US012606937B2

(12) United States Patent
Bazirgan et al.

(10) Patent No.: US 12,606,937 B2
(45) Date of Patent: *Apr. 21, 2026

(54) HUMANIZED ANTIBODIES WITH ULTRALONG COMPLEMENTARY DETERMINING REGIONS

(71) Applicant: Taurus Biosciences, LLC, Emeryville, CA (US)

(72) Inventors: Omar Bazirgan, Emeryville, CA (US); Miguel De Los Rios, Emeryville, CA (US)

(73) Assignee: TAURUS BIOSCIENCES, LLC, Emeryville, CA (US)

( * ) Notice: Subject to any disclaimer, the term of this patent is extended or adjusted under 35 U.S.C. 154(b) by 590 days.

This patent is subject to a terminal disclaimer.

(21) Appl. No.: 18/054,045

(22) Filed: Nov. 9, 2022

(65) Prior Publication Data

US 2023/0287598 A1      Sep. 14, 2023

Related U.S. Application Data

(63) Continuation of application No. 16/831,508, filed on Mar. 26, 2020, now Pat. No. 11,530,493, which is a continuation of application No. 14/905,765, filed as application No. PCT/US2014/047315 on Jul. 18, 2014, now Pat. No. 10,640,574.

(60) Provisional application No. 61/856,010, filed on Jul. 18, 2013.

(51) Int. Cl.
*C40B 40/10*       (2006.01)
*C07K 16/00*       (2006.01)
*C07K 16/46*       (2006.01)

(52) U.S. Cl.
CPC .............. *C40B 40/10* (2013.01); *C07K 16/00* (2013.01); *C07K 16/005* (2013.01); *C07K 16/464* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,877,293 | A | 3/1999 | Adair et al. |
| 6,740,747 | B2 | 5/2004 | Kaushik et al. |
| 7,196,185 | B2 | 3/2007 | Kaushik et al. |
| 7,575,893 | B2 | 8/2009 | Simmons |
| 7,592,010 | B2 | 9/2009 | Rosen et al. |
| 9,221,902 | B2 | 12/2015 | Smider et al. |
| 9,403,904 | B2 | 8/2016 | Smider et al. |
| 9,644,021 | B2 | 5/2017 | Wang et al. |
| 10,101,333 | B2 | 10/2018 | Smider et al. |
| 2003/0039649 | A1 | 2/2003 | Foote |

(Continued)

FOREIGN PATENT DOCUMENTS

| | | |
|---|---|---|
| CN | 1656121 A | 8/2005 |
| JP | 2005-522197 | 7/2005 |

(Continued)

OTHER PUBLICATIONS

U.S. Appl. No. 14/946,445, filed Nov. 19, 2015, Smider et al.

(Continued)

*Primary Examiner* — Christian C Boesen
(74) *Attorney, Agent, or Firm* — James S. Keddie; Bozicevic, Field & Francis LLP

(57)      ABSTRACT

The present disclosure provides humanized antibodies, including antibodies comprising an ultralong CDR3 and uses thereof.

10 Claims, 113 Drawing Sheets

Specification includes a Sequence Listing.

Non Reduced          Reduced

A  B  C  D          A  B  C  D

A = ShK 1x (HEK)
B = ShK 1x (CHO)
C = ShK 0x (HEK)
D = ShK 0x (CHO)

(56) References Cited

U.S. PATENT DOCUMENTS

| | | |
|---|---|---|
| 2003/0088074 A1 | 5/2003 | Hamers et al. |
| 2003/0170646 A1 | 9/2003 | Kaushik et al. |
| 2003/0215880 A1 | 11/2003 | Burton |
| 2005/0261480 A1 | 11/2005 | Foote |
| 2006/0275254 A1 | 12/2006 | Kim et al. |
| 2007/0071764 A1 | 3/2007 | Sullivan et al. |
| 2009/0148455 A1 | 6/2009 | Fischer et al. |
| 2009/0304580 A1 | 12/2009 | Goldenberg et al. |
| 2010/0311119 A1 | 12/2010 | Hermans et al. |
| 2011/0039761 A1 | 2/2011 | Eckert et al. |
| 2011/0172125 A1 | 7/2011 | Ladner |
| 2011/0293513 A1 | 12/2011 | Govindan et al. |
| 2011/0318339 A1 | 12/2011 | Smider et al. |
| 2012/0058906 A1 | 3/2012 | Smider et al. |
| 2012/0316071 A1 | 12/2012 | Smider et al. |
| 2014/0050720 A1 | 2/2014 | Smider et al. |
| 2014/0086871 A1 | 3/2014 | Smider et al. |
| 2014/0227267 A1 | 8/2014 | Wang et al. |
| 2015/0011431 A1 | 1/2015 | Smider et al. |
| 2015/0376264 A1 | 12/2015 | Wang et al. |
| 2016/0069894 A1 | 3/2016 | Smider et al. |
| 2016/0159928 A1 | 6/2016 | Bazirgan et al. |
| 2016/0168231 A1 | 6/2016 | De Los Rios et al. |
| 2016/0194627 A1 | 7/2016 | Smider et al. |
| 2016/0237156 A1 | 8/2016 | Wang et al. |
| 2018/0222999 A1 | 8/2018 | Smider et al. |

FOREIGN PATENT DOCUMENTS

| | | |
|---|---|---|
| WO | WO 93/20210 A1 | 10/1993 |
| WO | WO-1993/20210 | 10/1993 |
| WO | WO-1994/018221 | 8/1994 |
| WO | WO-2002/022809 | 3/2002 |
| WO | WO-2003/030821 | 4/2003 |
| WO | WO 2003/085086 | 10/2003 |
| WO | WO-2005/056759 | 6/2005 |
| WO | WO-2010/028791 | 3/2010 |
| WO | WO-2010/054007 | 5/2010 |
| WO | WO-2010/054010 | 5/2010 |
| WO | WO-2011/044542 | 4/2011 |
| WO | WO-2011/056997 | 5/2011 |
| WO | WO-2012/170977 | 12/2012 |
| WO | WO-2013/106485 | 7/2013 |
| WO | WO-2013/106489 | 7/2013 |
| WO | WO-2014/110368 | 7/2014 |
| WO | WO-2015/010100 | 1/2015 |
| WO | WO-2015/017146 | 2/2015 |

OTHER PUBLICATIONS

U.S. Appl. No. 15/140,175, filed Apr. 27, 2016, Smider et al.

Baker, P.J., "The pain of "chronic Lyme disease": moving the discourse in a different direction," The FASEB Journal, 26(1):11-12 (2012).

Brumeanu et al., "Efficient loading of identical viral peptide onto class II molecules by antigenized immunoglobulin and influenza virus," J. Exp. Med 178(5):1795-1799 (1993).

Casset et al., "A peptide mimetic of an anti-CD4 monoclonal antibody by rational design," BBRC 307(1):198-205 (2003).

Chen et al., "Selection and analysis of an optimized anti-VEGF antibody: crystal structure of an affinity-matured Fab in complex with antigen," J. Mol. Bio. 293(4): 865-881 (1999).

Haakenson et al., "Diversity in the cow Ultralong CDR H3 Antibody repertoire," Frontiers in Immunology (2018) 9:1262.

Hosseini et al., "Duplicated copies of the bovine JH locus contribute to the Ig repertoire," Int. Immunol. (2004) 16(6):843-852.

Hust et al., "Single chain Fab (scFab) fragment," BMC Biotechnology (2007) 7:14.

Inoue et al., "Affinity transfer to a human protein by CDR3 grafting of camelid VHH," Protein Science. 20(12):1971-1981 (2011).

Lefranc et al., "IMGT, the international ImMunoGeneTics information system." Nucleic Acids Res. Jan. 2009;37(Database issue):D1006-12.

Muyldermans et al., "Distinct Antibody Species: Structural Differences Creating Therapeutic Opportunities," Curr Opin Immunol. Jun. 2016 ; 40: 7-13.

NCBI, GenBank accession No. DM113215.1 (Jun. 18, 2009).

Nuttal et al., "Selection and affinity maturation of IgNAR variable domains targeting Plasmodium falciparum AMA1," Proteins: Structure, Function. and Bioinformatics. 55(1):187-197 (2004).

Pistillo et al., "Molecular Characterization and Applications of Recombinant SCFV Antibodies to CD152 Co-Stimulatory Molecule," Tissue Antigens 55(3):229-238.

Qin et al., "Fusion protein of CDR mimetic peptide with Fc inhibit TNF-alpha induced cytotoxicity," Molecular Immunology 43(6):660-666.

Qiu et al. "Small antibody mimetics comprising two complementarity determining regions and a framework region for tumor targeting," Nature Biotechnology 25(8):921-929 (2007).

Rader et al., "The rabbit antibody repertoire as a novel source for the generation of therapeutic human antibodies," Journal of Biological Chemistry. 275:13668-13676 (2000).

Ramsland et al., "Incorporation of long CDR3s into V domains: implications for the structural evolution of the antibody combining site," Experimental and Clinical Immunogenetics. 18(4):176-198 (2001).

Roche et al., "Invited review: Body condition score and its association with dairy cow productivity, health, and welfare," J. Dairy Sci., 92(12):5769-5801 (2009).

Sain et al., "Bovine IgM antibodies with exceptionally long complementarity-determining region 3 of the heavy chain share unique structural properties conferring restricted VH + Vlambda pairings," international immunology, 15(7):845-853 (2003).

Simmons et al., "Shark IgNAR antibody mimotopes target a murine immunoglobulin through extended CDR3 loop structures," Proteins: Structure, Function, and Bioinformatics. 71(1): 119-130 (2008).

Sok et al., "Rapid elicitation of broadly neutralizing antibodies to HIV by immunization in cows," Nature. Aug. 3, 2017; 548(7665): 108-111.

Streltsov et al., "Crystal Structure of the Amyloid-p3 Fragment Provides a Model for Oligomer Formation in Alzheimer's Disease," Journal of Neuroscience. 31(4) 1419-1426 (2011).

Streltsov et al., "Supplemental Material Crystal Structure of the Amyloid-p3 Fragment Provides a Model for Oligomer Formation in Alzheimer's Disease," (2011) Journal of Neuroscience. 31(4) 1419-1426 (2011).

Wells "Additivity of Mutational Effects in Proteins," Biochemistry 29:8509-8517 (1990).

Wold et al., "Antibody Therapeutics in Oncology," Immunotherapy (Los Angel). Mar. 2016 ; 2(1):pii:108.

Wynne et al., "Oxyntomodulin increases energy expenditure in addition to decreasing energy intake in overweight and obese humans: a randomised controlled trial," International Journal of Obesity 30(12) • 1729-1736 (2006).

Yang et al., "The three complementarity-determining region-like loops in the second extracellular domain of human Fc alpha/mu receptor contribute to its binding of IgA and IgM," Immunobiology 218(5):798-809 (2013).

Zhao et al., "The bovine antibody repertoire," Developmental and Comparative Immunology. 30• 175-186 (2006).

Saini et al., "Exceptionally long CDR3H region with multiple cysteine residues in functional bovine IgM antibodies," European Journal of Immunology, (1999) 29(8): 2420-2426.

Smider, "Cow Antibodies: A New Structural Class of Antibody Using Ultralong CDR3s," World ADC, Oct. 16, 2013. Retrieved from http://adc-summit.com/uploads/files/2463_ADC_/Vaughn_Smider.pdf.

Stanfield et al., "Conservation and diversity in the ultralong third heavy-chain complementarity-determining region of bovine antibodies," Science Immunology (2016) 1:aaf7962.

Wang et al., "Reshaping Antibody Diversity," Cell (2013) 153(6):1379-1393.

Zhang et al., "An Antibody CDR3-Erythropoietin Fusion Protein," ACS Chem Biol (2013) 8(10):2117-2121.

(56) References Cited

OTHER PUBLICATIONS

Zhang et al., "Functional Antibody CDR3 Fusion Proteins with Enhanced Pharmacological Properties," Angew Chem Int Ed Engl (2013) 52(32):8295-8298.

Zhang et al., "Rational Design of humanized dual-agonist antibodies," Journal of the American Chemical Society (2015) 137(1):38-41.

U.S. Appl. No. 15/660,852, filed Jul. 26, 2017, by Smider et al.

Koti et al., "Novel atypical nucleotide insertions specifically at VH-DH junction generate exceptionally long CDR3H in cattle antibodies", Molecular Immunology, 2010, 47(11-12): 2119-2128.

Saini et al., "Exceptionally long CDR3H region with multiple cysteine residues in functional bovine IgM antibodies", Eur. J. Immunol., 1999, 29: 2420-2426.

Almagro et al., "Humanization of antibodies", Frontiers in Bioscience, 2008; 1(13): 1619-1633.

De Genst et al., "Antibody repertoire development in camelids", Developmental and Comparative Immunology, 2006; 30: 187-198.

Ward et al., "Binding activities of a repertoire of single immunoglobulin variable domains secreted from *Escherichia coli*" Nature, 1989; 341: 544-546.

Barthelemy et al., "Comprehensive analysis of the factors contributing to the stability and solubility of autonomous human VH domains", Journal of Biological Chemistry, 2008; 283(6): 3639-3654.

Choi et al., "Predicting antibody complementarity determining region structures without classification", 2011, Molecular BioSystems, 2011; 7: 3327-3334.

Griffiths et al., "Human anti-self antibodies with high specificity from phage display libraries.", The European Molecular Biology Organization Journal, 1993; 12(2): 725-734.

Klimka et al., "Human anti-CD30 recombinant antibodies by guided phage antibody selection using cell panning", British Journal of Cancer, 2000; 83(2): 252-260.

Beiboer et al., "Guided selection of a pan carcinoma specific antibody reveals similar binding characteristics yet structural divergence between the original murine antibody and its human equivalent", Journal of Molecular Biology, 2000; 296(3): 833-849.

Ottensmeier et al., "Isotype switch variants reveal clonally related subpopulations in diffuse large B-cell lymphoma", Blood, 2000; 96(7): 2550-2556.

Pistillo et al., "Molecular Characterization and Applications of Recombinant SCFV Antibodies to CD152 Co-Stimulatory Molecule", Tissue Antigens, Mar. 2000, 55(3): 229-238.

Qin et al., "Fusion protein of CDR mimetic peptide with Fc inhibit TNF-alpha induced cytotoxicity", Molecular Immunology, Feb. 2006, 43(6): 660-666.

Figure 1:
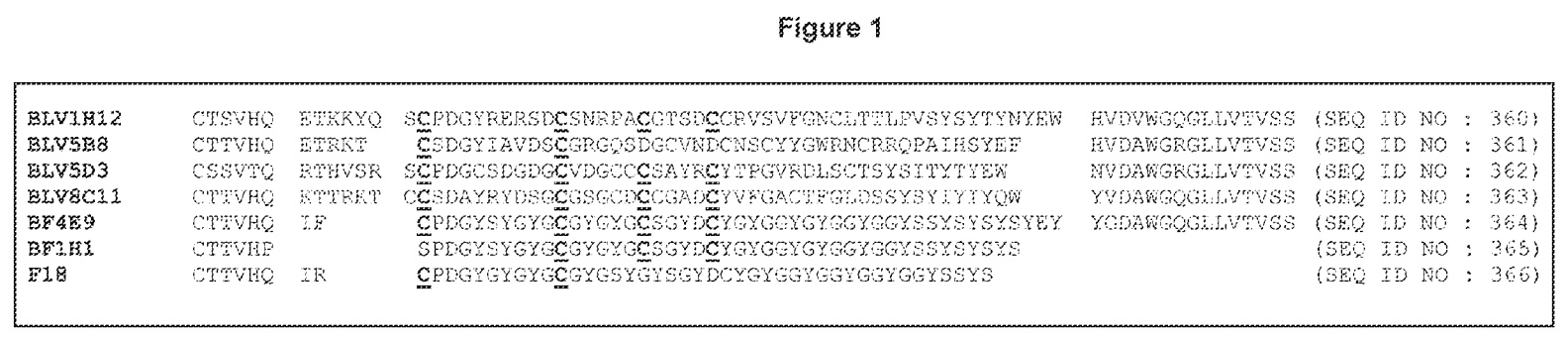

Figure 2A:
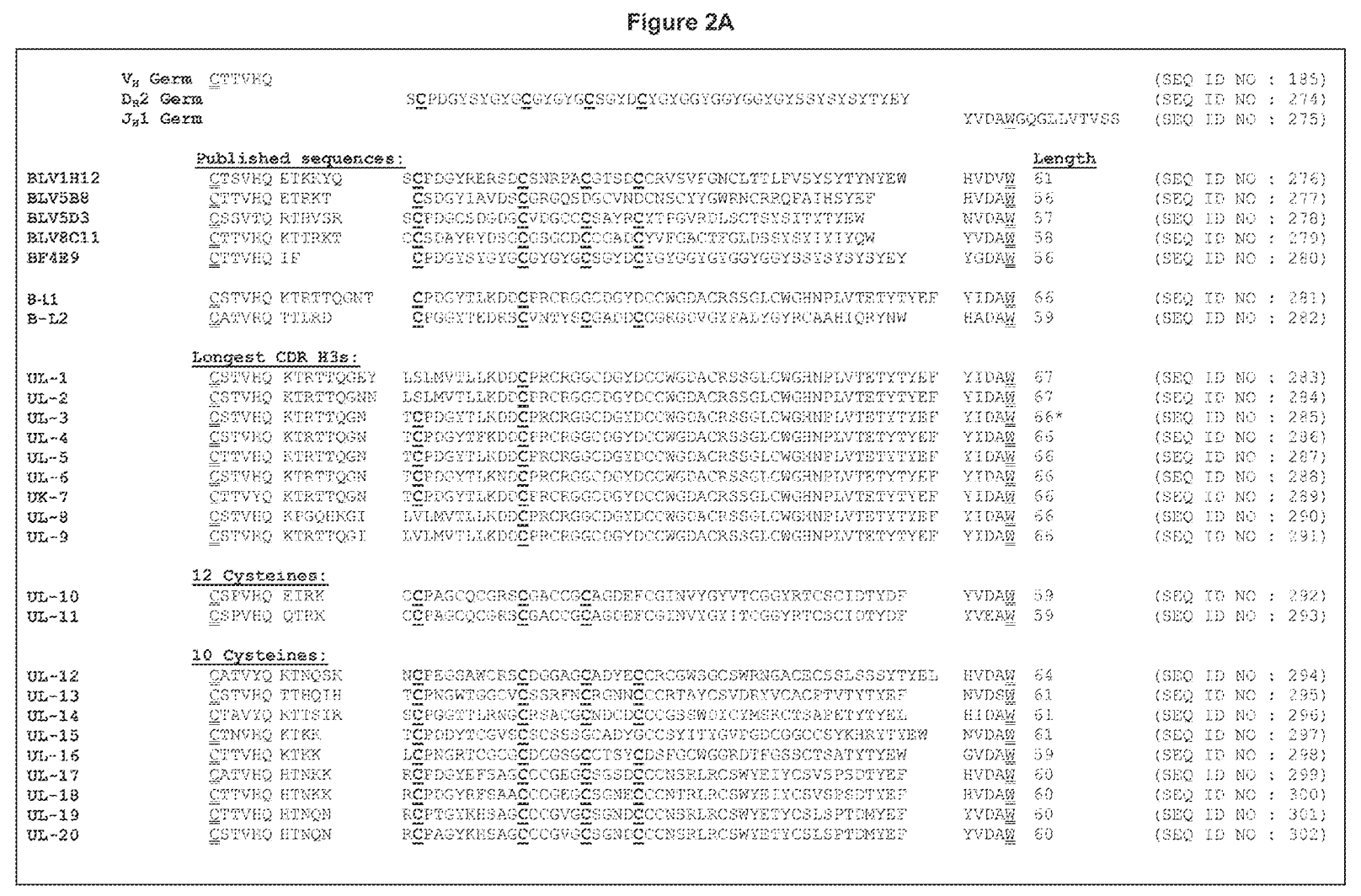

Figure 2B:
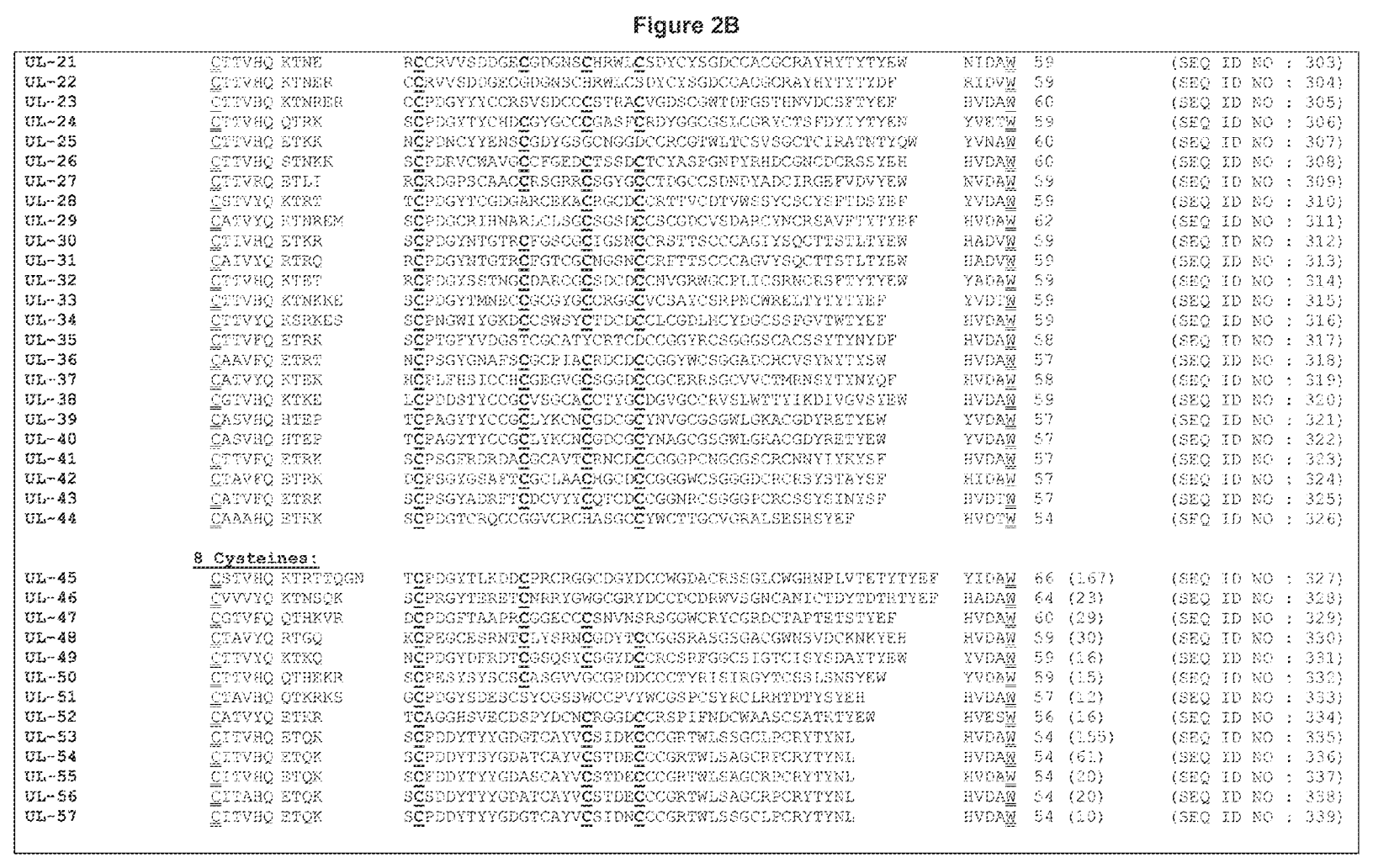

Figure 2C:
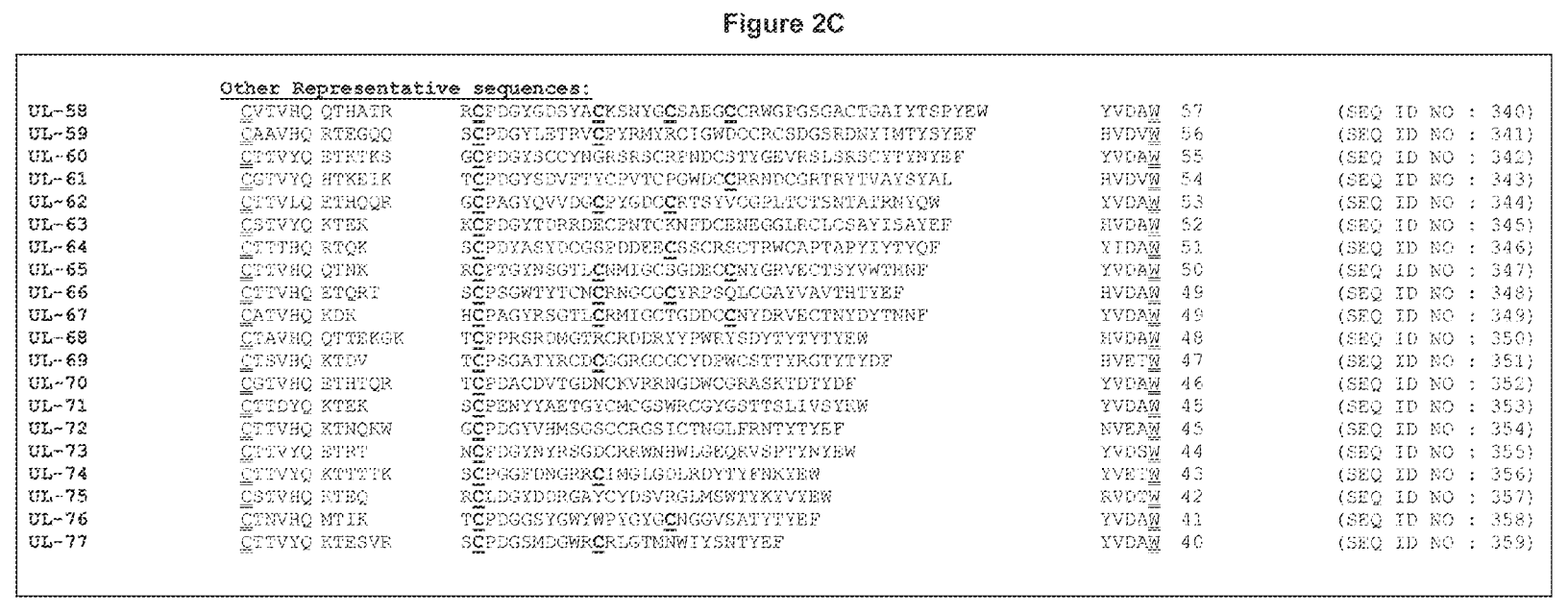

BLV1H12

SVHQETKKYQSCPDGYRERSDCSNRPACGTSDCCRVSVFGNCLTTLPVSYSYTYNYEWHVD
(SEQ ID NO : 22)

BLV5B8
TVHQETRKTCSDGYIAVDSCGRGQSDGCVNDCNSCYYGWRNCRRQPAIHSYEFHVD
(SEQ ID NO : 23)

BLV5D3
SVTQRTHVSRSCPDGCSDGDGCVDGCCCSAYRCYTPGVRDLSCTSYSITYTYEWNVD
(SEQ ID NO : 24)

BLV8C11
TVHQKTTRKTCCSDAYRYDSGCGSGCDCCGADCYVFGACTFGLDSSYSYIYIYQWYVD
(SEQ ID NO : 25)

BF4E9
TVHQIFCPDGYSYGYGCGYGYGCSGYDCYGYGGYGYGGYGGYSSYSYSYSYEYYGD
(SEQ ID NO : 26)

BF1H1
TVHPSPDGYSYGYGCGYGYGCSGYDCYGYGGYGYGGYGGYSSYSYSYS
(SEQ ID NO : 27)

F18
TVHQIRCPDGYGYGYGCGYGSYGYSGYDCYGYGGYGGYGGYGGYSSYS
(SEQ ID NO : 28)

Figure 4

Bovine VH-UL:

```
        caggtgcagctgcgggagtcgggccccagcctggtgaagccctcacagaccctctcgctc
         Q   V   Q   L   R   E   S   G   P   S   L   V   K   P   S   Q   T   L   S   L
        acctgcacggcctctggattctcattgagcgacaaggctgtaggctgggtccgccaggct
         T   C   T   A   S   G   F   S   L   S   D   K   A   V   G   W   V   P   Q   A
        ccagggaaggcgctggagtggctcggtggtatagacactggtggaagcacaggctataac
         P   G   K   A   L   E   W   L   G   G   I   D   T   G   G   S   T   G   Y   N
        ccaggcctgaaatcccggctcagcatcaccaaggacaactccaagagccaagtctctctg
         P   G   L   K   S   R   L   S   I   T   K   D   N   S   K   S   Q   V   S   L
        tcagtgagcagcgtgacaactgaggactcggccacatactactgtactactgtgcaccag   (SEQ ID NO: 367)
         S   V   S   S   V   T   T   E   D   S   A   T   Y   Y   C   T   T   V   H   Q   (SEQ ID NO: 29)

QVQLRESGPSLVKPSQTLSLTCTASGFSLSDKAVGWVRQAPGKALEWLGGIDTGGSTGYN
        PGLKSRLSITKDNSKSQVSLSVSSVTTEDSATYYCTTVHQ   (SEQ ID NO: 29)
```

Figure 5A

4-39:
Cagctgcagctgcaggagtcgggcccaggactggtgaagccttcggagaccctgtccctcacctgcactgtctctgg
tggctccatcagcagtagttactactggggctggatccgccagcccccagggaaggggctggagtggattgggga
gtatctattatagtgggagcacctactacaacccgtccctcaagagtcgagtcaccatatccgtagacacgtccaag
aaccagttctccctgaagctgagctctgtgaccgccgcagacacggctgtgtattactgtgcgagacacacagtgag
ggg
(SEQ ID NO: 368)

QLQLQESGPGLVKPSETLSLTCTVSGGSISSSSYYWGWIRQPPGKGLEWIGSIYYSGSTYYNPSLKSRVTISVDTSK
NQFSLKLSSVTAADTAVYYCAR
(SEQ ID NO: 31)

4-59*03:
Caggtgcagctgcaggagtcgggcccaggactggtgaagccttcggagaccctgtccctcacctgcactgtctctgg
tggctccatcagtagttactactggagctggatccggcagcccccagggaagggggactggagtggattgggtatatct
attacagtgggagcaccaactacaaccccctccctcaagagtcgagtcaccatatcagtagacacgtccaagaaccaa
ttctccctgaagctgagctctgtgaccgctgcggacacggccgtgtattactgtgcg
(SEQ ID NO: 369)

QVQLQESGPGLVKPSETLSLTCTVSGGSISSYYWSWIRQPPGKGLEWIGYIYYSGSTNYNPSLKSRVTISVDTSKNQ
FSLKLSSVTAADTAVYYCA
(SEQ ID NO: 32)

4-34*09:
Caggtgcagctgcaggagtcgggcccaggactggtgaagccttcacagaccctgtccctcacctgcgctgtctatgg
tgggtccttcagtggttactactggagctggatccgccagcccccagggaagggggactggagtggattggggaaatca
atcatagtggaagcaccaactacaaccccgtccctcaagagtcgagttaccatatcagtagacacgtctaagaaccag
ttctccctgaagctgagctctgtgactgccgcggacacggccgtgtattactgtgcgaga
(SEQ ID NO: 370)

QVQLQESGPGLVKPSQTLSLTCAVYGGSFSGYYWSWIRQPPGKGLEWIGEINHSGSTNYNPSLKSRVTISVDTSKNQ
FSLKLSSVTAADTAVYYCAR
(SEQ ID NO: 33)

4-34*02:
Caggtgcagctacaacagtggggcgcaggactgttgaagccttcggagaccctgtccctcacctgcgctgtctatgg
tgggtccttcagtggttactactggagctggatccgccagcccccagggaagggggctggagtggattggggaaatca
atcatagtggaagcaccaactacaaccccgtccctcaagagtcgagtcaccatatcagtagacacgtccaagaaccag
ttctccctgaagctgagctctgtgaccgccgcggacacggctgtgtattactgtgcgagagg
(SEQ ID NO: 371)

QVQLQQWGAGLLKPSETLSLTCAVYGGSFSGYYWSWIRQPPGKGLEWIGEINHSGSTNYNPSLKSRVTISVDTSKNQ
FSLKLSSVTAADTAVYYCAR
(SEQ ID NO: 34)

Figure 5B

```
4-39        QLQLQESGPGLVKPSETLSLTCTVSGGSISSSSYYWGWIRQPPGKGLEWIGSIYYSGSTY 60
4-59*03     QVQLQESGPGLVKPSETLSLTCTVSGGSISS--YYWSWIRQPPGKGLEWIGYIYYSGSTN 58
4-34*02     QVQLQQWGAGLLKPSETLSLTCAVYGGSFSG--YYWSWIRQPPGKGLEWIGEINHSGSTN 58
4-34*09     QVQLQESGPGLVKPSQTLSLTCAVYGGSFSG--YYWSWIRQPPGKGLEWIGEINHSGSTN 58
VH-UL       QVQLPESGPSLVKPSQTLSLTCTASGFSLSD--KAVGWVRQAPGKALEWLGGIDTGGSTG 58
            *:**:: *,,*:***;*****:, * *;*          .*:**,***,***;* *   ,***

4-39        YNPSLKSRVTISVDTSKNQFSLKLSSVTAADTAVYYCAR----- 99  (SEQ ID NO: 31)
4-59*03     YNPSLKSRVTISVDTSKNQFSLKLSSVTAADTAVYYCA------- 96  (SEQ ID NO: 32)
4-34*02     YNPSLKSRVTISVDTSKNQFSLKLSSVTAADTAVYYCAR----- 97  (SEQ ID NO: 33)
4-34*09     YNPSLKSRVTISVDTSKNQFSLKLSSVTAADTAVYYCAR----- 97  (SEQ ID NO: 34)
VH-UL       YNPGLKSRLSITKDNSKSQVSLSVSSVTTEDSATYYCTTVHQTQ 102 (SEQ ID NO: 29)
            ***,****::*: *,**,*,*,**.;***;
```

Figure 6

BLV1H12 VL:

Caggctgtgctgaatcagccatcatccgtgtccgggtccctgggccagagggtctccatcacctgctctggaagcag
cagcaatgttggaaatggatatgtgagctggtaccaactgatcccaggatcggcccccagaaccctcatctatggtg
acaccagtcgagcctcggggggtccccgaccgattctccggctccaggtctgggaacacagccaccctgaccatcagc
tcgctccaggctgaggacgaggcagattatttctgtgcatctgctgaggatagtagcagtaatgctgttttcggcag
cgggaccacactgaccgtcctg
(SEQ ID NO: 372)

QAVLNQPSSVSGSLGQRVSITCSGSSSNVGNGYVSWYQLIPGSAPRTLIYGDTSRASGVPDRFSGSRSGNTATLTIS
SLQAEDEADYFCASAEDSSSNAVFGSGTTLTVL
(SEQ ID NO: 35)

Cagtctgtgctgactcagccaccctcagcgtctggggacccccgggcagagggtcaccatctcttgttctggaagcag
ctccaacatcggaagtaattatgtatactggtaccagcagctcccaggaacggcccccaaactcctcatctataggga
ataatcagcggccctcaggggtccctgaccgattctctggctccaagtctggcacctcagcctccctggccatcagt
gggctccggtccgaggatgaggctgattattactgtgcagcatgggatgacagcctgagtggtcc
(SEQ ID NO: 373)

QSVLTQPPSASGTPGQRVTISCSGSSSNIGSNYVYWYQQLPGTAPKLLIYRNNQRPSGVPDRFSGSESGTSASLAIS
GLRSEDEADYYCAAWDDSLSG
(SEQ ID NO: 36)

V11-40*1:
Cagtctgtgctgacgcagccgccctcagtgtctggggcccccagggcagagggtcaccatctcctgcactgggagcag
ctccaacatcggggcaggttatgatgtacactggtaccagcagcttccaggaacagcccccaaactcctcatctatg
gtaacagcaatcggccctcaggggtccctgaccgattctctggctccaagtctggcacctcagcctccctggccatc
actgggctccaggctgaggatgaggctgattattactgccagtcctatgacagcagcctgagtggttc
(SEQ ID NO: 374)

QSVLTQPPSVSGAPGQRVTISCTGSSSNIGAGYDVHWYQQLPGTAPKLLIYGNSNRPSGVPDRFSGSKSGTSASLAI
TGLQAEDEADYYCQSYDSSLSG
(SEQ ID NO: 37)

V11-51 *01:
Cagtctgtgttgacgcagccgccctcagtgtctgggcccaggacagaaggtcaccatctcctgctctggaagcag
ctccaacattgggaataattatgtatcctggtaccagcagctcccaggaacagcccccaaactcctcatttatgaca
ataataagcgaccctcagggattcctgaccgattctctggctccaagtctggcacgtcagccaccctgggcatcacc
ggactccagactggggacgaggccgattattactgcggaacatgggatagcagcctgagtgctgg
SEQ ID NO: 375)

QSVLTQPPSVSAAPGQKVTISCSGSSSNIGNNYVSWYQQLPGTAPKLLIYDNNKRPSGIPDRFSGSESGTSATLGIT
GLQTGDEADYYCGTWDSSLSA
SEQ ID NO: 38)

V12-18*02:
Cagtctgccctgactcagcctccctccgtgtccgggtctcctggacagtcagtcaccatctcctgcactggaaccagcagtgacgt
tggtagttataaccgtgtctcctggtaccagcagcccccaggcacagcccccaaactcatgatttatgaggtcagtaatcggccct
caggggtccctgatcgcttctctgggtccaagtctggcaacacggcctcctgaccatctctgggctccaggctgaggacgaggct
gattattactgcagctcatatacaagcagcagcactttc
(SEQ ID NO: 376)

QSALTQPPSVSGSPGQSVTISCTGTSSDVGSYNRVSWYQQPPGTAPKLMIYEVSNRPSGVPDRFSGSKSGNTASLTI
SGLQAEDEADYYCSSYTSSSTF
(SEQ ID NO: 39)

Figure 7B

```
Vl1-47        QSVLTQPPSASGTPGQRVTISCSGSSSNIGSNY-VYWYQQLPGTAPKLLIYRNNQRPSGV 59
Vl1-51        QSVLTQPPSVSAAPGQKVTISCSGSSSNIGNNY-VSWYQQLPGTAPKLLIYDNNKRPSGI 59
Vl1-40*1      QSVLTQPPSVSGAPGQRVTISCTGSSSNIGAGYDVHWYQQLPGTAPKLLIYGNSNRPSGV 60
Vl2-18*02     QSALTQPPSVSGSPGQSVTISCTGTSSDVGSYNRVSWYQQPPGTAPKLMIYEVSNRPSGV 60
Vl1x (cow)    QAVLTQPSSVSGSLGQRVSITCSGSSSNVGNGY-VSWYQLIPGSAPRTLIYGDTSPASGV 59
              *:.****.*.*.:.** *:*:*:*:**::*    * *** **:**: :** ..*.**:

Vl1-47        PDRFSGSKSGTSASLAISGLRSEDEADYYCAAWDDSLSG 98    (SEQ ID NO: 36)
Vl1-51        PDRFSGSKSGTSATLGITGLQTGDEADYYCGTWDSSLSA 98    (SEQ ID NO: 37)
Vl1-40*1      PDRFSGSKSGTSASLAITGLQAEDEADYYCQSYDSSLSG 99    (SEQ ID NO: 38)
Vl2-18*02     PDRFSGSKSGNTASLTISGLQAEDEADYYCSSYTSSSTF 99    (SEQ ID NO: 39)
Vl1x          PDRFSGSRSGNTATLTISSLQAEDEADYFCASAEDSSSN 98    (SEQ ID NO: 35)
              *******:**.:*:* *:.*:: *****:* :  .* :
```

Figure 8

| Designation | V1 Alternative A | V1 Alternative B |
|---|---|---|
| VH4-34_Q5RQ6E | QVQLREWGAGLLKPSETLSLTCAVYGGSFSGYYWSWIRQPPGKGLEWIGEINHSGSTNYNPSLKSRVTISVDTSKNQFSLKLSSVTAADTAVYY (SEQ ID NO: 734) | QVQLREWGAGLLKPSETLSLTCAVYGGSFSGYYWSWIRQPPGKGLEWIGEINHSGSTNYNPSLKSRVTISVDTSKNQFSLKLSSVTAADTAVYYC (SEQ ID NO: 735) |
| VH4-34_CDR1-G31DY32K_Q5RQ6E | QVQLREWGAGLLKPSETLSLTCAVYGGSFSDKYWSWIRQPPGKGLEWIGEINHSGSTNYNPSLKSRVTISVDTSKNQFSLKLSSVTAADTAVYY (SEQ ID NO: 736) | QVQLREWGAGLLKPSETLSLTCAVYGGSFSDKYWSWIRQPPGKGLEWIGEINHSGSTNYNPSLKSRVTISVDTSKNQFSLKLSSVTAADTAVYYC (SEQ ID NO: 737) |
| VH4-34_CDR2-E50S_Q5RQ6E | QVQLREWGAGLLKPSETLSLTCAVYGGSFSGYYWSWIRQPPGKGLEWIGSINHSGSTNYNPSLKSRVTISVDTSKNQFSLKLSSVTAADTAVYY (SEQ ID NO: 738) | QVQLREWGAGLLKPSETLSLTCAVYGGSFSGYYWSWIRQPPGKGLEWIGSINHSGSTNYNPSLKSRVTISVDTSKNQFSLKLSSVTAADTAVYYC (SEQ ID NO: 739) |
| VH4-34_CDR1-G31DY32K_CDR2-E50S_Q5RQ6E | QVQLREWGAGLLKPSETLSLTCAVYGGSFSDKYWSWIRQPPGKGLEWIGSINHSGSTNYNPSLKSRVTISVDTSKNQFSLKLSSVTAADTAVYY (SEQ ID NO: 740) | QVQLREWGAGLLKPSETLSLTCAVYGGSFSDKYWSWIRQPPGKGLEWIGSINHSGSTNYNPSLKSRVTISVDTSKNQFSLKLSSVTAADTAVYYC (SEQ ID NO: 741) |
| VH4-34_CDR1-Cow_Q5RQ6E | QVQLREWGAGLLKPSETLSLTCTASGFSLSDKAVGWIRQPPGKGLEWIGEINHSGSTNYNPSLKSRVTISVDTSKNQFSLKLSSVTAADTAVYY (SEQ ID NO: 742) | QVQLREWGAGLLKPSETLSLTCTASGFSLSDKAVGWIRQPPGKGLEWIGEINHSGSTNYNPSLKSRVTISVDTSKNQFSLKLSSVTAADTAVYYC (SEQ ID NO: 743) |
| VH4-34_CDR2-Cow_Q5RQ6E | QVQLREWGAGLLKPSETLSLTCAVYGGLGSIDTGGNTGSFSGYYWSWIRQPPGKGLEWYNPSLKSRVTISVDTSKNQFSLKLSSVTAADTAVYY (SEQ ID NO: 744) | QVQLREWGAGLLKPSETLSLTCAVYGGLGSIDTGGNTGSFSGYYWSWIRQPPGKGLEWYNPSLKSRVTISVDTSKNQFSLKLSSVTAADTAVYYC (SEQ ID NO: 745) |
| VH4-34_CDR1-Cow_CDR2-E50S_Q5RQ6E | QVQLREWGAGLLKPSETLSLTCTASGFSLSDKAVGWIRQPPGKGLEWIGSINHSGSTNYNPSLKSRVTISVDTSKNQFSLKLSSVTAADTAVYY (SEQ ID NO: 746) | QVQLREWGAGLLKPSETLSLTCTASGFSLSDKAVGWIRQPPGKGLEWIGSINHSGSTNYNPSLKSRVTISVDTSKNQFSLKLSSVTAADTAVYYC (SEQ ID NO: 747) |
| VH4-34_CDR1-Cow_CDR2-Cow_Q5RQ6E | QVQLREWGAGLLKPSETLSLTCTASGFSLSDKAVGWIRQPPGKGLEWLGSIDTGGNTGYNPSLKSRVTISVDTSKNQFSLKLSSVTAADTAVYY (SEQ ID NO: 748) | QVQLREWGAGLLKPSETLSLTCTASGFSLSDKAVGWIRQPPGKGLEWLGSIDTGGNTGYNPSLKSRVTISVDTSKNQFSLKLSSVTAADTAVYYC (SEQ ID NO: 749) |

Figure 9

| Designation | VL Amino Acid Sequence |
|---|---|
| VL1-51 S2A, T5N, P8S, A12G ,A13S, P14L, K46R, L47T, D51G, N52D, N53T | QAVLNQPSSVSGSLGQKVTISCSGSSNIGNNYVSWYQQLPGTAPRTLIYGDTKRPSGIP DRFSGGSKSGTSATLGITGLQTGDEADYYC (SEQ ID NO: 750) |
| VL1-51 S2A, T5N, P8S, A12G ,A13S, P14L, K46R, L47T, D51G, N52D, N53T, K54S, P56A | QAVLNQPSSVSGSLGQKVTISCSGSSNIGNNYVSWYQQLPGTAPRTLIYGDTSRASGIP DRFSGGSKSGTSATLGITGLQTGDEADYYC (SEQ ID NO: 751) |
| VL1-51 I29V, N32G, K46R, L47T, D51G, N52D, N53T | QSVLTQPPSVSAAPGQKVTISCSGSSNVGNGYVSWYQQLPGTAPRTLIYGDTKRPSGI PDRFSGGSKSGTSATLGITGLQTGDEADYYC (SEQ ID NO: 752) |
| VL1-51 I29V, N32G, K46R, L47T, D51G, N52D, N53T, K54S, P56A | QSVLTQPPSVSAAPGQKVTISCSGSSNVGNGYVSWYQQLPGTAPRTLIYGDTSRASGI PDRFSGGSKSGTSATLGITGLQTGDEADYYC (SEQ ID NO: 753) |
| VL1-51 S2A, T5N, P8S, A12G ,A13S, P14L, K46R, L47T, D51G, N52D, N53T, with CDR3 in BLV1H12 Light Chain and J region after CDR3 in BLV1H12 Light Chain | QAVLNQPSSVSGSLGQKVTISCSGSSNIGNNYVSWYQQLPGTAPRTLIYGDTKRPSGIP DRFSGGSKSGTSATLGITGLQTGDEADYYCASAEDSSSNAVFGSGTTLTVL(SEQ ID NO: 959) |

Figure 10

| Designation | VH Nucleic Acid Sequence | VH Amino Acid Sequence |
|---|---|---|
| VH4-34+CDR3-IL8_Q5RQ6E | CAGGTGCAGCTAAGAGAGTGGGGCGCAGGACTGTTGAAGCCTTCGGAGACGCTGTCCCTCACCTGCGCTGTGTCTATGGTGGGTTCCTTCAGTGGTTACTACTGGAGCTGGATTCGGCAGCCCCCAGGAAGGGGCTGGAGTGGATGGGAAATCAATCATAGTGGAAGCACCAACTACAACCCGTCCCTCAAGAGTCGAGTCACCATATCAGTAGACACGTCCAAGAACCAGTTCTCCCTGAAGCTGAGCTCTGTGACCGCCGCGGACACGGCTGTGTATTACTGTACCTCTGTGCACCAGGAAACTAAGAAATACCAGAGCCCAAGGAGTGCTAAGAACTTAGATGTCAGTGCATAAAAGACATACTCCAAACCTTTCCACCCCAAGTTCATCAAGGAGCTGAGAGTGATTGAGAGTGGAGAGCTCTGCCTGGACCCCAAGGAAAACTGGGTGCAGTAAAGCTTTCTGATGGGAGAAGTTCTTGAAGAGGTCGTGGAGAAGTTCTTGAAGAGGTCGTGGAGAAGTTCTTGATGGGAGAAGTTCTTGATGTGGATGCATGTGGATGTGTGGATGTCTGGGGACAGGGCCTGCTGGTGGTGACAGTCTACAATTATGAATGGCATGTGGATGTGTGGGGACAGGGCCTGCTGGTGGTGACAGTCTCTAGT (SEQ ID NO: 490) | QVQLREWGAGLLKPSETLSLTCAVYGGSFSGYWSWIRQPPGKGLEWIGEINHSGSTNYNPSLKSRVTISVDTSKNQFSLKLSSVTAADTAVYYCTSVHQETKKYQSPRSAKELRCQCIKTYSKPFHPKFIKELRVIESGPHCANTEIIVKLSDGRELCLDPKENWVQRVVEKFLKRAENSGSGSYTYNYEWHVDVWGQGLLVTVSS (SEQ ID NO: 784) |
| VH4-34+CDR3-IL8_CDR1-G31DY32K_Q5RQ6E | CAGGTGCAGCTAAGAGAGTGGGGCGCAGGACTGTTGAAGCCTTCGGAGACGCTGTCCCTCACCTGCGCTGTGTCTATGGTGGGTTCCTTCAGTGACAAGTACTGGAGCTGGATTCGCCAGCCCCCAGGAAGGGGCTGGAGTGGATGGGAAATCAATCATAGTGGAAGCACCAACTACAACCCGTCCCTCAAGAGTCGAGTCACCATATCAGTAGACACGTCCAAGAACCAGTTCTCCCTGAAGCTGAGCTCTGTGACCGCCGCGGACACGGCTGTGTATTACTGTACCTCTGTGCACCAGGAAACTAAGAAATACCAGAGCCCAAGGAGTGCTAAGAACTTAGATGTCAGTGCATAAAAGACATACTCCAAACCTTTCCACCCCAAGTTCATCAAGGAGCTGAGAGTGATTGAGAGTGGAGAGCTCTGCCTGGACCCCAAGGAAAACTGGGTGCAGTAAAGCTTTCTGATGGGAGAAGTTCTTGAAGAGGTCGTGGAGAAGTTCTTGATGGGAGAAGTTCTTGATGTGGATGCATGTGGATGTGTGGGGACAGGGCCTGCTGGTGGTGACAGTCTACAATTATGAATGGCATGTGGATGTGTGGGGACAGGGCCTGCTGGTGGTGACAGTCTCTAGT (SEQ ID NO: 491) | QVQLREWGAGLLKPSETLSLTCAVYGGSFSDKYWSWIRQPPGKGLEWIGEINHSGSTNYNPSLKSRVTISVDTSKNQFSLKLSSVTAADTAVYYCTSVHQETKKYQSPRSAKELRCQCIKTYSKPFHPKFIKELRVIESGPHCANTEIIVKLSDGRELCLDPKENWVQRVVEKFLKRAENSGSGSYTYNYEWHVDVWGQGLLVTVSS (SEQ ID NO: 785) |

Figure 10 (continued)

| Designation | VH Nucleic Acid Sequence | VH Amino Acid Sequence |
|---|---|---|
| VH4-34+CDR3-IL8_CDR2-E50S_Q5RQ6 E | CAGGTGCAGCTAAGAGAGTGGGGCGCAGGACTGTTGAAGCCTTCGGAGACGCTGT CCCTCACCTGCGCTGTCTGTGGTGGTTCCTTCAGTGGTTACTACTGGAGCTGGATT CGCCAGCCCCAGGGAAGGGCTGGAGTGGATTGGGAGCATCAATCATAGTGGAA GCACCAACTACAACCCGTCCCTCAAGAGTCGAGTCACCATATCAGTAGACACGTCC AAGAACCAGTTCTCCCTGAAGCTGAGCTCTGTGACCGCGGACACGGCTGTGTA TTACTGTACCTCTGTGCACCAGGAAACTAAGAAATACCAGAGCCCAAGGAGTGCTAA AGAACTTAGATGTCAGTGCATAAAAGACATACTCCAAACCTTTCCACCCCAAGTTCAT CAAGGAGCTGAGAGTGATTGAGAGTGGACCACACTGCGCCAACACAGAGATTATTG TAAAGCTTTCTGATGGGAGAAGTTCTTGAAGAGGGCTGAGAAGGGCTGAGAAACTGGGTGCAG AGGGTCGTGGAGAAGTTCTTGAAGAGGCATGTGGGATGTCTGGGGACAGGGCCTGGTGGTGACAGTCT CTACAATTATGAATGGCATGTGGGATGTCTGGGGACAGGGCCTGGTGGTGACAGTCT CTAGT (SEQ ID NO: 492) | QVQLREWGAGLLKPSETLSLTC AVYGGSFSGYYWSWIRQPPGK GLEWIGSINHSGSTNYNPSLKS RVTISVDTSKNQFSLKLSSVTAA DTAVYYCTSVHQETKKYQSPRS AKELRCQCIKTYSKPFHPKFIKE LRVIESGPHCANTEIIVKLSDGR ELCLDPKENWVQRVVEKFLKRA ENSGGSYTYNYEWHVDVWG QGLLVTVSS (SEQ ID NO: 786) |
| VH4-34+CDR3-IL8_CDR1-G31DY32K_C DR2-E50S_Q5RQ6 E | CAGGTGCAGCTAAGAGAGTGGGGGCGCAGGACTGTTGAAGCCTTCGGAGACGCTGT CCCTCACCTGCGCTGTCTGTATGGTGGTTCCTTCAGTGACAAGTACTGGAGCTGGATT CGCCAGCCCCAGGGAAGGGCTGGAGTGGATTGGGAGCATCAATCATAGTGGAA GCACCAACTACAACCCGTCCCTCAAGAGTCGAGTCACCATATCAGTAGACACGTCC AAGAACCAGTTCTCCCTGAAGCTGAGCTCTGTGACCGCGGACACGGCTGTGTA TTACTGTACCTCTGTGCACCAGGAAACTAAGAAATACCAGAGCCCAAGGAGTGCTAA AGAACTTAGATGTCAGTGCATAAAAGACATACTCCAAACCTTTCCACCCCAAGTTCAT CAAGGAGCTGAGAGTGATTGAGAGTGGACCACACTGCGCCAACACAGAGATTATTG TAAAGCTTTCTGATGGGAGAAGTTCTTGAAGAGGGCTGAGAAAGGGCTGAGAAACTGGGTGCAG AGGGTCGTGGAGAAGTTCTTGAAGAGGCATGTGGGATGTCTGGGGACAGGGCCTGGTGGTGACAGTCT CTACAATTATGAATGGCATGTGGGATGTCTGGGGACAGGGCCTGGTGGTGACAGTCT CTAGT (SEQ ID NO: 493) | QVQLREWGAGLLKPSETLSLTC AVYGGSFSDKYWSWIRQPPGK GLEWIGSINHSGSTNYNPSLKS RVTISVDTSKNQFSLKLSSVTAA DTAVYYCTSVHQETKKYQSPRS AKELRCQCIKTYSKPFHPKFIKE LRVIESGPHCANTEIIVKLSDGR ELCLDPKENWVQRVVEKFLKRA ENSGGSYTYNYEWHVDVWG QGLLVTVSS (SEQ ID NO: 787) |

Figure 10 (continued)

| Designation | VH Nucleic Acid Sequence | VH Amino Acid Sequence |
|---|---|---|
| VH4-34+CDR3-IL8_CDR1-Cow_Q5RQ6E | CAGGTGCAGCTAAGAGAGTGGGGCGCAGGACTGTTGAAGCCTTCGGAGACGCTGTCCCTCACCTGCACAGCAAGCGGGTTTCACTGAGCGACAAGGCAGTGGGATGGATTCGCCAGCCCCAGGGAAGGGGCTGGAGTGGATTGGGAAATCAATCATAGTGGAAGCACCAACTACAACCCGTCCCTCAAGAGTCGAGTCACCATATCAGTAGACACGTCCAAGAACCAGTTCTCCCTGAAGCTGAGCTCTGTGACCGCCGGGACACGGCTGTGTATTACTGTACCTCTGTGCACCAGGAAACTAAGAAATACCAGAGCCCAAGGAGTGCTAAAGAACTTAGATGTCAGTGCATAAAGACATACTCCAAACCTTTCCACCCCAAGTTCATCAAGGAGCTGAGAGTGATTGAGAGGTGGACCAGACCACACTGCGCCAACACAGAGATTATTGTAAAGCTTTCTGATGGGAGAGAGCTCTTGGGACCCCAAGGAAAACTGGGTGCAGAGGGTCGTGGAGAAGTTCTTGAAGAGGGCATGGCATGGGATGTGCTGGGGACAGGGCCTGGTGGTGACAGTCTCTAGT (SEQ ID NO: 494) | QVQLREWGAGLLKPSETLSLTCTASGFSLSDKAVGWIRQPPGKGLEWIGEINHSGSTNYNPSLKSRVTISVDTSKNQFSLKLSSVTAADTAVYYCTSVHQETKKYQSPRSAKELRCQCIKTYSKPFHPKFIKELRVIESGPHCANTEIIVKLSDGRELCLDPKENWVQRVVEKFLKRAENSGSGSYTYNYEWHVDVWGQGLLVTVSS (SEQ ID NO: 788) |
| VH4-34+CDR3-IL8_CDR2-Cow_Q5RQ6E | CAGGTGCAGCTAAGAGAGTGGGGCGCAGGACTGTTGAAGCCTTCGGAGACGCTGTCCCTCACCTGCGCTGTCTATGGTGGTGGCAGCGTGGCTGGCATGGACACAGGGTCCTTCAGTGGTTACTGCTGGAGCTGGATTCGCCAGCCCCCAGGGAAGGGGCTGGAGTGGATTGGGAGTCAACACCGTCCCTCAAGAGTCGAGTCTCTGTGACCGCGGGGACACGGCTGTGTCAAGAACCAGTTCTCCCTGAAGCTGAGCTCTGTGACCGCCGGGAAACTAAGAAATACCAGAGCCCAAGGAGTGCTAATTACTGTACCTCTGTGCACCAGGAAACTAAGAAATACCAGAGCCCAAGGAGTGCTAAGAACTTAGATGTCAGTGCATAAAGACATACTCCAAACCTTTCCACCCCAAGTTCATCAAGGAGCTGAGAGTGATTGAGAGGTGGACCAGACCACACTGCGCCAACACAGAGATTATTGTAAAGCTTTCTGATGGGAGAGAGCTCTTGGGACCCCAAGGAAAACTGGGTGCAGAGGGTCGTGGAGAAGTTCTTGAAGAGGGCATGGCATGGGATGTGCTGGGGACAGGGCCTGGTGGTGACAGTCTCTAGT (SEQ ID NO: 495) | QVQLREWGAGLLKPSETLSLTCAVYGGLGSIDTGGNTGSFSGYYWSWIRQPPGKGLEWYNPSLKSRVTISVDTSKNQFSLKLSSVTAADTAVYYCTSVHQETKKYQSPRSAKELRCQCIKTYSKPFHPKFIKELRVIESGPHCANTEIIVKLSDGRELCLDPKENWVQRVVEKFLKRAENSGSGSYTYNYEWHVDVWGQGLLVTVSS (SEQ ID NO: 789) |

Figure 10 (continued)

| Designation | VH Nucleic Acid Sequence | VH Amino Acid Sequence |
|---|---|---|
| VH4-34+CDR3-IL8_CDR1-Cow_CDR2-E50S_Q5RQ6E | CAGGTGCAGCTAAGAGAGTGGGGCGCAGGACTGTTGAAGCCTTCGGAGACGCTGTCCCTCACCTGCACAGCAGCGGGTTTCACTGAGCGACAAGGCAGTGGGATGGATTCGCCAGCCCCCAGGGAAGGGGCTGGAGTGGATGGCATCAATCATAGTGGAAGCACCAACTACAACCCGTCCCTCAAGAGTCGAGTCACCATATCAGTAGACACGTCCAAGAACCAGTTCTCCCTGAAGCTGAGCTCTGTGACCGGCGGACACGGCTGTGTATTACTGTACCTCTGTGCACCAGGAAACTAAGAAACTAACCAGAGCCCAAGGAGTGCTAAAGAACTTAGATGTCAGTGCATAAAGACATACTCCAAACCTTTCCACCCCAAGTTCATCAAGGAGCTGAGAGTGATTGAGAGTGGAGAGCTGTGCCTGAGAAACTGGGTGCAGTAAAGCTTTCTGATGGGAGAAGTTCTTGAAGAGGGCATGTGGATGTCTGGGGACGTCGTGGTGACAGTCTCTACAATTATGAATGGCATGTGGATGTCTGGGGACGTCGTGGTGACAGTCTCTAGT (SEQ ID NO: 496) | QVQLREWGAGLLKPSETLSLTCTASGFSLSDKAVGWIRQPPGKGLEWIGSINHSGSTNYNPSLKSRVTISVDTSKNQFSLKLSSVTAADTAVYYCTSVHQETKKYQSPRSAKELRCQIKTYSKPFHPKFIKELRVIESGPHCANTEIIVKLSDGRELCLDPKENWVQRVVEKFLKRAENSGGSYYNYEWHVDVWGQGLLVTVSS (SEQ ID NO: 790) |
| VH4-34+CDR3-IL8_CDR1-Cow_CDR2-Cow_Q5RQ6E | CAGGTGCAGCTAAGAGAGTGGGGCGCAGGACTGTTGAAGCCTTCGGAGACGCTGTCCCTCACCTGCACAGCAGCGGGTTTCACTGAGCGACAAGGCAGTGGGATGGATTCGCCAGCCCCCAGGGAAGGGGCTGGAGTGGCTGGGCATCGATACCGGCGGGAACACAGGGTACAACCCGTCCCTCAAGAGTCGAGTCAGTGTCGTGACAGTCAAGAACCAGTTCTCCCTGAAGCTGAGCTCTGTGACCGGCGGACACGGCTGTGTATTACTGTACCTCTGTGCACCAGGAAACTAAGAAAGACATACTCCAAACCTTTCCACCCCAAGTTCAAGAACTTAGATGTCAGTGCATAAAGACATACTCCAAACCTTTCCACCCCAAGTTCATCAAGGAGCTGAGAGTGATTGAGAGTGGAGAGCTGTGCCTGAGAAACTGGGTGCAGTAAAGCTTTCTGATGGGAGAAGTTCTTGAAGAGGGCATGTGGATGTCTGGGGACAGGGCTCAGGGGCATCAGGGCTCAGGGCGGTTCTTATAGAGGGTCGTGTGGAAGTTCTTGATGGGAGAAGTTCTTGAAGAGGGCATGTGGATGTCTGGGGACAGGGCCTGCTGGTGACAGTCCCTACAATTATGAATGGCATGTGGATGTCTGGGGACAGGGCCTGCTGGTGACAGTCTCTAGT (SEQ ID NO: 497) | QVQLREWGAGLLKPSETLSLTCTASGFSLSDKAVGWIRQPPGKGLEWLGSIDTGGNTGYNPSLKSRVTISVDTSKNQFSLKLSSVTAADTAVYYCTSVHQETKKYQSPRSAKELRCQIKTYSKPFHPKFIKELRVIESGPHCANTEIIVKLSDGRELCLDPKENWVQRVVEKFLKRAENSGGSYYNYEWHVDVWGQGLLVTVSS (SEQ ID NO: 791) |

Figure 11

| Designation | VL-CL Nucleic Acid Sequence | VL-CL Amino Acid Sequence |
|---|---|---|
| VL1-51 S2A, T5N, P8S, A12G ,A13S, P14L, K46R, L47T, D51G, N52D, N53T | CAGGCCGTCCTGAACCAGCCAAGCCAGCGGTCTCCGGGTCTCTGGGGCAGAAGGTGA CTATCAGCTGCTGCTCTGGCTCATCAAGCAACATCGGGAATAATTACGTCAGCTGGTACC AGCAGCTGCCTGGAACAGCTCCTAGAACCCTCATTTATGGCGACACAAAGCGCCCA TCCGGAATCCCTGACCGATTCAGCGGAAGCAAATCAGGGACCTCTGCAACTCTGGG AATCACTGGCTTCAGGACAGGAGATGAGGCAGATTACTATTGCGCCTCTGCAGAGG ACAGCTCCAGCAATGCCGTGTTCGGGTCTGGTACCACTCTTACAGTCCTAGGTCAG CCCAAGGCTGCCCCCTCGGTCACTCTGTTCCCGCCCTCCTCTGAGGAGCTTCAAGC CAACAAGGCCACACTGGTGTGTCTCATAAGTGACTTCTACCCGGGAGCCGGTGACAG TGGCCTGGAAGGCAGTAGCAGCCCCGTCAAGGCGGGAGTGGAAACAACCACACC CTCCAACAAGAGCAACAAGCAGTCCCACAGAAGCTACAGCTGCCAGGTCACGGGAGCAC GTTCA CGTGGGAGAAGACAGTGGCCCCTACAGAATGTTCA (SEQ ID NO: 486) | QAVLNQPSSVSGSLGQKVTISC SGSSSNIGNNYVSWYQQLPGT APRTLIYGDTKRPSGIPDRFSGS KSGTSATLGITGLQTGDEADYY CASAEDSSSNAVFGSGTTLTVL GQPKAAPSVTLFPPSSEELQAN KATLVCLISDFYPGAVTVAWKA DSSPVKAGVETTTPSKQSNNKY AASSYLSLTPEQWKSHRSYSC QVTHEGSTVEKTVAPTECS (SEQ ID NO: 780) |
| VL1-51 S2A, T5N, P8S, A12G ,A13S, P14L, K46R, L47T, D51G, N52D, N53T, K54S, P56A | CAGGCCGTCCTGAACCAGCCAAGCCAGCGGTCTCCGGGTCTCTGGGGCAGAAGGTGA CTATCAGCTGCTGCTCTGGCTCATCAAGCAACATCGGGAATAATTACGTCAGCTGGTACC AGCAGCTGCCTGGAACAGCTCCTAGAACCCTCATTTATGGCGACACATCCAGAGCT TCCGGAATCCCTGACCGATTCAGCGGAAGCAAATCAGGGACCTCTGCAACTCTGGG AATCACTGGGCTTCAGGACAGGAGATGAGGCAGATTACTATTGCGCCTCTGCAGAGG CCCAAGGCTGCCCCCTCGGTCACTCTGTTCCCGCCCTCCTCTGAGGAGCTTCAAGC CAACAAGGCCACACTGGTGTGTCTCATAAGTGACTTCTACCCGGGAGCCGGTGACAG TGGCCTGGAAGGCAGTAGCAGCCCCGTCAAGGCGGGAGTGGAAACAACCACACC CTCCAAACAAAGCAACAAGCAGTCCCACAGAAGCTACAGCTGCCAGGTCACGGGAGCAC AGCAGTGGAAGTCCCACAGAAGCTACAGCTGCCAGGTCACGGGAGCAC CGTGGGAGAAGACAGTGGCCCCTACAGAATGTTCA (SEQ ID NO: 487) | QAVLNQPSSVSGSLGQKVTISC SGSSSNIGNNYVSWYQQLPGT APRTLIYGDTSRASGIPDRFSGS KSGTSATLGITGLQTGDEADYY CASAEDSSSNAVFGSGTTLTVL GQPKAAPSVTLFPPSSEELQAN KATLVCLISDFYPGAVTVAWKA DSSPVKAGVETTTPSKQSNNKY AASSYLSLTPEQWKSHRSYSC QVTHEGSTVEKTVAPTECS (SEQ ID NO: 781) |

Figure 11 (continued)

| Designation | VL-CL Nucleic Acid Sequence | VL-CL Amino Acid Sequence |
|---|---|---|
| VL1-51 I29V, N32G, K46R, L4TT, D51G, N52D, N53T | CAGTCCGTGCTGACCCAACCCCGTCAGTGTCTGCTGCCCCGGGCAGAAGGTGA CTATCAGCGTGCTGTCTGGCTCATCCTCCAATGTCGGCAACGGTACGTCAGCTGGTAC CAGCAGCTGCCTGGAACAGCTCCTAGAACCCTCATTTATGGCGACACAAAGCGCCC ATCCGGAATCCCTGACCGATTCAGCGGAAGCAAATCAGGAGACCTCTGCAACTCTGG GAATCACTGGGCTTCAGCACTGGAGGATGAGGCAGATTACTATTGGCGCCTCTGCAGAG GACAGCTCCAGCAATGCCGGTTGGGGTCTGGTGTACCCACTCTTACAGTCCTAGGTCA GCCCAAGGCTGCCCCTCGGTCACTCTGTTCCCGCCCTCCTCTGAGGAGCTTCAAG CCAACAAGGCCACACTGGTGTGTCTCATAAGTGACTTCTACCCGGGAGCCGTGACA GTGGCCTGGAAGGCAGATAGCAGCCCGTCAAGGCGGGAGTGGAAACAACCACAC CCTCCAAACAAGCAACAACAAGTACGCGGCCAGCTACAGCTGCCAGGTCACGCCTGACGCCT GAGCAGTGGAAGTCCCACAGAAGCTACAGCTGCCAGGTCACGCACGCATGAAGGGAGCA CCGTGGAGAAGACAGTGGCCCCTACAGAATGTTCA (SEQ ID NO: 488) | QSVLTQPPSVSAAPGQKVTISC SGSSSNVGNGYVSWYQQLPGT APRTLIYGDTKRPSGIPDRFSGS KSGTSATLGITGLQTGDEADYY CASAEDSSSNAVFGSGTTLTVL GQPKAAPSVTLFPPSSEELQAN KATLVCLISDFYPGAVTVAWKA DSSPVKAGVETTTPSKQSNNKY AASSYLSLTPEQWKSHRSYSC QVTHEGSTVEKTVAPTECS (SEQ ID NO: 782) |
| VL1-51 I29V, N32G, K46R, L4TT, D51G, N52D, N53T, K54S, P56A | CAGTCCGTGCTGACCCAACCCCGTCAGTGTCTGCTGCCCCGGGCAGAAGGTGA CTATCAGCGTGCTGTCTGGCTCATCCTCCAATGTCGGCAACGGTACGTCAGCTGGTAC CAGCAGCTGCCTGGAACAGCTCCTAGAACCCTCATTTATGGCGACACATCCAGAGC TTCCGGAATCCCTGACCGATTCAGCGGAAGCAAATCAGGAGACCTCTGCAACTCTGG GAATCACTGGGCTTCAGCACTGGAGGATGAGGCAGATTACTATTGGCGCCTCTGCAGAG GACAGCTCCAGCAATGCCGGTTGGGGTCTGGTGTACCCACTCTTACAGTCCTAGGTCA GCCCAAGGCTGCCCCTCGGTCACTCTGTTCCCGCCCTCCTCTGAGGAGCTTCAAG CCAACAAGGCCACACTGGTGTGTCTCATAAGTGACTTCTACCCGGGAGCCGTGACA GTGGCCTGGAAGGCAGATAGCAGCCCCGTCAAGGCGGGAGTGGAAACAACCACAC CCTCCAAACAAAGCAACAACAAGTACGCGGCGCAGCTACAGCTGCCAGGTCATCTGACGCCT GAGCAGTGGAAGTCCCACAGAAGCTACAGCTGCCAGGTCACGCACGCATGAAGGGAGCA CCGTGGAGAAGACAGTGGCCCCTACAGAATGTTCA (SEQ ID NO: 489) | QSVLTQPPSVSAAPGQKVTISC SGSSSNVGNGYVSWYQQLPGT APRTLIYGDTSRASGIPDRFSGS KSGTSATLGITGLQTGDEADYY CASAEDSSSNAVFGSGTTLTVL GQPKAAPSVTLFPPSSEELQAN KATLVCLISDFYPGAVTVAWKA DSSPVKAGVETTTPSKQSNNKY AASSYLSLTPEQWKSHRSYSC QVTHEGSTVEKTVAPTECS (SEQ ID NO: 783) |

Figure 12

| Designation | Amino Acid Sequence |
|---|---|
| Heavy Chain CDR3 Ascending Stalk | TSVHQETKKYQS (SEQ ID NO: 498) |
| Heavy Chain CDR3 Descending Stalk | SYTYNYEWHVDV(SEQ ID NO: 499) |
| BLV1H12 Heavy Chain J region outside of CDR3 | WGQGLLVTVSS(SEQ ID NO: 500) |
| CDR3 in BLV1H12 Light Chain | ASAEDSSSNAV(SEQ ID NO: 754) |
| J region after CDR3 in BLV1H12 Light Chain | FGSGTTLTVL(SEQ ID NO: 755) |
| Human Light Chain Lambda Constant Region | GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS(SEQ ID NO: 756) |
| Human Light Chain Lambda Variable Region | QAVLNQPSSVSGSLGQRVSITCSGSSSNVGNGYVSWYQLIPGSAPRTLIYGDTSRASGV PDRFSGSRSGNTATLTISSLQAEDEADYFCASAEDSSSNAVFGSGTTLTVL(SEQ ID NO: 956) |

Figure 13

| Designation | Nucleic Acid Sequence |
|---|---|
| BLV1H12-CDR3-GGS1:1-BsaI | CAGGTCCAGCTGAGAGAGAGCGGCGCCCTTCACTGGTCAAGCCATCCCAGACACTGAGCCTGACATGCACAGCAGCAAGCGGGTTTTCACTGAGCGACAAGGCAGTGGGATGGGTCCGGACAGGCACCAGGAAAGCCCTGGAATGGCTGGGCAGCATCGATACCGGCGGGAACACAGGGTACAATCCCGGACTGAAGAGACAGACTGTCCATTACCAAGGACAACTCTAAAAGTCAGGTGTCACTGAGCGTGAGCGTCCGTCACCACAGAGGATAGTGCAACTTACTATTGCACCTCTGTGCACCAGGAAACTAAGAAATACCAGAGCGGAGGAAGCGGAGACCTACTATGGTTCGGGTCTCGGGACAGGGCCTGCTGGTGACAGTTGAATGGCATGTGGATGTCTGGGGACAGGGCCTGCTGGTGACAGTCTCTAGTCTCTAGTGC TAGC (SEQ ID NO: 757) |
| BLV1H12-CDR3-GGS1:2-BsaI | CAGGTCCAGCTGAGAGAGAGCGGCGCCCTTCACTGGTCAAGCCATCCCAGACACTGAGCCTGACATGCACAGCAGCAAGCGGGTTTTCACTGAGCGACAAGGCAGTGGGATGGGTCCGACAGGCACCAGGAAAGCCCTGGAATGGCTGGGCAGCATCGATACCGGCGGGAACACAGGGTACAATCCCGGACTGGTCACTGAGCGTGCACTGAGCGTCACTGAGCGGTGAGCGTCCGTCACCACAGAGGATAGTCAACTCTAAAAGTCAGGTGTCACTGAGCGTGCACTGAGCGTCACTGAGCGGTGAGCGTCCGTCACCACAGAGGATAGTGCAACTTACTATTGCACCTCTGTGCACCTATGGTTCGGGTCTCGGGTGGTGGCATGTGGATGTCTGGGGACAGGGCCTGCTGGTGACAGCCTACAATTATGAATGGCATGTGGATGTCTGGGGACAGGGCCTGCTGGTGACAGTCTCTAGTGCTAGC (SEQ ID NO: 758) |
| BLV1H12-CDR3-GGS2:1-BsaI | CAGGTCCAGCTGAGAGAGAGCGGCGCCCTTCACTGGTCAAGCCATCCCAGACACTGAGCCTGACATGCACAGCAGCAAGCGGGTTTTCACTGAGCGACAAGGCAGTGGGATGGGTCCGGACAGGCACCAGGAAAGCCCTGGAATGGCTGGGCAGCATCGATACCGGCGGGAACACAGGGTACAATCCCGGACTGAAGAGACAGACTGTCCATTACCAAGGACAACTCTAAAAGTCAGGTGTCACTGAGCGTGAGCGTCCGTCACCACAGAGGATAGTGCAACTTACTATTGCACCTCTGTGCACCAGGAAACTAAGAAATACCAGAGCGGAGGAAGCGGAGAAGGCGGAGGAAGCGGAGGAAGCGGAGCCTACAATTATGAATGGCATGTGGATGTCTGGGGACAGGGCCTGCTGGTGACAGCCTACACAATTATGAATGGCATGTGGATGTCTGGGGACAGGGCCTGCTGGTGACAGTCTCTAGTGCTAGC (SEQ ID NO: 759) |

Figure 13 (continued)

| Designation | Nucleic Acid Sequence |
|---|---|
| BLV1H12-CDR3-GGS2.2-BsaI | CAGGTCCAGCTGGAGAGAGAGAGCGGCGGCCCTTCACTGGTCAAGCCATCCAGACACTGAGCCTGACACTGCACAGCACAGGTACAATGCCTGGGTTTTCACTGAGCGACAAGGCAGTGGGATGGGTCCGACAGGCACCAGGAAAAGCCCTGGAATGGCTGGGCAGCATCGGATACCGGCGGGAACACAGGTACAATCCCGGACTGAAGAGCAGACTGTCCATTACCAAGGACAACTCTAAAAGTCAGGTGTCACTGAGCGTGACCCTCTGTGCACCAGAGGATAGTGCAACTTACTATTGCACCTCGTGTGCACCAGGAACTAAGAAATACCAGAGCGGGAGGAAGCGGGAGGAAGCGGAGACCTACTATGGCATGTCGGGTCTCGGGGACAGGGCCTGCAGCTCTTATACCTACACAATTATGAATGGCATGTGGATGTCTGGGGACAGGGCCTGCTGGTGACAGTCTCTAGTGCTAGC (SEQ ID NO: 760) |
| BLV1H12-CDR3-GGS2.3-BsaI | CAGGTCCAGCTGGAGAGAGAGAGCGGCGGCCCTTCACTGGTCAAGCCATCCAGACACTGAGCCTGACACTGCACAGCACAGGTACAATGCCTGGGTTTTCACTGAGCGACAAGGCAGTGGGATGGGTCCGACAGGCACCAGGAAAAGCCCTGGAATGGCTGGGCAGCATCGGATACCGGCGGGAACACAGGTACAATCCCGGACTGAAGAGCAGACTGTCCATTACCAAGGACAACTCTAAAAGTCAGGTGTCACTGAGCGTGACCCTCTGTGCACCAGAGGATAGTGCAACTTACTATTGCACCTCTGTGCACCAGGAACTAAGAAATACCAGAGCGGGAGGAAGCGGGAGGAAGCGGAGAGCGGGAGGAAGCGGGAGGAAGCGGGAGAGCGGAGGAAGCGGGAGAGCTTATACCTACACAATTATGAATGGCATGTGGATGTCTGGGGACAGGGCCTGCTGGTGACAGTCTCTAGTGCTAGC (SEQ ID NO: 761) |
| BLV1H12-CDR3-GGS2.4-BsaI | CAGGTCCAGCTGGAGAGAGAGAGCGGCGGCCCTTCACTGGTCAAGCCATCCAGACACTGAGCCTGACACTGCACAGCACAGGTACAATGCCTGGGTTTTCACTGAGCGACAAGGCAGTGGGATGGGTCCGACAGCAGCACCAGGAAAAGCCCTGGAATGGCTGGGCAGCATCGGATACCGGCGGGAACACAGGTACAATCCCGGACTGAAGAGCAGACTGTCCATTACCAAGGACAACTCTAAAAGTCAGGTGTCACTGAGCGTGACCCTCTGTGCACCAGAGGATAGTGCAACTTACTATTGCACCTCTGTGCACCAGGAACTAAGAAATACCAGAGCGGGAGGAAGCGGGAGGAAGCGGGAGGAAGCGGGAGGAAGCGGGAGAGCGGGAGGAAGCGGGAGGAAGCGGAGGAAGCGGAGGAAGCGGGAGAGCTCTTATACCTACACAATTATGAATGGCATGTGGATGTCTGGGGACAGGGCCTGCTGGTGACAGTCTCTAGTGCTAGC (SEQ ID NO: 762) |

Figure 13 (continued)

| Designation | Nucleic Acid Sequence |
|---|---|
| BLV1H12-CDR3-GGS3:2-Bsal | CAGGTCCAGCTGAGAGAGAGAGCGGCGGCCCTTCACTGGTCAAGCCATCCCAGACACTGAGCCTGACATGCACAGCAGGCACCAGGAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACCTGTCACTGAGCGTGAGCTCCGTCACCACAGAGGATAGTGCAACTTACTATTGCACCTCTGTGCACCAGGAAGGAGACCTACTATGGTTCGGGTCTCGGAGGAGAAGCGGGAGGAGGAAGCGGAGGAGGAAGCTCTTATACCTACAATTATGAATGGCATGTGGATGTCTGGGGACAGGGCCTGCTGGTGACAGTCTCTAGTGCTAGC (SEQ ID NO: 763) |
| BLV1H12-CDR3-GGS3:3-Bsal | CAGGTCCAGCTGAGAGAGAGAGCGGCGGCCCTTCACTGGTCAAGCCATCCCAGACACTGAGCCTGACATGCACAGCAGGCACCAGGAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACCTGTCACTGAGCGTGAGCTCCGTCACCACAGAGGATAGTGCAACTTACTATTGCACCTCTGTGCACCAGGAAGGAGACCTACTATGGTTCGGGTCTCGGAGGAGAAGCGGGAGGAGGAAGCGGAGGAGGAAGCTCTTATACCTACAATTATCCTACAATTATGAATGGCATGTGGATGTCTGGGGACAGGGCCTGCTGGTGACAGTCTCTAGTGCTAGC (SEQ ID NO: 764) |
| BLV1H12-CDR3-GGS4:2-Bsal | CAGGTCCAGCTGAGAGAGAGAGCGGCGGCCCTTCACTGGTCAAGCCATCCCAGACACTGAGCCTGACATGCACAGCAGGCACCAGGAAAGCCCTGGAATGGCTGGGCAGCATCGATACCGGCGGGAACACAGGGTACAATCCCGGACTGAAGAGCAGACTGTCCATTACCAAGGACAACTCTAAAAGTCAGGTGTCACCTGTCACTGAGCGTGAGCTCCGTCACCACAGAGGATAGTGCAACTTACTATTGCACCTCTGTGCACCAGGAAGGAGACCTACTATGGTTCGGGTCTCGGAGGAGAAGCGGAGGAGGAAGCGGAGGAGGAAGCTCTTATACCTACAATTATGAATGGCATGTGGATGTCTGGGGACAGGGCCTGCTGGTGACAGTCTCTAGTGCTAGC (SEQ ID NO: 765) |

Figure 13 (continued)

| Designation | Nucleic Acid Sequence |
|---|---|
| BLV1H12-CDR3-G4Sx1-Bsal | CAGGTCCAGCTGGAGAGAGAGCGGCCGCCCTTCACTGGTCAAGCCATCCCAGACACTG AGCCTGACACTGCCACAGCAAGGCAAGCGGGTTTTCACTGAGCGACCAAGGCAGTGGGATGG GTCCGACAGGCCACCAGGAAAAGCCCTGGAATGGCTGGGCAGCATCGATACCGG CGGGAACACAGGGTACAATCCCGGACTGAAGAGCAGAGACTGTCCATTACCAAGGA CAACTCTAAAAGTCAGGTGTCACTGAGCGTGACCAGGAAACTAAGAAATACCAGAGGATAGT GCAACTTACTATTGCACCTCTGTGCACCAGGAGACCTACTATGGTTCAGGGTCTCTGGAGGTGGTG GAGGAGGTTCTGGAGGATGAGACCTACTATGGTTCAGGGTCTCTGGAGGTGGTG GATCTTCTTATACCTACACAATTATGGCATGTGCATGTCTGGGGACAGGGCCT GCTGGTGACAGTCTCTAGTGCTAGC (SEQ ID NO: 766) |
| BLV1H12-CDR3-G4Sx3-Bsal | CAGGTCCAGCTGGAGAGAGAGCGGCCGCCCTTCACTGGTCAAGCCATCCCAGACACTG AGCCTGACATGCACAGCAAGCGGGTTTTCACTGAGCGACCAAGGCAGTGGGATGG GTCCGACAGGCCACCAGGAAAAGCCCTGGAATGGCTGGGCAGCATCGATACCGG CGGGAACACAGGGTACAATCCCGGACTGAAGAGCAGAGACTGTCCATTACCAAGGA CAACTCTAAAAGTCAGGTGTCACCCTCTGTGCACCAGGAAACTAAGAAATACCAGAGGATAGT GCAACTTACTATTGCACCTCTGTGCACCAGGAAACTAAGAAATACCAGAGCGGTG GAGGAGGTTCTGGAGGCGGTGGAAGTGGTGGCGGAGGTGGATCTGGTGGAGGAGGCAGTGGA CTACTATGGTGGCAGCTCTTATACCTACACAATTATGAATGGCATGTGCATGTCTGGGGAC GGTGGTGGCAGCTTCAGGGTCTCTGGAGGTGGATCTGGTGGAGGAGGCAGTGGA AGGGCCTGCTGGTGACAGTCTCTAGTGCTAGC (SEQ ID NO: 767) |
| Bsal containing Nucleotide sequence I | GAGACCTACTATGGTTCGGGTCTC (SEQ ID NO: 768) |
| Bsal containing Nucleotide sequence II | GAGACCTACTATGGTTCAGGGTCTC (SEQ ID NO: 769) |

Figure 14

| Designation | Amino Acid Sequence |
|---|---|
| BLV1H12-CDR3-GGS1:1-Moka | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSGGSSYTYNYEWHVDVWGQGLLVTV KCSLPQQCIKPCKDAGMRFGKCMNKKCRCYSGGSSYTYNYEWHVDVWGQGLLVTV SSAS (SEQ ID NO: 770) |
| BLV1H12-CDR3-GGS1:2-Moka | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGSGGINV KCSLPQQCIKPCKDAGMRFGKCMNKKCRCYSGGSSYTYNYEWHVDVWGQGL LVTVSSAS (SEQ ID NO: 771) |
| BLV1H12-CDR3-GGS2:1-Moka | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGSGGS GINVKCSLPQQCIKPCKDAGMRFGKCMNKKCRCYSGGSSYTYNYEWHVDVWGQGL LVTVSSAS (SEQ ID NO: 772) |
| BLV1H12-CDR3-GGS2:2-Moka | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGSGGS GINVKCSLPQQCIKPCKDAGMRFGKCMNKKCRCYSGGSSYTYNYEWHVDVWG QGLLVTVSSAS (SEQ ID NO: 773) |
| BLV1H12-CDR3-GGS3:3-Moka | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGSGGS GGSGINVKCSLPQQCIKPCKDAGMRFGKCMNKKCRCYSGGSGGSSYTYNYEW HVDVWGQGLLVTVSSAS (SEQ ID NO: 774) |
| BLV1H12-CDR3-G4Sx3-ProTxII | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGGSG GGSGGGGSGGYCQKWMWTCDSERKCCEGMVCRLWCKKLWGGGGSGGGGGS GGGGSSYTYNYEWHVDVWGQGLLVTVSSAS (SEQ ID NO: 775) |
| BLV1H12-CDR3-G4Sx3-GPTX toxin | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGGGSG GGSGGGGSGGGDCLGFMRKCIPDNDKCCRPNLVCSRTHKWCKYVFGGGGSGGGGS SGGGGSSYTYNYEWHVDVWGQGLLVTVSSAS (SEQ ID NO: 776) |

Figure 14 (continued)

| Designation | Amino Acid Sequence |
|---|---|
| BLV1H12-CDR3-G4Sx3-OSK1 P12, K16, D20 toxin | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGGGSG GGGSGGGGSGGGGVIINVCKISPQCLKPCKDAGMRFGKCMNGKCHCTPKGGGGSG GGGSGGGGSSYTYNYEWHVDVWGQGLLVTVSSAS  (SEQ ID NO: 777) |
| BLV1H12-CDR3-G4Sx3-OSK1 K16, D20 toxin | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGGGSG GGGSGGGGSGGGGVIINVCKKISRQCLKPCKDAGMRFGKCMNGKCHCTPKGGGGGSG GGGSGGGGGSSYTYNYEWHVDVWGQGLLVTVSSAS (SEQ ID NO: 778) |
| BLV1H12-CDR3-G4Sx3-ShK toxin | QVQLRESGPSLVKPSQTLSLTCTASGFSLSDKAVGWVRQAPGKALEWLGSIDTGGN TGYNPGLKSRLSITKDNSKSQVSLSVSSVTTEDSATYYCTSVHQETKKYQSGGGGSG GGGSGGGGSGGGRSCIDTIPKSRCTAFQCKHSMKYRLSFCRKTCGTCGGGGSGGGGG SGGGGSSYTYNYEWHVDVWGQGLLVTVSSAS (SEQ ID NO: 779) |

Figure 15

| Designation | Amino Acid Sequence | Cross reference Nucleic Acid Sequence |
|---|---|---|
| VL1-51 S2A, T5N, P8S, A12G, A13S, P14L, D51G, N52D, N53T | QAVLNQPSSVSGSLGQKVTISCSGSSSNIGNNYVSWYQQLPGTAPKLLIYG DTKRPSGIPDRFSGSKSGTSATLGITGLQTGDEADYYCASAEDSSSNAVFG SGTTLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGS TVEKTVAPTECS (SEQ ID NO: 792) | (SEQ ID NO: 444) |
| VH4-34+CDR3-IL8 | QVQLQQWGAGLLKPSETLSLTCAVYGGSFSGYYWSWIRQPPGKGLEWIGE INHSGSTNYNPSLKSRVTISVDTSKNQFSLKLSSVTAADTAVYYCTSVHQET KKYQSPRSAKELRCQCIKTYSKPFHPKFIKELRVIESGPHCANTEIIVKLSDGR ELCLDPKENWVQRVVEKFLKRAENSGSGSYTYNYEWHVDVWGQGLLVTV SSAS (SEQ ID NO: 793) | (SEQ ID NO: 430) |
| VH4-34+CDR3-IL8_CDR1 Cow | QVQLQQWGAGLLKPSETLSLTCTASGFSLSDKAVGWIRQPPGKGLEWIGEI NHSGSTNYNPSLKSRVTISVDTSKNQFSLKLSSVTAADTAVYYCTSVHQETK KYQSPRSAKELRCQCIKTYSKPFHPKFIKELRVIESGPHCANTEIIVKLSDGRE LCLDPKENWVQRVVEKFLKRAENSGSGSYTYNYEWHVDVWGQGLLVTVS SAS (SEQ ID NO: 794) | (SEQ ID NO: 432) |
| VH4-34+CDR3-IL8_CDR2 Cow | QVQLQQWGAGLLKPSETLSLTCAVYGGSFSGYYWSWIRQPPGKGLEWLG SIDTGGNTGYNPSLKSRVTISVDTSKNQFSLKLSSVTAADTAVYYCTSVHQE TKKYQSPRSAKELRCQCIKTYSKPFHPKFIKELRVIESGPHCANTEIIVKLSDG RELCLDPKENWVQRVVEKFLKRAENSGSGSYTYNYEWHVDVWGQGLLVT VSSAS (SEQ ID NO: 795) | (SEQ ID NO: 433) |
| VH4-34+CDR3-IL8_CDR1 G31D, Y32K | QVQLQQWGAGLLKPSETLSLTCAVYGGSFSDKYWSWIRQPPGKGLEWIGE INHSGSTNYNPSLKSRVTISVDTSKNQFSLKLSSVTAADTAVYYCTSVHQET KKYQSPRSAKELRCQCIKTYSKPFHPKFIKELRVIESGPHCANTEIIVKLSDGR ELCLDPKENWVQRVVEKFLKRAENSGSGSYTYNYEWHVDVWGQGLLVTV SSAS (SEQ ID NO: 796) | (SEQ ID NO: 434) |
| VH4-34+CDR3-IL8_CDR2 E50S | QVQLQQWGAGLLKPSETLSLTCAVYGGSFSGYYWSWIRQPPGKGLEWIGS INHSGSTNYNPSLKSRVTISVDTSKNQFSLKLSSVTAADTAVYYCTSVHQET KKYQSPRSAKELRCQCIKTYSKPFHPKFIKELRVIESGPHCANTEIIVKLSDGR ELCLDPKENWVQRVVEKFLKRAENSGSGSYTYNYEWHVDVWGQGLLVTV SSAS (SEQ ID NO: 797) | (SEQ ID NO: 435) |

Figure 15 (continued)

| Designation | Amino Acid Sequence | Cross reference Nucleic Acid Sequence |
|---|---|---|
| VH4-34+CDR3-IL8_CDR1 Cow_CDR2 Cow | QVQLQQWGAGLLKPSETLSLTCTASGFSLSDKAVGWIRQPPGKGLEWLGSI DTGGNTGYNPSLKSRVTISVDTSKNQFSLKLSSVTAADTAVYYCTSVHQETK KYQSPRSAKELRCQCIKTYSKPFHPKFIKELRVIESGPHCANTEIIVKLSDGRE LCLDPKENWVQRVVEKFLKRAENSGSGSYTYNYEWHVDVWGQGLLVTVS SAS (SEQ ID NO: 798) | (SEQ ID NO: 436) |
| VH4-34+CDR3-IL8_CDR1 Cow_CDR2 E50S | QVQLQQWGAGLLKPSETLSLTCTASGFSLSDKAVGWIRQPPGKGLEWIGSI NHSGSTNYNPSLKSRVTISVDTSKNQFSLKLSSVTAADTAVYYCTSVHQETK KYQSPRSAKELRCQCIKTYSKPFHPKFIKELRVIESGPHCANTEIIVKLSDGRE LCLDPKENWVQRVVEKFLKRAENSGSGSYTYNYEWHVDVWGQGLLVTVS SAS (SEQ ID NO: 799) | (SEQ ID NO: 437) |
| VH4-34+CDR3-IL8_CDR1 G31D,Y32K_CDR2 E50S | QVQLQQWGAGLLKPSETLSLTCAVYGGSFSDKYWSWIRQPPGKGLEWIGS INHSGSTNYNPSLKSRVTISVDTSKNQFSLKLSSVTAADTAVYYCTSVHQET KKYQSPRSAKELRCQCIKTYSKPFHPKFIKELRVIESGPHCANTEIIVKLSDGR ELCLDPKENWVQRVVEKFLKRAENSGSGSYTYNYEWHVDVWGQGLLVTV SSAS (SEQ ID NO: 800) | (SEQ ID NO: 439) |
| VL1-51 I29V, N32G | QSVLTQPPSVSAAPGQKVTISCSGSSSNVGNGYVSWYQQLPGTAPKLLIYD NNKRPSGIPDRFSGSKSGTSATLGITGLQTGDEADYYCASAEDSSSNAVFG SGTTLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGS TVEKTVAPTECS (SEQ ID NO: 801) | (SEQ ID NO: 440) |
| VL1-51 D51G, N52D, N53T | QSVLTQPPSVSAAPGQKVTISCSGSSSNIGNNYVSWYQQLPGTAPKLLIYGD TKRPSGIPDRFSGSKSGTSATLGITGLQTGDEADYYCASAEDSSSNAVFGS GTTLTVLGQPKAAPSVTLFPPSSEELQANKATLVCLISDFYPGAVTVAWKAD SSPVKAGVETTTPSKQSNNKYAASSYLSLTPEQWKSHRSYSCQVTHEGST VEKTVAPTECS (SEQ ID NO: 802) | (SEQ ID NO: 441) |
| VL1-51 D51G, N52D, N53T, K54S, P56A | QSVLTQPPSVSAAPGQKVTISCSGSSSNIGNNYVSWYQQLPGTAPKLLIYGD TSRASGIPDRFSGSKSGTSATLGITGLQTGDEADYYCASAEDSSSNAVFGS GTTLTVLGQPKAAPSVTLFPPSSEELQANKATLVCLISDFYPGAVTVAWKAD SSPVKAGVETTTPSKQSNNKYAASSYLSLTPEQWKSHRSYSCQVTHEGST VEKTVAPTECS (SEQ ID NO: 803) | (SEQ ID NO: 442) |

Figure 15 (continued)

| Designation | Amino Acid Sequence | Cross reference Nucleic Acid Sequence |
| --- | --- | --- |
| VL1-51 S2A, T5N, P8S, A12G, A13S, P14L | QAVLNQPSSVSVSGSLGQKVTISCSGSGSSSNIGNNYVSWYQQLPGTAPKLLIYD NNKRPSGIPDRFSGSKSGTSATLGITGLQTGDEADYYCASAEDSSSNAVFG SGTTLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGS TVEKTVAPTECS (SEQ ID NO: 804) | (SEQ ID NO: 443) |
| VL1-51 | QSVLTQPPSVSAAPGQKVTISCSGSGSSSNIGNNYVSWYQQLPGTAPKLLIYDN NKRPSGIPDRFSGSKSGTSATLGITGLQTGDEADYYCASAEDSSSNAVFGS GTTLTVLGQPKAAPSVTLFPPSSEELQANKATLVCLISDFYPGAVTVAWKAD SSPVKAGVETTTPSKQSNNKYAASSYLSLTPEQWKSHRSYSCQVTHEGST VEKTVAPTECS (SEQ ID NO: 805) | (SEQ ID NO: 456) |
| Lambda LC translation | QAVLNQPSSVSVSGSLGQRVSITCSGSSSNVGNGYVSWYQLIPGSAPRTLIYG DTSRASGVPDRFSGSRSGNTATLTISSLQAEDEADYFCASAEDSSSNAVFG SGTTLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGS TVEKTVAPTECS (SEQ ID NO: 807) | (SEQ ID NO: 474) |

Figure 16

| SEQ ID NO: | Amino Acid Sequence |
|---|---|
| 575 | GGGGS |
| 576 | GGGGS GGGGS |
| 577 | GGGGS GGGGS GGGGS |
| 578 | GGGGS GGGGS GGGGS GGGGS |
| 579 | GGS |
| 580 | GGS GGS |
| 581 | GGS GGS GGS |
| 582 | GGS GGS GGS GGS |
| 583 | ASG |
| 584 | ASG ASG |
| 585 | ASG ASG ASG |
| 586 | ASG ASG ASG ASG |
| 587 | GCGGGGS |
| 588 | GCGGGGS GGGGS |
| 589 | GCGGGGS GGGGS GGGGS |
| 590 | GCGGGGS GGGGS GGGGS GGGGS |
| 591 | GCGGS |
| 592 | GCGGS GGS |
| 593 | GCGGS GGS GGS |
| 594 | GCGGS GGS GGS GGS |
| 595 | GCASG |
| 596 | GCGCASG ASG |
| 597 | GCASG ASG ASG |
| 598 | GCASG ASG ASG ASG |
| 699 | SGGGG |
| 700 | SGGGG SGGGG |
| 701 | SGGGG SGGGG SGGGG |
| 702 | SGGGG SGGGG SGGGG SGGGG |
| 703 | SGG |
| 704 | SGG SGG |
| 705 | SGG SGG SGG |

Figure 16 (continued)

| SEQ ID NO: | Amino Acid Sequence |
|---|---|
| 706 | SGG SGG SGG SGG |
| 707 | GSA |
| 708 | GSA GSA |
| 709 | GSA GSA GSA |
| 710 | GSA GSA GSA GSA |
| 711 | SGGGGCG |
| 712 | SGGGG SGGGGCG |
| 713 | SGGGG SGGGG SGGGGCG |
| 714 | SGGGG SGGGG SGGGG SGGGGCG |
| 715 | SGGCG |
| 716 | SGG SGGCG |
| 717 | SGG SGG SGGCG |
| 718 | SGG SGG SGG SGGCG |
| 719 | GSACG |
| 720 | GSA GSACGCG |
| 721 | GSA GSA GSACG |
| 722 | GSA GSA GSA GSACG |
| 723 | GGGGS GG |
| 724 | GGGGS GGGGS GGGGS GG |
| 725 | GG SGGGG |
| 726 | GG SGGGG SGGGG GGGGS |
| 813 | G |
| 814 | GG |
| 815 | GGG |
| 816 | GGGG |
| 817 | GGGGGGGS |
| 818 | GGGGGGGGSGG |
| 819 | GGGGSGGS |
| 820 | GGGGSGGGSGGGS |
| 821 | GGGGSGGGSGGGGS |
| 822 | GGSG |
| 823 | GGSGG |

Figure 16 (continued)

| SEQ ID NO: | Amino Acid Sequence |
|---|---|
| 824 | GGSGGGSG |
| 825 | GGSGGGSGG |
| 826 | GGSGGGSGGSG |
| 827 | GGSGGGSGGSGG |
| 828 | GGSGGGSGGSGGSGG |
| 829 | GSG |
| 830 | GSGG |

Figure 17

| Peptide Name | Amino Acid Sequence | Target |
|---|---|---|
| ADWX-1 | VGINVKCKHSRQCLKPCKDAGMRFGKCTNGKCHCTPK (SEQ ID NO: 599) | Kv1.3 |
| HsTx1 | ASCRTPKDCADPCRKETGCPYGKCMNRKCKCNRC (SEQ ID NO: 600) | Kv1.3 |
| OSK1 | GVIINVKCKISRQCLEPCKKAGMRFGKCMNGKCHCTPK (SEQ ID NO: 601) | Kv1.3 |
| Pi2 | TISCTNPKQCYPHCKKETGYPNAKCMNRKCKCFGR (SEQ ID NO: 602) | Kv1.3 |
| Hongotoxin (HgTX) | TVIDVKCTSPKQCLPPCKAQFGIRAGAKCMNGKCKCYPH (SEQ ID NO: 603) | Kv1.3 |
| Margatoxin | TIINVKCTSPKQCLPPCKAQFGQSAGAKCMNGKCKCYPH (SEQ ID NO: 604) | Kv1.3 |
| Agitoxin-2 | GVPINVSCTGSPQCIKPCKDAGMRFGKCMNRKCHCTPK (SEQ ID NO: 605) | Kv1.3 |
| Pi3 | TISCTNEKQCYPHCKKETGYPNAKCMNRKCKCFGR (SEQ ID NO: 606) | Kv1.3 |
| Kaliotoxin | GVEINVKCSGSPQCLKPCKDAGMRFGKCMNRKCHCTPK (SEQ ID NO: 607) | Kv1.3 |
| Anuroctoxin | ZKECTGPQHCTNFCRKNKCTHGKCMNRKCKCFNCK (SEQ ID NO: 608) | Kv1.3 |
| Charybdotoxin | ZFTNVSCTTSKECWSVCQRLHNTSRGKCMNKKCRCYS (SEQ ID NO: 609) | Kv1.3 |
| Tityustoxin -K- alpha | VFINAKCRGSPECLPKCKEAIGKAAGKCMNGKCKCYP (SEQ ID NO: 610) | Kv1.3 |
| Maurotoxin | VSCTGSKDCYAPCRKQTGCPNAKCINKSCKCYGC (SEQ ID NO: 611) | Kv1.3 |
| Ceratotoxin 1 (CcoTx1) | DCLGWFKSCDPKNDKCCKNYTCSRRDRWCKYDL (SEQ ID NO: 612) | |
| CcoTx2 | DCLGWFKSCDPKNDKCCKNYTCSRRDRWCKYYL (SEQ ID NO: 613) | |
| CcoTx3 | GVDKEGCRKLLGGCTIDDDCCPHLGCNKKYWHCGWDGTF (SEQ ID NO: 614) | |
| Phrixotoxin 3 (PaurTx3) | DCLGFLWKCNPSNDKCCCRPNLVCSRKDKWCKYQI (SEQ ID NO: 615) | |

Figure 17 (continued)

| Peptide Name | Amino Acid Sequence | Target |
|---|---|---|
| Hanatoxin 1 | ECRYLFGGCKTTSDCCKHLGCKFRDKYCAWDFTFS (SEQ ID NO: 616) | |
| Phrixotoxin 1 | YCQKWMWTCDSARKCCEGLVCRLWCKKII (SEQ ID NO: 617) | |
| Huwentoxin-IV | ECLEIFKACNPSNDQCCKSSKLVCSRKTRWCKYQI (SEQ ID NO: 618) | |
| α-conotoxin ImI | GCCSDPRCAWRC (SEQ ID NO: 619) | |
| α-conotoxin EpI | GCCSDPRCMNNPDYC (SEQ ID NO: 620) | |
| α-conotoxin PnIA | GCCSLPPCAANNPDYC (SEQ ID NO: 621) | |
| α-conotoxin PnIB | GCCSLPPCALSNPDYC (SEQ ID NO: 622) | |
| α-conotoxin MII | GCCSNPVCHLEHSNLC (SEQ ID NO: 623) | |
| α-conotoxin AuIA | GCCSYPPCFATNSDYC (SEQ ID NO: 624) | |
| α-conotoxin AuIB | GCCSYPPCFATNPDC (SEQ ID NO: 625) | |
| α-conotoxin AuIC | GCCSYPPCFATNSGYC (SEQ ID NO: 626) | |
| conotoxin κ-PVIIA | CRIPNQKCFQHLDDCCSRKCNRFNKCV (SEQ ID NO: 627) | |
| charybdotoxin | ZFTNVSCTTSKECWSVCQRLHNTSRGKCMNKKCRCYS (SEQ ID NO: 628) | |
| neurotoxin B-IV | ASATWGAAYPACENNCRKKYDLCIRCQGKWAGKGRGKCAAHCIIQKNNCKG KCKKE (SEQ ID NO: 629) | |
| crotamine | YKQCHKKGGHCFPKEKICLPPSSDFGKMDCCRWRWKCCKKGSG (SEQ ID NO: 630) | |
| ω-GVIA (conotoxin) | CKSPGSSSCSPTSYNCCRSCNPYTKRCY (SEQ ID NO: 631) | |
| κ-hefutoxin 1 | GHACYRNCWREGNDEETCKERC (SEQ ID NO: 632) | |

Figure 17 (continued)

| Peptide Name | Amino Acid Sequence | Target |
|---|---|---|
| Css4 | KEGYLVNSYTGCKFECFKLGDNDYCLRECRQQYGKGSSGYCYAFGCWCT HLYEQAVVWPLPNKTCN (SEQ ID NO: 633) | |
| Bj-xtrIT | KKNGYPLDRNGKTTECSGVNAIAPHYCNSECTKVYVAESGYCCWGACYCF GLEDDKPIGPMKDITKKYCDVQIIPS (SEQ ID NO: 634) | |
| BclV | GLPCDCHGHTGTYWLNYYSKCPKGYGYTGRCRYLVGSCCYK (SEQ ID NO: 635) | |
| Hm-1 | GCIPYGKTCEFWSGPWCCAGKCKLNVWSMTLSCTRNF (SEQ ID NO: 636) | |
| Hm-2 | GCIPSFGECAWFSGESCCTGICKWVFFTSKFMCRRVWGKD (SEQ ID NO: 637) | |
| GsAF-I (β-theraphotoxin-Gr1b) | YCQKWLWTCDSERKCCEDMVCRLWCKKRL (SEQ ID NO: 638) | |
| Protoxin I (ProTx-I, β-theraphotoxin-Tp1a) | ECRYWLGGCSAGQTCCKHLVCSRRHGWCVWDGTFS (SEQ ID NO: 639) | |
| Protoxin II (ProTx II) | YCQKWMWTCDSERKCCEGMVCRLWCKKLW (SEQ ID NO: 640) | |
| Huwentoxin I | ACKGVFDACTPGKNECCPNRVCSDKHKWCKWKL (SEQ ID NO: 641) | |
| μ-Conotoxin PIIIA | ERLCCGFPKSCRSRQCKPHRCC (SEQ ID NO: 642) | |
| Jingzhaotoxin-III (β-TRTX-Cj1α) | DGECGGFWWKCGRGKPPCCKGYACSKTWGWCAVEAP (SEQ ID NO: 643) | |
| GsAF-II (Kappa-theraphotoxin-Gr2c) | YCQKWMWTCDEERKCCEGLVCRLWCKKIEW (SEQ ID NO: 644) | |
| ShK, K16,E30 | RSCIDTIPKSRCTAFKCKHSMKYRLSFCRETCGTC (SEQ ID NO: 645) | |
| ShK (Stichodactyla toxin) | RSCIDTIPKSRCTAFQCKHSMKYRLSFCRKTCGTC (SEQ ID NO: 646) | Kv1.3 |
| HsTx1 | ASCRTPKDCADPCRKETGCPYGKCMNRKCKCNRC (SEQ ID NO: 647) | |
| Guangxitoxin 1E, GxTx-1E | EGECGGFWWKCGSGKPACCPKYVCSPKWGLCNFPMP (SEQ ID NO: 648) | |
| Charybdotoxin, ChTX | EFTNVSCTTSKECWSVCQRLHNTSRGKCMNKKCRCYS (SEQ ID NO: 649) | |

Figure 17 (continued)

| Peptide Name | Amino Acid Sequence | Target |
|---|---|---|
| Iberiotoxin, ibTx | EFTDVDCSVSKECWSVCKDLFGVDRGKCMGKKCRCYQ (SEQ ID NO: 650) | |
| Leiurotoxin 1, scyllatoxin | AFCNLRMCQLSCRSLGLLGKCIGDKCECVKH (SEQ ID NO: 651) | |
| Tamapin | AFCNLRRCELSCRSLGLLGKCIGEECKCVPY (SEQ ID NO: 652) | |
| Kaliotoxin-1, KTX | GVEINVKCSGSPQCLKPCKDAGMRFGKCMNRKCHCTPK (SEQ ID NO: 653) | |
| Purotoxin1, PT-1 | GYCAEKGIRCDDIHCCTGLKCKCNASGYNCVCRKK (SEQ ID NO: 654) | |
| GpTx-1 | DCLGFMRKCIPDNDKCCRPNLVCSRTHKWCKYVF (SEQ ID NO: 655) | Nav1.7 |
| MOKA Toxin | INVKCSLPQQCIKPCKDAGMRFGKCMNKKCRCYS (SEQ ID NO: 727) | |
| OSK1, P12, K16, D20 | GVIINVKCKISPQCLKPCKDAGMRFGKCMNGKCHCTPK (SEQ ID NO: 728) | Kv1.3 |
| OSK1 K16, D20 | GVIINVKCKISRQCLKPCKDAGMRFGKCMNGKCHCTPK (SEQ ID NO: 729) | Kv1.3 |
| HmK | RTCKDLIPVSECTDIRCRTSMKYRLNLCRKTCGSC (SEQ ID NO: 730) | Kv1.3 |
| ShK, K16,Y26, K29 | RSCIDTIPKSRCTAFKCKHSMKYRLYFCKKTCGTC (SEQ ID NO: 731) | Kv1.3 |
| ShK, K16 | RSCIDTIPKSRCTAFKCKHSMKYRLSFCRKTCGTC (SEQ ID NO: 732) | Kv1.3 |
| ShK-A, K16 | RSCIDTIPKSRCTAFKCKHSMKYRLSFCRKTCGTCA (SEQ ID NO: 733) | Kv1.3 |
| Shk toxin | GVPDRFSGSSRSGNTATLTISSLQAEDEADYFCASAEDSSSNAVFGSGTTLT VLGQPKAAP (SEQ ID NO: 808) | |
| ProTxil toxin | SVTLFPPSSEELQANKATLVCLISDFYPGAVTVAWKADSSPVKAGVETTTPS KQSNNKYA (SEQ ID NO: 809) | |
| GPTX toxin | ASSYLSLTPEQWKSHRSYSCQVTHEGSTVEKTVAPTECS (SEQ ID NO: 810) | |
| ShK, Q21 | RSCIDTIPKSRCTAFQCKHSQKYRLSFCRKTCGTC (SEQ ID NO: 831) | Kv1.3 |

FIGURE 17 (continued)

| Peptide Name | Amino Acid Sequence | Target |
|---|---|---|
| ShK, L21 | RSCIDTIPKSRCTAFQCKHSLKYRLSFCRKTCGTC (SEQ ID NO: 832) | Kv1.3 |
| ShK, F21 | RSCIDTIPKSRCTAFQCKHSFKYRLSFCRKTCGTC (SEQ ID NO: 833) | Kv1.3 |
| ShK, I21 | RSCIDTIPKSRCTAFQCKHSIKYRLSFCRKTCGTC (SEQ ID NO: 834) | Kv1.3 |
| ShK, A21 | RSCIDTIPKSRCTAFQCKHSAKYRLSFCRKTCGTC (SEQ ID NO: 835) | Kv1.3 |

Figure 17 (continued)

| Toxin | Block 1 Seq | Linker A Seq | Block 2 Seq | Linker B Seq | Block 3 Seq |
|---|---|---|---|---|---|
| ADWX-1 | VGINVKCKHSR (SEQ ID NO: 666) | QC | LKPCKDAGMRFG (SEQ ID NO: 677) | KCM | NGKCHCTPK (SEQ ID NO: 688) |
| HsTx1 | ASCRTPK (SEQ ID NO: 667) | QC | ADPCRKETGCPYG (SEQ ID NO: 678) | KCM | NRKCKCNRC (SEQ ID NO: 689) |
| OSK1 | GVIINVKCKISR (SEQ ID NO: 668) | QC | LEPCKKAGMRFG (SEQ ID NO: 679) | KCM | NGKCHCTPK (SEQ ID NO: 690) |
| Pi2 | TISCTNPK (SEQ ID NO: 669) | QC | YPHCKKETGYPNA (SEQ ID NO: 680) | KCM | NRKCKCFGR (SEQ ID NO: 691) |
| Hongotoxin (HgTX) | TVIDVKCTSPK (SEQ ID NO: 670) | QC | LPPCKAQFGIRAGA (SEQ ID NO: 681) | KCM | NGKCKCYPH (SEQ ID NO: 692) |
| Margatoxin | TIINVKCTSPK (SEQ ID NO: 671) | QC | LPPCKAQFGQSAGA (SEQ ID NO: 682) | KCM | NGKCKCYPH (SEQ ID NO: 693) |
| Agitoxin-2 | GVPINVSCTGSP (SEQ ID NO: 672) | QC | IKPCKDAGMRFG (SEQ ID NO: 683) | KCM | NRKCHCTPK (SEQ ID NO: 694) |
| Pi3 | TISCTNEK (SEQ ID NO: 673) | QC | YPHCKKETGYPNA (SEQ ID NO: 684) | KCM | NRKCKCFGR (SEQ ID NO: 695) |
| Kaliotoxin | GVEINVKCSGSP (SEQ ID NO: 674) | QC | LKPCKDAGMRFG (SEQ ID NO: 685) | KCM | NRKCHCTPK (SEQ ID NO: 696) |
| Anuroctoxin | ZKECTGPQ (SEQ ID NO: 675) | QC | TNFCRKNKCTHG (SEQ ID NO: 686) | KCM | NRKCKCFNCK (SEQ ID NO: 697) |
| Charybdotoxin | ZFTNVSCTTSK (SEQ ID NO: 676) | QC | WSVCQRLHNTSRG (SEQ ID NO: 687) | KCM | NKKCRCYS (SEQ ID NO: 698) |

Figure 18

| Designation | Nucleic Acid Sequence |
|---|---|
| MOKA Toxin | GGCATCAACGTGAAGTGCAGCCTGCCCCAGCAGTGCATCAAGCCCTGCAAGGACGCGGGCATGAGATTCGGGCAAGTGCATGAACAAGAAGTGCAGATGCAGATGCTACAGC (SEQ ID NO: 806) |
| OSK1 toxin (P12, K16, D20) | GGCGTGATCATCAACGTGAAATGCAAGATCAGCCCCAGTGCCTGAAGCCCTGCCTGCAAGGACGCCGGCATGAGGTTCGGGAAGTGCATGAACGTGAAGTGCCACTGCACCCCCAAG (SEQ ID NO: 811) |
| OSK1 toxin (K16 and D20) | GGCGTGATCATCAACGTGAAGTGCAAGATCAGCAGGGCAGTGCCTGAAGCCCTGCAAGGACGCCCTGCAAGGACGCCGGCATGAGGTTCGGGTAAGTGCATGAACGTGAAGTGCCACTGCACCCCCAAG (SEQ ID NO: 812) |

Figure 19

| Ab Name | Ultralong CDR3 | | | V2 region |
| --- | --- | --- | --- | --- |
| | A region | Insert | D region | |
| PGT145 | GSKHRLRDYFLYNE (SEQ ID NO: 501) | | YGPNYEEWGDYLATLDV (SEQ ID NO: 536) | WGHGTAVTVSS (SEQ ID NO: 570) |
| | GSKHRLRDYFLYN (SEQ ID NO: 502) | | GPNYEEWGDYLATLDV (SEQ ID NO: 537) | |
| | GSKHRLRDYFLY (SEQ ID NO: 503) | | PNYEEWGDYLATLDV (SEQ ID NO: 538) | |
| | GSKHRLRDYFL (SEQ ID NO: 504) | | NYEEWGDYLATLDV (SEQ ID NO: 539) | |
| | GSKHRLRDYF (SEQ ID NO: 505) | | YEEWGDYLATLDV (SEQ ID NO: 540) | |
| | GSKHRLRDY (SEQ ID NO: 506) | | EEWGDYLATLDV (SEQ ID NO: 541) | |
| | GSKHRLRD (SEQ ID NO: 507) | | | |
| PG9 | EAGGPDYRNGYNY (SEQ ID NO: 508) | | YDFYDGYYNYHYMDV (SEQ ID NO: 542) | WGKGTTVTVSS (SEQ ID NO: 571) |
| | EAGGPDYRNGYN (SEQ ID NO: 509) | | DFYDGYYNYHYMDV (SEQ ID NO: 543) | |
| | EAGGPDYRNGY (SEQ ID NO: 510) | | FYDGYYNYHYMDV (SEQ ID NO: 544) | |
| | EAGGPDYRNG (SEQ ID NO: 511) | | YDGYYNYHYMDV (SEQ ID NO: 545) | |
| | EAGGPDYRN (SEQ ID NO: 512) | | DGYYNYHYMDV (SEQ ID NO: 546) | |
| | EAGGPDYR (SEQ ID NO: 513) | | GYYNYHYMDV (SEQ ID NO: 547) | |

Figure 19 (continued)

| Ab Name | Ultralong CDR3 | | | V2 region |
| --- | --- | --- | --- | --- |
| | A region | Insert | D region | |
| PG16 | EAGGPDY (SEQ ID NO: 514) | | YYNYHYMDV (SEQ ID NO: 548) | |
| | EAGGPD (SEQ ID NO: 515) | | | |
| | EAGGPIWHDDDVKY (SEQ ID NO: 516) | | YDFNDGYYNYHYM DV (SEQ ID NO: 549) | WGKGTTVTVSS (SEQ ID NO: 572) |
| | EAGGPIWHDDDVK (SEQ ID NO: 517) | | DFYDGYYNYHYMD V (SEQ ID NO: 550) | |
| | EAGGPIWHDDDV (SEQ ID NO: 518) | | FYDGYYNYHYMDV (SEQ ID NO: 551) | |
| | EAGGPIWHDD (SEQ ID NO: 519) | | YDGYYNYHYMDV (SEQ ID NO: 552) | |
| | EAGGPIWHD (SEQ ID NO: 520) | | DGYYNYHYMDV (SEQ ID NO: 553) | |
| | EAGGPIWH (SEQ ID NO: 521) | | GYYNYHYMDV (SEQ ID NO: 554) | |
| | EAGGPIW (SEQ ID NO: 522) | | | |
| | EAGGPI (SEQ ID NO: 523) | | | |
| CHO4 | GTDYTIDDQGI (SEQ ID NO: 524) | | QGIRYQGSGTFWY FDV (SEQ ID NO: 555) | WGRGTLVTVSS (SEQ ID NO: 573) |
| | GTDYTIDDQG (SEQ ID NO: 525) | | GIRYQGSGTFWYFD V (SEQ ID NO: 556) | |
| | GTDYTIDDQ (SEQ ID NO: 526) | | IRYQGSGTFWYFDV (SEQ ID NO: 557) | |
| | GTDYTIDD (SEQ ID NO: 527) | | RYQGSGTFWYFDV (SEQ ID NO: 558) | |

Figure 19 (continued)

| Ab Name | Ultralong CDR3 | | | |
| | A region | Insert | D region | V2 region |
| --- | --- | --- | --- | --- |
| | GTDYTID (SEQ ID NO: 528) | | YQGSGTFWYFDV (SEQ ID NO: 559) | |
| | GTDYTI (SEQ ID NO: 529) | | QGSGTFWYFDV (SEQ ID NO: 560) | |
| | | | GSGTFWYFDV (SEQ ID NO: 561) | |
| | | | SGTFWYFDV (SEQ ID NO: 562) | |
| | | | GTFWYFDV (SEQ ID NO: 563) | |
| 2909 | DKGDSDYDYNL (SEQ ID NO: 530) | | YNLGYSYFYYMDG (SEQ ID NO: 564) | WGKGTTVTVSS (SEQ ID NO: 574) |
| | DKGDSDYDYN (SEQ ID NO: 531) | | NLGYSYFYYMDG (SEQ ID NO: 565) | |
| | DKGDSDYDY (SEQ ID NO: 532) | | LGYSYFYYMDG (SEQ ID NO: 566) | |
| | DKGDSDYD (SEQ ID NO: 533) | | GYSYFYYMDG (SEQ ID NO: 567) | |
| | DKGDSDY (SEQ ID NO: 534) | | YSYFYYMDG (SEQ ID NO: 568) | |
| | DKGDSD (SEQ ID NO: 535) | | SYFYYMDG (SEQ ID NO: 569) | |

A = ShK 1x (HEK)
B = ShK 1x (CHO)
C = ShK 0x (HEK)
D = ShK 0x (CHO)

Figure 21

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 201 | BLV1H12 GGS1.1 ProTxII | BLV1H12 HC GGS1.1 ProTxII | 131-34 | caggtccagctgagagagagcggccctcactggtcaagccatccc agacactgagctgcacatggtgtcgacagcaagcgggtttcactgagcga caaggcagtgggatgggtcgacaggcaccaggaaaagccctgg aatgctgggcagcatcgataccggcgggaaacacaggtacaatc ccggactgaagagagacttgtccattaccaaggacaactctaaaa gtcaggtgtcactgagcgtgagctccgtcaccacagaggatagtgc aacttactacattgcacctctgtgccaggaaaactaagaaaataccaga gcggaggaagctattgccagaagtgcatggtgtgccgctgcgatagcg aacggaaatgttgcgaaggcatggtgtgccgctggtgttgtcaagaa gaaactctgggggaggaaagctcttatacctacacaattatgaagtgcatgt ggatgtctgggggacaggcctgctgtggtgggtgacagtctctagtgctagc | 836 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSYCQKW MWTCDSERKCCEGMVCRL WCKKKLWGGSSYTYNYEW HVDVWGQGLLVTVSSAS | 903 |
| 202 | BLV1H12 GGS1.2 ProTxII | BLV1H12 HC GGS1.2 ProTxII | 131-35 | caggtccagctgagagagagcggccctcactgggtcaagccatccc agacactgagctgcacatggtgtcgacagcaagcgggtttcactgagcga caaggcagtgggatgggtcgacaggcaccaggaaaagccctgg aatgctgggcagcatcgataccggcgggaaacacaggtacaatc ccggactgaagagagacttgtccattaccaaggacaactctaaaa gtcaggtgtcactgagcgtgagctccgtcaccacagaggatagtgc aacttactacattgcacctctgtgccaggaaaactaagaaaataccaga gcggaggaagctattgccagaagtgcatggtgtgccgctgcgatagcg aacggaaatgttgcgaaggcatggtgtgccgctggtgttgtcaagaa gaaactctggggggaggaaagctcttatacctacacacaattat gaatggcatgtgtggatgtctgggggacaggcctgctgtggtgacagtctc tagtgctagc | 837 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSYCQKW MWTCDSERKCCEGMVCRL WCKKKLWGGSGGSSYTYN YEWHVDVWGQGLLVTVSS AS | 904 |

Figure 21 (continued)

| BID's | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 203 | BLV1H12 GGS2:1 ProTxII | BLV1H12 HC GGS2:1 ProTxII | 131-36 | caggtccagctgtgagagagagcggcccttcactggtcaagccatccc agacaactgagcctggcatggtcacagcaagcgggtttcactgagcga caaggcagtggatgggtcgacaggcaccaggaaaagcccctgg aatgctgggcagcagcatcgatacggcgcggaacacacaggtacaatc ccggactgaagagcagactgtccattaccaaggacaactcaaaa gtcaggtgtcactgagcgtgagctccgtcaccacagaggatagtgc aacttactattgcaccctgtgcaccaggaaactaagaaataccaga gcggaggaagcggaggaagctattgccagaagtggatggaccct gcgatagcgaacgaaatctgggaggaagctctataccacaattatg aatggcatgtggatgtctgtggggacaggggctgctggtgtcagtctct agtgctagc | 838 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSYC CRLWCKKKLWGGSSYTYN YEWHVDVWGQGLLVTVSS AS | 905 |
| 32, 204 | BLV1H12 GGS1:1 Moka | BLV1H12 Hc CowV,HuC 1:1GGS G-Moka | 131-40 | caggtccagctgtgagagagagcggccccttcactggtcaagccatccc agacaactgagcctggatgggtcgacagcaagcgggtttcactgagcga caaggcagtggatgggtcgacaggcaccaggaaaagcccctgg aatgctgggcagcagcatcgatacggcgcggaacacacaggtacaatc ccggactgaagagcagactgtccattaccaaggacaactcaaaa gtcaggtgtcactgagcgtgagctccgtcaccagaggatagtgc aacttactattgcaccctgtgcaccaggaaactaagaaataccaga gcggaggaagcggaggaagctattgccagaagtggatggaccct gcgatagcgaacgaaatctgggaggaagctctataccacaattatg atgaacaagaagtgcagatgctacagcggaggaagctcttatacct acaattatgaatggcatgtggatgtctgtggggacaggggcctgtggtg acagtctcagtgctagc | 839 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGINVKC SLPQQCIKPCKDAGMRFGK CMNKKCRCYSGGSSYTYN YEWHVDVWGQGLLVTVSS AS | 770 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 30, 205, 227 | BLV1H12 GGS1.2 Moka | BLV1H12 Hc CowV,HuC 1.2GGS G-Moka | 131-41 | caggtccagctgagagagagacggcccttcactggtcaagccatccc agacactgagctgcacagcagcaagcgcggtttcactgagcga caaggcagtggatgggtccgacaggcaccaggaaaagccctgg aatggctgggcagctcgatacggcgggaacacaggtacaatc ccggactgaagagcagactgtccattaccaaggacaactctaaaa gtcaggtgtcactgagcgtgagctcgtcaccacagagaatagtgc aacttactattgcacctctgtgcaccaggaaactaagaaataccaga gcggaggaagcgggcaatcaaagtgaagtgcagctgcccagcag tgcatcaagccctgcaaggacgccggcatgagattcggcaagtgc atgaacaagaagtgcagatgctacagcggcggaagcggaggaacagg gctcttatacctacgacagtctcagtgctagc | 840 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGINVKC SLPQQCIKPCKDAGMRFGK CMNKKCRCYSGSGSSY TYNYEWHVDVWGQGLLVT VSSAS | 771 |
| 31, 206 | BLV1H12 GGS2.1 Moka | BLV1H12 Hc CowV,HuC 2.1GGS G-Moka | 131-42 | caggtccagctgagagagagacggcccttcactggtcaagccatccc agacactgagctgcacagcagcaagcgcggtttcactgagcga caaggcagtggatgggtccgacaggcaccaggaaaagccctgg aatggctgggcagctcgatacggcgggaacacaggtacaatc ccggactgaagagcagactgtccattaccaaggacaactctaaaa gtcaggtgtcactgagcgtgagctcgtcaccacagagaatagtgc aacttactattgcacctctgtgcaccaggaaactaagaaataccaga gcggaggaagcggaggaagcggcatcaacgtgaagtgcagcct gccccagcagtgcatcaagccctgcaaggacgccggcatgagaatt cggcaagtgcatgaacaagaagtgcagatgctacagcggcggaggaacagg gctcttatacctacaattatgaatgcatgtggatggtgggacagg gcctgctgctgacagtctctagtgctagc | 841 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGIN VKCSLPQQCIKPCKDAGMR FGKCMNKKCRCYSCGSSYT YNYEWHVDVWGQGLLVTV SSAS | 772 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 33, 41, 207 | BLV1H12 GGS3.3 Moka | BLV1H12 Hc CowV,HuC 3.3GGS G-Moka | 131-43 | caggtccagctgagagagagcggcccttcactggtcaagccatccc agacaactgagcctgacatgcacagcaggcgttttcactgagcga caaggcagtggatggtccgacaggcaccaggaaaagcccctgg aatggctgggcagcatcgatacggcggaacacaggtacaatc ccggactgaagagcagactgtccattaccaaggacaactctaaaa gtcaggtgtcactgagcgtgagctccgtcaccacaggaggatagtgc aacttactattgcacctgtgtgtcaccaggaaactaagaaataccaga gcggaggaagcggaggaagcggaggaagcggcatcaacgtga agtgcagcctgccccagcagtgcatcaagccctgcaaggacgccg gcatgagattcggcaagtgcatgaacaagaagtgcagatgctaca gcggaggaagcggaggaagcggaggaagcggctggacagtc atgaatggcatggatgtctgggtcggggacaaggcctgctggtgacagtc tctagtgctagc | 842 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG SGINVKCSLPQQCJKPCKDA GMRFGKCMNKKCRCYSGG SGGSGGSSYTYNYEWHVD VWGQGLLVTVSSAS | 774 |
| 208 | BLV1H12 GGS1:1 GG-ProTxII-GG | BLV1H12 HC GGS1:1 GG-ProTxII-GG | 131-37 | caggtccagctgagagagagcggcccttcactggtcaagccatccc agacaactgagcctgacatgcacagcaggcgttttcactgagcga caaggcagtggatggtccgacaggcaccaggaaaagcccctgg aatggctgggcagcatcgatacggcggaacacaggtacaatc ccggactgaagagcagactgtccattaccaaggacaactctaaaa gtcaggtgtcactgagcgtgagctccgtcaccacaggaggatagtgc aacttactattgcaccctgtgtgtcaccaggaaactaagaaataccaga gccggaggaagcggcggctattgccaagtgaagtggacctgcg atagcgaacggaaatctggggcggcggaggcatggtgtgccgcctggtg caagaagaaactctggggcggcggaggctcttatacctacaa ttatgaatggcatggatgtctgggtcggggacaaggcctgctggtgacagt ctctagtgctagc | 843 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSYCQ KWMWTDDSERKCCEGMVC RLWCKKKLWGGGSSYTY NYEWHVDVWGQGLLVTVS SAS | 906 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 209 | BLV1H12 GGS1.2 GG-ProTxll-GG | BLV1H12 HC GGS1.2 GG-ProTxll-GG | 131-38 | caggtccagctgcagagagagcgcccctcactggtcaagccatccc agacactgagcctgagctggatggtcgacagcaaggcggtttcactgagcga caaggcagtggatgggtcgacaggcaccaggaaaagccctgg aatgctggcggcagcagcatcgatacggcgcggaacacacaggtacaatc ccggactgaagagcagactgtccattaccaaggacaactctaaaa gtcaggtgtcactgagctgagctccgtcaccacagaggatagtgc aacttactattgcaccctctgtgcaccaggaaactaagaaaataccaga gcggaggaagcggcggctattgccgaaggcatggtgtgccgcctgggtg caagaagaaactctgggcgggcggaggaagcgcgaggaagctctt atacctacaattatgaatgcatggaatggcatcagtctctagtgcctg ctggtgacagtctctagtgctagc | 844 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGYCQ KWMWTCDSERKCCEGMVC RLWCKKKLWGGGSGGSSS YTYNYEWHVDVWGQGLLV TVSSAS | 907 |
| 210 | BLV1H12 GGS2.1 GG-ProTxll-GG | BLV1H12 HC GGS2.1 GG-ProTxll-GG | 131-39 | caggtccagctgcagagagagcgcccctcactggtcaagccatccc agacactgagcctgagctggatggtcgacagcaaggcggtttcactgagcga caaggcagtggatgggtcgacaggcaccaggaaaagccctgg aatgctggcggcagcagcatcgatacggcgcggaacacacaggtacaatc ccggactgaagagcagactgtccattaccaaggacaactctaaaa gtcaggtgtcactgagctgagctccgtcaccacagaggatagtgc aacttactattgcaccctgtgtgcaccaggaaactaagaaaataccaga gcggaggaagcggcggaagcggcggctattgccgaaggcatggtgtcc tggacctcggcatagcgaacgaaagaaactctgggcgcggcggaagctt gcctgtggtcaagaagaaactctgggcgcggcggaggaagctctt atacctacaattatgaatgcatggaatggcatcagtctctagtgcctg ctggtgacagtctctagtgctagc | 845 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG YCQKWMWTCDSERKCCEG MVCRLWCKKKLWGGGSS YTYNYEWHVDVWGQGLLV TVSSAS | 908 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 211 | BLV1H12 GGS2.2 ProTxII | BLV1H12 HC GGS2.2 ProTxII | 131-44 | caggtccagctgagagagagcggccccttcactgtcaagccatccc agacaactgagctgacatgcacagccagcggcgggtttcactgagcga caaggcagtggatggtcgacaggcaccaggaaaagccctgg aatggctgggccagcatcgatacggcgcggaacacaggtacaatc ccggactgaagacgagcagactgtccattaccaaggacaacttcaaaa gtcaggtgtcactgagcgtgagctccgtcaccacagaggatagtgc aacttactattgcaccctgtgcaccaggaaactaagaaataccaga gcggaggaagcggaggaagctattgccgaaggccatggtgtgccgcctgtg gtgcaagaagaacgaacggaaatgttgcgaaggccatgggtgccgcctggt ctacaattatgaatggcatgtggatgtctcgtgggacaggccctgctggt gacagtctctagtgctagc | 846 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGSGSGSYC QKWMWTCDSERKCCEGMV CRLWCKKKLWGGSGSGSSY TYNYEWHVDVWGQGLLVT VSSAS | 909 |
| 212 | BLV1H12 GGS2.4 ProTxII | BLV1H12 HC GGS2.4 ProTxII | 131-45 | caggtccagctgagagagagcggccccttcactgtcaagccatccc agacaactgagctgacatgcacagccagcggcgggtttcactgagcga caaggcagtggatggtcgacaggcaccaggaaaagccctgg aatggctgggccagcatcgatacggcgcggaacacaggtacaatc ccggactgaagacgagcagactgtccattaccaaggacaacttcaaaa gtcaggtgtcactgagcgtgagctccgtcaccacagaggatagtgc aacttactattgcaccctgtgcaccaggaaactaagaaataccaga gcggaggaagcggaggaagctattgccgaaggccatggtgtgccgcctgtg gtgcaagaagaacgaacggaaatgttgcgaaggccatgggtgccgcctgg aagcggaggaagctcttatacctacaattatgaatggcatgtggatgt ctggggacaggccctgctggtgacagtctctagtgctagc | 847 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGSGSGSYC QKWMWTCDSERKCCEGMV CRLWCKKKLWGGSGSGSG SGGSSYTYNYEWHVDVWG QGLLVTVSSAS | 910 |

FIGURE 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 213 | BLV1H12 GGS4.2 ProTxII | BLV1H12 HC GGS4.2 ProTxII | 131-46 | caggtccagctgagagagagcggccccttcactggtcaagccatccagacaactgagcctgacatgcacagcaagcggtttcactgagcgacaaggcagtggatggtggtccgacatcggaacaccaggaaagcccggaatggctgggcagcatcgataccggcggaacacaggtacaatcccgactgaagagcagactgtccattaccaaggacaactctaaaagtcaggtgtcactgagcgtgagctcgtcaccacagaggatagtgcaacttactattgcaccctctgtgtcaccaggaaactaagaaataccagagcggaggaagcggaggaagcggaggaagcggaggaagctattgccagaagtggatgtggacctgcgcgcctgtggtgtcaagaagaacctcgggagaaggcatgggcgcagggcctctatacctacaattatgaatggcatgtggatgtctgggggacaggggctgctggtgacagtctcagtgctagc | 848 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG SGGSYCQKWMWTCDSERK CCEGMVCRLWCKKLWGG SGGSSYTYNYEWHVDVWG QGLLVTVSSAS | 911 |
| 214 | BLV1H12 GGS2.2 GG-ProTxII-GG | BLV1H12 HC GGS2.2 GG-ProTxII-GG | 131-47 | caggtccagctgagagagagcggccccttcactggtcaagccatccagacaactgagcctgacatgcacagcaagcggtttcactgagcgacaaggcagtggatggtggtccgacatcggaacacaggaaagcccggaatggctgggcagcatcgataccggcggaacacaggtacaatcccgactgaagagcagactgtccattaccaaggacaactctaaaagtcaggtgtcactgagcgtgagctcgtcaccacagaggatagtgcaacttactattgcaccctctgtgtcaccaggaaactaagaaataccagagcggaggaagcggaggaagcggcgctattgccagaagtggatgtggacctgcgcgcctgtggtgtcaagaagaacctcgggagaaggcatgggcgcagggcctctatacctacaattatgaatggcatgtggatgtctggggaccagggcctgctggtggtgacagtctcagtgctagc | 849 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG YCQKWMWTCDSERKCCEG MVCRLWCKKLWGGSGGSG GSSYTYNYEWHVDVWGQG LLVTVSSAS | 912 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 215 | BLV1H12 GGS 2:3 GG-ProTxII-GG | BLV1H12 HC GGS 2:3 GG-ProTxII-GG | 131-48 | caggtccagctgagagagagcggcccctcactggtcaagccatccc agacaactgagcctgacatggcacagcaagcggggtttcactgagcga caaggcagtggatggtggtccgacatgcgcaccaggaaaagcccctgg aatggctcggcgcagcatcgatacggccggaaacacaggtacaatc ccggactgaagagcagactgtccattaccaaggacaactctaaaa gtcaggtgtcactgagcgtgagctccgtcaccacagaggatagtgc aacttactattgcacctgtgcaccaggaaactaagaaaaataccaga gcggaggaagcggaggaagcggcggcggcggaagtggatg tggaacctgcgatagcgaacgtgaaatgttcgaaggcatggtgtgcc gcctgtggtgcaaagaagaaactctgggcggcggcggaagcgga ggaagcggaggaagcggccctgctgctgtgacagtctctagtgctagc | 850 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG YCQKWMWTCDSERKCCEG MVCRLWCKKLWGGGSSG GSGGSGGSSYTYNYEWHVDVW GQGLLVTVSSAS | 913 |
| 216 | BLV1H12 GGS 2:4 GG-ProTxII-GG | BLV1H12 HC GGS 2:4 GG-ProTxII-GG | 131-49 | caggtccagctgagagagagcggcccctcactggtcaagccatccc agacaactgagcctgacatggcacagcaagcggggtttcactgagcga caaggcagtggatggtggtccgacatgcgcaccaggaaaagcccctgg aatggctcggcgcagcatcgatacggccggaaacacaggtacaatc ccggactgaagagcagactgtccattaccaaggacaactctaaaa gtcaggtgtcactgagcgtgagctccgtcaccacagaggatagtgc aacttactattgcacctgtgcaccaggaaactaagaaaaataccaga gcggaggaagcggaggaagcggcggcggcggaagtggatg tggaacctgcgatagcgaacgtgaaatgttcgaaggcatggtgtgcc gcctgtggtgcaaagaagaaactctgggcggcggcggaagcgga ggaagcggaggaagcggctctatacctaccacaattatgaat ggcatgtggatgtctggggacagggcctgctggtgacagtctctagt gctagc | 851 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG YCQKWMWTCDSERKCCEG MVCRLWCKKLWGGGSSG GSGGSGGSSYTYNYEWHV DVWGQGLLVTVSSAS | 914 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|------|----------|------------------|----------------------|-----------------|---------------------|------------------------|--------------------|
| 217 | BLV1H12 GGS 3:2 GG-ProTxII-GG | BLV1H12 HC GGS 3:2 GG-ProTxII-GG | 131-50 | caggtccagctgagagagagcggcccttcactggtcaagccatccc agacaactgagcctgacatgcacagcaagcgggtttcactgagcga caaggcagtggatggtccgacagcaccaggaaaagccctgg aatggctgggcagcatcgatacggcggaacacacaggtacaatc ccggactgaagagcagactgtccattaccaaggacaactctaaaa gtcaggtgtcactgagcgtgagctccgtcaccacagaggatagtgc aacttactattgcaccctgtgccaccaggaaaactaagaaaataccaga gcggaggaagcggaggaagcggaggaagcggcgttattgcca gaagtggggatggtccgctggtgtcaagaagaaactctgggcggcgg catggtgtgccgcctgtggtcaagaagctctatacctacaattgaatgcatgtgg atgtctgggacagggccctggtgacagtctctagtgctagc | 852 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG SGGYCQKWMWTCDSERKC CEGMVCRLWCKKKLWGGG GSGGSSYTYNYEWHVDVW GQGLLVTVSSAS | 915 |
| 218 | BLV1H12 GGS 3:3 GG-ProTxII-GG | BLV1H12 HC GGS 3:3 GG-ProTxII-GG | 131-51 | caggtccagctgagagagagcggccctcactggtcaagccatccc agacaactgagcctggatggtccgacagcaccaggaaaagccctgg aatggctgggcagcatcgatacggcggaacacacaggtacaatc ccggactgaagagcagactgtccattaccaaggacaactctaaaa gtcaggtgtcactgagcgtgagctccgtcaccacagaggatagtgc aacttactattgcaccctgtgccaccaggaagaacaagaaaataccaga gcggaggaagcggaggaagcggaggaagcggcggctattgcca gaagtggtgatggtccgctggtgtcaagaagaaactctgggcggcgg catggtgtgccgcctgtggtcaagaagctctatacctacaattatga aggcatgtggatgtctgggacagggccctggtgacagtctctcta gtgctagc | 853 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG SGGYCQKWMWTCDSERKC CEGMVCRLWCKKKLWGGG GSGGSSYTYNYEWHV DVWGQGLLVTVSSAS | 916 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 219 | BLV1H12 GGS 4:2 GG-ProTxII-GG | BLV1H12 HC GGS 4:2 GG-ProTxII-GG | 131-52 | caggtccagctgagagagagcggccctcactggtcaagccatccagacactgagcctgacatgcacagcaggcggtttcactgagcgacaaggcagtggatggtcgacagcaggcaccagaaagccctggaatggctggccagcagcgatacgtcgggaacacaggtacaatccggactgaagagcagactgtccattaccaaggacaactctaaagtcaggtgtcactgagcgtgagctcgtcaccagaggatagtgcaacttactattgcaacctctgtcaccaggaaactaagaaataccagagcggaggaagcggaggaagcggaggaagcggaggaagcggcggctattgccagaagtggatgtggacctgcgatagcgaacggaaatgttcgaaggcatgtgtccgcctgtggggggcggcgaggaaggcgaggaagctcttatacctacaattatgaatggcatgtgggtggggacagggcctgctgtgtgacagtctctagtgctagc | 854 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGSGG SGGSGGYCQKWMWTCDS ERKCCEGMVCRLWCKKKL WGGGSGSGGSSYTYNYEWH VDVWGQGLLVTVSSAS | 917 |
| 220 | BLV1H12 GTLV 3xG4S ProTxII | BLV1H12 GTLV 3xG4S ProTxII | 131-56 | caggtccagctgagagagagcggccctcactggtcaagccatccagacactgagcctgacatgcacagcaggcggtttcactgagcgacaaggcagtggatggtcgacagcaggcaccagaaagccctggaatggctggccagcagcgatacgtcgggaacacaggtacaatccggactgaagagcagactgtccattaccaaggacaactctaaagtcaggtgtcactgagcgtgagctcgtcaccagaggaaactaagaaataccagagcggtggaggaggttctggcggcggttgaagtggcggcggcagcgcggaggatactgccagaagtggatggtcaggctgtggtcaagaagaagaagctgtggggaggtggtggatctggtggtggaggcagtggaggtggtgtggcagctctacctacaattatgaatggcatgtgggtcaggaaccctggtcaccgtctcctcagctagc | 855 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGSGGGG GSGGGGSGGYCQKWMWT CDSERKCCEGMVCRLWCK KKLWGGGSGGGGSGGSGGG GSSYTYNYEWHVDVWGQG TLVTVSSAS | 918 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 221 | BLV1H12 GTLV 3xG4S ShK | BLV1H12 GTLV 3xG4S ShK | 131-59 | caggtccagctgcagagagcggccccttcactggtcaagccatccc agacactgagcctgacatgcacagcaagcgggtttcactgagcga caaggcagtggcatggctcgacaggcaccaggaaaagccctgg aatggctggcagcagcatcgatacggcgggaacacaggtacaatc ccggactgaagacagagctgtcattaccaaggacaactctaaaa gtcaggtgtcactgagcgtgagctccgtcaccacagaggatagtgc aacttactattgcacctctgtgcaccaaggaaaactaagaaaataccaga gcggtgaggaggttctggagcggcggttgaagtgtgtgcggaggta gcggaggaagagctgcaagcacagccatcccaagagcccgatgc accgccttcagtgcaagctgcctctgctctgtcgagctgtctggg ag gaggcagtggaggttggtggcagctctataaccttatacttacttaatatgaatgg catgtgaggatgtctgtggggggacaaaacctgtcaccgtctcctcagc tagc | 856 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGSGGGG GSGGGSSGRSCIDTIPKS RCTAFQCKHSMKYRLSFCR KTCGTCGGGGSGGGGSGG GGSSYTYNYEWHVDVWGQ GTLVTVSSAS | 919 |
| 222 | BLV1H12 GTLV 3xG4S OSK1 (K16, D20) | BLV1H12 GTLV 3xG4S OSK1 (K16, D20) | 131-60 | caggtccagctgcagagagcggccccttcactggtcaagccatccc agacactgagcctgacatgcacagcaagcgggtttcactgagcga caaggcagtggcatggctcgacaggcaccaggaaaagccctgg aatggctggcagcagcatcgatacggcgggaacacaggtacaatc ccggactgaagacagagctgtcattaccaaggacaactctaaaa gtcaggtgtcactgagcgtgagctccgtcaccacagaggatagtgc aacttactattgcacctctgtgcaccaaggaaaactaagaaaataccaga gcggtgaggaggttctggagcggcggtgaagtgtgtgcggaggta gcggaggaggcgtgatcatcaacgtgaagtgcaagatcagcagg cagtgcctgaaccctgcaaggacgccggcatgaggttcggtaagt gcatgaacggcaagtgccactgcaccctgcccaaggggaggttggtgat tatgaatgcatggaggtctggatgtctgggggccaagaacccctgtcaccgt ctcctcagctagc | 857 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGSGGGG GSGGGSGGGVIINVKCKIS RQCLKPCKDAGMRFGKCM NGKCHCTPKGGGGSGGGG SGGGGSSYTYNYEWHVDV WGQGTLVTVSSAS | 920 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|------|----------|------------------|----------------------|-----------------|---------------------|------------------------|---------------------|
| 223 | BLV1H12 GTLV 3xG4S OSK1 (P12,K16,D 20) | BLV1H12 GTLV 3xG4S OSK1 (P12,K16,D 20) | 131-61 | caggtccagctgcgagagagagcggccctcactggtcaagccatccc agacaactgagcctgagctggagcatgcacagcaagcgggtttcactgagcga caaggcagtggaggatggtcgacagcgcaccaggaaaagccctgg aatggctgggcagccatcgatacggcgggaacacacagggtacaatc ccgactgaagagcagagactgtccattaccaaggacaactaaaa gtcaggtgtcactgagcgtgagctccgtcaccacagaggatagtgc aacttactattgcaacctctgtgcaccaggaaaactaagaaaataccaga gcggtggaggaggttctgagcgcgttgaagtgtggcgaggta gcggaggaggcgtgatcatcaacgtgaaatgcaagatcagccccc agtgtgcgaagccctgcaagggacgccgcatgaggttcggaagt gcatgaacggcaagtgccactgccactgccaaggagagtggtggat ctggtgtggaggaggttggatgctggagtctcatgaattgaaatgggat tatgaatgcatgtggatgtctgggggccaaggaacctgtcaccgt ctcctcagctagc | 858 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGSGGG GSGGSGGGVIINVKCKIS PQCLKPCKDAGMRFGKCM NGKCHCTPKGGGGSGGGG SGGGSSYTYNYEWHVDV WGQGTLVTVSSAS | 921 |
| 79, 224 | BLV1H12 GTLV 3xG4S GpTx-1 | BLV1H12 cowV HumanC 3xG4S GPTX | 131-62 | caggtccagctgcgagagagagcggccctcactggtcaagccatccc agacaactgagcctgagctggagcatgcacagcaagcgggtttcactgagcga caaggcagtggaggatggtcgacagcgcaccaggaaaagccctgg aatggctgggcagccatcgatacggcgggaacacacagggtacaatc ccgactgaagagcagagactgtccattaccaaggacaactaaaa gtcaggtgtcactgagcgtgagctccgtcaccacagaggatagtgc aacttactattgcaacctctgtgcaccaggaaaactaagaaaataccaga gcggtggaggaggttctgagcgcggttgtgtggcgcgaggta gcggagagactgcctggcttcatgagcaagtgcatcccgaca acgacaagtgctgcaggccccaacctgtgtgcagcaggacccac aagtgtgcaagtacgttcggtggatctgtggtggag gcagtgaggtgtggcgagctcttatacctacacatatgaattgaatggcatg tggatgtctggggggccaaggaaccctgtcaccgtctcctcagctagc | 859 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGSGGG GSGGGGGGDCLGFMPKC IPDNDKCCRPNLVCSRTHK WCKYVFGGGGSGGGGSG GGGSSYTYNYEWHVDVWG QGTLVTVSSAS | 922 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|------|----------|------------------|----------------------|-----------------|---------------------|------------------------|--------------------|
| 225 | BLV1H12 GTLV 6xG4S | BLV1H12 GTLV 6xG4S | 131-64 | caggtccagctgtgagagagagcggcccttcactggtcaagccatccc agacacctgagcctgacatgcacagcagcaagcgggttttcactgagccga caaggcagtggatgggtccgacaggcaccaggaaaagccctgg aatggctgggtcagcatcgatacggcgggaaacacaggtacaatc ccggactgaagagcagactgtccattaccaaggacaactctaaaaa gtcaggtgtcactgagcgtgagctccgtcaccacagaggatagtgc aacttactactgtcacctgttcgaggcggtgaagttggctgcggaggta gcggaggaggttctggatggtggtggaggaggcagtggtggggc gcggaggaggttctggatgggtggaggaggcagtggtgatgtctcggggggccaa ggaaccctggtcaccgtctcctcagctagc | 860 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGSGGGG GSGGGSGGGSGGGSGGGS GGGGSSYTYNYEWHVDVW GQGTLVTVSSAS | 923 |
| 226 | BLV1H12 GTLV 1xG4S Bsals (wStop) | BLV1H12 GTLV 1xG4S Bsals (wStop) | 131-65 | caggtccagctgtgagagagagcggcccttcactggtcaagccatccc agacacctgagcctgacatgcacagcagcaagcgggttttcactgagcga caaggcagtggatgggtccgacaggcaccaggaaaagcccctgg aatggctgggtcagcatcgatacggcgcgggaaacacaggtacaatc ccggactgaagagcagactgtccattaccaaggacaactctaaaaa gtcaggtgtcactgagcgtgagctccgtcaccacagaggatagtgc aacttactactgtcacctgttcgaggcggtgaagttggctgcggaggtc tcggaggtggtggatctcttatacctacacaattatgaatggcatgtgga tgtctgggggccaaggaaacctggtcaccgtctcctcagctagc | 861 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGGSGG* DLLWFRVSGGGGGSYTYNV EWHVDVWGQGTLVTVSSA S | 924 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 25, 228 | BLV1H12 GLLV 3xG4S ProTxII | BLV1H12 GLLV 3xG4S ProTxII | 131-66 | caggtccagctgcagagagagcggccctccttcactggtcaagccatccc agacaactgagcctgacctgctacagcagccggatttttcactgagcga caaggcagtggatggtccgacaggcacccaggaaaagccctgg aatgctgggcagcagccatcgataccggcggaacacaggtgacaatc cggactgaagagcagactgtccattaccaaggacaacttcaaaa gtcaggtgtcacttgagcgtgagctccgtcaccacagaggatagtgc aacttactattgcacctctgtcaccaggaaaactaagaaaataccaga gcggtggaggaggttctgcgaggcgttgaagtgtgtgcggaggta gcggaggatactgccagaaagtgcatggtcaggtgtcgcagcagag aggaagtgctgcgaggcagcatggtggatctggtcaggtgtgtcaagaag aagctgtggggaggtggttggatctggtggaggcagtggaggt ggtggcagctcttacacctacacaattatgaatggcatgtggtgatgtctggg gacagggcctgctggtgacagtctcagtgctago | 862 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGGSGGG GSGGGGSGGYCQKWMWT CDSERKCCEGMVCRLWCK KKLWGGGGSGGGGSGGGG GSSYTYNYEWHVDVWGQG LLVTVSSAS | 775 |
| 29, 40, 229 | BLV1H12 GLLV 3xG4S ShK | BLV1H12 Hc CowV,HuC GLLV 3xG4S ShKtoxin | 131-67 | caggtccagctgcagagagagcggccctccttcactggtcaagccatccc agacaactgagcctgacctgctacagcagccggatttttcactgagcga caaggcagtggatggtccgacaggcacccaggaaaagccctgg aatgctgggcagcagccatcgataccggcggggaacacaggtgacaatc ccgactgaagagcagactgtccattaccaaggacaactctaaaa gtcaggtgtcacttgagcgtgagctccgtcaccacagaggatagtgc aacttactattgcacctctgtcaccaggaaaactaagaaaataccaga gcggtggaggaggttctgcgaggcgttgaagtgtggtgcggaggta gcggaggagagagctgcatgcaacctcatgggtcagccgatgc accgccttccagtgcaagcacagcatgaagtacagactgtcgagcttct gcaggaagacctgcggcacctgcggcagtggtgggggatctggtggag gaggcagtggaggtggtggcagctcttatacctacaattatgaatgg catgtggatgtctggggacagggcctgctggtgacagtctctagtgct agc | 863 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGGSGGG GSGGGGSGGRSCIDTIPKS RCTAFQCKHSMKYRLSFCR KTCGTCGGSGGGGSGGSGG GGSSYTYNYEWHVDVWGQ GLLVTVSSAS | 779 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 26, 230 | BLV1H12 GLLV 3xG4S OSK1 (K16,D20) | BLV1H12 GLLV 3xG4S OSK1 (K16,D20) | 131-68 | caggtccagctgcagagagagcggccccttcactggtcaagccatccc agacaactgagcctgacatgcacagcaaggcggttttcactgagcga caaggcagtggatggtggtcgacaggcaccaggaaaagccctgg aatggctggcagcatcgatcacgtcgggaacacacaggtacaatc ccggactgaagacagactgtccattaccaaggacacaactctaaaa gtcaggtgtcactgagctgagctccgtcaccacaggatagtgc aacttactattgcacctgtgcaccaggaaaactaagaaaataccaga gcggtgaggaggttctgagtgcggtgaagtgtgtgcggaggta gcgcagtggcgtgatccctgcaaggacgccggcatgaggttcggtaagt cagtgcctgaccgcaagtgccactgcaggaccggaggggaggttggttgat ctgttggaggaggcagtgagtgtggtgcagctcttatacctacaat tatgaatggcatggtggtgtctgggggacaggcctgctggtgacagt ctctagtgctagc | 864 | QVQLRESGPSLVKPSQTLS LTCTASGFSLSDKAVGWVR QAPGKALEWLGSIDTGGNT GYNPGLKSRLSITKDNSKSQ VSLSVSVTTEDSATYYCTS VHQETKKYQSGGGGSGG GSGGGGSGGVIINVKCKIS RQCLKPCKDAGMRFGKCM NGKCHCTPKGGGSGGGG SGGGGSSYTYNYEWHVDV WGQGLLVTVSSAS | 778 |
| 27, 231 | BLV1H12 GLLV 3xG4S OSK1 (P12,K16,D 20) | BLV1H12 GLLV 3xG4S OSK1 (P12,K16,D 20) | 131-69 | caggtccagctgcagagagagcggccccttcactggtcaagccatccc agacaactgagcctgacatgcacagcaaggcggttttcactgagcga caaggcagtggatggtggtcgacaggcaccaggaaaagccctgg aatggctggcagcatcgatacggcggggaacacacaggtacaatc ccggactgaagacagactgtccattaccaaggacacaactctaaaa gtcaggtgtcactgagctgagctccgtcaccacaggatagtgc aacttactattgcacctgtgcaccaggaaaactaagaaaataccaga gcggtgaggaggttctgagtgcggtgaagtgtgtgcggaggta gcgcagtggcgtgatccctgcaaggacgccggcatgaggttcggtaagt agtgcctgaacaggcccctgcaaggacgccgtcatgaggttgggaagt gcatgaatggcatggtggtgtctgggggacaggcctgctggtgacagt ctgttggaggaggcagtgagtgtggtgcagctcttatacctacaat tatgaatggcatggtggtgtctgggggacaggcctgctggtgacagt ctctagtgctagc | 865 | QVQLRESGPSLVKPSQTLS LTCTASGFSLSDKAVGWVR QAPGKALEWLGSIDTGGNT GYNPGLKSRLSITKDNSKSQ VSLSVSVTTEDSATYYCTS VHQETKKYQSGGGGSGGGG GSGGGGSGGVIINVKCKIS PQCLKPCKDAGMRFGKCM NGKCHCTPKGGGSGGGG SGGGGSSYTYNYEWHVDV WGQGLLVTVSSAS | 777 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 28, 232 | BLV1H12 GLLV 3xG4S GpTx-1 | BLV1H12 GLLV 3xG4S GpTx-1 | 131-70 | caggtccagctgagagagagcggcccctcactggtcaagccatccc agacactgagctgcacagcgtcaggcttttcactgagcga caaggcagtggatggtcgacagcgcaggcaccaggaaaagccctgg aatggctgggcagcatcgatacgggtgggaaacacaggtacaatc ccggactgaagagcagactgtccattaccaaggacaactctaaaa gtcaggtgtcactgagcgtgagctccgtcaccacagaggatagtgc aacttactattgcacctctgtgcaccaggaaactaagaaaataccaga gcgtggaggaggttctgaggcgcggtggaagtggtggtggaggta gcggaggagactgcctggctggcttcatgaagaagtgcatcccgaca acgacaagtgctgcaggcccaacctggtgtgcagcaggaccac aagtggttgcaagtacgtcttcggaggtggaggtggtggaggag gcagtggaggtggtggcagctcttatacctacaattatgaatggcatg tggatgtctgtgggacagggcctgctggtgacagtctctagtgctagc | 866 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGGSGGG GSGGGGSGGDQLGFMKKC IPDNDKCCRPNLVCSRTHK WCKYVFGGGGSGGGGSG GGGSSYTYNYEWHVDVWG QGLLVTVSSAS | 776 |
| 34 | VH4-34 MutA IL-8 CD1Cow | VH4-34 CD3 iL8_CDR1-Cow_CDR2-Human | 132-07 | caggtgcagctacagcagtggggcgcaggactgttgaagccttcgg agaccctgtccctcacctgcacagcgtcaggcttttcactgagcgac aaggcagtggatggattcgccagcccccagggaaggggctgga gtgattgggaaatcaatcataggtgaagcaccaactacaaccc gtcccctcaagagtcgagtcaccatatcagtagacacgtccaagaac cagttctccctgaagctgagctctgtgaccgccgcggacacggctgt gtattactgtacctctgtgcaccaggaaactaagaaatacaagagcc caagagagctctgtaaagaactagatgtcagtgaaagacatactc caaacctttcacccccaagttcatcaaggagctgagagttattgatg gaagagagctgtgcctggatccggaccccaagttcatcaaggagctgagagttgaatg gtcttggagaagttcttaaagaggggctgaaactgggtcagcggtt cttatacctacaattatgaatggcatgtggatgtctgggacagggcc tgctggtgacagtctctagtgctagc | 867 | QVQLQQWGAGLLKPSETLS LTCTASGFSLSDKAVGWIR QPPGKGLEWIGEINHSGST NYNPSLKSRVTISVDTSKNQ FSLKLSSVTAADTAVYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSSAS | 794 |

Figure 21 (continued)

| BIDs | IgG Name | Heavy Chain Name | VH DNA Sequence | SEQ ID NO: (VH DNA) | VH Amino Acid Sequence | SEQ ID NO: (VH aa) |
|---|---|---|---|---|---|---|
| 35 | VH4-34 IL-8 CDR1cow CDR2cow | VH4-34 CD3 iL8_CDR1-Cow_CDR 2-Cow | 132-09 | caggtgcagctacacagcagtgggtcggcgcaggactgttgaagccttcgg agacgctgtccctcacctgcacagcagtcgggttttcactgagcgac aaggcagtgggatggattcgccagccccccaggggaagggggctgga gtggtgggcagcatcgatacggctcgggaacacaggtacaacc cgtccccaagagtcgagtcaagtctctggtgaccgcgccgacacggctg ccagttctccctgaagctgagctgcagctccaccaagaaaataccagagc ccaaggagtgcaaagaaccttagatgtcagtgcataaagacatact ccaaaccttccaccccaagttcatcaaggagctgagagtgattgag agtggaccaccactgcccaacacagagatatttcagtctaaagctttctgat gggagagagctcgtcctgaagagggctgagaactcaggcagcggt ggtcgtggagaagttcttgaagagggctgagaactcaggcagcggt tcttatacctacaattatgaatggcatgtgtgatgtctgggacagggc ctgctcggtgacagtctctagtgctagc | 868 | QVQLQQWGAGLLKPSETLS LTCTASGFSLSDKAVGWIR QPPGKGLEWLGSIDTGGNT GYNPSLKSRVTISVDTSKNQ FSLKLSSVTAADTAVYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSSAS | 798 |
| 36 | VH4-34 MutB iL-8 CDR1cow CDR2cow | VH4-34 CD3 iL8_CDR1-Cow_CDR 2-Cow | 132-09 | caggtgcagctacacagcagtgggtcggcgcaggactgttgaagccttcgg agacgctgtccctcacctgcacagcagtcgggttttcactgagcgac aaggcagtgggatggattcgccagccccccaggggaagggggctgga gtggtgggcagcatcgatacggctcgggaacacaggtacaacc cgtccccaagagtcgagtcaagtctctggtgaccgcgccgacacggctg ccagttctccctgaagctgagctgcagctccaccaagaaaataccagagc ccaaggagtgcaaagaaccttagatgtcagtgcataaagacatact ccaaaccttccaccccaagttcatcaaggagctgagagtgattgag agtggaccaccactgcccaacacagagatatttcagtctaaagctttctgat gggagagagctcgtcctgaagagggctgagaactcaggcagcggt ggtcgtggagaagttcttgaagagggctgagaactcaggcagcggt tcttatacctacaattatgaatggcatgtgtgatgtctgggacagggc ctgctcggtgacagtctctagtgctagc | 869 | QVQLQQWGAGLLKPSETLS LTCTASGFSLSDKAVGWIR QPPGKGLEWLGSIDTGGNT GYNPSLKSRVTISVDTSKNQ FSLKLSSVTAADTAVYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSSAS | 798 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 37 | VH4-34 MutC IL-8 31D32K50S | VH4-34 CD3 iL8_CDR1-G31DY32K_CDR2-E50S | 132-05 | caggtgcagctacaagcagtggggcgcaggacttgttgaagcctcgg agagcgctgtcctcacctgcgctggtgtctcattgggtggtggtcttcagtgaca agtactggagctggatctgccagcagcccccaggggaaggggctggagt ggattgggagcatcaatcatcaggtgaagcaccaactacaaaccgtc cctcaagagtcgagtcaccatatcagtagacacgtccaagaacca gttctccctgaagctgagctctgtgaccgccgcggacacggctgtgt attactgtacctctgtgcaccaggaaaactaagataccaggaccc aaggagtgtcaaagaactagatgtcagtcgagagtgattgagag aaaccttcacccccgccaacacagagattattattgaaagctttctgatgg gagagagctctgcctggaagggctgagaactcaggcagcgggttct tatacctacaattatgaatggcatgtggatgtctgggggacagggcctg ctggtgacagtctctagtgctagc | 870 | QVQLQQWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSSAS | 800 |
| 38 | VH4-34 MutE IL-8 5R6E31D3 2K50S | VH4-34 CD3 IL8 Q5RQ6E_ CDR1-G31DY32K_CDR2-E50S | 132-13 | caggtgcagctaagagagtgggcgcaggacttgttgaagcctcg gagacgctgtcctcacctgcgctggtgtctcattgggtggtccttcagtgac aagtactggagctggatctgccagcagcccccaggggaaggggctggag tggattgggagcatcaatcatcagtgaagcaccaactacaaccgt ccctcaagagtcgagtcaccatatcagtagacacgtccaagaacc agttctccctgaagctgagctctgtgaccgccgcggacacggctgtgt tattactgtacctctgtgcaccaggaaaactaagataccagagccc aaggagtgtcaaagaactagatgtcagtcgagagtgattgagag aaaccttcacccccgccaacacagagattattattgaaagctttctgatgg tggaccacactgcgtcctgcctggaagggctgagaactcaggcagcgggttct tatacctacaattatgaatggcatgtggatgtctgggggacagggcctg ctggtgacagtctctagt | 493 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSS | 737 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 39 | VH4-34 MutD IL-8 CDR1cow CDR2cow | VH4-34 CD3 iL8_CDR1-Cow_CDR 2-Cow | 132-09 | caggtgcagctacagcagtgggggcgcaggagtgttgaagccttcgg agacgctgtccctgacctgcactgtctctggtggctccatcagtagtggt tactactactggagctggatccgccagcccccaggaaaggggactgga gtggattgggtgcagtctggagcctcaaggtgaaacagaggcagtactgaactgtctggag cgtcctccaagagtcgagtcaccatatcagtagacacgtccaagaac ccagtccctgaagctgagctgttgacctgcggaccggcgacgctg tgtattactgtgcgagctgagctgttgaccgcgccggacacgggctg ccaaggagtgctaaagaaacttagatgtcagtgcataaagacatact ccaaaccttccaccccagtccaacacagagattattgtaaagctttctgat agtgaccaccactgcgccaacacagagatttgaagctgagagtcgagag gggagagagagctgcctgcctgaccagaacaaaaactggtgcagag gtcgtggaagttctttgaagaggggtgagaactcaggcagcggt tcttatacctacaattatgaatggcatgtctggatgtctgggacagggc ctgctggtgacagtctcttagtgctagc | 871 | QVQLQQWGAGLLKPSETLS LTCTASGFSLSDKAVGWIR QPPGKGLEWLGSIDTGGNT GYNPSLKSRVTISVDTSKNQ FSLKLSSVTAADTAVYYCTS VHQETKKYQSPRSAKELRC QCIKTYSKPFHPKFIKELRVI ESGPHCAANTEIIVKLSDGRE LCLDPKENWVQRWEKFLK RAENSGSGSYTYNYEWHV DVWGQGLLVTVSSAS | 798 |
| 42 | BLV1H12 | BLV1H12 HC CowV. Human CH1-2-3 (107) | 131-74 | caggtccagctgcagcagagagagcgcggccctccactggtcaagccatccc agacactgagctgagctgggatgggatcgcacagcaagcgcggtttttcactgagcga caaggcagtgagctggtggatggtccgaccaggaaaagccctgg aatgctggcgcagcatcgatgatccgggggaacacagggtgacaatc ccggactgaagagcgcagactgtccattaccaagcagcaactctaaaa gtcaggtgtcactgagcgtagccgtccgtcaccacagaggatagtgc aacttactattgcacctctgtgcaccggagaaactaagaaaataccaga gctgtcctgacggctatcgagatctgcggtctcggaactcggaactgcc tgactaccctgcctgtgtctccatctcttatactacaattatgaatggcat gttggatgtctgggggacaggggcctgctgggacagtctcttagtgctag c | 872 | QVQLRESGPSLVKPSQTLS LTCTASGFSLSDKAVGWVR QAPGKALEWLGSIDTGGNT GYNPGLKSRLSITKDNSKSQ VSLSVSSVTEDSATYYCTS VHQETKKYQSCPDGYRERS DCSNRPACGTSDCCRVSVF GNCLTTLPVSYSYTNYEW HVDVWGQGLLVTVSSAS | 925 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 43 | VH4-34 MutF IL-8 5R6E CD1cow | VH4-34 IL-8 CDR3 Q5RQ6E_CDR1-Cow_CDR2-Human | 132-11 | caggtgcagctaagagagtggggcgcaggactgttgaagccttcg gagacgctgtccctcacctgcacagcaagcgggttttcactgagcg acaagcagtggatgtgatcgccagccccccagggaagggggctg gagttggattgggaaatcaatcaatacagtggaagcaccaactacaac ccgttccctcaagagtcgagtcaacatatcagtagacacgtccaaga accagttctccctgaagctgagctctgtgaccgccgcggacacggct gtgtattacttgacctctgtgtgtcaccaggaaactaagaaataccagag cccaaggagtgctaaagaaacttagatgtcagtgcataaagacatac tccaaaccttccacccaagttcatcaaggagctgagagtgattga gagtggaccacactgcgccaacacagagattattgtaaagcttctg atgggagagagctgcctgctgaagaggggctgagaactcaggcagc aggtcgtggagaagttctgaagaggggctgagaactcaggcagc ggttcttatacctacaaaatatgaatggcatggatgtctgggggacagg gcctgctggtgacagtctcagt | 494 | QVQLREWGAGLLKPSETLS LTCTASGFSLSDKAVGWIR QPPGKGLEWIGEINHSGST NYNPSLKSRVTISVDTSKNQ FSLKLSSVTAADTAVYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSS | 788 |
| 44 | BLV1H12-IL8 | BLV1H12 HC CowV, CDR3 IL-8, Human CH1-2-3 (105) | 131-76 | caggtccagctgagagagcggccctcactggtcaagccatccc agacactgagcctgacatgcacagcaagcgggtttcactgagcga caaggcagtggatggtccgcacaggcaccaggaaaagccctgg aatggctgggcagcatcgatacggcgggaacacagggtacaatc ccggactgaagagcagacgtccattaccaaggacaactctaaaa gtcagtgtcactgagcgtgagctccgtcaccacagaggtagtgc aactactattgcacctgtgtcaaagaacttagatgtcagtgcataaagacata ctccaaacctctcaccccaagttcatcaaggagctgagagtgca agagttcgtgagaagttcttgaagagggctgagaactcaggcag cggttcttatacctacaaatatgaatggcatggatgtctgggggacag ggcctgctggtgacagtctcagtgctagc | 873 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSPRSAKELRC QCIKTYSKPFHPKFIKELRVI ESGPHCANTEIIVKLSDGRE LCLDPKENWVQRVVEKFLK RAENSGSGSYTYNYEWHV DVWGQGLLVTVSSAS | 926 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 45 | BLV1H12 HC CowV, CDR3 IL-8, 1xG4S | BLV1H12 CowV 1xGGGGS linker- IL-8 - HumanCH 123 | 131-71 | caggtccagctgagagagagcggcccctttcactggtcaagccatccc agacaactgagcctgacatgcacagccagcggcttttcactgagcga caaggcagtggcatgggtcgacaggcaccaggaaaagccctgg aatggctgggcagcattgacactggaggaaacacaggtacaatc ccggactgaagagcagactgtccattaccaagagacaactctaaaa gtcaggtgtcactgagctgagctccgtcaccacagaggatagtgc aacttactactgtgcacctctgtgcaccagagaaataagaaaataccaga gcggtgaggaggttctgaggaccaaggagtgtaaagaacttta gatgtcagtcagtaagacatactccaaaacctttccaccccaagttc atcaaggctgagagtgattgagagtggaccaactgcgccaac acagagagattattgtaaagctttctgatgtgggagagagagctgtcctgac cccaaggaaaactgggtgcagagagctcgtggagaagttcttgaag agggctgagaactcaggagagtggtggtgatcttctttatacctacaattat gaatggcatgtgatgtctgggacaggcctgctggtgacagtctc tagtgctagc | 874 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGGSGGP RSAKELRCQCIKTYSKPFHP KFIKELRVIESGPHCANTEIIV KLSDGRELCLDPKENWVQR VVEKFLKRAENSGGGSSY TYNYEWHVDVWGQGLLVT VSSAS | 927 |
| 46 | BLV1H12 HC CowV, CDR3 IL-8, 3xG4S | BLV1H12 CowV 3xGGGGS linker- IL-8 - HumanCH 123 | 131-72 | caggtccagctgagagagagcggcccctttcactggtcaagccatccc agacaactgagcctgacatgcacagccagcggcttttcactgagcga caaggcagtggcatgggtcgacaggcaccaggaaaagccctgg aatggctgggcagcattgacactggaggaaacacaggtacaatc ccggactgaagagcagactgtccattaccaagagacaactctaaaa gtcaggtgtcactgagctgagctccgtcaccacagaggatagtgc aacttactactgtgcacctctgtgcaccaccagagaaataagaaataccaga gcggtgaggaggttctgaggccggtgaagtgtggcgtgaggta gcggaggaccaaggagtgtaaagaacttagatgtcagtcatgtcataa agacatactccaaaacctttccaccccaagttcatcaaggagctgag agtgattgagagtggaggtcatcaaggagctgag agtgattctgatgtgggagagagctgtcctgac cccaaggaaaactgggtgcagagactgagaagttcttgaagagctgag aggaggtggatctgtgtgaggagcatgtggatgtctgggggacaggg cctgctggtgtgacgtctctagtgctagc | 875 | QVQLRESGPSLVKPSQTLS LTCTASGFSLSDKAVGWVR QAPGKALEWLGSIDTGGNT GYNPGLKSRLSITKDNSKSQ VSLSVSSVTTEDSATYYCTS VHQETKKYQSGGGGSGGG GSGGGGSGGPRSAKELRC QCIKTYSKPFHPKFIKELRVI ESGPHCANTEIIVKLSDGRE LCLDPKENWVQRVVEKFLK RAENSGGGSGGGGSGG GGSSYTYNYEWHVDVWGQ GLLVTVSSAS | 928 |

Figure 21 (continued)

| BIDs | IgG Name | Heavy Chain Name | VH DNA Sequence | SEQ ID NO: (VH DNA) | VH Amino Acid Sequence | SEQ ID NO: (VH aa) |
|---|---|---|---|---|---|---|
| 47 | VH4-34 MutE 3xG4S IL-8 | VH4-34 Q5RQ6E, G31DY32K, E50S, 3xG4S, IL-8 | caggtgcagctaagagagagtggggcgcaggactgttgaagccttcg gagacgctgtccctcacctgcgctgtgtatggtggtccttcagtgac aagtactggagctggattcgccagcccccaggaaggggctggag tggattgggagcatcaatcatagtggaagcaccaactacaaccgt ccctcaagagtcgagtcaccatatcagtagacacgtccaagaacc agttctccctgaagctgagctctgtgaccgccgcggacacggctgtg tattactgtacctctgtgcaccaggaaactaagaaataccagagcgg tggaggaggttctggaggcggtggaagtggtggcggaggtagcgg aggaccaagaggagtcaagctaga... | 876 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGPRSAKELRC QCIKTYSKPFHPKFIKELRVI ESGPHCANTEIIVKLSDGRE LCLDPKENWVQRVVEKFLK RAENSGGGSGGGGSGG GGSSYTYNYEWHVDVWGQ GLLVTVSSAS | 929 |
| 48, 68, 72, 75, 80, 94, 100, 101, 111, 115,1 20, 123, 135 | VH4-34 MutE 3xG4S ShK | VH4-34 Q5RQ6E, G31DY32K, E50S, 3xG4S, ShK | caggtgcagctaagagagagtggggcgcaggactgttgaagccttcg gagacgctgtccctcacctgcgctgtgtatggtggtccttcagtgac aagtactggagctggattcgccagcccccaggaaggggctggag tggattgggagcatcaatcatagtggaagcaccaactacaaccgt ccctcaagagtcgagtcaccatatcagtagacacgtccaagaacc agttctccctgaagctgagctctgtgaccgccgcggacacggctgtg tattactgtacctctgtgcaccaggaaactaagaaataccagagcgg tggaggaggttctggaggcggtggaagtggtggcggaggtagcgg aggaaggagctgcatcgacacatcccaagagtacagccgatgcaccg ccttccagtgcaagcacagcatgaagtacaggctgagcttctgcag gaagacctgcggtggttgtcagctcggaggtggtggtatctggtgtggaggg cagtggaggtggttgtcagctctatacctacaaattatgaatggcatgt ggatgtctgggggacaggtgcctgggtgacagtctcagtgctagc | 877 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGRSCIDTIPKS RCTAFQCKHSMKYRLSFCR KTCGTCGGGSGGGGSGG GGSSYTYNYEWHVDVWGQ GLLVTVSSAS | 930 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 49 | VH4-34 MutE 3xGGS MOKA | VH4-34 Q5RQ6E, G31DY32K, E50S, 3:3GGS, MOKA | 132-36 | caggtgcagctaagagagtggggcgcaggactgttgaagccttcg gagacgctgtccctcacctgcgctgtctggtgtcggtccttcagtgac aagtactgggagctggattgccagccccagggaaggggctggag tggattgggagcatcaatcatagtggaagcaccaacacaaccgt ccctcaagagtcgagtcaccatatcagtagacacgtccaagaaacc agttctcctgaagctgagctgctgtgtaccgccgcgacacggctgtg tattactgtacctctgtgcaccaggaaactaagaaataccagagcgg aggaagcggaggaagcggaggaagcggcatcaacgtgaagtgc agcctgccccagcagtgcatgaaaagcagaggtcagggacgccggcatg agattcggcaagatgaataagaagtgctacagcggaagacgcggga ggaagcggaggaagcggaggaagctcttatacctacaattatgaat ggcatgtggatgtctggggacagggcctgctggtgacagtctctagt gctagc | 878 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGSGGSGGG SGINVKCSLPQQCIKPCKDA GMRFGKCMNKKCRCYSGG SGGSGGSGGSSYTYNYEWHVD VWGQGLLVTVSSAS | 931 |
| 50 | VH4-34 MutF 3xG4S ShK | VH4-34 Q5RQ6E, CDR1 Cow, 3xG4S, ShK | 132-38 | caggtgcagctaagagagtggggcgcaggactgttgaagccttcg gagacgctgtccctcacctgcaccagcaagcgggtttcactgagcg acaaggcagtgggatggattcgccagccccagggaaggggctg gagtggattgggagaatcaatcatagtggaagcaccaacacaaac cgttcccctcaagagtcgagtcaccatatcagtagacacgtccaaga accagttctcctgaagctgagctgtgtaccgccgcggacacggct gtgtattactgtacctctgtgcaccaggaaactaagaaataccagag cggtggaggaggttctggagcggtggaagtggtgcggggtag cggaggaggagtggagctgcatcgacaccatcccaagagccgatgca ccgccttccagtgcaagcacagcatgaagtacagactgagcttctg caggaagacctgcggcacctgcggagtgtggatctggtggtggagg aggcagtggagtggtgtcagtctataccttataccacaattatgaatggc atgtggatgtctggggacagggcctgctggtgacagtctctagtgcta gc | 879 | QVQLREWGAGLLKPSETLS LTCTASGFSLSDKAVGWIR QPPGKGLEWIGEINHSGST NYNPSLKSRVTISVDTSKNQ FSLKLSSVTAADTAVYYCTS VHQETKKYQSGGGSGGGG GSGGGGSGGGRSCIDTIPKS RCTAFQCKHSMKYRLSFCR KTCGTCGGSGGGGSGGGGG GGSSYTYNYEWHVDVWGQ GLLVTVSSAS | 932 |

Figure 21 (continued)

| BIDs | IgG Name | Heavy Chain Name | VH DNA Sequence | SEQ ID NO: (VH DNA) | VH Amino Acid Sequence | SEQ ID NO: (VH aa) |
|---|---|---|---|---|---|---|
| 51 | VH4-34 MutF 3xG4S IL-8 | VH4-34 Q5RQ6E. CDR1 Cow, 3xG4S, IL-8 | caggtgcagctaagagagtggggcgcaggactgttgaagccttcg gagacgctgtccctcacctgcacagcaagcgggttttcactgagcg acaaggcagtgggatggattcgccagcccccaggggaaggggctg gagtggattgggaaatcaatcatagtggaagcaccaactacaac ccgtccctcaagagtgagtcaccatatcagtagacacgtccaaga accagttctcctgaagctgagctctgtgaccgcgcgggacacggct gtgtattactgtgtccctgtgtccaccaggaaactaagaaataccagag cggtggaggaggttctggaggcggttggaagtgtggcggagttag cggaggaccaaggagtgctaaagaactagatgtcagtcagtaa gacatactccaaaccttccacccaagttcatcaaggagctgaga gtgattgagagtggaccacactgcgccaacacagagattattgtaa agcttctgatgggagagagctctgccctgaacgaaggctgagaactca ggaggtgtggatctgtggaggaagttcttgaaagggtcagtggtggcagc tcttatactacaattatgaatgcacaagtctgatgtctgggacagggc ctgctgttgacagtctgacagtctagc | 880 | QVQLREWGAGLLKPSETLS LTCTASGFSLSDKAVGWIR QPPGKGLEWIGEINHSGST NYNPSLKSRVTISVDTSKNQ FSLKLSSVTAADTAVYYCTS VHQETKKYQSGGGGSGGG GSGGGGSGGPRSAKELRC QCIKTYSKPFHPKFIKELRVI ESGPHCANTEIIVKLSDGRE LCLDPKENWVQRVVEKFLK RAENSGGGGSGGGGSGG GGSSYTYNYEWHVDVWGQ GLLVTVSSAS | 933 |
| 52 | VH4-34 MutF 3xGGS MOKA | VH4-34 Q5RQ6E, CDR1 Cow, 3:3GGS, MOKA | caggtgcagctaagagagtggggcgcaggactgttgaagccttcg gagacgctgtccctcacctgcacagcaagcgggttttcactgagcg acaaggcagtgggatggattcgccagcccccaggggaaggggctg gagtggattgggaaatcaatcatagtggaagcaccaactacaac ccgtccctcaagagtgagtcaccatatcagtagacacgtccaaga accagttctcctgaagctgagctctgtgaccgcgcgggacacggct gtgtattactgtgtccctgtgtccaccaggaaactaagaaataccagag cggaggaagcggaggaagcggaggaagcggcatcaacgtgaa gtgcagcctgccccagcagtgcatcaagcccctgcaaggacgccgg catgagaatcggcaagtgcatgaacaagaagtgcagatgctacag cggaggaagcggaggaagcggaggaagctctataccacaatta tgaatggcatgtggatgtggggacaggggcctgttacctattacctaatta ctagtgctagc | 881 | QVQLREWGAGLLKPSETLS LTCTASGFSLSDKAVGWIR QPPGKGLEWIGEINHSGST NYNPSLKSRVTISVDTSKNQ FSLKLSSVTAADTAVYYCTS VHQETKKYQSGGGGSGGG SGINVKCSLPQQCIKPCKDA GMRFGKCMNKKCRCYSGG SGGSGGSSYTYNYEWHVD VWGQGLLVTVSSAS | 934 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 53, 155 | VH4-34 MutE 3xG4S ProTxII | VH4-34 Q5RQ6E. G31DY32K , E50S, 3xG4S, ProTxII | 132-31 | caggtgcagctaagagagagtggggcgcaggactgttgaagccttcg gagacgctgtccctcacctgcgtcgctcatgstggtcttcagtgac aagtactggagctggatccgccagcccccaggggaaggggctggag tggattgggagcatcaatcatagtggaagcaccaacacacaaccgt ccctcaagagtcgagtcaccatatcagtagacacgtccaagaaacc agttccctgaagctgagctcttgaccgccgcggacacggctgtg tattactgtacctctgtgcaccaggaaaataaccagagcgg tggaggaggttctggaggcggtggaagtggtgtggcggtagcgg aggatactgccagaagtggatgtggtgccatctgcacagcgagagga agtgctgcgagggcatggtgttgcagctgtcgtggtcaagaagaagct gtgggaggtggatctggtggaggcagtggaggtggtgg cagctcttatacctacaattatgaataccacagtctctagtgtggaca gggcctgctggtgacagtctcagtgctagc | 882 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGYCQKVMWVT CDSERKCCEGMVCRLWCK KKLWGGGSGGGSGGGG GSSYTNYEWHVDVWGQG LLVTVSSAS | 935 |
| 54, 78, 156 | VH4-34 MutE 3xG4S GPTX1 | VH4-34 Q5RQ6E. G31DY32K , E50S, 3xG4S, GPTX1 | 132-34 | caggtgcagctaagagagagtggggcgcaggactgttgaagccttcg gagacgctgtccctcacctgcgtcgctcatgstggtcttcagtgac aagtactggagctggatccgccagcccccaggggaaggggctggag tggattgggagcatcaatcatagtggaagcaccaacacacaaccgt ccctcaagagtcgagtcaccatatcagtagacacgtccaagaaacc agttccctgaagctgagctctgtgaccgccgcggacacggctgtg tattactgtacctctgtgcaccaggaaaataaccagagcgg tggaggaggttctggaggcggtggaagtggtggcggtagcgg aggagagctgcctggtcaggccccaaccgttgtcatccgcgacaacga caagtgctgcgaggccccaaccgtgtgccgacggaccccacaagtg gtgcaagtacgtgttcggaggcggtggtggaatcggtggaagtggcagt ggaggtggtggcagtctctataccctacaattatgaatggcatgtggat gtctgggggacagggcctgctggtgacagtctcagtgctagc | 883 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGDCLGFMRKC IPDNDKCCRPNLVCSRTHK WCKYVFGGGSGGGGSG GGGSSYTNYEWHVDVWG QGLLVTVSSAS | 936 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 55, 64, 102, 110, 112, 121, 125, 160, 163, 166, 169 | VH4-34 MutE No Knob | VH4-34 Q5RQ6E, G31DY32K, E50S, CDR3 CowStalks-3xGGS | 132-49 | caggtgcagctaagagagtggggcgcaggacttgaagccttcg gagacgctgtcctcacctgcgctgtctatggtgtgggtcctcagtgac aagtactggagctggatccgccagcccccaggggaagggggctggag tggattgggagcatcaatcatagtggaagcaccacactacaacccgt ccctcaagagtcgagtccacatatcagtagacacgtccaagaacc agttctccctgaagctgagctgtgttgaccgccgcgacacggctgtg tattactgtacctctgtgcaccaggaaaactaagaaataccagagcgg aggaagcggaggaagcggaggaagctcttatacctatacacaattatga atggcatggtgatgtctggggacagggcctgctcgtggtgacagtctcta gtgctagc | 884 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGSGGSGGG SSYTYNYEWHVDVWGQGL LVTVSSAS | 937 |
| 56, 124, 145, 146, 147, 148 | VH4-34 MutE 1xG4S ShK | VH4-34 Q5RQ6E, G31DY32K, E50S, CDR3 CowStalks-1xG4S ShK | 132-53 | caggtgcagctaagagagtggggcgcaggacttgaagccttcg gagacgctgtcctcacctgcgctgtctatggtgtgggtcctcagtgac aagtactggagctggatccgccagcccccaggggaagggggctggag tggattgggagcatcaatcatagtggaagcaccacactacaacccgt ccctcaagagtcgagtcaccatatcagtagacacgtccaagaacc agttctccctgaagctgagctctgtgaccgccgcgacacggctgtg tattactgtacctctgtgcaccaggaaaactaagaaataccagagcgg tggaggaggttctggaggaggagctgaagtcatcagacaatccccaa gagccgatgcacctggcaggaagacctgcggcacctgcggaggtggtgga tcttctatacctaacaattgaatgcatggcatgtctgggatgtctgggacagg gcctgctggtgacagtctctagtgctagc | 885 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGGSGGGR SCIDTIPKSRCTAFQCKHSM KYRLSFCRKTCGTCGGGGS SYTYNYEWHVDVWGQGLL VTVSSAS | 938 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 57 | VH4-34 MutE ShK-16K 1xG4S | VH4-34 Q5RQ6E, G31DY32K ,E50S, CDR3 CowStalks-1xG4S ShK-16K | 132-52 | caggtgcagctaagagagtggggcgcaggacttgaagccttcg gagacgctgtccctcacctgcgctgtctatggttggtccttcagtgac aagtactggagctggattcgccagcccccagggaaggggctggag tggattgggagcatcaatcatagtggaagcaccaactacaacccgt ccctcaagagtcgagtcaccatatcagtagacacgtccaagaacc agttctccctgaagctgagctctgtgaccgccgcggacacgctgtg tattactgtacctctgtgcaccaggaaactaagaaataccagagcgg tggaggaggttctggaggaggaggctctgcatccaccatcccaa gagccgatgcaccgccttcaagtgcaagacactgaagtacag gctgagctttctgcaggaagactgcggcactcgcggaggtgggga tcttcttatacctacaaattatgaatgtctcgcggaggtgggacagg gcctgctggtgacagtctctagtgctagc | 886 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGGSGGGR SCIDTIPKSRCTAFKCKHSM KYRLSFCRKTCGTCGGGGS SYTYNYEWHVDVWGQGLL VTVSSAS | 939 |
| 58 | MutE ShK-16K 3xG4S | VH4-34 Q5RQ6E, G31DY32K ,E50S, CDR3 CowStalks-3xG4S ShK-16K | 132-56 | caggtgcagctaagagagtggggcgcaggacttgaagccttcg gagacgctgtccctcacctgcgctgtctatggttggtccttcagtgac aagtactggagctggattcgccagcccccagggaaggggctggag tggattgggagcatcaatcatagtggaagcaccaactacaacccgt ccctcaagagtcgagtcaccatatcagtagacacgtccaagaacc agttctccctgaagctgagctctgtgaccgccgcggacacgctgtg tattactgtacctctgtgcaccaggaaactaagaaataccagagcgg tggaggaggttctggaggcggtggaagtggtggcgggtagcgg aggaaggagctgatcgacacaccatcccaagagccgatgcaccg cctcaagagtcgatgcacaccatgaagagcatgaagtaccggcag cagtggaggtggtggcagctcttatacctacaaattgaatggcatgt ggatgtctggggacaggggcctgctggtgacagtctctagtgctagc | 887 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGGSGGGG GSGGGGSGGGRSCIDTIPKS RCTAFKCKHSMKYRLSFCR KTCGTCGGGGSGGGGSGG GGSSYTYNYEWHVDVWGQ GLLVTVSSAS | 940 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 59, 137, 144, 149, 153, 159, 161, 162, 164, 165, 167, 168, 170, 171, 172, 173, 175, 176, 177, 178, 179 | VH4-34 MutE Shk-No Linker | VH4-34 Q5RQ6E. G31DY32K, E50S, CDR3 Shk-No Linker | 132-61 | caggtgcagctaaagagagagtggggcgcaggactgttgaagccttcg gagacgctgtccctcacctgcgctgtctatggtgggtccttcagtgac aagtactggagctggattcgccagcccccaggggaaggggctggag tggattgggagcatcaatcatagtggaagcaccaactacaaccgt ccctcaagagtcgagtcaccatatcagtagacacgtccaagaacc agttctccctgaagctgagctctgtgaccgccgcggacacggctgtg tattactgtacctctgtcaccaggaaaataccagagcag gagctgcaatgcacaccatcccaagagcggatgccaccgtccttcca gtgcaagcacagcatgaagtacaggcgagcttctgcaggaagac ctgcggcacctgctcttatacctacaattatgaatggcatggatgtct ggggacacaggggcctgctggtgacagtctctagtgtctagc | 888 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSRSCIDTIPKS RCTAFQCKHSMKYRLSFCR KTCGTCSYTNYEWHVDV WGQGLLVTVSSAS | 941 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 60, 69, 73, 76, 138 | VH4-34 MutE G-ShK-G | VH4-34 Q5RQ6E, G31DY32K, E50S, CDR3 G-ShK-G | 132-62 | caggtgcagctaagagagtggggcgcaggactgttgaagccttcg gagacgctgtcctcacctgcgctgtctatggtggtggttccttcagtgac aagtactggagctggatccgccagcccccagggaaggggctggag tggattgggagcatcaatcatagtggaagcaccacaaactacaaccgt ccctcaagagtcgagtcaccatatcagtagacacgtccaagaacc agttctccctgaagctgagctctgtgaccgcgcggacacggctgtg tattactgtacctctgtcaccaggaaaataccagagcgg caggagctgcaagcacagcatgaagtacaggctgctctcgcaggaa gacctgcgcgcacctgcgatcttatacctacaattatgaatggcatgt ggatgtctgggggacaggcctgctcgtgtgacagtctctagtgctagc | 889 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGRSCIDTIPK SRCTAFQCKHSMKYRLSFC RKTCGTCGGSYTNYEWHVD VWGQGLLVTVSSAS | 942 |
| 61, 139 | VH4-34 MutE GG-ShK-GG | VH4-34 MutE GG-ShK-GG | 132-63 | caggtgcagctaagagagtggggcgcaggactgttgaagccttcg gagacgctgtcctcacctgcgctgtctatggtggtggttccttcagtgac aagtactggagctggatccgccagcccccagggaaggggctggag tggattgggagcatcaatcatagtggaagcaccacaaactacaaccgt ccctcaagagtcgagtcaccatatcagtagacacgtccaagaacc agttctccctgaagctgagctctgtgaccgcgcggacacggctgtg tattactgtacctctgtcaccaggaaaatcaccagagcgg cgggaggagctgcatcgaacatcgacaccatcccaagacgccaccg cctccagtgcaagcacagcatgaagtacaggctgctctcgcag gaagacctgcgcgcacctgcgcgaggcttcttacctacaattatgaat ggcatgtggatgtctgggggacaggccctgctcgtgtgacagtctctagt gctagc | 890 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGRSCIDTIP KSRCTAFQCKHSMKYRLSF CRKTCGTCGGSYTNYEW HVDVWGQGLLVTVSSAS | 943 |

Figure 21 (continued)

| BID's | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 65,140 | VH4-34 MutE GSGG-Shk-GGGG | VH4-34 Q5RQ6E, G31DY32K, E50S, CDR3 GSGG-GGGG-Shk-GGGG | 132-75 | caggtgcagctaagagagtggggcgcaggacttgttgaagccttcg gagacgctgtccctcacctgcgctgtctatggtggtggttccttcagtgac aagtactggagctggattcgccagcccccaggggaagggggctggag tggattgggagcatcaatcatagtggaagcaccaactacaacccgt ccctcaagagtcgagtcaccatatcagtagacacgtccaagaacc agttctccctgaagctgagctcgtgaccgccgcggacacggctgtg tattactgtgccgtgtaccttgtcaccaggaaaactaagaaataccagagcgg ttctggaggaggagctgcatcgcaagcacagcatgaagtacaggctgagcttc caccgccttccagtgcaagacctgcggcgaggttggtgatcttatacctag tgcaggaagacctgcggcgaggttggtgatgtctgggacagggcctgctggtga caattatgaatgcatgtctgggacagggcctgctggtga cagtctctagtgtgctagc | 891 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGSGGRSCID TIPKSRCTAFQCKHSMKYRL SFCRKTCGTCGGGGSYTYN YEWHVDVWGQGLLVTVSS AS | 944 |
| 66, 141 | VH4-34 MutE GGGG-Shk-GGGG | VH4-34 Q5RQ6E, G31DY32K, E50S, CDR3 GGGG-Shk-GGGG | 132-76 | caggtgcagctaagagagtggggcgcaggacttgttgaagccttcg gagacgctgtccctcacctgcgctgtctatggtggtggttccttcagtgac aagtactggagctggattcgccagcccccaggggaagggggctggag tggattgggagcatcaatcatagtggaagcaccaactacaacccgt ccctcaagagtcgagtcaccatatcagtagacacgtccaagaacc agttctccctgaagctgagctcgtgaccgccgcggacacggctgtg tattactgtgccgtgtaccttgtcaccaggaaaactaagaaataccagagcgg ttctggaggaggagctgcatcgcaagcacagcatgaagtacaggctgagcttc caccgccttccagtgcaagacctgcggcgaggttggtgatcttatacctag tgcaggaagacctgcggcgaggttggtgatgtctgggacagggcctgctggtga caattatgaatgcatgtctgggacagggcctgctggtga cagtctctagtgtgctagc | 892 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGSGGRSCID TIPKSRCTAFQCKHSMKYRL SFCRKTCGTCGGGGSYTYN YEWHVDVWGQGLLVTVSS AS | 945 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 67, 70, 74, 77, 142 | VH4-34 MutE GGG-Shk-GGG | VH4-34 Q5RQ6E. G31DY32K E50S, CDR3 GGG-Shk-GGG | 132-77 | caggtgcagctaagagagagtggggcgcaggactgttgaagccttcg gagacgctgtccctcacctgcgctgtctatggctcatggtggtcttcagtgac aagtactggagctggattcgccagcccccaggagaggggctggag tggattgggagcatcaatcatagtggaagcaccaacacacccgt ccctcaagagtcgagtcaccatatcagtagacacgtccaagaaacc agttctcctgaagctgagctgtgtgaccgccgcggacacggctgtg tattactgactctgtgtccaggaaaataaccagagcggg aggaggtaggagctgcaagcacagcatgaagtacaggccgatgca ccgccttccagtgcaagacctgcggtggtggacaaggccctgctgagccttctg caggaagacctgcggcacctgcggtggtgtgggacacaggggcctgctggtgacagtc tctagtgctagc | 893 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGRSCIDTI PKSRCTAFQCKHSMKYRLS FCRKTCGTCGGGSYTYNYE WHVDVWGQGLLVTVSSAS | 946 |
| 92, 95, 103 | VH4-34 MutE 3xG4S ShK S62G | VH4-34 Q5RQ6E S62G MutE CD1_G31D Y32K_CD2 _E50S_CD 3_3XG4S_ ShK | 133-76 | caggtgcagctaagagagagtggggcgcaggactgttgaagccttcg gagacgctgtccctcacctgcgctgtctatggctcatggtggtcttcagtgac aagtactggagctggattcgccagcccccaggagaggggctggag tggattgggagcatcaatcatagtggaagcaccaacacacccgg gcctcaagagtcgagtcagtcaccatatcagtagacacgtccaagaaacc agttctcctgaagctgagtctgtgaccgccgcggacacggctgtg tattactgactctgtgtccaggaaaataaccagagcggg tggaggaggagctgcaagcacaccatcccaagacgccgatgccaccg cctccagtgcaagacagtcaagacagctgagctgagtctctgcag gaagacctgcggcacctgcggcagggaggtggtggatctggtggaggagg cagtggaggtggtgcagtcttataccacaattatgaatggcatgt ggatgtctgggggacacaggggcctgctggtgtgacagtctctagtgctagc | 894 | QVQLREWGAGLLKPSETLS LTCAVYGGSFSDKYWSWIR QPPGKGLEWIGSINHSGST NYNPGLKSRVTISVDTSKNQ FSLKLSSVTAADTAVYYCTS VHQETKKYQSGGGSGGG GSGGGGSGGGRSCIDTIPKS RCTAFQCKHSMKYRLSFCR KTCGTCGGGSGGGGSGG GGSSYTYNYEWHVDVWGQ GLLVTVSSAS | 947 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 104, 113, 119, 122 | VH4-34 MutE 2xG4S ShK | VH4-34 Q5RQ6E MutE_CD1 G31DY32K CD2_E50 S_CDR3_2 xG4S ShK | 134-12 | caggtgcagctaagagagtggggcgcaggactgttgaagccttcg gagacgcttccctcacctgcgctgcgtgtggttggtttccagtgac aagtactggagctggatcgccagcccccaggggaaggggctggag tggattgggagcatcaatcatagtggaagcaccaacacacaaccgt cccttcaagactcgagtcaccatcagtagacacgtccaagaaacc agttctccctgaagctgagctctgtgaccgccgcggacacggctgtg tattactgtacctctgtgcaccaggaaaataccagagcgg aggcggtggaagtggtggcgaggtagcgagggaaggagtgc atggacaccatcccaagactaagcgcgatgcaccgcctcagtcaag cacagcatgaagtacagctgagcttctgcaggaagacctgcggc acctgcggtggaggaggcagtggaggtggtggcagctctatacct acaattatgaagtggcatgtgatgtctgggacagggcctgctggtg acagtctctagtgctagc | 895 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYCTS VHQETKKYQSGGGSGGG GSGGRSCIDTIPKSRCTAFQ CKHSMKYRLSFCRKTCGTC GGGSGGGGSSYTYNYEW HVDWGQGLLVTVSSAS | 948 |
| 105 | VH4-34 MutE 3xG4S ShK (M21Q) | VH4-34 Q5RQ6E MutE_CD1 G31DY32K CD2_E50 S_CDR3_3 xG4S ShK (M21Q) | 134-13 | caggtgcagctaagagagtggggcgcaggactgttgaagccttcg gagacgcttccctcacctgcgctgcgtgtggttggtttccagtgac aagtactggagctggatcgccagcccccaggggaaggggctggag tggattgggagcatcaatcatagtggaagcaccaacacacaaccgt cccttcaagactcgagtcaccatcagtagacacgtccaagaaacc agttctccctgaagctgagctctgtgaccgccgcggacacggctgtg tattactgtacctctgtgcaccaggaaaataccagagcgg tggaggaggcgtcttggaagtggtggaagtggttgtcggagtagcgg aggaagagagctgcatcgacaccatcccaagactaagcgccatgcaccg ccttccagtgcaagtgcatcacacagagagctacagggttgctgcgcag gaacctgcggcggtggtggtggttggttgatctggtggatggaggagg cagtggaggtggtggcagtcttataccctacaattatgaatggcatgt ggatgtctggggacagggcctgctggtgacagtctctagtgctagc | 896 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYCTS VHQETKKYQSGGGSGGG GSGGGGSGGRSCIDTIPKS RCTAFQCKHSQKYRLSFCR KTCGTCGGGSGGGGSGGG GGSSYTYNYEWHVDWGQ GLLVTVSSAS | 949 |

Figure 21 (continued)

| ID# | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 106 | VH4-34 MutE 3xG4S ShK (M21L) | VH4-34 Q5RQ6E MutE_CD1 _G31DY32K _CD2_E50 S_CDR3_3 xG4S ShK (M21L) | 134-14 | caggtgcagctaagagagtggggcgcaggactgttgaagcctcg gagaacgctgtccctcacctgcgctgtctatggtggttctttcagtgac aagtactggagctggatctgccagcccccagggaaggggctggag tggattgggagcatcaatcatagtggaagcaccacctacaacccgt ccctcaagagtcgagtcaccatatcagtagacacgtccaagaacc agttctccctgaagctgagctctgtgaccgccgcggacacggctgtg tattactgtacctctgtgcaccaggaaaataccagagcgcgg tggaggaggtgtcgagcggtggtcggtggaggtcggcg aggaaggagctgcatcgacaccatcccaagagccgatgcaccg ccttcagtgcaaggcacctgcgagttgtggatcggttggaggagg cagtgaggtgttggcagctcatacctacaattatgaatggcatgt ggatgtctgggggacagggcctggtggtgacagtctctagtgctagc | 897 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGRSCIDTIPKS RCTAFQCKHSLKYRLSFCR KTCGTCGGGGSGGGGGSGG GGSSYTYNYEWHVDVWGQ GLLVTVSSAS | 950 |
| 107, 114 | VH4-34 MutE 3xG4S ShK (M21F) | VH4-34 Q5RQ6E MutE_CD1 _G31DY32K _CD2_E50 S_CDR3_3 xG4S ShK (M21F) | 134-15 | caggtgcagctaagagagtggggcgcaggactgttgaagcctcg gagaacgctgtccctcacctgcgctgtctatggtggttctttcagtgac aagtactggagctggatctgccagcccccagggaaggggctggag tggattgggagcatcaatcatagtggaagcaccacctacaacccgt ccctcaagagtcgagtcaccatatcagtagacacgtccaagaacc agttctccctgaagctgagctctgtgaccgccgcggacacggctgtg tattactgtacctctgtgcaccaggaaaataccagagcgcgg tggaggaggtgtcgagcggtggtcggtggaggtcggcg aggaaggagctgcatcgacaccatcccaagagcctgagcttctcagg aagacctgcggcacctgcgagttgtggatcggttggaggagc agtggaggtggtgcagctcatacctacaattatgaatggcatgtg gatgtctgggggacagggcctggtggtgacagtctctagtgctagc | 898 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGRSCIDTIPKS RCTAFQCKHSFKYRLSFCR KTCGTCGGGGSGGGGGSGG GGSSYTYNYEWHVDVWGQ GLLVTVSSAS | 951 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 108 | VH4-34 MutE 3xG4S ShK (M21I) | VH4-34 Q5RQ6E MutE_CD1 G31DY32K CD2_E50 S_CDR3_3 xG4S ShK (M21I) | 134-16 | caggtgcagctaagagagtggggcgcaggacttgttgaagccttcg gagacgctgtccctcacctgcgctgtctatggtggtggtatcagtgac aagtactggagctggattcgccagcccccaggaagggctggag tggattggagcatccaatcatcatagtggaagcaccaacacaaccgt ccctcaagagtcgagtcaccatcagtagacacgtccaagaacc agttctccctgaagctgagctctgtgaccgccgccggacacggtgtg tattactgtacctcctgtcaccaggaaactaagaataccagacgcgg tggaggaggctcaggcctcggtggaggtggcgggagctagcgg aggaaggagctgcaagcacagcatcaagtacaggctgagcttctgcag gaagacctgcggcacctgcggggtggagtgttggatctggtcgaggagg cagtggaggtggttggcagctcttatacctacaaattatgaatggcatgt ggatgtctgtggggacagggcctgctcggtgtgacagtctcagtgctagc | 899 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGG GSGGGSGGGRSCIDTIPKS RCTAFQCKHSIKYRLSFCRK TCGTCGGGSGGGGSGGGG GSSYTNYEWHVDVWGQG LLVTVSSAS | 952 |
| 109 | VH4-34 MutE 3xG4S ShK (M21A) | VH4-34 Q5RQ6E MutE_CD1 G31DY32K CD2_E50 S_CDR3_3 xG4S ShK (M21A) | 134-17 | caggtgcagctaagagagtggggcgcaggacttgttgaagccttcg gagacgctgtccctcacctgcgctgtctatggtggtggtatcagtgac aagtactggagctggattcgccagcccccaggaagggctggag tggattggagcatccaatcatcatagtggaagcaccaacacaaccgt ccctcaagagtcgagtcaccatcagtagacacgtccaagaacc agttctccctgaagctgagtctgtgaccgccgccggacacggtgtg tattactgtacctcctgtcaccaggaaactaagaataccagacgcgg tggaggaggctcaggccggttcggtggaggtggcgggagctagcgg aggaaggagctgcaagcacagcatcaagtacaggctgagcgatgcaccg ccttcagtgcaagctggcagctcttatacctacaaattatgaatggcatgt ggatgtctgtggggacagggcctgctcggtgtgacagtctcagtgctagc | 900 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGSGGGG GSGGGSGGGRSCIDTIPKS RCTAFQCKHSAKYRLSFCR KTCGTCGGGSGGGGSGGGG GGSSYTNYEWHVDVWGQ GLLVTVSSAS | 953 |

Figure 21 (continued)

| BIDs | IgG Name | Heavy Chain Name | Heavy Chain Plasmid # | VH DNA Sequence | SEQ ID NO: (VH DNA) | VH Amino Acid Sequence | SEQ ID NO: (VH aa) |
|---|---|---|---|---|---|---|---|
| 157 | VH4-34MutE 1xG4S ProTxII | VH4-34 Q5RQ6E, G31DY32K, E50S, CDR3 CowStalks-1xG4S ProTxII | 132-54 | caggtgcagctaagagagtggggcgcaggactgttgaagccttcg gagacgctgtcctcacctgcgctgtctatggtggtggtcttcagtgac aagtactggagctggatccagccagcccccaggaaagggggctggag tggattgggagcatcaatcatagtggaagcaccacaaactacaaccgt ccctcaagagtcgagtcaccatatcagtagacacgtccaagaacc agtctccctgaagctgagctctgttgaccgcgcggacacggctgtg tattactgtacctctgttgaccaggaaaataccagagcgg tggaggaggttctggaggatactgccagaagtggatgtggacctgc gacagcggaggaagctgtcgcgagggcatggtgtgcaggtgtgg tgcaagaagaagctgtggggaggtggttggatcttcttatacctacaaat tatgaaatggcatgtgcatgtctgggaggacaaggggctgtgctgtgacagt ctctagtgctagc | 901 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGGSGGY CQKWMWTCDSERKCCEG MVCRLWCKKKLWGGGSS YTYNYEWHVDVWGQGLLV TVSSAS | 954 |
| 158 | VH4-34MutE 1xG4S GPTX1 | VH4-34 Q5RQ6E, G31DY32K, E50S, CDR3 CowStalks-1xG4S GPTX1 | 132-55 | caggtgcagctaagagagtggggcgcaggactgttgaagccttcg gagacgctgtcctcacctgcgctgtctatggtggtggtcttcagtgac aagtactggagctggatccagccagcccccaggaaagggggctggag tggattgggagcatcaatcatagtggaagcaccacaaactacaaccgt ccctcaagagtcgagtcaccatatcagtagacacgtccaagaacc agtctccctgaagctgagctctgttgaccgcgcggacacggctgtg tattactgtacctctgttgaccaggaaaataccagagcgg tggaggaggttctggaggagactgccctggcttcatgaggaagtgc atcccgacaacgacaagtgttgcaggtacgttgcagtgttggtggtggtcagc aggacccacaaagtggtgcaagtacgttgcgaggtggtggtggatcttc ttatacctacaattatgaatggcatgtggatgtggatgtctgggggacagggcct gctggtgacagtctctagtgctagc | 902 | QVQLREWGAGLLKPSETLS LTCAVYGGSFSDKYWSWIR QPPGKGLEWIGSINHSGST NYNPSLKSRVTISVDTSKNQ FSLKLSSVTAADTAVYYCTS VHQETKKYQSGGGGSGGGD CLGFMRKCIPDNDKCCRPN LVCSRTHKVWCKYVFGGGG SSYTYNYEWHVDVWGQGL LVTVSSAS | 955 |

Figure 22

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 201 | BLV1H12 GGS1.1 ProTxII | BLV1H12 LC CowV HuLamC | 131-73 | caggccgtcctgaaccagccaagcagcgtctccggtctctggggc agcgggtcaatcacctgagcgggtcttcctccaatgtgggcaac ggctacgtgtcttggtatcagtctgatccctggcagtgcccacgaacc ctgatctacggcgacacatcagagcttctgggtcccgatcggttc tcaggggagcagatccggaaacacagctactctgaccatcagctccc tgcaggctgaggacgaagcagagttattctgcgcatctccgaggac tctagttcaaatgccgtgtttggaagcggcaccacactgacagtccta ggtcagcccaaggctgccccctccgtcacctgttccccgccctctct gaggagcttcaagccaacaaggccacagtggcctggaaggcagatgca actctaccccggagccggagcgtgacagtggccaccacccctccaaacaa gccccgtcaaggcgggagtggagaccaccctccagcctatctgacgcct gagcagtggaagtgaagagcacaagacacagtggcccctacagaatgtc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 202 | BLV1H12 GGS1.2 ProTxII | BLV1H12 LC CowV HuLamC | 131-73 | caggccgtcctgaaccagccaagcagcgtctccggtctctggggc agcgggtcaatcacctgagcgggtcttcctccaatgtgggcaac ggctacgtgtcttggtatcagtctgatccctggcagtgcccacgaacc ctgatctacggcgacacatcagagcttctgggtcccgatcggttc tcaggggagcagatccggaaacacagctactctgaccatcagctccc tgcaggctgaggacgaagcagagttattctgcgcatctccgaggac tctagttcaaatgccgtgtttggaagcggcaccacactgacagtccta ggtcagcccaaggctgccccctccgtcacctgttccccgccctctct gaggagcttcaagccaacaaggccacagtggcctggaaggcagatagca actctaccccggagccggagcgtgacagtggccaccacccctccaaacaa agcaacaacaagtacagcggggagtggagaccaccctccagcctatctgacgcct gagcagtggaagtgaagagcacaagacacagtggccccctacagaatgtc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 203 | BLV1H12 GGS2.1 ProTxII | BLV1H12 LC CowV HuLamC | 131-73 | caggccgtcctgaaccagccaagcagcgtctccggctctctggggc agcgggtcttcaatcacctgtagcgggtcttcctccaatgtcggcaac ggctacgttgtctggtatcagtgccagtgcccccacgaacc ctgatctacggcgacaccatccagagcttctgggtccccgatcggttc tcaggggagcagatccggacgaacacagctactctgaccatcagctccc tgcaggctgaggacgaagcagattatttctgcgcatctgccgaggac tctagttcaaaatgccgtgtttggaagcggcaccacactgacagtccta ggtcagcccaaggctgccccctcgttccactcgttccgccctcctct gaggagcttcaagccacaaggccacactggtgtctcataagtg actctaccggggagccggagtggagaccaccaccactcccaaacaa gccccgtcaaggcgggaggccgccagctactctgagcctgacgcct gagcagtggaagtccacaggccatctgagcctgcaggtcacgcat gaaggggagcaccgtggagaagacagtgccctacacgaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 32, 204 | BLV1H12 GGS1.1 Moka | BLV1H12 LC CowV HuLamC | 131-73 | caggccgtcctgaaccagccaagcagcgtctccggctctctggggc agcgggtcttcaatcacctgtagcgggtcttcctccaatgtcggcaac ggctacgttgtctggtatcagtgccagtgcccccacgaacc ctgatctacggcgacaccatccagagcttctgggtccccgatcggttc tcaggggagcagatccggacgaacacagctactctgaccatcagctccc tgcaggctgaggacgaagcagattatttctgcgcatctgccgaggac tctagttcaaaatgccgtgtttggaagcggcaccacactgacagtccta ggtcagcccaaggctgccccctcgttccactcgttccgccctcctct gaggagcttcaagccacaaggccacactggtgtctcataagtg actctaccggggagccggagtggagaccaccaccactcccaaacaa gccccgtcaaggcgggaggccgccagctactctgagcctgacgcct gagcagtggaagtccacaggccatctgagcctgcaggtcacgcat gaaggggagcaccgtggagaagacagtgccctacacgaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| IIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|----------------------|-------------------|---------------------|---------------------------|---------------------|
| 30, 205, 227 | BLV1H12 GGS1.2 Moka | BLV1H12 LC CowV HuLamC | 131-73 | caggccgtcctgaaccagccaagcagcgtctccggtctctggggc agcgggtcaatcacctgagcgggttccttcctccaatgtcggcaac ggctacgtgtcttggtatcagcctggatccctggcagtgcccacgaacc ctgatctacgcgcacacatccagagctctgggtccccgatcggttc tcaggggagcagcacagcgatcggggaaacacactactctgaccatcagctccc tgcaggctgaggacgaagcagattattctgcgcatcgccgaggac tctagttcaaatgccgtgtttggaggcggcaccacactgacagtccta ggtcagcccaaggctgcccctcggtcactgttccgcccctctct gaggagcttcaagccaacaaggccacactggtgtcctggaaggcagatgca actctaccccggacgcggggagtggagaccacccaacacctccaaacaa gccccgtcaaggcggtggccagtgcctgagcctgacgcct gagcagtgaagtccccacagacctacagtccagttcacgcat gaagggagcaccgtggagaagacagtgccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 31, 206 | BLV1H12 GGS2.1 Moka | BLV1H12 LC CowV HuLamC | 131-73 | caggccgtcctgaaccagccaagcagcgtctccggtctctggggc agcgggtcaatcacctgagcgggttccttcctccaatgtcggcaac ggctacgtgtcttggtatcagcctggatccctggcagtgcccacgaacc ctgatctacgcgcacacatccagagctctgggtccccgatcggttc tcaggggagcagcacagcgatcggggaaacacactactctgaccatcagctccc tgcaggctgaggacgaagcagattattctgcgcatcgccgaggac tctagttcaaatgccgtgtttggaggcggcaccacactgacagtccta ggtcagcccaaggctgcccctcggtcactgttccgcccctctct gaggagcttcaagccaacaaggccacactggtgtcctggaaggcagatgca actctaccccggacgcggggagtggagaccacccaacacctccaaacaa gccccgtcaaggcggtggccagtgcctgagcctgacgcct gagcagtgaagtccccacagacctacagtccagttcacgcat gaagggagcaccgtggagaagacagtgccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 33, 41, 207 | BLV1H12 GGS3.3 Moka | BLV1H12 LC CowV HuLamC | 131-73 | caggccgtcctgaaccagccaagcagcgtctccggtctctggggc agcgggtcaatcacctgtagcgggtcttcctccaatgtcggcaac ggctacgtgtcttggtatcagcttggatcctggcagtgcccacgaacc ctgatcttacgcggcacacatccagagcttctgggtcccgatcggttc tcaggagcagcagatccggaaacacagctactctgaccatcagctccc tgcaggctgaggacgaagcagattattctggccatctgccggaggac tctagttcaaatgccgtgtttggcggcggcaccacactgacagtccta ggtcagcccaaggctgccccctggtcactctgttccgccctcctct gaggagcttcaagcaacaaggccacactggtgtctcataagtg actctaccgcggaggcgtgacagtggcctggaaggcagatagca gcccgtcaaggcgggagtgagaccacaccctccaaacaa agcaacaacaagtacgcggccagcagctacagtctgacgcat gagcagtggaagtccacacagagctacagctgccaggtcacgcat gaaggggagcaccgtggagaagacagtggccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 208 | BLV1H12 GGS1.1 GG-ProTxII-GG | BLV1H12 LC CowV HuLamC | 131-73 | caggccgtcctgaaccagccaagcagcgtctccggtctctggggc agcgggtcaatcacctgtagcgggtcttcctccaatgtcggcaac ggctacgtgtcttggtatcagcttggatcctggcagtgcccacgaacc ctgatcttacgcggcacacatccagagcttctgggtcccgatcggttc tcaggagcagcagatccggaaacacagctactctgaccatcagctccc tgcaggctgaggacgaagcagattattctggccatctgccggaggac tctagttcaaatgccgtgtttggcggcggcaccacactgacagtccta ggtcagcccaaggctgccccctggtcactctgttccgccctcctct gaggagcttcaagcaacaaggccacactggtgtctcataagtg actctaccgcggaggcgtgacagtggcctggaaggcagatagca gcccgtcaaggcgggagtgagaccacaccctccaaacaa agcaacaacaagtacgcggccagcagctacagtctgacgcct gagcagtggaagtccacacagagctacagctgccaggtcacgcat gaaggggagcaccgtggagaagacagtggccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 209 | BLV1H12 GGS1.2 GG-ProTxII-GG | BLV1H12 LC CowV HuLamC | 131-73 | caggccgtcctgaaccagccaagcagcgtctccgggtctctggggc agcgggtcaatcacctgtagcgggtcttcctccaatgtcggcaac ggctacgtgtcttggtatcagcagcacccggccagtcccccacgaacc ctgatctacgggcgacacatcagagctctggggtccccgatcggttc tcaggagcagcagatccggaaacacactactctgaccatcagctccc tgcaggctgaggacgaagcagattattctgcgcatctgccgaggac tctagttcaaatgccgtgtttggaggcggcaccacactgacagtccta ggtcagcccaaggctgccccctcggtcactgttccccgcctctct gaggagcttcaagccaacaaggccacacctgggaaggcagatagca actctaccccggagcccggagtggaggaccacccaccacctccaaacaa gccccgtcaaggcggagtgggtccgcagctacagctgagctgacgcct gagcagtgaagtcccacagagctacagctgccaggtcacgcat gaaggggagcaccgtgagaagaagacagtggccccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 210 | BLV1H12 GGS2.1 GG-ProTxII-GG | BLV1H12 LC CowV HuLamC | 131-73 | caggccgtcctgaaccagccaagcagcgtctccgggtctctggggc agcgggtcaatcacctgtagcgggtcttcctccaatgtcggcaac ggctacgtgtcttggtatcagcagcacccggccagtcccccacgaacc ctgatctacgggcgacacatcagagctctggggtccccgatcggttc tcaggagcagcagatccggaaacacactactctgaccatcagctccc tgcaggctgaggacgaagcagattattctgcgcatctgccgaggac tctagttcaaatgccgtgtttggaggcggcaccacactgacagtccta ggtcagcccaaggctgccccctcggtcactgttccccgcctctct gaggagcttcaagccaacaaggccacacctgggaaggcagatagca actctaccccggagcccggagtggaggaccacccaccacctccaaacaa gccccgtcaaggcggagtgggtccgcagctacagctgagctgacgcct gagcagtgaagtcccacagagctacagctgccaggtcacgcat gaaggggagcaccgtgagaagaagacagtggccccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 211 | BLV1H12 GGS2.2 ProTxII | BLV1H12 LC CowV HuLamC | 131-73 | caggccgtcctgaaccagccaagcagcgtctccggtctctggggc agcgggtctcaatcacctgtagcgggtcttcctccaatgtcggcaac ggctacgtgtctgttggtatcagctgatcctggcagttcccacgaacc ctgatctacggcgacacatccagagcttctgggtccccgatcggttc tcaggagcagatccggaaacacactactctgaccatcagctccc tgcaggctgaggacgaagcggacactactgcgcatccgaccgaggac tctagttcaaatgccgtgttggaagcggcaccacactgacagtccta ggtcagcccaaggctgccccctggtcactcttccgccctcctct gaggagcttcaagccacaaggccacaactggtgtctcataagtg acttcacccggagcctgcagttgaccaccacctccaaacaa gccccgtcaaggcggggagtggaggacgcagtctacagctgcagctgacgcat agcacaacaagtacgccggccagcagctacagctgcaggtcacgcat gagcaggtggagtccacagagacagctgcaggtcacgcagatgcat gaagggagcaccgtgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 212 | BLV1H12 GGS2.4 ProTxII | BLV1H12 LC CowV HuLamC | 131-73 | caggccgtcctgaaccagccaagcagcgtctccggtctctggggc agcgggtctcaatcacctgtagcgggtcttcctccaatgtcggcaac ggctacgtgtctgttggtatcagctgatcctggcagttcccacgaacc ctgatctacggcgacacatccagagcttctgggtccccgatcggttc tcaggagcagatccggaaacacactactctgaccatcagctccc tgcaggctgaggacgaagcggacactactgcgcatccgaccgaggac tctagttcaaatgccgtgttggaagcggcaccacactgacagtccta ggtcagcccaaggctgccccctggtcactcttccgccctcctct gaggagcttcaagccacaaggccacaactggtgtctcataagtg acttctacccggagcctgcagttgaccaccacctccaaacaa gccccgtcaaggcggggagtggaggacgcagtctacagctgcagctgacgcct gagcagcaaagtacgccggccagcagctacagctgcaggtcacgcat gaagggagcaccgtgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| SID# | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|----------------------|---------------------|---------------------|---------------------------|---------------------|
| 213 | BLV1H12 GGS4.2 ProTxII | BLV1H12 LC CowV HuLamC | 131-73 | caggccgtcctgaaccagccaagcagcgtctccggtctgggggc agcgggtcaatcacctgtagcgggtcttcctccaatgtcggcaac ggctacgtgtcttggtatcagctgatccctggcagtcccacgaacc ctgatctacggcgacacatccagagctctggggtcccgatcggttc tcaggggagcagatccggagacacagctactctgaccatcagctccc tgcaggctgaggacgaagcagattatttctgcgcatcggccggac tctagttcaaaatgccgtgtttggaagcggcaccacactgacagtccta ggtcagcgccaaggctgcccctcggtcactctgttccgccctcctcti gaggagcttcaagccaacaaggccacactggttcctgaaggcagagca actttcacccggagcgggagtgcgtgcagtgcctggaaggcacaatgca gccccgtcaaggcgggagtggggagaccacccacccctccaaacaa agcaacaacaagtacgcgtgccagagctacagctacagtgtcacgcat gagcagtgcaccgtgcaggtaccagagaagacacagtggccccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 214 | BLV1H12 GGS2.2 GG-ProTxII-GG | BLV1H12 LC CowV HuLamC | 131-73 | caggccgtcctgaaccagccaagcagcgtctccggtctgggggc agcgggtcaatcacctgtagcgggtcttcctccaatgtcggcaac ggctacgtgtcttggtatcagcagatccctggcagtcccacgaacc ctgatctacggcgacacatccagagctctgggtcccgatcggttc tcaggggagcagatccggagacacagctactctgaccatcagctccc tgcaggctgaggacgaagcagattatttctgcgcatcggccggac tctagttcaaaatgccgtgtttggaagcggcaccacactgacagtccta ggtcagcgccaaggctgcccctcggtcactctgttccgccctcctcti gaggagcttcaagccaacaaggccacactggttcctgaaggcagagca actttcacccggagcgggagtggggagaccacccacccctccaaacaa agcaacaacaagtacgcgtgccagagctacagctacagtgtcacgcat gagcagtgcaccgtgcaggtaccagagaagacacagtggccccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 215 | BLV1H12 GGS 2:3 GG-ProTxII-GG | BLV1H12 LC CowV HuLamC | 131-73 | caggccgtcctgaaccagccaagcagcgtctccgggtctcggggc agcgggtcaatcacctgtagcgggtcttcctccaatgtcggcaac ggctacgtgtcttggtatcagtcacctggcagtgcccacgaacc ctgatcttacggcgacacatccagagctttcggtcccgatcggttc tcaggagcagatccggaaaacacagctacctcgaccatcagctccc tgcaggctgaggacgaagcagattattctgcgcatctgccgaggac tctagttcaaatgccgtgttggaaggcggcaccacactgacagtccta ggtcagcccaaggctgccccctggtcactctgttccgcccctctct gaggagcttcaagccaacaaggccacacctggtgtctcataagtg actctaccgggagccggagtggacgtgcctggaaggcagatagca gccccgtcaaggcgggagtggagaccaacccctccaaacaa agcaacaacaagtacgcggccagcagctacagctgcacctgccat gagcagtggaagtcccacagaagctacagctgccaggtcacgcat gaaggggagcaccgtggagaagaacagtggccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 216 | BLV1H12 GGS 2:4 GG-ProTxII-GG | BLV1H12 LC CowV HuLamC | 131-73 | caggccgtcctgaaccagccaagcagcgtctccgggtctcggggc agcgggtcaatcacctgtagcgggtcttcctccaatgtcggcaac ggctacgtgtcttggtatcagtcacctggcagtgcccacgaacc ctgatcttacggcgacacatccagagctttcggtcccgatcggttc tcaggagcagatccggaaaacacagctacctcgaccatcagctccc tgcaggctgaggacgaagcagattattctgcgcatctgccgaggac tctagttcaaatgccgtgttggaaggcggcaccacactgacagtccta ggtcagcccaaggctgccccctggtcactctgttccgcccctctct gaggagcttcaagccaacaaggccacacctggtgtctcataagtg actctaccgggagccggagtggacgtgcctggaaggcagatagca gccccgtcaaggcgggagtggagaccaacccctccaaacaa agcaacaacaagtacgcggccagcagctacagctgcacctgccat gagcagtggaagtcccacagaagctacagctgccaggtcacgcat gaaggggagcaccgtggagaagaacagtggccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 217 | BLV1H12 GGS 3:2 GG-ProTxII-GG | BLV1H12 LC CowV HuLamC | 131-73 | caggccgtcctgaaccagccaagcagcgtctccggtctctggggc agcgggtcaatcacctgtagcgggtcttcctccaatgtcggcaac ggctacgtgtcttggtatcagtgatccctggcagtgcccacgaacc ctgatctacggcgacacatcagagctctgggtccgatcggttc tcaggagcagatccggaaacacagctactctgaccatcagctccc tgcaggctgaggacgaagcagattatttctgcgcatcgccgaggac tctagttcaaatgccgtgttggaagcggcaccacactgacagtccta ggtcagcccaaggctgcccctcgtccactcgttccgcccctctct gaggagcttcaagccaacaaggccacactggtgctggaaggcagagca actctacccgggacgggagtggagaccacccaccctccaaacaa gccccgtcaaagccggctactggccagcagctacagcgtcacgcgcat gagcagtggaagtccacagtacctacagcgtccagggtcacgcat gaaggtgagcaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 218 | BLV1H12 GGS 3:3 GG-ProTxII-GG | BLV1H12 LC CowV HuLamC | 131-73 | caggccgtcctgaaccagccaagcagcgtctccggtctctggggc agcgggtcaatcacctgtagcgggtcttcctccaatgtcggcaac ggctacgtgtcttggtatcagtgatccctggcagtgcccacgaacc ctgatctacggcgacacatcagagctctgggtccgatcggttc tcaggagcagatccggaaacacagctactctgaccatcagctccc tgcaggctgaggacgaagcagattatttctgcgcatcgccgaggac tctagttcaaatgccgtgttggaagcggcaccacactgacagtccta ggtcagcccaaggctgcccctcgtccactcgttccgcccctctct gaggagcttcaagccaacaaggccacactggtgctggaaggcagagca actctacccgggacgggagtggagaccacccacctccaaacaa agcaacaacaagtacgccgtgcagtggaaggagtacctatccaaacaa gagcagtggaagtccacagtacctacagcgtccagggtcacgcat gaaggtgagcaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|----------------------|--------------------|--------------------|---------------------------|--------------------|
| 219 | BLV1H12 GGS 4:2 GG-ProTxII-GG | BLV1H12 LC CowV HuLamC | 131-73 | caggccgtcctgaaccagccaagcagcgtctccggtctctggggc agcgggtctcaatcacctgtagcgggtcttcctccaatgtcggcaac ggctacgtgtcttggtatcagtcagccggcagcttcctgatcgtcccacgaacc ctgatctacgcgcacacatccagagcttctgggtccccgatcggttc tcaggagcagatccggaaacacactactctgaccatcagctccc tgcaggctgaggacgaagcagattatttctgccatctgccgaggac tctagttcaaatgccgtgtttggaagcggcaccacactgacagtccta ggtcagcccaaggctgccccctgcgtcactctgttcccgcccctctct gaggagcttcaagccaacaaggccacactggtgtgtctcataagtg acttcaccccgggacggtgacagtggcctggaaggcagatagca gccccgtcaaggcggagtggagaccacacacctccaaacaa agcaacaacaagtacgcggccagcagctacctgagcctgacgcat gagcagtggaagtcccacagaagcctacagctgccaggtcacgcat gaagggagcaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 220 | BLV1H12 GTLV 3xG4S ProTxII | BLV1H12 LC CowV HuLamC | 131-73 | caggccgtcctgaaccagccaagcagcgtctccggtctctgggggc agcgggtctcaatcacctgtagcgggtcttcctccaatgtcggcaac ggctacgtgtcttggtatcagtcagccggcagcttcctgatcgtcccacgaacc ctgatctacgcgcacacatccagagcttctgggtccccgatcggttc tcaggagcagatccggaaacacactactctgaccatcagctccc tgcaggctgaggacgaagcagattatttctgccatctgccgaggac tctagttcaaatgccgtgtttggaagcggcaccacactgacagtccta ggtcagcccaaggctgccccctgcgtcactctgttcccgcccctctct gaggagcttcaagccaacaaggccacactggtgtgtctcataagtg acttcaccccgggacggtgacagtggcctggaaggcagatagca gccccgtcaaggcggagtggagaccacacacctccaaacaa agcaacaacaagtacgcggccagcagctacctgagcctgacgcat gagcagtggaagtcccacagaagcctacagctgccaggtcacgcat gaagggagcaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 221 | BLV1H12 GTLV 3xG4S ShK | BLV1H12 LC CowV HuLamC | 131-73 | caggccgtcctgaaccagccaagcagcagcgtgtccggtctctggggc agcggggtctcaatcacctgtagcggggtcttcctccaatgtcggcaac ggctacgtgtcttggtatcagctgatccctggcagtgcccacgaacc ctgatctacggcgacacatccagagcttctgggtcccgatcggttc tcaggggacagatccgaaacacagccagtacttctgaccatcagctccc tgcaggctgaggacgaagcagattattctgcgcatcgccggaggac tctagttcaaatgccgtgttggaaggcggcaccacactgacagtcctta ggtcagcccaaggctgcccctggtcactctgttcccgccctctct gaggaggtcaagccacaaggccacactggtggcctggaaggcagatagca gccccgtcaaggcggaggtggagaccacacaccctccaaacaa agcaacaacaagtacggccagagctcttgagcctgacgcct gagcagtggaagtcccacagaagctacacagtgccaggtcacgcat gaaggggagcaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 222 | BLV1H12 GTLV 3xG4S OSK1 (K16, D20) | BLV1H12 LC CowV HuLamC | 131-73 | caggccgtcctgaaccagccaagcagcagcgtgtccggtctctggggc agcggggtctcaatcacctgtagcggggtcttcctccaatgtcggcaac ggctacgtgtcttggtatcagctgatccctggcagtgcccacgaacc ctgatctacggcgacacatccagagcttctgggtcccgatcggttc tcaggggacagatccgaaacacagccagtacttctgaccatcagctccc tgcaggctgaggacgaagcagattattctgcgcatcgccggaggac tctagttcaaatgccgtgttggaaggcggcaccacactgacagtcctta ggtcagcccaaggctgcccctggtcactctgttcccgccctctct gaggaggtcaagccacaaggccacactggtggcctggaaggcagatagca gccccgtcaaggcggaggtggagaccacacaccctccaaacaa agcaacaacaagtacggccagagctcttgagcctgacgcct gagcagtggaagtcccacagaagctacacagtgccaggtcacgcat gaaggggagcaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 223 | BLV1H12 GTLV 3xG4S OSK1 (P12,K16,D 20) | BLV1H12 LC CowV HuLamC | 131-73 | caggccgtcctgaaccagccaagcagcgtctccggtctctggggc agcgggtcaatcaacctgtagcgggtcttcctccaatgtcggcaac ggctacgtgtcttggtatcagtcgatcccctggcagtgcccacgaacc ctgatctacggcgacacatccagagcttctggggtccccgatcggttc tcaggggagcagatccggaaacacagctactctgaccatcagctccc tgcaggctgaggacgaaggcagattatttctgcgcatctgccgaggac tctagttcaaatgccgtgttggaaggcggcaccacactgacagtccta ggtcagcccaaggctcaagccaacaaggccacagtggctgtgaaggcagatagca actttcacccggaggcggtgccgtgacagtgcctgaaggcagatagca gccccgtcaaggcgggagtgacagccaccaccacctccaaacaa agcaacaacaagtacgccgcagctatctgacctgcaggtcacgcat gagcagtggagaagacagtgccccctacacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 79, 224 | BLV1H12 GTLV 3xG4S GpTx-1 | BLV1H12 LC CowV HuLamC | 131-73 | caggccgtcctgaaccagccaagcagcgtctccggtctctggggc agcgggtcaatcaacctgtagcgggtcttcctccaatgtcggcaac ggctacgtgtcttggtatcagtcgatcccctggcagtgcccacgaacc ctgatctacggcgacacatccagagcttctggggtcccgatcggttc tcaggggagcagatccggaaacacagctactctgaccatcagctccc tgcaggctgaggacgaaggcagattatttctgcgcatctgccgaggac tctagttcaaatgccgtgttggaaggcggcaccacactgacagtccta ggtcagcccaaggctcaagccaacaaggccacagtggctgtgaaggcagatagca actttcacccggaggcggtgcctgacagtgcctgaaggcagatagca gccccgtcaaggcgggagtgacagtgccaccaccacctccaaacaa agcaacaacaagtacgccgcagctatctgacctgcaggtcacgcat gagcagtggagaagacagtgcccctacatctgagcctgacgcct gaaggcagacccacaggctgccctgacacgcat a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 225 | BLV1H12 GTLV 6xG4S | BLV1H12 LC CowV HuLamC | 131-73 | caggccgtcctgaaccagccaagcagcgtgtccggtctctggggc agcgggtctcaatcaactgtagcgggtcttcctccaatgtcggcaac ggctacgtgtcttggtatcagtcgcagtgcccacgaaacc ctgatctacggcgacacatccagagcttctgggtcccgatcggttc tcagggagcagatccggaaacacacgctactctgaccatcagctcc tgcaggctgaggacgaagcagattattctgcgcatcgccgaggac tctagttcaaatgccgtgttggaagcggcaccacactgacagtccta ggtcagccaaggctgcccctcgtcactctgtccgcctcctct gaggagcttcaagccaacaaggccacactggtctgtgtctcataagtg acttctaccggggagcccgtgacagtggcctggaaggcagatagca gcccgtcaaggcgggagtggagaccacacaaccctccaaacaa agcaacaacaagtacgcggccagcttctgagcctgacgcct gagcagtggaagtcccacagaagctacagctgccaggtcacgcat gaagggagcaccgtggagaagacagtggccctacagaatgttc a | 474 | QAVLNQPSSVSGSLGQRVS ITCSGSSSNVGNGYVSWYQ LPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 226 | BLV1H12 GTLV 1xG4S Bsals (wStop) | BLV1H12 LC CowV HuLamC | 131-73 | caggccgtcctgaaccagccaagcagcgtgtccggtctctggggc agcgggtctcaatcaactgtagcgggtcttcctccaatgtcggcaac ggctacgtgtcttggtatcagtcgcagtgcccacgaaacc ctgatctacggcgacacatccagagcttctgggtcccgatcggttc tcagggagcagatccggaaacacacgctactctgaccatcagctcc tgcaggctgaggacgaagcagattattctgcgcatcgccgaggac tctagttcaaatgccgtgttggaagcggcaccacactgacagtccta ggtcagccaaggctgcccctcgtcactctgtccgcctcctct gaggagcttcaagccaacaaggccacactggtctgtgtctcataagtg acttctaccggggagcccgtgacagtggcctggaaggcagatagca gcccgtcaaggcgggagtggagaccacacaaccctccaaacaa agcaacaacaagtacgcggccagcttctgagcctgacgcct gagcagtggaagtcccacagaagctacagctgccaggtcacgcat gaagggagcaccgtggagaagacagtggccctacagaatgttc a | 474 | QAVLNQPSSVSGSLGQRVS ITCSGSSSNVGNGYVSWYQ LPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 25, 228 | BLV1H12 GLLV 3xG4S ProTxII | BLV1H12 LC CowV HuLamC | 131-73 | caggccgtcctgaaccagccaagcagcgtctccggtctctggggc agcgggtccaatcacctgtagcgggtccttcctcaatgtcggcaac ggctacgtgtcttggtatcagctgatccctggcagtgccccacgaacc ctgatctacggcgacacatccagagcttctggggtcccgatcggttc tcaggagcagatccgaaacacacgctactctgaccatcagctccc tgcaggctgaggacgaagcagattattfctgcgcatctgccgaggac tctagttcaaatgccgttggaaagcggcaccaacactgacagtccta ggtcagcccaaggctgcccctcggtcacttctgttccgccctcct gaggagcttcaagccaacaaggccacactggttgtctcataagtg acttctaccgggagccggtgacagtggcctggaaggcagatagca gccccgtcaaggcgggagtggagaccacacccctcaaacaa agcaacaacaagtacgcggccagctacctatctgagcctgaccct gagccagtggaagtcccacagaagctacagctgccaggtcacgcat gaagggagcaccgtggagaagaccgtggccccctacagaaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 29, 40, 229 | BLV1H12 GLLV 3xG4S ShK | BLV1H12 LC CowV HuLamC | 131-73 | caggccgtcctgaaccagccaagcagcgtctccggtctctggggc agcgggtccaatcacctgtagcgggtccttcctcaatgtcggcaac ggctacgtgtcttggtatcagctgatccctggcagtgccccacgaacc ctgatctacggcgacacatccagagcttctggggtcccgatcggttc tcaggagcagatccgaaacacacgctactctgaccatcagctccc tgcaggctgaggacgaagcagattattfctgcgcatctgccgaggac tctagttcaaatgccgttggaaagcggcaccaacactgacagtccta ggtcagcccaaggctgcccctcggtcacttctgttccgccctcct gaggagcttcaagccaacaaggccacactggttgtctcataagtg acttctaccgggagccggtgacagtggcctggaaggcagatagca gccccgtcaaggcgggagtggagaccacacccctcaaacaa agcaacaacaagtacgcggccagctacctatctgagcctgaccct gagccagtggaagtcccacagaagctacagctgccaggtcacgcat gaagggagcaccgtggagaagaccgtggccccctacagaaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 26, 230 | BLV1H12 GLLV 3xG4S OSK1 (K16,D20) | BLV1H12 LC CowV HuLamC | 131-73 | caggccgtcctgaaccagccaagcagcgtctccggctctctgggc agcgggtctcaatcacctgagcgggtcttcctccaatgtcggcaac ggctacgttgtctcttggtatcagctgaccctggccagtgccccacgaacc ctgatctacggcgacacatccagagcttctgggtccccgatcggttc tcaggagcagtccggaaacacagctactctgaccatcagctccc tgcaggctgaggacgaagcagattattctgcgcatcgccgaggac tctagttcaaatgccgtgttggaagcggcaccacactgacagtccta ggtcagcccaaggctgccccctggtcactctgttccgccctcctct gaggagcttcaagccaacaaggccacactggtgtctcataagtg acttctacccgggagcggtgacgtgaggccagcagtagca gccccgtcaaggcggagtggggaggacaccacacctccaaacaa agcaacaacaagtacgcggccacagctacagctgcctgacgcat gagcagtggaagtcccacagagctacagctgccaggtcacgcat gaagggagcaccgtggagaagacagtggccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 27, 231 | BLV1H12 GLLV 3xG4S OSK1 (P12,K16,D 20) | BLV1H12 LC CowV HuLamC | 131-73 | caggccgtcctgaaccagccaagcagcgtctccggctctctgggc agcgggtctcaatcacctgagcgggtgcttcctccaatgtcggcaac ggctacgttgtctcttggtatcagctgaccctggccagtgccccacgaacc ctgatctacggcgacacatccagagcttctgggtcccgatcggttc tcaggagcagtccggaacgaagcagattattctgcgcatcagctccc tgcaggctgaggacgaagcagattattctgcgcatcgccgaggac tctagttcaaatgccgtgttggaagcggcaccacactgacagtccta ggtcagcccaaggctgccccctggtcactctgttccgccctcctct gaggagcttcaagccaacaaggccacactggtgtctcataagtg acttctacccgggagcggtgacgtggcctggaaggcagatgca gccccgtcaaggcggagtgggggaggaccaacccctccaaacaa agcaacaacaagtacgcggccacagctacagctgcctgacgcat gagcagtggaagtcccacagagctacagctgccaggtcacgcat gaagggagcaccgtggagaagacagtggccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| IDs | IgG Name | Light Chain Name | Light Chain Plasmid # | VL-CL DNA Sequence | SEQ ID NO. (VL DNA) | VL-CL Amino Acid Sequence | Seq ID NO: (VL aa) |
|---|---|---|---|---|---|---|---|
| 28, 232 | BLV1H12 GLLV 3xG4S GpTx-1 | BLV1H12 LC CowV HuLamC | 131-73 | caggccgtcctgaaccagccaagcagcgtctccgggtctctgggc acgggtctcaatcacctgtagcgggtcttcctccaatgtcggcaac ggctacgtgtcttggtatcagctgatccctggcagtgccccacgaacc ctgatctacggcgacacatcagagctctgggtcccgatcggttc tcaggcagcagatccggaaacacagctactctgaccatcagctccc tgcaggctgaggacgaagcagattatttctgcgcatctgccgaggac tctagttcaaatgccgtgtttggaagcggcaccacactgacagtccta ggtcagcccaaggctgcccctgtcactctgttccgcccctcctct gaggagctcaagccaacaaggccacactggtctctcataagtg actctaccccgggagccggaggtgaccagccaccacctccaaacaa gcccgtcaaggcggggagttgaccaccaccaccaccaccaaccacctcccaggcct agcaacaacaagtacgccagcagctactacagctacagcctgacgcat gagcagtggaagagctccacagagagctacagagacagtggcccccacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 34 | VH4-34 MutA IL-8 CD1Cow | VL1-51 S2A, T5N, P8S, A12G, A13S, P14L | 132-25 | caggccgtcctgaaccagccaagcagcgtctccgggtctctgggc agaaggtgactatcagctgtctggctcatcaagcaacatcgggaat aattacgtcagctggtaccagcagctgcctggaacagctcctaaact gctcatttatgacaataacaagcgcccatccggaatcctgaccgat tcagcggaagcaaatcaggagacctctcaactctggaatcactcgg gcttcagacaggagagatgaggcagattacatcgcctctgcagag gacagctccagcaatgcggttggtttcggggtctgtgctaccactacagtc ctaggtcagcccaaggctgcccctcggtcactctgttccgcccctcc tctgaggagcttcaagccaacaaggccacactggtgtctcataag tgactctaccccgggagccggagtgaccgacagtggctgcctgaagacatagc agccccgtcaaggcggggagttgagacccaccaccaccccaaaca aagcaacaacaagtacgcggccagcagctactacagctacagcctgacgc ctgagcagtggaagtcccacagaagctacagctgccaggtcacgc atgaaggggagcaccgtggagaagacagtggcccctacagaatgtt ca | 443 | QAVLNQPSSVSGSLGQKVTI SCSGSSSNIGNNYVSWYQQ LPGTAPKLLIYDNNKRPSGIP DRFSGSKSGTSATLGITGLQ TGDEADYYCASAEDSSSNA VFGSGTTLTVLGQPKAAPS VTLFPPSSEELQANKATLVC LISDFYPGAVTVAWKADSSP VKAGVETTTPSKQSNNKYA ASSYLSLTPEQWKSHRSYS CQVTHEGSTVEKTVAPTEC S | 804 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 35 | VH4-34 IL-8 CDR1cow CDR2cow | VL1-51 Lc | 132-21 | caggccgtcctgacccagccaagcagcgtctccgggtctctggggc agaaggtgactatcagctgctctggctcatcaagcaacatcgggaat aattacgtcagctggtaccagcagctgcctggaacagctcctagaa ccctcatttatgcgacacaaagcgcccatccggaatcctgaccg atttcagcggaagcaaatcaggaccctgcaactctggaatcact gggcttcagacaggaggatgaggcagattactattgcgcctctgcag aggacagctccagcaatgcgtgttcgggtctggtaccactcttaca gtcctagttcagccccaaggctgcccctcggtcactctgttccggccc tcctctgaggagcttcaccgggagcggggttgacagtggcctgaaggcagat aagtgacttctaccggagcccgtacaacaaccacacccctccaa agcagccccgtcaaggcgccagctggccagcgatacagtgccaggtca cgcctgagcagcagtggaagtccacagaagctacagtgccaggtca cgcatgaagggaggcaccgtggagaagacagtggccctacagaa tgttca | 456 | QSVLTQPPSVSAAPGQKVTI SCSGSSSNIGNNYVSWYQQ LPGTAPKLLIYDNNKRPSGIP DRFSGSKSGTSATLGITGLQ TGDEADYYCASAEDSSSNA VFGSGTTLTVLGQPKAAPS VTLFPPSSEELQANKATLVC LISDFYPGAVTVAWKADSSP VKAGVETTTPSKQSNNKYA ASSYLSLTPEQWKSHRSYS CQVTHEGSTVEKTVAPTEC S | 805 |
| 36 | VH4-34 MutB IL-8 CDR1cow CDR2cow | VL1-51 S2A, T5N, P8S, A12G, A13S, P14L | 132-25 | caggccgtcctgacccagccaagcagcgtctccgggtctctggggc agaaggtgactatcagctgctctggctcatcaagcaacatcgggaat aattacgtcagctggtaccagcagctgcctggaacagctcctagaa ccctcatttatgcgacacaaagcgcccatccggaatcctgaccg atttcagcggaagcaaatcaggaccctgcaactctggaatcact gggcttcagacaggaggatgaggcagattactattgcgcctctgcag aggacagctccagcaatgcgtgttcgggtctggtaccactcttaca gtcctagttcagccccaaggctgcccctcggtcactctgttccggccc tcctctgaggagcttcaccgggagcggggttgacagtggcctgaaggcagat aagtgacttctaccggagcccgtacaacaaccacacccctccaa agcagccccgtcaaggcgccagctggccagcgatacagtgccaggtca cgcctgagcagcagtggaagtccacagaagctacagtgccaggtca cgcatgaagggaggcaccgtggagaagacagtggccctacagaa tgttca | 443 | QAVLNQPSSVSGSLGQKVTI SCSGSSSNIGNNYVSWYQQ LPGTAPKLLIYDNNKRPSGIP DRFSGSKSGTSATLGITGLQ TGDEADYYCASAEDSSSNA VFGSGTTLTVLGQPKAAPS VTLFPPSSEELQANKATLVC LISDFYPGAVTVAWKADSSP VKAGVETTTPSKQSNNKYA ASSYLSLTPEQWKSHRSYS CQVTHEGSTVEKTVAPTEC S | 804 |

Figure 22 (continued)

| BIDs | IgG Name | Light Chain Name | Light Chain Plasmid # | VL-CL DNA Sequence | SEQ ID NO. (VL DNA) | VL-CL Amino Acid Sequence | Seq ID NO. (VL aa) |
|---|---|---|---|---|---|---|---|
| 37 | VH4-34 MutC IL-8 31D32K50S | VL1-51 S2A, T5N, P8S, A12G, A13S, P14L, K46R, L47T, D51G, N52D, N53T | 132-27 | caggccgtcctgaaccagccaagcagcgtctccgggtctctggggcagaaggtgactatcagctgctctggctctcatcaaagcaacatcgggaataattacgtcagctggtaccagcagctgcctggaacagctcctagaacccctcatttatggcgacacaaagcgcccatccggaatccgaccgatcagcggaagcaaatcaggaacctctgcaactctggaatcactgggcttcagacacaggagatgaggcagattactattcgccctctgcagaggacagctccagcaatgccgttgggtctggtgttcactcttaccagtcctaggtcagccaaggctcaagccaacaaaggccacactggtgtgtctcattccctgaggagcttcaccggagcccgtgacagtggcctggaaaacaccacctccaaaagtgcaacaacaagtacggccagcagctatcagctgccaggtcacgccctgaagggggagcaccgtggagaagaccgtggcccctacagaatgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 38 | VH4-34 MutE IL-8 5R6E31D32K50S | VL1-51 S2A, T5N, P8S, A12G, A13S, P14L, K46R, L47T, D51G, N52D, N53T | 132-27 | caggccgtcctgaaccagccaagcagcgtctccgggtctctggggcagaaggtgactatcagctgctctggctctcatcaaagcaacatcgggaataattacgtcagctggtaccagcagctgcctggaacagctcctagaacccctcatttatggcgacacaaagcgcccatccggaatccgaccgatcagcggaagcaaatcaggaacctctgcaactctggaatcactgggcttcagacacaggagatgaggcagattactattcgccctctgcagaggacagctccagcaatgccgttgggtctggtgttcactcttaccagtcctaggtcagccaaggctcaagccaacaaaggccacacatggtgtgtctcattccctgaggagcttcaccggagcccgtgacagtggcctggaaaacaccacctccaaaagtgcaacaacaagtacggccagcagctatcagctgccaggtcacgcctgagcctgacccgtcaaggccagtgggagttgaagtgaagaacaacaagtacggccagcagctatcagctgccaggtcacgccctgagcctgagcctgacccgtcaaggccagtgggagcaccgtggagaagaccgtggcccctacagaatgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 39 | VH4-34 MutD IL-8 CDR1cow CDR2cow | VL1-51 S2A, T5N, P8S, A12G, A13S, P14L, K46R, L47T, D51G, N52D, N53T | 132-27 | caggccgtcctgaaccagccaagcagcgtctccggctctctggggc agaaggtgactatcagctgctctggctctcatcaagcaacatcgggaat aattacgtcagctggtaccagcagctgccfggaacagtcctagaa ccctcatttatggcgacacaaagcgcccatccggaatcctgaccg atfcagcggaagcaaatcaggagacctctgcaactctggaatcact gggcttcagacagcagagatgaggcagattactattgcgcctctgcag aggacagctccagcaatgccgtgttcggtctgtgtaccactcttaca gtccfaggtcagtcccaagctgcccctcggtcactctgttccgccc tccctgaggaggcttcaagccaacaagccacactgtgtgtctcat aagtgacttctaccccggcaaggcggggagttgaaacacacacccaa agcagcgcccgtcaaggcgggagtaacaagagctacagctgccaggtca acaaagcaacaagtacgcgccagcagctacagcgccagtca cgcctgagcagtgaagtccacacagaagctacagctgccaggtca cgcatgaagggagcaccgtggagaagacagtggcccctacagaa tgttca | 486 | QAVLNQPSSVSGSLGQKVTI SCSGSGSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 42 | BLV1H12 | BLV1H12 LC CowV HuLamC | 131-73 | caggccgtcctgaaccagccaagcagcgtctccggctctctggggc agcgggtcaatcacctgtagcgggtcttcctccaatgtgggcaac ggctacgtgtcttggtatcagctgatccctggcagtgcccacgaacc ctgatctacggcgacaccagcagagctttcggggtccccgatcggttc tcaggcagcagatccggaaacacagctactctgaccatcagctccc tgcaggctgaggacgaagcagattatttctgcgcatctgccgaggac tctagttcaaatgccgtgtttggaagcggcaccacactgacagtccta ggtcagcccaaggctgccccctccgtcactctgttccgccctctct gaggagcttcaagccaacaaggccacactggtgtctcataagtg actctaccccggggaggcggggagttgaaggcctgaaggcagatagca gccccgtcaaggcgggagtggagcaccaccacccctcccaaacaa agcaacaacaagtacgcggccagcagctatctgagcctgacccct gagcagtggaagtccacacgacagagaagctacagctgccaggtca gaagggagcaccgtggagaagacagtgccctacagctgccctacagtttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BID∞ | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 43 | VH4-34 MutF IL-8 5R6E CD1cow | VL1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgctctggctctaatcaaagcaacatcgggaat aattacgtcagctggtaccagcagctgcctggaacagctcctagaa ccctcatttatggcgacacaaagcgccatccggaatcctgaccg atcagcggagcaaatcagggacctctgcaactctggaatcact gggcttcagacacaggagatgaggcagattactatgcgcctctgcag aggacagctccagcaatgcgcgtttcggtctgttctggtggtaccactcttaca gtcctaggtcagcccaaggctgccccctcggtcactctgttccccgccc tcctctgaggagcttcaagccaagctccaaaggccaccaccctccaa aagtgacttcaccgggagccgggaagttgaaacaaccacccctccaa agcagcaacaaacaagtacgcggccagcagctgctggccctgaggcagat acaaagcaacaacaagtacgcggccagcagctatctgagcctga cgcctgagcagtggaagtccacagaagctacagctgccaggtca cgcatgaagggagccaccgtggagaagacagtggcccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 44 | BLV1H12-IL8 | BLV1H12 LC CowV HuLamC | 131-73 | caggccgtcctgaaccagccaagcagcgtctccgggtctctgggc agcgggtctcaatcactgtagcgggtgttcttctccaagtgcggcaac ggctacgtgtcttggtatcagctgatcctggcagtgcccaccagaacc ctgatctacgtgcgacaacatccagagcttctgggtcccgatcggttc tcaggagcagatcggcaacacacagctactctgaccatcagctccc tgcaggctgaggacgaggcagattattctgcgcatctgccgagggac tctagttcaaaatgccgtgttggaagcggcaccacactgacagtccta ggtcagcccaaggctgccccctcggtcacctcgttccccgccctctct gaggagcttcaagccaacaaggccacactggtgtgtctcataagtg acttcaccggagccggagtgacagtgcctgaaggcagagtagca gccccgtcaaggtcggagtggagaccacaccacctccaaacaa agcagcaacaaagtacgcggccagcagctatctgagcctgacgcct gagcagtggaagtcccacagaagctacagctgccaggtcacgcat gaaggggagccaccgtggagaagacagtggcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|-----------------------|---------------------|---------------------|----------------------------|---------------------|
| 45 | BLV1H12 HC CowV, CDR3 IL-8, 1xG4S | BLV1H12 LC CowV HuLamC | 131-73 | caggccgtcctgaaccagccaagcagcgtctccggtctctgggc agcgggtctcaatcacctgtagcgggtcttcctccaatgtcggcaac ggctacgtgtcttggtatcagcctccggcagtgcccacgaacc ctgatctacgggcacacatccagagcttctgggtcccgatcggttc tcaggagcagtccggaaacacagcttactctgaccatcagctcc tgcaggctgaggacgaaggcagattattctgcgcatcgccgaggac tctagttcaaatgccgtgttggaagcggcaccacactgacagtcta ggtcagcccaaggctgccccctcggtcactctgttccgccctcctct gaggagcttcaagccaacaaggccacactggtgtgtctcataagtg acttctacccgggacggtgacgtgacctgaggccaggtcacgcat gccccgtcaaggcggagtggagaccaacagctactacagctgccct agcaacaacaagtacgcgggccagcagcatctgagcctgacgcat gagcagtggaagtcccacagaggctacacgctgcaggtcacgcat gaaggggagcaccgtgagaagagacagtgcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |
| 46 | BLV1H12 HC CowV, CDR3 IL-8, 3xG4S | BLV1H12 LC CowV HuLamC | 131-73 | caggccgtcctgaaccagccaagcagcgtctccggtctctgggc agcgggtctcaatcacctgtagcgggtcttcctccaatgtcggcaac ggctacgtgtcttggtatcagcctccggcagtgcccacgaacc ctgatctacgggcacacatccagagcttctgggtcccgatcggttc tcaggagcagtccggaaacacagcttactctgaccatcagctcc tgcaggctgaggacgaaggcagattattctgcgcatcgccgaggac tctagttcaaatgccgtgttggaagcggcaccacactgacagtcta ggtcagcccaaggctgccccctcggtcactctgttccgccctcctct gaggagcttcaagccaacaaggccacactggtgtgtctcataagtg acttctacccgggacggtgacgtggcctggaaggcagatagca gccccgtcaaggcggaggtggagaccaacacctccaaacaa agcaacaacaagtacgcggccagcagctacagctgcacgcat gagcagtggaagtcccacagaggctacagctgcaggtcacgcat gaaggggagcaccgtggagaagacagtgcccctacagaatgttc a | 474 | QAVLNQPSSVSGSLGQRVS ITCSGSSSNVGNGYVSWYQ LIPGSAPRTLIYGDTSRASG VPDRFSGSRSGNTATLTISS LQAEDEADYFCASAEDSSS NAVFGSGTTLTVLGQPKAA PSVTLFPPSSEELQANKATL VCLISDFYPGAVTVAWKADS SPVKAGVETTTPSKQSNNK YAASSYLSLTPEQWKSHRS YSCQVTHEGSTVEKTVAPT ECS | 807 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 47 | VH4-34 MutE 3xG4S IL-8 | VL1-51 S2A, T5N, P8S, A12G, A13S, P14L, K46R, L47T, D51G, N52D, N53T | 132-27 | caggccgtcctgaaccagccaagcagcgtctccggtgtctctgggggc agaaggtgactatcagctcgtctggctcatcaagcaacatcgggaat aattacgtcagctggtaccagcagctgcctggaaacagctcctagaa ccctcatttatggcgacacaaagcgcccatccgaatccctgaccg atccagcggaagcaaatcaggagacctctgcaactctggaatcact gggcttcagacacaggagatgaggcagattactattcgcgcctctgcag aggacagctccagcaatgccgtgttcggtcttcggtctgctaccactcttaca gtccctaggtcagcccaaggctgcccctcggtcactcttgttcccgccc tcctctgaggagcttcaagccacaaggccacactggtgttgctcat aagtgacttctaccggggagccggaggtgaaacaacaccacccctccaa acaaaagcaacaacaagtacggcggccagcagctatcgtgagcctga cgcctgagcagtggaagtccacagaagctacagctgccaggtca cgcatgaagggggagcaccgtggaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 48, 68, 72, 75, 80, 94, 100, 101, 111, 115.1 20, 123, 135 | VH4-34 MutE 3xG4S ShK | VL1-51 S2A, T5N, P8S, A12G, A13S, P14L, K46R, L47T, D51G, N52D, N53T | 132-27 | caggccgtcctgaaccagccaagcagcgtctccggtgtctctgggggc agaaggtgactatcagctcgtctggctcatcaagcaacatcgggaat aattacgtcagctggtaccagcagctgcctggaaacagctcctagaa ccctcatttatggcgacacaaagcgcccatccgaatccctgaccg atccagcggaagcaaatcaggagacctctgcaactctggaatcact gggcttcagacacaggagatgaggcagattactattggcgcctctgcag aggacagctccagcaatgccgtgttcggtcttcggtctgctaccactcttaca gtccctaggtcagcccaaggctgcccctcggtcactcttgttcccgccc tcctctgaggagcttcaagccacaaggccacactggtgttgctcat aagtgacttctaccggggagccggaggtgaaacaacaccacccctccaa acaaaagcaacaacaagtacggcggccagcagctatcgtgagcctga cgcctgagcagtggaagtccacagaagctacagctgccaggtca cgcatgaagggggagcaccgtggaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 49 | VH4-34 MutE 3xGGS MOKA | VL1-51 S2A, T5N, P8S, A12G, A13S, P14L, K46R, L47T, D51G, N52D, N53T | 132-27 | caggccgtcctgaaccagccaagcagcgtctccggtctcgggggc agaaggtgactatcagctgctctggctcatcaagcaacatcgggaat aattacgtcagctggtaccagcagctgcctggaacagctcctagaa ccctcatttatgcgacacaaagcgcccatccggaatccgtaccg atcagcggcgaagcaacaggagacctctgcaactctggaatcact gggcttcagacacaggagatgaggcaggattactattgcgcctctgcag aggacagctccagcaatgcggttcgggtctggtgtaccactctaca gtcctaggtcagcccaaggctgccccctcggtcactctgttcccgccc tccctgagggagcttcagccacaaggccacactggtgtctctcat aagtgacttcaccggagccgtcaaggccgtggaagtgcagat agcagccccgtcaagcgcgggagttgaaaacaacacacacccctccaa acaaagcaacaacaagtacgcggccagctatcctgagcctga cgcctgagcgaaggcagtgaagtccacacagaagctacagctgccaggtca cgatgaaggagcaccgtggagaagaacagaggggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 50 | VH4-34 MutF 3xG4S ShK | VL1-51 S2A, T5N, P8S, A12G, A13S, P14L, K46R, L47T, D51G, N52D, N53T | 132-27 | caggccgtcctgaaccagccaagcagcgtctccggtctcgggggc agaaggtgactatcagctgctctggctcatcaagcaacatcgggaat aattacgtcagctggtaccagcagctgcctggaacagctcctagaa ccctcatttatgcgacacaaagcgcccatccggaatccgtaccg atcagcggcgaagcaacaggagacctctgcaactctggaatcact gggcttcagacacaggagatgaggcaggattactattgcgcctctgcag aggacagctccagcaatgcggttcgggtctggtgtaccactctaca gtcctaggtcagcccaaggctgccccctcggtcactctgttcccgccc tccctgagggagcttcagccacaaggccacactggtgtctctcat aagtgacttcaccggagccgtcaaggccgtggaagtgcagat agcagccccgtcaagcgcgggagttgaaaacaacacacacccctccaa acaaagcaacaacaagtacgcggccagctatcctgagcctga cgcctgagcgaaggcagtgaagtccacacagaagctacagctgccaggtca cgatgaaggagcaccgtggagaagaacagaggggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 51 | VH4-34 MutF 3xG4S IL-8 | VL1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgctctgcctcatcaagcaacatcgggaat aattacgtcagctggtaccagcagctgcctggaacagtcctagaa ccctcatttatggcgacacaaagcgcccatccgaatcctgaccg atcagcggagcaaatcagggaccctcgcaactctggaatcact gggcttcagacacaggagatgaggcagattactattgcgcctctgcag aggacagctccagcaatgcgtgttcggggtcgtggtaccactcttaca gtccgaggtcagcccaaggtgcccctcgtcactctgttcccgccc tcctctgaggacttcagccggggagcctgacagtggcctgaaggcagat aagtgacttctaccccgggagcgggagttgaaacaacaccacacctccaa acaaagcaacaacaagtacgcggccagcagctacagtcgagcctga cgcctgagcagtgaaggaagtccacacagaagctacagtccaggtca cgcatgaagggagcaccgtggagaagagacagcagggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 52 | VH4-34 MutF 3xGGS MOKA | VL1-51 S2A, T5N, P8S, A12G, A13S, P14L, K46R, L47T, D51G, N52D, N53T | 132-27 | caggccgtcctgaaccagccaagcagcgtctccgggtctctgggggc agaaggtgactatcagctgctctgcctcatcaagcaacatcgggaat aattacgtcagctggtaccagcagctgcctggaacagtcctagaa ccctcatttatggcgacacaaagcgcccatccgaatcctgaccg atcagcggagcaaatcagggaccctcgcaactctggaatcact gggcttcagacacaggagatgaggcagattactattgcgcctctgcag aggacagctccagcaatgcgtgttcggggtcgtggtaccactcttaca gtccgaggtcagcccaaggtgcccctcgtcactctgttcccgccc tcctctgaggacttcagccggggagtgacagtggcctgaaggcagat aagtgacttctaccccgggagcgggagttgaaacaacaccacacctccaa acaaagcaacaacaagtacgcggccagcagctacagtcgagcctga cgcctgagcagtgaaggaagtccacacagaagtcagcgtccaggtca cgcatgaagggagcaccgtggagaagagacagcagggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 53, 155 | VH4-34 MutE 3xG4S ProTxII | VL1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgctctggctcatcaagcaacatcgggaat aattacgtcagctggtaccagcagctgcctggaacagctcctagaa ccctcatttatggcgacacaaagcgcccatccgaatccctgaccg atcagcggcttcagacaggagatggaggcagattactattgcgcctctgcag aggacagctccagcaatgcggttcggtctggtgtaccacttctacaa gtcctaggtcagccaaggtccccctcggtcactctgttccgcccc tcctctgaggagcttcaagccaacaaggccacactggttctgtctcat aagtgacttctaccgggagcccgggagttgaaacaacaccacacccctccaa acaaagcaacaacaagtacgcggccagcagctacacgctgccaggtca cgcctgagcagtgaagtccacacagaagctacagctgccatctgagcctga cgcatgaagggagcaccgtggagaagacagtggccccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGGGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 54, 78, 156 | VH4-34 MutE 3xG4S GPTX1 | VL1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgctctggctcatcaagcaacatcgggaat aattacgtcagctggtaccagcagctgcctggaacagctcctagaa ccctcatttatggcgacacaaagcgcccatccgaatccctgaccg atcagcggcttcagacaggagatggaggcagattactattgcgcctctgcag aggacagctccagcaatgcggttcggtctggtgtaccacttctacaa gtcctaggtcagccaaggtccccctcggtcactctgttccgcccc tcctctgaggagcttcaagccaacaaggccacactggtgttctcat aagtgacttctaccgggagcccgggagttgaaacaacaccacacccctccaa acaaagcaacaacaagtacgcggccagcagctacacgctgccaggtca cgcctgagcagtgaagtccacacagaagctacacagctgccatctgagcctga cgcatgaagggagcaccgtggagaagacagtggccccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGGGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 55, 64, 102, 110, 112, 121, 125, 160, 163, 166, 169 | VH4-34 MutE No Knob | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctggctctcatcaagcaacatcgggaat aattacgtcagctggtaccagcagctgcctggaacagctcctagaa ccctcatttatggcgacacaaagcgccatccggaatccctgaccg attcagcggaagcaaatcaggagacctctgcaactctggaatcact gggcttcagacacaggagatgaggcagattactattcgcctctgcag aggacagctccagcaatgcgtgttcggtctgttggtaccactcttaca gtccaggtcagtccaaggctgcccctcggtcactctgttccgccc tcctctgagggagttcagccacaaggccgtgacagtggcctgaaggcagat agtgacttctaccggcgtcaaggcgggggagttgaaaacaccacaccctccaa acaaagcaacaacaagtacggccagcagctacagctgccaggtca cgcctgagcgtggaagtccacacagaagctacagctgccaggtca cgcatgaagggagcaccgtggagaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 56, 124, 145, 146, 147, 148 | VH4-34 MutE 1xG4S ShK | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctggctctcatcaagcaacatcgggaat aattacgtcagctggtaccagcagctgcctggaacagctcctagaa ccctcatttatggcgacacaaagcgccatccggaatccctgaccg attcagcggaagcaaatcaggagacctctgcaactctggaatcact gggcttcagacacaggagatgaggcagattactattcgcctctgcag aggacagctccagcaatgcgtgttcggtctgttggtaccactcttaca gtccaggtcagtccaaggctgcccctcggtcactctgttccgccc tcctctgagggagttcagccacaaggccgtgacagtggcctgaaggcagat agcagccctcactcaccccgggaggccgtgacagtggcctgaaggcagat acaaagcaacaacaagtacggccagcagctacagctgccaggtca cgcctgagcgtggaagtccacacagaagctacagctgccaggtca cgcatgaagggagcaccgtggagaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|----------------------|--------------------|--------------------|---------------------------|--------------------|
| 57 | VH4-34 MutE ShK-16K 1xG4S | VL 1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgctctggctcatcaagcaacatcgggaat aattacgtcagctggtaccagcagctgcctggaacagctcctagaa ccctcatttatggcgacacaaagcgccatccggaatcctgaccg atcagcggaagcaaatcaggaggcctctgcaactctggaatcact gggcttcagacaggagatgaggcagattactattgcgcctctgcag aggacagctccagcaggtccagcctggcttcaagctcttcaccg gtcctaggtcagccccaaggttctcccctcctgttccgccc tcctctgaggagcttcaagccaacaaggccacacggtgtctcat aagtgacttctaccggctcaaggcgcgtgacagtggcctggaaggcagat agcagccccgtcaaggtggaggttgaaacaccacaccctccaa acaaagcaacaacaagtacgcggccacaagaagctacagctgccaggtca cgcctgagcagtggaagtccacaagagaagctacagctgccaggtca cgcatgaagggaggcaccgtggagaagaacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 58 | MutE ShK-16K 3xG4S | VL 1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgctctggctcatcaagcaacatcgggaat aattacgtcagctggtaccagcagctgcctggaacagctcctagaa ccctcatttatggcgacacaaagcgccatccggaatcctgaccg atcagcggaagcaaatcaggaggcctctgcaactctggaatcact gggcttcagacaggagatgaggcagattactattgcgcctctgcag aggacagctccagcaggtccagcctggcttcaagctcttcaccg gtcctaggtcagccccaaggttctcccctcctgttccgccc tcctctgaggagcttcaagccaacaaggccacacggtgtctcat aagtgacttctaccggctcaaggcgcgggacagtggcctggaaggcagat agcagccccgtcaaggtggaggttgaaacaccacaccctccaa acaaagcaacaacaagtacgcggccacaagaagctacagctgccaggtca cgcctgagcagtggaagtccacaagagaagctacagctgccaggtca cgcatgaagggaggcaccgtggagaagaacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|----------------------|--------------------|---------------------|---------------------------|---------------------|
| 59, 137, 144, 149, 153, 159, 161, 162, 164, 165, 167, 168, 170, 171, 172, 173, 175, 176, 177, 178, 179 | VH4-34 MutE Shk-No Linker | VL 1-51 S2A, T5N, P8S, A12G, A13S, P14L, K46R, L47T, D51G, N52D, N53T | 132-27 | caggccgtcctgaaccagccaagcagcgtctccgggtctctggggc agaaggtgactatcagctgcctctggctcatcaagcaacatcgggaat aattacgtcagctggtaccagcagctgcctggaacagtcctagaa ccctcatttatggcgacacaaagcgccatccgaatccctgaccg attcagcggaagcaaatcaggagacctctgcaactctgggaatcact gggcttcaagacaggagatgaggcagattactattgcgcctctgcag aggacagctccagcaatgccgtgttcgggtctggtaccactcttaca gtcctaggtcagcccaaggctgcccctcggtcacttgttccgcccc tcctcgaggagcttcacccggagccgtgacagtggcctgaaggcagat agtgacttcacccggcaaggcggagttgaaaccacacacctccaa acaaagtcaacaacaagtacgcggccagcagctatctgagcctga cgcctgagcagtggaagtcccacagaagctacagctgccaggtca cgcatgaagggaggcaccgtggagaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 60, 69, 73, 76, 138 | VH4-34 MutE G-ShK-G | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctggctcatcaagcaacatcgggaat aattacgtcagctggtaccagcagctgcctggaacagctcctagaa ccctcatttatggcgacacaaagcgcccatccggaatccctgaccg atcagcggaagcaaatcaggagaccctctgcaactctggaatcact gggcttcagacacaggaggatgaggcaatgcggtctgttcccctgcgcc aggacagctccagcaatgcgggtttcggggtctgttccccctggttccgccc gtcctaggtcagtcccaaggctgcccctcggtcactctgttccgcccc tcctctgaggagcttcaagccaacaaggccacactggtgtgtctcat aagtgacttctaccgggagccggggagtgggagttgaaaccaccacacccctccaa acaaaagcaacaacaagtacgcggccagcagctacctgagcctga cgcctgagcagtggaagtccacagaagctacagctgccaggtca cgcatgaagggagcaccgtggagaagaccgtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 61, 139 | VH4-34 MutE GG-ShK-GG | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctggctcatcaagcaacatcgggaat aattacgtcagctggtaccagcagctgcctggaacagctcctagaa ccctcatttatggcgacacaaagcgccatccggaatccctgaccg atcagcggaagcaaatcaggagaccctgcaactctggaatcact gggcttcagacacaggaggatgaggcaatgcggttcggggtctgttccccctgcgcc aggacagctccagcaatgcgggtttcggggtctgttccccctggttccgccc gtcctaggtcagtcccaaggctgcccctcggtcactctgttccgcccc tcctctgaggagcttcaagccaacaaggccacactgtgtgtctcat aagtgacttctaccgggagccgggagtgggagttgaaaccaccacccctccaa agcagcccgtcaaggtggagttgaaacaccacccctccaa acaaaagcaacaacaagtacgcggccagcagctacctgagcctga cgcctgagcagtggaagtccacagaagctacagctgccaggtca cgcatgaagggagcaccgtggagaagaccgtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 65, 140 | VH4-34 MutE GSGG-Shk-GGGG | VL1-51 S2A, T5N, P8S, A12G, A13S, P14L, K46R, L47T, D51G, N52D, N53T | 132-27 | caggccgtcctgaccagccaagcagcgtctccggtctctgggc agaaggtgactatcagctgctctggctcatcaagcaacatcgggaat aattacgtcagctggtaccagcagctgcctgaacagctcctagaa ccctcatttatggcgacacaaagcgcccatccgaatccctgaccg attcagcggaagcaaatcaggagacctctgcaactctggaatcact gggcttcagacacaggagatgaggcagattactattcgcctctgcag aggacagctccagcaatgcggttcgccctcggtcactctgttccgccc gtcctaggtcagccaaggctgcccctcggtcactctgttccgccc tcctctgaggagcttcaagccaacaaggccacactggtgtctcat aagtgacttctaccccgggcgggagtgccgtgacagtggcctggaaggcagat agcagcccgtcaaggcgggagtgccagcagctcagcctga cgcatgatgaagggagcaccgtggagaagacagtgcccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 66, 141 | VH4-34 MutE GGGG-Shk-GGGG | VL1-51 S2A, T5N, P8S, A12G, A13S, P14L, K46R, L47T, D51G, N52D, N53T | 132-27 | caggccgtcctgaccagccaagcagcgtctccggtctctgggc agaaggtgactatcagctgctctggctcatcaagcaacatcgggaat aattacgtcagctggtaccagcagctgcctgaacagctcctagaa ccctcatttatggcgacacaaagcgcccatccgaatccctgaccg attcagcggaagcaaatcaggagacctctgcaactctggaatcact gggcttcagacacaggagatgaggcagattactattcgcctctgcag aggacagctccagcaatgcggttcgccctcggtcactctgttccgccc tcctctgaggagcttcaagccaacaaggccacactggtgtctcat aagtgacttctaccccgggcgggagtgccgtgacagtggcctggaaggcagat agcagcccgtcaaggcgggagtgccagcagctcagcctga cgcatgatgaagggagcaccgtggagaagacagtgcccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| SIDs | IgG Name | Light Chain Name | Light Chain Plasmid # | VL-CL DNA Sequence | SEQ ID NO: (VL DNA) | VL-CL Amino Acid Sequence | SEQ ID NO: (VL aa) |
|---|---|---|---|---|---|---|---|
| 67, 70, 74, 77, 142 | VH4-34 MutE GGG-Shk-GGG | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctgcctcatcaagcaacatcgggaat aattacgtcagctggtaccagcagctgcctggaacagctcctagaa ccctcattatggcgacacaaagcgccatccggaatccctgaccg attcagcggaagcaaatcaggagacctctgcaactctggaatcact gggcttcagacacaggagatgaggcagattactattcgcctctgcag aggacagctccagcaatgcgtgttcggttctggtctgtaccactcttaca gtccagctcagcccaaggctgcccctcggtcactctgttccgcgccc tcctctgaggacttcaagccaggtcaacaaggccacactggtgtctcat aagtgacttctaccggagccgtgacagttgcctgaaggcagat agcagccccgtcaaggcgggagttgaaaacaacacacccctccaa acaaagcaacaacaagtacgcggccagcagttacagctggccctga cgcctgagcgagtgaagtccacacagaagaagtaccagtgcccaggtca cgcatgaagggagcaccgtggagacagaggtggcctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 92, 95, 103 | VH4-34 MutE 3xG4S ShK S62G | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctgcctcatcaagcaacatcgggaat aattacgtcagctggtaccagcagctgcctggaacagctcctagaa ccctcattatggcgacacaaagcgccatccggaatccctgaccg atcagcggaagcaaatcaggagacctctgcaactctggaatcact gggcttcagacacaggagatgaggcagattactattcgcctctgcag aggacagctccagcaatgcgtgttcggttctggtctgtaccactcttaca gtccagctcagcccaaggctgcccctcgtcactctgttccgcgccc tcctctgaggacttcaagccaggtcaacaaggccacactggtgtctcat aagtgacttctaccggagccgtgacagttgcctgaaggcagat agcagccccgtcaaggcgggagttgaaaacaacacacccctccaa acaaagcaacaacaagtacgcggccagcagttacagctggccctga cgcctgagcgagtgaagtccacacagaagaagtaccagtgcccaggtca cgcatgaagggagcaccgtggagacagaggtggcctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 104, 113, 119, 122 | VH4-34 MutE 2xG4S ShK | VL1-51 S2A, T5N, P8S, A12G, A13S, P14L, K46R, L47T, D51G, N52D, N53T | 132-27 | caggccgtcctgaaccagccaagcagcgtctccggctctctgggc agaaggtgactatcagctgctctggctcatcaagcaacatcgggaat aattacgtcagctggtaccagcagctgcctggaacagctcctagaa ccctcatttatggcgacacaaagcgcccatccgaatccctgaccg attcagcggaagcaaatcaggagacctctgcaactctgggaatcact gggcttcagacacaggagatgaggcagattactatggcgcctctgcag aggacagctccagcaatgcggttccctcggtcactctgttccgcccc gtcctaggtcagcccaaggctgccccctcggtcacctggcctgaaggcagat tcctctgaggagcttcaagccaacaaggccacactggtgtgtctcat aagtgactttctacccggaggcggggagttgacagtggcctgaaggccagat agcagccccgtcaaggggcggggagttgaaacaacccacaccctccaa acaaagcaacaacaagtacgcggccagcagctacatcgagcctga cgcctgagcagtggaagtccacagaagctacagctgccaggtca cgcatgaagggagcacgtggagaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGGGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 105 | VH4-34 MutE 3xG4S ShK (M21Q) | VL1-51 S2A, T5N, P8S, A12G, A13S, P14L, K46R, L47T, D51G, N52D, N53T | 132-27 | caggccgtcctgaaccagccaagcagcgtctccggctctctgggc agaaggtgactatcagctgctctggctcatcaagcaacatcgggaat aattacgtcagctggtaccagcagctgcctggaacagctcctagaa ccctcatttatggcgacacaaagcgccatccgaatccctgaccg attcagcggaagcaaatcaggagacctctgcaactctgggaatcact gggcttcagacacaggagatgaggcagattactatggcgcctctgcag aggacagctccagcaatgcggttccctcggtcactctgttccgcccc gtcctaggtcagcccaaggctgccccctcggtcacctggcctgaaggcagat tcctctgaggagcttcaagccaacaaggccacactggtgtgtctcat aagtgactttctaccccggaggcggggagttgacagtggcctgaaggccagat agcagccccgtcaaggggcggggagttgaaacaacccacaccctccaa acaaagcaacaacaagtacgcggccagcagctacatcgagcctga cgcctgagcagtggaagtccacagaagctacagctgccaggtca cgcatgaagggagcacgtggagaagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGGGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|------|----------|------------------|----------------------|---------------------|--------------------|---------------------------|--------------------|
| 106 | VH4-34 MutE 3xG4S ShK (M21L) | VL1-51 S2A, T5N, P8S, A12G, A13S, P14L, K46R, L47T, D51G, N52D, N53T | 132-27 | caggccgtcctgaaccagccaagcagcgtctccggtctctgggc agaaggtgactatcagctgtctctggctcatcaagcaacatcgggaat aattacgtcagctggtaccagcagctgcctggaacagctcctagaa ccctcatttatggcgacacaaaagcgccatccgaatcctgaccg attcagcggaagcaaatcaggagacctctgcaactctggaatcact gggcttcagacacaggagatgaggcagattactattgcgctctgcag aggacagctccagcaatgcgtgttcgggtctggtaccactcttaca gtcctaggtcagcccaaggctgcccctcggtcactctgttcccgccc tcctctgaggagcttcaagccaacaaggccacactggtgttctcat aagtgacttctaccggagccgtgacagtgcctgaaggcagat agcagcccgtcaaggtgcgggagttgaaacaacacacctccaa acaaagcaacaacaagtacgcggccagcagctatctgagcctga cgcctgagcagtgaagtccacacagaagctacagctgccaggtca cgcatgaagggagcacggtggaagagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 107, 114 | VH4-34 MutE 3xG4S ShK (M21F) | VL1-51 S2A, T5N, P8S, A12G, A13S, P14L, K46R, L47T, D51G, N52D, N53T | 132-27 | caggccgtcctgaaccagccaagcagcgtctccggtctctgggc agaaggtgactatcagctgtctctggctcatcaagcaacatcgggaat aattacgtcagctggtaccagcagctgcctggaacagctcctagaa ccctcatttatggcgacacaaaagcgccatccgaatcctgaccg attcagcggaagcaaatcaggagacctctgcaactctggaatcact gggcttcagacacaggagatgaggcagattactattgcgctctgcag aggacagctccagcaatgcgtgttcgggtctggtaccactcttaca gtcctaggtcagcccaaggctgcccctcggtcactctgttcccgccc tcctctgaggagcttcaagccaacaaggccacactggtgtttctcat aagtgacttctaccggagccgtggacagtgcctgaaggcagat agcagcccgtcaaggtgcgggagttgaaacaacacacctccaa acaaagcaacaacaagtacgcggccagcagctatctgagcctga cgcctgagcagtgaagtccacacagaagctacagctgccaggtca cgcatgaagggagcacggtggaagagacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 108 | VH4-34 MutE 3xG4S ShK (M21I) | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctggctcatcaagcaacatcgggaat aattacgtcagctggtaccagcagctgcctgaacagctcctagaa ccctcatttatggcgacacaaagcgcccatccggaatctgaccg atttcagcggaagcaagaatcaggacctctgcaactctggaatcact gggcttcagacacaggagatgaggcagattactattgcgcctctgcag aggacagctccagccaaggctgcccctcggtcactctgttcccgccc tcctctgaggagcttcaagccaacaaggccacactggtgtgtctcat aagtgactttacccgggagtccggacagtggcctggaaggcagat agcagccccgtcaaggcggaggtggaaaacaacacacctccaa acaaagcaacaacaaagtacgcggccagcagagctacagcgtgccctga cgcctgagcagcagtgaagtccacagagaagacacagtgccaggtca cgcatgaagggagcacgtggagaagacacagaaccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 109 | VH4-34 MutE 3xG4S ShK (M21A) | VL1-51 S2A, T5N, P8S, A12G, A13S, P14L, K46R, L47T, D51G, N52D, N53T | 132-27 | caggccgtcctgaaccagccaagcagcgtctccggtctctggggc agaaggtgactatcagctgctctggctcatcaagcaacatcgggaat aattacgtcagctggtaccagcagctgcctgaacagctcctagaa ccctcatttatggcgacacaaagcgccatccggaatctgaccg atttcagcggaagcaagaatcaggacctctgcaactctggaatcact gggcttcagacacaggagatgaggcagattactattgcgcctctgcag aggacagctccagccaaggctgcccctcggtcactctgttcccgccc tcctctgaggagcttcaagccaacaaggccacactggtgtgtctcat aagtgactttacccgggagtccggacagtggcctggaaggcagat agcagccccgtcaaggcggaggtggaaaacaacacacctccaa acaaagcaacaacaaagtacgcggccagcagagctacagcgtgccctga cgcctgagcagcagtgaagtccacagagaagacacagtgccaggtca cgcatgaagggagcacgtggagaagacacagaaccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

Figure 22 (continued)

| BIDs | IgG Name | Light Chain Name | Light Chain Plasmid # | VL-CL DNA Sequence | SEQ ID NO: (VL DNA) | VL-CL Amino Acid Sequence | Seq ID NO: (VL aa) |
|---|---|---|---|---|---|---|---|
| 157 | VH4-34MutE 1xG4S ProTxII | VL1-51 S2A, T5N, P8S, A12G, A13S, P14L, K46R, L47T, D51G, N52D, N53T | 132-27 | caggccgtcctgaaccagccaagcagcgtgtccggtctgggc agaaggtgactcagctgtcttctggctcatcaagcaacatcgggaat aattacgtcagctggtaccagcagctgcctggaacagctcctagaa ccctcatttatggcgacacaaagcgccatccgaatccgtgaccg attcagacggaagcaaatcaggagcctctgcaactctggaatcact gggcttcagacaggaggatgaggcagattactattcgcctctgcag aggacagctccagcgccaagctgcccctcggtcactcttcccgccc tcctctgaggagcttcaagccaacaaggccacactggttgtctcat aagtgacttctaccgggagccgtgacagtggcctggaaggcagat agcagcccgtcaagtgggggagtggaaaacaaccacacctccaa acaaagcaacaacaagtacgcgggccagcagagctcagcgctga cgccctgagcagtggaagtccacagaagaagtcacagctgcaggtca cgcatgagaagggagcaccgtggagacacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |
| 158 | VH4-34MutE 1xG4S GPTX1 | VL1-51 S2A, T5N, P8S, A12G, A13S, P14L, K46R, L47T, D51G, N52D, N53T | 132-27 | caggccgtcctgaaccagccaagcagcgtgtccggtctgggc agaaggtgactcagctgtcttctggctcatcaagcaacatcgggaat aattacgtcagctggtaccagcagctgcctggaacagctcctagaa ccctcatttatggcgacacaaagcgccatccgaatccgtgaccg attcagacggaagcaaatcaggagcctctgcaactctggaatcact gggcttcagacaggaggatgaggcagattactattcgcctctgcag aggacagctccagcgccaagctgcccctcggtcactcttcccgccc tcctctgaggagcttcaagccaacaaggccacactggttgtctcat aagtgacttctaccgggagccgtgacagtggcctggaaggcagat agcagcccgtcaagtgggggagtggaaaacaaccacacctccaa acaaagcaacaacaagtacgcgggccagcagagctcagcgctga cgccctgagcagtggaagtccacagaagaagtcacagctgcaggtca cgcatgagaagggagcaccgtggagacacagtggccctacagaa tgttca | 486 | QAVLNQPSSVSGSLGQKVTI SCSGSSSNIGNNYVSWYQQ LPGTAPRTLIYGDTKRPSGI PDRFSGSKSGTSATLGITGL QTGDEADYYCASAEDSSSN AVFGSGTTLTVLGQPKAAP SVTLFPPSSEELQANKATLV CLISDFYPGAVTVAWKADSS PVKAGVETTTPSKQSNNKY AASSYLSLTPEQWKSHRSY SCQVTHEGSTVEKTVAPTE CS | 780 |

SEQUENCE LISTING

```
Sequence total quantity: 959
SEQ ID NO: 1            moltype = AA   length = 6
FEATURE                 Location/Qualifiers
source                  1..6
                        mol_type = protein
                        organism = synthetic construct
```

-continued

```
SEQUENCE: 1
CTTVHQ                                                                    6

SEQ ID NO: 2         moltype = AA   length = 6
FEATURE              Location/Qualifiers
source               1..6
                     mol_type = protein
                     organism = synthetic construct
SEQUENCE: 2
CTSVHQ                                                                    6

SEQ ID NO: 3         moltype = AA   length = 6
FEATURE              Location/Qualifiers
source               1..6
                     mol_type = protein
                     organism = synthetic construct
SEQUENCE: 3
CSSVTQ                                                                    6

SEQ ID NO: 4         moltype = AA   length = 6
FEATURE              Location/Qualifiers
source               1..6
                     mol_type = protein
                     organism = synthetic construct
SEQUENCE: 4
CTTVHP                                                                    6

SEQ ID NO: 5         moltype = AA   length = 48
FEATURE              Location/Qualifiers
source               1..48
                     mol_type = protein
                     organism = synthetic construct
SEQUENCE: 5
SCPDGYSYGY GCGYGYGCSG YDCYGYGGYG GYGGYGYSSY SYSYTYEY                      48

SEQ ID NO: 6         moltype = AA   length = 48
FEATURE              Location/Qualifiers
source               1..48
                     mol_type = protein
                     organism = synthetic construct
SEQUENCE: 6
SCPDGYRERS DCSNRPACGT SDCCRVSVFG NCLTTLPVSY SYTYNYEW                      48

SEQ ID NO: 7         moltype = AA   length = 44
FEATURE              Location/Qualifiers
source               1..44
                     mol_type = protein
                     organism = synthetic construct
SEQUENCE: 7
CSDGYIAVDS CGRGQSDGCV NDCNSCYYGW RNCRRQPAIH SYEF                          44

SEQ ID NO: 8         moltype = AA   length = 44
FEATURE              Location/Qualifiers
source               1..44
                     mol_type = protein
                     organism = synthetic construct
SEQUENCE: 8
SCPDGCSDGD GCVDGCCCSA YRCYTPGVRD LSCTSYSITY TYEW                          44

SEQ ID NO: 9         moltype = AA   length = 45
FEATURE              Location/Qualifiers
source               1..45
                     mol_type = protein
                     organism = synthetic construct
SEQUENCE: 9
CCSDAYRYDS GCGSGCDCCG ADCYVFGACT FGLDSSYSYI YIYQW                         45

SEQ ID NO: 10        moltype = AA   length = 47
FEATURE              Location/Qualifiers
source               1..47
                     mol_type = protein
                     organism = synthetic construct
SEQUENCE: 10
CPDGYSYGYG CGYGYGCSGY DCYGYGGYGY GGYGGYSSYS YSYSYEY                       47

SEQ ID NO: 11        moltype = AA   length = 44
FEATURE              Location/Qualifiers
source               1..44
                     mol_type = protein
```

-continued

```
                          organism = synthetic construct
SEQUENCE: 11
SPDGYSYGYG CGYGYGCSGY DCYGYGGYGY GGYGGYSSYS YSYS                            44

SEQ ID NO: 12             moltype = AA  length = 42
FEATURE                   Location/Qualifiers
source                    1..42
                          mol_type = protein
                          organism = synthetic construct
SEQUENCE: 12
CPDGYGYGYG CGYGSYGYSG YDCYGYGGYG GYGGYGGYSS YS                              42

SEQ ID NO: 13             moltype = AA  length = 15
FEATURE                   Location/Qualifiers
source                    1..15
                          mol_type = protein
                          organism = synthetic construct
SEQUENCE: 13
YVDAWGQGLL VTVSS                                                           15

SEQ ID NO: 14             moltype = AA  length = 15
FEATURE                   Location/Qualifiers
source                    1..15
                          mol_type = protein
                          organism = synthetic construct
SEQUENCE: 14
HVDVWGQGLL VTVSS                                                           15

SEQ ID NO: 15             moltype = AA  length = 15
FEATURE                   Location/Qualifiers
source                    1..15
                          mol_type = protein
                          organism = synthetic construct
SEQUENCE: 15
HVDAWGRGLL VTVSS                                                           15

SEQ ID NO: 16             moltype = AA  length = 15
FEATURE                   Location/Qualifiers
source                    1..15
                          mol_type = protein
                          organism = synthetic construct
SEQUENCE: 16
NVDAWGRGLL VTVSS                                                           15

SEQ ID NO: 17             moltype = AA  length = 15
FEATURE                   Location/Qualifiers
source                    1..15
                          mol_type = protein
                          organism = synthetic construct
SEQUENCE: 17
YGDAWGQGLL VTVSS                                                           15

SEQ ID NO: 18             moltype = AA  length = 6
FEATURE                   Location/Qualifiers
source                    1..6
                          mol_type = protein
                          organism = synthetic construct
SEQUENCE: 18
ETKKYQ                                                                      6

SEQ ID NO: 19             moltype = AA  length = 5
FEATURE                   Location/Qualifiers
source                    1..5
                          mol_type = protein
                          organism = synthetic construct
SEQUENCE: 19
ETRKT                                                                       5

SEQ ID NO: 20             moltype = AA  length = 6
FEATURE                   Location/Qualifiers
source                    1..6
                          mol_type = protein
                          organism = synthetic construct
SEQUENCE: 20
RTHVSR                                                                      6

SEQ ID NO: 21             moltype = AA  length = 6
FEATURE                   Location/Qualifiers
source                    1..6
```

-continued

```
                          mol_type = protein
                          organism = synthetic construct
SEQUENCE: 21
KTTRKT                                                        6

SEQ ID NO: 22        moltype = AA  length = 61
FEATURE              Location/Qualifiers
source               1..61
                     mol_type = protein
                     organism = synthetic construct
SEQUENCE: 22
SVHQETKKYQ SCPDGYRERS DCSNRPACGT SDCCRVSVFG NCLTTLPVSY SYTYNYEWHV  60
D                                                            61

SEQ ID NO: 23        moltype = AA  length = 56
FEATURE              Location/Qualifiers
source               1..56
                     mol_type = protein
                     organism = synthetic construct
SEQUENCE: 23
TVHQETRKTC SDGYIAVDSC GRGQSDGCVN DCNSCYYGWR NCRRQPAIHS YEFHVD      56

SEQ ID NO: 24        moltype = AA  length = 57
FEATURE              Location/Qualifiers
source               1..57
                     mol_type = protein
                     organism = synthetic construct
SEQUENCE: 24
SVTQRTHVSR SCPDGCSDGD GCVDGCCCSA YRCYTPGVRD LSCTSYSITY TYEWNVD     57

SEQ ID NO: 25        moltype = AA  length = 58
FEATURE              Location/Qualifiers
source               1..58
                     mol_type = protein
                     organism = synthetic construct
SEQUENCE: 25
TVHQKTTRKT CCSDAYRYDS GCGSGCDCCG ADCYVFGACT FGLDSSYSYI YIYQWYVD    58

SEQ ID NO: 26        moltype = AA  length = 56
FEATURE              Location/Qualifiers
source               1..56
                     mol_type = protein
                     organism = synthetic construct
SEQUENCE: 26
TVHQIFCPDG YSYGYGCGYG YGCSGYDCYG YGGYGYGGYG GYSSYSYSYS YEYYGD      56

SEQ ID NO: 27        moltype = AA  length = 48
FEATURE              Location/Qualifiers
source               1..48
                     mol_type = protein
                     organism = synthetic construct
SEQUENCE: 27
TVHPSPDGYS YGYGCGYGYG CSGYDCYGYG GYGYGGYGGY SSYSYSYS             48

SEQ ID NO: 28        moltype = AA  length = 48
FEATURE              Location/Qualifiers
source               1..48
                     mol_type = protein
                     organism = synthetic construct
SEQUENCE: 28
TVHQIRCPDG YGYGYGCGYG SYGYSGYDCY GYGGYGGYGG YGGYSSYS             48

SEQ ID NO: 29        moltype = AA  length = 100
FEATURE              Location/Qualifiers
source               1..100
                     mol_type = protein
                     organism = synthetic construct
SEQUENCE: 29
QVQLRESGPS LVKPSQTLSL TCTASGFSLS DKAVGWVRQA PGKALEWLGG IDTGGSTGYN  60
PGLKSRLSIT KDNSKSQVSL SVSSVTTEDS ATYYCTTVHQ                   100

SEQ ID NO: 30        moltype = AA  length = 97
FEATURE              Location/Qualifiers
source               1..97
                     mol_type = protein
                     organism = synthetic construct
SEQUENCE: 30
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SAEDSSS                      97
```

-continued

```
SEQ ID NO: 31              moltype = AA   length = 99
FEATURE                    Location/Qualifiers
source                     1..99
                           mol_type = protein
                           organism = synthetic construct
SEQUENCE: 31
QLQLQESGPG LVKPSETLSL TCTVSGGSIS SSSYYWGWIR QPPGKGLEWI GSIYYSGSTY  60
YNPSLKSRVT ISVDTSKNQF SLKLSSVTAA DTAVYYCAR                         99

SEQ ID NO: 32              moltype = AA   length = 96
FEATURE                    Location/Qualifiers
source                     1..96
                           mol_type = protein
                           organism = synthetic construct
SEQUENCE: 32
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCA                            96

SEQ ID NO: 33              moltype = AA   length = 97
FEATURE                    Location/Qualifiers
source                     1..97
                           mol_type = protein
                           organism = synthetic construct
SEQUENCE: 33
QVQLQQWGAG LLKPSETLSL TCAVYGGSFS GYYWSWIRQP PGKGLEWIGE INHSGSTNYN  60
PSLKSRVTIS VDTSKNQFSL KLSSVTAADT AVYYCAR                           97

SEQ ID NO: 34              moltype = AA   length = 97
FEATURE                    Location/Qualifiers
source                     1..97
                           mol_type = protein
                           organism = synthetic construct
SEQUENCE: 34
QVQLQESGPG LVKPSQTLSL TCAVYGGSFS GYYWSWIRQP PGKGLEWIGE INHSGSTNYN  60
PSLKSRVTIS VDTSKNQFSL KLSSVTAADT AVYYCAR                           97

SEQ ID NO: 35              moltype = AA   length = 110
FEATURE                    Location/Qualifiers
source                     1..110
                           mol_type = protein
                           organism = synthetic construct
SEQUENCE: 35
QAVLNQPSSV SGSLGQRVSI TCSGSSSNVG NGYVSWYQLI PGSAPRTLIY GDTSRASGVP  60
DRFSGSRSGN TATLTISSLQ AEDEADYFCA SAEDSSSNAV FGSGTTLTVL            110

SEQ ID NO: 36              moltype = AA   length = 98
FEATURE                    Location/Qualifiers
source                     1..98
                           mol_type = protein
                           organism = synthetic construct
SEQUENCE: 36
QSVLTQPPSA SGTPGQRVTI SCSGSSSNIG SNYVYWYQQL PGTAPKLLIY RNNQRPSGVP  60
DRFSGSKSGT SASLAISGLR SEDEADYYCA AWDDSLSG                          98

SEQ ID NO: 37              moltype = AA   length = 99
FEATURE                    Location/Qualifiers
source                     1..99
                           mol_type = protein
                           organism = synthetic construct
SEQUENCE: 37
QSVLTQPPSV SGAPGQRVTI SCTGSSSNIG AGYDVHWYQQ LPGTAPKLLI YGNSNRPSGV  60
PDRFSGSKSG TSASLAITGL QAEDEADYYC QSYDSSLSG                         99

SEQ ID NO: 38              moltype = AA   length = 98
FEATURE                    Location/Qualifiers
source                     1..98
                           mol_type = protein
                           organism = synthetic construct
SEQUENCE: 38
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSA                          98

SEQ ID NO: 39              moltype = AA   length = 99
FEATURE                    Location/Qualifiers
source                     1..99
                           mol_type = protein
                           organism = synthetic construct
SEQUENCE: 39
```

```
QSALTQPPSV SGSPGQSVTI SCTGTSSDVG SYNRVSWYQQ PPGTAPKLMI YEVSNRPSGV  60
PDRFSGSKSG NTASLTISGL QAEDEADYYC SSYTSSSTF                          99

SEQ ID NO: 40            moltype =   length =
SEQUENCE: 40
000

SEQ ID NO: 41            moltype = AA  length = 28
FEATURE                  Location/Qualifiers
REGION                   2..11
                         note = misc_feature - Xaa can be any naturally occurring
                          amino acid
REGION                   13..17
                         note = misc_feature - Xaa can be any naturally occurring
                          amino acid
SITE                     19
                         note = misc_feature - Xaa can be any naturally occurring
                          amino acid
REGION                   21..27
                         note = misc_feature - Xaa can be any naturally occurring
                          amino acid
source                   1..28
                         mol_type = protein
                         organism = synthetic construct
SEQUENCE: 41
CXXXXXXXXX XCXXXXXCXC XXXXXXXC                                      28

SEQ ID NO: 42            moltype = AA  length = 43
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
SITE                     26
                         note = misc_feature - Xaa can be any naturally occurring
                          amino acid
REGION                   28..42
                         note = misc_feature - Xaa can be any naturally occurring
                          amino acid
source                   1..43
                         mol_type = protein
                         organism = synthetic construct
SEQUENCE: 42
CXXXXXXXXX XCXXXXXCX XXXXCXCXXX XXXXXXXXXX XXC                      43

SEQ ID NO: 43            moltype = AA  length = 21
FEATURE                  Location/Qualifiers
REGION                   2..12
                         note = misc_feature - Xaa can be any naturally occurring
                          amino acid
SITE                     14
                         note = misc_feature - Xaa can be any naturally occurring
                          amino acid
REGION                   16..20
                         note = misc_feature - Xaa can be any naturally occurring
                          amino acid
source                   1..21
                         mol_type = protein
                         organism = synthetic construct
SEQUENCE: 43
CXXXXXXXXX XXCXCXXXXX C                                             21

SEQ ID NO: 44            moltype = AA  length = 35
FEATURE                  Location/Qualifiers
REGION                   2..12
                         note = misc_feature - Xaa can be any naturally occurring
                          amino acid
REGION                   14..18
                         note = misc_feature - Xaa can be any naturally occurring
                          amino acid
REGION                   20..24
                         note = misc_feature - Xaa can be any naturally occurring
                          amino acid
SITE                     26
```

-continued

```
                         note = misc_feature - Xaa can be any naturally occurring
                          amino acid
REGION                   28..34
                         note = misc_feature - Xaa can be any naturally occurring
                          amino acid
source                   1..35
                         mol_type = protein
                         organism = synthetic construct
SEQUENCE: 44
CXXXXXXXXX XXCXXXXXCX XXXXCXCXXX XXXXC                              35

SEQ ID NO: 45            moltype = AA  length = 41
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
SITE                     26
                         note = misc_feature - Xaa can be any naturally occurring
                          amino acid
REGION                   28..40
                         note = misc_feature - Xaa can be any naturally occurring
                          amino acid
source                   1..41
                         mol_type = protein
                         organism = synthetic construct
SEQUENCE: 45
CXXXXXXXXX XCXXXXXXCX XXXXCXCXXX XXXXXXXXXX C                       41

SEQ ID NO: 46            moltype = AA  length = 34
FEATURE                  Location/Qualifiers
REGION                   2..11
                         note = misc_feature - Xaa can be any naturally occurring
                          amino acid
REGION                   13..17
                         note = misc_feature - Xaa can be any naturally occurring
                          amino acid
SITE                     19
                         note = misc_feature - Xaa can be any naturally occurring
                          amino acid
REGION                   21..24
                         note = misc_feature - Xaa can be any naturally occurring
                          amino acid
REGION                   26..33
                         note = misc_feature - Xaa can be any naturally occurring
                          amino acid
source                   1..34
                         mol_type = protein
                         organism = synthetic construct
SEQUENCE: 46
CXXXXXXXXX XCXXXXCXC XXXXCXXXXX XXXC                                34

SEQ ID NO: 47            moltype = AA  length = 36
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..25
                         note = misc_feature - Xaa can be any naturally occurring
                          amino acid
SITE                     27
                         note = misc_feature - Xaa can be any naturally occurring
                          amino acid
REGION                   29..35
                         note = misc_feature - Xaa can be any naturally occurring
                          amino acid
source                   1..36
                         mol_type = protein
                         organism = synthetic construct
SEQUENCE: 47
CXXXXXXXXX XCXXXXXXCX XXXXXCXCXX XXXXXC                             36
```

-continued

```
SEQ ID NO: 48           moltype = AA  length = 36
FEATURE                 Location/Qualifiers
REGION                  2..11
                        note = misc_feature - Xaa can be any naturally occurring
                         amino acid
REGION                  13..16
                        note = misc_feature - Xaa can be any naturally occurring
                         amino acid
REGION                  18..24
                        note = misc_feature - Xaa can be any naturally occurring
                         amino acid
SITE                    26
                        note = misc_feature - Xaa can be any naturally occurring
                         amino acid
REGION                  28..35
                        note = misc_feature - Xaa can be any naturally occurring
                         amino acid
source                  1..36
                        mol_type = protein
                        organism = synthetic construct
SEQUENCE: 48
CXXXXXXXXX XCXXXXCXXX XXXXCXCXXX XXXXXC                                 36

SEQ ID NO: 49           moltype = AA  length = 35
FEATURE                 Location/Qualifiers
REGION                  2..11
                        note = misc_feature - Xaa can be any naturally occurring
                         amino acid
REGION                  13..16
                        note = misc_feature - Xaa can be any naturally occurring
                         amino acid
REGION                  18..24
                        note = misc_feature - Xaa can be any naturally occurring
                         amino acid
SITE                    26
                        note = misc_feature - Xaa can be any naturally occurring
                         amino acid
REGION                  28..34
                        note = misc_feature - Xaa can be any naturally occurring
                         amino acid
source                  1..35
                        mol_type = protein
                        organism = synthetic construct
SEQUENCE: 49
CXXXXXXXXX XCXXXXCXXX XXXXCXCXXX XXXXC                                  35

SEQ ID NO: 50           moltype = AA  length = 33
FEATURE                 Location/Qualifiers
REGION                  2..14
                        note = misc_feature - Xaa can be any naturally occurring
                         amino acid
REGION                  16..23
                        note = misc_feature - Xaa can be any naturally occurring
                         amino acid
REGION                  25..32
                        note = misc_feature - Xaa can be any naturally occurring
                         amino acid
source                  1..33
                        mol_type = protein
                        organism = synthetic construct
SEQUENCE: 50
CXXXXXXXXX XXXXCXXXXX XXXCXXXXXX XXC                                    33

SEQ ID NO: 51           moltype = AA  length = 35
FEATURE                 Location/Qualifiers
REGION                  2..11
                        note = misc_feature - Xaa can be any naturally occurring
                         amino acid
REGION                  13..18
                        note = misc_feature - Xaa can be any naturally occurring
                         amino acid
REGION                  20..24
                        note = misc_feature - Xaa can be any naturally occurring
                         amino acid
SITE                    26
                        note = misc_feature - Xaa can be any naturally occurring
                         amino acid
REGION                  28..34
```

```
                         note = misc_feature - Xaa can be any naturally occurring
                           amino acid
source                   1..35
                         mol_type = protein
                         organism = synthetic construct
SEQUENCE: 51
CXXXXXXXX XCXXXXXCX XXXXCXCXXX XXXXC                                      35

SEQ ID NO: 52            moltype = AA  length = 24
FEATURE                  Location/Qualifiers
REGION                   2..11
                         note = misc_feature - Xaa can be any naturally occurring
                           amino acid
REGION                   13..17
                         note = misc_feature - Xaa can be any naturally occurring
                           amino acid
REGION                   19..23
                         note = misc_feature - Xaa can be any naturally occurring
                           amino acid
source                   1..24
                         mol_type = protein
                         organism = synthetic construct
SEQUENCE: 52
CXXXXXXXX XCXXXXCXX XXXC                                                  24

SEQ ID NO: 53            moltype = AA  length = 35
FEATURE                  Location/Qualifiers
REGION                   2..11
                         note = misc_feature - Xaa can be any naturally occurring
                           amino acid
REGION                   13..17
                         note = misc_feature - Xaa can be any naturally occurring
                           amino acid
REGION                   19..24
                         note = misc_feature - Xaa can be any naturally occurring
                           amino acid
SITE                     26
                         note = misc_feature - Xaa can be any naturally occurring
                           amino acid
REGION                   28..34
                         note = misc_feature - Xaa can be any naturally occurring
                           amino acid
source                   1..35
                         mol_type = protein
                         organism = synthetic construct
SEQUENCE: 53
CXXXXXXXX XCXXXXXCXX XXXXCXCXXX XXXXC                                     35

SEQ ID NO: 54            moltype = AA  length = 43
FEATURE                  Location/Qualifiers
REGION                   2..11
                         note = misc_feature - Xaa can be any naturally occurring
                           amino acid
REGION                   13..18
                         note = misc_feature - Xaa can be any naturally occurring
                           amino acid
REGION                   20..24
                         note = misc_feature - Xaa can be any naturally occurring
                           amino acid
REGION                   26..32
                         note = misc_feature - Xaa can be any naturally occurring
                           amino acid
REGION                   34..42
                         note = misc_feature - Xaa can be any naturally occurring
                           amino acid
source                   1..43
                         mol_type = protein
                         organism = synthetic construct
SEQUENCE: 54
CXXXXXXXX XCXXXXXCX XXXXCXXXXX XXCXXXXXXX XXC                             43

SEQ ID NO: 55            moltype = AA  length = 35
FEATURE                  Location/Qualifiers
REGION                   2..10
                         note = misc_feature - Xaa can be any naturally occurring
                           amino acid
REGION                   12..18
                         note = misc_feature - Xaa can be any naturally occurring
                           amino acid
```

```
REGION              20..24
                    note = misc_feature - Xaa can be any naturally occurring
                     amino acid
SITE                26
                    note = misc_feature - Xaa can be any naturally occurring
                     amino acid
REGION              28..34
                    note = misc_feature - Xaa can be any naturally occurring
                     amino acid
source              1..35
                    mol_type = protein
                    organism = synthetic construct
SEQUENCE: 55
CXXXXXXXXX CXXXXXXXCX XXXXCXCXXX XXXXC                                          35

SEQ ID NO: 56       moltype = AA  length = 37
FEATURE             Location/Qualifiers
REGION              2..11
                    note = misc_feature - Xaa can be any naturally occurring
                     amino acid
REGION              13..18
                    note = misc_feature - Xaa can be any naturally occurring
                     amino acid
REGION              20..24
                    note = misc_feature - Xaa can be any naturally occurring
                     amino acid
SITE                26
                    note = misc_feature - Xaa can be any naturally occurring
                     amino acid
REGION              28..36
                    note = misc_feature - Xaa can be any naturally occurring
                     amino acid
source              1..37
                    mol_type = protein
                    organism = synthetic construct
SEQUENCE: 56
CXXXXXXXXX XCXXXXXXCX XXXXCXCXXX XXXXXXC                                        37

SEQ ID NO: 57       moltype = AA  length = 37
FEATURE             Location/Qualifiers
REGION              2..11
                    note = misc_feature - Xaa can be any naturally occurring
                     amino acid
SITE                13
                    note = misc_feature - Xaa can be any naturally occurring
                     amino acid
REGION              15..18
                    note = misc_feature - Xaa can be any naturally occurring
                     amino acid
REGION              20..24
                    note = misc_feature - Xaa can be any naturally occurring
                     amino acid
REGION              26..36
                    note = misc_feature - Xaa can be any naturally occurring
                     amino acid
source              1..37
                    mol_type = protein
                    organism = synthetic construct
SEQUENCE: 57
CXXXXXXXXX XCXCXXXXCX XXXXCXXXXX XXXXXXC                                        37

SEQ ID NO: 58       moltype = AA  length = 45
FEATURE             Location/Qualifiers
REGION              2..8
                    note = misc_feature - Xaa can be any naturally occurring
                     amino acid
REGION              10..12
                    note = misc_feature - Xaa can be any naturally occurring
                     amino acid
REGION              14..19
                    note = misc_feature - Xaa can be any naturally occurring
                     amino acid
REGION              21..25
                    note = misc_feature - Xaa can be any naturally occurring
                     amino acid
SITE                27
                    note = misc_feature - Xaa can be any naturally occurring
                     amino acid
REGION              29..33
```

```
                         note = misc_feature - Xaa can be any naturally occurring
                          amino acid
REGION                   35..44
                         note = misc_feature - Xaa can be any naturally occurring
                          amino acid
source                   1..45
                         mol_type = protein
                         organism = synthetic construct
SEQUENCE: 58
CXXXXXXXCX XXCXXXXXXC XXXXXCXCXX XXXCXXXXXX XXXXC                              45

SEQ ID NO: 59           moltype = AA  length = 34
FEATURE                 Location/Qualifiers
REGION                  2..11
                        note = misc_feature - Xaa can be any naturally occurring
                         amino acid
SITE                    13
                        note = misc_feature - Xaa can be any naturally occurring
                         amino acid
REGION                  15..18
                        note = misc_feature - Xaa can be any naturally occurring
                         amino acid
REGION                  20..24
                        note = misc_feature - Xaa can be any naturally occurring
                         amino acid
SITE                    26
                        note = misc_feature - Xaa can be any naturally occurring
                         amino acid
REGION                  28..29
                        note = misc_feature - Xaa can be any naturally occurring
                         amino acid
REGION                  31..33
                        note = misc_feature - Xaa can be any naturally occurring
                         amino acid
source                  1..34
                        mol_type = protein
                        organism = synthetic construct
SEQUENCE: 59
CXXXXXXXXX XCXCXXXXCX XXXXCXCXXC XXXC                                          34

SEQ ID NO: 60           moltype = AA  length = 26
FEATURE                 Location/Qualifiers
REGION                  2..17
                        note = misc_feature - Xaa can be any naturally occurring
                         amino acid
REGION                  19..23
                        note = misc_feature - Xaa can be any naturally occurring
                         amino acid
SITE                    25
                        note = misc_feature - Xaa can be any naturally occurring
                         amino acid
source                  1..26
                        mol_type = protein
                        organism = synthetic construct
SEQUENCE: 60
CXXXXXXXXX XXXXXXXCXX XXXCXC                                                   26

SEQ ID NO: 61           moltype = AA  length = 26
FEATURE                 Location/Qualifiers
REGION                  2..7
                        note = misc_feature - Xaa can be any naturally occurring
                         amino acid
REGION                  9..12
                        note = misc_feature - Xaa can be any naturally occurring
                         amino acid
SITE                    14
                        note = misc_feature - Xaa can be any naturally occurring
                         amino acid
REGION                  16..19
                        note = misc_feature - Xaa can be any naturally occurring
                         amino acid
REGION                  21..25
                        note = misc_feature - Xaa can be any naturally occurring
                         amino acid
source                  1..26
                        mol_type = protein
                        organism = synthetic construct
SEQUENCE: 61
CXXXXXXCXX XXCXCXXXXC XXXXXC                                                   26
```

```
SEQ ID NO: 62              moltype = AA   length = 35
FEATURE                    Location/Qualifiers
REGION                     2..12
                           note = misc_feature - Xaa can be any naturally occurring
                            amino acid
REGION                     14..17
                           note = misc_feature - Xaa can be any naturally occurring
                            amino acid
REGION                     19..23
                           note = misc_feature - Xaa can be any naturally occurring
                            amino acid
REGION                     25..30
                           note = misc_feature - Xaa can be any naturally occurring
                            amino acid
REGION                     32..34
                           note = misc_feature - Xaa can be any naturally occurring
                            amino acid
source                     1..35
                           mol_type = protein
                           organism = synthetic construct
SEQUENCE: 62
CXXXXXXXXX XXCXXXXCXX XXXCXXXXXX CXXXC                                    35

SEQ ID NO: 63              moltype = AA   length = 26
FEATURE                    Location/Qualifiers
REGION                     2..9
                           note = misc_feature - Xaa can be any naturally occurring
                            amino acid
REGION                     11..12
                           note = misc_feature - Xaa can be any naturally occurring
                            amino acid
REGION                     14..19
                           note = misc_feature - Xaa can be any naturally occurring
                            amino acid
REGION                     21..25
                           note = misc_feature - Xaa can be any naturally occurring
                            amino acid
source                     1..26
                           mol_type = protein
                           organism = synthetic construct
SEQUENCE: 63
CXXXXXXXXC XXCXXXXXXC XXXXXC                                              26

SEQ ID NO: 64              moltype = AA   length = 37
FEATURE                    Location/Qualifiers
REGION                     2..11
                           note = misc_feature - Xaa can be any naturally occurring
                            amino acid
REGION                     13..17
                           note = misc_feature - Xaa can be any naturally occurring
                            amino acid
REGION                     19..23
                           note = misc_feature - Xaa can be any naturally occurring
                            amino acid
SITE                       25
                           note = misc_feature - Xaa can be any naturally occurring
                            amino acid
REGION                     27..36
                           note = misc_feature - Xaa can be any naturally occurring
                            amino acid
source                     1..37
                           mol_type = protein
                           organism = synthetic construct
SEQUENCE: 64
CXXXXXXXXX XCXXXXCXX XXXCXCXXXX XXXXXC                                    37

SEQ ID NO: 65              moltype = AA   length = 28
FEATURE                    Location/Qualifiers
REGION                     2..11
                           note = misc_feature - Xaa can be any naturally occurring
                            amino acid
SITE                       13
                           note = misc_feature - Xaa can be any naturally occurring
                            amino acid
REGION                     15..20
                           note = misc_feature - Xaa can be any naturally occurring
                            amino acid
REGION                     22..25
```

```
                        note = misc_feature - Xaa can be any naturally occurring
                          amino acid
SITE                    27
                        note = misc_feature - Xaa can be any naturally occurring
                          amino acid
source                  1..28
                        mol_type = protein
                        organism = synthetic construct
SEQUENCE: 65
CXXXXXXXXX XCXCXXXXXX CXXXXCXC                                            28

SEQ ID NO: 66           moltype = AA  length = 29
FEATURE                 Location/Qualifiers
REGION                  2..11
                        note = misc_feature - Xaa can be any naturally occurring
                          amino acid
REGION                  13..17
                        note = misc_feature - Xaa can be any naturally occurring
                          amino acid
REGION                  19..23
                        note = misc_feature - Xaa can be any naturally occurring
                          amino acid
SITE                    25
                        note = misc_feature - Xaa can be any naturally occurring
                          amino acid
REGION                  27..28
                        note = misc_feature - Xaa can be any naturally occurring
                          amino acid
source                  1..29
                        mol_type = protein
                        organism = synthetic construct
SEQUENCE: 66
CXXXXXXXXX XCXXXXXCXX XXXCXCXXC                                           29

SEQ ID NO: 67           moltype = AA  length = 27
FEATURE                 Location/Qualifiers
REGION                  2..15
                        note = misc_feature - Xaa can be any naturally occurring
                          amino acid
REGION                  17..18
                        note = misc_feature - Xaa can be any naturally occurring
                          amino acid
REGION                  20..22
                        note = misc_feature - Xaa can be any naturally occurring
                          amino acid
SITE                    24
                        note = misc_feature - Xaa can be any naturally occurring
                          amino acid
SITE                    26
                        note = misc_feature - Xaa can be any naturally occurring
                          amino acid
source                  1..27
                        mol_type = protein
                        organism = synthetic construct
SEQUENCE: 67
CXXXXXXXXX XXXXXCXXCX XXCXCXC                                             27

SEQ ID NO: 68           moltype = AA  length = 25
FEATURE                 Location/Qualifiers
REGION                  2..16
                        note = misc_feature - Xaa can be any naturally occurring
                          amino acid
REGION                  18..22
                        note = misc_feature - Xaa can be any naturally occurring
                          amino acid
SITE                    24
                        note = misc_feature - Xaa can be any naturally occurring
                          amino acid
source                  1..25
                        mol_type = protein
                        organism = synthetic construct
SEQUENCE: 68
CXXXXXXXXX XXXXXCXXX XXCXC                                                25

SEQ ID NO: 69           moltype = AA  length = 38
FEATURE                 Location/Qualifiers
REGION                  2..5
                        note = misc_feature - Xaa can be any naturally occurring
                          amino acid
```

-continued

```
REGION                  7..12
                        note = misc_feature - Xaa can be any naturally occurring
                         amino acid
REGION                  14..22
                        note = misc_feature - Xaa can be any naturally occurring
                         amino acid
REGION                  24..25
                        note = misc_feature - Xaa can be any naturally occurring
                         amino acid
REGION                  27..37
                        note = misc_feature - Xaa can be any naturally occurring
                         amino acid
source                  1..38
                        mol_type = protein
                        organism = synthetic construct
SEQUENCE: 69
CXXXXCXXXX XXCXXCXXXX XXCXXCXXXX XXXXXXXC                            38

SEQ ID NO: 70           moltype = AA  length = 38
FEATURE                 Location/Qualifiers
REGION                  2..7
                        note = misc_feature - Xaa can be any naturally occurring
                         amino acid
REGION                  9..12
                        note = misc_feature - Xaa can be any naturally occurring
                         amino acid
REGION                  14..18
                        note = misc_feature - Xaa can be any naturally occurring
                         amino acid
REGION                  20..24
                        note = misc_feature - Xaa can be any naturally occurring
                         amino acid
REGION                  26..37
                        note = misc_feature - Xaa can be any naturally occurring
                         amino acid
source                  1..38
                        mol_type = protein
                        organism = synthetic construct
SEQUENCE: 70
CXXXXXXCXX XXCXXXXXCX XXXXCXXXXX XXXXXXXC                            38

SEQ ID NO: 71           moltype = AA  length = 38
FEATURE                 Location/Qualifiers
REGION                  2..8
                        note = misc_feature - Xaa can be any naturally occurring
                         amino acid
REGION                  10..12
                        note = misc_feature - Xaa can be any naturally occurring
                         amino acid
SITE                    14
                        note = misc_feature - Xaa can be any naturally occurring
                         amino acid
SITE                    16
                        note = misc_feature - Xaa can be any naturally occurring
                         amino acid
REGION                  18..21
                        note = misc_feature - Xaa can be any naturally occurring
                         amino acid
REGION                  23..27
                        note = misc_feature - Xaa can be any naturally occurring
                         amino acid
REGION                  29..37
                        note = misc_feature - Xaa can be any naturally occurring
                         amino acid
source                  1..38
                        mol_type = protein
                        organism = synthetic construct
SEQUENCE: 71
CXXXXXXXCX XXCXCXCXXX XCXXXXXCXX XXXXXXXC                            38

SEQ ID NO: 72           moltype = AA  length = 25
FEATURE                 Location/Qualifiers
REGION                  2..11
                        note = misc_feature - Xaa can be any naturally occurring
                         amino acid
REGION                  13..18
                        note = misc_feature - Xaa can be any naturally occurring
                         amino acid
REGION                  20..24
```

```
                              note = misc_feature - Xaa can be any naturally occurring
                               amino acid
source                        1..25
                              mol_type = protein
                              organism = synthetic construct
SEQUENCE: 72
CXXXXXXXXX XCXXXXXXCX XXXXC                                                25

SEQ ID NO: 73                 moltype = AA  length = 35
FEATURE                       Location/Qualifiers
REGION                        2..8
                              note = misc_feature - Xaa can be any naturally occurring
                               amino acid
REGION                        10..12
                              note = misc_feature - Xaa can be any naturally occurring
                               amino acid
REGION                        14..18
                              note = misc_feature - Xaa can be any naturally occurring
                               amino acid
REGION                        20..24
                              note = misc_feature - Xaa can be any naturally occurring
                               amino acid
REGION                        26..34
                              note = misc_feature - Xaa can be any naturally occurring
                               amino acid
source                        1..35
                              mol_type = protein
                              organism = synthetic construct
SEQUENCE: 73
CXXXXXXXCX XXCXXXXXCX XXXXCXXXXX XXXXC                                     35

SEQ ID NO: 74                 moltype = AA  length = 20
FEATURE                       Location/Qualifiers
REGION                        2..8
                              note = misc_feature - Xaa can be any naturally occurring
                               amino acid
REGION                        10..14
                              note = misc_feature - Xaa can be any naturally occurring
                               amino acid
SITE                          16
                              note = misc_feature - Xaa can be any naturally occurring
                               amino acid
REGION                        18..19
                              note = misc_feature - Xaa can be any naturally occurring
                               amino acid
source                        1..20
                              mol_type = protein
                              organism = synthetic construct
SEQUENCE: 74
CXXXXXXXCX XXXXCXCXXC                                                      20

SEQ ID NO: 75                 moltype = AA  length = 21
FEATURE                       Location/Qualifiers
REGION                        2..11
                              note = misc_feature - Xaa can be any naturally occurring
                               amino acid
SITE                          13
                              note = misc_feature - Xaa can be any naturally occurring
                               amino acid
REGION                        15..20
                              note = misc_feature - Xaa can be any naturally occurring
                               amino acid
source                        1..21
                              mol_type = protein
                              organism = synthetic construct
SEQUENCE: 75
CXXXXXXXXX XCXCXXXXXX C                                                    21

SEQ ID NO: 76                 moltype = AA  length = 43
FEATURE                       Location/Qualifiers
REGION                        2..11
                              note = misc_feature - Xaa can be any naturally occurring
                               amino acid
REGION                        13..15
                              note = misc_feature - Xaa can be any naturally occurring
                               amino acid
REGION                        17..19
                              note = misc_feature - Xaa can be any naturally occurring
                               amino acid
```

```
REGION                  21..25
                        note = misc_feature - Xaa can be any naturally occurring
                         amino acid
REGION                  27..33
                        note = misc_feature - Xaa can be any naturally occurring
                         amino acid
SITE                    35
                        note = misc_feature - Xaa can be any naturally occurring
                         amino acid
REGION                  37..42
                        note = misc_feature - Xaa can be any naturally occurring
                         amino acid
source                  1..43
                        mol_type = protein
                        organism = synthetic construct
SEQUENCE: 76
CXXXXXXXX XCXXXCXXXC XXXXXCXXXX XXXCXCXXXX XXC                      43

SEQ ID NO: 77           moltype = AA  length = 39
FEATURE                 Location/Qualifiers
REGION                  2..11
                        note = misc_feature - Xaa can be any naturally occurring
                         amino acid
REGION                  13..16
                        note = misc_feature - Xaa can be any naturally occurring
                         amino acid
REGION                  18..22
                        note = misc_feature - Xaa can be any naturally occurring
                         amino acid
REGION                  24..35
                        note = misc_feature - Xaa can be any naturally occurring
                         amino acid
REGION                  37..38
                        note = misc_feature - Xaa can be any naturally occurring
                         amino acid
source                  1..39
                        mol_type = protein
                        organism = synthetic construct
SEQUENCE: 77
CXXXXXXXX XCXXXXCXXX XXCXXXXXXX XXXXXCXXC                      39

SEQ ID NO: 78           moltype = AA  length = 43
FEATURE                 Location/Qualifiers
REGION                  2..13
                        note = misc_feature - Xaa can be any naturally occurring
                         amino acid
REGION                  15..18
                        note = misc_feature - Xaa can be any naturally occurring
                         amino acid
REGION                  20..24
                        note = misc_feature - Xaa can be any naturally occurring
                         amino acid
SITE                    26
                        note = misc_feature - Xaa can be any naturally occurring
                         amino acid
SITE                    28
                        note = misc_feature - Xaa can be any naturally occurring
                         amino acid
REGION                  30..38
                        note = misc_feature - Xaa can be any naturally occurring
                         amino acid
REGION                  40..42
                        note = misc_feature - Xaa can be any naturally occurring
                         amino acid
source                  1..43
                        mol_type = protein
                        organism = synthetic construct
SEQUENCE: 78
CXXXXXXXX XXXCXXXXCX XXXXCXCXCX XXXXXXXXCX XXC                      43

SEQ ID NO: 79           moltype = AA  length = 41
FEATURE                 Location/Qualifiers
REGION                  2..13
                        note = misc_feature - Xaa can be any naturally occurring
                         amino acid
REGION                  15..18
                        note = misc_feature - Xaa can be any naturally occurring
                         amino acid
REGION                  20..24
```

-continued

```
                         note = misc_feature - Xaa can be any naturally occurring
                          amino acid
REGION                   26..37
                         note = misc_feature - Xaa can be any naturally occurring
                          amino acid
REGION                   39..40
                         note = misc_feature - Xaa can be any naturally occurring
                          amino acid
source                   1..41
                         mol_type = protein
                         organism = synthetic construct
SEQUENCE: 79
CXXXXXXXX XXXCXXXXCX XXXXCXXXXX XXXXXXXCXX C                            41

SEQ ID NO: 80            moltype = AA  length = 39
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
SITE                     26
                         note = misc_feature - Xaa can be any naturally occurring
                          amino acid
REGION                   28..38
                         note = misc_feature - Xaa can be any naturally occurring
                          amino acid
source                   1..39
                         mol_type = protein
                         organism = synthetic construct
SEQUENCE: 80
CXXXXXXXX XCXXXXXXCX XXXXCXCXXX XXXXXXXC                               39

SEQ ID NO: 81            moltype = AA  length = 43
FEATURE                  Location/Qualifiers
REGION                   2..17
                         note = misc_feature - Xaa can be any naturally occurring
                          amino acid
REGION                   19..23
                         note = misc_feature - Xaa can be any naturally occurring
                          amino acid
SITE                     25
                         note = misc_feature - Xaa can be any naturally occurring
                          amino acid
SITE                     27
                         note = misc_feature - Xaa can be any naturally occurring
                          amino acid
REGION                   29..42
                         note = misc_feature - Xaa can be any naturally occurring
                          amino acid
source                   1..43
                         mol_type = protein
                         organism = synthetic construct
SEQUENCE: 81
CXXXXXXXX XXXXXXXCXX XXXCXCXCXX XXXXXXXXXX XXC                         43

SEQ ID NO: 82            moltype = AA  length = 36
FEATURE                  Location/Qualifiers
REGION                   2..11
                         note = misc_feature - Xaa can be any naturally occurring
                          amino acid
REGION                   13..17
                         note = misc_feature - Xaa can be any naturally occurring
                          amino acid
SITE                     19
                         note = misc_feature - Xaa can be any naturally occurring
                          amino acid
REGION                   21..28
                         note = misc_feature - Xaa can be any naturally occurring
                          amino acid
REGION                   30..35
                         note = misc_feature - Xaa can be any naturally occurring
                          amino acid
source                   1..36
                         mol_type = protein
```

-continued

```
                          organism = synthetic construct
SEQUENCE: 82
CXXXXXXXXX XCXXXXCXC XXXXXXXXCX XXXXXC                                36

SEQ ID NO: 83            moltype = AA  length = 37
FEATURE                  Location/Qualifiers
REGION                   2..13
                         note = misc_feature - Xaa can be any naturally occurring
                          amino acid
REGION                   15..18
                         note = misc_feature - Xaa can be any naturally occurring
                          amino acid
REGION                   20..24
                         note = misc_feature - Xaa can be any naturally occurring
                          amino acid
REGION                   26..33
                         note = misc_feature - Xaa can be any naturally occurring
                          amino acid
REGION                   35..36
                         note = misc_feature - Xaa can be any naturally occurring
                          amino acid
source                   1..37
                         mol_type = protein
                         organism = synthetic construct
SEQUENCE: 83
CXXXXXXXXX XXXCXXXXCX XXXXCXXXXX XXXCXXC                              37

SEQ ID NO: 84            moltype = AA  length = 37
FEATURE                  Location/Qualifiers
REGION                   2..13
                         note = misc_feature - Xaa can be any naturally occurring
                          amino acid
REGION                   15..19
                         note = misc_feature - Xaa can be any naturally occurring
                          amino acid
REGION                   21..25
                         note = misc_feature - Xaa can be any naturally occurring
                          amino acid
SITE                     27
                         note = misc_feature - Xaa can be any naturally occurring
                          amino acid
REGION                   29..36
                         note = misc_feature - Xaa can be any naturally occurring
                          amino acid
source                   1..37
                         mol_type = protein
                         organism = synthetic construct
SEQUENCE: 84
CXXXXXXXXX XXXCXXXXC XXXXXCXCXX XXXXXXC                               37

SEQ ID NO: 85            moltype = AA  length = 44
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
SITE                     26
                         note = misc_feature - Xaa can be any naturally occurring
                          amino acid
REGION                   28..31
                         note = misc_feature - Xaa can be any naturally occurring
                          amino acid
SITE                     33
                         note = misc_feature - Xaa can be any naturally occurring
                          amino acid
REGION                   35..43
                         note = misc_feature - Xaa can be any naturally occurring
                          amino acid
source                   1..44
                         mol_type = protein
                         organism = synthetic construct
SEQUENCE: 85
CXXXXXXXXX XCXXXXXCX XXXXCXCXXX XCXCXXXXXX XXXC                       44
```

```
SEQ ID NO: 86            moltype = AA  length = 36
FEATURE                  Location/Qualifiers
REGION                   2..12
                         note = misc_feature - Xaa can be any naturally occurring
                          amino acid
REGION                   14..17
                         note = misc_feature - Xaa can be any naturally occurring
                          amino acid
REGION                   19..23
                         note = misc_feature - Xaa can be any naturally occurring
                          amino acid
REGION                   25..32
                         note = misc_feature - Xaa can be any naturally occurring
                          amino acid
REGION                   34..35
                         note = misc_feature - Xaa can be any naturally occurring
                          amino acid
source                   1..36
                         mol_type = protein
                         organism = synthetic construct
SEQUENCE: 86
CXXXXXXXXX XXCXXXXCXX XXXCXXXXXX XXCXXC                                  36

SEQ ID NO: 87            moltype = AA  length = 37
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
REGION                   26..33
                         note = misc_feature - Xaa can be any naturally occurring
                          amino acid
REGION                   35..36
                         note = misc_feature - Xaa can be any naturally occurring
                          amino acid
source                   1..37
                         mol_type = protein
                         organism = synthetic construct
SEQUENCE: 87
CXXXXXXXXX XCXXXXXXCX XXXXCXXXXX XXXCXXC                                 37

SEQ ID NO: 88            moltype = AA  length = 36
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
SITE                     26
                         note = misc_feature - Xaa can be any naturally occurring
                          amino acid
REGION                   28..35
                         note = misc_feature - Xaa can be any naturally occurring
                          amino acid
source                   1..36
                         mol_type = protein
                         organism = synthetic construct
SEQUENCE: 88
CXXXXXXXXX XCXXXXXXCX XXXXCXCXXX XXXXXC                                  36

SEQ ID NO: 89            moltype = AA  length = 43
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
```

```
                         amino acid
SITE                     26
                         note = misc_feature - Xaa can be any naturally occurring
                          amino acid
REGION                   28..30
                         note = misc_feature - Xaa can be any naturally occurring
                          amino acid
REGION                   32..39
                         note = misc_feature - Xaa can be any naturally occurring
                          amino acid
REGION                   41..42
                         note = misc_feature - Xaa can be any naturally occurring
                          amino acid
source                   1..43
                         mol_type = protein
                         organism = synthetic construct
SEQUENCE: 89
CXXXXXXXXX XCXXXXXXCX XXXXCXCXXX CXXXXXXXXC XXC                                    43

SEQ ID NO: 90            moltype = AA  length = 38
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
REGION                   26..28
                         note = misc_feature - Xaa can be any naturally occurring
                          amino acid
REGION                   30..37
                         note = misc_feature - Xaa can be any naturally occurring
                          amino acid
source                   1..38
                         mol_type = protein
                         organism = synthetic construct
SEQUENCE: 90
CXXXXXXXXX XCXXXXXXCX XXXXCXXXCX XXXXXXXC                                          38

SEQ ID NO: 91            moltype = AA  length = 43
FEATURE                  Location/Qualifiers
REGION                   2..11
                         note = misc_feature - Xaa can be any naturally occurring
                          amino acid
REGION                   13..18
                         note = misc_feature - Xaa can be any naturally occurring
                          amino acid
REGION                   20..24
                         note = misc_feature - Xaa can be any naturally occurring
                          amino acid
SITE                     26
                         note = misc_feature - Xaa can be any naturally occurring
                          amino acid
REGION                   28..29
                         note = misc_feature - Xaa can be any naturally occurring
                          amino acid
REGION                   31..36
                         note = misc_feature - Xaa can be any naturally occurring
                          amino acid
REGION                   38..42
                         note = misc_feature - Xaa can be any naturally occurring
                          amino acid
source                   1..43
                         mol_type = protein
                         organism = synthetic construct
SEQUENCE: 91
CXXXXXXXXX XCXXXXXXCX XXXXCXCXXC XXXXXXCXXX XXC                                    43

SEQ ID NO: 92            moltype = AA  length = 34
FEATURE                  Location/Qualifiers
REGION                   2..8
                         note = misc_feature - Xaa can be any naturally occurring
                          amino acid
REGION                   10..15
                         note = misc_feature - Xaa can be any naturally occurring
                          amino acid
```

-continued

```
REGION                  17..19
                        note = misc_feature - Xaa can be any naturally occurring
                         amino acid
REGION                  21..23
                        note = misc_feature - Xaa can be any naturally occurring
                         amino acid
REGION                  25..33
                        note = misc_feature - Xaa can be any naturally occurring
                         amino acid
source                  1..34
                        mol_type = protein
                        organism = synthetic construct
SEQUENCE: 92
CXXXXXXXCX XXXXXCXXXC XXXCXXXXXX XXXC                                        34

SEQ ID NO: 93           moltype = AA  length = 39
FEATURE                 Location/Qualifiers
REGION                  2..10
                        note = misc_feature - Xaa can be any naturally occurring
                         amino acid
REGION                  12..19
                        note = misc_feature - Xaa can be any naturally occurring
                         amino acid
REGION                  21..25
                        note = misc_feature - Xaa can be any naturally occurring
                         amino acid
REGION                  27..32
                        note = misc_feature - Xaa can be any naturally occurring
                         amino acid
REGION                  34..38
                        note = misc_feature - Xaa can be any naturally occurring
                         amino acid
source                  1..39
                        mol_type = protein
                        organism = synthetic construct
SEQUENCE: 93
CXXXXXXXXX CXXXXXXXC XXXXXCXXXX XXCXXXXXC                                     39

SEQ ID NO: 94           moltype = AA  length = 46
FEATURE                 Location/Qualifiers
REGION                  2..11
                        note = misc_feature - Xaa can be any naturally occurring
                         amino acid
REGION                  13..14
                        note = misc_feature - Xaa can be any naturally occurring
                         amino acid
REGION                  16..17
                        note = misc_feature - Xaa can be any naturally occurring
                         amino acid
REGION                  19..25
                        note = misc_feature - Xaa can be any naturally occurring
                         amino acid
SITE                    27
                        note = misc_feature - Xaa can be any naturally occurring
                         amino acid
REGION                  29..39
                        note = misc_feature - Xaa can be any naturally occurring
                         amino acid
REGION                  41..45
                        note = misc_feature - Xaa can be any naturally occurring
                         amino acid
source                  1..46
                        mol_type = protein
                        organism = synthetic construct
SEQUENCE: 94
CXXXXXXXXX XCXXCXXCXX XXXXXCXCXX XXXXXXXXXC XXXXXC                           46

SEQ ID NO: 95           moltype = AA  length = 44
FEATURE                 Location/Qualifiers
REGION                  2..11
                        note = misc_feature - Xaa can be any naturally occurring
                         amino acid
REGION                  13..18
                        note = misc_feature - Xaa can be any naturally occurring
                         amino acid
REGION                  20..24
                        note = misc_feature - Xaa can be any naturally occurring
                         amino acid
SITE                    26
```

```
                            note = misc_feature - Xaa can be any naturally occurring
                              amino acid
REGION                      28..29
                            note = misc_feature - Xaa can be any naturally occurring
                              amino acid
REGION                      31..38
                            note = misc_feature - Xaa can be any naturally occurring
                              amino acid
REGION                      40..43
                            note = misc_feature - Xaa can be any naturally occurring
                              amino acid
source                      1..44
                            mol_type = protein
                            organism = synthetic construct
SEQUENCE: 95
CXXXXXXXX XCXXXXXXCX XXXXCXCXXC XXXXXXXXCX XXXC                              44

SEQ ID NO: 96               moltype = AA  length = 42
FEATURE                     Location/Qualifiers
REGION                      3..5
                            note = misc_feature - Xaa can be any naturally occurring
                              amino acid
SITE                        7
                            note = misc_feature - Xaa can be any naturally occurring
                              amino acid
REGION                      9..11
                            note = misc_feature - Xaa can be any naturally occurring
                              amino acid
REGION                      13..14
                            note = misc_feature - Xaa can be any naturally occurring
                              amino acid
SITE                        17
                            note = misc_feature - Xaa can be any naturally occurring
                              amino acid
REGION                      19..23
                            note = misc_feature - Xaa can be any naturally occurring
                              amino acid
REGION                      25..33
                            note = misc_feature - Xaa can be any naturally occurring
                              amino acid
REGION                      35..39
                            note = misc_feature - Xaa can be any naturally occurring
                              amino acid
SITE                        41
                            note = misc_feature - Xaa can be any naturally occurring
                              amino acid
source                      1..42
                            mol_type = protein
                            organism = synthetic construct
SEQUENCE: 96
CCXXXCXCXX XCXXCCXCXX XXXCXXXXXX XXXCXXXXXC XC                               42

SEQ ID NO: 97               moltype = AA  length = 39
FEATURE                     Location/Qualifiers
REGION                      2..7
                            note = misc_feature - Xaa can be any naturally occurring
                              amino acid
REGION                      9..10
                            note = misc_feature - Xaa can be any naturally occurring
                              amino acid
REGION                      12..16
                            note = misc_feature - Xaa can be any naturally occurring
                              amino acid
REGION                      18..21
                            note = misc_feature - Xaa can be any naturally occurring
                              amino acid
SITE                        24
                            note = misc_feature - Xaa can be any naturally occurring
                              amino acid
REGION                      26..29
                            note = misc_feature - Xaa can be any naturally occurring
                              amino acid
REGION                      31..36
                            note = misc_feature - Xaa can be any naturally occurring
                              amino acid
SITE                        38
                            note = misc_feature - Xaa can be any naturally occurring
                              amino acid
source                      1..39
```

```
                           mol_type = protein
                           organism = synthetic construct
SEQUENCE: 97
CXXXXXXCXX CXXXXXCXXX XCCXCXXXXC XXXXXXCXC                            39

SEQ ID NO: 98             moltype = AA  length = 38
FEATURE                   Location/Qualifiers
REGION                    2..8
                          note = misc_feature - Xaa can be any naturally occurring
                            amino acid
SITE                      10
                          note = misc_feature - Xaa can be any naturally occurring
                            amino acid
REGION                    12..16
                          note = misc_feature - Xaa can be any naturally occurring
                            amino acid
REGION                    18..21
                          note = misc_feature - Xaa can be any naturally occurring
                            amino acid
REGION                    25..28
                          note = misc_feature - Xaa can be any naturally occurring
                            amino acid
REGION                    30..35
                          note = misc_feature - Xaa can be any naturally occurring
                            amino acid
SITE                      37
                          note = misc_feature - Xaa can be any naturally occurring
                            amino acid
source                    1..38
                          mol_type = protein
                          organism = synthetic construct
SEQUENCE: 98
CXXXXXXXCX CXXXXXCXXX XCCCXXXXCX XXXXXCXC                             38

SEQ ID NO: 99             moltype = AA  length = 36
FEATURE                   Location/Qualifiers
REGION                    2..10
                          note = misc_feature - Xaa can be any naturally occurring
                            amino acid
REGION                    12..14
                          note = misc_feature - Xaa can be any naturally occurring
                            amino acid
SITE                      16
                          note = misc_feature - Xaa can be any naturally occurring
                            amino acid
REGION                    18..19
                          note = misc_feature - Xaa can be any naturally occurring
                            amino acid
SITE                      21
                          note = misc_feature - Xaa can be any naturally occurring
                            amino acid
REGION                    25..30
                          note = misc_feature - Xaa can be any naturally occurring
                            amino acid
REGION                    32..35
                          note = misc_feature - Xaa can be any naturally occurring
                            amino acid
source                    1..36
                          mol_type = protein
                          organism = synthetic construct
SEQUENCE: 99
CXXXXXXXXX CXXXCXCXXC XCCCXXXXXX CXXXXC                               36

SEQ ID NO: 100            moltype = AA  length = 39
FEATURE                   Location/Qualifiers
REGION                    2..6
                          note = misc_feature - Xaa can be any naturally occurring
                            amino acid
REGION                    8..10
                          note = misc_feature - Xaa can be any naturally occurring
                            amino acid
SITE                      12
                          note = misc_feature - Xaa can be any naturally occurring
                            amino acid
REGION                    14..17
                          note = misc_feature - Xaa can be any naturally occurring
                            amino acid
REGION                    19..22
                          note = misc_feature - Xaa can be any naturally occurring
```

```
                         amino acid
REGION                   25..34
                         note = misc_feature - Xaa can be any naturally occurring
                          amino acid
REGION                   36..37
                         note = misc_feature - Xaa can be any naturally occurring
                          amino acid
source                   1..39
                         mol_type = protein
                         organism = synthetic construct
SEQUENCE: 100
CXXXXXCXXX CXCXXXXCXX XXCCXXXXXX XXXXCXXCC                                39

SEQ ID NO: 101           moltype = AA  length = 38
FEATURE                  Location/Qualifiers
REGION                   2..6
                         note = misc_feature - Xaa can be any naturally occurring
                          amino acid
SITE                     8
                         note = misc_feature - Xaa can be any naturally occurring
                          amino acid
SITE                     10
                         note = misc_feature - Xaa can be any naturally occurring
                          amino acid
SITE                     12
                         note = misc_feature - Xaa can be any naturally occurring
                          amino acid
REGION                   14..16
                         note = misc_feature - Xaa can be any naturally occurring
                          amino acid
REGION                   19..21
                         note = misc_feature - Xaa can be any naturally occurring
                          amino acid
REGION                   23..26
                         note = misc_feature - Xaa can be any naturally occurring
                          amino acid
REGION                   28..37
                         note = misc_feature - Xaa can be any naturally occurring
                          amino acid
source                   1..38
                         mol_type = protein
                         organism = synthetic construct
SEQUENCE: 101
CXXXXXCXCX CXCXXXCCXX XCXXXXCXXX XXXXXXXC                                 38

SEQ ID NO: 102           moltype = AA  length = 37
FEATURE                  Location/Qualifiers
REGION                   2..10
                         note = misc_feature - Xaa can be any naturally occurring
                          amino acid
REGION                   14..16
                         note = misc_feature - Xaa can be any naturally occurring
                          amino acid
REGION                   18..21
                         note = misc_feature - Xaa can be any naturally occurring
                          amino acid
REGION                   25..29
                         note = misc_feature - Xaa can be any naturally occurring
                          amino acid
REGION                   31..36
                         note = misc_feature - Xaa can be any naturally occurring
                          amino acid
source                   1..37
                         mol_type = protein
                         organism = synthetic construct
SEQUENCE: 102
CXXXXXXXXX CCCXXXCXXX XCCCXXXXXC XXXXXC                                   37

SEQ ID NO: 103           moltype = AA  length = 36
FEATURE                  Location/Qualifiers
REGION                   3..10
                         note = misc_feature - Xaa can be any naturally occurring
                          amino acid
REGION                   12..16
                         note = misc_feature - Xaa can be any naturally occurring
                          amino acid
REGION                   18..21
                         note = misc_feature - Xaa can be any naturally occurring
                          amino acid
```

```
REGION                   23..25
                         note = misc_feature - Xaa can be any naturally occurring
                          amino acid
REGION                   27..30
                         note = misc_feature - Xaa can be any naturally occurring
                          amino acid
SITE                     33
                         note = misc_feature - Xaa can be any naturally occurring
                          amino acid
SITE                     35
                         note = misc_feature - Xaa can be any naturally occurring
                          amino acid
source                   1..36
                         mol_type = protein
                         organism = synthetic construct
SEQUENCE: 103
CCXXXXXXXX CXXXXXCXXX XCXXXCXXXX CCXCXC                                  36

SEQ ID NO: 104           moltype = AA  length = 41
FEATURE                  Location/Qualifiers
REGION                   3..8
                         note = misc_feature - Xaa can be any naturally occurring
                          amino acid
REGION                   11..15
                         note = misc_feature - Xaa can be any naturally occurring
                          amino acid
REGION                   19..22
                         note = misc_feature - Xaa can be any naturally occurring
                          amino acid
REGION                   24..27
                         note = misc_feature - Xaa can be any naturally occurring
                          amino acid
REGION                   29..40
                         note = misc_feature - Xaa can be any naturally occurring
                          amino acid
source                   1..41
                         mol_type = protein
                         organism = synthetic construct
SEQUENCE: 104
CCXXXXXXCC XXXXXCCCXX XXCXXXXCXX XXXXXXXXXX C                            41

SEQ ID NO: 105           moltype = AA  length = 36
FEATURE                  Location/Qualifiers
REGION                   2..7
                         note = misc_feature - Xaa can be any naturally occurring
                          amino acid
REGION                   9..10
                         note = misc_feature - Xaa can be any naturally occurring
                          amino acid
REGION                   12..14
                         note = misc_feature - Xaa can be any naturally occurring
                          amino acid
REGION                   18..21
                         note = misc_feature - Xaa can be any naturally occurring
                          amino acid
REGION                   23..27
                         note = misc_feature - Xaa can be any naturally occurring
                          amino acid
REGION                   29..31
                         note = misc_feature - Xaa can be any naturally occurring
                          amino acid
REGION                   33..35
                         note = misc_feature - Xaa can be any naturally occurring
                          amino acid
source                   1..36
                         mol_type = protein
                         organism = synthetic construct
SEQUENCE: 105
CXXXXXXCXX CXXXCCCXXX XCXXXXXCXX XCXXXC                                  36

SEQ ID NO: 106           moltype = AA  length = 39
FEATURE                  Location/Qualifiers
REGION                   2..4
                         note = misc_feature - Xaa can be any naturally occurring
                          amino acid
REGION                   6..10
                         note = misc_feature - Xaa can be any naturally occurring
                          amino acid
REGION                   12..17
```

```
                              note = misc_feature - Xaa can be any naturally occurring
                               amino acid
REGION                        19..22
                              note = misc_feature - Xaa can be any naturally occurring
                               amino acid
SITE                          25
                              note = misc_feature - Xaa can be any naturally occurring
                               amino acid
REGION                        27..31
                              note = misc_feature - Xaa can be any naturally occurring
                               amino acid
REGION                        33..36
                              note = misc_feature - Xaa can be any naturally occurring
                               amino acid
SITE                          38
                              note = misc_feature - Xaa can be any naturally occurring
                               amino acid
source                        1..39
                              mol_type = protein
                              organism = synthetic construct
SEQUENCE: 106
CXXXCXXXXX CXXXXXXCXX XXCCXCXXXX XCXXXXCXC                         39

SEQ ID NO: 107                moltype = AA  length = 41
FEATURE                       Location/Qualifiers
REGION                        2..5
                              note = misc_feature - Xaa can be any naturally occurring
                               amino acid
REGION                        7..10
                              note = misc_feature - Xaa can be any naturally occurring
                               amino acid
REGION                        13..16
                              note = misc_feature - Xaa can be any naturally occurring
                               amino acid
REGION                        18..21
                              note = misc_feature - Xaa can be any naturally occurring
                               amino acid
SITE                          23
                              note = misc_feature - Xaa can be any naturally occurring
                               amino acid
REGION                        25..35
                              note = misc_feature - Xaa can be any naturally occurring
                               amino acid
REGION                        37..38
                              note = misc_feature - Xaa can be any naturally occurring
                               amino acid
SITE                          40
                              note = misc_feature - Xaa can be any naturally occurring
                               amino acid
source                        1..41
                              mol_type = protein
                              organism = synthetic construct
SEQUENCE: 107
CXXXXCXXXX CCXXXXCXXX XCXCXXXXXX XXXXXCXXCX C                       41

SEQ ID NO: 108                moltype = AA  length = 36
FEATURE                       Location/Qualifiers
REGION                        2..6
                              note = misc_feature - Xaa can be any naturally occurring
                               amino acid
REGION                        8..9
                              note = misc_feature - Xaa can be any naturally occurring
                               amino acid
REGION                        12..16
                              note = misc_feature - Xaa can be any naturally occurring
                               amino acid
REGION                        18..21
                              note = misc_feature - Xaa can be any naturally occurring
                               amino acid
REGION                        24..26
                              note = misc_feature - Xaa can be any naturally occurring
                               amino acid
REGION                        29..35
                              note = misc_feature - Xaa can be any naturally occurring
                               amino acid
source                        1..36
                              mol_type = protein
                              organism = synthetic construct
SEQUENCE: 108
```

-continued

```
CXXXXXCXXC CXXXXXCXXX XCCXXXCCXX XXXXXC                                   36

SEQ ID NO: 109          moltype = AA  length = 38
FEATURE                 Location/Qualifiers
REGION                  2..6
                        note = misc_feature - Xaa can be any naturally occurring
                         amino acid
REGION                  8..12
                        note = misc_feature - Xaa can be any naturally occurring
                         amino acid
REGION                  14..16
                        note = misc_feature - Xaa can be any naturally occurring
                         amino acid
REGION                  18..19
                        note = misc_feature - Xaa can be any naturally occurring
                         amino acid
SITE                    21
                        note = misc_feature - Xaa can be any naturally occurring
                         amino acid
REGION                  24..27
                        note = misc_feature - Xaa can be any naturally occurring
                         amino acid
REGION                  29..35
                        note = misc_feature - Xaa can be any naturally occurring
                         amino acid
SITE                    37
                        note = misc_feature - Xaa can be any naturally occurring
                         amino acid
source                  1..38
                        mol_type = protein
                        organism = synthetic construct
SEQUENCE: 109
CXXXXXCXXX XXCXXXCXXC XCCXXXXCXX XXXXXCXC                                 38

SEQ ID NO: 110          moltype = AA  length = 37
FEATURE                 Location/Qualifiers
REGION                  2..4
                        note = misc_feature - Xaa can be any naturally occurring
                         amino acid
REGION                  6..12
                        note = misc_feature - Xaa can be any naturally occurring
                         amino acid
REGION                  14..16
                        note = misc_feature - Xaa can be any naturally occurring
                         amino acid
REGION                  18..21
                        note = misc_feature - Xaa can be any naturally occurring
                         amino acid
SITE                    24
                        note = misc_feature - Xaa can be any naturally occurring
                         amino acid
REGION                  26..27
                        note = misc_feature - Xaa can be any naturally occurring
                         amino acid
REGION                  29..33
                        note = misc_feature - Xaa can be any naturally occurring
                         amino acid
REGION                  35..36
                        note = misc_feature - Xaa can be any naturally occurring
                         amino acid
source                  1..37
                        mol_type = protein
                        organism = synthetic construct
SEQUENCE: 110
CXXXCXXXXX XXCXXXCXXX XCCXCXXCXX XXXCXXC                                  37

SEQ ID NO: 111          moltype = AA  length = 38
FEATURE                 Location/Qualifiers
REGION                  2..10
                        note = misc_feature - Xaa can be any naturally occurring
                         amino acid
REGION                  12..14
                        note = misc_feature - Xaa can be any naturally occurring
                         amino acid
SITE                    16
                        note = misc_feature - Xaa can be any naturally occurring
                         amino acid
REGION                  18..21
                        note = misc_feature - Xaa can be any naturally occurring
```

```
                              amino acid
REGION                        24..28
                              note = misc_feature - Xaa can be any naturally occurring
                                amino acid
REGION                        32..37
                              note = misc_feature - Xaa can be any naturally occurring
                                amino acid
source                        1..38
                              mol_type = protein
                              organism = synthetic construct
SEQUENCE: 111
CXXXXXXXX CXXXCXCXXX XCCXXXXXCC CXXXXXXC                                38

SEQ ID NO: 112                moltype = AA  length = 38
FEATURE                       Location/Qualifiers
REGION                        2..10
                              note = misc_feature - Xaa can be any naturally occurring
                                amino acid
REGION                        12..14
                              note = misc_feature - Xaa can be any naturally occurring
                                amino acid
SITE                          16
                              note = misc_feature - Xaa can be any naturally occurring
                                amino acid
REGION                        18..19
                              note = misc_feature - Xaa can be any naturally occurring
                                amino acid
SITE                          21
                              note = misc_feature - Xaa can be any naturally occurring
                                amino acid
REGION                        24..29
                              note = misc_feature - Xaa can be any naturally occurring
                                amino acid
REGION                        31..33
                              note = misc_feature - Xaa can be any naturally occurring
                                amino acid
REGION                        35..37
                              note = misc_feature - Xaa can be any naturally occurring
                                amino acid
source                        1..38
                              mol_type = protein
                              organism = synthetic construct
SEQUENCE: 112
CXXXXXXXX CXXXCXCXXC XCCXXXXXXC XXXCXXXC                                38

SEQ ID NO: 113                moltype = AA  length = 33
FEATURE                       Location/Qualifiers
REGION                        2..9
                              note = misc_feature - Xaa can be any naturally occurring
                                amino acid
SITE                          12
                              note = misc_feature - Xaa can be any naturally occurring
                                amino acid
REGION                        14..16
                              note = misc_feature - Xaa can be any naturally occurring
                                amino acid
REGION                        19..21
                              note = misc_feature - Xaa can be any naturally occurring
                                amino acid
SITE                          23
                              note = misc_feature - Xaa can be any naturally occurring
                                amino acid
REGION                        25..27
                              note = misc_feature - Xaa can be any naturally occurring
                                amino acid
REGION                        29..32
                              note = misc_feature - Xaa can be any naturally occurring
                                amino acid
source                        1..33
                              mol_type = protein
                              organism = synthetic construct
SEQUENCE: 113
CXXXXXXXXC CXCXXXCCXX XCXCXXXCXX XXC                                    33

SEQ ID NO: 114                moltype = AA  length = 34
FEATURE                       Location/Qualifiers
REGION                        2..10
                              note = misc_feature - Xaa can be any naturally occurring
                                amino acid
```

-continued

```
REGION                13..16
                      note = misc_feature - Xaa can be any naturally occurring
                       amino acid
REGION                18..19
                      note = misc_feature - Xaa can be any naturally occurring
                       amino acid
SITE                  21
                      note = misc_feature - Xaa can be any naturally occurring
                       amino acid
SITE                  24
                      note = misc_feature - Xaa can be any naturally occurring
                       amino acid
REGION                26..29
                      note = misc_feature - Xaa can be any naturally occurring
                       amino acid
REGION                31..33
                      note = misc_feature - Xaa can be any naturally occurring
                       amino acid
source                1..34
                      mol_type = protein
                      organism = synthetic construct
SEQUENCE: 114
CXXXXXXXXX CCXXXXCXXC XCCXCXXXXC XXXC                             34

SEQ ID NO: 115        moltype = AA  length = 37
FEATURE               Location/Qualifiers
REGION                2..11
                      note = misc_feature - Xaa can be any naturally occurring
                       amino acid
SITE                  13
                      note = misc_feature - Xaa can be any naturally occurring
                       amino acid
REGION                15..17
                      note = misc_feature - Xaa can be any naturally occurring
                       amino acid
REGION                19..20
                      note = misc_feature - Xaa can be any naturally occurring
                       amino acid
SITE                  22
                      note = misc_feature - Xaa can be any naturally occurring
                       amino acid
REGION                25..28
                      note = misc_feature - Xaa can be any naturally occurring
                       amino acid
REGION                30..34
                      note = misc_feature - Xaa can be any naturally occurring
                       amino acid
SITE                  36
                      note = misc_feature - Xaa can be any naturally occurring
                       amino acid
source                1..37
                      mol_type = protein
                      organism = synthetic construct
SEQUENCE: 115
CXXXXXXXXX XCXCXXXCXX CXCCXXXXCX XXXXCXC                          37

SEQ ID NO: 116        moltype = AA  length = 36
FEATURE               Location/Qualifiers
REGION                2..10
                      note = misc_feature - Xaa can be any naturally occurring
                       amino acid
SITE                  12
                      note = misc_feature - Xaa can be any naturally occurring
                       amino acid
REGION                14..16
                      note = misc_feature - Xaa can be any naturally occurring
                       amino acid
REGION                18..19
                      note = misc_feature - Xaa can be any naturally occurring
                       amino acid
SITE                  21
                      note = misc_feature - Xaa can be any naturally occurring
                       amino acid
REGION                24..27
                      note = misc_feature - Xaa can be any naturally occurring
                       amino acid
REGION                29..33
                      note = misc_feature - Xaa can be any naturally occurring
                       amino acid
```

-continued

```
SITE                       35
                           note = misc_feature - Xaa can be any naturally occurring
                            amino acid
source                     1..36
                           mol_type = protein
                           organism = synthetic construct
SEQUENCE: 116
CXXXXXXXXX CXCXXXCXXC XCCXXXXCXX XXXCXC                          36

SEQ ID NO: 117             moltype = AA  length = 34
FEATURE                    Location/Qualifiers
REGION                     2..7
                           note = misc_feature - Xaa can be any naturally occurring
                            amino acid
SITE                       10
                           note = misc_feature - Xaa can be any naturally occurring
                            amino acid
REGION                     12..16
                           note = misc_feature - Xaa can be any naturally occurring
                            amino acid
REGION                     18..21
                           note = misc_feature - Xaa can be any naturally occurring
                            amino acid
SITE                       24
                           note = misc_feature - Xaa can be any naturally occurring
                            amino acid
REGION                     26..30
                           note = misc_feature - Xaa can be any naturally occurring
                            amino acid
REGION                     32..33
                           note = misc_feature - Xaa can be any naturally occurring
                            amino acid
source                     1..34
                           mol_type = protein
                           organism = synthetic construct
SEQUENCE: 117
CXXXXXXCCX CXXXXXCXXX XCCXCXXXXX CXXC                            34

SEQ ID NO: 118             moltype = AA  length = 28
FEATURE                    Location/Qualifiers
REGION                     2..7
                           note = misc_feature - Xaa can be any naturally occurring
                            amino acid
SITE                       10
                           note = misc_feature - Xaa can be any naturally occurring
                            amino acid
REGION                     12..14
                           note = misc_feature - Xaa can be any naturally occurring
                            amino acid
SITE                       16
                           note = misc_feature - Xaa can be any naturally occurring
                            amino acid
REGION                     19..21
                           note = misc_feature - Xaa can be any naturally occurring
                            amino acid
REGION                     23..26
                           note = misc_feature - Xaa can be any naturally occurring
                            amino acid
source                     1..28
                           mol_type = protein
                           organism = synthetic construct
SEQUENCE: 118
CXXXXXXCCX CXXXCXCCXX XCXXXXCC                                   28

SEQ ID NO: 119             moltype = AA  length = 36
FEATURE                    Location/Qualifiers
REGION                     2..7
                           note = misc_feature - Xaa can be any naturally occurring
                            amino acid
SITE                       10
                           note = misc_feature - Xaa can be any naturally occurring
                            amino acid
REGION                     12..14
                           note = misc_feature - Xaa can be any naturally occurring
                            amino acid
SITE                       16
                           note = misc_feature - Xaa can be any naturally occurring
                            amino acid
REGION                     18..19
```

```
                        note = misc_feature - Xaa can be any naturally occurring
                           amino acid
SITE                    21
                        note = misc_feature - Xaa can be any naturally occurring
                           amino acid
REGION                  23..26
                        note = misc_feature - Xaa can be any naturally occurring
                           amino acid
REGION                  28..35
                        note = misc_feature - Xaa can be any naturally occurring
                           amino acid
source                  1..36
                        mol_type = protein
                        organism = synthetic construct
SEQUENCE: 119
CXXXXXXCCX CXXXCXCXXC XCXXXXCXXX XXXXXC                          36

SEQ ID NO: 120          moltype = AA  length = 29
FEATURE                 Location/Qualifiers
REGION                  2..5
                        note = misc_feature - Xaa can be any naturally occurring
                           amino acid
REGION                  7..8
                        note = misc_feature - Xaa can be any naturally occurring
                           amino acid
REGION                  11..13
                        note = misc_feature - Xaa can be any naturally occurring
                           amino acid
SITE                    15
                        note = misc_feature - Xaa can be any naturally occurring
                           amino acid
REGION                  17..20
                        note = misc_feature - Xaa can be any naturally occurring
                           amino acid
REGION                  23..24
                        note = misc_feature - Xaa can be any naturally occurring
                           amino acid
REGION                  26..28
                        note = misc_feature - Xaa can be any naturally occurring
                           amino acid
source                  1..29
                        mol_type = protein
                        organism = synthetic construct
SEQUENCE: 120
CXXXXCXXCC XXXCXCXXXX CCXXCXXXC                                  29

SEQ ID NO: 121          moltype = AA  length = 32
FEATURE                 Location/Qualifiers
REGION                  2..4
                        note = misc_feature - Xaa can be any naturally occurring
                           amino acid
REGION                  6..10
                        note = misc_feature - Xaa can be any naturally occurring
                           amino acid
REGION                  12..14
                        note = misc_feature - Xaa can be any naturally occurring
                           amino acid
REGION                  18..21
                        note = misc_feature - Xaa can be any naturally occurring
                           amino acid
REGION                  23..31
                        note = misc_feature - Xaa can be any naturally occurring
                           amino acid
source                  1..32
                        mol_type = protein
                        organism = synthetic construct
SEQUENCE: 121
CXXXCXXXXX CXXXCCCXXX XCXXXXXXXX XC                              32

SEQ ID NO: 122          moltype = AA  length = 29
FEATURE                 Location/Qualifiers
REGION                  3..11
                        note = misc_feature - Xaa can be any naturally occurring
                           amino acid
REGION                  13..15
                        note = misc_feature - Xaa can be any naturally occurring
                           amino acid
SITE                    17
                        note = misc_feature - Xaa can be any naturally occurring
```

-continued

```
                        amino acid
REGION                  20..22
                        note = misc_feature - Xaa can be any naturally occurring
                         amino acid
REGION                  24..28
                        note = misc_feature - Xaa can be any naturally occurring
                         amino acid
source                  1..29
                        mol_type = protein
                        organism = synthetic construct
SEQUENCE: 122
CCXXXXXXXX XCXXXCXCCX XXCXXXXXC                                    29

SEQ ID NO: 123          moltype = AA  length = 35
FEATURE                 Location/Qualifiers
REGION                  2..10
                        note = misc_feature - Xaa can be any naturally occurring
                         amino acid
REGION                  12..13
                        note = misc_feature - Xaa can be any naturally occurring
                         amino acid
REGION                  15..17
                        note = misc_feature - Xaa can be any naturally occurring
                         amino acid
REGION                  19..22
                        note = misc_feature - Xaa can be any naturally occurring
                         amino acid
REGION                  25..28
                        note = misc_feature - Xaa can be any naturally occurring
                         amino acid
REGION                  30..34
                        note = misc_feature - Xaa can be any naturally occurring
                         amino acid
source                  1..35
                        mol_type = protein
                        organism = synthetic construct
SEQUENCE: 123
CXXXXXXXXX CXXCXXXCXX XXCCXXXXCX XXXXC                             35

SEQ ID NO: 124          moltype = AA  length = 39
FEATURE                 Location/Qualifiers
REGION                  2..10
                        note = misc_feature - Xaa can be any naturally occurring
                         amino acid
REGION                  12..18
                        note = misc_feature - Xaa can be any naturally occurring
                         amino acid
REGION                  20..23
                        note = misc_feature - Xaa can be any naturally occurring
                         amino acid
SITE                    26
                        note = misc_feature - Xaa can be any naturally occurring
                         amino acid
REGION                  28..34
                        note = misc_feature - Xaa can be any naturally occurring
                         amino acid
REGION                  36..38
                        note = misc_feature - Xaa can be any naturally occurring
                         amino acid
source                  1..39
                        mol_type = protein
                        organism = synthetic construct
SEQUENCE: 124
CXXXXXXXXX CXXXXXXXCX XXXCCXCXXX XXXXCXXXC                         39

SEQ ID NO: 125          moltype = AA  length = 35
FEATURE                 Location/Qualifiers
REGION                  2..10
                        note = misc_feature - Xaa can be any naturally occurring
                         amino acid
REGION                  12..14
                        note = misc_feature - Xaa can be any naturally occurring
                         amino acid
REGION                  18..27
                        note = misc_feature - Xaa can be any naturally occurring
                         amino acid
REGION                  29..30
                        note = misc_feature - Xaa can be any naturally occurring
                         amino acid
```

-continued

```
REGION                  32..34
                        note = misc_feature - Xaa can be any naturally occurring
                         amino acid
source                  1..35
                        mol_type = protein
                        organism = synthetic construct
SEQUENCE: 125
CXXXXXXXX CXXXCCCXXX XXXXXXXCXX CXXXC                                  35

SEQ ID NO: 126          moltype = AA  length = 41
FEATURE                 Location/Qualifiers
REGION                  2..4
                        note = misc_feature - Xaa can be any naturally occurring
                         amino acid
REGION                  6..10
                        note = misc_feature - Xaa can be any naturally occurring
                         amino acid
REGION                  12..16
                        note = misc_feature - Xaa can be any naturally occurring
                         amino acid
REGION                  18..21
                        note = misc_feature - Xaa can be any naturally occurring
                         amino acid
REGION                  24..33
                        note = misc_feature - Xaa can be any naturally occurring
                         amino acid
REGION                  35..40
                        note = misc_feature - Xaa can be any naturally occurring
                         amino acid
source                  1..41
                        mol_type = protein
                        organism = synthetic construct
SEQUENCE: 126
CXXXCXXXXX CXXXXXCXXX XCCXXXXXXX XXXCXXXXXX C                          41

SEQ ID NO: 127          moltype = AA  length = 36
FEATURE                 Location/Qualifiers
REGION                  2..10
                        note = misc_feature - Xaa can be any naturally occurring
                         amino acid
REGION                  12..16
                        note = misc_feature - Xaa can be any naturally occurring
                         amino acid
REGION                  18..21
                        note = misc_feature - Xaa can be any naturally occurring
                         amino acid
SITE                    24
                        note = misc_feature - Xaa can be any naturally occurring
                         amino acid
REGION                  26..30
                        note = misc_feature - Xaa can be any naturally occurring
                         amino acid
REGION                  32..35
                        note = misc_feature - Xaa can be any naturally occurring
                         amino acid
source                  1..36
                        mol_type = protein
                        organism = synthetic construct
SEQUENCE: 127
CXXXXXXXXX CXXXXXCXXX XCCXCXXXXX CXXXXC                                36

SEQ ID NO: 128          moltype = AA  length = 36
FEATURE                 Location/Qualifiers
REGION                  2..8
                        note = misc_feature - Xaa can be any naturally occurring
                         amino acid
SITE                    10
                        note = misc_feature - Xaa can be any naturally occurring
                         amino acid
REGION                  12..17
                        note = misc_feature - Xaa can be any naturally occurring
                         amino acid
REGION                  19..22
                        note = misc_feature - Xaa can be any naturally occurring
                         amino acid
REGION                  26..35
                        note = misc_feature - Xaa can be any naturally occurring
                         amino acid
source                  1..36
```

-continued

```
                        mol_type = protein
                        organism = synthetic construct
SEQUENCE: 128
CXXXXXXXCX XXXXXXCXX XXCCCXXXXX XXXXXC                            36

SEQ ID NO: 129          moltype = AA  length = 32
FEATURE                 Location/Qualifiers
REGION                  2..9
                        note = misc_feature - Xaa can be any naturally occurring
                         amino acid
REGION                  11..12
                        note = misc_feature - Xaa can be any naturally occurring
                         amino acid
REGION                  14..17
                        note = misc_feature - Xaa can be any naturally occurring
                         amino acid
REGION                  20..23
                        note = misc_feature - Xaa can be any naturally occurring
                         amino acid
REGION                  25..27
                        note = misc_feature - Xaa can be any naturally occurring
                         amino acid
REGION                  29..31
                        note = misc_feature - Xaa can be any naturally occurring
                         amino acid
source                  1..32
                        mol_type = protein
                        organism = synthetic construct
SEQUENCE: 129
CXXXXXXXXC XXCXXXXCCX XXXCXXXCXX XC                               32

SEQ ID NO: 130          moltype = AA  length = 36
FEATURE                 Location/Qualifiers
REGION                  2..8
                        note = misc_feature - Xaa can be any naturally occurring
                         amino acid
REGION                  10..14
                        note = misc_feature - Xaa can be any naturally occurring
                         amino acid
SITE                    16
                        note = misc_feature - Xaa can be any naturally occurring
                         amino acid
REGION                  18..21
                        note = misc_feature - Xaa can be any naturally occurring
                         amino acid
REGION                  24..30
                        note = misc_feature - Xaa can be any naturally occurring
                         amino acid
REGION                  32..35
                        note = misc_feature - Xaa can be any naturally occurring
                         amino acid
source                  1..36
                        mol_type = protein
                        organism = synthetic construct
SEQUENCE: 130
CXXXXXXXCX XXXXCXCXXX XCCXXXXXXX CXXXXC                           36

SEQ ID NO: 131          moltype = AA  length = 36
FEATURE                 Location/Qualifiers
REGION                  2..12
                        note = misc_feature - Xaa can be any naturally occurring
                         amino acid
REGION                  14..16
                        note = misc_feature - Xaa can be any naturally occurring
                         amino acid
REGION                  18..21
                        note = misc_feature - Xaa can be any naturally occurring
                         amino acid
REGION                  25..32
                        note = misc_feature - Xaa can be any naturally occurring
                         amino acid
REGION                  34..35
                        note = misc_feature - Xaa can be any naturally occurring
                         amino acid
source                  1..36
                        mol_type = protein
                        organism = synthetic construct
SEQUENCE: 131
CXXXXXXXXX XXCXXXXCXXX XCCCXXXXXX XXCXXC                          36
```

```
SEQ ID NO: 132            moltype = AA  length = 41
FEATURE                   Location/Qualifiers
REGION                    2..3
                          note = misc_feature - Xaa can be any naturally occurring
                           amino acid
REGION                    5..7
                          note = misc_feature - Xaa can be any naturally occurring
                           amino acid
REGION                    9..12
                          note = misc_feature - Xaa can be any naturally occurring
                           amino acid
REGION                    15..18
                          note = misc_feature - Xaa can be any naturally occurring
                           amino acid
REGION                    20..24
                          note = misc_feature - Xaa can be any naturally occurring
                           amino acid
REGION                    26..40
                          note = misc_feature - Xaa can be any naturally occurring
                           amino acid
source                    1..41
                          mol_type = protein
                          organism = synthetic construct
SEQUENCE: 132
CXXCXXXCXX XXCCXXXXCX XXXXCXXXXX XXXXXXXXXX C                        41

SEQ ID NO: 133            moltype = AA  length = 31
FEATURE                   Location/Qualifiers
REGION                    2..10
                          note = misc_feature - Xaa can be any naturally occurring
                           amino acid
REGION                    12..16
                          note = misc_feature - Xaa can be any naturally occurring
                           amino acid
REGION                    18..21
                          note = misc_feature - Xaa can be any naturally occurring
                           amino acid
REGION                    24..30
                          note = misc_feature - Xaa can be any naturally occurring
                           amino acid
source                    1..31
                          mol_type = protein
                          organism = synthetic construct
SEQUENCE: 133
CXXXXXXXXX CXXXXXCXXX XCCXXXXXXX C                                   31

SEQ ID NO: 134            moltype = AA  length = 33
FEATURE                   Location/Qualifiers
REGION                    2..10
                          note = misc_feature - Xaa can be any naturally occurring
                           amino acid
REGION                    12..18
                          note = misc_feature - Xaa can be any naturally occurring
                           amino acid
REGION                    20..22
                          note = misc_feature - Xaa can be any naturally occurring
                           amino acid
REGION                    24..25
                          note = misc_feature - Xaa can be any naturally occurring
                           amino acid
REGION                    27..32
                          note = misc_feature - Xaa can be any naturally occurring
                           amino acid
source                    1..33
                          mol_type = protein
                          organism = synthetic construct
SEQUENCE: 134
CXXXXXXXXX CXXXXXXXCX XXCXXCXXXX XXC                                 33

SEQ ID NO: 135            moltype = AA  length = 38
FEATURE                   Location/Qualifiers
REGION                    2..10
                          note = misc_feature - Xaa can be any naturally occurring
                           amino acid
REGION                    12..16
                          note = misc_feature - Xaa can be any naturally occurring
                           amino acid
REGION                    18..21
```

-continued

```
                          note = misc_feature - Xaa can be any naturally occurring
                           amino acid
REGION                    24..37
                          note = misc_feature - Xaa can be any naturally occurring
                           amino acid
source                    1..38
                          mol_type = protein
                          organism = synthetic construct
SEQUENCE: 135
CXXXXXXXXX CXXXXXCXXX XCCXXXXXXX XXXXXXXC                              38

SEQ ID NO: 136            moltype = AA  length = 32
FEATURE                   Location/Qualifiers
REGION                    2..10
                          note = misc_feature - Xaa can be any naturally occurring
                           amino acid
REGION                    12..16
                          note = misc_feature - Xaa can be any naturally occurring
                           amino acid
REGION                    18..21
                          note = misc_feature - Xaa can be any naturally occurring
                           amino acid
REGION                    24..31
                          note = misc_feature - Xaa can be any naturally occurring
                           amino acid
source                    1..32
                          mol_type = protein
                          organism = synthetic construct
SEQUENCE: 136
CXXXXXXXXX CXXXXXCXXX XCCXXXXXXX XC                                    32

SEQ ID NO: 137            moltype = AA  length = 26
FEATURE                   Location/Qualifiers
REGION                    2..10
                          note = misc_feature - Xaa can be any naturally occurring
                           amino acid
REGION                    12..17
                          note = misc_feature - Xaa can be any naturally occurring
                           amino acid
REGION                    19..22
                          note = misc_feature - Xaa can be any naturally occurring
                           amino acid
SITE                      25
                          note = misc_feature - Xaa can be any naturally occurring
                           amino acid
source                    1..26
                          mol_type = protein
                          organism = synthetic construct
SEQUENCE: 137
CXXXXXXXXX CXXXXXCXX XXCCXC                                            26

SEQ ID NO: 138            moltype = AA  length = 33
FEATURE                   Location/Qualifiers
REGION                    2..6
                          note = misc_feature - Xaa can be any naturally occurring
                           amino acid
REGION                    9..15
                          note = misc_feature - Xaa can be any naturally occurring
                           amino acid
REGION                    17..20
                          note = misc_feature - Xaa can be any naturally occurring
                           amino acid
REGION                    22..33
                          note = misc_feature - Xaa can be any naturally occurring
                           amino acid
source                    1..33
                          mol_type = protein
                          organism = synthetic construct
SEQUENCE: 138
CXXXXXCCXX XXXXXCXXXX CXXXXXXXXX XXX                                   33

SEQ ID NO: 139            moltype = AA  length = 27
FEATURE                   Location/Qualifiers
REGION                    2..11
                          note = misc_feature - Xaa can be any naturally occurring
                           amino acid
REGION                    13..15
                          note = misc_feature - Xaa can be any naturally occurring
                           amino acid
```

```
REGION                   17..20
                         note = misc_feature - Xaa can be any naturally occurring
                          amino acid
REGION                   23..26
                         note = misc_feature - Xaa can be any naturally occurring
                          amino acid
source                   1..27
                         mol_type = protein
                         organism = synthetic construct
SEQUENCE: 139
CXXXXXXXXX XCXXXCXXXX CCXXXXC                                         27

SEQ ID NO: 140           moltype = AA  length = 28
FEATURE                  Location/Qualifiers
REGION                   2..10
                         note = misc_feature - Xaa can be any naturally occurring
                          amino acid
REGION                   12..15
                         note = misc_feature - Xaa can be any naturally occurring
                          amino acid
REGION                   18..22
                         note = misc_feature - Xaa can be any naturally occurring
                          amino acid
REGION                   24..27
                         note = misc_feature - Xaa can be any naturally occurring
                          amino acid
source                   1..28
                         mol_type = protein
                         organism = synthetic construct
SEQUENCE: 140
CXXXXXXXXX CXXXXCCXXX XXCXXXXC                                        28

SEQ ID NO: 141           moltype = AA  length = 31
FEATURE                  Location/Qualifiers
REGION                   2..11
                         note = misc_feature - Xaa can be any naturally occurring
                          amino acid
REGION                   13..15
                         note = misc_feature - Xaa can be any naturally occurring
                          amino acid
REGION                   17..20
                         note = misc_feature - Xaa can be any naturally occurring
                          amino acid
REGION                   22..28
                         note = misc_feature - Xaa can be any naturally occurring
                          amino acid
SITE                     30
                         note = misc_feature - Xaa can be any naturally occurring
                          amino acid
source                   1..31
                         mol_type = protein
                         organism = synthetic construct
SEQUENCE: 141
CXXXXXXXXX XCXXXCXXXX CXXXXXXXCX C                                    31

SEQ ID NO: 142           moltype = AA  length = 27
FEATURE                  Location/Qualifiers
REGION                   2..8
                         note = misc_feature - Xaa can be any naturally occurring
                          amino acid
REGION                   10..16
                         note = misc_feature - Xaa can be any naturally occurring
                          amino acid
REGION                   18..19
                         note = misc_feature - Xaa can be any naturally occurring
                          amino acid
REGION                   21..22
                         note = misc_feature - Xaa can be any naturally occurring
                          amino acid
REGION                   24..26
                         note = misc_feature - Xaa can be any naturally occurring
                          amino acid
source                   1..27
                         mol_type = protein
                         organism = synthetic construct
SEQUENCE: 142
CXXXXXXXCX XXXXXXCXXC XXCXXXC                                         27

SEQ ID NO: 143           moltype = AA  length = 29
```

-continued

```
FEATURE              Location/Qualifiers
REGION               2..10
                     note = misc_feature - Xaa can be any naturally occurring
                      amino acid
REGION               12..15
                     note = misc_feature - Xaa can be any naturally occurring
                      amino acid
REGION               17..20
                     note = misc_feature - Xaa can be any naturally occurring
                      amino acid
REGION               23..28
                     note = misc_feature - Xaa can be any naturally occurring
                      amino acid
source               1..29
                     mol_type = protein
                     organism = synthetic construct
SEQUENCE: 143
CXXXXXXXXX CXXXXCXXXX CCXXXXXXC                                    29

SEQ ID NO: 144       moltype = AA  length = 24
FEATURE              Location/Qualifiers
REGION               2..8
                     note = misc_feature - Xaa can be any naturally occurring
                      amino acid
SITE                 10
                     note = misc_feature - Xaa can be any naturally occurring
                      amino acid
REGION               12..14
                     note = misc_feature - Xaa can be any naturally occurring
                      amino acid
SITE                 16
                     note = misc_feature - Xaa can be any naturally occurring
                      amino acid
REGION               18..23
                     note = misc_feature - Xaa can be any naturally occurring
                      amino acid
source               1..24
                     mol_type = protein
                     organism = synthetic construct
SEQUENCE: 144
CXXXXXXXCX CXXXCXCXXX XXXC                                         24

SEQ ID NO: 145       moltype = AA  length = 23
FEATURE              Location/Qualifiers
REGION               2..8
                     note = misc_feature - Xaa can be any naturally occurring
                      amino acid
SITE                 10
                     note = misc_feature - Xaa can be any naturally occurring
                      amino acid
REGION               12..15
                     note = misc_feature - Xaa can be any naturally occurring
                      amino acid
SITE                 17
                     note = misc_feature - Xaa can be any naturally occurring
                      amino acid
REGION               19..22
                     note = misc_feature - Xaa can be any naturally occurring
                      amino acid
source               1..23
                     mol_type = protein
                     organism = synthetic construct
SEQUENCE: 145
CXXXXXXXCX CXXXXCXCXX XXC                                          23

SEQ ID NO: 146       moltype = AA  length = 22
FEATURE              Location/Qualifiers
REGION               2..10
                     note = misc_feature - Xaa can be any naturally occurring
                      amino acid
REGION               12..16
                     note = misc_feature - Xaa can be any naturally occurring
                      amino acid
REGION               18..21
                     note = misc_feature - Xaa can be any naturally occurring
                      amino acid
source               1..22
                     mol_type = protein
                     organism = synthetic construct
```

```
SEQUENCE: 146
CXXXXXXXXX CXXXXXCXXX XC                                            22

SEQ ID NO: 147          moltype = AA  length = 21
FEATURE                 Location/Qualifiers
REGION                  2..4
                        note = misc_feature - Xaa can be any naturally occurring
                         amino acid
REGION                  6..11
                        note = misc_feature - Xaa can be any naturally occurring
                         amino acid
REGION                  13..20
                        note = misc_feature - Xaa can be any naturally occurring
                         amino acid
source                  1..21
                        mol_type = protein
                        organism = synthetic construct
SEQUENCE: 147
CXXXCXXXXX XCXXXXXXXX C                                             21

SEQ ID NO: 148          moltype = AA  length = 19
FEATURE                 Location/Qualifiers
REGION                  2..11
                        note = misc_feature - Xaa can be any naturally occurring
                         amino acid
SITE                    13
                        note = misc_feature - Xaa can be any naturally occurring
                         amino acid
REGION                  15..18
                        note = misc_feature - Xaa can be any naturally occurring
                         amino acid
source                  1..19
                        mol_type = protein
                        organism = synthetic construct
SEQUENCE: 148
CXXXXXXXXX XCXCXXXXC                                                19

SEQ ID NO: 149          moltype = AA  length = 18
FEATURE                 Location/Qualifiers
REGION                  2..11
                        note = misc_feature - Xaa can be any naturally occurring
                         amino acid
REGION                  14..17
                        note = misc_feature - Xaa can be any naturally occurring
                         amino acid
source                  1..18
                        mol_type = protein
                        organism = synthetic construct
SEQUENCE: 149
CXXXXXXXXX XCCXXXC                                                  18

SEQ ID NO: 150          moltype =   length =
SEQUENCE: 150
000

SEQ ID NO: 151          moltype =   length =
SEQUENCE: 151
000

SEQ ID NO: 152          moltype =   length =
SEQUENCE: 152
000

SEQ ID NO: 153          moltype = AA  length = 5
FEATURE                 Location/Qualifiers
source                  1..5
                        mol_type = protein
                        organism = synthetic construct
SEQUENCE: 153
TTVHQ                                                               5

SEQ ID NO: 154          moltype = AA  length = 5
FEATURE                 Location/Qualifiers
source                  1..5
                        mol_type = protein
                        organism = synthetic construct
SEQUENCE: 154
TSVHQ                                                               5
```

-continued

```
SEQ ID NO: 155          moltype = AA   length = 5
FEATURE                 Location/Qualifiers
source                  1..5
                        mol_type = protein
                        organism = synthetic construct
SEQUENCE: 155
SSVTQ                                                                    5

SEQ ID NO: 156          moltype = AA   length = 5
FEATURE                 Location/Qualifiers
source                  1..5
                        mol_type = protein
                        organism = synthetic construct
SEQUENCE: 156
STVHQ                                                                    5

SEQ ID NO: 157          moltype = AA   length = 5
FEATURE                 Location/Qualifiers
source                  1..5
                        mol_type = protein
                        organism = synthetic construct
SEQUENCE: 157
ATVRQ                                                                    5

SEQ ID NO: 158          moltype = AA   length = 5
FEATURE                 Location/Qualifiers
source                  1..5
                        mol_type = protein
                        organism = synthetic construct
SEQUENCE: 158
TTVYQ                                                                    5

SEQ ID NO: 159          moltype = AA   length = 5
FEATURE                 Location/Qualifiers
source                  1..5
                        mol_type = protein
                        organism = synthetic construct
SEQUENCE: 159
SPVHQ                                                                    5

SEQ ID NO: 160          moltype = AA   length = 5
FEATURE                 Location/Qualifiers
source                  1..5
                        mol_type = protein
                        organism = synthetic construct
SEQUENCE: 160
ATVYQ                                                                    5

SEQ ID NO: 161          moltype = AA   length = 5
FEATURE                 Location/Qualifiers
source                  1..5
                        mol_type = protein
                        organism = synthetic construct
SEQUENCE: 161
TAVYQ                                                                    5

SEQ ID NO: 162          moltype = AA   length = 5
FEATURE                 Location/Qualifiers
source                  1..5
                        mol_type = protein
                        organism = synthetic construct
SEQUENCE: 162
TNVHQ                                                                    5

SEQ ID NO: 163          moltype = AA   length = 5
FEATURE                 Location/Qualifiers
source                  1..5
                        mol_type = protein
                        organism = synthetic construct
SEQUENCE: 163
ATVHQ                                                                    5

SEQ ID NO: 164          moltype = AA   length = 5
FEATURE                 Location/Qualifiers
source                  1..5
                        mol_type = protein
                        organism = synthetic construct
SEQUENCE: 164
STVYQ                                                                    5
```

```
SEQ ID NO: 165          moltype = AA  length = 5
FEATURE                 Location/Qualifiers
source                  1..5
                        mol_type = protein
                        organism = synthetic construct
SEQUENCE: 165
TIVHQ                                                                        5

SEQ ID NO: 166          moltype = AA  length = 5
FEATURE                 Location/Qualifiers
source                  1..5
                        mol_type = protein
                        organism = synthetic construct
SEQUENCE: 166
AIVYQ                                                                        5

SEQ ID NO: 167          moltype = AA  length = 5
FEATURE                 Location/Qualifiers
source                  1..5
                        mol_type = protein
                        organism = synthetic construct
SEQUENCE: 167
TTVFQ                                                                        5

SEQ ID NO: 168          moltype = AA  length = 5
FEATURE                 Location/Qualifiers
source                  1..5
                        mol_type = protein
                        organism = synthetic construct
SEQUENCE: 168
AAVFQ                                                                        5

SEQ ID NO: 169          moltype = AA  length = 5
FEATURE                 Location/Qualifiers
source                  1..5
                        mol_type = protein
                        organism = synthetic construct
SEQUENCE: 169
GTVHQ                                                                        5

SEQ ID NO: 170          moltype = AA  length = 5
FEATURE                 Location/Qualifiers
source                  1..5
                        mol_type = protein
                        organism = synthetic construct
SEQUENCE: 170
ASVHQ                                                                        5

SEQ ID NO: 171          moltype = AA  length = 5
FEATURE                 Location/Qualifiers
source                  1..5
                        mol_type = protein
                        organism = synthetic construct
SEQUENCE: 171
TAVFQ                                                                        5

SEQ ID NO: 172          moltype = AA  length = 5
FEATURE                 Location/Qualifiers
source                  1..5
                        mol_type = protein
                        organism = synthetic construct
SEQUENCE: 172
ATVFQ                                                                        5

SEQ ID NO: 173          moltype = AA  length = 5
FEATURE                 Location/Qualifiers
source                  1..5
                        mol_type = protein
                        organism = synthetic construct
SEQUENCE: 173
AAAHQ                                                                        5

SEQ ID NO: 174          moltype = AA  length = 5
FEATURE                 Location/Qualifiers
source                  1..5
                        mol_type = protein
                        organism = synthetic construct
SEQUENCE: 174
```

-continued

```
VVVYQ                                                          5

SEQ ID NO: 175        moltype = AA   length = 5
FEATURE               Location/Qualifiers
source                1..5
                      mol_type = protein
                      organism = synthetic construct

SEQUENCE: 175
GTVFQ                                                          5

SEQ ID NO: 176        moltype = AA   length = 5
FEATURE               Location/Qualifiers
source                1..5
                      mol_type = protein
                      organism = synthetic construct

SEQUENCE: 176
TAVHQ                                                          5

SEQ ID NO: 177        moltype = AA   length = 5
FEATURE               Location/Qualifiers
source                1..5
                      mol_type = protein
                      organism = synthetic construct

SEQUENCE: 177
ITVHQ                                                          5

SEQ ID NO: 178        moltype = AA   length = 5
FEATURE               Location/Qualifiers
source                1..5
                      mol_type = protein
                      organism = synthetic construct

SEQUENCE: 178
ITAHQ                                                          5

SEQ ID NO: 179        moltype = AA   length = 5
FEATURE               Location/Qualifiers
source                1..5
                      mol_type = protein
                      organism = synthetic construct

SEQUENCE: 179
VTVHQ                                                          5

SEQ ID NO: 180        moltype = AA   length = 5
FEATURE               Location/Qualifiers
source                1..5
                      mol_type = protein
                      organism = synthetic construct

SEQUENCE: 180
AAVHQ                                                          5

SEQ ID NO: 181        moltype = AA   length = 5
FEATURE               Location/Qualifiers
source                1..5
                      mol_type = protein
                      organism = synthetic construct

SEQUENCE: 181
GTVYQ                                                          5

SEQ ID NO: 182        moltype = AA   length = 5
FEATURE               Location/Qualifiers
source                1..5
                      mol_type = protein
                      organism = synthetic construct

SEQUENCE: 182
TTVLQ                                                          5

SEQ ID NO: 183        moltype = AA   length = 5
FEATURE               Location/Qualifiers
source                1..5
                      mol_type = protein
                      organism = synthetic construct

SEQUENCE: 183
TTTHQ                                                          5

SEQ ID NO: 184        moltype = AA   length = 5
FEATURE               Location/Qualifiers
source                1..5
                      mol_type = protein
                      organism = synthetic construct
```

-continued

```
SEQUENCE: 184
TTDYQ                                                                    5

SEQ ID NO: 185           moltype = AA  length = 6
FEATURE                  Location/Qualifiers
source                   1..6
                         mol_type = protein
                         organism = synthetic construct
SEQUENCE: 185
CTTVHQ                                                                   6

SEQ ID NO: 186           moltype = AA  length = 6
FEATURE                  Location/Qualifiers
source                   1..6
                         mol_type = protein
                         organism = synthetic construct
SEQUENCE: 186
CTSVHQ                                                                   6

SEQ ID NO: 187           moltype = AA  length = 6
FEATURE                  Location/Qualifiers
source                   1..6
                         mol_type = protein
                         organism = synthetic construct
SEQUENCE: 187
CSSVTQ                                                                   6

SEQ ID NO: 188           moltype = AA  length = 6
FEATURE                  Location/Qualifiers
source                   1..6
                         mol_type = protein
                         organism = synthetic construct
SEQUENCE: 188
CSTVHQ                                                                   6

SEQ ID NO: 189           moltype = AA  length = 6
FEATURE                  Location/Qualifiers
source                   1..6
                         mol_type = protein
                         organism = synthetic construct
SEQUENCE: 189
CATVRQ                                                                   6

SEQ ID NO: 190           moltype = AA  length = 6
FEATURE                  Location/Qualifiers
source                   1..6
                         mol_type = protein
                         organism = synthetic construct
SEQUENCE: 190
CTTVYQ                                                                   6

SEQ ID NO: 191           moltype = AA  length = 6
FEATURE                  Location/Qualifiers
source                   1..6
                         mol_type = protein
                         organism = synthetic construct
SEQUENCE: 191
CSPVHQ                                                                   6

SEQ ID NO: 192           moltype = AA  length = 6
FEATURE                  Location/Qualifiers
source                   1..6
                         mol_type = protein
                         organism = synthetic construct
SEQUENCE: 192
CATVYQ                                                                   6

SEQ ID NO: 193           moltype = AA  length = 6
FEATURE                  Location/Qualifiers
source                   1..6
                         mol_type = protein
                         organism = synthetic construct
SEQUENCE: 193
CTAVYQ                                                                   6

SEQ ID NO: 194           moltype = AA  length = 6
FEATURE                  Location/Qualifiers
source                   1..6
                         mol_type = protein
```

```
                          organism = synthetic construct
SEQUENCE: 194
CTNVHQ                                                            6

SEQ ID NO: 195          moltype = AA  length = 6
FEATURE                 Location/Qualifiers
source                  1..6
                        mol_type = protein
                        organism = synthetic construct
SEQUENCE: 195
CATVHQ                                                            6

SEQ ID NO: 196          moltype = AA  length = 6
FEATURE                 Location/Qualifiers
source                  1..6
                        mol_type = protein
                        organism = synthetic construct
SEQUENCE: 196
CSTVYQ                                                            6

SEQ ID NO: 197          moltype = AA  length = 6
FEATURE                 Location/Qualifiers
source                  1..6
                        mol_type = protein
                        organism = synthetic construct
SEQUENCE: 197
CTIVHQ                                                            6

SEQ ID NO: 198          moltype = AA  length = 6
FEATURE                 Location/Qualifiers
source                  1..6
                        mol_type = protein
                        organism = synthetic construct
SEQUENCE: 198
CAIVYQ                                                            6

SEQ ID NO: 199          moltype = AA  length = 6
FEATURE                 Location/Qualifiers
source                  1..6
                        mol_type = protein
                        organism = synthetic construct
SEQUENCE: 199
CTTVFQ                                                            6

SEQ ID NO: 200          moltype = AA  length = 6
FEATURE                 Location/Qualifiers
source                  1..6
                        mol_type = protein
                        organism = synthetic construct
SEQUENCE: 200
CAAVFQ                                                            6

SEQ ID NO: 201          moltype = AA  length = 6
FEATURE                 Location/Qualifiers
source                  1..6
                        mol_type = protein
                        organism = synthetic construct
SEQUENCE: 201
CGTVHQ                                                            6

SEQ ID NO: 202          moltype = AA  length = 6
FEATURE                 Location/Qualifiers
source                  1..6
                        mol_type = protein
                        organism = synthetic construct
SEQUENCE: 202
CASVHQ                                                            6

SEQ ID NO: 203          moltype = AA  length = 6
FEATURE                 Location/Qualifiers
source                  1..6
                        mol_type = protein
                        organism = synthetic construct
SEQUENCE: 203
CTAVFQ                                                            6

SEQ ID NO: 204          moltype = AA  length = 6
FEATURE                 Location/Qualifiers
source                  1..6
```

-continued

```
                             mol_type = protein
                             organism = synthetic construct
SEQUENCE: 204
CATVFQ                                                                  6

SEQ ID NO: 205               moltype = AA  length = 6
FEATURE                      Location/Qualifiers
source                       1..6
                             mol_type = protein
                             organism = synthetic construct
SEQUENCE: 205
CAAAHQ                                                                  6

SEQ ID NO: 206               moltype = AA  length = 6
FEATURE                      Location/Qualifiers
source                       1..6
                             mol_type = protein
                             organism = synthetic construct
SEQUENCE: 206
CVVVYQ                                                                  6

SEQ ID NO: 207               moltype = AA  length = 6
FEATURE                      Location/Qualifiers
source                       1..6
                             mol_type = protein
                             organism = synthetic construct
SEQUENCE: 207
CGTVFQ                                                                  6

SEQ ID NO: 208               moltype = AA  length = 6
FEATURE                      Location/Qualifiers
source                       1..6
                             mol_type = protein
                             organism = synthetic construct
SEQUENCE: 208
CTAVHQ                                                                  6

SEQ ID NO: 209               moltype = AA  length = 6
FEATURE                      Location/Qualifiers
source                       1..6
                             mol_type = protein
                             organism = synthetic construct
SEQUENCE: 209
CITVHQ                                                                  6

SEQ ID NO: 210               moltype = AA  length = 6
FEATURE                      Location/Qualifiers
source                       1..6
                             mol_type = protein
                             organism = synthetic construct
SEQUENCE: 210
CITAHQ                                                                  6

SEQ ID NO: 211               moltype = AA  length = 6
FEATURE                      Location/Qualifiers
source                       1..6
                             mol_type = protein
                             organism = synthetic construct
SEQUENCE: 211
CVTVHQ                                                                  6

SEQ ID NO: 212               moltype = AA  length = 6
FEATURE                      Location/Qualifiers
source                       1..6
                             mol_type = protein
                             organism = synthetic construct
SEQUENCE: 212
CAAVHQ                                                                  6

SEQ ID NO: 213               moltype = AA  length = 6
FEATURE                      Location/Qualifiers
source                       1..6
                             mol_type = protein
                             organism = synthetic construct
SEQUENCE: 213
CGTVYQ                                                                  6

SEQ ID NO: 214               moltype = AA  length = 6
FEATURE                      Location/Qualifiers
```

-continued

```
source                     1..6
                           mol_type = protein
                           organism = synthetic construct
SEQUENCE: 214
CTTVLQ                                                                  6

SEQ ID NO: 215             moltype = AA   length = 6
FEATURE                    Location/Qualifiers
source                     1..6
                           mol_type = protein
                           organism = synthetic construct
SEQUENCE: 215
CTTTHQ                                                                  6

SEQ ID NO: 216             moltype = AA   length = 6
FEATURE                    Location/Qualifiers
source                     1..6
                           mol_type = protein
                           organism = synthetic construct
SEQUENCE: 216
CTTDYQ                                                                  6

SEQ ID NO: 217             moltype = AA   length = 8
FEATURE                    Location/Qualifiers
source                     1..8
                           mol_type = protein
                           organism = synthetic construct
SEQUENCE: 217
CYTYNYEF                                                                8

SEQ ID NO: 218             moltype = AA   length = 8
FEATURE                    Location/Qualifiers
source                     1..8
                           mol_type = protein
                           organism = synthetic construct
SEQUENCE: 218
HYTYTYDF                                                                8

SEQ ID NO: 219             moltype = AA   length = 8
FEATURE                    Location/Qualifiers
source                     1..8
                           mol_type = protein
                           organism = synthetic construct
SEQUENCE: 219
HYTYTYEW                                                                8

SEQ ID NO: 220             moltype = AA   length = 8
FEATURE                    Location/Qualifiers
source                     1..8
                           mol_type = protein
                           organism = synthetic construct
SEQUENCE: 220
KHRYTYEW                                                                8

SEQ ID NO: 221             moltype = AA   length = 8
FEATURE                    Location/Qualifiers
source                     1..8
                           mol_type = protein
                           organism = synthetic construct
SEQUENCE: 221
NYIYKYSF                                                                8

SEQ ID NO: 222             moltype = AA   length = 8
FEATURE                    Location/Qualifiers
source                     1..8
                           mol_type = protein
                           organism = synthetic construct
SEQUENCE: 222
PYIYTYQF                                                                8

SEQ ID NO: 223             moltype = AA   length = 8
FEATURE                    Location/Qualifiers
source                     1..8
                           mol_type = protein
                           organism = synthetic construct
SEQUENCE: 223
SFTYTYEW                                                                8

SEQ ID NO: 224             moltype = AA   length = 8
```

-continued

```
FEATURE                 Location/Qualifiers
source                  1..8
                        mol_type = protein
                        organism = synthetic construct
SEQUENCE: 224
SYIYIYQW                                                                  8

SEQ ID NO: 225          moltype = AA  length = 8
FEATURE                 Location/Qualifiers
source                  1..8
                        mol_type = protein
                        organism = synthetic construct
SEQUENCE: 225
SYNYTYSW                                                                  8

SEQ ID NO: 226          moltype = AA  length = 8
FEATURE                 Location/Qualifiers
source                  1..8
                        mol_type = protein
                        organism = synthetic construct
SEQUENCE: 226
SYSYSYEY                                                                  8

SEQ ID NO: 227          moltype = AA  length = 8
FEATURE                 Location/Qualifiers
source                  1..8
                        mol_type = protein
                        organism = synthetic construct
SEQUENCE: 227
SYTYNYDF                                                                  8

SEQ ID NO: 228          moltype = AA  length = 8
FEATURE                 Location/Qualifiers
source                  1..8
                        mol_type = protein
                        organism = synthetic construct
SEQUENCE: 228
SYTYNYEW                                                                  8

SEQ ID NO: 229          moltype = AA  length = 8
FEATURE                 Location/Qualifiers
source                  1..8
                        mol_type = protein
                        organism = synthetic construct
SEQUENCE: 229
SYTYNYQF                                                                  8

SEQ ID NO: 230          moltype = AA  length = 8
FEATURE                 Location/Qualifiers
source                  1..8
                        mol_type = protein
                        organism = synthetic construct
SEQUENCE: 230
SYVWTHNF                                                                  8

SEQ ID NO: 231          moltype = AA  length = 8
FEATURE                 Location/Qualifiers
source                  1..8
                        mol_type = protein
                        organism = synthetic construct
SEQUENCE: 231
TYKYVYEW                                                                  8

SEQ ID NO: 232          moltype = AA  length = 8
FEATURE                 Location/Qualifiers
source                  1..8
                        mol_type = protein
                        organism = synthetic construct
SEQUENCE: 232
TYTYTYEF                                                                  8

SEQ ID NO: 233          moltype = AA  length = 8
FEATURE                 Location/Qualifiers
source                  1..8
                        mol_type = protein
                        organism = synthetic construct
SEQUENCE: 233
TYTYTYEW                                                                  8
```

-continued

```
SEQ ID NO: 234          moltype = AA   length = 8
FEATURE                 Location/Qualifiers
source                  1..8
                        mol_type = protein
                        organism = synthetic construct
SEQUENCE: 234
VFTYTYEF                                                                8

SEQ ID NO: 235          moltype = AA   length = 6
FEATURE                 Location/Qualifiers
source                  1..6
                        mol_type = protein
                        organism = synthetic construct
SEQUENCE: 235
AYTYEW                                                                  6

SEQ ID NO: 236          moltype = AA   length = 6
FEATURE                 Location/Qualifiers
source                  1..6
                        mol_type = protein
                        organism = synthetic construct
SEQUENCE: 236
DYIYTY                                                                  6

SEQ ID NO: 237          moltype = AA   length = 6
FEATURE                 Location/Qualifiers
source                  1..6
                        mol_type = protein
                        organism = synthetic construct
SEQUENCE: 237
IHSYEF                                                                  6

SEQ ID NO: 238          moltype = AA   length = 6
FEATURE                 Location/Qualifiers
source                  1..6
                        mol_type = protein
                        organism = synthetic construct
SEQUENCE: 238
SFTYEF                                                                  6

SEQ ID NO: 239          moltype = AA   length = 6
FEATURE                 Location/Qualifiers
source                  1..6
                        mol_type = protein
                        organism = synthetic construct
SEQUENCE: 239
SHSYEF                                                                  6

SEQ ID NO: 240          moltype = AA   length = 6
FEATURE                 Location/Qualifiers
source                  1..6
                        mol_type = protein
                        organism = synthetic construct
SEQUENCE: 240
THTYEF                                                                  6

SEQ ID NO: 241          moltype = AA   length = 6
FEATURE                 Location/Qualifiers
source                  1..6
                        mol_type = protein
                        organism = synthetic construct
SEQUENCE: 241
TWTYEF                                                                  6

SEQ ID NO: 242          moltype = AA   length = 6
FEATURE                 Location/Qualifiers
source                  1..6
                        mol_type = protein
                        organism = synthetic construct
SEQUENCE: 242
TYNYEW                                                                  6

SEQ ID NO: 243          moltype = AA   length = 6
FEATURE                 Location/Qualifiers
source                  1..6
                        mol_type = protein
                        organism = synthetic construct
SEQUENCE: 243
TYSYEF                                                                  6
```

-continued

```
SEQ ID NO: 244          moltype = AA   length = 6
FEATURE                 Location/Qualifiers
source                  1..6
                        mol_type = protein
                        organism = synthetic construct
SEQUENCE: 244
TYSYEH                                                             6

SEQ ID NO: 245          moltype = AA   length = 6
FEATURE                 Location/Qualifiers
source                  1..6
                        mol_type = protein
                        organism = synthetic construct
SEQUENCE: 245
TYTYDF                                                             6

SEQ ID NO: 246          moltype = AA   length = 6
FEATURE                 Location/Qualifiers
source                  1..6
                        mol_type = protein
                        organism = synthetic construct
SEQUENCE: 246
TYTYEF                                                             6

SEQ ID NO: 247          moltype = AA   length = 6
FEATURE                 Location/Qualifiers
source                  1..6
                        mol_type = protein
                        organism = synthetic construct
SEQUENCE: 247
TYTYEW                                                             6

SEQ ID NO: 248          moltype = AA   length = 4
FEATURE                 Location/Qualifiers
source                  1..4
                        mol_type = protein
                        organism = synthetic construct
SEQUENCE: 248
AYEF                                                               4

SEQ ID NO: 249          moltype = AA   length = 4
FEATURE                 Location/Qualifiers
source                  1..4
                        mol_type = protein
                        organism = synthetic construct
SEQUENCE: 249
AYSF                                                               4

SEQ ID NO: 250          moltype = AA   length = 4
FEATURE                 Location/Qualifiers
source                  1..4
                        mol_type = protein
                        organism = synthetic construct
SEQUENCE: 250
AYSY                                                               4

SEQ ID NO: 251          moltype = AA   length = 4
FEATURE                 Location/Qualifiers
source                  1..4
                        mol_type = protein
                        organism = synthetic construct
SEQUENCE: 251
CYSF                                                               4

SEQ ID NO: 252          moltype = AA   length = 4
FEATURE                 Location/Qualifiers
source                  1..4
                        mol_type = protein
                        organism = synthetic construct
SEQUENCE: 252
DYTY                                                               4

SEQ ID NO: 253          moltype = AA   length = 4
FEATURE                 Location/Qualifiers
source                  1..4
                        mol_type = protein
                        organism = synthetic construct
SEQUENCE: 253
```

-continued

```
KYEH                                                                      4

SEQ ID NO: 254              moltype = AA   length = 4
FEATURE                    Location/Qualifiers
source                     1..4
                           mol_type = protein
                           organism = synthetic construct
SEQUENCE: 254
KYEW                                                                      4

SEQ ID NO: 255              moltype = AA   length = 4
FEATURE                    Location/Qualifiers
source                     1..4
                           mol_type = protein
                           organism = synthetic construct
SEQUENCE: 255
MYEF                                                                      4

SEQ ID NO: 256              moltype = AA   length = 4
FEATURE                    Location/Qualifiers
source                     1..4
                           mol_type = protein
                           organism = synthetic construct
SEQUENCE: 256
NWIY                                                                      4

SEQ ID NO: 257              moltype = AA   length = 4
FEATURE                    Location/Qualifiers
source                     1..4
                           mol_type = protein
                           organism = synthetic construct
SEQUENCE: 257
NYDY                                                                      4

SEQ ID NO: 258              moltype = AA   length = 4
FEATURE                    Location/Qualifiers
source                     1..4
                           mol_type = protein
                           organism = synthetic construct
SEQUENCE: 258
NYQW                                                                      4

SEQ ID NO: 259              moltype = AA   length = 4
FEATURE                    Location/Qualifiers
source                     1..4
                           mol_type = protein
                           organism = synthetic construct
SEQUENCE: 259
NYSF                                                                      4

SEQ ID NO: 260              moltype = AA   length = 4
FEATURE                    Location/Qualifiers
source                     1..4
                           mol_type = protein
                           organism = synthetic construct
SEQUENCE: 260
PYEW                                                                      4

SEQ ID NO: 261              moltype = AA   length = 4
FEATURE                    Location/Qualifiers
source                     1..4
                           mol_type = protein
                           organism = synthetic construct
SEQUENCE: 261
RYNW                                                                      4

SEQ ID NO: 262              moltype = AA   length = 4
FEATURE                    Location/Qualifiers
source                     1..4
                           mol_type = protein
                           organism = synthetic construct
SEQUENCE: 262
RYTY                                                                      4

SEQ ID NO: 263              moltype = AA   length = 4
FEATURE                    Location/Qualifiers
source                     1..4
                           mol_type = protein
                           organism = synthetic construct
```

-continued

```
SEQUENCE: 263
SYEF                                                              4

SEQ ID NO: 264        moltype = AA  length = 4
FEATURE               Location/Qualifiers
source                1..4
                      mol_type = protein
                      organism = synthetic construct
SEQUENCE: 264
SYEH                                                              4

SEQ ID NO: 265        moltype = AA  length = 4
FEATURE               Location/Qualifiers
source                1..4
                      mol_type = protein
                      organism = synthetic construct
SEQUENCE: 265
SYEW                                                              4

SEQ ID NO: 266        moltype = AA  length = 4
FEATURE               Location/Qualifiers
source                1..4
                      mol_type = protein
                      organism = synthetic construct
SEQUENCE: 266
SYKW                                                              4

SEQ ID NO: 267        moltype = AA  length = 4
FEATURE               Location/Qualifiers
source                1..4
                      mol_type = protein
                      organism = synthetic construct
SEQUENCE: 267
SYTY                                                              4

SEQ ID NO: 268        moltype = AA  length = 4
FEATURE               Location/Qualifiers
source                1..4
                      mol_type = protein
                      organism = synthetic construct
SEQUENCE: 268
TYDF                                                              4

SEQ ID NO: 269        moltype = AA  length = 4
FEATURE               Location/Qualifiers
source                1..4
                      mol_type = protein
                      organism = synthetic construct
SEQUENCE: 269
TYEF                                                              4

SEQ ID NO: 270        moltype = AA  length = 4
FEATURE               Location/Qualifiers
source                1..4
                      mol_type = protein
                      organism = synthetic construct
SEQUENCE: 270
TYEW                                                              4

SEQ ID NO: 271        moltype = AA  length = 4
FEATURE               Location/Qualifiers
source                1..4
                      mol_type = protein
                      organism = synthetic construct
SEQUENCE: 271
TYQW                                                              4

SEQ ID NO: 272        moltype = AA  length = 4
FEATURE               Location/Qualifiers
source                1..4
                      mol_type = protein
                      organism = synthetic construct
SEQUENCE: 272
TYTY                                                              4

SEQ ID NO: 273        moltype = AA  length = 4
FEATURE               Location/Qualifiers
source                1..4
                      mol_type = protein
```

-continued

```
                                 organism = synthetic construct
SEQUENCE: 273
VYEW                                                                4

SEQ ID NO: 274          moltype = AA  length = 48
FEATURE                 Location/Qualifiers
source                  1..48
                        mol_type = protein
                        organism = synthetic construct
SEQUENCE: 274
SCPDGYSYGY GCGYGYGCSG YDCYGYGGYG GYGGYGYSSY SYSYTYEY             48

SEQ ID NO: 275          moltype = AA  length = 15
FEATURE                 Location/Qualifiers
source                  1..15
                        mol_type = protein
                        organism = synthetic construct
SEQUENCE: 275
YVDAWGQGLL VTVSS                                                 15

SEQ ID NO: 276          moltype = AA  length = 65
FEATURE                 Location/Qualifiers
source                  1..65
                        mol_type = protein
                        organism = synthetic construct
SEQUENCE: 276
CTSVHQETKK YQSCPDGYRE RSDCSNRPAC GTSDCCRVSV FGNCLTTLPV SYSYTYNYEW 60
HVDVW                                                            65

SEQ ID NO: 277          moltype = AA  length = 60
FEATURE                 Location/Qualifiers
source                  1..60
                        mol_type = protein
                        organism = synthetic construct
SEQUENCE: 277
CTTVHQETRK TCSDGYIAVD SCGRGQSDGC VNDCNSCYYG WRNCRRQPAI HSYEFHVDAW 60

SEQ ID NO: 278          moltype = AA  length = 61
FEATURE                 Location/Qualifiers
source                  1..61
                        mol_type = protein
                        organism = synthetic construct
SEQUENCE: 278
CSSVTQRTHV SRSCPDGCSD GDGCVDGCCC SAYRCYTPGV RDLSCTSYSI TYTYEWNVDA 60
W                                                               61

SEQ ID NO: 279          moltype = AA  length = 62
FEATURE                 Location/Qualifiers
source                  1..62
                        mol_type = protein
                        organism = synthetic construct
SEQUENCE: 279
CTTVHQKTTR KTCCSDAYRY DSGCGSGCDC CGADCYVFGA CTFGLDSSYS YIYIYQWYVD 60
AW                                                              62

SEQ ID NO: 280          moltype = AA  length = 60
FEATURE                 Location/Qualifiers
source                  1..60
                        mol_type = protein
                        organism = synthetic construct
SEQUENCE: 280
CTTVHQIFCP DGYSYGYGCG YGYGCSGYDC YGYGGYGYGG YGGYSSYSYS YSYEYYGDAW 60

SEQ ID NO: 281          moltype = AA  length = 70
FEATURE                 Location/Qualifiers
source                  1..70
                        mol_type = protein
                        organism = synthetic construct
SEQUENCE: 281
CSTVHQKTRT TQGNTCPDGY TLKDDCPRCR GGCDGYDCCW GDACRSSGLC WGHNPLVTET 60
YTYEFYIDAW                                                      70

SEQ ID NO: 282          moltype = AA  length = 63
FEATURE                 Location/Qualifiers
source                  1..63
                        mol_type = protein
                        organism = synthetic construct
SEQUENCE: 282
CATVRQTTLR DCPGGYTEDR SCVNTYSCGA DDCCGRGDVG YPALYGYRCA AHIQRYNWHA 60
```

```
DAW                                                                   63

SEQ ID NO: 283              moltype = AA   length = 71
FEATURE                    Location/Qualifiers
source                     1..71
                           mol_type = protein
                           organism = synthetic construct
SEQUENCE: 283
CSTVHQKTRT TQGEYLSLMV TLLKDDCPRC RGGCDGYDCC WGDACRSSGL CWGHNPLVTE  60
TYTYEFYIDA W                                                       71

SEQ ID NO: 284              moltype = AA   length = 71
FEATURE                    Location/Qualifiers
source                     1..71
                           mol_type = protein
                           organism = synthetic construct
SEQUENCE: 284
CSTVHQKTRT TQGNNLSLMV TLLKDDCPRC RGGCDGYDCC WGDACRSSGL CWGHNPLVTE  60
TYTYEFYIDA W                                                       71

SEQ ID NO: 285              moltype = AA   length = 70
FEATURE                    Location/Qualifiers
source                     1..70
                           mol_type = protein
                           organism = synthetic construct
SEQUENCE: 285
CSTVHQKTRT TQGNTCPDGY TLKDDCPRCR GGCDGYDCCW GDACRSSGLC WGHNPLVTET  60
YTYEFYIDAW                                                         70

SEQ ID NO: 286              moltype = AA   length = 70
FEATURE                    Location/Qualifiers
source                     1..70
                           mol_type = protein
                           organism = synthetic construct
SEQUENCE: 286
CSTVHQKTRT TQGNTCPDGY TFKDDCPRCR GGCDGYDCCW GDACRSSGLC WGHNPLVTET  60
YTYEFYIDAW                                                         70

SEQ ID NO: 287              moltype = AA   length = 70
FEATURE                    Location/Qualifiers
source                     1..70
                           mol_type = protein
                           organism = synthetic construct
SEQUENCE: 287
CTTVHQKTRT TQGNTCPDGY TLKDDCPRCR GGCDGYDCCW GDACRSSGLC WGHNPLVTET  60
YTYEFYIDAW                                                         70

SEQ ID NO: 288              moltype = AA   length = 70
FEATURE                    Location/Qualifiers
source                     1..70
                           mol_type = protein
                           organism = synthetic construct
SEQUENCE: 288
CSTVHQKTRT TQGNTCPDGY TLKNDCPRCR GGCDGYDCCW GDACRSSGLC WGHNPLVTET  60
YTYEFYIDAW                                                         70

SEQ ID NO: 289              moltype = AA   length = 70
FEATURE                    Location/Qualifiers
source                     1..70
                           mol_type = protein
                           organism = synthetic construct
SEQUENCE: 289
CTTVYQKTRT TQGNTCPDGY TLKDDCPRCR GGCDGYDCCW GDACRSSGLC WGHNPLVTET  60
YTYEFYIDAW                                                         70

SEQ ID NO: 290              moltype = AA   length = 70
FEATURE                    Location/Qualifiers
source                     1..70
                           mol_type = protein
                           organism = synthetic construct
SEQUENCE: 290
CSTVHQKPGQ HKGILVLMVT LLKDDCPRCR GGCDGYDCCW GDACRSSGLC WGHNPLVTET  60
YTYEFYIDAW                                                         70

SEQ ID NO: 291              moltype = AA   length = 70
FEATURE                    Location/Qualifiers
source                     1..70
                           mol_type = protein
                           organism = synthetic construct
```

-continued

```
SEQUENCE: 291
CSTVHQKTRT TQGILVLMVT LLKDDCPRCR GGCDGYDCCW GDACRSSGLC WGHNPLVTET  60
YTYEFYIDAW                                                         70

SEQ ID NO: 292           moltype = AA  length = 63
FEATURE                  Location/Qualifiers
source                   1..63
                         mol_type = protein
                         organism = synthetic construct
SEQUENCE: 292
CSPVHQEIRK CCPAGCQCGR SCGACCGCAG DEFCGINVYG YVTCGGYRTC SCIDTYDFYV  60
DAW                                                               63

SEQ ID NO: 293           moltype = AA  length = 63
FEATURE                  Location/Qualifiers
source                   1..63
                         mol_type = protein
                         organism = synthetic construct
SEQUENCE: 293
CSPVHQQTRK CCPAGCQCGR SCGACCGCAG DEFCGINVYG YITCGGYRTC SCIDTYDFYV  60
EAW                                                               63

SEQ ID NO: 294           moltype = AA  length = 68
FEATURE                  Location/Qualifiers
source                   1..68
                         mol_type = protein
                         organism = synthetic construct
SEQUENCE: 294
CATVYQKTNQ SKNCPEGSAW CRSCDGGAGC ADYECCRCGW SGCSWRNGAC ECSSLSSSYT  60
YELHVDAW                                                          68

SEQ ID NO: 295           moltype = AA  length = 65
FEATURE                  Location/Qualifiers
source                   1..65
                         mol_type = protein
                         organism = synthetic construct
SEQUENCE: 295
CSTVHQTTHQ IHTCPNGWTG GCVCSSRFNC RGNNCCCRTA YCSVDRYVCA CPTVTYTYEF  60
NVDSW                                                             65

SEQ ID NO: 296           moltype = AA  length = 65
FEATURE                  Location/Qualifiers
source                   1..65
                         mol_type = protein
                         organism = synthetic construct
SEQUENCE: 296
CTAVYQKTTS IRSCPGGTTL RNGCRSACGC NDCDCCCGSS WDICYMSKCT SAPETYTYEL  60
HIDAW                                                             65

SEQ ID NO: 297           moltype = AA  length = 65
FEATURE                  Location/Qualifiers
source                   1..65
                         mol_type = protein
                         organism = synthetic construct
SEQUENCE: 297
CTNVHQKTKK TCPDDYTCGV SCSCSSSGCA DYGCCSYITY GVPGDCGGCC SYKHRYTYEW  60
NVDAW                                                             65

SEQ ID NO: 298           moltype = AA  length = 63
FEATURE                  Location/Qualifiers
source                   1..63
                         mol_type = protein
                         organism = synthetic construct
SEQUENCE: 298
CTTVHQKTKK LCPNGRTCGC GCDCGSGCCT SYCDSFGCWG GRDTFGSSCT SATYTYEWGV  60
DAW                                                               63

SEQ ID NO: 299           moltype = AA  length = 64
FEATURE                  Location/Qualifiers
source                   1..64
                         mol_type = protein
                         organism = synthetic construct
SEQUENCE: 299
CATVHQHTNK KRCPDGYEFS AGCCCGEGCS GSDCCCNSRL RCSWYEIYCS VSPSDTYEFH  60
VDAW                                                              64

SEQ ID NO: 300           moltype = AA  length = 64
FEATURE                  Location/Qualifiers
source                   1..64
```

-continued

```
                          mol_type = protein
                          organism = synthetic construct
SEQUENCE: 300
CTTVHQHTNK KRCPDGYRFS AACCCGEGCS GNECCCNTRL RCSWYEIYCS VSPSDTYEFH    60
VDAW                                                                 64

SEQ ID NO: 301            moltype = AA  length = 64
FEATURE                   Location/Qualifiers
source                    1..64
                          mol_type = protein
                          organism = synthetic construct
SEQUENCE: 301
CTTVHQHTNQ NRCPTGYKHS AGCCCGVGCS GNDCCCNSRL RCSWYETYCS LSPTDMYEFY    60
VDAW                                                                 64

SEQ ID NO: 302            moltype = AA  length = 64
FEATURE                   Location/Qualifiers
source                    1..64
                          mol_type = protein
                          organism = synthetic construct
SEQUENCE: 302
CSTVHQHTNQ NRCPAGYKHS AGCCCGVGCS GNDCCCNSRL RCSWYETYCS LSPTDMYEFY    60
VDAW                                                                 64

SEQ ID NO: 303            moltype = AA  length = 63
FEATURE                   Location/Qualifiers
source                    1..63
                          mol_type = protein
                          organism = synthetic construct
SEQUENCE: 303
CTTVHQKTNE RCCRVVSDDG ECGDGNSCHR WLCSDYCYSG DCCACGCRAY HYTYTYEWNI    60
DAW                                                                  63

SEQ ID NO: 304            moltype = AA  length = 63
FEATURE                   Location/Qualifiers
source                    1..63
                          mol_type = protein
                          organism = synthetic construct
SEQUENCE: 304
CTTVHQKTNE RCCRVVSDDG ECGDGNSCHR WLCSDYCYSG DCCACGCRAY HYTYTYDFRI    60
DVW                                                                  63

SEQ ID NO: 305            moltype = AA  length = 64
FEATURE                   Location/Qualifiers
source                    1..64
                          mol_type = protein
                          organism = synthetic construct
SEQUENCE: 305
CTTVHQKTNR ERCCPDGYYY CCRSVSDCCC STRACVGDSC GWTDFGSTHN VDCSFTYEFH    60
VDAW                                                                 64

SEQ ID NO: 306            moltype = AA  length = 63
FEATURE                   Location/Qualifiers
source                    1..63
                          mol_type = protein
                          organism = synthetic construct
SEQUENCE: 306
CTTVHQQTRK SCPDGYTYCH DCGYGCCCGA SFCRDYGGCG SLCGRYCTSF DYIYTYENYV    60
ETW                                                                  63

SEQ ID NO: 307            moltype = AA  length = 64
FEATURE                   Location/Qualifiers
source                    1..64
                          mol_type = protein
                          organism = synthetic construct
SEQUENCE: 307
CTTVHQETKK NCPDNCYYEN SCGDYGSGCN GGDCCRCGTW LTCSVSGCTC IRATNTYQWY    60
VNAW                                                                 64

SEQ ID NO: 308            moltype = AA  length = 64
FEATURE                   Location/Qualifiers
source                    1..64
                          mol_type = protein
                          organism = synthetic construct
SEQUENCE: 308
CTTVHQSTNK KSCPDRVCWA VGCCFGEDCT SSDCTCYASP GNPYRHDCGN CDCRSSYEHH    60
VDAW                                                                 64

SEQ ID NO: 309            moltype = AA  length = 63
```

-continued

```
FEATURE                 Location/Qualifiers
source                  1..63
                        mol_type = protein
                        organism = synthetic construct
SEQUENCE: 309
CTTVRQETLI RCRDGPSCAA CCRSGRRCSG YGCCTDGCCS DNDYADCIRG EFVDVYEWNV  60
DAW                                                                63

SEQ ID NO: 310          moltype = AA  length = 63
FEATURE                 Location/Qualifiers
source                  1..63
                        mol_type = protein
                        organism = synthetic construct
SEQUENCE: 310
CSTVYQKTRT TCPDGYTCGD GARCEKACRG CDCCRTTVCD TVWSSYCSCY SFTDSYEFYV  60
DAW                                                                63

SEQ ID NO: 311          moltype = AA  length = 66
FEATURE                 Location/Qualifiers
source                  1..66
                        mol_type = protein
                        organism = synthetic construct
SEQUENCE: 311
CATVYQKTNR EMSCPDGCRI HNARLCLSGC SGSDCCSCGD CVSDARCYNC RSAVFTYTYE  60
FHVDAW                                                             66

SEQ ID NO: 312          moltype = AA  length = 63
FEATURE                 Location/Qualifiers
source                  1..63
                        mol_type = protein
                        organism = synthetic construct
SEQUENCE: 312
CTIVHQETKR SCPDGYNTGT RCFGSCGCIG SNCCRSTTSC CCAGIYSQCT TSTLTYEWHA  60
DVW                                                                63

SEQ ID NO: 313          moltype = AA  length = 63
FEATURE                 Location/Qualifiers
source                  1..63
                        mol_type = protein
                        organism = synthetic construct
SEQUENCE: 313
CAIVYQRTRQ RCPDGYNTGT RCFGTCGCNG SNCCRFTTSC CCAGVYSQCT TSTLTYEWHA  60
DVW                                                                63

SEQ ID NO: 314          moltype = AA  length = 63
FEATURE                 Location/Qualifiers
source                  1..63
                        mol_type = protein
                        organism = synthetic construct
SEQUENCE: 314
CTTVHQKTET RCPDGYSSTN GCDARCGCSD CDCCNVGRWG CPLICSRNCR SFTYTYEWYA  60
DAW                                                                63

SEQ ID NO: 315          moltype = AA  length = 63
FEATURE                 Location/Qualifiers
source                  1..63
                        mol_type = protein
                        organism = synthetic construct
SEQUENCE: 315
CTTVHQKTNK KESCPDGYTM NECCGCGYGC CRGGCVCSAY CSRPNCWREL TYTYTYEFYV  60
DTW                                                                63

SEQ ID NO: 316          moltype = AA  length = 63
FEATURE                 Location/Qualifiers
source                  1..63
                        mol_type = protein
                        organism = synthetic construct
SEQUENCE: 316
CTTVYQKSRK ESSCPNGWIY GKDCCSWSYC TDCDCCLCGD LHCYDGCSSF GVTWTYEFHV  60
DAW                                                                63

SEQ ID NO: 317          moltype = AA  length = 62
FEATURE                 Location/Qualifiers
source                  1..62
                        mol_type = protein
                        organism = synthetic construct
SEQUENCE: 317
CTTVFQETRK SCPTGFYVDG STCGCATYCR TCDCCGGYRC SGGGSCACSS YTYNYDFHVD  60
AW                                                                 62
```

-continued

```
SEQ ID NO: 318           moltype = AA  length = 61
FEATURE                  Location/Qualifiers
source                   1..61
                         mol_type = protein
                         organism = synthetic construct
SEQUENCE: 318
CAAVFQETRT NCPSGYGNAF SCGCPIACRD CDCCGGYWCS GGADCHCVSY NYTYSWHVDA   60
W                                                                   61

SEQ ID NO: 319           moltype = AA  length = 62
FEATURE                  Location/Qualifiers
source                   1..62
                         mol_type = protein
                         organism = synthetic construct
SEQUENCE: 319
CATVYQKTEK HCPLFHSICC HCGEGVGCSG GDCCGCERRS GCVVCTMRNS YTYNYQFHVD   60
AW                                                                  62

SEQ ID NO: 320           moltype = AA  length = 63
FEATURE                  Location/Qualifiers
source                   1..63
                         mol_type = protein
                         organism = synthetic construct
SEQUENCE: 320
CGTVHQKTKE LCPDDSTYCC GCVSGCACCT YGCDGVGCCR VSLWTTYIKD IVGVSYEWHV   60
DAW                                                                 63

SEQ ID NO: 321           moltype = AA  length = 61
FEATURE                  Location/Qualifiers
source                   1..61
                         mol_type = protein
                         organism = synthetic construct
SEQUENCE: 321
CASVHQHTEP TCPAGYTYCC GCLYKCNCGD CGCYNVGCGS GWLGKACGDY RETYEWYVDA   60
W                                                                   61

SEQ ID NO: 322           moltype = AA  length = 61
FEATURE                  Location/Qualifiers
source                   1..61
                         mol_type = protein
                         organism = synthetic construct
SEQUENCE: 322
CASVHQHTEP TCPAGYTYCC GCLYKCNCGD CGCYNAGCGS GWLGKACGDY RETYEWYVDA   60
W                                                                   61

SEQ ID NO: 323           moltype = AA  length = 61
FEATURE                  Location/Qualifiers
source                   1..61
                         mol_type = protein
                         organism = synthetic construct
SEQUENCE: 323
CTTVFQETRK SCPSGFRDRD ACGCAVTCRN CDCCGGGPCN GGGSCRCNNY IYKYSFHVDA   60
W                                                                   61

SEQ ID NO: 324           moltype = AA  length = 61
FEATURE                  Location/Qualifiers
source                   1..61
                         mol_type = protein
                         organism = synthetic construct
SEQUENCE: 324
CTAVFQETRK DCPSGYGSAF TCGCLAACHG CDCCGGGWCS GGGDCRCRSY STAYSFHIDA   60
W                                                                   61

SEQ ID NO: 325           moltype = AA  length = 61
FEATURE                  Location/Qualifiers
source                   1..61
                         mol_type = protein
                         organism = synthetic construct
SEQUENCE: 325
CATVFQETRK SCPSGYADRF TCDCVYYCQT CDCCGGNRCS GGGPCRCSSY SINYSFHVDT   60
W                                                                   61

SEQ ID NO: 326           moltype = AA  length = 58
FEATURE                  Location/Qualifiers
source                   1..58
                         mol_type = protein
                         organism = synthetic construct
SEQUENCE: 326
```

-continued

```
CAAAHQETKK SCPDGTCRQC CGGVCRCHAS GCCYWCTTGC VGRALSESHS YEFHVDTW      58

SEQ ID NO: 327          moltype = AA   length = 70
FEATURE                 Location/Qualifiers
source                  1..70
                        mol_type = protein
                        organism = synthetic construct
SEQUENCE: 327
CSTVHQKTRT TQGNTCPDGY TLKDDCPRCR GGCDGYDCCW GDACRSSGLC WGHNPLVTET      60
YTYEFYIDAW                                                             70

SEQ ID NO: 328          moltype = AA   length = 68
FEATURE                 Location/Qualifiers
source                  1..68
                        mol_type = protein
                        organism = synthetic construct
SEQUENCE: 328
CVVVYQKTNS QKSCPRGYTE RETCNRRYGW GCGRYDCCDC DRWVSGNCAN ICTDYTDTHT      60
YEFHADAW                                                               68

SEQ ID NO: 329          moltype = AA   length = 64
FEATURE                 Location/Qualifiers
source                  1..64
                        mol_type = protein
                        organism = synthetic construct
SEQUENCE: 329
CGTVFQQTHK VRDCPDGFTA APRCGGECCC SNVNSRSGGW CRYCGRDCTA PTETSTYEFH      60
VDAW                                                                   64

SEQ ID NO: 330          moltype = AA   length = 63
FEATURE                 Location/Qualifiers
source                  1..63
                        mol_type = protein
                        organism = synthetic construct
SEQUENCE: 330
CTAVYQRTGQ KCPEGCESRN TCLYSRNCGD YTCCGGSRAS GSGACGWNSV DCKNKYEHHV      60
DAW                                                                    63

SEQ ID NO: 331          moltype = AA   length = 63
FEATURE                 Location/Qualifiers
source                  1..63
                        mol_type = protein
                        organism = synthetic construct
SEQUENCE: 331
CTTVYQKTKQ NCPDGYDFRD TCGSQSYCSG YDCCRCSRFG GCSIGTCISY SDAYTYEWYV      60
DAW                                                                    63

SEQ ID NO: 332          moltype = AA   length = 63
FEATURE                 Location/Qualifiers
source                  1..63
                        mol_type = protein
                        organism = synthetic construct
SEQUENCE: 332
CTTVHQQTHE KRSCPESYSY SCSCASGVVG CGPDDCCCTY RISIRGYTCS SLSNSYEWYV      60
DAW                                                                    63

SEQ ID NO: 333          moltype = AA   length = 61
FEATURE                 Location/Qualifiers
source                  1..61
                        mol_type = protein
                        organism = synthetic construct
SEQUENCE: 333
CTAVHQQTKR KSGCPDGYSD ESCSYCGSSW CCPVYWCGSP CSYRCLRHTD TYSYEHHVDA      60
W                                                                      61

SEQ ID NO: 334          moltype = AA   length = 60
FEATURE                 Location/Qualifiers
source                  1..60
                        mol_type = protein
                        organism = synthetic construct
SEQUENCE: 334
CATVYQETKR TCAGGHSVEC DSPYDCNCRG GDCCRSPIFN DCWAASCSAT KTYEWHVESW      60

SEQ ID NO: 335          moltype = AA   length = 58
FEATURE                 Location/Qualifiers
source                  1..58
                        mol_type = protein
                        organism = synthetic construct
SEQUENCE: 335
```

```
CITVHQETQK SCPDDYTYYG DGTCAYVCSI DKCCCGRTWL SSGCLPCRYT YNLHVDAW        58

SEQ ID NO: 336          moltype = AA   length = 58
FEATURE                 Location/Qualifiers
source                  1..58
                        mol_type = protein
                        organism = synthetic construct
SEQUENCE: 336
CITVHQETQK SCPDDYTSYG DATCAYVCST DECCCGRTWL SAGCRPCRYT YNLHVDAW        58

SEQ ID NO: 337          moltype = AA   length = 58
FEATURE                 Location/Qualifiers
source                  1..58
                        mol_type = protein
                        organism = synthetic construct
SEQUENCE: 337
CITVHQETQK SCFDDYTYYG DASCAYVCST DECCCGRTWL SAGCRPCRYT YNLHVDAW        58

SEQ ID NO: 338          moltype = AA   length = 58
FEATURE                 Location/Qualifiers
source                  1..58
                        mol_type = protein
                        organism = synthetic construct
SEQUENCE: 338
CITAHQETQK SCSDDYTYYG DATCAYVCST DECCCGRTWL SAGCRPCRYT YNLHVDAW        58

SEQ ID NO: 339          moltype = AA   length = 58
FEATURE                 Location/Qualifiers
source                  1..58
                        mol_type = protein
                        organism = synthetic construct
SEQUENCE: 339
CITVHQETQK SCPDDYTYYG DGTCAYVCSI DNCCCGRTWL SSGCLPCRYT YNLHVDAW        58

SEQ ID NO: 340          moltype = AA   length = 61
FEATURE                 Location/Qualifiers
source                  1..61
                        mol_type = protein
                        organism = synthetic construct
SEQUENCE: 340
CVTVHQQTHA TRRCPDGYGD SYACKSNYGC SAEGCCRWGP GSGACTGAIY TSPYEWYVDA      60
W                                                                     61

SEQ ID NO: 341          moltype = AA   length = 60
FEATURE                 Location/Qualifiers
source                  1..60
                        mol_type = protein
                        organism = synthetic construct
SEQUENCE: 341
CAAVHQRTEG QQSCPDGYLE TRVCPYRMYR CIGWDCCRCS DGSRDNYIMT YSYEFHVDVW      60

SEQ ID NO: 342          moltype = AA   length = 59
FEATURE                 Location/Qualifiers
source                  1..59
                        mol_type = protein
                        organism = synthetic construct
SEQUENCE: 342
CTTVYQETKT KSGCPDGYSC CYNGRSRSCR PNDCSTYGEV RSLSRSCYTY NYEFYVDAW       59

SEQ ID NO: 343          moltype = AA   length = 58
FEATURE                 Location/Qualifiers
source                  1..58
                        mol_type = protein
                        organism = synthetic construct
SEQUENCE: 343
CGTVYQHTKE IKTCPDGYSD VFTYCPVTCP GWDCCRRNDC GRTRYTVAYS YALHVDVW        58

SEQ ID NO: 344          moltype = AA   length = 57
FEATURE                 Location/Qualifiers
source                  1..57
                        mol_type = protein
                        organism = synthetic construct
SEQUENCE: 344
CTTVLQETHQ QRGCPAGYQV VDGCPYGDCC RTSYVCGPLT CTSNTATRNY QWYVDAW         57

SEQ ID NO: 345          moltype = AA   length = 56
FEATURE                 Location/Qualifiers
source                  1..56
                        mol_type = protein
```

-continued

```
                          organism = synthetic construct
SEQUENCE: 345
CSTVYQKTEK KCPDGYTDRR DECPNTCKNF DCENEGGLRC LCSAYISAYE FHVDAW          56

SEQ ID NO: 346            moltype = AA  length = 55
FEATURE                   Location/Qualifiers
source                    1..55
                          mol_type = protein
                          organism = synthetic construct
SEQUENCE: 346
CTTTHQRTQK SCPDYASYDC GSPDDEECSS CRSCTRWCAP TAPYIYTYQF YIDAW           55

SEQ ID NO: 347            moltype = AA  length = 54
FEATURE                   Location/Qualifiers
source                    1..54
                          mol_type = protein
                          organism = synthetic construct
SEQUENCE: 347
CTTVHQQTNK RCPTGYNSGT LCNMIGCSGD ECCNYGRVEC TSYVWTHNFY VDAW            54

SEQ ID NO: 348            moltype = AA  length = 53
FEATURE                   Location/Qualifiers
source                    1..53
                          mol_type = protein
                          organism = synthetic construct
SEQUENCE: 348
CTTVHQETQR TSCPSGWTYT CNCRNGCGCY RPSQLCGAYV AVTHTYEFHV DAW            53

SEQ ID NO: 349            moltype = AA  length = 53
FEATURE                   Location/Qualifiers
source                    1..53
                          mol_type = protein
                          organism = synthetic construct
SEQUENCE: 349
CATVHQKDKH CPAGYRSGTL CRMIGCTGDD CCNYDRVECT NYDYTNNFYV DAW            53

SEQ ID NO: 350            moltype = AA  length = 52
FEATURE                   Location/Qualifiers
source                    1..52
                          mol_type = protein
                          organism = synthetic construct
SEQUENCE: 350
CTAVHQQTTE KGKTCPPRSR DMGTRCRDDR YYPWRYSDYT YTYTYEWHVD AW             52

SEQ ID NO: 351            moltype = AA  length = 51
FEATURE                   Location/Qualifiers
source                    1..51
                          mol_type = protein
                          organism = synthetic construct
SEQUENCE: 351
CTSVHQKTDV TCPSGATYRC DCGGRGCGCY DPWCSTTYRG TYTYDFHVET W              51

SEQ ID NO: 352            moltype = AA  length = 50
FEATURE                   Location/Qualifiers
source                    1..50
                          mol_type = protein
                          organism = synthetic construct
SEQUENCE: 352
CGTVHQETHT QRTCPDACDV TGDNCKVRRN GDWCGRASKT DTYDFYVDAW                50

SEQ ID NO: 353            moltype = AA  length = 49
FEATURE                   Location/Qualifiers
source                    1..49
                          mol_type = protein
                          organism = synthetic construct
SEQUENCE: 353
CTTDYQKTEK SCPENYYAET GYCMCGSWRC GYGSTTSLIV SYKWYVDAW                 49

SEQ ID NO: 354            moltype = AA  length = 49
FEATURE                   Location/Qualifiers
source                    1..49
                          mol_type = protein
                          organism = synthetic construct
SEQUENCE: 354
CTTVHQKTNQ KWGCPDGYVH MSGSCCRGSI CTNGLFRNTY TYEFNVEAW                 49

SEQ ID NO: 355            moltype = AA  length = 48
FEATURE                   Location/Qualifiers
source                    1..48
```

-continued

```
                          mol_type = protein
                          organism = synthetic construct
SEQUENCE: 355
CTTVYQETRT NCPDGYNYRS GDCRRWNHWL GEQRVSPTYN YEWYVDSW                48

SEQ ID NO: 356            moltype = AA  length = 47
FEATURE                   Location/Qualifiers
source                    1..47
                          mol_type = protein
                          organism = synthetic construct
SEQUENCE: 356
CTTVYQKTTT TKSCPGGFDN GRRCIMGLGD LRDYTYFNKY EWYVETW                 47

SEQ ID NO: 357            moltype = AA  length = 46
FEATURE                   Location/Qualifiers
source                    1..46
                          mol_type = protein
                          organism = synthetic construct
SEQUENCE: 357
CSTVHQKTEQ RCLDGYDDRG AYCYDSVRGL MSWTYKYVYE WRVDTW                  46

SEQ ID NO: 358            moltype = AA  length = 45
FEATURE                   Location/Qualifiers
source                    1..45
                          mol_type = protein
                          organism = synthetic construct
SEQUENCE: 358
CTNVHQMTIK TCPDGGSYGW YWPYGYGCNG GVSATYTYEF YVDAW                   45

SEQ ID NO: 359            moltype = AA  length = 44
FEATURE                   Location/Qualifiers
source                    1..44
                          mol_type = protein
                          organism = synthetic construct
SEQUENCE: 359
CTTVYQKTES VRSCPDGSMD GWRCRLGTMN WIYSNTYEFY VDAW                    44

SEQ ID NO: 360            moltype = AA  length = 75
FEATURE                   Location/Qualifiers
source                    1..75
                          mol_type = protein
                          organism = synthetic construct
SEQUENCE: 360
CTSVHQETKK YQSCPDGYRE RSDCSNRPAC GTSDCCRVSV FGNCLTTLPV SYSYTYNYEW   60
HVDVWGQGLL VTVSS                                                    75

SEQ ID NO: 361            moltype = AA  length = 70
FEATURE                   Location/Qualifiers
source                    1..70
                          mol_type = protein
                          organism = synthetic construct
SEQUENCE: 361
CTTVHQETRK TCSDGYIAVD SCGRGQSDGC VNDCNSCYYG WRNCRRQPAI HSYEFHVDAW   60
GRGLLVTVSS                                                          70

SEQ ID NO: 362            moltype = AA  length = 71
FEATURE                   Location/Qualifiers
source                    1..71
                          mol_type = protein
                          organism = synthetic construct
SEQUENCE: 362
CSSVTQRTHV SRSCPDGCSD GDGCVDGCCC SAYRCYTPGV RDLSCTSYSI TYTYEWNVDA   60
WGRGLLVTVS S                                                        71

SEQ ID NO: 363            moltype = AA  length = 72
FEATURE                   Location/Qualifiers
source                    1..72
                          mol_type = protein
                          organism = synthetic construct
SEQUENCE: 363
CTTVHQKTTR KTCCSDAYRY DSGCGSGCDC CGADCYVFGA CTFGLDSSYS YIYIYQWYVD   60
AWGQGLLVTV SS                                                       72

SEQ ID NO: 364            moltype = AA  length = 70
FEATURE                   Location/Qualifiers
source                    1..70
                          mol_type = protein
                          organism = synthetic construct
SEQUENCE: 364
```

-continued

```
CTTVHQIFCP DGYSYGYGCG YGYGCSGYDC YGYGGYGYGG YGGYSSYSYS YSYEYYGDAW   60
GQGLLVTVSS                                                          70

SEQ ID NO: 365         moltype = AA  length = 50
FEATURE                Location/Qualifiers
source                 1..50
                       mol_type = protein
                       organism = synthetic construct
SEQUENCE: 365
CTTVHPSPDG YSYGYGCGYG YGCSGYDCYG YGGYGYGGYG GYSSYSYSYS               50

SEQ ID NO: 366         moltype = AA  length = 50
FEATURE                Location/Qualifiers
source                 1..50
                       mol_type = protein
                       organism = synthetic construct
SEQUENCE: 366
CTTVHQIRCP DGYGYGYGCG YGSYGYSGYD CYGYGGYGGY GGYGGYSSYS               50

SEQ ID NO: 367         moltype = DNA  length = 300
FEATURE                Location/Qualifiers
source                 1..300
                       mol_type = other DNA
                       organism = synthetic construct
SEQUENCE: 367
caggtgcagc tgcgggagtc gggcccagc ctggtgaagc cctcacagac cctctcgctc    60
acctgcacgg cctctggatt ctcattgagc gacaaggctg taggctgggt ccgccaggct   120
ccagggaagg cgctggagtg gctcggtggt atagacactg gtggaagcac aggctataac   180
ccaggcctga aatcccggct cagcatcacc aaggacaact ccaagagcca gtctctctg    240
tcagtgagca gcgtgacaac tgaggactcg gccacatact actgtactac tgtgcaccag   300

SEQ ID NO: 368         moltype = DNA  length = 311
FEATURE                Location/Qualifiers
source                 1..311
                       mol_type = other DNA
                       organism = synthetic construct
SEQUENCE: 368
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct gggagtggat tgggagtatct attatagtgg gagcacctac   180
tacaacccgt ccctcaagag tcgagtcacc atatccgtag acacgtccaa gaaccagttc    240
tccctgaagc tgagctctgt gaccgccgca gacacggctg tgtattactg tgcgagacac    300
acagtgaggg g                                                        311

SEQ ID NO: 369         moltype = DNA  length = 288
FEATURE                Location/Qualifiers
source                 1..288
                       mol_type = other DNA
                       organism = synthetic construct
SEQUENCE: 369
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgagt caccatatca gtagacacgt ccaagaacca attctccctg   240
aagctgagct ctgtgaccgc tgcggacacg gccgtgtatt actgtgcg                288

SEQ ID NO: 370         moltype = DNA  length = 291
FEATURE                Location/Qualifiers
source                 1..291
                       mol_type = other DNA
                       organism = synthetic construct
SEQUENCE: 370
caggtgcagc tgcaggagtc gggcccagga ctggtgaagc cttcacagac cctgtccctc    60
acctgcgctg tctatggtgg gtccttcagt ggttactact ggagctggat ccgccagccc   120
ccagggaagg gactggagtg gattggggaa atcaatcata gtggaagcac caactacaac   180
ccgtccctca agagtcgagt taccatatca gtagacacgt ctaagaacca gttctccctg   240
aagctgagct ctgtgactgc cgcggacacg gccgtgtatt actgtgcgag a            291

SEQ ID NO: 371         moltype = DNA  length = 293
FEATURE                Location/Qualifiers
source                 1..293
                       mol_type = other DNA
                       organism = synthetic construct
SEQUENCE: 371
caggtgcagc tacaacagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtgcgag agg          293
```

-continued

```
SEQ ID NO: 372          moltype = DNA  length = 330
FEATURE                 Location/Qualifiers
source                  1..330
                        mol_type = other DNA
                        organism = synthetic construct
SEQUENCE: 372
caggctgtgc tgaatcagcc atcatccgtg tccgggtccc tgggccagag ggtctccatc   60
acctgctctg gaagcagcag caatgttgga aatggatatg tgagctggta ccaactgatc  120
ccaggatcgg cccccagaac cctcatctat ggtgacacca gtcgagcctc ggggtcccc   180
gaccgattct ccggctccag gtctgggaac acagccaccc tgaccatcag ctcgctccag  240
gctgaggacg aggcagatta tttctgtgca tctgctgagg atagtagcag taatgctgtt  300
ttcggcagcg ggaccacact gaccgtcctg                                   330

SEQ ID NO: 373          moltype = DNA  length = 296
FEATURE                 Location/Qualifiers
source                  1..296
                        mol_type = other DNA
                        organism = synthetic construct
SEQUENCE: 373
cagtctgtgc tgactcagcc accctcagcg tctgggaccc ccgggcagag ggtcaccatc   60
tcttgttctg gaagcagctc caacatcgga agtaattatg tatactggta ccagcagctc  120
ccaggaacgg cccccaaact cctcatctat aggaataatc agcggccctc aggggtccct  180
gaccgattct ctggctccaa gtctggcacc tcagcctccc tggccatcag tgggctccgg  240
tccgaggatg aggctgatta ttactgtgca gcatgggata cagcctgag tggtcc       296

SEQ ID NO: 374          moltype = DNA  length = 299
FEATURE                 Location/Qualifiers
source                  1..299
                        mol_type = other DNA
                        organism = synthetic construct
SEQUENCE: 374
cagtctgtgc tgacgcagcc gccctcagtg tctgggggcc cagggcagag ggtcaccatc   60
tcctgcactg ggagcagctc caacatcggg gcaggttatg atgtacactg gtaccagcag  120
cttccaggaa cagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggttc   299

SEQ ID NO: 375          moltype = DNA  length = 296
FEATURE                 Location/Qualifiers
source                  1..296
                        mol_type = other DNA
                        organism = synthetic construct
SEQUENCE: 375
cagtctgtgt tgacgcagcc gccctcagtg tctgcggccc caggacgaa ggtcaccatc    60
tcctgctctg gaagcagctc caacattggg aataattatg tatcctggta ccagcagctc  120
ccaggaacag cccccaaact cctcatttat gacaataata agcgaccctc agggattcct  180
gaccgattct ctggctccaa gtctggcacg tcagccaccc tgggcatcac cggactccag  240
actggggacg aggccgatta ttactgcgga acatgggata gcagcctgag tgctgg      296

SEQ ID NO: 376          moltype = DNA  length = 297
FEATURE                 Location/Qualifiers
source                  1..297
                        mol_type = other DNA
                        organism = synthetic construct
SEQUENCE: 376
cagtctgccc tgactcagcc tccctccgtg tccgggtctc ctggacagtc agtcaccatc   60
tcctgcactg gaaccagcag tgacgttggt agttataacc gtgtctcctg gtaccagcag  120
cccccaggca gcccccaa actcatgatt tatgaggtca gtaatcggcc ctcagggggtc  180
cctgatcgct tctctgggtc caagtctggc aacacggcct ccctgaccat ctctgggctc  240
caggctgagg acgaggctga ttattactgc agctcatata caagcagcag cactttc     297

SEQ ID NO: 377          moltype = DNA  length = 514
FEATURE                 Location/Qualifiers
source                  1..514
                        mol_type = other DNA
                        organism = synthetic construct
SEQUENCE: 377
cagctgcagc tgcaggagtc gggcccagga ctggtgaagc cttcggagac cctgtccctc   60
acctgcactg tctctggtgg ctccatcagc agtagtagtt actactgggg ctggatccgc  120
cagcccccag ggaaggggct ggagtggatt gggagtatct attatagtgg gagcacctac  180
tacaacccgt ccctcaagag tcgagtcacc atatccgtag acacgtccaa gaaccagttc  240
tccctgaagc tgagctctgt gaccgccgca gacacggctg tgtattactg tactactgtg  300
caccaggaaa caaaaaaata ccaaagttgt cctgatgggt atagagaacg ttcggattgt  360
agtaacagac ctgcttgtgg tactagtgat tgttgtcgtg ttagtgtttt tggtaattgt  420
cttactactc ttcctgtgag ttatagttat acttacaatt acgaatggca cgtcgatgtc  480
tggggccagg gaaccctggt caccgtctcc tcag                               514

SEQ ID NO: 378          moltype = AA  length = 171
```

-continued

```
FEATURE                Location/Qualifiers
source                 1..171
                       mol_type = protein
                       organism = synthetic construct
SEQUENCE: 378
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCTTV HQETKKYQSC PDGYRERSDC   120
SNRPACGTSD CCRVSVFGNC LTTLPVSYSY TYNYEWHVDV WGQGTLVTVS S            171

SEQ ID NO: 379         moltype = DNA   length = 493
FEATURE                Location/Qualifiers
source                 1..493
                       mol_type = other DNA
                       organism = synthetic construct
SEQUENCE: 379
caggtgcagc tacaacagtg gggcgcagga ctgttgaagc cttcggagac cctgtccctc    60
acctgcgctg tctatggtgg gtccttcagt ggttactact ggagctggat ccgccagccc   120
ccaggaaggg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtactac tgtgcaccag   300
gaaaccagaa aaacctgttc tgatggttat atggctgtag atagttgtgg tcgtggtcag   360
agtgatggtt gtgtcaatga ttgcaattgt tgttattatg gttggcggaa ctgtcgcagg   420
cagcctgcaa ttcaaagtta cgaatttcac gtcgatgcct ggggccgtgg caccctggtc   480
actgtctcct cag                                                     493

SEQ ID NO: 380         moltype = AA   length = 164
FEATURE                Location/Qualifiers
source                 1..164
                       mol_type = protein
                       organism = synthetic construct
SEQUENCE: 380
QVQLQQWGAG LLKPSETLSL TCAVYGGSFS GYYWSWIRQP PGKGLEWIGE INHSGSTNYN    60
PSLKSRVTIS VDTSKNQFSL KLSSVTAADT AVYYCTTVHQ ETRKTCSDGY MAVDSCGRGQ   120
SDGCVNDCNC CYYGWRNCRR QPAIQSYEFH VDAWGRGTLV TVSS                   164

SEQ ID NO: 381         moltype = DNA   length = 63
FEATURE                Location/Qualifiers
source                 1..63
                       mol_type = other DNA
                       organism = synthetic construct
SEQUENCE: 381
cctatcccct gtgtgccttg gcagtctcag acgagtgcgt ttgagcgaca aggctgtagg    60
ctg                                                                 63

SEQ ID NO: 382         moltype = DNA   length = 62
FEATURE                Location/Qualifiers
source                 1..62
                       mol_type = other DNA
                       organism = synthetic construct
SEQUENCE: 382
ccatctcatc cctgcgtgtc tccgactcag acgagtgcgt ctttcggggc tgtggtggag    60
gc                                                                 62

SEQ ID NO: 383         moltype = DNA   length = 63
FEATURE                Location/Qualifiers
source                 1..63
                       mol_type = other DNA
                       organism = synthetic construct
SEQUENCE: 383
cctatcccct gtgtgccttg gcagtctcag tctctatgcg ttgagcgaca aggctgtagg    60
ctg                                                                 63

SEQ ID NO: 384         moltype = DNA   length = 66
FEATURE                Location/Qualifiers
source                 1..66
                       mol_type = other DNA
                       organism = synthetic construct
SEQUENCE: 384
ccatctcatc cctgcgtgtc tccgactcag tctctatgcg agtgaagact ctcgggtgtg    60
attcac                                                             66

SEQ ID NO: 385         moltype = DNA   length = 63
FEATURE                Location/Qualifiers
source                 1..63
                       mol_type = other DNA
                       organism = synthetic construct
SEQUENCE: 385
cctatcccct gtgtgccttg gcagtctcag tgatacgtct ttgagcgaca aggctgtagg    60
ctg                                                                 63
```

```
SEQ ID NO: 386           moltype = DNA   length = 66
FEATURE                  Location/Qualifiers
source                   1..66
                         mol_type = other DNA
                         organism = synthetic construct
SEQUENCE: 386
ccatctcatc cctgcgtgtc tccgactcag tgatacgtct agtgaagact ctcgggtgtg   60
attcac                                                              66

SEQ ID NO: 387           moltype = DNA   length = 23
FEATURE                  Location/Qualifiers
source                   1..23
                         mol_type = other DNA
                         organism = synthetic construct
SEQUENCE: 387
ttgagcgaca aggctgtagg ctg                                           23

SEQ ID NO: 388           moltype = DNA   length = 22
FEATURE                  Location/Qualifiers
source                   1..22
                         mol_type = other DNA
                         organism = synthetic construct
SEQUENCE: 388
ctttcggggc tgtggtggag gc                                            22

SEQ ID NO: 389           moltype = DNA   length = 20
FEATURE                  Location/Qualifiers
source                   1..20
                         mol_type = other DNA
                         organism = synthetic construct
SEQUENCE: 389
agatccaagc tgtgaccggc                                               20

SEQ ID NO: 390           moltype = DNA   length = 1002
FEATURE                  Location/Qualifiers
source                   1..1002
                         mol_type = other DNA
                         organism = synthetic construct
SEQUENCE: 390
gctagcacca agggcccatc ggtcttcccc ctggcaccct cctccaagag cacctctggg   60
ggcacagcgg ccctgggctg cctggtcaag gactacttcc ccgagccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctggggdga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gtgtggtcag cgtcctcacc gtcctgcacc aggactggct gaatggcaag  600
gagtacaagt gcaaggtgtc caacaaagcc ctcccagccc ccatcgagaa aaccatctcc  660
aaagccaaag ggcagccccg agaaccacag gtgtacaccc tgcccccatc ccgggatgag  720
ctgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa tgataatcta ga                    1002

SEQ ID NO: 391           moltype = AA   length = 330
FEATURE                  Location/Qualifiers
source                   1..330
                         mol_type = protein
                         organism = synthetic construct
SEQUENCE: 391
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 392           moltype = DNA   length = 513
FEATURE                  Location/Qualifiers
source                   1..513
                         mol_type = other DNA
                         organism = synthetic construct
SEQUENCE: 392
caggtccagc tgagagagag cggcccttca ctggtcaagc catcccagac actgagcctg   60
acatgcacag caagcgggtt ttcactgagc gacaaggcag tggatggggt ccgacaggca  120
```

```
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag ctgtcctgac ggctatcggg agagatctga ttgcagtaat    360
aggccagctt gtggcacatc cgactgctgt cgcgtgtctg tcttcgggaa ctgcctgact    420
accctgcctg tgtcctactc ttatacctac aattatgaat ggcatgtgga tgtctgggga    480
cagggcctgc tggtgacagt ctctagtgct agc                                513

SEQ ID NO: 393          moltype = DNA  length = 1563
FEATURE                 Location/Qualifiers
source                  1..1563
                        mol_type = other DNA
                        organism = synthetic construct
SEQUENCE: 393
atgcgcagga tgcaactcct gttgctgatt gcactaagtc ttgcacttgt cacgaattcg    60
caggtccagc tgagagagag cggcccttca ctggtcaagc catcccagac actgagcctg    120
acatgcacag caagcgggtt ttcactgagc gacaaggcag tgggatgggt ccgacaggca    180
ccaggaaaag ccctggaatg gctgggcagc atcgataccg gcgggaacac agggtacaat    240
cccggactga agagcagact gtccattacc aaggacaact ctaaaagtca ggtgtcactg    300
agcgtgagct ccgtcaccac agaggatagt gcaacttact attgcacctc tgtgcaccag    360
gaaactaaga aataccagag ctgtcctgac ggctatcggg agagatctga ttgcagtaat    420
aggccagctt gtggcacatc cgactgctgt cgcgtgtctg tcttcgggaa ctgcctgact    480
accctgcctg tgtcctactc ttatacctac aattatgaat ggcatgtgga tgtctgggga    540
cagggcctgc tggtgacagt ctctagtgct agcaccaagg gcccatcggt cttccccctg    600
gcaccctcct ccaagagcac ctctgggggc acagcggccc tgggctgcct ggtcaaggac    660
tacttccccg agccggtgac ggtgtcgtgg aactcaggcg ccctgaccag cggcgtgcac    720
accttccccg ctgtcctaca gtcctcagga ctctactccc tcagcagcgt ggtgaccgtg    780
ccctccagca gcttgggcac ccagacctac atctgcaacg tgaatcacaa gcccagcaac    840
accaaggtgg acaagaaagt tgagcccaaa tcttgtgaca aaactcacac atgcccaccg    900
tgcccagcac ctgaactcct ggggggaccg tcagtcttcc tcttcccccc aaaacccaag    960
gacaccctca tgatctcccg gacccctgag gtcacatgcg tggtggtgga cgtgagccac    1020
gaagaccctg aggtcaagtt caactggtac gtggacggcg tggaggtgca taatgccaag    1080
acaaagccgc gggaggagca gtacaacagc acgtaccgtg tggtcagcgt cctcaccgtc    1140
ctgcaccagg actggctgaa tggcaaggag tacaagtgca aggtctccaa caaagccctc    1200
ccagccccca tcgagaaaac catctccaaa gccaaagggc agccccgaga accacaggtg    1260
tacaccctgc ccccatcccg ggatgagctg accaagaacc aggtcagcct gacctgcctg    1320
gtcaaaggct tctatcccag cgacatcgcc gtggagtggg agagcaatgg gcagccggag    1380
aacaactaca agaccacgcc tcccgtgctg gactccgacg gctccttctt cctctacagc    1440
aagctcaccg tggacaagag caggtggcag caggggaacg tcttctcatg ctccgtgatg    1500
catgaggctc tgcacaacca ctacacgcag aagagcctct ccctgtctcc gggtaaatga    1560
taa                                                                 1563

SEQ ID NO: 394          moltype = AA  length = 519
FEATURE                 Location/Qualifiers
source                  1..519
                        mol_type = protein
                        organism = synthetic construct
SEQUENCE: 394
MRRMQLLLLI ALSLALVTNS QVQLRESGPS LVKPSQTLSL TCTASGFSLS DKAVGWVRQA    60
PGKALEWLGS IDTGGNTGYN PGLKSRLSIT KDNSKSQVSL SVSSVTTEDS ATYYCTSVHQ    120
ETKKYQSCPD GYRERSDCSN RPACGTSDCC RVSVFGNCLT TLPVSYSYTY NYEWHVDVWG    180
QGLLVTVSSA STKGPSVFPL APSSKSTSGG TAALGCLVKD YFPEPVTVSW NSGALTSGVH    240
TFPAVLQSSG LYSLSSVVTV PSSSLGTQTY ICNVNHKPSN TKVDKKVEPK SCDKTHTCPP    300
CPAPELLGGP SVFLFPPKPK DTLMISRTPE VTCVVVDVSH EDPEVKFNWY VDGVEVHNAK    360
TKPREEQYNS TYRVVSVLTV LHQDWLNGKE YKCKVSNKAL PAPIEKTISK AKGQPREPQV    420
YTLPPSRDEL TKNQVSLTCL VKGFYPSDIA VEWESNGQPE NNYKTTPPVL DSDGSFFLYS    480
KLTVDKSRWQ QGNVFSCSVM HEALHNHYTQ KSLSLSPGK                          519

SEQ ID NO: 395          moltype = DNA  length = 1470
FEATURE                 Location/Qualifiers
source                  1..1470
                        mol_type = other DNA
                        organism = synthetic construct
SEQUENCE: 395
atgcgcagga tgcaactcct gttgctgatt gcactaagtc ttgcacttgt cacgaattcg    60
caggtccagc tgagagagag cggcccttca ctggtcaagc catcccagac actgagcctg    120
acatgcacag caagcgggtt ttcactgagc gacaaggcag tgggatgggt ccgacaggca    180
ccaggaaaag ccctggaatg gctgggcagc atcgataccg gcgggaacac agggtacaat    240
cccggactga agagcagact gtccattacc aaggacaact ctaaaagtca ggtgtcactg    300
agcgtgagct ccgtcaccac agaggatagt gcaacttact attgcacctc tgtgcaccag    360
gaaactaaga aataccagag cgagacctac atggttcgg gtctctctta tacctacaat    420
tatgaatggc atgtggatgt ctgggacag ggctgctgg tgacagtctc tagtgctagc    480
accaaggggcc catcggtctt ccccctggca ccctcctcca gagcacctc tggggggcaca    540
gcggccctgg gctgcctggt caaggactac ttccccgagc cggtgacggt gtcgtggaac    600
tcaggcgccc tgaccagcgg cgtgcacacc ttccccggctg cctacagtc ctcaggactc    660
tactccctca gcagcgtggt gaccgtgccc tccagcagct tgggcaccca gacctacatc    720
tgcaacgtga atcacaagcc cagcaacacc aaggtggaca gaaagttga gcccaaatct    780
tgtgacaaaa ctcacacatg cccaccgtgc ccagcacctg aactcctggg gggaccgtca    840
gtcttcctct tccccccaaa acccaaggac accctcatga tctcccggac ccctgaggtc    900
```

```
acatgcgtgg tggtggacgt gagccacgaa gaccctgagg tcaagttcaa ctggtacgtg    960
gacggcgtgg aggtgcataa tgccaagaca aagccgcggg aggagcagta caacagcacg   1020
taccgtgtgg tcagcgtcct caccgtcctg caccaggact ggctgaatgg caaggagtac   1080
aagtgcaagg tgtccaacaa agccctccca gcccccatcg agaaaaccat ctccaaagcc   1140
aaagggcagc cccgagaacc acaggtgtac accctgcccc catcccggga tgagctgacc   1200
aagaaccagg tcagcctgac ctgcctggtc aaaggcttct atcccagcga catcgccgtg   1260
gagtgggaga gcaatgggca gccggagaac aactacaaga ccacgcctcc cgtgctggac   1320
tccgacggct ccttcttcct ctacagcaag ctcaccgtgg acaagagcag gtggcagcag   1380
gggaacgtct tctcatgctc cgtgatgcat gaggctctgc acaaccacta cacgcagaag   1440
agcctctccc tgtctccggg taaatgataa                                    1470

SEQ ID NO: 396          moltype = AA   length = 488
FEATURE                 Location/Qualifiers
source                  1..488
                        mol_type = protein
                        organism = synthetic construct
SEQUENCE: 396
MRRMQLLLLI ALSLALVTNS QVQLRESGPS LVKPSQTLSL TCTASGFSLS DKAVGWVRQA    60
PGKALEWLGS IDTGGNTGYN PGLKSRLSIT KDNSKSQVSL SVSSVTTEDS ATYYCTSVHQ   120
ETKKYQSETY YGSGLSYTYN YEWHVDVWGQ GLLVTVSSAS TKGPSVFPLA PSSKSTSGGT   180
AALGCLVKDY FPEPVTVSWN SGALTSGVHT FPAVLQSSGL YSLSSVVTVP SSSLGTQTYI   240
CNVNHKPSNT KVDKKVEPKS CDKTHTCPPC PAPELLGGPS VFLFPPKPKD TLMISRTPEV   300
TCVVVDVSHE DPEVKFNWYV DGVEVHNAKT KPREEQYNST YRVVSVLTVL HQDWLNGKEY   360
KCKVSNKALP APIEKTISKA KGQPREPQVY TLPPSRDELT KNQVSLTCLV KGFYPSDIAV   420
EWESNGQPEN NYKTTPPVLD SDGSFFLYSK LTVDKSRWQQ GNVFSCSVMH EALHNHYTQK   480
SLSLSPGK                                                            488

SEQ ID NO: 397          moltype = DNA   length = 258
FEATURE                 Location/Qualifiers
source                  1..258
                        mol_type = other DNA
                        organism = synthetic construct
SEQUENCE: 397
aattcgggtc tcaagagccc aaggagtgct aaagaactta gatgtcagtg cataaagaca    60
tactccaaac ctttccaccc caagttcatc aaggagctga gagtgattga gagtggacca   120
cactgcgcca acacagagat tattgtaaag ctttctgatg ggagagagct ctgcctggac   180
cccaaggaaa actgggtgca gagggtcgtg gagaagttct tgaagagggc tgagaactca   240
tcttatgaga ccagctaa                                                 258

SEQ ID NO: 398          moltype = AA   length = 85
FEATURE                 Location/Qualifiers
source                  1..85
                        mol_type = protein
                        organism = synthetic construct
SEQUENCE: 398
NSGLKSPRSA KELRCQCIKT YSKPFHPKFI KELRVIESGP HCANTEIIVK LSDGRELCLD    60
PKENWVQRVV EKFLKRAENS SYETS                                          85

SEQ ID NO: 399          moltype = DNA   length = 267
FEATURE                 Location/Qualifiers
source                  1..267
                        mol_type = other DNA
                        organism = synthetic construct
SEQUENCE: 399
aattcgggtc tcaagagccc aaggagtgct aaagaactta gatgtcagtg cataaagaca    60
tactccaaac ctttccaccc caagttcatc aaggagctga gagtgattga gagtggacca   120
cactgcgcca acacagagat tattgtaaag ctttctgatg ggagagagct ctgcctggac   180
cccaaggaaa actgggtgca gagggtcgtg gagaagttct tgaagagggc tgagaactca   240
ggcagcggtt cttatgagac cagctaa                                       267

SEQ ID NO: 400          moltype = AA   length = 88
FEATURE                 Location/Qualifiers
source                  1..88
                        mol_type = protein
                        organism = synthetic construct
SEQUENCE: 400
NSGLKSPRSA KELRCQCIKT YSKPFHPKFI KELRVIESGP HCANTEIIVK LSDGRELCLD    60
PKENWVQRVV EKFLKRAENS GSGSYETS                                       88

SEQ ID NO: 401          moltype = DNA   length = 435
FEATURE                 Location/Qualifiers
source                  1..435
                        mol_type = other DNA
                        organism = synthetic construct
SEQUENCE: 401
aattcgggtc tcaagagcca aggtcaagat cgccacatga tcagaatgcg tcagctcata    60
gatattgttg atcagctgaa gaactacgtg aacgacttgg tccctgaatt tctgccagct   120
cccgaagatg tagagacaaa ctgtgagtgg tcagccttct cctgctttca gaaggcccaa   180
ctaaagtcag caaataccgg caacaacgag aggataatca atgtatcaat caaaaagctg   240
```

-continued

```
aagaggaagc caccttccac aaatgcaggg agacggcaga aacaccgcct gacatgccct   300
tcatgtgatt cttacgagaa gaagccaccc aaagagttcc tagagcggtt caagtcactt   360
ctcgacaaga tgattgatca gcatctgtcc tctcgcacac acggaagtga agattcctct   420
tatgagacca gctaa                                                     435

SEQ ID NO: 402            moltype = AA   length = 144
FEATURE                   Location/Qualifiers
source                    1..144
                          mol_type = protein
                          organism = synthetic construct
SEQUENCE: 402
NSGLKSQGQD RHMIRMRQLI DIVDQLKNYV NDLVPEFLPA PEDVETNCEW SAFSCFQKAQ   60
LKSANTGNNE RIINVSIKKL KRKPPSTNAG RRQKHRLTCP SCDSYEKKPP KEFLERFKSL   120
LDKMIDQHLS SRTHGSEDSS YETS                                          144

SEQ ID NO: 403            moltype = DNA   length = 435
FEATURE                   Location/Qualifiers
source                    1..435
                          mol_type = other DNA
                          organism = synthetic construct
SEQUENCE: 403
aattcgggtc tcaagagcca aggtcaagat cgccacatga tcagaatgcg tcagctcata   60
gatattgttg atcagctgaa gaactacgtg aacgacttgg tccctgaatt tctgccagct   120
cccgaagatg tagagacaaa ctgtgagtgg tcagccttct cctgctttca gaaggcccaa   180
ctaaagtcag caaataccgg caacaacgag aggataatca atgtatcaat caaaaagctg   240
aagaggaagc caccttccac aaatgcaggg agacggcaga aacaccgcct gacatgccct   300
tcatgtgatt cttacgagaa gaagccaccc aaagagttcc tagagcggtt caagtcactt   360
ctcgacaaga tgattgatca gcatctgtcc tctcgcacac acggaagtga agattcctct   420
tatgagacca gctaa                                                     435

SEQ ID NO: 404            moltype = AA   length = 144
FEATURE                   Location/Qualifiers
source                    1..144
                          mol_type = protein
                          organism = synthetic construct
SEQUENCE: 404
NSGLKSQGQD RHMIRMRQLI DIVDQLKNYV NDLVPEFLPA PEDVETNCEW SAFSCFQKAQ   60
LKSANTGNNE RIINVSIKKL KRKPPSTNAG RRQKHRLTCP SCDSYEKKPP KEFLERFKSL   120
LDKMIDQHLS SRTHGSEDSS YETS                                          144

SEQ ID NO: 405            moltype = DNA   length = 249
FEATURE                   Location/Qualifiers
source                    1..249
                          mol_type = other DNA
                          organism = synthetic construct
SEQUENCE: 405
aattcgggtc tcaagagcaa gcccgtcagc ctgagctaca gatgcccatg ccgattcttc   60
gaaagccatg ttgccagagc caacgtcaag catctcaaaa ttctcaacac tccaaactgt   120
gcccttcaga ttgtagcccg gctgaagaac aacaacagac aagtgtgcat tgacccgaag   180
ctaaagtgga ttcaggagta cctggagaaa gctttaaaca agggcagcgg ttcttatgag   240
accagctaa                                                           249

SEQ ID NO: 406            moltype = DNA   length = 78
FEATURE                   Location/Qualifiers
source                    1..78
                          mol_type = other DNA
                          organism = synthetic construct
SEQUENCE: 406
aattcgggtc tcaagagcgc tggctgcaag aatttcttct ggaagacttt cacatcctgt   60
tcttatgaga ccagctaa                                                 78

SEQ ID NO: 407            moltype = AA   length = 25
FEATURE                   Location/Qualifiers
source                    1..25
                          mol_type = protein
                          organism = synthetic construct
SEQUENCE: 407
NSGLKSAGCK NFFWKTFTSC SYETS                                         25

SEQ ID NO: 408            moltype = DNA   length = 126
FEATURE                   Location/Qualifiers
source                    1..126
                          mol_type = other DNA
                          organism = synthetic construct
SEQUENCE: 408
aattcgggtc tcaagagcta ttgccagaag tggatgtgga cctgcgatag cgaacggaaa   60
tgttgcgaag gcatggtgtg ccgcctgtgg tgcaagaaga aactctggtc ttatgagacc   120
agctaa                                                              126
```

```
SEQ ID NO: 409           moltype = AA   length = 41
FEATURE                  Location/Qualifiers
source                   1..41
                         mol_type = protein
                         organism = synthetic construct
SEQUENCE: 409
NSGLKSYCQK WMWTCDSERK CCEGMVCRLW CKKKLWSYET S                     41

SEQ ID NO: 410           moltype = DNA   length = 138
FEATURE                  Location/Qualifiers
source                   1..138
                         mol_type = other DNA
                         organism = synthetic construct
SEQUENCE: 410
aattcgggtc tcaagagcat gtgtatgccc tgcttcacga ccgatcacca gatggcgcgc   60
aaatgcgatg actgttgcgg cggtaaaggt cgcggaaagt gctatggccc gcagtgtctg  120
tcttatgaga ccagctaa                                                 138

SEQ ID NO: 411           moltype = DNA   length = 111
FEATURE                  Location/Qualifiers
source                   1..111
                         mol_type = other DNA
                         organism = synthetic construct
SEQUENCE: 411
aattcgggtc tcaagagctg caagggcaaa ggtgcgaaat gcagccgcct gatgtatgat   60
tgctgtaccg ggtcctgccg cagtggcaag tgctcttatg agaccagcta a            111

SEQ ID NO: 412           moltype = DNA   length = 672
FEATURE                  Location/Qualifiers
source                   1..672
                         mol_type = other DNA
                         organism = synthetic construct
SEQUENCE: 412
tcacgaattc gcaggccgtc ctgaaccagc caagcagcgt ctccgggtct ctggggcagc   60
gggtctcaat cacctggtagc gggtcttcct ccaatgtcgg caacggctac gtgtcttggt  120
atcagctgat ccctggcagt gccccacgaa ccctgatcta cggcgacaca tccagagctt  180
ctgggggtccc cgatcggttc tcagggagca gatccggaaa cacagctact ctgaccatca  240
gctccctgca ggctgaggac gaagcagatt atttctgcgc atctgccgag gactctagtt  300
caaatgccgt gtttggaagc ggcaccacac tgacagtcct ggggcagccc aagagtcccc  360
cttcagtgac tctgttccca ccctctaccg aggaactgaa cggaaacaag gccacactgg  420
tgtgtctgat cagcgacttt taccctggat ccgtcactgt ggtctggaag gcagatggca  480
gcacaattac taggaacgtg gaaactaccc gcgcctccaa gcagtctaat agtaaatacg  540
ccgccagctc ctatctgagc ctgacctcta gtgattggaa gtccaaaggg tcatatagct  600
gcgaagtgac ccatgaaggc tcaaccgtga ctaagactgt gaaaccatcc gagtgctcct  660
aggctagctg gc                                                       672

SEQ ID NO: 413           moltype = AA   length = 7
FEATURE                  Location/Qualifiers
source                   1..7
                         mol_type = protein
                         organism = synthetic construct
SEQUENCE: 413
SRIRRPS                                                             7

SEQ ID NO: 414           moltype = AA   length = 34
FEATURE                  Location/Qualifiers
source                   1..34
                         mol_type = protein
                         organism = synthetic construct
SEQUENCE: 414
TSQAASPGLW GSGSQSPVAG LPPMSATATC LGIS                              34

SEQ ID NO: 415           moltype = AA   length = 8
FEATURE                  Location/Qualifiers
source                   1..8
                         mol_type = protein
                         organism = synthetic construct
SEQUENCE: 415
SLAVPHEP                                                            8

SEQ ID NO: 416           moltype = AA   length = 25
FEATURE                  Location/Qualifiers
source                   1..25
                         mol_type = protein
                         organism = synthetic construct
SEQUENCE: 416
STATHPELLG SPIGSQGADP ETQLL                                        25

SEQ ID NO: 417           moltype = AA   length = 32
```

```
FEATURE                Location/Qualifiers
source                 1..32
                       mol_type = protein
                       organism = synthetic construct
SEQUENCE: 417
PSAPCRLRTK QIISAHLPRT LVQMPCLEAA PH                                             32

SEQ ID NO: 418         moltype = AA  length = 11
FEATURE                Location/Qualifiers
source                 1..11
                       mol_type = protein
                       organism = synthetic construct
SEQUENCE: 418
QSWGSPRVPL Q                                                                    11

SEQ ID NO: 419         moltype = AA  length = 9
FEATURE                Location/Qualifiers
source                 1..9
                       mol_type = protein
                       organism = synthetic construct
SEQUENCE: 419
LCSHPLPRN                                                                        9

SEQ ID NO: 420         moltype = AA  length = 9
FEATURE                Location/Qualifiers
source                 1..9
                       mol_type = protein
                       organism = synthetic construct
SEQUENCE: 420
TETRPHWCV                                                                        9

SEQ ID NO: 421         moltype = AA  length = 42
FEATURE                Location/Qualifiers
source                 1..42
                       mol_type = protein
                       organism = synthetic construct
SEQUENCE: 421
SATFTLDPSL WSGRQMAAQL LGTWKLPAPP SSLIVNTPPA PI                                  42

SEQ ID NO: 422         moltype = AA  length = 14
FEATURE                Location/Qualifiers
source                 1..14
                       mol_type = protein
                       organism = synthetic construct
SEQUENCE: 422
PLVIGSPKGH IAAK                                                                 14

SEQ ID NO: 423         moltype = AA  length = 6
FEATURE                Location/Qualifiers
source                 1..6
                       mol_type = protein
                       organism = synthetic construct
SEQUENCE: 423
PMKAQP                                                                           6

SEQ ID NO: 424         moltype = AA  length = 10
FEATURE                Location/Qualifiers
source                 1..10
                       mol_type = protein
                       organism = synthetic construct
SEQUENCE: 424
NHPSAPRLAG                                                                      10

SEQ ID NO: 425         moltype = DNA  length = 641
FEATURE                Location/Qualifiers
source                 1..641
                       mol_type = other DNA
                       organism = synthetic construct
SEQUENCE: 425
tcacgaattc gcaggtccag ctggtacagt ctggggctga ggtgaagaag cctgggcct    60
cagtgaaggt gtcctgcaag gtttccggat acaccctcac tgaattatcc atgcactggg   120
tgcgacaggc tcctggaaaa gggcttgagt ggatgggagg ttttgatcct gaagatggtg   180
aaacaatcta cgcacagaag ttccagggca gagtcaccat gaccgaggac acatctcag   240
acacagccta catggagctg agcagcctga gatctgagga cacggccgtg tattactgca   300
cctctgtgca ccaggaaact aagaaatacc agagcccaag gagtgctaaa gaacttagat   360
gtcagtgcat aaagacatac tccaaacctt ccaccccaa gttcatcaag gagctgagag   420
tgattgagag tggaccacac tgcgccaaca cagagattat tgtaaagctt tctgatggga   480
gagagctctg cctggacccc aaggaaaact gggtgcagag gtcgtggag aagttcttga   540
agagggctga gaactcaggc agcggttctt atacctacaa ttatgaatgg catgtggatg   600
```

-continued

```
tctggggaca gggcctgctg gtgacagtct ctagtgctag c                    641

SEQ ID NO: 426        moltype = DNA   length = 641
FEATURE               Location/Qualifiers
source                1..641
                      mol_type = other DNA
                      organism = synthetic construct
SEQUENCE: 426
tcacgaattc gcaggtgcag ctggtgcagt ctggggctga ggtgaagaag cctggggcct    60
cagtgaaggt ttcctgcaag gcatctggat acaccttcac cagctactat atgcactggg   120
tgcgacaggc ccctggacaa gggcttgagt ggatgggaat aatcaaccct agtggtggta   180
gcacaagcta cgcacagaag ttccagggca gagtcaccat gaccagggac acgtccacga   240
gcacagtcta catggagctg agcagcctga gatctgagga cacggccgtg tattactgca   300
cctctgtgca ccaggaaact aagaaatacc agagcccaag gagtgctaaa gaacttagat   360
gtcagtgcat aaagacatac tccaaacctt ccaccccaa gttcatcaag gagctgagag    420
tgattgagag tggaccacac tgcgccaaca cagagattat tgtaaagctt tctgatggga   480
gagagctctg cctggacccc aaggaaaact gggtgcagag ggtcgtggag aagttcttga   540
agagggctga gaactcaggc agcggttctt atacctacaa ttatgaatgg catgtggatg   600
tctggggaca gggcctgctg gtgacagtct ctagtgctag c                    641

SEQ ID NO: 427        moltype = DNA   length = 641
FEATURE               Location/Qualifiers
source                1..641
                      mol_type = other DNA
                      organism = synthetic construct
SEQUENCE: 427
tcacgaattc gcaggtgcag ctggtgcagt ctggggctga ggtgaagaag cctgggtcct    60
cggtgaaggt gtcctgcaag gcttctggag gcaccttcag cagctatgct atcagctggg   120
tgcgacaggc ccctggacaa gggcttgagt ggatgggagg gatcatccct atctttggta   180
cagcaaacta cgcacagaag ttccagggca gagtcacgat taccgcggac aaatccacga   240
gcacagccta catggagctg agcagcctga gatctgagga cacggccgtg tattactgca   300
cctctgtgca ccaggaaact aagaaatacc agagcccaag gagtgctaaa gaacttagat   360
gtcagtgcat aaagacatac tccaaacctt ccacccccaa gttcatcaag gagctgagag   420
tgattgagag tggaccacac tgcgccaaca cagagattat tgtaaagctt tctgatggga   480
gagagctctg cctggacccc aaggaaaact gggtgcagag ggtcgtggag aagttcttga   540
agagggctga gaactcaggc agcggttctt atacctacaa ttatgaatgg catgtggatg   600
tctggggaca gggcctgctg gtgacagtct ctagtgctag c                    641

SEQ ID NO: 428        moltype = DNA   length = 641
FEATURE               Location/Qualifiers
source                1..641
                      mol_type = other DNA
                      organism = synthetic construct
SEQUENCE: 428
tcacgaattc ggaggtgcag ctgttggagt ctgggggagg cttggtacag cctggggggt    60
ccctgagact ctcctgtgca gcctctggat tcacctttag cagctatgcc atgagctggg   120
tccgccaggc tccagggaag gggctggagt gggtgagcgc aattagtggt agtggcggta   180
gcacatacta cgcagactcc gtgaaggggc ggttcaccat ctcacgtgac aattccaaga   240
acacgctgta tctgcaaatg aacagcctga gagccgagga cacggccgtg tattactgca   300
cctctgtgca ccaggaaact aagaaatacc agagcccaag gagtgctaaa gaacttagat   360
gtcagtgcat aaagacatac tccaaacctt ccacccccaa gttcatcaag gagctgagag   420
tgattgagag tggaccacac tgcgccaaca cagagattat tgtaaagctt tctgatggga   480
gagagctctg cctggacccc aaggaaaact gggtgcagag ggtcgtggag aagttcttga   540
agagggctga gaactcaggc agcggttctt atacctacaa ttatgaatgg catgtggatg   600
tctggggaca gggcctgctg gtgacagtct ctagtgctag c                    641

SEQ ID NO: 429        moltype = DNA   length = 638
FEATURE               Location/Qualifiers
source                1..638
                      mol_type = other DNA
                      organism = synthetic construct
SEQUENCE: 429
tcacgaattc gcaggtgcag ctgcaggagt cgggcccagg actggtgaag ccttcggaga    60
cgctgtccct cacctgcact gtctctggtg gctccatcag tagttactac tggagctgga   120
ttcggcagcc cgccgggaag ggactggagt ggattgggcg tatctatacc agtgggagca   180
ccaactacaa cccctccctc aagagtcgag tcaccatgtc agtagacacg tccaagaacc   240
agttctccct gaagctgagc tctgtgaccg ccgcggacac ggccgtgtat tactgcacct   300
ctgtgcacca ggaaactaag aataccaga gcccaaggag tgctaaagaa cttagatgtc      360
agtgcataaa gacatactcc aaacctttcc accccaagtt catcaaggag ctgagagtgg    420
ttgagagtgg accacactgc gccaacacag agattattgt aaagctttct gatggagag    480
agctctgcct ggaccccaag gaaaactggg tgcagaggt cgtggagaag ttcttgaaga     540
gggctgagaa ctcaggcagc ggttcttata cctacaatta tgaatggcat gtggatgtct   600
ggggacaggg cctgctggtg acagtctcta gtgctagc                         638

SEQ ID NO: 430        moltype = DNA   length = 638
FEATURE               Location/Qualifiers
source                1..638
                      mol_type = other DNA
                      organism = synthetic construct
```

```
SEQUENCE: 430
tcacgaattc gcaggtgcag ctacagcagt ggggcgcagg actgttgaag ccttcggaga    60
cgctgtccct cacctgcgct gtctatggtg ggtccttcag tggttactac tggagctgga   120
ttcgccagcc cccagggaag gggctggagt ggattgggga aatcaatcat agtggaagca   180
ccaactacaa cccgtccctc aagagtcgag tcaccatatc agtagacacg tccaagaacc   240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtga   420
ttgagagtgg accacactgc gccaacacag agattattgt aaagctttct gatgggagag   480
agctctgcct ggaccccaag gaaaactggg tgcagagggt cgtggagaag ttcttgaaga   540
gggctgagaa ctcaggcagc ggttcttata cctacaatta tgaatggcat gtggatgtct   600
ggggacaggg cctgctggtg acagtctcta gtgctagc                           638

SEQ ID NO: 431          moltype = DNA   length = 431
FEATURE                 Location/Qualifiers
source                  1..431
                        mol_type = other DNA
                        organism = synthetic construct
SEQUENCE: 431
tcacgaattc gcaggtgcag ctgcaggagt cgggcccagg actggtgaag ccttcggaga    60
cgctgtccct cacctgcact gtctctggtg gctccatcag tagttactac tggagctgga   120
ttcggcagcc cgccgggaag ggactggagt ggattgggcg tatctatacc agtgggaca    180
ccaactacaa cccctccctc aagagtcgag tcaccatgtc agtagacacg tccaagaacc   240
agttctccct gaagctgagc tctgtgaccg ccgcggacac ggccgtgtat tactgcacct   300
ctgtgcacca ggaaactaag aaataccaga gcgagaccta ctatggttcg ggtctctctt   360
atacctacaa ttatgaatgg catgtggatg tctggggaca gggcctgctg gtgacagtct   420
ctagtgctag c                                                        431

SEQ ID NO: 432          moltype = DNA   length = 638
FEATURE                 Location/Qualifiers
source                  1..638
                        mol_type = other DNA
                        organism = synthetic construct
SEQUENCE: 432
tcacgaattc gcaggtgcag ctacagcagt ggggcgcagg actgttgaag ccttcggaga    60
cgctgtccct cacctgcaca gcaagcgggt tttcactgag cgacaaggca gtgggatgga   120
ttcgccagcc cccagggaag gggctggagt ggattgggga aatcaatcat agtggaagca   180
ccaactacaa cccgtccctc aagagtcgag tcaccatatc agtagacacg tccaagaacc   240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtga   420
ttgagagtgg accacactgc gccaacacag agattattgt aaagctttct gatgggagag   480
agctctgcct ggaccccaag gaaaactggg tgcagagggt cgtggagaag ttcttgaaga   540
gggctgagaa ctcaggcagc ggttcttata cctacaatta tgaatggcat gtggatgtct   600
ggggacaggg cctgctggtg acagtctcta gtgctagc                           638

SEQ ID NO: 433          moltype = DNA   length = 638
FEATURE                 Location/Qualifiers
source                  1..638
                        mol_type = other DNA
                        organism = synthetic construct
SEQUENCE: 433
tcacgaattc gcaggtgcag ctacagcagt ggggcgcagg actgttgaag ccttcggaga    60
cgctgtccct cacctgcgct gtctatggtg ggtccttcag tggttactac tggagctgga   120
ttcgccagcc cccagggaag gggctggagt ggctggtgcg catcgatacc ggcgggaaca   180
cagggtacaa cccgtccctc aagagtcgag tcaccatatc agtagacacg tccaagaacc   240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtga   420
ttgagagtgg accacactgc gccaacacag agattattgt aaagctttct gatgggagag   480
agctctgcct ggaccccaag gaaaactggg tgcagagggt cgtggagaag ttcttgaaga   540
gggctgagaa ctcaggcagc ggttcttata cctacaatta tgaatggcat gtggatgtct   600
ggggacaggg cctgctggtg acagtctcta gtgctagc                           638

SEQ ID NO: 434          moltype = DNA   length = 638
FEATURE                 Location/Qualifiers
source                  1..638
                        mol_type = other DNA
                        organism = synthetic construct
SEQUENCE: 434
tcacgaattc gcaggtgcag ctacagcagt ggggcgcagg actgttgaag ccttcggaga    60
cgctgtccct cacctgcgct gtctatggtg ggtccttcag tgacaagtac tggagctgga   120
ttcgccagcc cccagggaag gggctggagt ggattgggga aatcaatcat agtggaagca   180
ccaactacaa cccgtccctc aagagtcgag tcaccatatc agtagacacg tccaagaacc   240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtga   420
ttgagagtgg accacactgc gccaacacag agattattgt aaagctttct gatgggagag   480
agctctgcct ggaccccaag gaaaactggg tgcagagggt cgtggagaag ttcttgaaga   540
```

```
gggctgagaa ctcaggcagc ggttcttata cctacaatta tgaatggcat gtggatgtct  600
ggggacaggg cctgctggtg acagtctcta gtgctagc                          638

SEQ ID NO: 435              moltype = DNA   length = 638
FEATURE                     Location/Qualifiers
source                      1..638
                            mol_type = other DNA
                            organism = synthetic construct
SEQUENCE: 435
tcacgaattc gcaggtgcag ctacagcagt ggggcgcagg actgttgaag ccttcggaga  60
cgctgtccct cacctgcgct gtctatggtg ggtccttcag tggttactac tggagctgga  120
ttcgccagcc cccagggaag gggctggagt ggattgggag catcaatcat agtggaagca  180
ccaactacaa cccgtccctc aagagtcgag tcaccatatc agtagacacg tccaagaacc  240
agttctccct gaagctgagc tctgtgaccg ccgcggacac ggctgtgtat tactgtacct  300
ctgtgcacca ggaaactaag aaataccaga gcccaaggag tgctaaagaa cttagatgtc  360
agtgcataaa gacatactcc aaacctttcc accccaagtt catcaaggag ctgagagtga  420
ttgagagtgg accacactgc gccaacacag agattattgt aaagctttct gatgggagag  480
agctctgcct ggaccccaag gaaaactggg tgcagagggt cgtggagaag ttcttgaaga  540
gggctgagaa ctcaggcagc ggttcttata cctacaatta tgaatggcat gtggatgtct  600
ggggacaggg cctgctggtg acagtctcta gtgctagc                          638

SEQ ID NO: 436              moltype = DNA   length = 638
FEATURE                     Location/Qualifiers
source                      1..638
                            mol_type = other DNA
                            organism = synthetic construct
SEQUENCE: 436
tcacgaattc gcaggtgcag ctacagcagt ggggcgcagg actgttgaag ccttcggaga  60
cgctgtccct cacctgcaca gcaagcgggt tttcactgag cgacaaggca gtgggatgga  120
ttcgccagcc cccagggaag gggctggagt ggctgggcag catcgatacc ggcgggaaca  180
cagggtacaa cccgtccctc aagagtcgag tcaccatatc agtagacacg tccaagaacc  240
agttctccct gaagctgagc tctgtgaccg ccgcggacac ggctgtgtat tactgtacct  300
ctgtgcacca ggaaactaag aaataccaga gcccaaggag tgctaaagaa cttagatgtc  360
agtgcataaa gacatactcc aaacctttcc accccaagtt catcaaggag ctgagagtga  420
ttgagagtgg accacactgc gccaacacag agattattgt aaagctttct gatgggagag  480
agctctgcct ggaccccaag gaaaactggg tgcagagggt cgtggagaag ttcttgaaga  540
gggctgagaa ctcaggcagc ggttcttata cctacaatta tgaatggcat gtggatgtct  600
ggggacaggg cctgctggtg acagtctcta gtgctagc                          638

SEQ ID NO: 437              moltype = DNA   length = 638
FEATURE                     Location/Qualifiers
source                      1..638
                            mol_type = other DNA
                            organism = synthetic construct
SEQUENCE: 437
tcacgaattc gcaggtgcag ctacagcagt ggggcgcagg actgttgaag ccttcggaga  60
cgctgtccct cacctgcaca gcaagcgggt tttcactgag cgacaaggca gtgggatgga  120
ttcgccagcc cccagggaag gggctggagt ggattgggag catcaatcat agtggaagca  180
ccaactacaa cccgtccctc aagagtcgag tcaccatatc agtagacacg tccaagaacc  240
agttctccct gaagctgagc tctgtgaccg ccgcggacac ggctgtgtat tactgtacct  300
ctgtgcacca ggaaactaag aaataccaga gcccaaggag tgctaaagaa cttagatgtc  360
agtgcataaa gacatactcc aaacctttcc accccaagtt catcaaggag ctgagagtga  420
ttgagagtgg accacactgc gccaacacag agattattgt aaagctttct gatgggagag  480
agctctgcct ggaccccaag gaaaactggg tgcagagggt cgtggagaag ttcttgaaga  540
gggctgagaa ctcaggcagc ggttcttata cctacaatta tgaatggcat gtggatgtct  600
ggggacaggg cctgctggtg acagtctcta gtgctagc                          638

SEQ ID NO: 438              moltype = DNA   length = 638
FEATURE                     Location/Qualifiers
source                      1..638
                            mol_type = other DNA
                            organism = synthetic construct
SEQUENCE: 438
tcacgaattc gcaggtgcag ctacagcagt ggggcgcagg actgttgaag ccttcggaga  60
cgctgtccct cacctgcgct gtctatggtg ggtccttcag tgacaagtac tggagctgga  120
ttcgccagcc cccagggaag gggctggagt ggctgggcag catcgatacc ggcgggaaca  180
cagggtacaa cccgtccctc aagagtcgag tcaccatatc agtagacacg tccaagaacc  240
agttctccct gaagctgagc tctgtgaccg ccgcggacac ggctgtgtat tactgtacct  300
ctgtgcacca ggaaactaag aaataccaga gcccaaggag tgctaaagaa cttagatgtc  360
agtgcataaa gacatactcc aaacctttcc accccaagtt catcaaggag ctgagagtga  420
ttgagagtgg accacactgc gccaacacag agattattgt aaagctttct gatgggagag  480
agctctgcct ggaccccaag gaaaactggg tgcagagggt cgtggagaag ttcttgaaga  540
gggctgagaa ctcaggcagc ggttcttata cctacaatta tgaatggcat gtggatgtct  600
ggggacaggg cctgctggtg acagtctcta gtgctagc                          638

SEQ ID NO: 439              moltype = DNA   length = 638
FEATURE                     Location/Qualifiers
source                      1..638
                            mol_type = other DNA
```

```
                          organism = synthetic construct
SEQUENCE: 439
tcacgaattc gcaggtgcag ctacagcagt ggggcgcagg actgttgaag ccttcggaga    60
cgctgtccct cacctgcgct gtctatggtg ggtccttcag tgacaagtac tggagctgga   120
ttcgccagcc cccagggaag gggctggagt ggattgggag catcaatcat agtggaagca   180
ccaactacaa cccgtcctc aagagtcgag tcaccatatc agtagacacg tccaagaacc    240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtgg   420
ttgagagtgg accacactgc gccaacacag agattattgt aaagctttct gatgggagag   480
agctctgcct ggaccccaag gaaaactggg tgcagagggt cgtggagaag ttcttgaaga   540
gggctgagaa ctcaggcagc ggttcttata cctacaatta tgaatggcat gtggatgtct   600
ggggacaggg cctgctggtg acagtctcta gtgctagc                           638

SEQ ID NO: 440        moltype = DNA   length = 671
FEATURE               Location/Qualifiers
source                1..671
                      mol_type = other DNA
                      organism = synthetic construct
SEQUENCE: 440
tcacgaattc gcagtccgtg ctgacccaac ccccgtcagt gtctgctgcc cccgggcaga    60
aggtgactat cagctgctct ggctcatcct ccaatgtcgg caacggctac gtcagctggt   120
accagcagct gcctggaaca gctcctaaac tgctcattta tgacaataac aagcgcccat   180
ccggaatccc tgaccgattc agcggaagca aatcagggac ctctgcaact ctgggaatca   240
ctgggcttca gacaggagat gaggcagatt actattgcgc ctctgcagag gacagctcca   300
gcaatgccgt gttcgggtct ggtaccactc ttacagtcct aggtcagccc aaggctgccc   360
cctcggtcac tctgttcccg ccctcctctg aggagcttca agccaacaag gccacactgg   420
tgtgtctcat aagtgacttc tacccgggag ccgtgacagt ggcctggaag gcagatagca   480
gccccgtcaa ggcgggagtg aaacaacca caccctccaa acaaagcaac aacaagtacg    540
cggccagcag ctatctgagc ctgacgcctg agcagtggaa gtcccacaga agctacagct   600
gccaggtcac gcatgaaggg agcaccgtgg agaagacagt ggcccctaca gaatgttcat   660
aatgagctag c                                                        671

SEQ ID NO: 441        moltype = DNA   length = 671
FEATURE               Location/Qualifiers
source                1..671
                      mol_type = other DNA
                      organism = synthetic construct
SEQUENCE: 441
tcacgaattc gcagtccgtg ctgacccaac ccccgtcagt gtctgctgcc cccgggcaga    60
aggtgactat cagctgctct ggctcatcaa gcaacatcgg gaataattac gtcagctggt   120
accagcagct gcctggaaca gctcctaaac tgctcattta tggcgacaca aagcgcccat   180
ccggaatccc tgaccgattc agcggaagca aatcagggac ctctgcaact ctgggaatca   240
ctgggcttca gacaggagat gaggcagatt actattgcgc ctctgcagag gacagctcca   300
gcaatgccgt gttcgggtct ggtaccactc ttacagtcct aggtcagccc aaggctgccc   360
cctcggtcac tctgttcccg ccctcctctg aggagcttca agccaacaag gccacactgg   420
tgtgtctcat aagtgacttc tacccgggag ccgtgacagt ggcctggaag gcagatagca   480
gccccgtcaa ggcgggagtg aaacaacca caccctccaa acaaagcaac aacaagtacg    540
cggccagcag ctatctgagc ctgacgcctg agcagtggaa gtcccacaga agctacagct   600
gccaggtcac gcatgaaggg agcaccgtgg agaagacagt ggcccctaca gaatgttcat   660
aatgagctag c                                                        671

SEQ ID NO: 442        moltype = DNA   length = 671
FEATURE               Location/Qualifiers
source                1..671
                      mol_type = other DNA
                      organism = synthetic construct
SEQUENCE: 442
tcacgaattc gcagtccgtg ctgacccaac ccccgtcagt gtctgctgcc cccgggcaga    60
aggtgactat cagctgctct ggctcatcaa gcaacatcgg gaataattac gtcagctggt   120
accagcagct gcctggaaca gctcctaaac tgctcattta tggcgacaca tccagagctt   180
ccggaatccc tgaccgattc agcggaagca aatcagggac ctctgcaact ctgggaatca   240
ctgggcttca gacaggagat gaggcagatt actattgcgc ctctgcagag gacagctcca   300
gcaatgccgt gttcgggtct ggtaccactc ttacagtcct aggtcagccc aaggctgccc   360
cctcggtcac tctgttcccg ccctcctctg aggagcttca agccaacaag gccacactgg   420
tgtgtctcat aagtgacttc tacccgggag ccgtgacagt ggcctggaag gcagatagca   480
gccccgtcaa ggcgggagtg aaacaacca caccctccaa acaaagcaac aacaagtacg    540
cggccagcag ctatctgagc ctgacgcctg agcagtggaa gtcccacaga agctacagct   600
gccaggtcac gcatgaaggg agcaccgtgg agaagacagt ggcccctaca gaatgttcat   660
aatgagctag c                                                        671

SEQ ID NO: 443        moltype = DNA   length = 671
FEATURE               Location/Qualifiers
source                1..671
                      mol_type = other DNA
                      organism = synthetic construct
SEQUENCE: 443
tcacgaattc gcaggccgtc ctgaaccagc caagcagcgt ctccgggtct ctggggcaga    60
aggtgactat cagctgctct ggctcatcaa gcaacatcgg gaataattac gtcagctggt   120
```

-continued

```
accagcagct gcctggaaca gctcctaaac tgctcattta tgacaataac aagcgcccat    180
ccggaatccc tgaccgattc agcggaagca aatcagggac ctctgcaact ctgggaatca    240
ctgggcttca gacaggagat gaggcagatt actattgcgc ctctgcagag gacagctcca    300
gcaatgccgt gttcgggtct ggtaccactc ttacagtcct aggtcagccc aaggctgccc    360
cctcggtcac tctgttcccg ccctcctctg aggagcttca agccaacaag gccacactgg    420
tgtgtctcat aagtgacttc tacccgggag ccgtgacagt ggcctggaag gcagatagca    480
gccccgtcaa ggcgggagtg gaaacaacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aatgagctag c                                                        671
```

SEQ ID NO: 444   moltype = DNA length = 671
FEATURE      Location/Qualifiers
source       1..671
          mol_type = other DNA
          organism = synthetic construct
SEQUENCE: 444

```
tcacgaattc gcaggccgtc ctgaaccagc caagcagcgt ctccgggtct ctggggcaga    60
aggtgactat cagctgctct ggctcatcaa gcaacatcgg gaataattac gtcagctggt    120
accagcagct gcctggaaca gctcctaaac tgctcattta tggcgacaca aagcgcccat    180
ccggaatccc tgaccgattc agcggaagca aatcagggac ctctgcaact ctgggaatca    240
ctgggcttca gacaggagat gaggcagatt actattgcgc ctctgcagag gacagctcca    300
gcaatgccgt gttcgggtct ggtaccactc ttacagtcct aggtcagccc aaggctgccc    360
cctcggtcac tctgttcccg ccctcctctg aggagcttca agccaacaag gccacactgg    420
tgtgtctcat aagtgacttc tacccgggag ccgtgacagt ggcctggaag gcagatagca    480
gccccgtcaa ggcgggagtg gaaacaacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aatgagctag c                                                        671
```

SEQ ID NO: 445   moltype = DNA length = 657
FEATURE      Location/Qualifiers
source       1..657
          mol_type = other DNA
          organism = synthetic construct
SEQUENCE: 445

```
gacatccaga tgacccagtc tccatcctcc ctgtctgcat ctgtaggaga cagagtcacc    60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg cccctccgtg gacgttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaatg agctagc       657
```

SEQ ID NO: 446   moltype = DNA length = 657
FEATURE      Location/Qualifiers
source       1..657
          mol_type = other DNA
          organism = synthetic construct
SEQUENCE: 446

```
gaaattgtgt tgacacagtc tccagccacc ctgtctttgt ctccagggga aagagccacc    60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgtg gacgttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaatg agctagc       657
```

SEQ ID NO: 447   moltype = DNA length = 660
FEATURE      Location/Qualifiers
source       1..660
          mol_type = other DNA
          organism = synthetic construct
SEQUENCE: 447

```
gaaatagtga tgacgcagtc tccagccacc ctgtctttgt ctccagggga aagagccacc    60
ctctcctgca gggccagtca gagtgttagc agcagctact atcctggta ccagcagaaa    120
cctgggcagg ctcccaggct cctcatctat ggtgcatcca ccagggccac tggcatccca    180
gccaggttca gtggcagtgg gtctgggaca gacttcactc tcaccatcag cagcctgcag    240
cctgaagatt ttgcagtttta ttactgtcag caggattata acttacctcc gtggacgttc    300
ggccaaggga ccaaggtgga aatcaaacgt acggtggctg caccatctgt cttcatcttc    360
ccgccatctg atgagcagtt gaaatctgga actgcctctg ttgtgtgcct gctgaataac    420
```

-continued

```
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgtta atgagctagc  660
```

SEQ ID NO: 448          moltype = DNA   length = 663
FEATURE                 Location/Qualifiers
source                  1..663
                        mol_type = other DNA
                        organism = synthetic construct
SEQUENCE: 448

```
cagtctgccc tgactcagcc tccctccgcg tccgggtctc ctggacagtc agtcaccatc  60
tcctgcactg gaaccagcag tgacgttggt ggttataact atgtctcctg gtaccaacag  120
cacccaggca aagcccccaa actcatgatt tatgaggtca gtaagcggcc ctcaggggtc  180
cctgatcgct tctctggctc caagtctggc aacacggcct ccctgaccgt ctctgggctc  240
caggctgagg atgaggctga ttattactgc agctcatatg caggcagcaa caatttcgct  300
gtgttcggag gaggcaccca gctgaccgtc ctaggtcagc ccaaggctgc ccctcggtc   360
actctgttcc cgccctcctc tgaggagctt caagccaaca aggccacact ggtgtgtctc  420
ataagtgact tctacccggg agccgtgaca gtggcctgga aggcagatag cagccccgtc  480
aaggcgggag tggagaccac cacaccctcc aaacaaagca acaacaagta cgcggccagc  540
agctatctga gcctgacgcc tgagcagtgg aagtcccaca gaagctacag ctgccaggtc  600
acgcatgaag ggagcaccgt ggagaagaca gtggcccccta cagaatgttc ataatgagct  660
agc                                                                663
```

SEQ ID NO: 449          moltype = DNA   length = 663
FEATURE                 Location/Qualifiers
source                  1..663
                        mol_type = other DNA
                        organism = synthetic construct
SEQUENCE: 449

```
cagtctgccc tgactcagcc tgcctccgtg tctggctccc ctggacagtc gatcaccatc  60
tcctgcactg gaaccagcag tgatgttggg agttataacc ttgtctcctg gtaccaacag  120
cacccaggca aagcccccaa actcatgatt tatgagggca gtaagcggcc ctcaggggtt  180
tctaatcgct tctctggctc caagtctggc aacacggcct ccctgacaat ctctgggctc  240
caggctgagg acgaggctga ttattactgc tgctcatatg caggtagtag cactttctat  300
gtcttcggaa ctgggaccaa ggtcaccgtc ctaggtcagc ccaaggctgc ccctcggtc   360
actctgttcc cgccctcctc tgaggagctt caagccaaca aggccacact ggtgtgtctc  420
ataagtgact tctacccggg agccgtgaca gtggcctgga aggcagatag cagccccgtc  480
aaggcgggag tggagaccac cacaccctcc aaacaaagca acaacaagta cgcggccagc  540
agctatctga gcctgacgcc tgagcagtgg aagtcccaca gaagctacag ctgccaggtc  600
acgcatgaag ggagcaccgt ggagaagaca gtggccccta cagaatgttc ataatgagct  660
agc                                                                663
```

SEQ ID NO: 450          moltype = DNA   length = 663
FEATURE                 Location/Qualifiers
source                  1..663
                        mol_type = other DNA
                        organism = synthetic construct
SEQUENCE: 450

```
cagtctgtgc tgactcagcc accctcggtg tctgaagccc ccaggcagag ggtcaccatc  60
tcctgttctg gaagcagctc caacatcgga aataatgctg taaactggta ccagcagctc  120
ccaggaaagg ctcccaaact cctcatctat tatgatgatc tgctgccctc aggggtctct  180
gaccgattct ctggctccaa gtctggcacc tcagcctccc tggccatcag tgggctccag  240
tctgaggatg aggctgatta ttactgtgca gcatgggatg acagcctgaa tggtcctgtg  300
gtattcggcg gagggaccaa gctgaccgtc ctaggtcagc ccaaggctgc ccctcggtc   360
actctgttcc cgccctcctc tgaggagctt caagccaaca aggccacact ggtgtgtctc  420
ataagtgact tctacccggg agccgtgaca gtggcctgga aggcagatag cagccccgtc  480
aaggcgggag tggagaccac cacaccctcc aaacaaagca acaacaagta cgcggccagc  540
agctatctga gcctgacgcc tgagcagtgg aagtcccaca gaagctacag ctgccaggtc  600
acgcatgaag ggagcaccgt ggagaagaca gtggccccta cagaatgttc ataatgagct  660
agc                                                                663
```

SEQ ID NO: 451          moltype = DNA   length = 336
FEATURE                 Location/Qualifiers
source                  1..336
                        mol_type = other DNA
                        organism = synthetic construct
SEQUENCE: 451

```
ccagtctgtg ctgactcagc caccctcagc gtctgggacc cccgggcaga gggtcaccat  60
ctcttgttct ggaagcagct ccaacatcgg aagtaatact gtaaactggt accagcagct  120
cccaggaacg gcccccaaac tcctcatcta tagtaataat cagcggccct caggggtccc  180
tgaccgattc tctggctcca gtctggcac ctcagcctcc ctggccatca gtgggctcca  240
gtctgaggat gaggctgatt attactgtgc agcatgggat gacagcctga atggtcctaa  300
tgtgttcggc agtggcacca aggtgaccgt cctagg                            336
```

SEQ ID NO: 452          moltype = DNA   length = 657
FEATURE                 Location/Qualifiers
source                  1..657
                        mol_type = other DNA
```

```
                              organism = synthetic construct
SEQUENCE: 452
tcctatgagc tgacacagcc accctcggtg tcagtgtccc caggacagac ggccaggatc   60
acctgctctg gagatgcatt gccaaagcaa tatgcttatt ggtaccagca gaagccaggc   120
caggcccctg tgctggtgat atataaagac agtgagaggc cctcaggcat ccctgagcga   180
ttctctggct ccagctcagg gacaacagtc acgttgacca tcagtggagt ccaggcagaa   240
gatgaggctg actattactg tcaatcagca gacagcagtg gtacttatcc tgtggtattc   300
ggcggaggga ccaagctgac cgtcctaggt cagcccaagg ctgcccctc ggtcactctg    360
ttcccgccct cctctgagga gcttcaagcc aacaaggcca cactggtgtg tctcataagt   420
gacttctacc cgggagccgt gacagtggcc tggaaggcag atagcagccc cgtcaaggcg   480
ggagtggaaa caaccacacc ctccaaacaa agcaacaaca agtacgcggc cagcagctat   540
ctgagcctga cgcctgagca gtggaagtcc cacagaagct acagctgcca ggtcacgcat   600
gaagggagca ccgtggagaa gacagtggcc cctacagaat gttcataatg agctagc      657

SEQ ID NO: 453            moltype = DNA   length = 663
FEATURE                   Location/Qualifiers
source                    1..663
                          mol_type = other DNA
                          organism = synthetic construct SEQUENCE: 453
cagactgtgg tgacccagga gccatcgttc tcagtgtccc ctggagggac agtcacactc   60
acttgtggct tgagctctgg ctcagtctct actagttact accccagctg gtaccagcag   120
accccaggcc aggctccacg cacgctcatc tacagcacaa acactcgctc ttctgggtc    180
cctgatcgct tctctggctc catccttggg aacaaagctg ccctcaccat cacggggcc    240
caggcagatg atgaatctga ttattactgt gtgctgtata tgggtagtgg catttcttat   300
gtcttcggaa ctgggaccaa ggtcaccgtc ctaggtcagc ccaaggctgc ccctcggtc    360
actctgttcc cgccctcctc tgaggagctt caagccaaca ggccacact ggtgtgtctc     420
ataagtgact tctacccggg agccgtgaca gtggcctgga aggcagatag cagccccgtc   480
aaggcgggag tggagaccac cacaccctcc aaacaaagca caacaagta cgcggccagc     540
agctatctga gcctgacgcc tgagcagtgg aagtcccaca gaagctacag ctgccaggtc   600
acgcatgaag ggagcaccgt ggagaagaca gtggccccta cagaatgttc ataatgagct   660
agc                                                                 663

SEQ ID NO: 454            moltype = DNA   length = 666
FEATURE                   Location/Qualifiers
source                    1..666
                          mol_type = other DNA
                          organism = synthetic construct SEQUENCE: 454
cagcctgtgc tgactcaatc atcctctgcc tctgcttccc tgggctcctc ggtcaagctc   60
acctgcactc tgagcagtgg gcacagtagc tacatcatcg catggcatca gcagcagcca   120
gggaaggccc ctcggtactt gatgaagctt gaaggtagtg gaagctacaa caaggggagc   180
ggagttcctg atcgcttctc aggctccagc tctggggctg accgtacct caccatctcc    240
aacctccagt ttgaggatga ggctgattat tactgtgaga cctgggacag taacactcat   300
gtggtattcg gcggagggac caagctgacc gtcctaggtc agcccaaggc tgcccctcg    360
gtcactctgt tcccgcctc ctctgaggag cttcaagcca caaggccac actggtgtgt      420
ctcataagtg acttctaccc gggagccgtg acagtggcct ggaagtcagc agccccc      480
gtcaaggcgg gagtggagac caccacaccc tccaaacaaa gcaacaacaa gtacgcggcc   540
agcagctatc tgagcctgac gcctgagcag tggaagtccc acagaagcta cagctgccag   600
gtcacgcatg aagggagcac cgtggagaag acagtggccc ctacagaatg ttcataatga   660
gctagc                                                              666

SEQ ID NO: 455            moltype = DNA   length = 660
FEATURE                   Location/Qualifiers
source                    1..660
                          mol_type = other DNA
                          organism = synthetic construct SEQUENCE: 455
caatcagttt tgacccagcc accctccgca tccggcaccc ccgggcaacg cgttacaata   60
agctgtagcg gcagctcatc taatattggc agcaactacg tttattggta ccagcagctt   120
ccagggaccg cccccaaatt gcttatctac cggaataatc agaggccttc cggggtgcca   180
gataggttct ctgggagtaa atctggcact agcgcaagtc tggctatcag cgggctccgg   240
tctgaggatg aagccgacta ttattgcgcg agcgctgagg actcatcttc taatgctgtg   300
tttggctccg gtaccacact caccgtccta ggtcagccca aggctgccc tcggtcact     360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg aaacaaccac accctccaaa caaagcaaca caagtacgc ggccagcagc     540
tatctgagcc tgacgcctga gcagtggaag tcccacagaa gctacagctg ccaggtcacg   600
catgaaggga gcaccgtgga agacagtg ccctacag aatgttcata atgagctagc        660

SEQ ID NO: 456            moltype = DNA   length = 660
FEATURE                   Location/Qualifiers
source                    1..660
                          mol_type = other DNA
                          organism = synthetic construct SEQUENCE: 456
cagtccgtgc tgacccaacc cccgtcagtg tctgctgccc ccgggcagaa ggtgactatc   60
agctgctctg gctcatcaag caacatcggg aataattacg tcagctggta ccagcagctg   120
cctggaacag ctcctaaact gctcatttat gacaataaca gcgcccatc cggaatccct    180
```

-continued

```
gaccgattca gcggaagcaa atcagggacc tctgcaactc tgggaatcac tgggcttcag    240
acaggagatg aggcagatta ctattgcgcg tctgcagagg acagctccag caatgccgtg    300
ttcgggtctg gtaccactct tacagtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcac ccccgtcaag    480
gcgggagtgg aaacaaccac accctccaaa caaagcaaca caagtacgc ggccagcagc     540
tatctgagcc tgacgcctga gcagtggaag tcccacagaa gctacagctg ccaggtcacg    600
catgaaggga gcaccgtgga gaagacagtg gcccctacag aatgttcata atgagctagc    660

SEQ ID NO: 457        moltype = DNA  length = 4188
FEATURE               Location/Qualifiers
source                1..4188
                      mol_type = other DNA
                      organism = synthetic construct
SEQUENCE: 457
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgaaggggtgg ggagaaccgt   180
atataagtgc agtagtcgcc gtgaacgttc tttttcgcaa cgggtttgcc gccagaaaac     240
agctgaagct tcgagggggct cgcatctctc cttcacgcgc ccgccgccct acctgaggcc    300
gccatccacg ccgttgagt cgcgttctgc cgcctcccgc ctgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca    600
ttgcactaag tcttgcactt gtcacgaatt cgatatcggc catggttaga tctgtggagt     660
gcccaccttg cccagcacca cctgtggcag gaccttcagt cttcctcttc cccccaaaac     720
ccaaggacac cctgatgatc tccagaaccc ctgaggtcac gtgcgtggtg gtggacgtga    780
gccacgaaga ccccgaggtc cagttcaact ggtacgtgga cggcatggag gtgcataatg    840
ccaagacaaa gccacgggag gagcagttca acagcacgtt ccgtgtggtc agcgtcctca    900
ccgtcgtgca ccaggactgg ctgaacggca aggagtacaa gtgcaaggtc tccaacaaag    960
gcctcccagc ccccatcgag aaaaccatct ccaaaaccaa agggcagccc cgagaaccac   1020
aggtgtacac cctgccccca tcccgggagg agatgaccaa gaaccaggtc agcctgacct   1080
gcctggtcaa aggcttctac cccagcgaca tcgccgtgga gtgggagagc aatgggcagc   1140
cggagaacaa ctacaagacc acacctccca tgctggactc cgacggctcc ttcttcctct   1200
acagcaagct caccgtggac aagagcaggt ggcagcaggg gaacgtcttc tcatgctccg   1260
tgatgcatga ggctctgcac aaccactaca cacagaagag cctctccctg tctccgggta   1320
aatgagtgcc acggctagct ggccagacat gataagatac attgatgagt ttggacaaac   1380
cacaactaga atgcagtgaa aaaaatgctt tatttgtgaa atttgtgatg ctattgcttt   1440
atttgtaacc attataagct gcaataaaca agttaacaac aacaattgca ttcattttat   1500
gtttcaggtt cagggggagg tgtgggaggt ttttttaaagc aagtaaaacc tctacaaatg    1560
tggtatggaa ttaattctaa aatacagcat agcaaaactt aacctccaa atcaagcctc     1620
tacttgaatc ctttttctgag ggatgaataa ggcataggca tcaggggctg ttgccaatgt   1680
gcattagctg tttgcagcct caccttcttt catggagttt aagatatagt gtattttccc    1740
aaggtttgaa ctagctcttc atttctttat gttttaaatg cactgacctc ccacattccc   1800
ttttttagtaa aatattcaga aataatttaa atacatcatt gcaatgaaaa taaatgtttt  1860
ttattaggaa gaatccagat gctcaaggcc cttcataata tcccccagtt tagtagttgg   1920
acttaggaa caaaggaacc tttaataga attggacagc aagaaagcga gcttctagct      1980
tatcctcagt cctgctcctc tgccacaaag tgcacgcagt gccggccgg gtcgcgcagg     2040
gcgaactccc gcccccacgg ctgctcgccg atctcggtca tggccggccc ggaggcgtcc   2100
cggaagttcg tggacacgac ctccgaccac tcggcgtaca gctcgtccag gccgcgcacc   2160
cacacccagg ccagggtgtt gtccggcacc acctggtcct ggaccgcgct gatgaacagg   2220
gtcacgtcgt cccggaccac accggcgaag tcgtcctcca cgaagtcccg ggagaacccg   2280
agccggtcgg tccagaactc gaccgctccg gcgacgtcgc gcgcggtgag caccggaacg   2340
gcactggtca acttggccat gatggctcct cctgtcagga gaggaaagag aagaaggtta   2400
gtacaattgc tatagtgagt tgtattatac tatgcagata tactatgcca atgattaatt   2460
gtcaaactag ggctgcaggg ttcatagtgc cactttttcct gcactgcccc atctcctgcc   2520
cacccttttcc caggcataga cagtcagtga cttaccaaac tcacaggagg gagaaggcag   2580
aagcttgaga cagacccgcg ggaccgccga actgcgaggg gacgtggcta gggcggcttc   2640
ttttatggtg cgccggccct cggaggcagg gcgctcaggg aggctagcg gccaatctgc   2700
ggtggcagga ggcggggccg aaggccgtgc ctgaccaatc cggagcacat aggagtctca   2760
gcccccccgcc ccaaagcaag gggaagtcac gcgcctgtag cgccagcgtg ttgtgaaatg   2820
ggggcttggg ggggttgggg ccctgactag tcaaaacaaa ctcccattga cgtcaatggg   2880
gtggagactt ggaaatcccc gtgagtcaaa ccgctatcca ccgctccattga tgtactgcca 2940
aaaccgcatc atcatggtaa tagcgatgac taatacgtag atgtactgcc aagtaggaaa   3000
gtcccataag gtcatgtact gggcataatg ccaggcgggc catttaccgt cattgacgtc   3060
aatagggggc gtacttggca tatgatacac ttgatgtact gccaagtggg cagtttaccg   3120
taaatactcc acccattgac gtcaatggaa agtccctatt ggcgttacta tgggaacata   3180
cgtcattatt gacgtcaatg ggcggggggtc gttgggcggt cagccaggcg ggccatttac   3240
cgtaagttat gtaacgcctg caggttaatt aagaacatgt gagcaaaagg ccagcaaaag   3300
gccaggaacc gtaaaaaggc cgcgttgctg gcgtttttcc ataggctccg ccccccctgac   3360
gagcatcaca aaaatcgacg ctcaagtcag aggtggcgaa acccgacagg actataaaga   3420
taccaggcgt ttccccctgg aagctccctc gtgcgctctc ctgttccgac cctgccgctt   3480
accggatacc tgtccgcctt tctcccttcg ggaagcgtgg cgctttctca tagctcacgc   3540
tgtaggtatc tcagttcggt gtaggtcgtt cgctccaagc tgggctgtgt gcacgaaccc   3600
cccgttcagc ccgaccgctg cgccttatcc ggtaactatc gtcttgagtc caacccggta   3660
agacacgact tatcgccact ggcagcagcc actggtaaca ggattagcag agcgaggtat   3720
gtaggcggtg ctacagagtt cttgaagtgg tggcctaact acggctacac tagaagaaca   3780
gtatttggta tctgcgctct gctgaagcca gttaccttcg gaaaaagagt tggtagctct   3840
```

-continued

```
tgatccggca aacaaaccac cgctggtagc ggtggttttt ttgtttgcaa gcagcagatt   3900
acgcgcagaa aaaaggatc tcaagaagat cctttgatct tttctacggg gtctgacgct     3960
cagtggaacg aaaactcacg ttaagggatt ttggtcatgg ctagttaatt aacatttaaa    4020
tcagcggccg caataaaata tctttatttt cattacatct gtgtgttggt tttttgtgtg    4080
aatcgtaact aacatacgct ctccatcaaa acaaaacgaa acaaaacaaa ctagcaaaat    4140
aggctgtccc cagtgcaagt gcaggtgcca gaacatttct ctatcgaa              4188
```

SEQ ID NO: 458          moltype = DNA   length = 4495
FEATURE                 Location/Qualifiers
source                  1..4495
                        mol_type = other DNA
                        organism = synthetic construct
SEQUENCE: 458

```
ggatctgcga tcgctccggt gcccgtcagt gggcagagcg cacatcgccc acagtccccg    60
agaagttggg ggggaggggtc ggcaattgaa cgggtgccta gagaaggtgg cgcggggtaa   120
actgggaaag tgatgtcgtg tactggctcc gccttttttcc cgagggtggg ggagaaccgt   180
atataagtgc agtagtcgcc gtgaacgttc ttttttcgcaa cgggtttgcc gccagaacac   240
agctgaagct tcgaggggct cgcatctctc cttcacgcgc ccgccgcct acctgaggcc     300
gccatccacg ccggttgagt cgcgttctgc cgcctcccgc ctgtggtgcc tcctgaactg    360
cgtccgccgt ctaggtaagt ttaaagctca ggtccagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgccag gatgcaactc ctgttgctga    600
ttgcactaag tcttgcactt gtcacgaatt cgccatggct cctcagctag caccaagggc    660
ccatcggtct tcccctggc acctcctcc aagagcacct ctgggggcac agcggccctg     720
ggctgcctgg tcaaggacta cttcccgag ccggtgacgg tgtcgtggaa ctcaggcgcc    780
ctgaccagcg gcgtgcacac cttcccggct gtcctacagt cctcaggact ctactccctc    840
agcagcgtgg tgaccgtgcc ctccagcagc ttgggcaccc agacctacat ctgcaacgtg    900
aatcacaagc ccagcaacac caaggtggac aagaaagttg agcccaaatc ttgtgacaaa   960
actcacacat gcccaccgtg cccagcacct gaactcctgg ggggaccgtc agtcttcctc   1020
ttccccccaa aacccaagga caccctcatg atctcccgga cccctgaggt cacatgcgtg   1080
gtggtggacg tgagccacga agaccctgag gtcaagttca actggtacgt ggacggcgtg    1140
gaggtgcata atgccaagac aaagccgcgg gaggagcagt acaacagcac gtaccgtgtg     1200
gtcagcgtcc tcaccgtcct gcaccaggac tggctgaatg gcaaggagta caagtgcaag    1260
gtgtccaaca aagccctccc agcccccatc gagaaaacca tctccaaagc caaagggcag   1320
ccccgagaac cacaggtgta caccctgccc ccatccgggg atgagctgac caagaaccag   1380
gtcagcctga cctgcctggt caaaggcttc tatcccagcg acatcgccgt ggagtgggag    1440
agcaatgggc agccggagaa caactacaag accacgcctc ccgtgctgga ctccgacggc    1500
tccttcttcc tctacagcaa gctcaccgtg gacaagagca ggtggcagca gggaaacgtc    1560
ttctcatgct ccgtgatgca tgaggctctg cacaaccact acacgcagaa gagcctctcc    1620
ctgtctccgg gtaaatgata atctagtggc cagacatgat aagatacatt gatgagtttg    1680
gacaaaccac aactagaatg cagtgaaaaa aatgctttat ttgtgaaatt tgtgatgcta    1740
ttgcttttatt tgtaaccatt ataagctgca ataaacaagt taacaacaac aattgcattc    1800
attttatgtt tcaggttcag ggggaggtgt gggaggtttt ttaaagcaag taaaacctct    1860
acaaatgtgg tatggaatta attctaaaat acagcatagc aaaactttaa cctccaaatc    1920
aagcctctac ttgaatcctt ttctgaggga tgaataaggc ataggcatca ggggctgttg    1980
ccaatgtgca ttagctgttt gcagcctcac cttctttcat ggagtttaag atatagtgta    2040
ttttcccaag gtttgaacta gctcttcatt tctttatgtt ttaaatgcac tgacctccca    2100
cattcccttt ttagtaaaat attcagaaat aatttaaata catcattgca atgaaaataa    2160
atgtttttta ttaggcagaa tccagatgct caaggccctt cataatatcc cccagtttag    2220
tagttggact tagggaacaa aggaacctt aatagaaatt ggacagcaag aaagcgagct    2280
tctagcttat cctcagtcct gctcctctgc cacaaagtgc acgcagttgc cggccgggtc    2340
gcgcagggcg aactcccgcc cccacggctg ctcgccgatc tcggtcatgg ccggcccgga    2400
ggcgtcccg aagttcgtgg acacgacctc cgaccactcg cgctacagct cgtccaggcc    2460
gcgcacccac acccaggcca gggtgttgtc cggcaccacc tggtcctgga gcgcgctgat    2520
gaacagggtc acgtcgtccc ggaccacacc ggcgaagtcg tcctccacga agtcccggga    2580
gaacccgagc cggtcggtcc agaactcgac cgctccggcg acgtcgcgcg cggtgagcac    2640
cggaacggca ctggtcaact tggccatgat ggctcctcct gtcaggagag gaaagagaag    2700
aaggttagta caattgctat agtgagttgt attatactat gcagatatac tatgccaatg    2760
attaattgtc aaactagggc tgcagggttc atagtgccac ttttcctgca ctgccccatc    2820
tcctgcccac cctttcccag gcatagacag tcagtgactt accaaactca caggagggag    2880
aaggcagaag cttgagacag acccgcggga ccgccgaact gcgaggggac gtggctaggg    2940
cggcttcttt tatggtgcgc cggccctcgg aggcagggcg ctcggggagg cctagcggcc    3000
aatctgcggt ggcaggaggc ggggccgaag gccgtgccct accaatccgg agcacatagg    3060
agtctcagcc ccccgcccca aagcaagggg aagtcacgcg cctgtagcgc cagcgtgttg    3120
tgaaatgggg gcttggggggg gttggggccc tgactagtca aaacaaactc ccattgacgt    3180
caatggggtg gagacttgga aatccccgtg agtcaaaccg ctatccacgc ccattgatgt    3240
actgccaaaa ccgcatcatc atggtaatag cgatgactaa tacgtagatg tactgccaag    3300
taggaaagtc ccataaggtc ttattactggg cataatgcca ggcgggccat ttaccgtcat    3360
tgacgtcaat aggggcgta cttggcatat gatacacttg atgtactgcc aagtgggcag    3420
tttaccgtaa atactccacc cattgacgtc aatggaaagt ccctattggc gttactatgg    3480
gaacatacgc cattattgac gtcaatgggc gggggtcgtt gggcggtcag ccaggcgggc    3540
catttaccgt aagttatgta acgcctgcag gttaattaag aacatgtgag caaaaggcca    3600
gcaaaaggcc aggaaccgta aaaaggccgc gttgctggcg tttttccata ggctccgccc    3660
ccctgacgag catcacaaaa atcgacgctc aagtcagagg tggcgaaacc cgacaggact    3720
ataaagatac caggcgtttc ccctggaag ctccctcgtg cgctctcctg ttccgaccct    3780
gccgcttacc ggatacctgt ccgcctttct cccttcggga agcgtggcgc tttctcatag    3840
ctcacgctgt aggtatctca gttcggtgta ggtcgttcgc tccaagctgg gctgtgtgca    3900
cgaacccccc gttcagcccg accgctgcgc cttatccggt aactatcgtc ttgagtccaa    3960
```

-continued

```
cccggtaaga cacgacttat cgccactggc agcagccact ggtaacagga ttagcagagc    4020
gaggtatgta ggcggtgcta cagagttctt gaagtggtgg cctaactacg gctacactag    4080
aagaacagta tttggtatct gcgctctgct gaagccagtt accttcggaa aaagagttgg    4140
tagctcttga tccggcaaac aaaccaccgc tggtagcggt ggtttttttg tttgcaagca    4200
gcagattacg cgcagaaaaa aaggatctca agaagatcct ttgatctttt ctacggggtc    4260
tgacgctcag tggaacgaaa actcacgtta agggattttg gtcatggcta gttaattaac    4320
atttaaatca gcggccgcaa taaaatatct ttattttcat tacatctgtg tgttggtttt    4380
ttgtgtgaat cgtaactaac atacgctctc catcaaaaca aaacgaaaca aaacaaacta    4440
gcaaaatagg ctgtccccag tgcaagtgca ggtgccagaa catttctcta tcgaa         4495

SEQ ID NO: 459          moltype = DNA   length = 3822
FEATURE                 Location/Qualifiers
source                  1..3822
                        mol_type = other DNA
                        organism = synthetic construct
SEQUENCE: 459
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaaacac    240
agctgaagct tcgagggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtccagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgcgacg gatgcaactc ctgttgctga     600
ttgcactaag tcttgcactt gtcacgaatt cgccatggcc ctaggtcagc ccaaggctgc     660
cccctcggtc actctgttcc cgccctcctc tgaggagctt caagccaaca aggccacact     720
ggtgtgtctc ataagtgact tctacccggg agccgtgaca gtggcctgga aggcagatag     780
cagccccgtc aaggcgggag tggaaacaac cacacccctcc aaacaaagca acaacaagta    840
cgcggccagc agctatctga gcctgacgcc tgagcagtgg aagtcccaca gaagctcag     900
ctgccaggtc acgcatgaag ggagcaccgg ggagaagaca gtggcccta cagaatgttc     960
ataatgagct agctggccag acatgataag atacattgat gagtttggac aaaccacaac    1020
tagaatgcag tgaaaaaaat gctttatttg tgaaatttgt gatgctattg ctttatttgt    1080
aaccattata agctgcaata aacaagttaa caacaacaat tgcattcatt ttatgtttca    1140
ggttcagggg gaggtgtggg aggttttttta aagcaagtaa aacctctaca aatgtggtat    1200
ggaattaatt ctaaaataca gcatagcaaa actttaacct ccaaatcaag cctctacttg    1260
aatccttttc tgagggatga ataaggcata ggcatcaggg gctgttgcca atgtgcatta    1320
gctgtttgca gcctcacctt ctttcatgga gtttaagata tagtgtattt tcccaaggtt    1380
tgaactagct cttcatttct ttatgtttta aatgcactga cctcccacat tccctttta     1440
gtaaaatatt cagaaataat ttaaatacat cattgcaatg aaaatataatg tttttattaa   1500
ggcagaatcc agatgctcaa ggcccttcat aatatccccc agtttagtag ttggacttag    1560
ggaacaaagg aacctttaat agaaattgga cagcaagaaa gcgagcttct agcttatcct    1620
cagtcctgct cctctgccac aaagtgcacg cagttgccgg ccgggtcgcg cagggcgaac    1680
tcccgccccc acggctgctc gccgatctcg gtcatggccg gcccggaggc gtcccggaag    1740
ttcgtggaca cgacctccga ccactcggcg tacagctcgt ccaggccgcg cacccacacc    1800
caggccaggg tgttgtccgg caccacctgg tcctggaccg cgctgatgaa cagggtcacg    1860
tcgtcccgga ccacaccggc gaagtcgtcc tccacgaagt cccggagaa cccgagccgg    1920
tcggtccaga actcgaccgc tccggcgacg tcgcgcgcgg tgagcaccgg aacggcactg    1980
gtcaacttgg ccatgatggc tcctcctgtc aggagaggaa agagaagaag gttagtacaa    2040
ttgctatagt gagttgtatt atactatgca gatatactat gccaatgatt aattgtcaaa    2100
ctagggctgc agggttcata gtgccacttt tcctgcactg ccccatctcc tgcccacctt    2160
ttcccaggca tagacagtca gtgacttacc aaactcacag gagggagaag gcagaagctt    2220
gagacagacc cgcgggaccg ccgaactgcg aggggacgtg gctagggcgg cttctttat     2280
ggtgcgccgg ccctcggagg cagggcgctc ggggaggcct agcggccaat ctgcggtggc    2340
aggaggcggg gccgaaggcc gtgcctgacc aatccggagc acataggagt ctcagccccc    2400
cgcccccaaag caaggggaag tcacgcgcct gtagcgccag cgtgttgtga aatgggggct    2460
tggggggggtt ggggccctga ctagtcaaaa caaactccca ttgacgtcaa tggggtggag    2520
acttggaaat ccccgtgagt caaaccgcta tccacgccca ttgatgtact gccaaaaccg    2580
catcatcatg gtaatagcga tgactaatac gtagatgtac tgccaagtag gaaagtccca    2640
taaggtcatg tactgggcat aatgccaggc gggccattta ccgtcattga cgtcaatagg    2700
gggcgtactt ggcatatgat acacttgatg tactgccaag tgggcagttt accgtaaata    2760
ctccacccat tgacgtcaat ggaaagtccc tattggcgtt actatgggaa catacgtcat    2820
tattgacgtc aatgggcggg ggtcgttggg cggtcagcca ggcgggccat ttaccgtaag    2880
ttatgtaacg cctgcaggtt aattaagaac atgtgagcaa aaggccagca aaaggccagg    2940
aaccgtaaaa aggccgcgtt gctggcgttt ttccataggc tccgcccccc tgacgagcat    3000
cacaaaaatc gacgctcaag tcagaggtgg cgaaacccga caggactata aagataccag    3060
gcgtttcccc ctggaagctc cctcgtgcgc tctcctgttc cgaccctgcc gcttaccgga    3120
tacctgtccg cctttctccc ttcgggaagc gtggcgcttt ctcatagctc acgctgtagg    3180
tatctcagtt cggtgtaggt cgttcgctcc aagctgggct gtgtgcacga accccccgtt    3240
cagcccgacc gctgcgcctt atccggtaac tatcgtcttg agtccaaccc ggtaagacac    3300
gacttatcgc cactggcagc agccactggt aacaggatta gcagagcgag gtatgtaggc    3360
ggtgctacag agttcttgaa gtggtggcct aactacggct acactagaag aacagtattt    3420
ggtatctgcg ctctgctgaa gccagttacc ttcggaaaaa gagttggtag ctcttgatcc    3480
ggcaaacaaa ccaccgctgg tagcggtggt tttttgttt gcaagcagca gattacgcgc     3540
agaaaaaaag gatctcaaga gatcctttga tctttcta cggggtctga cgctcagtgg     3600
aacgaaaact cacgttaagg gattttggtc atggctagtt aattaacatt aaatcagcg     3660
gccgcaataa aatatcttta ttttcattac atctgtgtgt tggttttttg tgtgaatcgt    3720
aactaacata cgctctccat caaaacaaaa cgaaacaaaa caaactagca aaataggctg    3780
```

```
tccccagtgc aagtgcaggt gccagaacat ttctctatcg aa                          3822

SEQ ID NO: 460          moltype = AA   length = 107
FEATURE                 Location/Qualifiers
source                  1..107
                        mol_type = protein
                        organism = synthetic construct
SEQUENCE: 460
QVQLQQWGAG LLKPSETLSL TCAVYGGSFS GYYWSWIRQP PGKGLEWIGE INHSGSTNYN        60
PSLKSRVTIS VDTSKNQFSL KLSSVTAADT AVYYCTSVHQ ETKKYQS                      107

SEQ ID NO: 461          moltype = AA   length = 107
FEATURE                 Location/Qualifiers
source                  1..107
                        mol_type = protein
                        organism = synthetic construct
SEQUENCE: 461
QVQLQQWGAG LLKPSETLSL TCTASGFSLS DKAVGWIRQP PGKGLEWIGE INHSGSTNYN        60
PSLKSRVTIS VDTSKNQFSL KLSSVTAADT AVYYCTSVHQ ETKKYQS                      107

SEQ ID NO: 462          moltype = AA   length = 107
FEATURE                 Location/Qualifiers
source                  1..107
                        mol_type = protein
                        organism = synthetic construct
SEQUENCE: 462
QVQLQQWGAG LLKPSETLSL TCAVYGGSFS GYYWSWIRQP PGKGLEWLGS IDTGGNTGYN        60
PSLKSRVTIS VDTSKNQFSL KLSSVTAADT AVYYCTSVHQ ETKKYQS                      107

SEQ ID NO: 463          moltype = AA   length = 107
FEATURE                 Location/Qualifiers
source                  1..107
                        mol_type = protein
                        organism = synthetic construct
SEQUENCE: 463
QVQLQQWGAG LLKPSETLSL TCAVYGGSFS DKYWSWIRQP PGKGLEWIGE INHSGSTNYN        60
PSLKSRVTIS VDTSKNQFSL KLSSVTAADT AVYYCTSVHQ ETKKYQS                      107

SEQ ID NO: 464          moltype = AA   length = 107
FEATURE                 Location/Qualifiers
source                  1..107
                        mol_type = protein
                        organism = synthetic construct
SEQUENCE: 464
QVQLQQWGAG LLKPSETLSL TCAVYGGSFS GYYWSWIRQP PGKGLEWIGS INHSGSTNYN        60
PSLKSRVTIS VDTSKNQFSL KLSSVTAADT AVYYCTSVHQ ETKKYQS                      107

SEQ ID NO: 465          moltype = AA   length = 107
FEATURE                 Location/Qualifiers
source                  1..107
                        mol_type = protein
                        organism = synthetic construct
SEQUENCE: 465
QVQLQQWGAG LLKPSETLSL TCTASGFSLS DKAVGWIRQP PGKGLEWLGS IDTGGNTGYN        60
PSLKSRVTIS VDTSKNQFSL KLSSVTAADT AVYYCTSVHQ ETKKYQS                      107

SEQ ID NO: 466          moltype = AA   length = 107
FEATURE                 Location/Qualifiers
source                  1..107
                        mol_type = protein
                        organism = synthetic construct
SEQUENCE: 466
QVQLQQWGAG LLKPSETLSL TCTASGFSLS DKAVGWIRQP PGKGLEWIGS INHSGSTNYN        60
PSLKSRVTIS VDTSKNQFSL KLSSVTAADT AVYYCTSVHQ ETKKYQS                      107

SEQ ID NO: 467          moltype = AA   length = 107
FEATURE                 Location/Qualifiers
source                  1..107
                        mol_type = protein
                        organism = synthetic construct
SEQUENCE: 467
QVQLQQWGAG LLKPSETLSL TCAVYGGSFS DKYWSWIRQP PGKGLEWLGS IDTGGNTGYN        60
PSLKSRVTIS VDTSKNQFSL KLSSVTAADT AVYYCTSVHQ ETKKYQS                      107

SEQ ID NO: 468          moltype = AA   length = 107
FEATURE                 Location/Qualifiers
source                  1..107
                        mol_type = protein
                        organism = synthetic construct
```

```
SEQUENCE: 468
QVQLQQWGAG LLKPSETLSL TCAVYGGSFS DKYWSWIRQP PGKGLEWIGS INHSGSTNYN  60
PSLKSRVTIS VDTSKNQFSL KLSSVTAADT AVYYCTSVHQ ETKKYQS               107

SEQ ID NO: 469           moltype = AA   length = 25
FEATURE                  Location/Qualifiers
source                   1..25
                         mol_type = protein
                         organism = synthetic construct
SEQUENCE: 469
SYTYNYEWHV DVWGQGLLVT VSSAS                                        25

SEQ ID NO: 470           moltype = AA   length = 6
FEATURE                  Location/Qualifiers
source                   1..6
                         mol_type = protein
                         organism = synthetic construct
SEQUENCE: 470
DNNKRP                                                             6

SEQ ID NO: 471           moltype = AA   length = 6
FEATURE                  Location/Qualifiers
source                   1..6
                         mol_type = protein
                         organism = synthetic construct
SEQUENCE: 471
GDTSRA                                                             6

SEQ ID NO: 472           moltype = DNA   length = 420
FEATURE                  Location/Qualifiers
source                   1..420
                         mol_type = other DNA
                         organism = synthetic construct
SEQUENCE: 472
caggtgcagc tacagcagtg gggcgcagga ctgttgaagc cttcggagac gctgtccctc  60
acctgcacag caagcgggtt ttcactgagc gacaaggcag tgggatggat tcgccagccc  120
ccagggaagg ggctggagtg gattggggaa atcaatcata gtggaagcac caactacaac  180
ccgtccctca agagtcgagt caccatatca gtagacacgt ccaagaacca gttctccctg  240
aagctgagct ctgtgaccgc cgcggacacg gctgtgtatt actgtacctc tgtgcaccag  300
gaaactaaga ataccagag cgagacctac tatggttcgg tctctctta tacctacaat  360
tatgaatggc atgtggatgt ctggggacag ggcctgctgg tgacagtctc tagtgctagc  420

SEQ ID NO: 473           moltype = AA   length = 133
FEATURE                  Location/Qualifiers
SITE                     107
                         note = MISC_FEATURE - X is an insert of a non-bovine
                          sequence
SITE                     108
                         note = misc_feature - Xaa can be any naturally occurring
                          amino acid
source                   1..133
                         mol_type = protein
                         organism = synthetic construct
SEQUENCE: 473
QVQLQQWGAG LLKPSETLSL TCTASGFSLS DKAVGWIRQP PGKGLEWIGE INHSGSTNYN  60
PSLKSRVTIS VDTSKNQFSL KLSSVTAADT AVYYCTSVHQ ETKKYQSXSY TYNYEWHVDV  120
WGQGLLVTVS SAS                                                     133

SEQ ID NO: 474           moltype = DNA   length = 662
FEATURE                  Location/Qualifiers
source                   1..662
                         mol_type = other DNA
                         organism = synthetic construct
SEQUENCE: 474
tcacgaattc gcaggccgtc ctgaaccagc caagcagcgt ctccgggtct ctggggcagc  60
gggtctcaat cacctgtagc gggtcttcct ccaatgtcgg caacggctac gtgtcttggt  120
atcagctgat ccctggcagt gccccacgaa ccctgatcta cggcgacaca tccagagctt  180
ctggggtccc cgatcggttc tcagggagca gatccggaaa cacagctact ctgaccatca  240
gctccctgca ggctgaggac gaagcagatt atttctgccg atctgccgag gactctagtt  300
caaatgccgt gtttggaagc ggcaccacac tgacagtcct aggtcagccc aaggctgccc  360
cctcggtcac tctgttcccg ccctcctctg aggagcttca agccaacaag gccacactgg  420
tgtgtctcat aagtgacttc tacccgggag ccgtgacagt ggcctggaag gcagatagca  480
gccccgtcaa ggcgggagtg gagaccacca caccctccaa acaaagcaac aacaagtacg  540
cggccagcag ctatctgagc ctgacgcctg agcagtggaa gtcccacaga agctacagct  600
gccaggtcac gcatgaaggg agcaccgtgg agaagacagt ggccctaca gaatgttcat  660
aa                                                                662

SEQ ID NO: 475           moltype = AA   length = 74
FEATURE                  Location/Qualifiers
```

-continued

```
source                  1..74
                        mol_type = protein
                        organism = synthetic construct
SEQUENCE: 475
PRSAKELRCQ CIKTYSKPFH PKFIKELRVI ESGPHCANTE IIVKLSDGRE LCLDPKENWV   60
QRVVEKFLKR AENS                                                     74

SEQ ID NO: 476          moltype = AA  length = 25
FEATURE                 Location/Qualifiers
source                  1..25
                        mol_type = protein
                        organism = synthetic construct
SEQUENCE: 476
CKGKGAKCSR LMYDCCTGSC RSGKC                                         25

SEQ ID NO: 477          moltype = AA  length = 15
FEATURE                 Location/Qualifiers
source                  1..15
                        mol_type = protein
                        organism = synthetic construct
SEQUENCE: 477
AGCKNFFWKT FTSCG                                                    15

SEQ ID NO: 478          moltype = AA  length = 34
FEATURE                 Location/Qualifiers
source                  1..34
                        mol_type = protein
                        organism = synthetic construct
SEQUENCE: 478
MCMPCFTTDH QMARKCDDCC GGKGRGKCYG PQCL                               34

SEQ ID NO: 479          moltype = AA  length = 68
FEATURE                 Location/Qualifiers
source                  1..68
                        mol_type = protein
                        organism = synthetic construct
SEQUENCE: 479
KPVSLSYRCP CRFFESHVAR ANVKHLKILN TPNCALQIVA RLKNNNRQVC IDPKLKWIQE   60
YLEKALNK                                                            68

SEQ ID NO: 480          moltype = AA  length = 133
FEATURE                 Location/Qualifiers
source                  1..133
                        mol_type = protein
                        organism = synthetic construct
SEQUENCE: 480
QGQDRHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDS                                                     133

SEQ ID NO: 481          moltype = AA  length = 30
FEATURE                 Location/Qualifiers
source                  1..30
                        mol_type = protein
                        organism = synthetic construct
SEQUENCE: 481
YCQKWMWTCD SERKCCEGMV CRLWCKKKLW                                    30

SEQ ID NO: 482          moltype = AA  length = 274
FEATURE                 Location/Qualifiers
source                  1..274
                        mol_type = protein
                        organism = synthetic construct
SEQUENCE: 482
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSCPD GYRERSDCSN  120
RPACGTSDCC RVSVFGNCLT TLPVSYSYTY NYEWHVDVWG QGLLVTVSSA STTAPKVYPL  180
SSCCGDKSSS TVTLGCLVSS YMPEPVTVTW NSGALKSGVH TFPAVLQSSG LYSLSSMVTV  240
PGSTSGQTFT CNVAHPASST KVDKAVEPKS CDGS                              274

SEQ ID NO: 483          moltype = AA  length = 216
FEATURE                 Location/Qualifiers
source                  1..216
                        mol_type = protein
                        organism = synthetic construct
SEQUENCE: 483
QAVLNQPSSV SGSLGQRVSI TCSGSSSNVG NGYVSWYQLI PGSAPRTLIY GDTSRASGVP   60
DRFSGSRSGN TATLTISSLQ AEDEADYFCA SAEDSSSNAV FGSGTTLTVL GQPKSPPSVT  120
LFPPSTEELN GNKATLVCLI SDFYPGSVTV VWKADGSTIT RNVETTRASK QSNSKYAASS  180
```

-continued

```
YLSLTSSDWK SKGSYSCEVT HEGSTVTKTV KPSECS                       216

SEQ ID NO: 484            moltype = AA  length = 269
FEATURE                   Location/Qualifiers
source                    1..269
                          mol_type = protein
                          organism = synthetic construct
SEQUENCE: 484
QVQLRESGPS LVQPSQTLSL TCTASGFSLS DKAVGWVRQA PGKALEWLGS IDTGGSTGYN 60
PGLKSRLSIT KDNSKSQVSL SVSSVTTEDS ATYYCTTVHQ ETRKTCSDGY IAVDSCGRGQ 120
SDGCVNDCNS CYYGWRNCRR QPAIHSYEPH VDAWGRGLLV TVSSASTTAP KVYPLSSCCG 180
DKSSSTVTLG CLVSSYMPEP VTVTWNSGAL KSGVHTFPAV LQSSGLYSLS SMVTVPGSTS 240
GQTFTCNVAH PASSTKVDKA VEPKSCDGS                               269

SEQ ID NO: 485            moltype = AA  length = 216
FEATURE                   Location/Qualifiers
source                    1..216
                          mol_type = protein
                          organism = synthetic construct
SEQUENCE: 485
QAVLNQPSSV SGSLGQRVSI TCSGSSSNVG NGYVSWYQLI PGSAPRTLIY GDTSRASGVP 60
DRFSGSRSGN TATLTISSLQ AEDEADYFCA SAEDSSSNAV FGSGTTLTVL GQPKSPPSVT 120
LFPPSTEELN GNKATLVCLI SDFYPGSVTV VWKADGSTIT RNVETTRASK QSNSKYAASS 180
YLSLTSSDWK SKGSYSCEVT HEGSTVTKTV KPSECS                       216

SEQ ID NO: 486            moltype = DNA  length = 648
FEATURE                   Location/Qualifiers
source                    1..648
                          mol_type = other DNA
                          organism = synthetic construct
SEQUENCE: 486
caggccgtcc tgaaccagcc aagcagcgtc tccgggtctc tggggcagaa ggtgactatc 60
agctgctctg gctcatcaag caacatcggg aataattacg tcagctggta ccagcagctg 120
cctggaacag ctcctagaac cctcatttat ggcgacacaa agcgcccatc cggaatccct 180
gaccgattca gcggaagcaa atcagggacc tctgcaactc tgggaatcac tgggcttcag 240
acaggagatg aggcagatta ctattgcgcc tctgcagagg acagctccag caatgccgtg 300
ttcgggtctg gtaccactct tacagtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg aaacaaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca              648

SEQ ID NO: 487            moltype = DNA  length = 648
FEATURE                   Location/Qualifiers
source                    1..648
                          mol_type = other DNA
                          organism = synthetic construct
SEQUENCE: 487
caggccgtcc tgaaccagcc aagcagcgtc tccgggtctc tggggcagaa ggtgactatc 60
agctgctctg gctcatcaag caacatcggg aataattacg tcagctggta ccagcagctg 120
cctggaacag ctcctagaac cctcatttat ggcgacacat ccagagcttc cggaatccct 180
gaccgattca gcggaagcaa atcagggacc tctgcaactc tgggaatcac tgggcttcag 240
acaggagatg aggcagatta ctattgcgcc tctgcagagg acagctccag caatgccgtg 300
ttcgggtctg gtaccactct tacagtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg aaacaaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca              648

SEQ ID NO: 488            moltype = DNA  length = 648
FEATURE                   Location/Qualifiers
source                    1..648
                          mol_type = other DNA
                          organism = synthetic construct
SEQUENCE: 488
cagtccgtgc tgacccaacc cccgtcagtg tctgctgccc ccgggcagaa ggtgactatc 60
agctgctctg gctcatcctc caatgtcggc aacggctacg tcagctggta ccagcagctg 120
cctggaacag ctcctagaac cctcatttat ggcgacacaa agcgcccatc cggaatccct 180
gaccgattca gcggaagcaa atcagggacc tctgcaactc tgggaatcac tgggcttcag 240
acaggagatg aggcagatta ctattgcgcc tctgcagagg acagctccag caatgccgtg 300
ttcgggtctg gtaccactct tacagtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg aaacaaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca              648
```

-continued

```
SEQ ID NO: 489          moltype = DNA   length = 648
FEATURE                 Location/Qualifiers
source                  1..648
                        mol_type = other DNA
                        organism = synthetic construct
SEQUENCE: 489
cagtccgtgc tgacccaacc cccgtcagtg tctgctgccc ccgggcagaa ggtgactatc    60
agctgctctg gctcatcctc caatgtcggc aacggctacg tcagctggta ccagcagctg   120
cctggaacag ctcctagaac cctcatttat ggcgacacat ccagagcttc cggaatccct   180
gaccgattca gcggaagcaa atcagggacc tctgcaactc tgggaatcac tgggcttcag   240
acaggagatg aggcagatta ctattgcgcc tctgcagagg acagctccag caatgccgtg   300
ttcgggtctg gtaccactct tacagtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg aaacaaccac accctccaaa caaagcaaca caagtacgcg ggccagcagc   540
tatctgagcc tgacgcctga gcagtggaag tcccacagaa gctacagctg ccaggtcacg   600
catgaaggga gcaccgtgga gaagacagtg gcccctacag aatgttca                648

SEQ ID NO: 490          moltype = DNA   length = 621
FEATURE                 Location/Qualifiers
source                  1..621
                        mol_type = other DNA
                        organism = synthetic construct
SEQUENCE: 490
caggtgcagc taagagagtg gggcgcagga ctgttgaagc cttcggagac gctgtccctc    60
acctgcgctg tctatggtgg gtccttcagt ggttactact ggagctggat tcgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga ataccagag cccaaggagt gctaaagaac ttagatgtca gtgcataaag   360
acatactcca aacctttcca ccccaagttc atcaaggagc tgagagtgat tgagagtgga   420
ccacactgcg ccaacacaga gattattgta aagctttctg atgggagaga gctctgcctg   480
gaccccaagg aaaactgggt gcagagggtc gtggagaagt tcttgaagag ggctgagaac   540
tcaggcagcg gttcttatac ctacaattat gaatggcatg tggatgtctg gggacagggc   600
ctgctggtga cagtctctag t                                             621

SEQ ID NO: 491          moltype = DNA   length = 621
FEATURE                 Location/Qualifiers
source                  1..621
                        mol_type = other DNA
                        organism = synthetic construct
SEQUENCE: 491
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga ataccagag cccaaggagt gctaaagaac ttagatgtca gtgcataaag   360
acatactcca aacctttcca ccccaagttc atcaaggagc tgagagtgat tgagagtgga   420
ccacactgcg ccaacacaga gattattgta aagctttctg atgggagaga gctctgcctg   480
gaccccaagg aaaactgggt gcagagggtc gtggagaagt tcttgaagag ggctgagaac   540
tcaggcagcg gttcttatac ctacaattat gaatggcatg tggatgtctg gggacagggc   600
ctgctggtga cagtctctag t                                             621

SEQ ID NO: 492          moltype = DNA   length = 621
FEATURE                 Location/Qualifiers
source                  1..621
                        mol_type = other DNA
                        organism = synthetic construct
SEQUENCE: 492
caggtgcagc taagagagtg gggcgcagga ctgttgaagc cttcggagac gctgtccctc    60
acctgcgctg tctatggtgg gtccttcagt ggttactact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga ataccagag cccaaggagt gctaaagaac ttagatgtca gtgcataaag   360
acatactcca aacctttcca ccccaagttc atcaaggagc tgagagtgat tgagagtgga   420
ccacactgcg ccaacacaga gattattgta aagctttctg atgggagaga gctctgcctg   480
gaccccaagg aaaactgggt gcagagggtc gtggagaagt tcttgaagag ggctgagaac   540
tcaggcagcg gttcttatac ctacaattat gaatggcatg tggatgtctg gggacagggc   600
ctgctggtga cagtctctag t                                             621

SEQ ID NO: 493          moltype = DNA   length = 621
FEATURE                 Location/Qualifiers
source                  1..621
                        mol_type = other DNA
                        organism = synthetic construct
SEQUENCE: 493
caggtgcagc taagagagtg gggcgcagga ctgttgaagc cttcggagac gctgtccctc    60
```

-continued

```
acctgcgctg tctatggtgg gtccttcagt gacaagtact ggagctggat tcgccagccc    120
ccagggaagg ggctggagtg gattgggagc atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtacctc tgtgcaccag    300
gaaactaaga aataccagag cccaaggagt gctaaagaac ttagatgtca gtgcataaag    360
acatactcca aacctttcca ccccaagttc atcaaggagc tgagagtgat tgagagtgga    420
ccacactgcg ccaacacaga gattattgta aagctttctg atgggagaga gctctgcctg    480
gaccccaagg aaaactgggt gcagagggtc gtggagaagt tcttgaagag ggctgagaac    540
tcaggcagcg gttcttatac ctacaattat gaatggcatg tggatgtctg gggacagggc    600
ctgctggtga cagtctctag t                                             621
```

SEQ ID NO: 494         moltype = DNA   length = 621
FEATURE                Location/Qualifiers
source                 1..621
                       mol_type = other DNA
                       organism = synthetic construct
SEQUENCE: 494
```
caggtgcagc taagagagtg gggcgcagga ctgttgaagc cttcggagac gctgtccctc     60
acctgcacag caagcgggtt ttcactgagc gacaaggcag tgggatggat tcgccagccc    120
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtacctc tgtgcaccag    300
gaaactaaga aataccagag cccaaggagt gctaaagaac ttagatgtca gtgcataaag    360
acatactcca aacctttcca ccccaagttc atcaaggagc tgagagtgat tgagagtgga    420
ccacactgcg ccaacacaga gattattgta aagctttctg atgggagaga gctctgcctg    480
gaccccaagg aaaactgggt gcagagggtc gtggagaagt tcttgaagag ggctgagaac    540
tcaggcagcg gttcttatac ctacaattat gaatggcatg tggatgtctg gggacagggc    600
ctgctggtga cagtctctag t                                             621
```

SEQ ID NO: 495         moltype = DNA   length = 621
FEATURE                Location/Qualifiers
source                 1..621
                       mol_type = other DNA
                       organism = synthetic construct
SEQUENCE: 495
```
caggtgcagc taagagagtg gggcgcagga ctgttgaagc cttcggagac gctgtccctc     60
acctgcgctg tctatggtgg gctgggcagc atcgataccg gcgggaacac agggtccttc    120
agtggttact actggagctg gattcgccag cccccaggga aggggctgga gtggtacaac    180
ccgtccctca agagtcgagt caccatatca gtagacacgt ccaagaacca gttctccctg    240
aagctgagct ctgtgaccgc cgcggacacg gctgtgtatt actgtacctc tgtgcaccag    300
gaaactaaga aataccagag cccaaggagt gctaaagaac ttagatgtca gtgcataaag    360
acatactcca aacctttcca ccccaagttc atcaaggagc tgagagtgat tgagagtgga    420
ccacactgcg ccaacacaga gattattgta aagctttctg atgggagaga gctctgcctg    480
gaccccaagg aaaactgggt gcagagggtc gtggagaagt tcttgaagag ggctgagaac    540
tcaggcagcg gttcttatac ctacaattat gaatggcatg tggatgtctg gggacagggc    600
ctgctggtga cagtctctag t                                             621
```

SEQ ID NO: 496         moltype = DNA   length = 621
FEATURE                Location/Qualifiers
source                 1..621
                       mol_type = other DNA
                       organism = synthetic construct
SEQUENCE: 496
```
caggtgcagc taagagagtg gggcgcagga ctgttgaagc cttcggagac gctgtccctc     60
acctgcacag caagcgggtt ttcactgagc gacaaggcag tgggatggat tcgccagccc    120
ccagggaagg ggctggagtg gattgggagc atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtacctc tgtgcaccag    300
gaaactaaga aataccagag cccaaggagt gctaaagaac ttagatgtca gtgcataaag    360
acatactcca aacctttcca ccccaagttc atcaaggagc tgagagtgat tgagagtgga    420
ccacactgcg ccaacacaga gattattgta aagctttctg atgggagaga gctctgcctg    480
gaccccaagg aaaactgggt gcagagggtc gtggagaagt tcttgaagag ggctgagaac    540
tcaggcagcg gttcttatac ctacaattat gaatggcatg tggatgtctg gggacagggc    600
ctgctggtga cagtctctag t                                             621
```

SEQ ID NO: 497         moltype = DNA   length = 621
FEATURE                Location/Qualifiers
source                 1..621
                       mol_type = other DNA
                       organism = synthetic construct
SEQUENCE: 497
```
caggtgcagc taagagagtg gggcgcagga ctgttgaagc cttcggagac gctgtccctc     60
acctgcacag caagcgggtt ttcactgagc gacaaggcag tgggatggat tcgccagccc    120
ccagggaagg ggctggagtg gctgggcagc atcgataccg gcgggaacac agggtacaac    180
ccgtccctca agagtcgagt caccatatca gtagacacgt ccaagaacca gttctccctg    240
aagctgagct ctgtgaccgc cgcggacacg gctgtgtatt actgtacctc tgtgcaccag    300
gaaactaaga aataccagag cccaaggagt gctaaagaac ttagatgtca gtgcataaag    360
acatactcca aacctttcca ccccaagttc atcaaggagc tgagagtgat tgagagtgga    420
ccacactgcg ccaacacaga gattattgta aagctttctg atgggagaga gctctgcctg    480
```

```
gaccccaagg aaaactgggt gcagagggtc gtggagaagt tcttgaagag ggctgagaac   540
tcaggcagcg gttcttatac ctacaattat gaatggcatg tggatgtctg gggacagggc   600
ctgctggtga cagtctctag t                                             621

SEQ ID NO: 498            moltype = AA   length = 12
FEATURE                   Location/Qualifiers
source                    1..12
                          mol_type = protein
                          organism = synthetic construct
SEQUENCE: 498
TSVHQETKKY QS                                                        12

SEQ ID NO: 499            moltype = AA   length = 12
FEATURE                   Location/Qualifiers
source                    1..12
                          mol_type = protein
                          organism = synthetic construct
SEQUENCE: 499
SYTYNYEWHV DV                                                        12

SEQ ID NO: 500            moltype = AA   length = 11
FEATURE                   Location/Qualifiers
source                    1..11
                          mol_type = protein
                          organism = synthetic construct
SEQUENCE: 500
WGQGLLVTVS S                                                         11

SEQ ID NO: 501            moltype = AA   length = 14
FEATURE                   Location/Qualifiers
source                    1..14
                          mol_type = protein
                          organism = synthetic construct
SEQUENCE: 501
GSKHRLRDYF LYNE                                                      14

SEQ ID NO: 502            moltype = AA   length = 13
FEATURE                   Location/Qualifiers
source                    1..13
                          mol_type = protein
                          organism = synthetic construct
SEQUENCE: 502
GSKHRLRDYF LYN                                                       13

SEQ ID NO: 503            moltype = AA   length = 12
FEATURE                   Location/Qualifiers
source                    1..12
                          mol_type = protein
                          organism = synthetic construct
SEQUENCE: 503
GSKHRLRDYF LY                                                        12

SEQ ID NO: 504            moltype = AA   length = 11
FEATURE                   Location/Qualifiers
source                    1..11
                          mol_type = protein
                          organism = synthetic construct
SEQUENCE: 504
GSKHRLRDYF L                                                         11

SEQ ID NO: 505            moltype = AA   length = 10
FEATURE                   Location/Qualifiers
source                    1..10
                          mol_type = protein
                          organism = synthetic construct
SEQUENCE: 505
GSKHRLRDYF                                                           10

SEQ ID NO: 506            moltype = AA   length = 9
FEATURE                   Location/Qualifiers
source                    1..9
                          mol_type = protein
                          organism = synthetic construct
SEQUENCE: 506
GSKHRLRDY                                                            9

SEQ ID NO: 507            moltype = AA   length = 8
FEATURE                   Location/Qualifiers
source                    1..8
```

-continued

```
                               mol_type = protein
                               organism = synthetic construct
SEQUENCE: 507
GSKHRLRD                                                          8

SEQ ID NO: 508         moltype = AA  length = 13
FEATURE                Location/Qualifiers
source                 1..13
                       mol_type = protein
                       organism = synthetic construct
SEQUENCE: 508
EAGGPDYRNG YNY                                                    13

SEQ ID NO: 509         moltype = AA  length = 12
FEATURE                Location/Qualifiers
source                 1..12
                       mol_type = protein
                       organism = synthetic construct
SEQUENCE: 509
EAGGPDYRNG YN                                                     12

SEQ ID NO: 510         moltype = AA  length = 11
FEATURE                Location/Qualifiers
source                 1..11
                       mol_type = protein
                       organism = synthetic construct
SEQUENCE: 510
EAGGPDYRNG Y                                                      11

SEQ ID NO: 511         moltype = AA  length = 10
FEATURE                Location/Qualifiers
source                 1..10
                       mol_type = protein
                       organism = synthetic construct
SEQUENCE: 511
EAGGPDYRNG                                                        10

SEQ ID NO: 512         moltype = AA  length = 9
FEATURE                Location/Qualifiers
source                 1..9
                       mol_type = protein
                       organism = synthetic construct
SEQUENCE: 512
EAGGPDYRN                                                         9

SEQ ID NO: 513         moltype = AA  length = 8
FEATURE                Location/Qualifiers
source                 1..8
                       mol_type = protein
                       organism = synthetic construct
SEQUENCE: 513
EAGGPDYR                                                          8

SEQ ID NO: 514         moltype = AA  length = 7
FEATURE                Location/Qualifiers
source                 1..7
                       mol_type = protein
                       organism = synthetic construct
SEQUENCE: 514
EAGGPDY                                                           7

SEQ ID NO: 515         moltype = AA  length = 6
FEATURE                Location/Qualifiers
source                 1..6
                       mol_type = protein
                       organism = synthetic construct
SEQUENCE: 515
EAGGPD                                                            6

SEQ ID NO: 516         moltype = AA  length = 13
FEATURE                Location/Qualifiers
source                 1..13
                       mol_type = protein
                       organism = synthetic construct
SEQUENCE: 516
EAGGPIWHDD VKY                                                    13

SEQ ID NO: 517         moltype = AA  length = 12
FEATURE                Location/Qualifiers
```

-continued

```
source                   1..12
                         mol_type = protein
                         organism = synthetic construct
SEQUENCE: 517
EAGGPIWHDD VK                                                              12

SEQ ID NO: 518           moltype = AA   length = 11
FEATURE                  Location/Qualifiers
source                   1..11
                         mol_type = protein
                         organism = synthetic construct
SEQUENCE: 518
EAGGPIWHDD V                                                               11

SEQ ID NO: 519           moltype = AA   length = 10
FEATURE                  Location/Qualifiers
source                   1..10
                         mol_type = protein
                         organism = synthetic construct
SEQUENCE: 519
EAGGPIWHDD                                                                 10

SEQ ID NO: 520           moltype = AA   length = 9
FEATURE                  Location/Qualifiers
source                   1..9
                         mol_type = protein
                         organism = synthetic construct
SEQUENCE: 520
EAGGPIWHD                                                                  9

SEQ ID NO: 521           moltype = AA   length = 8
FEATURE                  Location/Qualifiers
source                   1..8
                         mol_type = protein
                         organism = synthetic construct
SEQUENCE: 521
EAGGPIWH                                                                   8

SEQ ID NO: 522           moltype = AA   length = 7
FEATURE                  Location/Qualifiers
source                   1..7
                         mol_type = protein
                         organism = synthetic construct
SEQUENCE: 522
EAGGPIW                                                                    7

SEQ ID NO: 523           moltype = AA   length = 6
FEATURE                  Location/Qualifiers
source                   1..6
                         mol_type = protein
                         organism = synthetic construct
SEQUENCE: 523
EAGGPI                                                                     6

SEQ ID NO: 524           moltype = AA   length = 11
FEATURE                  Location/Qualifiers
source                   1..11
                         mol_type = protein
                         organism = synthetic construct
SEQUENCE: 524
GTDYTIDDQG I                                                              11

SEQ ID NO: 525           moltype = AA   length = 10
FEATURE                  Location/Qualifiers
source                   1..10
                         mol_type = protein
                         organism = synthetic construct
SEQUENCE: 525
GTDYTIDDQG                                                                10

SEQ ID NO: 526           moltype = AA   length = 9
FEATURE                  Location/Qualifiers
source                   1..9
                         mol_type = protein
                         organism = synthetic construct
SEQUENCE: 526
GTDYTIDDQ                                                                  9

SEQ ID NO: 527           moltype = AA   length = 8
```

-continued

```
FEATURE                 Location/Qualifiers
source                  1..8
                        mol_type = protein
                        organism = synthetic construct
SEQUENCE: 527
GTDYTIDD                                                          8

SEQ ID NO: 528          moltype = AA  length = 7
FEATURE                 Location/Qualifiers
source                  1..7
                        mol_type = protein
                        organism = synthetic construct
SEQUENCE: 528
GTDYTID                                                           7

SEQ ID NO: 529          moltype = AA  length = 6
FEATURE                 Location/Qualifiers
source                  1..6
                        mol_type = protein
                        organism = synthetic construct
SEQUENCE: 529
GTDYTI                                                            6

SEQ ID NO: 530          moltype = AA  length = 11
FEATURE                 Location/Qualifiers
source                  1..11
                        mol_type = protein
                        organism = synthetic construct
SEQUENCE: 530
DKGDSDYDYN L                                                      11

SEQ ID NO: 531          moltype = AA  length = 10
FEATURE                 Location/Qualifiers
source                  1..10
                        mol_type = protein
                        organism = synthetic construct
SEQUENCE: 531
DKGDSDYDYN                                                        10

SEQ ID NO: 532          moltype = AA  length = 9
FEATURE                 Location/Qualifiers
source                  1..9
                        mol_type = protein
                        organism = synthetic construct
SEQUENCE: 532
DKGDSDYDY                                                         9

SEQ ID NO: 533          moltype = AA  length = 8
FEATURE                 Location/Qualifiers
source                  1..8
                        mol_type = protein
                        organism = synthetic construct
SEQUENCE: 533
DKGDSDYD                                                          8

SEQ ID NO: 534          moltype = AA  length = 7
FEATURE                 Location/Qualifiers
source                  1..7
                        mol_type = protein
                        organism = synthetic construct
SEQUENCE: 534
DKGDSDY                                                           7

SEQ ID NO: 535          moltype = AA  length = 6
FEATURE                 Location/Qualifiers
source                  1..6
                        mol_type = protein
                        organism = synthetic construct
SEQUENCE: 535
DKGDSD                                                            6

SEQ ID NO: 536          moltype = AA  length = 17
FEATURE                 Location/Qualifiers
source                  1..17
                        mol_type = protein
                        organism = synthetic construct
SEQUENCE: 536
YGPNYEEWGD YLATLDV                                                17
```

-continued

```
SEQ ID NO: 537          moltype = AA  length = 16
FEATURE                 Location/Qualifiers
source                  1..16
                        mol_type = protein
                        organism = synthetic construct
SEQUENCE: 537
GPNYEEWGDY LATLDV                                                    16

SEQ ID NO: 538          moltype = AA  length = 15
FEATURE                 Location/Qualifiers
source                  1..15
                        mol_type = protein
                        organism = synthetic construct
SEQUENCE: 538
PNYEEWGDYL ATLDV                                                     15

SEQ ID NO: 539          moltype = AA  length = 14
FEATURE                 Location/Qualifiers
source                  1..14
                        mol_type = protein
                        organism = synthetic construct
SEQUENCE: 539
NYEEWGDYLA TLDV                                                      14

SEQ ID NO: 540          moltype = AA  length = 13
FEATURE                 Location/Qualifiers
source                  1..13
                        mol_type = protein
                        organism = synthetic construct
SEQUENCE: 540
YEEWGDYLAT LDV                                                       13

SEQ ID NO: 541          moltype = AA  length = 12
FEATURE                 Location/Qualifiers
source                  1..12
                        mol_type = protein
                        organism = synthetic construct
SEQUENCE: 541
EEWGDYLATL DV                                                        12

SEQ ID NO: 542          moltype = AA  length = 15
FEATURE                 Location/Qualifiers
source                  1..15
                        mol_type = protein
                        organism = synthetic construct
SEQUENCE: 542
YDFYDGYYNY HYMDV                                                     15

SEQ ID NO: 543          moltype = AA  length = 14
FEATURE                 Location/Qualifiers
source                  1..14
                        mol_type = protein
                        organism = synthetic construct
SEQUENCE: 543
DFYDGYYNYH YMDV                                                      14

SEQ ID NO: 544          moltype = AA  length = 13
FEATURE                 Location/Qualifiers
source                  1..13
                        mol_type = protein
                        organism = synthetic construct
SEQUENCE: 544
FYDGYYNYHY MDV                                                       13

SEQ ID NO: 545          moltype = AA  length = 12
FEATURE                 Location/Qualifiers
source                  1..12
                        mol_type = protein
                        organism = synthetic construct
SEQUENCE: 545
YDGYYNYHYM DV                                                        12

SEQ ID NO: 546          moltype = AA  length = 11
FEATURE                 Location/Qualifiers
source                  1..11
                        mol_type = protein
                        organism = synthetic construct
SEQUENCE: 546
DGYYNYHYMD V                                                         11
```

-continued

```
SEQ ID NO: 547          moltype = AA  length = 10
FEATURE                 Location/Qualifiers
source                  1..10
                        mol_type = protein
                        organism = synthetic construct
SEQUENCE: 547
GYYNYHYMDV                                                        10

SEQ ID NO: 548          moltype = AA  length = 9
FEATURE                 Location/Qualifiers
source                  1..9
                        mol_type = protein
                        organism = synthetic construct
SEQUENCE: 548
YYNYHYMDV                                                         9

SEQ ID NO: 549          moltype = AA  length = 15
FEATURE                 Location/Qualifiers
source                  1..15
                        mol_type = protein
                        organism = synthetic construct
SEQUENCE: 549
YDFNDGYYNY HYMDV                                                  15

SEQ ID NO: 550          moltype = AA  length = 14
FEATURE                 Location/Qualifiers
source                  1..14
                        mol_type = protein
                        organism = synthetic construct
SEQUENCE: 550
DFYDGYYNYH YMDV                                                   14

SEQ ID NO: 551          moltype = AA  length = 13
FEATURE                 Location/Qualifiers
source                  1..13
                        mol_type = protein
                        organism = synthetic construct
SEQUENCE: 551
FYDGYYNYHY MDV                                                    13

SEQ ID NO: 552          moltype = AA  length = 12
FEATURE                 Location/Qualifiers
source                  1..12
                        mol_type = protein
                        organism = synthetic construct
SEQUENCE: 552
YDGYYNYHYM DV                                                     12

SEQ ID NO: 553          moltype = AA  length = 11
FEATURE                 Location/Qualifiers
source                  1..11
                        mol_type = protein
                        organism = synthetic construct
SEQUENCE: 553
DGYYNYHYMD V                                                      11

SEQ ID NO: 554          moltype = AA  length = 10
FEATURE                 Location/Qualifiers
source                  1..10
                        mol_type = protein
                        organism = synthetic construct
SEQUENCE: 554
GYYNYHYMDV                                                        10

SEQ ID NO: 555          moltype = AA  length = 16
FEATURE                 Location/Qualifiers
source                  1..16
                        mol_type = protein
                        organism = synthetic construct
SEQUENCE: 555
QGIRYQGSGT FWYFDV                                                 16

SEQ ID NO: 556          moltype = AA  length = 15
FEATURE                 Location/Qualifiers
source                  1..15
                        mol_type = protein
                        organism = synthetic construct
SEQUENCE: 556
```

-continued

```
GIRYQGSGTF WYFDV                                                        15

SEQ ID NO: 557          moltype = AA  length = 14
FEATURE                 Location/Qualifiers
source                  1..14
                        mol_type = protein
                        organism = synthetic construct SEQUENCE: 557
IRYQGSGTFW YFDV                                                         14

SEQ ID NO: 558          moltype = AA  length = 13
FEATURE                 Location/Qualifiers
source                  1..13
                        mol_type = protein
                        organism = synthetic construct SEQUENCE: 558
RYQGSGTFWY FDV                                                          13

SEQ ID NO: 559          moltype = AA  length = 12
FEATURE                 Location/Qualifiers
source                  1..12
                        mol_type = protein
                        organism = synthetic construct SEQUENCE: 559
YQGSGTFWYF DV                                                           12

SEQ ID NO: 560          moltype = AA  length = 11
FEATURE                 Location/Qualifiers
source                  1..11
                        mol_type = protein
                        organism = synthetic construct SEQUENCE: 560
QGSGTFWYFD V                                                            11

SEQ ID NO: 561          moltype = AA  length = 10
FEATURE                 Location/Qualifiers
source                  1..10
                        mol_type = protein
                        organism = synthetic construct SEQUENCE: 561
GSGTFWYFDV                                                             10

SEQ ID NO: 562          moltype = AA  length = 9
FEATURE                 Location/Qualifiers
source                  1..9
                        mol_type = protein
                        organism = synthetic construct SEQUENCE: 562
SGTFWYFDV                                                               9

SEQ ID NO: 563          moltype = AA  length = 8
FEATURE                 Location/Qualifiers
source                  1..8
                        mol_type = protein
                        organism = synthetic construct SEQUENCE: 563
GTFWYFDV                                                                8

SEQ ID NO: 564          moltype = AA  length = 13
FEATURE                 Location/Qualifiers
source                  1..13
                        mol_type = protein
                        organism = synthetic construct SEQUENCE: 564
YNLGYSYFYY MDG                                                          13

SEQ ID NO: 565          moltype = AA  length = 12
FEATURE                 Location/Qualifiers
source                  1..12
                        mol_type = protein
                        organism = synthetic construct SEQUENCE: 565
NLGYSYFYYM DG                                                           12

SEQ ID NO: 566          moltype = AA  length = 11
FEATURE                 Location/Qualifiers
source                  1..11
                        mol_type = protein
                        organism = synthetic construct
```

-continued

```
SEQUENCE: 566
LGYSYFYYMD G                                                   11

SEQ ID NO: 567          moltype = AA  length = 10
FEATURE                 Location/Qualifiers
source                  1..10
                        mol_type = protein
                        organism = synthetic construct
SEQUENCE: 567
GYSYFYYMDG                                                     10

SEQ ID NO: 568          moltype = AA  length = 9
FEATURE                 Location/Qualifiers
source                  1..9
                        mol_type = protein
                        organism = synthetic construct
SEQUENCE: 568
YSYFYYMDG                                                      9

SEQ ID NO: 569          moltype = AA  length = 8
FEATURE                 Location/Qualifiers
source                  1..8
                        mol_type = protein
                        organism = synthetic construct
SEQUENCE: 569
SYFYYMDG                                                       8

SEQ ID NO: 570          moltype = AA  length = 11
FEATURE                 Location/Qualifiers
source                  1..11
                        mol_type = protein
                        organism = synthetic construct
SEQUENCE: 570
WGHGTAVTVS S                                                   11

SEQ ID NO: 571          moltype = AA  length = 11
FEATURE                 Location/Qualifiers
source                  1..11
                        mol_type = protein
                        organism = synthetic construct
SEQUENCE: 571
WGKGTTVTVS S                                                   11

SEQ ID NO: 572          moltype = AA  length = 11
FEATURE                 Location/Qualifiers
source                  1..11
                        mol_type = protein
                        organism = synthetic construct
SEQUENCE: 572
WGKGTTVTVS S                                                   11

SEQ ID NO: 573          moltype = AA  length = 11
FEATURE                 Location/Qualifiers
source                  1..11
                        mol_type = protein
                        organism = synthetic construct
SEQUENCE: 573
WGRGTLVTVS S                                                   11

SEQ ID NO: 574          moltype = AA  length = 11
FEATURE                 Location/Qualifiers
source                  1..11
                        mol_type = protein
                        organism = synthetic construct
SEQUENCE: 574
WGKGTTVTVS S                                                   11

SEQ ID NO: 575          moltype = AA  length = 5
FEATURE                 Location/Qualifiers
source                  1..5
                        mol_type = protein
                        organism = synthetic construct
SEQUENCE: 575
GGGGS                                                          5

SEQ ID NO: 576          moltype = AA  length = 10
FEATURE                 Location/Qualifiers
source                  1..10
                        mol_type = protein
```

-continued

```
                               organism = synthetic construct
SEQUENCE: 576
GGGGSGGGGS                                                              10

SEQ ID NO: 577          moltype = AA  length = 15
FEATURE                 Location/Qualifiers
source                  1..15
                        mol_type = protein
                        organism = synthetic construct
SEQUENCE: 577
GGGGSGGGGS GGGGS                                                        15

SEQ ID NO: 578          moltype = AA  length = 20
FEATURE                 Location/Qualifiers
source                  1..20
                        mol_type = protein
                        organism = synthetic construct
SEQUENCE: 578
GGGGSGGGGS GGGGSGGGGS                                                   20

SEQ ID NO: 579          moltype =   length =
SEQUENCE: 579
000

SEQ ID NO: 580          moltype = AA  length = 6
FEATURE                 Location/Qualifiers
source                  1..6
                        mol_type = protein
                        organism = synthetic construct
SEQUENCE: 580
GGSGGS                                                                  6

SEQ ID NO: 581          moltype = AA  length = 9
FEATURE                 Location/Qualifiers
source                  1..9
                        mol_type = protein
                        organism = synthetic construct
SEQUENCE: 581
GGSGGSGGS                                                               9

SEQ ID NO: 582          moltype = AA  length = 12
FEATURE                 Location/Qualifiers
source                  1..12
                        mol_type = protein
                        organism = synthetic construct
SEQUENCE: 582
GGSGGSGGSG GS                                                           12

SEQ ID NO: 583          moltype =   length =
SEQUENCE: 583
000

SEQ ID NO: 584          moltype = AA  length = 6
FEATURE                 Location/Qualifiers
source                  1..6
                        mol_type = protein
                        organism = synthetic construct
SEQUENCE: 584
ASGASG                                                                  6

SEQ ID NO: 585          moltype = AA  length = 9
FEATURE                 Location/Qualifiers
source                  1..9
                        mol_type = protein
                        organism = synthetic construct
SEQUENCE: 585
ASGASGASG                                                               9

SEQ ID NO: 586          moltype = AA  length = 12
FEATURE                 Location/Qualifiers
source                  1..12
                        mol_type = protein
                        organism = synthetic construct
SEQUENCE: 586
ASGASGASGA SG                                                           12

SEQ ID NO: 587          moltype = AA  length = 7
FEATURE                 Location/Qualifiers
source                  1..7
```

```
                         mol_type = protein
                         organism = synthetic construct
SEQUENCE: 587
GCGGGGS                                                                      7

SEQ ID NO: 588          moltype = AA   length = 12
FEATURE                 Location/Qualifiers
source                  1..12
                         mol_type = protein
                         organism = synthetic construct
SEQUENCE: 588
GCGGGGSGGG GS                                                                12

SEQ ID NO: 589          moltype = AA   length = 17
FEATURE                 Location/Qualifiers
source                  1..17
                         mol_type = protein
                         organism = synthetic construct
SEQUENCE: 589
GCGGGGSGGG GSGGGGS                                                           17

SEQ ID NO: 590          moltype = AA   length = 22
FEATURE                 Location/Qualifiers
source                  1..22
                         mol_type = protein
                         organism = synthetic construct
SEQUENCE: 590
GCGGGGSGGG GSGGGGSGGG GS                                                     22

SEQ ID NO: 591          moltype = AA   length = 5
FEATURE                 Location/Qualifiers
source                  1..5
                         mol_type = protein
                         organism = synthetic construct
SEQUENCE: 591
GCGGS                                                                        5

SEQ ID NO: 592          moltype = AA   length = 8
FEATURE                 Location/Qualifiers
source                  1..8
                         mol_type = protein
                         organism = synthetic construct
SEQUENCE: 592
GCGGSGGS                                                                     8

SEQ ID NO: 593          moltype = AA   length = 11
FEATURE                 Location/Qualifiers
source                  1..11
                         mol_type = protein
                         organism = synthetic construct
SEQUENCE: 593
GCGGSGGSGG S                                                                 11

SEQ ID NO: 594          moltype = AA   length = 14
FEATURE                 Location/Qualifiers
source                  1..14
                         mol_type = protein
                         organism = synthetic construct
SEQUENCE: 594
GCGGSGGSGG SGGS                                                              14

SEQ ID NO: 595          moltype = AA   length = 5
FEATURE                 Location/Qualifiers
source                  1..5
                         mol_type = protein
                         organism = synthetic construct
SEQUENCE: 595
GCASG                                                                        5

SEQ ID NO: 596          moltype = AA   length = 10
FEATURE                 Location/Qualifiers
source                  1..10
                         mol_type = protein
                         organism = synthetic construct
SEQUENCE: 596
GCGCASGASG                                                                   10

SEQ ID NO: 597          moltype = AA   length = 11
FEATURE                 Location/Qualifiers
```

-continued

```
source                   1..11
                         mol_type = protein
                         organism = synthetic construct
SEQUENCE: 597
GCASGASGAS G                                                          11

SEQ ID NO: 598           moltype = AA  length = 14
FEATURE                  Location/Qualifiers
source                   1..14
                         mol_type = protein
                         organism = synthetic construct
SEQUENCE: 598
GCASGASGAS GASG                                                       14

SEQ ID NO: 599           moltype = AA  length = 37
FEATURE                  Location/Qualifiers
source                   1..37
                         mol_type = protein
                         organism = synthetic construct
SEQUENCE: 599
VGINVKCKHS RQCLKPCKDA GMRFGKCTNG KCHCTPK                              37

SEQ ID NO: 600           moltype = AA  length = 34
FEATURE                  Location/Qualifiers
source                   1..34
                         mol_type = protein
                         organism = synthetic construct
SEQUENCE: 600
ASCRTPKDCA DPCRKETGCP YGKCMNRKCK CNRC                                 34

SEQ ID NO: 601           moltype = AA  length = 38
FEATURE                  Location/Qualifiers
source                   1..38
                         mol_type = protein
                         organism = synthetic construct
SEQUENCE: 601
GVIINVKCKI SRQCLEPCKK AGMRFGKCMN GKCHCTPK                             38

SEQ ID NO: 602           moltype = AA  length = 35
FEATURE                  Location/Qualifiers
source                   1..35
                         mol_type = protein
                         organism = synthetic construct
SEQUENCE: 602
TISCTNPKQC YPHCKKETGY PNAKCMNRKC KCFGR                                35

SEQ ID NO: 603           moltype = AA  length = 39
FEATURE                  Location/Qualifiers
source                   1..39
                         mol_type = protein
                         organism = synthetic construct
SEQUENCE: 603
TVIDVKCTSP KQCLPPCKAQ FGIRAGAKCM NGKCKCYPH                            39

SEQ ID NO: 604           moltype = AA  length = 39
FEATURE                  Location/Qualifiers
source                   1..39
                         mol_type = protein
                         organism = synthetic construct
SEQUENCE: 604
TIINVKCTSP KQCLPPCKAQ FGQSAGAKCM NGKCKCYPH                            39

SEQ ID NO: 605           moltype = AA  length = 38
FEATURE                  Location/Qualifiers
source                   1..38
                         mol_type = protein
                         organism = synthetic construct
SEQUENCE: 605
GVPINVSCTG SPQCIKPCKD AGMRFGKCMN RKCHCTPK                             38

SEQ ID NO: 606           moltype = AA  length = 35
FEATURE                  Location/Qualifiers
source                   1..35
                         mol_type = protein
                         organism = synthetic construct
SEQUENCE: 606
TISCTNEKQC YPHCKKETGY PNAKCMNRKC KCFGR                                35

SEQ ID NO: 607           moltype = AA  length = 38
```

-continued

```
FEATURE                    Location/Qualifiers
source                     1..38
                           mol_type = protein
                           organism = synthetic construct
SEQUENCE: 607
GVEINVKCSG SPQCLKPCKD AGMRFGKCMN RKCHCTPK                      38

SEQ ID NO: 608             moltype = AA  length = 35
FEATURE                    Location/Qualifiers
source                     1..35
                           mol_type = protein
                           organism = synthetic construct
SEQUENCE: 608
ZKECTGPQHC TNFCRKNKCT HGKCMNRKCK CFNCK                         35

SEQ ID NO: 609             moltype = AA  length = 37
FEATURE                    Location/Qualifiers
source                     1..37
                           mol_type = protein
                           organism = synthetic construct
SEQUENCE: 609
ZFTNVSCTTS KECWSVCQRL HNTSRGKCMN KKCRCYS                       37

SEQ ID NO: 610             moltype = AA  length = 37
FEATURE                    Location/Qualifiers
source                     1..37
                           mol_type = protein
                           organism = synthetic construct
SEQUENCE: 610
VFINAKCRGS PECLPKCKEA IGKAAGKCMN GKCKCYP                       37

SEQ ID NO: 611             moltype = AA  length = 34
FEATURE                    Location/Qualifiers
source                     1..34
                           mol_type = protein
                           organism = synthetic construct
SEQUENCE: 611
VSCTGSKDCY APCRKQTGCP NAKCINKSCK CYGC                          34

SEQ ID NO: 612             moltype = AA  length = 33
FEATURE                    Location/Qualifiers
source                     1..33
                           mol_type = protein
                           organism = synthetic construct
SEQUENCE: 612
DCLGWFKSCD PKNDKCCKNY TCSRRDRWCK YDL                           33

SEQ ID NO: 613             moltype = AA  length = 33
FEATURE                    Location/Qualifiers
source                     1..33
                           mol_type = protein
                           organism = synthetic construct
SEQUENCE: 613
DCLGWFKSCD PKNDKCCKNY TCSRRDRWCK YYL                           33

SEQ ID NO: 614             moltype = AA  length = 39
FEATURE                    Location/Qualifiers
source                     1..39
                           mol_type = protein
                           organism = synthetic construct
SEQUENCE: 614
GVDKEGCRKL LGGCTIDDDC CPHLGCNKKY WHCGWDGTF                     39

SEQ ID NO: 615             moltype = AA  length = 34
FEATURE                    Location/Qualifiers
source                     1..34
                           mol_type = protein
                           organism = synthetic construct
SEQUENCE: 615
DCLGFLWKCN PSNDKCCRPN LVCSRKDKWC KYQI                          34

SEQ ID NO: 616             moltype = AA  length = 35
FEATURE                    Location/Qualifiers
source                     1..35
                           mol_type = protein
                           organism = synthetic construct
SEQUENCE: 616
ECRYLFGGCK TTSDCCKHLG CKFRDKYCAW DFTFS                         35
```

-continued

```
SEQ ID NO: 617          moltype = AA  length = 29
FEATURE                 Location/Qualifiers
source                  1..29
                        mol_type = protein
                        organism = synthetic construct
SEQUENCE: 617
YCQKWMWTCD SARKCCEGLV CRLWCKKII                                 29

SEQ ID NO: 618          moltype = AA  length = 35
FEATURE                 Location/Qualifiers
source                  1..35
                        mol_type = protein
                        organism = synthetic construct
SEQUENCE: 618
ECLEIFKACN PSNDQCCKSS KLVCSRKTRW CKYQI                          35

SEQ ID NO: 619          moltype = AA  length = 12
FEATURE                 Location/Qualifiers
source                  1..12
                        mol_type = protein
                        organism = synthetic construct
SEQUENCE: 619
GCCSDPRCAW RC                                                   12

SEQ ID NO: 620          moltype = AA  length = 16
FEATURE                 Location/Qualifiers
source                  1..16
                        mol_type = protein
                        organism = synthetic construct
SEQUENCE: 620
GCCSDPRCNM NNPDYC                                               16

SEQ ID NO: 621          moltype = AA  length = 16
FEATURE                 Location/Qualifiers
source                  1..16
                        mol_type = protein
                        organism = synthetic construct
SEQUENCE: 621
GCCSLPPCAA NNPDYC                                               16

SEQ ID NO: 622          moltype = AA  length = 16
FEATURE                 Location/Qualifiers
source                  1..16
                        mol_type = protein
                        organism = synthetic construct
SEQUENCE: 622
GCCSLPPCAL SNPDYC                                               16

SEQ ID NO: 623          moltype = AA  length = 16
FEATURE                 Location/Qualifiers
source                  1..16
                        mol_type = protein
                        organism = synthetic construct
SEQUENCE: 623
GCCSNPVCHL EHSNLC                                               16

SEQ ID NO: 624          moltype = AA  length = 16
FEATURE                 Location/Qualifiers
source                  1..16
                        mol_type = protein
                        organism = synthetic construct
SEQUENCE: 624
GCCSYPPCFA TNSDYC                                               16

SEQ ID NO: 625          moltype = AA  length = 15
FEATURE                 Location/Qualifiers
source                  1..15
                        mol_type = protein
                        organism = synthetic construct
SEQUENCE: 625
GCCSYPPCFA TNPDC                                                15

SEQ ID NO: 626          moltype = AA  length = 16
FEATURE                 Location/Qualifiers
source                  1..16
                        mol_type = protein
                        organism = synthetic construct
SEQUENCE: 626
GCCSYPPCFA TNSGYC                                               16
```

-continued

```
SEQ ID NO: 627              moltype = AA   length = 27
FEATURE                     Location/Qualifiers
source                      1..27
                            mol_type = protein
                            organism = synthetic construct
SEQUENCE: 627
CRIPNQKCFQ HLDDCCSRKC NRFNKCV                                    27

SEQ ID NO: 628              moltype = AA   length = 37
FEATURE                     Location/Qualifiers
source                      1..37
                            mol_type = protein
                            organism = synthetic construct
SEQUENCE: 628
ZFTNVSCTTS KECWSVCQRL HNTSRGKCMN KKCRCYS                         37

SEQ ID NO: 629              moltype = AA   length = 55
FEATURE                     Location/Qualifiers
source                      1..55
                            mol_type = protein
                            organism = synthetic construct
SEQUENCE: 629
ASATWGAAYP ACENNCRKKY DLCIRCQGKW AGKRGKCAAH CIIQKNNCKG KCKKE     55

SEQ ID NO: 630              moltype = AA   length = 43
FEATURE                     Location/Qualifiers
source                      1..43
                            mol_type = protein
                            organism = synthetic construct
SEQUENCE: 630
YKQCHKKGGH CFPKEKICLP PSSDFGKMDC CRWRWKCCKK GSG                  43

SEQ ID NO: 631              moltype = AA   length = 27
FEATURE                     Location/Qualifiers
source                      1..27
                            mol_type = protein
                            organism = synthetic construct
SEQUENCE: 631
CKSPGSSCSP TSYNCCRSCN PYTKRCY                                    27

SEQ ID NO: 632              moltype = AA   length = 22
FEATURE                     Location/Qualifiers
source                      1..22
                            mol_type = protein
                            organism = synthetic construct
SEQUENCE: 632
GHACYRNCWR EGNDEETCKE RC                                         22

SEQ ID NO: 633              moltype = AA   length = 66
FEATURE                     Location/Qualifiers
source                      1..66
                            mol_type = protein
                            organism = synthetic construct
SEQUENCE: 633
KEGYLVNSYT GCKFECFKLG DNDYCLRECR QQYGKGSGGY CYAFGCWCTH LYEQAVVWPL 60
PNKTCN                                                           66

SEQ ID NO: 634              moltype = AA   length = 76
FEATURE                     Location/Qualifiers
source                      1..76
                            mol_type = protein
                            organism = synthetic construct
SEQUENCE: 634
KKNGYPLDRN GKTTECSGVN AIAPHYCNSE CTKVYVAESG YCCWGACYCF GLEDDKPIGP 60
MKDITKKYCD VQIIPS                                                76

SEQ ID NO: 635              moltype = AA   length = 41
FEATURE                     Location/Qualifiers
source                      1..41
                            mol_type = protein
                            organism = synthetic construct
SEQUENCE: 635
GLPCDCHGHT GTYWLNYYSK CPKGYGYTGR CRYLVGSCCY K                    41

SEQ ID NO: 636              moltype = AA   length = 37
FEATURE                     Location/Qualifiers
source                      1..37
                            mol_type = protein
```

```
                          organism = synthetic construct
SEQUENCE: 636
GCIPYGKTCE FWSGPWCCAG KCKLNVWSMT LSCTRNF                                    37

SEQ ID NO: 637           moltype = AA  length = 40
FEATURE                  Location/Qualifiers
source                   1..40
                         mol_type = protein
                         organism = synthetic construct
SEQUENCE: 637
GCIPSFGECA WFSGESCCTG ICKWVFFTSK FMCRRVWGKD                                 40

SEQ ID NO: 638           moltype = AA  length = 29
FEATURE                  Location/Qualifiers
source                   1..29
                         mol_type = protein
                         organism = synthetic construct
SEQUENCE: 638
YCQKWLWTCD SERKCCEDMV CRLWCKKRL                                             29

SEQ ID NO: 639           moltype = AA  length = 35
FEATURE                  Location/Qualifiers
source                   1..35
                         mol_type = protein
                         organism = synthetic construct
SEQUENCE: 639
ECRYWLGGCS AGQTCCKHLV CSRRHGWCVW DGTFS                                      35

SEQ ID NO: 640           moltype = AA  length = 30
FEATURE                  Location/Qualifiers
source                   1..30
                         mol_type = protein
                         organism = synthetic construct
SEQUENCE: 640
YCQKWMWTCD SERKCCEGMV CRLWCKKKLW                                            30

SEQ ID NO: 641           moltype = AA  length = 33
FEATURE                  Location/Qualifiers
source                   1..33
                         mol_type = protein
                         organism = synthetic construct
SEQUENCE: 641
ACKGVFDACT PGKNECCPNR VCSDKHKWCK WKL                                        33

SEQ ID NO: 642           moltype = AA  length = 22
FEATURE                  Location/Qualifiers
source                   1..22
                         mol_type = protein
                         organism = synthetic construct
SEQUENCE: 642
ERLCCGFPKS CRSRQCKPHR CC                                                    22

SEQ ID NO: 643           moltype = AA  length = 36
FEATURE                  Location/Qualifiers
source                   1..36
                         mol_type = protein
                         organism = synthetic construct
SEQUENCE: 643
DGECGGFWWK CGRGKPPCCK GYACSKTWGW CAVEAP                                     36

SEQ ID NO: 644           moltype = AA  length = 31
FEATURE                  Location/Qualifiers
source                   1..31
                         mol_type = protein
                         organism = synthetic construct
SEQUENCE: 644
YCQKWMWTCD EERKCCEGLV CRLWCKKKIE W                                          31

SEQ ID NO: 645           moltype = AA  length = 35
FEATURE                  Location/Qualifiers
source                   1..35
                         mol_type = protein
                         organism = synthetic construct
SEQUENCE: 645
RSCIDTIPKS RCTAFKCKHS MKYRLSFCRE TCGTC                                      35

SEQ ID NO: 646           moltype = AA  length = 35
FEATURE                  Location/Qualifiers
source                   1..35
```

-continued

```
                          mol_type = protein
                          organism = synthetic construct
SEQUENCE: 646
RSCIDTIPKS RCTAFQCKHS MKYRLSFCRK TCGTC                               35

SEQ ID NO: 647          moltype = AA  length = 34
FEATURE                 Location/Qualifiers
source                  1..34
                          mol_type = protein
                          organism = synthetic construct
SEQUENCE: 647
ASCRTPKDCA DPCRKETGCP YGKCMNRKCK CNRC                                34

SEQ ID NO: 648          moltype = AA  length = 36
FEATURE                 Location/Qualifiers
source                  1..36
                          mol_type = protein
                          organism = synthetic construct
SEQUENCE: 648
EGECGGFWWK CGSGKPACCP KYVCSPKWGL CNFPMP                              36

SEQ ID NO: 649          moltype = AA  length = 37
FEATURE                 Location/Qualifiers
source                  1..37
                          mol_type = protein
                          organism = synthetic construct
SEQUENCE: 649
EFTNVSCTTS KECWSVCQRL HNTSRGKCMN KKCRCYS                             37

SEQ ID NO: 650          moltype = AA  length = 37
FEATURE                 Location/Qualifiers
source                  1..37
                          mol_type = protein
                          organism = synthetic construct
SEQUENCE: 650
EFTDVDCSVS KECWSVCKDL FGVDRGKCMG KKCRCYQ                             37

SEQ ID NO: 651          moltype = AA  length = 31
FEATURE                 Location/Qualifiers
source                  1..31
                          mol_type = protein
                          organism = synthetic construct
SEQUENCE: 651
AFCNLRMCQL SCRSLGLLGK CIGDKCECVK H                                   31

SEQ ID NO: 652          moltype = AA  length = 31
FEATURE                 Location/Qualifiers
source                  1..31
                          mol_type = protein
                          organism = synthetic construct
SEQUENCE: 652
AFCNLRRCEL SCRSLGLLGK CIGEECKCVP Y                                   31

SEQ ID NO: 653          moltype = AA  length = 38
FEATURE                 Location/Qualifiers
source                  1..38
                          mol_type = protein
                          organism = synthetic construct
SEQUENCE: 653
GVEINVKCSG SPQCLKPCKD AGMRFGKCMN RKCHCTPK                            38

SEQ ID NO: 654          moltype = AA  length = 35
FEATURE                 Location/Qualifiers
source                  1..35
                          mol_type = protein
                          organism = synthetic construct
SEQUENCE: 654
GYCAEKGIRC DDIHCCTGLK CKCNASGYNC VCRKK                               35

SEQ ID NO: 655          moltype = AA  length = 34
FEATURE                 Location/Qualifiers
source                  1..34
                          mol_type = protein
                          organism = synthetic construct
SEQUENCE: 655
DCLGFMRKCI PDNDKCCRPN LVCSRTHKWC KYVF                                34

SEQ ID NO: 656          moltype =   length =
SEQUENCE: 656
```

-continued

```
000

SEQ ID NO: 657          moltype =   length =
SEQUENCE: 657
000

SEQ ID NO: 658          moltype =   length =
SEQUENCE: 658
000

SEQ ID NO: 659          moltype =   length =
SEQUENCE: 659
000

SEQ ID NO: 660          moltype =   length =
SEQUENCE: 660
000

SEQ ID NO: 661          moltype =   length =
SEQUENCE: 661
000

SEQ ID NO: 662          moltype =   length =
SEQUENCE: 662
000

SEQ ID NO: 663          moltype =   length =
SEQUENCE: 663
000

SEQ ID NO: 664          moltype =   length =
SEQUENCE: 664
000

SEQ ID NO: 665          moltype =   length =
SEQUENCE: 665
000

SEQ ID NO: 666          moltype = AA  length = 11
FEATURE                 Location/Qualifiers
source                  1..11
                        mol_type = protein
                        organism = synthetic construct
SEQUENCE: 666
VGINVKCKHS R                                               11

SEQ ID NO: 667          moltype = AA  length = 7
FEATURE                 Location/Qualifiers
source                  1..7
                        mol_type = protein
                        organism = synthetic construct
SEQUENCE: 667
ASCRTPK                                                    7

SEQ ID NO: 668          moltype = AA  length = 12
FEATURE                 Location/Qualifiers
source                  1..12
                        mol_type = protein
                        organism = synthetic construct
SEQUENCE: 668
GVIINVKCKI SR                                              12

SEQ ID NO: 669          moltype = AA  length = 8
FEATURE                 Location/Qualifiers
source                  1..8
                        mol_type = protein
                        organism = synthetic construct
SEQUENCE: 669
TISCTNPK                                                   8

SEQ ID NO: 670          moltype = AA  length = 11
FEATURE                 Location/Qualifiers
source                  1..11
                        mol_type = protein
                        organism = synthetic construct
SEQUENCE: 670
TVIDVKCTSP K                                               11

SEQ ID NO: 671          moltype = AA  length = 11
```

-continued

```
FEATURE                 Location/Qualifiers
source                  1..11
                        mol_type = protein
                        organism = synthetic construct
SEQUENCE: 671
TIINVKCTSP K                                                                11

SEQ ID NO: 672          moltype = AA  length = 12
FEATURE                 Location/Qualifiers
source                  1..12
                        mol_type = protein
                        organism = synthetic construct
SEQUENCE: 672
GVPINVSCTG SP                                                               12

SEQ ID NO: 673          moltype = AA  length = 8
FEATURE                 Location/Qualifiers
source                  1..8
                        mol_type = protein
                        organism = synthetic construct
SEQUENCE: 673
TISCTNEK                                                                    8

SEQ ID NO: 674          moltype = AA  length = 12
FEATURE                 Location/Qualifiers
source                  1..12
                        mol_type = protein
                        organism = synthetic construct
SEQUENCE: 674
GVEINVKCSG SP                                                               12

SEQ ID NO: 675          moltype = AA  length = 8
FEATURE                 Location/Qualifiers
source                  1..8
                        mol_type = protein
                        organism = synthetic construct
SEQUENCE: 675
ZKECTGPQ                                                                    8

SEQ ID NO: 676          moltype = AA  length = 11
FEATURE                 Location/Qualifiers
source                  1..11
                        mol_type = protein
                        organism = synthetic construct
SEQUENCE: 676
ZFTNVSCTTS K                                                                11

SEQ ID NO: 677          moltype = AA  length = 12
FEATURE                 Location/Qualifiers
source                  1..12
                        mol_type = protein
                        organism = synthetic construct
SEQUENCE: 677
LKPCKDAGMR FG                                                               12

SEQ ID NO: 678          moltype = AA  length = 13
FEATURE                 Location/Qualifiers
source                  1..13
                        mol_type = protein
                        organism = synthetic construct
SEQUENCE: 678
ADPCRKETGC PYG                                                              13

SEQ ID NO: 679          moltype = AA  length = 12
FEATURE                 Location/Qualifiers
source                  1..12
                        mol_type = protein
                        organism = synthetic construct
SEQUENCE: 679
LEPCKKAGMR FG                                                               12

SEQ ID NO: 680          moltype = AA  length = 13
FEATURE                 Location/Qualifiers
source                  1..13
                        mol_type = protein
                        organism = synthetic construct
SEQUENCE: 680
YPHCKKETGY PNA                                                              13
```

-continued

```
SEQ ID NO: 681                    moltype = AA   length = 14
FEATURE                           Location/Qualifiers
source                            1..14
                                  mol_type = protein
                                  organism = synthetic construct SEQUENCE: 681
LPPCKAQFGI RAGA                                                        14

SEQ ID NO: 682                    moltype = AA   length = 14
FEATURE                           Location/Qualifiers
source                            1..14
                                  mol_type = protein
                                  organism = synthetic construct SEQUENCE: 682
LPPCKAQFGQ SAGA                                                        14

SEQ ID NO: 683                    moltype = AA   length = 12
FEATURE                           Location/Qualifiers
source                            1..12
                                  mol_type = protein
                                  organism = synthetic construct SEQUENCE: 683
IKPCKDAGMR FG                                                          12

SEQ ID NO: 684                    moltype = AA   length = 13
FEATURE                           Location/Qualifiers
source                            1..13
                                  mol_type = protein
                                  organism = synthetic construct SEQUENCE: 684
YPHCKKETGY PNA                                                         13

SEQ ID NO: 685                    moltype = AA   length = 12
FEATURE                           Location/Qualifiers
source                            1..12
                                  mol_type = protein
                                  organism = synthetic construct SEQUENCE: 685
LKPCKDAGMR FG                                                          12

SEQ ID NO: 686                    moltype = AA   length = 12
FEATURE                           Location/Qualifiers
source                            1..12
                                  mol_type = protein
                                  organism = synthetic construct SEQUENCE: 686
TNFCRKNKCT HG                                                          12

SEQ ID NO: 687                    moltype = AA   length = 13
FEATURE                           Location/Qualifiers
source                            1..13
                                  mol_type = protein
                                  organism = synthetic construct SEQUENCE: 687
WSVCQRLHNT SRG                                                         13

SEQ ID NO: 688                    moltype = AA   length = 9
FEATURE                           Location/Qualifiers
source                            1..9
                                  mol_type = protein
                                  organism = synthetic construct SEQUENCE: 688
NGKCHCTPK                                                              9

SEQ ID NO: 689                    moltype = AA   length = 9
FEATURE                           Location/Qualifiers
source                            1..9
                                  mol_type = protein
                                  organism = synthetic construct SEQUENCE: 689
NRKCKCNRC                                                              9

SEQ ID NO: 690                    moltype = AA   length = 9
FEATURE                           Location/Qualifiers
source                            1..9
                                  mol_type = protein
                                  organism = synthetic construct SEQUENCE: 690
NGKCHCTPK                                                              9
```

-continued

```
SEQ ID NO: 691           moltype = AA   length = 9
FEATURE                  Location/Qualifiers
source                   1..9
                         mol_type = protein
                         organism = synthetic construct
SEQUENCE: 691
NRKCKCFGR                                                        9

SEQ ID NO: 692           moltype = AA   length = 9
FEATURE                  Location/Qualifiers
source                   1..9
                         mol_type = protein
                         organism = synthetic construct
SEQUENCE: 692
NGKCKCYPH                                                        9

SEQ ID NO: 693           moltype = AA   length = 9
FEATURE                  Location/Qualifiers
source                   1..9
                         mol_type = protein
                         organism = synthetic construct
SEQUENCE: 693
NGKCKCYPH                                                        9

SEQ ID NO: 694           moltype = AA   length = 9
FEATURE                  Location/Qualifiers
source                   1..9
                         mol_type = protein
                         organism = synthetic construct
SEQUENCE: 694
NRKCHCTPK                                                        9

SEQ ID NO: 695           moltype = AA   length = 9
FEATURE                  Location/Qualifiers
source                   1..9
                         mol_type = protein
                         organism = synthetic construct
SEQUENCE: 695
NRKCKCFGR                                                        9

SEQ ID NO: 696           moltype = AA   length = 9
FEATURE                  Location/Qualifiers
source                   1..9
                         mol_type = protein
                         organism = synthetic construct
SEQUENCE: 696
NRKCHCTPK                                                        9

SEQ ID NO: 697           moltype = AA   length = 10
FEATURE                  Location/Qualifiers
source                   1..10
                         mol_type = protein
                         organism = synthetic construct
SEQUENCE: 697
NRKCKCFNCK                                                       10

SEQ ID NO: 698           moltype = AA   length = 8
FEATURE                  Location/Qualifiers
source                   1..8
                         mol_type = protein
                         organism = synthetic construct
SEQUENCE: 698
NKKCRCYS                                                         8

SEQ ID NO: 699           moltype = AA   length = 5
FEATURE                  Location/Qualifiers
source                   1..5
                         mol_type = protein
                         organism = synthetic construct
SEQUENCE: 699
SGGGG                                                            5

SEQ ID NO: 700           moltype = AA   length = 10
FEATURE                  Location/Qualifiers
source                   1..10
                         mol_type = protein
                         organism = synthetic construct
SEQUENCE: 700
```

-continued

```
SGGGGSGGGG                                                        10

SEQ ID NO: 701          moltype = AA  length = 15
FEATURE                 Location/Qualifiers
source                  1..15
                        mol_type = protein
                        organism = synthetic construct
SEQUENCE: 701
SGGGGSGGGG SGGGG                                                  15

SEQ ID NO: 702          moltype = AA  length = 20
FEATURE                 Location/Qualifiers
source                  1..20
                        mol_type = protein
                        organism = synthetic construct
SEQUENCE: 702
SGGGGSGGGG SGGGGSGGGG                                             20

SEQ ID NO: 703          moltype =   length =
SEQUENCE: 703
000

SEQ ID NO: 704          moltype = AA  length = 6
FEATURE                 Location/Qualifiers
source                  1..6
                        mol_type = protein
                        organism = synthetic construct
SEQUENCE: 704
SGGSGG                                                            6

SEQ ID NO: 705          moltype = AA  length = 9
FEATURE                 Location/Qualifiers
source                  1..9
                        mol_type = protein
                        organism = synthetic construct
SEQUENCE: 705
SGGSGGSGG                                                         9

SEQ ID NO: 706          moltype = AA  length = 12
FEATURE                 Location/Qualifiers
source                  1..12
                        mol_type = protein
                        organism = synthetic construct
SEQUENCE: 706
SGGSGGSGGS GG                                                     12

SEQ ID NO: 707          moltype =   length =
SEQUENCE: 707
000

SEQ ID NO: 708          moltype = AA  length = 6
FEATURE                 Location/Qualifiers
source                  1..6
                        mol_type = protein
                        organism = synthetic construct
SEQUENCE: 708
GSAGSA                                                            6

SEQ ID NO: 709          moltype = AA  length = 9
FEATURE                 Location/Qualifiers
source                  1..9
                        mol_type = protein
                        organism = synthetic construct
SEQUENCE: 709
GSAGSAGSA                                                         9

SEQ ID NO: 710          moltype = AA  length = 12
FEATURE                 Location/Qualifiers
source                  1..12
                        mol_type = protein
                        organism = synthetic construct
SEQUENCE: 710
GSAGSAGSAG SA                                                     12

SEQ ID NO: 711          moltype = AA  length = 7
FEATURE                 Location/Qualifiers
source                  1..7
                        mol_type = protein
                        organism = synthetic construct
```

```
SEQUENCE: 711
SGGGGCG                                                                    7

SEQ ID NO: 712          moltype = AA  length = 12
FEATURE                 Location/Qualifiers
source                  1..12
                        mol_type = protein
                        organism = synthetic construct
SEQUENCE: 712
SGGGGSGGGG CG                                                              12

SEQ ID NO: 713          moltype = AA  length = 17
FEATURE                 Location/Qualifiers
source                  1..17
                        mol_type = protein
                        organism = synthetic construct
SEQUENCE: 713
SGGGGSGGGG SGGGGCG                                                         17

SEQ ID NO: 714          moltype = AA  length = 22
FEATURE                 Location/Qualifiers
source                  1..22
                        mol_type = protein
                        organism = synthetic construct
SEQUENCE: 714
SGGGGSGGGG SGGGGSGGGG CG                                                   22

SEQ ID NO: 715          moltype = AA  length = 5
FEATURE                 Location/Qualifiers
source                  1..5
                        mol_type = protein
                        organism = synthetic construct
SEQUENCE: 715
SGGCG                                                                      5

SEQ ID NO: 716          moltype = AA  length = 8
FEATURE                 Location/Qualifiers
source                  1..8
                        mol_type = protein
                        organism = synthetic construct
SEQUENCE: 716
SGGSGGCG                                                                   8

SEQ ID NO: 717          moltype = AA  length = 11
FEATURE                 Location/Qualifiers
source                  1..11
                        mol_type = protein
                        organism = synthetic construct
SEQUENCE: 717
SGGSGGSGGC G                                                               11

SEQ ID NO: 718          moltype = AA  length = 14
FEATURE                 Location/Qualifiers
source                  1..14
                        mol_type = protein
                        organism = synthetic construct
SEQUENCE: 718
SGGSGGSGGS GGCG                                                            14

SEQ ID NO: 719          moltype = AA  length = 5
FEATURE                 Location/Qualifiers
source                  1..5
                        mol_type = protein
                        organism = synthetic construct
SEQUENCE: 719
GSACG                                                                      5

SEQ ID NO: 720          moltype = AA  length = 10
FEATURE                 Location/Qualifiers
source                  1..10
                        mol_type = protein
                        organism = synthetic construct
SEQUENCE: 720
GSAGSACGCG                                                                 10

SEQ ID NO: 721          moltype = AA  length = 11
FEATURE                 Location/Qualifiers
source                  1..11
                        mol_type = protein
```

-continued

```
                       organism = synthetic construct
SEQUENCE: 721
GSAGSAGSAC G                                                    11

SEQ ID NO: 722        moltype = AA  length = 14
FEATURE               Location/Qualifiers
source                1..14
                      mol_type = protein
                      organism = synthetic construct
SEQUENCE: 722
GSAGSAGSAG SACG                                                 14

SEQ ID NO: 723        moltype = AA  length = 7
FEATURE               Location/Qualifiers
source                1..7
                      mol_type = protein
                      organism = synthetic construct
SEQUENCE: 723
GGGGSGG                                                         7

SEQ ID NO: 724        moltype = AA  length = 17
FEATURE               Location/Qualifiers
source                1..17
                      mol_type = protein
                      organism = synthetic construct
SEQUENCE: 724
GGGGSGGGGS GGGGSGG                                              17

SEQ ID NO: 725        moltype = AA  length = 7
FEATURE               Location/Qualifiers
source                1..7
                      mol_type = protein
                      organism = synthetic construct
SEQUENCE: 725
GGSGGGG                                                         7

SEQ ID NO: 726        moltype = AA  length = 17
FEATURE               Location/Qualifiers
source                1..17
                      mol_type = protein
                      organism = synthetic construct
SEQUENCE: 726
GGSGGGGSGG GGGGGGS                                              17

SEQ ID NO: 727        moltype = AA  length = 34
FEATURE               Location/Qualifiers
source                1..34
                      mol_type = protein
                      organism = synthetic construct
SEQUENCE: 727
INVKCSLPQQ CIKPCKDAGM RFGKCMNKKC RCYS                           34

SEQ ID NO: 728        moltype = AA  length = 38
FEATURE               Location/Qualifiers
source                1..38
                      mol_type = protein
                      organism = synthetic construct
SEQUENCE: 728
GVIINVKCKI SPQCLKPCKD AGMRFGKCMN GKCHCTPK                       38

SEQ ID NO: 729        moltype = AA  length = 38
FEATURE               Location/Qualifiers
source                1..38
                      mol_type = protein
                      organism = synthetic construct
SEQUENCE: 729
GVIINVKCKI SRQCLKPCKD AGMRFGKCMN GKCHCTPK                       38

SEQ ID NO: 730        moltype = AA  length = 35
FEATURE               Location/Qualifiers
source                1..35
                      mol_type = protein
                      organism = synthetic construct
SEQUENCE: 730
RTCKDLIPVS ECTDIRCRTS MKYRLNLCRK TCGSC                          35

SEQ ID NO: 731        moltype = AA  length = 35
FEATURE               Location/Qualifiers
source                1..35
```

-continued

```
                              mol_type = protein
                              organism = synthetic construct
SEQUENCE: 731
RSCIDTIPKS RCTAFKCKHS MKYRLYFCKK TCGTC                              35

SEQ ID NO: 732          moltype = AA  length = 35
FEATURE                 Location/Qualifiers
source                  1..35
                        mol_type = protein
                        organism = synthetic construct
SEQUENCE: 732
RSCIDTIPKS RCTAFKCKHS MKYRLSFCRK TCGTC                              35

SEQ ID NO: 733          moltype = AA  length = 36
FEATURE                 Location/Qualifiers
source                  1..36
                        mol_type = protein
                        organism = synthetic construct
SEQUENCE: 733
RSCIDTIPKS RCTAFKCKHS MKYRLSFCRK TCGTCA                             36

SEQ ID NO: 734          moltype = AA  length = 94
FEATURE                 Location/Qualifiers
source                  1..94
                        mol_type = protein
                        organism = synthetic construct
SEQUENCE: 734
QVQLREWGAG LLKPSETLSL TCAVYGGSFS GYYWSWIRQP PGKGLEWIGE INHSGSTNYN   60
PSLKSRVTIS VDTSKNQFSL KLSSVTAADT AVYY                               94

SEQ ID NO: 735          moltype = AA  length = 95
FEATURE                 Location/Qualifiers
source                  1..95
                        mol_type = protein
                        organism = synthetic construct
SEQUENCE: 735
QVQLREWGAG LLKPSETLSL TCAVYGGSFS GYYWSWIRQP PGKGLEWIGE INHSGSTNYN   60
PSLKSRVTIS VDTSKNQFSL KLSSVTAADT AVYYC                              95

SEQ ID NO: 736          moltype = AA  length = 94
FEATURE                 Location/Qualifiers
source                  1..94
                        mol_type = protein
                        organism = synthetic construct
SEQUENCE: 736
QVQLREWGAG LLKPSETLSL TCAVYGGSFS DKYWSWIRQP PGKGLEWIGE INHSGSTNYN   60
PSLKSRVTIS VDTSKNQFSL KLSSVTAADT AVYY                               94

SEQ ID NO: 737          moltype = AA  length = 95
FEATURE                 Location/Qualifiers
source                  1..95
                        mol_type = protein
                        organism = synthetic construct
SEQUENCE: 737
QVQLREWGAG LLKPSETLSL TCAVYGGSFS DKYWSWIRQP PGKGLEWIGE INHSGSTNYN   60
PSLKSRVTIS VDTSKNQFSL KLSSVTAADT AVYYC                              95

SEQ ID NO: 738          moltype = AA  length = 94
FEATURE                 Location/Qualifiers
source                  1..94
                        mol_type = protein
                        organism = synthetic construct
SEQUENCE: 738
QVQLREWGAG LLKPSETLSL TCAVYGGSFS GYYWSWIRQP PGKGLEWIGS INHSGSTNYN   60
PSLKSRVTIS VDTSKNQFSL KLSSVTAADT AVYY                               94

SEQ ID NO: 739          moltype = AA  length = 95
FEATURE                 Location/Qualifiers
source                  1..95
                        mol_type = protein
                        organism = synthetic construct
SEQUENCE: 739
QVQLREWGAG LLKPSETLSL TCAVYGGSFS GYYWSWIRQP PGKGLEWIGS INHSGSTNYN   60
PSLKSRVTIS VDTSKNQFSL KLSSVTAADT AVYYC                              95

SEQ ID NO: 740          moltype = AA  length = 94
FEATURE                 Location/Qualifiers
source                  1..94
                        mol_type = protein
```

-continued

```
                        organism = synthetic construct
SEQUENCE: 740
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYY                                94

SEQ ID NO: 741          moltype = AA   length = 95
FEATURE                 Location/Qualifiers
source                  1..95
                        mol_type = protein
                        organism = synthetic construct
SEQUENCE: 741
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYC                               95

SEQ ID NO: 742          moltype = AA   length = 94
FEATURE                 Location/Qualifiers
source                  1..94
                        mol_type = protein
                        organism = synthetic construct
SEQUENCE: 742
QVQLREWGAG LLKPSETLSL TCTASGFSLS DKAVGWIRQP PGKGLEWIGE INHSGSTNYN    60
PSLKSRVTIS VDTSKNQFSL KLSSVTAADT AVYY                                94

SEQ ID NO: 743          moltype = AA   length = 95
FEATURE                 Location/Qualifiers
source                  1..95
                        mol_type = protein
                        organism = synthetic construct
SEQUENCE: 743
QVQLREWGAG LLKPSETLSL TCTASGFSLS DKAVGWIRQP PGKGLEWIGE INHSGSTNYN    60
PSLKSRVTIS VDTSKNQFSL KLSSVTAADT AVYYC                               95

SEQ ID NO: 744          moltype = AA   length = 94
FEATURE                 Location/Qualifiers
source                  1..94
                        mol_type = protein
                        organism = synthetic construct
SEQUENCE: 744
QVQLREWGAG LLKPSETLSL TCAVYGGLGS IDTGGNTGSF SGYYWSWIRQ PPGKGLEWYN    60
PSLKSRVTIS VDTSKNQFSL KLSSVTAADT AVYY                                94

SEQ ID NO: 745          moltype = AA   length = 95
FEATURE                 Location/Qualifiers
source                  1..95
                        mol_type = protein
                        organism = synthetic construct
SEQUENCE: 745
QVQLREWGAG LLKPSETLSL TCAVYGGLGS IDTGGNTGSF SGYYWSWIRQ PPGKGLEWYN    60
PSLKSRVTIS VDTSKNQFSL KLSSVTAADT AVYYC                               95

SEQ ID NO: 746          moltype = AA   length = 94
FEATURE                 Location/Qualifiers
source                  1..94
                        mol_type = protein
                        organism = synthetic construct
SEQUENCE: 746
QVQLREWGAG LLKPSETLSL TCTASGFSLS DKAVGWIRQP PGKGLEWIGS INHSGSTNYN    60
PSLKSRVTIS VDTSKNQFSL KLSSVTAADT AVYY                                94

SEQ ID NO: 747          moltype = AA   length = 95
FEATURE                 Location/Qualifiers
source                  1..95
                        mol_type = protein
                        organism = synthetic construct
SEQUENCE: 747
QVQLREWGAG LLKPSETLSL TCTASGFSLS DKAVGWIRQP PGKGLEWIGS INHSGSTNYN    60
PSLKSRVTIS VDTSKNQFSL KLSSVTAADT AVYYC                               95

SEQ ID NO: 748          moltype = AA   length = 94
FEATURE                 Location/Qualifiers
source                  1..94
                        mol_type = protein
                        organism = synthetic construct
SEQUENCE: 748
QVQLREWGAG LLKPSETLSL TCTASGFSLS DKAVGWIRQP PGKGLEWLGS IDTGGNTGYN    60
PSLKSRVTIS VDTSKNQFSL KLSSVTAADT AVYY                                94

SEQ ID NO: 749          moltype = AA   length = 95
FEATURE                 Location/Qualifiers
```

-continued

```
source                  1..95
                        mol_type = protein
                        organism = synthetic construct
SEQUENCE: 749
QVQLREWGAG LLKPSETLSL TCTASGFSLS DKAVGWIRQP PGKGLEWLGS IDTGGNTGYN   60
PSLKSRVTIS VDTSKNQFSL KLSSVTAADT AVYYC                              95

SEQ ID NO: 750          moltype = AA  length = 89
FEATURE                 Location/Qualifiers
source                  1..89
                        mol_type = protein
                        organism = synthetic construct
SEQUENCE: 750
QAVLNQPSSV SGSLGQKVTI SCSGSSSNIG NNYVSWYQQL PGTAPRTLIY GDTKRPSGIP   60
DRFSGSKSGT SATLGITGLQ TGDEADYYC                                     89

SEQ ID NO: 751          moltype = AA  length = 89
FEATURE                 Location/Qualifiers
source                  1..89
                        mol_type = protein
                        organism = synthetic construct
SEQUENCE: 751
QAVLNQPSSV SGSLGQKVTI SCSGSSSNIG NNYVSWYQQL PGTAPRTLIY GDTSRASGIP   60
DRFSGSKSGT SATLGITGLQ TGDEADYYC                                     89

SEQ ID NO: 752          moltype = AA  length = 89
FEATURE                 Location/Qualifiers
source                  1..89
                        mol_type = protein
                        organism = synthetic construct
SEQUENCE: 752
QSVLTQPPSV SAAPGQKVTI SCSGSSSNVG NGYVSWYQQL PGTAPRTLIY GDTKRPSGIP   60
DRFSGSKSGT SATLGITGLQ TGDEADYYC                                     89

SEQ ID NO: 753          moltype = AA  length = 89
FEATURE                 Location/Qualifiers
source                  1..89
                        mol_type = protein
                        organism = synthetic construct
SEQUENCE: 753
QSVLTQPPSV SAAPGQKVTI SCSGSSSNVG NGYVSWYQQL PGTAPRTLIY GDTSRASGIP   60
DRFSGSKSGT SATLGITGLQ TGDEADYYC                                     89

SEQ ID NO: 754          moltype = AA  length = 11
FEATURE                 Location/Qualifiers
source                  1..11
                        mol_type = protein
                        organism = synthetic construct
SEQUENCE: 754
ASAEDSSSNA V                                                        11

SEQ ID NO: 755          moltype = AA  length = 10
FEATURE                 Location/Qualifiers
source                  1..10
                        mol_type = protein
                        organism = synthetic construct
SEQUENCE: 755
FGSGTTLTVL                                                          10

SEQ ID NO: 756          moltype = AA  length = 106
FEATURE                 Location/Qualifiers
source                  1..106
                        mol_type = protein
                        organism = synthetic construct
SEQUENCE: 756
GQPKAAPSVT LFPPSSEELQ ANKATLVCLI SDFYPGAVTV AWKADSSPVK AGVETTTPSK   60
QSNNKYAASS YLSLTPEQWK SHRSYSCQVT HEGSTVEKTV APTECS                 106

SEQ ID NO: 757          moltype = DNA  length = 438
FEATURE                 Location/Qualifiers
source                  1..438
                        mol_type = other DNA
                        organism = synthetic construct
SEQUENCE: 757
caggtccagc tgagagagag cggcccttca ctggtcaagc catcccagac actgagcctg   60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
cccggactga gagcagact gtccattacc aaggacaact ctaaaagtca ggtgtcactg  240
agcgtgagct ccgtcaccac agaggatagt gcaacttact attgcacctc tgtgcaccag  300
```

```
gaaactaaga aataccagag cggaggaagc gagacctact atggttcggg tctcggagga   360
agctcttata cctacaatta tgaatggcat gtggatgtct ggggacaggg cctgctggtg   420
acagtctcta gtgctagc                                                438

SEQ ID NO: 758          moltype = DNA   length = 447
FEATURE                 Location/Qualifiers
source                  1..447
                        mol_type = other DNA
                        organism = synthetic construct
SEQUENCE: 758
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga gagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc gagacctact atggtccggg tctcggagga   360
agcggaggaa gctcttatac ctacaattat gaatggcatg tggatgtctg gggacagggc   420
ctgctggtga cagtctctag tgctagc                                      447

SEQ ID NO: 759          moltype = DNA   length = 447
FEATURE                 Location/Qualifiers
source                  1..447
                        mol_type = other DNA
                        organism = synthetic construct
SEQUENCE: 759
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga gagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg agacctacta tggttcgggt   360
ctcggaggaa gctcttatac ctacaattat gaatggcatg tggatgtctg gggacagggc   420
ctgctggtga cagtctctag tgctagc                                      447

SEQ ID NO: 760          moltype = DNA   length = 456
FEATURE                 Location/Qualifiers
source                  1..456
                        mol_type = other DNA
                        organism = synthetic construct
SEQUENCE: 760
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga gagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg agacctacta tggttcgggt   360
ctcggaggaa gcggaggaag ctcttatacc tacaattatg aatggcatgt ggatgtctgg   420
ggacagggc tgctggtgac agtctctagt gctagc                             456

SEQ ID NO: 761          moltype = DNA   length = 465
FEATURE                 Location/Qualifiers
source                  1..465
                        mol_type = other DNA
                        organism = synthetic construct
SEQUENCE: 761
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga gagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg agacctacta tggttcgggt   360
ctcggaggaa gcggaggaag cggaggaagc tcttatacct acaattatga atggcatgtg   420
gatgtctggg gacagggcct gctggtgaca gtctctagtg ctagc                  465

SEQ ID NO: 762          moltype = DNA   length = 474
FEATURE                 Location/Qualifiers
source                  1..474
                        mol_type = other DNA
                        organism = synthetic construct
SEQUENCE: 762
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga gagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg agacctacta tggttcgggt   360
ctcggaggaa gcggaggaag cggaggaagc ggaggaagc cttatacct caattatgaa   420
tggcatgtg atgtctgggg acagggcctg ctggtgacag tctctagtgc tagc         474
```

```
SEQ ID NO: 763          moltype = DNA   length = 465
FEATURE                 Location/Qualifiers
source                  1..465
                        mol_type = other DNA
                        organism = synthetic construct
SEQUENCE: 763
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg gaggaagcga gacctactat   360
ggttcgggtc tcgaggaag cggaggaagc tcttatacct acaattatga atggcatgtg   420
gatgtctggg gacagggcct gctggtgaca gtctctagtc ctagc                   465

SEQ ID NO: 764          moltype = DNA   length = 474
FEATURE                 Location/Qualifiers
source                  1..474
                        mol_type = other DNA
                        organism = synthetic construct
SEQUENCE: 764
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg gaggaagcga gacctactat   360
ggttcgggtc tcgaggaag cggaggaagc ggaggaagct cttataccta caattatgaa   420
tggcatgtgg atgtctgggg acagggcctg ctggtgaca tctctagtgc tagc           474

SEQ ID NO: 765          moltype = DNA   length = 474
FEATURE                 Location/Qualifiers
source                  1..474
                        mol_type = other DNA
                        organism = synthetic construct
SEQUENCE: 765
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggaggaagc ggaggaagcg gaggaagcgg aggaagcgag   360
acctactatg gttcgggtct cggaggaagc ggaggaagct cttataccta caattatgaa   420
tggcatgtgg atgtctgggg acagggcctg ctggtgaca tctctagtgc tagc           474

SEQ ID NO: 766          moltype = DNA   length = 459
FEATURE                 Location/Qualifiers
source                  1..459
                        mol_type = other DNA
                        organism = synthetic construct
SEQUENCE: 766
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggtggagga ggttctggag gatgagacct actatggttc   360
agggtctctg gaggtggtgg atcttcttat acctacaatt atgaatggca tgtggatgtc   420
tggggacagg gcctgctggt gacagtctct agtgctagc                          459

SEQ ID NO: 767          moltype = DNA   length = 519
FEATURE                 Location/Qualifiers
source                  1..519
                        mol_type = other DNA
                        organism = synthetic construct
SEQUENCE: 767
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag   300
gaaactaaga aataccagag cggtggagga ggttctggag gcggtggaag tggtggcgga   360
ggtagcggag gatgagacct actatggttc agggtctctg gaggtggtgg atctggtgga   420
ggaggcagtg gaggtggtgg cagctcttat acctacaatt atgaatggca tgtggatgtc   480
tggggacagg gcctgctggt gacagtctct agtgctagc                          519

SEQ ID NO: 768          moltype = DNA   length = 24
FEATURE                 Location/Qualifiers
source                  1..24
```

-continued

```
                          mol_type = other DNA
                          organism = synthetic construct
SEQUENCE: 768
gagacctact atggttcggg tctc                                       24

SEQ ID NO: 769          moltype = DNA   length = 25
FEATURE                 Location/Qualifiers
source                  1..25
                        mol_type = other DNA
                        organism = synthetic construct
SEQUENCE: 769
gagacctact atggttcagg gtctc                                      25

SEQ ID NO: 770          moltype = AA   length = 173
FEATURE                 Location/Qualifiers
source                  1..173
                        mol_type = protein
                        organism = synthetic construct
SEQUENCE: 770
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSGGS GINVKCSLPQ  120
QCIKPCKDAG MRFGKCMNKK CRCYSGGSSY TYNYEWHVDV WGQGLLVTVS SAS         173

SEQ ID NO: 771          moltype = AA   length = 176
FEATURE                 Location/Qualifiers
source                  1..176
                        mol_type = protein
                        organism = synthetic construct
SEQUENCE: 771
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSGGS GINVKCSLPQ  120
QCIKPCKDAG MRFGKCMNKK CRCYSGGSGG SSYTYNYEWH VDVWGQGLLV TVSSAS      176

SEQ ID NO: 772          moltype = AA   length = 176
FEATURE                 Location/Qualifiers
source                  1..176
                        mol_type = protein
                        organism = synthetic construct
SEQUENCE: 772
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSGGS GGSGINVKCS  120
LPQQCIKPCK DAGMRFGKCM NKKCRCYSGG SSYTYNYEWH VDVWGQGLLV TVSSAS      176

SEQ ID NO: 773          moltype = AA   length = 179
FEATURE                 Location/Qualifiers
source                  1..179
                        mol_type = protein
                        organism = synthetic construct
SEQUENCE: 773
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSGGS GGSGINVKCS  120
LPQQCIKPCK DAGMRFGKCM NKKCRCYSGG SGGSSYTYNY EWHVDVWGQG LLVTVSSAS   179

SEQ ID NO: 774          moltype = AA   length = 185
FEATURE                 Location/Qualifiers
source                  1..185
                        mol_type = protein
                        organism = synthetic construct
SEQUENCE: 774
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSGGS GGSGGSGINV  120
KCSLPQQCIK PCKDAGMRFG KCMNKKCRCY SGGSGGSGGS SYTYNYEWHV DVWGQGLLVT  180
VSSAS                                                            185

SEQ ID NO: 775          moltype = AA   length = 194
FEATURE                 Location/Qualifiers
source                  1..194
                        mol_type = protein
                        organism = synthetic construct
SEQUENCE: 775
QVQLRESGPS LVKPSQTLSL TCTASGFSLS DKAVGWVRQA PGKALEWLGS IDTGGNTGYN   60
PGLKSRLSIT KDNSKSQVSL SVSSVTTEDS ATYYCTSVHQ ETKKYQSGGG GSGGGGSGGG  120
GSGGYCQKWM WTCDSERKCC EGMVCRLWCK KKLWGGGGSG GGGSGGGGSS YTYNYEWHVD  180
VWGQGLLVTV SSAS                                                  194

SEQ ID NO: 776          moltype = AA   length = 198
FEATURE                 Location/Qualifiers
source                  1..198
                        mol_type = protein
```

```
                          organism = synthetic construct
SEQUENCE: 776
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGG GSGGGGSGGG    120
GSGGDCLGFM RKCIPDNDKC CRPNLVCSRT HKWCKYVFGG GGSGGGGSGG GGSSYTYNYE    180
WHVDVWGQGL LVTVSSAS                                                  198

SEQ ID NO: 777          moltype = AA  length = 202
FEATURE                 Location/Qualifiers
source                  1..202
                        mol_type = protein
                        organism = synthetic construct
SEQUENCE: 777
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGG GSGGGGSGGG    120
GSGGGVIINV KCKISPQCLK PCKDAGMRFG KCMNGKCHCT PKGGGGSGGG GSGGGGSSYT    180
YNYEWHVDVW GQGLLVTVSS AS                                             202

SEQ ID NO: 778          moltype = AA  length = 202
FEATURE                 Location/Qualifiers
source                  1..202
                        mol_type = protein
                        organism = synthetic construct
SEQUENCE: 778
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGG GSGGGGSGGG    120
GSGGGVIINV KCKISRQCLK PCKDAGMRFG KCMNGKCHCT PKGGGGSGGG GSGGGGSSYT    180
YNYEWHVDVW GQGLLVTVSS AS                                             202

SEQ ID NO: 779          moltype = AA  length = 199
FEATURE                 Location/Qualifiers
source                  1..199
                        mol_type = protein
                        organism = synthetic construct
SEQUENCE: 779
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGG GSGGGGSGGG    120
GSGGRSCIDT IPKSRCTAFQ CKHSMKYRLS FCRKTCGTCG GGGSGGGGSG GGGSSYTYNY    180
EWHVDVWGQG LLVTVSSAS                                                 199

SEQ ID NO: 780          moltype = AA  length = 216
FEATURE                 Location/Qualifiers
source                  1..216
                        mol_type = protein
                        organism = synthetic construct
SEQUENCE: 780
QAVLNQPSSV SGSLGQKVTI SCSGSSSNIG NNYVSWYQQL PGTAPRTLIY GDTKRPSGIP    60
DRFSGSKSGT SATLGITGLQ TGDEADYYCA SAEDSSSNAV FGSGTTLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 781          moltype = AA  length = 216
FEATURE                 Location/Qualifiers
source                  1..216
                        mol_type = protein
                        organism = synthetic construct
SEQUENCE: 781
QAVLNQPSSV SGSLGQKVTI SCSGSSSNIG NNYVSWYQQL PGTAPRTLIY GDTSRASGIP    60
DRFSGSKSGT SATLGITGLQ TGDEADYYCA SAEDSSSNAV FGSGTTLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 782          moltype = AA  length = 216
FEATURE                 Location/Qualifiers
source                  1..216
                        mol_type = protein
                        organism = synthetic construct
SEQUENCE: 782
QSVLTQPPSV SAAPGQKVTI SCSGSSSNVG NGYVSWYQQL PGTAPRTLIY GDTKRPSGIP    60
DRFSGSKSGT SATLGITGLQ TGDEADYYCA SAEDSSSNAV FGSGTTLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 783          moltype = AA  length = 216
FEATURE                 Location/Qualifiers
source                  1..216
                        mol_type = protein
                        organism = synthetic construct
SEQUENCE: 783
```

-continued

```
QSVLTQPPSV SAAPGQKVTI SCSGSSSNVG NGYVSWYQQL PGTAPRTLIY GDTSRASGIP    60
DRFSGSKSGT SATLGITGLQ TGDEADYYCA SAEDSSSNAV FGSGTTLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 784              moltype = AA  length = 207
FEATURE                     Location/Qualifiers
source                      1..207
                            mol_type = protein
                            organism = synthetic construct
SEQUENCE: 784
QVQLREWGAG LLKPSETLSL TCAVYGGSFS GYYWSWIRQP PGKGLEWIGE INHSGSTNYN    60
PSLKSRVTIS VDTSKNQFSL KLSSVTAADT AVYYCTSVHQ ETKKYQSPRS AKELRCQCIK   120
TYSKPFHPKF IKELRVIESG PHCANTEIIV KLSDGRELCL DPKENWVQRV VEKFLKRAEN   180
SGSGSYTYNY EWHVDVWGQG LLVTVSS                                       207

SEQ ID NO: 785              moltype = AA  length = 207
FEATURE                     Location/Qualifiers
source                      1..207
                            mol_type = protein
                            organism = synthetic construct
SEQUENCE: 785
QVQLREWGAG LLKPSETLSL TCAVYGGSFS DKYWSWIRQP PGKGLEWIGE INHSGSTNYN    60
PSLKSRVTIS VDTSKNQFSL KLSSVTAADT AVYYCTSVHQ ETKKYQSPRS AKELRCQCIK   120
TYSKPFHPKF IKELRVIESG PHCANTEIIV KLSDGRELCL DPKENWVQRV VEKFLKRAEN   180
SGSGSYTYNY EWHVDVWGQG LLVTVSS                                       207

SEQ ID NO: 786              moltype = AA  length = 207
FEATURE                     Location/Qualifiers
source                      1..207
                            mol_type = protein
                            organism = synthetic construct
SEQUENCE: 786
QVQLREWGAG LLKPSETLSL TCAVYGGSFS GYYWSWIRQP PGKGLEWIGS INHSGSTNYN    60
PSLKSRVTIS VDTSKNQFSL KLSSVTAADT AVYYCTSVHQ ETKKYQSPRS AKELRCQCIK   120
TYSKPFHPKF IKELRVIESG PHCANTEIIV KLSDGRELCL DPKENWVQRV VEKFLKRAEN   180
SGSGSYTYNY EWHVDVWGQG LLVTVSS                                       207

SEQ ID NO: 787              moltype = AA  length = 207
FEATURE                     Location/Qualifiers
source                      1..207
                            mol_type = protein
                            organism = synthetic construct
SEQUENCE: 787
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSPRS AKELRCQCIK   120
TYSKPFHPKF IKELRVIESG PHCANTEIIV KLSDGRELCL DPKENWVQRV VEKFLKRAEN   180
SGSGSYTYNY EWHVDVWGQG LLVTVSS                                       207

SEQ ID NO: 788              moltype = AA  length = 207
FEATURE                     Location/Qualifiers
source                      1..207
                            mol_type = protein
                            organism = synthetic construct
SEQUENCE: 788
QVQLREWGAG LLKPSETLSL TCTASGFSLS DKAVGWIRQP PGKGLEWIGE INHSGSTNYN    60
PSLKSRVTIS VDTSKNQFSL KLSSVTAADT AVYYCTSVHQ ETKKYQSPRS AKELRCQCIK   120
TYSKPFHPKF IKELRVIESG PHCANTEIIV KLSDGRELCL DPKENWVQRV VEKFLKRAEN   180
SGSGSYTYNY EWHVDVWGQG LLVTVSS                                       207

SEQ ID NO: 789              moltype = AA  length = 207
FEATURE                     Location/Qualifiers
source                      1..207
                            mol_type = protein
                            organism = synthetic construct
SEQUENCE: 789
QVQLREWGAG LLKPSETLSL TCAVYGGLGS IDTGGNTGSF SGYYWSWIRQ PPGKGLEWYN    60
PSLKSRVTIS VDTSKNQFSL KLSSVTAADT AVYYCTSVHQ ETKKYQSPRS AKELRCQCIK   120
TYSKPFHPKF IKELRVIESG PHCANTEIIV KLSDGRELCL DPKENWVQRV VEKFLKRAEN   180
SGSGSYTYNY EWHVDVWGQG LLVTVSS                                       207

SEQ ID NO: 790              moltype = AA  length = 207
FEATURE                     Location/Qualifiers
source                      1..207
                            mol_type = protein
                            organism = synthetic construct
SEQUENCE: 790
QVQLREWGAG LLKPSETLSL TCTASGFSLS DKAVGWIRQP PGKGLEWIGS INHSGSTNYN    60
PSLKSRVTIS VDTSKNQFSL KLSSVTAADT AVYYCTSVHQ ETKKYQSPRS AKELRCQCIK   120
```

-continued

```
TYSKPFHPKF IKELRVIESG PHCANTEIIV KLSDGRELCL DPKENWVQRV VEKFLKRAEN    180
SGSGSYTYNY EWHVDVWGQG LLVTVSS                                         207

SEQ ID NO: 791          moltype = AA  length = 207
FEATURE                 Location/Qualifiers
source                  1..207
                        mol_type = protein
                        organism = synthetic construct
SEQUENCE: 791
QVQLREWGAG LLKPSETLSL TCTASGFSLS DKAVGWIRQP PGKGLEWLGS IDTGGNTGYN    60
PSLKSRVTIS VDTSKNQFSL KLSSVTAADT AVYYCTSVHQ ETKKYQSPRS AKELRCQCIK    120
TYSKPFHPKF IKELRVIESG PHCANTEIIV KLSDGRELCL DPKENWVQRV VEKFLKRAEN    180
SGSGSYTYNY EWHVDVWGQG LLVTVSS                                         207

SEQ ID NO: 792          moltype = AA  length = 216
FEATURE                 Location/Qualifiers
source                  1..216
                        mol_type = protein
                        organism = synthetic construct
SEQUENCE: 792
QAVLNQPSSV SGSLGQKVTI SCSGSSSNIG NNYVSWYQQL PGTAPKLLIY GDTKRPSGIP    60
DRFSGSKSGT SATLGITGLQ TGDEADYYCA SAEDSSSNAV GQPKAAPSVT               120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 793          moltype = AA  length = 209
FEATURE                 Location/Qualifiers
source                  1..209
                        mol_type = protein
                        organism = synthetic construct
SEQUENCE: 793
QVQLQQWGAG LLKPSETLSL TCAVYGGSFS GYYWSWIRQP PGKGLEWIGE INHSGSTNYN    60
PSLKSRVTIS VDTSKNQFSL KLSSVTAADT AVYYCTSVHQ ETKKYQSPRS AKELRCQCIK    120
TYSKPFHPKF IKELRVIESG PHCANTEIIV KLSDGRELCL DPKENWVQRV VEKFLKRAEN    180
SGSGSYTYNY EWHVDVWGQG LLVTVSSAS                                       209

SEQ ID NO: 794          moltype = AA  length = 209
FEATURE                 Location/Qualifiers
source                  1..209
                        mol_type = protein
                        organism = synthetic construct
SEQUENCE: 794
QVQLQQWGAG LLKPSETLSL TCTASGFSLS DKAVGWIRQP PGKGLEWIGE INHSGSTNYN    60
PSLKSRVTIS VDTSKNQFSL KLSSVTAADT AVYYCTSVHQ ETKKYQSPRS AKELRCQCIK    120
TYSKPFHPKF IKELRVIESG PHCANTEIIV KLSDGRELCL DPKENWVQRV VEKFLKRAEN    180
SGSGSYTYNY EWHVDVWGQG LLVTVSSAS                                       209

SEQ ID NO: 795          moltype = AA  length = 209
FEATURE                 Location/Qualifiers
source                  1..209
                        mol_type = protein
                        organism = synthetic construct
SEQUENCE: 795
QVQLQQWGAG LLKPSETLSL TCAVYGGSFS GYYWSWIRQP PGKGLEWLGS IDTGGNTGYN    60
PSLKSRVTIS VDTSKNQFSL KLSSVTAADT AVYYCTSVHQ ETKKYQSPRS AKELRCQCIK    120
TYSKPFHPKF IKELRVIESG PHCANTEIIV KLSDGRELCL DPKENWVQRV VEKFLKRAEN    180
SGSGSYTYNY EWHVDVWGQG LLVTVSSAS                                       209

SEQ ID NO: 796          moltype = AA  length = 209
FEATURE                 Location/Qualifiers
source                  1..209
                        mol_type = protein
                        organism = synthetic construct
SEQUENCE: 796
QVQLQQWGAG LLKPSETLSL TCAVYGGSFS DKYWSWIRQP PGKGLEWIGE INHSGSTNYN    60
PSLKSRVTIS VDTSKNQFSL KLSSVTAADT AVYYCTSVHQ ETKKYQSPRS AKELRCQCIK    120
TYSKPFHPKF IKELRVIESG PHCANTEIIV KLSDGRELCL DPKENWVQRV VEKFLKRAEN    180
SGSGSYTYNY EWHVDVWGQG LLVTVSSAS                                       209

SEQ ID NO: 797          moltype = AA  length = 209
FEATURE                 Location/Qualifiers
source                  1..209
                        mol_type = protein
                        organism = synthetic construct
SEQUENCE: 797
QVQLQQWGAG LLKPSETLSL TCAVYGGSFS GYYWSWIRQP PGKGLEWIGS INHSGSTNYN    60
PSLKSRVTIS VDTSKNQFSL KLSSVTAADT AVYYCTSVHQ ETKKYQSPRS AKELRCQCIK    120
TYSKPFHPKF IKELRVIESG PHCANTEIIV KLSDGRELCL DPKENWVQRV VEKFLKRAEN    180
SGSGSYTYNY EWHVDVWGQG LLVTVSSAS                                       209
```

```
SEQ ID NO: 798              moltype = AA  length = 209
FEATURE                     Location/Qualifiers
source                      1..209
                            mol_type = protein
                            organism = synthetic construct
SEQUENCE: 798
QVQLQQWGAG LLKPSETLSL TCTASGFSLS DKAVGWIRQP PGKGLEWLGS IDTGGNTGYN  60
PSLKSRVTIS VDTSKNQFSL KLSSVTAADT AVYYCTSVHQ ETKKYQSPRS AKELRCQCIK  120
TYSKPFHPKF IKELRVIESG PHCANTEIIV KLSDGRELCL DPKENWVQRV VEKFLKRAEN  180
SGSGSYTYNY EWHVDVWGQG LLVTVSSAS                                    209

SEQ ID NO: 799              moltype = AA  length = 209
FEATURE                     Location/Qualifiers
source                      1..209
                            mol_type = protein
                            organism = synthetic construct
SEQUENCE: 799
QVQLQQWGAG LLKPSETLSL TCTASGFSLS DKAVGWIRQP PGKGLEWIGS INHSGSTNYN  60
PSLKSRVTIS VDTSKNQFSL KLSSVTAADT AVYYCTSVHQ ETKKYQSPRS AKELRCQCIK  120
TYSKPFHPKF IKELRVIESG PHCANTEIIV KLSDGRELCL DPKENWVQRV VEKFLKRAEN  180
SGSGSYTYNY EWHVDVWGQG LLVTVSSAS                                    209

SEQ ID NO: 800              moltype = AA  length = 209
FEATURE                     Location/Qualifiers
source                      1..209
                            mol_type = protein
                            organism = synthetic construct
SEQUENCE: 800
QVQLQQWGAG LLKPSETLSL TCAVYGGSFS DKYWSWIRQP PGKGLEWIGS INHSGSTNYN  60
PSLKSRVTIS VDTSKNQFSL KLSSVTAADT AVYYCTSVHQ ETKKYQSPRS AKELRCQCIK  120
TYSKPFHPKF IKELRVIESG PHCANTEIIV KLSDGRELCL DPKENWVQRV VEKFLKRAEN  180
SGSGSYTYNY EWHVDVWGQG LLVTVSSAS                                    209

SEQ ID NO: 801              moltype = AA  length = 216
FEATURE                     Location/Qualifiers
source                      1..216
                            mol_type = protein
                            organism = synthetic construct
SEQUENCE: 801
QSVLTQPPSV SAAPGQKVTI SCSGSSSNVG NGYVSWYQQL PGTAPKLLIY DNNKRPSGIP  60
DRFSGSKSGT SATLGITGLQ TGDEADYYCA SAEDSSSNAV FGSGTTLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 802              moltype = AA  length = 216
FEATURE                     Location/Qualifiers
source                      1..216
                            mol_type = protein
                            organism = synthetic construct
SEQUENCE: 802
QSVLTQPPSV SAAPGQKVTI SCSGSSSNIG NNYVSWYQQL PGTAPKLLIY GDTKRPSGIP  60
DRFSGSKSGT SATLGITGLQ TGDEADYYCA SAEDSSSNAV FGSGTTLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 803              moltype = AA  length = 216
FEATURE                     Location/Qualifiers
source                      1..216
                            mol_type = protein
                            organism = synthetic construct
SEQUENCE: 803
QSVLTQPPSV SAAPGQKVTI SCSGSSSNIG NNYVSWYQQL PGTAPKLLIY GDTSRASGIP  60
DRFSGSKSGT SATLGITGLQ TGDEADYYCA SAEDSSSNAV FGSGTTLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 804              moltype = AA  length = 216
FEATURE                     Location/Qualifiers
source                      1..216
                            mol_type = protein
                            organism = synthetic construct
SEQUENCE: 804
QAVLNQPSSV SGSLGQKVTI SCSGSSSNIG NNYVSWYQQL PGTAPKLLIY DNNKRPSGIP  60
DRFSGSKSGT SATLGITGLQ TGDEADYYCA SAEDSSSNAV FGSGTTLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 805              moltype = AA  length = 216
```

-continued

```
FEATURE               Location/Qualifiers
source                1..216
                      mol_type = protein
                      organism = synthetic construct
SEQUENCE: 805
QSVLTQPPSV SAAPGQKVTI SCSGSSSNIG NNYVSWYQQL PGTAPKLLIY DNNKRPSGIP    60
DRFSGSKSGT SATLGITGLQ TGDEADYYCA SAEDSSSNAV FGSGTTLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 806        moltype = DNA   length = 105
FEATURE               Location/Qualifiers
source                1..105
                      mol_type = other DNA
                      organism = synthetic construct SEQUENCE: 806
ggcatcaacg tgaagtgcag cctgccccag cagtgcatca agccctgcaa ggacgccggc    60
atgagattcg gcaagtgcat gaacaagaag tgcagatgct acagc                   105

SEQ ID NO: 807        moltype = AA   length = 216
FEATURE               Location/Qualifiers
source                1..216
                      mol_type = protein
                      organism = synthetic construct SEQUENCE: 807
QAVLNQPSSV SGSLGQRVSI TCSGSSSNVG NGYVSWYQLI PGSAPRTLIY GDTSRASGVP    60
DRFSGSRSGN TATLTISSLQ AEDEADYFCA SAEDSSSNAV FGSGTTLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 808        moltype = AA   length = 60
FEATURE               Location/Qualifiers
source                1..60
                      mol_type = protein
                      organism = synthetic construct
SEQUENCE: 808
GVPDRFSGSR SGNTATLTIS SLQAEDEADY FCASAEDSSS NAVFGSGTTL TVLGQPKAAP    60

SEQ ID NO: 809        moltype = AA   length = 60
FEATURE               Location/Qualifiers
source                1..60
                      mol_type = protein
                      organism = synthetic construct
SEQUENCE: 809
SVTLFPPSSE ELQANKATLV CLISDFYPGA VTVAWKADSS PVKAGVETTT PSKQSNNKYA    60

SEQ ID NO: 810        moltype = AA   length = 39
FEATURE               Location/Qualifiers
source                1..39
                      mol_type = protein
                      organism = synthetic construct
SEQUENCE: 810
ASSYLSLTPE QWKSHRSYSC QVTHEGSTVE KTVAPTECS                           39

SEQ ID NO: 811        moltype = AA   length = 114
FEATURE               Location/Qualifiers
source                1..114
                      mol_type = protein
                      organism = synthetic construct
SEQUENCE: 811
GGCGTGATCA TCAACGTGAA ATGCAAGATC AGCCCCCAGT GCCTGAAGCC CTGCAAGGAC    60
GCCGGCATGA GGTTCGGGAA GTGCATGAAC GGCAAGTGCC ACTGCACCCC CAAG         114

SEQ ID NO: 812        moltype = AA   length = 114
FEATURE               Location/Qualifiers
source                1..114
                      mol_type = protein
                      organism = synthetic construct
SEQUENCE: 812
GGCGTGATCA TCAACGTGAA GTGCAAGATC AGCAGGCAGT GCCTGAAGCC CTGCAAGGAC    60
GCCGGCATGA GGTTCGGTAA GTGCATGAAC GGCAAGTGCC ACTGCACCCC CAAG         114

SEQ ID NO: 813        moltype =   length =
SEQUENCE: 813
000

SEQ ID NO: 814        moltype =   length =
SEQUENCE: 814
000
```

```
SEQ ID NO: 815          moltype =   length =
SEQUENCE: 815
000

SEQ ID NO: 816          moltype = AA  length = 4
FEATURE                 Location/Qualifiers
source                  1..4
                        mol_type = protein
                        organism = synthetic construct
SEQUENCE: 816
GGGG                                                            4

SEQ ID NO: 817          moltype = AA  length = 9
FEATURE                 Location/Qualifiers
source                  1..9
                        mol_type = protein
                        organism = synthetic construct
SEQUENCE: 817
GGGGGSGGS                                                       9

SEQ ID NO: 818          moltype = AA  length = 12
FEATURE                 Location/Qualifiers
source                  1..12
                        mol_type = protein
                        organism = synthetic construct
SEQUENCE: 818
GGGGSGGGGS GG                                                   12

SEQ ID NO: 819          moltype = AA  length = 8
FEATURE                 Location/Qualifiers
source                  1..8
                        mol_type = protein
                        organism = synthetic construct
SEQUENCE: 819
GGGGSGGS                                                        8

SEQ ID NO: 820          moltype = AA  length = 11
FEATURE                 Location/Qualifiers
source                  1..11
                        mol_type = protein
                        organism = synthetic construct
SEQUENCE: 820
GGGGSGGSGG S                                                    11

SEQ ID NO: 821          moltype = AA  length = 14
FEATURE                 Location/Qualifiers
source                  1..14
                        mol_type = protein
                        organism = synthetic construct
SEQUENCE: 821
GGGGSGGSGG SGGS                                                 14

SEQ ID NO: 822          moltype = AA  length = 4
FEATURE                 Location/Qualifiers
source                  1..4
                        mol_type = protein
                        organism = synthetic construct
SEQUENCE: 822
GGSG                                                            4

SEQ ID NO: 823          moltype = AA  length = 5
FEATURE                 Location/Qualifiers
source                  1..5
                        mol_type = protein
                        organism = synthetic construct
SEQUENCE: 823
GGSGG                                                           5

SEQ ID NO: 824          moltype = AA  length = 7
FEATURE                 Location/Qualifiers
source                  1..7
                        mol_type = protein
                        organism = synthetic construct
SEQUENCE: 824
GGSGGSG                                                         7

SEQ ID NO: 825          moltype = AA  length = 8
FEATURE                 Location/Qualifiers
```

-continued

```
source                  1..8
                        mol_type = protein
                        organism = synthetic construct
SEQUENCE: 825
GGSGGSGG                                                    8

SEQ ID NO: 826          moltype = AA  length = 10
FEATURE                 Location/Qualifiers
source                  1..10
                        mol_type = protein
                        organism = synthetic construct
SEQUENCE: 826
GGSGGSGGSG                                                  10

SEQ ID NO: 827          moltype = AA  length = 11
FEATURE                 Location/Qualifiers
source                  1..11
                        mol_type = protein
                        organism = synthetic construct
SEQUENCE: 827
GGSGGSGGSG G                                                11

SEQ ID NO: 828          moltype = AA  length = 14
FEATURE                 Location/Qualifiers
source                  1..14
                        mol_type = protein
                        organism = synthetic construct
SEQUENCE: 828
GGSGGSGGSG GSGG                                             14

SEQ ID NO: 829          moltype =    length =
SEQUENCE: 829
000

SEQ ID NO: 830          moltype = AA  length = 4
FEATURE                 Location/Qualifiers
source                  1..4
                        mol_type = protein
                        organism = synthetic construct
SEQUENCE: 830
GSGG                                                        4

SEQ ID NO: 831          moltype = AA  length = 35
FEATURE                 Location/Qualifiers
source                  1..35
                        mol_type = protein
                        organism = synthetic construct
SEQUENCE: 831
RSCIDTIPKS RCTAFQCKHS QKYRLSFCRK TCGTC                      35

SEQ ID NO: 832          moltype = AA  length = 35
FEATURE                 Location/Qualifiers
source                  1..35
                        mol_type = protein
                        organism = synthetic construct
SEQUENCE: 832
RSCIDTIPKS RCTAFQCKHS LKYRLSFCRK TCGTC                      35

SEQ ID NO: 833          moltype = AA  length = 35
FEATURE                 Location/Qualifiers
source                  1..35
                        mol_type = protein
                        organism = synthetic construct
SEQUENCE: 833
RSCIDTIPKS RCTAFQCKHS FKYRLSFCRK TCGTC                      35

SEQ ID NO: 834          moltype = AA  length = 35
FEATURE                 Location/Qualifiers
source                  1..35
                        mol_type = protein
                        organism = synthetic construct
SEQUENCE: 834
RSCIDTIPKS RCTAFQCKHS IKYRLSFCRK TCGTC                      35

SEQ ID NO: 835          moltype = AA  length = 35
FEATURE                 Location/Qualifiers
source                  1..35
                        mol_type = protein
                        organism = synthetic construct
```

-continued

```
SEQUENCE: 835
RSCIDTIPKS RCTAFQCKHS AKYRLSFCRK TCGTC                               35

SEQ ID NO: 836          moltype = DNA  length = 504
FEATURE                 Location/Qualifiers
source                  1..504
                        mol_type = other DNA
                        organism = synthetic construct
SEQUENCE: 836
caggtccagc tgagagagag cggcccttca ctggtcaagc catcccagac actgagcctg  60
acatgcacag caagcgggtt ttcactgagc gacaaggcag tgggatgggg ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggaggaagc tattgccaga agtggatgtg gacctgcgat  360
agcgaacgga aatgttgcga aggcatggtg tgccgcctgt ggtgcaagaa gaaactctgg  420
ggaggaagct cttatacctta caattatgaa tggcatgtgg atgtctgggg acagggcctg  480
ctggtgcacag tctctagtgc tagc                                        504

SEQ ID NO: 837          moltype = DNA  length = 513
FEATURE                 Location/Qualifiers
source                  1..513
                        mol_type = other DNA
                        organism = synthetic construct
SEQUENCE: 837
caggtccagc tgagagagag cggcccttca ctggtcaagc catcccagac actgagcctg  60
acatgcacag caagcgggtt ttcactgagc gacaaggcag tgggatgggg ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggaggaagc tattgccaga agtggatgtg gacctgcgat  360
agcgaacgga aatgttgcga aggcatggtg tgccgcctgt ggtgcaagaa gaaactctgg  420
ggaggaagcg gaggaagctc ttatacctac aattatgaat ggcatgtgga tgtctgggga  480
cagggcctgc tggtgacagt ctctagtgct agc                               513

SEQ ID NO: 838          moltype = DNA  length = 513
FEATURE                 Location/Qualifiers
source                  1..513
                        mol_type = other DNA
                        organism = synthetic construct
SEQUENCE: 838
caggtccagc tgagagagag cggcccttca ctggtcaagc catcccagac actgagcctg  60
acatgcacag caagcgggtt ttcactgagc gacaaggcag tgggatgggg ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggaggaagc ggaggaagct attgccagaa gtggatgtgg  360
acctgcgata cgaacgaa atgttgcgaa ggcatggtgt gccgcctgtg gtgcaagaag  420
aaactctggg gaggaagctc ttatacctac aattatgaat ggcatgtgga tgtctgggga  480
cagggcctgc tggtgacagt ctctagtgct agc                               513

SEQ ID NO: 839          moltype = DNA  length = 519
FEATURE                 Location/Qualifiers
source                  1..519
                        mol_type = other DNA
                        organism = synthetic construct
SEQUENCE: 839
caggtccagc tgagagagag cggcccttca ctggtcaagc catcccagac actgagcctg  60
acatgcacag caagcgggtt ttcactgagc gacaaggcag tgggatgggg ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggaggaagc ggcatcaacg tgaagtgcag cctgcccag  360
cagtgcatca gccctgcaa ggacgccggc atgagattcg gcaagtgcat gaacaagaag  420
tgcagatgct acagcggagg aagctcttat acctacaatt atgaatggca tgtggatgtc  480
tggggacagg gcctgctggt gacagtctct agtgctagc                         519

SEQ ID NO: 840          moltype = DNA  length = 528
FEATURE                 Location/Qualifiers
source                  1..528
                        mol_type = other DNA
                        organism = synthetic construct
SEQUENCE: 840
caggtccagc tgagagagag cggcccttca ctggtcaagc catcccagac actgagcctg  60
acatgcacag caagcgggtt ttcactgagc gacaaggcag tgggatgggg ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggaggaagc ggcatcaacg tgaagtgcag cctgcccag  360
```

```
cagtgcatca agccctgcaa ggacgccggc atgagattcg gcaagtgcat gaacaagaag   420
tgcagatgct acagcggagg aagcggagga agctcttata cctacaatta tgaatggcat   480
gtggatgtct ggggacaggg cctgctggtg acagtctcta gtgctagc                528

SEQ ID NO: 841           moltype = DNA   length = 528
FEATURE                  Location/Qualifiers
source                   1..528
                         mol_type = other DNA
                         organism = synthetic construct
SEQUENCE: 841
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag  300
gaaactaaga aataccagag cggaggaagc ggaggaagcg gcatcaacgt gaagtgcagc   360
ctgccccagc agtgcatcaa gccctgcaag gacgccggca tgagattcgg caagtgcatg   420
aacaagaagt gcagatgcta cagcggagga agctcttata cctacaatta tgaatggcat   480
gtggatgtct ggggacaggg cctgctggtg acagtctcta gtgctagc                528

SEQ ID NO: 842           moltype = DNA   length = 555
FEATURE                  Location/Qualifiers
source                   1..555
                         mol_type = other DNA
                         organism = synthetic construct
SEQUENCE: 842
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag  300
gaaactaaga aataccagag cggaggaagc ggaggaagcg gaggaagcgg catcaacgtg   360
aagtgcagcc tgccccagca gtgcatcaag ccctgcaagg acgccggcat gagattcggc   420
aagtgcatga acaagaagtg cagatgctac agcggaggaa gcgggaggaag cggaggaagc   480
tcttatacct acaattatga atggcatgtg gatgtctggg gacagggcct gctggtgaca   540
gtctctagtg ctagc                                                    555

SEQ ID NO: 843           moltype = DNA   length = 516
FEATURE                  Location/Qualifiers
source                   1..516
                         mol_type = other DNA
                         organism = synthetic construct
SEQUENCE: 843
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag  300
gaaactaaga aataccagag cggaggaagc ggcggctatt gccagaagtg gatgtggacc   360
tgcgatagcc aacggaaatg ttgcgaaggc atggtgtgcc gcctgtggtg caagaagaaa   420
ctctggggcg gcgaggaag ctcttatacc tacaattatg aatggcatgt ggatgtctgg    480
ggacagggcc tgctggtgac agtctctagt gctagc                             516

SEQ ID NO: 844           moltype = DNA   length = 525
FEATURE                  Location/Qualifiers
source                   1..525
                         mol_type = other DNA
                         organism = synthetic construct
SEQUENCE: 844
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgtcaccag  300
gaaactaaga aataccagag cggaggaagc ggcggctatt gccagaagtg gatgtggacc   360
tgcgatagcc aacggaaatg ttgcgaaggc atggtgtgcc gcctgtggtg caagaagaaa   420
ctctggggcg gcgaggaag cggaggaagc tcttatacct acaattatga atggcatgtg    480
gatgtctggg gacagggcct gctggtgaca gtctctagtg ctagc                   525

SEQ ID NO: 845           moltype = DNA   length = 525
FEATURE                  Location/Qualifiers
source                   1..525
                         mol_type = other DNA
                         organism = synthetic construct
SEQUENCE: 845
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
```

```
agcgtgagct ccgtcaccac agaggatagt gcaacttact attgcacctc tgtgcaccag    300
gaaactaaga aataccagag cggaggaagc ggaggaagcg gcggctattg ccagaagtgg    360
atgtggacct gcgatagcga acggaaatgt tgcgaaggca tggtgtgccg cctgtggtgc    420
aagaagaaac tctggggcgg cggaggaagc tcttatacct acaattatga atggcatgtg    480
gatgtctggg gacagggcct gctggtgaca gtctctagtg ctagc                    525

SEQ ID NO: 846              moltype = DNA   length = 522
FEATURE                    Location/Qualifiers
source                     1..522
                           mol_type = other DNA
                           organism = synthetic construct
SEQUENCE: 846
caggtccagc tgagagagag cggcccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag cggaggaagc ggaggaagct attgccagaa gtggatgtgg    360
acctgcgata gcgaacgaaa atgttgcgaa ggcatggtgt gccgcctgtg gtgcaagaag    420
aaaactctggg gaggaagcgg aggaagctct tatacctaca attatgaatg gcatgtggat    480
gtctggggac agggcctgct ggtgacagtc tctagtgcta gc                       522

SEQ ID NO: 847              moltype = DNA   length = 540
FEATURE                    Location/Qualifiers
source                     1..540
                           mol_type = other DNA
                           organism = synthetic construct
SEQUENCE: 847
caggtccagc tgagagagag cggcccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag cggaggaagc ggaggaagct attgccagaa gtggatgtgg    360
acctgcgata gcgaacgaaa atgttgcgaa ggcatggtgt gccgcctgtg gtgcaagaag    420
aaaactctggg gaggaagcgg aggaagcgga ggaagcggag gaagctctta tacctacaat    480
tatgaatggc atgtggatgt ctggggacag ggcctgctgg tgacagtctc tagtgctagc    540

SEQ ID NO: 848              moltype = DNA   length = 540
FEATURE                    Location/Qualifiers
source                     1..540
                           mol_type = other DNA
                           organism = synthetic construct
SEQUENCE: 848
caggtccagc tgagagagag cggcccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag cggaggaagc ggaggaagcg gaggaagcgg aggaagctat    360
tgccagaagt ggatgtggac ctgcgatagc gaacgaaat gttgcgaagg catgtggat    420
cgcctgtggt gcaagaagaa actctgggga ggaagcggag gaagctctta tacctacaat    480
tatgaatggc atgtggatgt ctggggacag ggcctgctgg tgacagtctc tagtgctagc    540

SEQ ID NO: 849              moltype = DNA   length = 534
FEATURE                    Location/Qualifiers
source                     1..534
                           mol_type = other DNA
                           organism = synthetic construct
SEQUENCE: 849
caggtccagc tgagagagag cggcccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag cggaggaagc ggaggaagcg gcggctattg ccagaagtgg    360
atgtggacct gcgatagcga acggaaatgt tgcgaaggca tggtgtgccg cctgtggtgc    420
aagaagaaac tctggggcgg cggaggaagc ggaggaagct cttatacctza caattatgaa    480
tggcatgtgg atgtctgggg acagggcctg ctggtgcacag tctctagtgc tagc          534

SEQ ID NO: 850              moltype = DNA   length = 543
FEATURE                    Location/Qualifiers
source                     1..543
                           mol_type = other DNA
                           organism = synthetic construct
SEQUENCE: 850
caggtccagc tgagagagag cggcccttca ctggtcaagc catcccagac actgagcctg    60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
```

```
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggaggaagc ggaggaagcg gcggctattg ccagaagtgg   360
atgtggacct gcgatagcga acggaaatgt tgcgaaggca tggtgtgccg cctgtggtgc   420
aagaagaaac tctggggcgg cggaggaagc ggaggaagcg gaggaagctc ttatacctac   480
aattatgaat ggcatgtgga tgtctgggga cagggcctgc tggtgacagt ctctagtgct   540
agc                                                                  543
```

SEQ ID NO: 851          moltype = DNA  length = 552
FEATURE                 Location/Qualifiers
source                  1..552
                        mol_type = other DNA
                        organism = synthetic construct
SEQUENCE: 851
```
caggtccagc tgagagagag cggcccttca ctggtcaagc catcccagac actgagcctg    60
acatgcacag caagcgggtt ttcactgagc gacaaggcag tgggatgggg ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggaggaagc ggaggaagcg gcggctattg ccagaagtgg   360
atgtggacct gcgatagcga acggaaatgt tgcgaaggca tggtgtgccg cctgtggtgc   420
aagaagaaac tctggggcgg cggaggaagc ggaggaagcg gaggaagctc ttatacctac   480
tatacctaca attatgaatg gcatgtggat gtctggggac agggcctgct ggtgacagtc   540
tctagtgcta gc                                                        552
```

SEQ ID NO: 852          moltype = DNA  length = 543
FEATURE                 Location/Qualifiers
source                  1..543
                        mol_type = other DNA
                        organism = synthetic construct
SEQUENCE: 852
```
caggtccagc tgagagagag cggcccttca ctggtcaagc catcccagac actgagcctg    60
acatgcacag caagcgggtt ttcactgagc gacaaggcag tgggatgggg ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggaggaagc ggaggaagcg gaggaagcgg cggctattgc   360
cagaagtgga tgtggacctg cgatagcgaa cggaaatgtt gcgaaggcat ggtgtgccgc   420
ctgtggtgca agaagaaact ctggggcggc ggaggaagcg gaggaagctc ttatacctac   480
aattatgaat ggcatgtgga tgtctgggga cagggcctgc tggtgacagt ctctagtgct   540
agc                                                                  543
```

SEQ ID NO: 853          moltype = DNA  length = 552
FEATURE                 Location/Qualifiers
source                  1..552
                        mol_type = other DNA
                        organism = synthetic construct
SEQUENCE: 853
```
caggtccagc tgagagagag cggcccttca ctggtcaagc catcccagac actgagcctg    60
acatgcacag caagcgggtt ttcactgagc gacaaggcag tgggatgggg ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggaggaagc ggaggaagcg gaggaagcgg cggctattgc   360
cagaagtgga tgtggacctg cgatagcgaa cggaaatgtt gcgaaggcat ggtgtgccgc   420
ctgtggtgca agaagaaact ctggggcggc ggaggaagcg gaggaagctc ttatacctac   480
tatacctaca attatgaatg gcatgtggat gtctggggac agggcctgct ggtgacagtc   540
tctagtgcta gc                                                        552
```

SEQ ID NO: 854          moltype = DNA  length = 552
FEATURE                 Location/Qualifiers
source                  1..552
                        mol_type = other DNA
                        organism = synthetic construct
SEQUENCE: 854
```
caggtccagc tgagagagag cggcccttca ctggtcaagc catcccagac actgagcctg    60
acatgcacag caagcgggtt ttcactgagc gacaaggcag tgggatgggg ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggaggaagc ggaggaagcg gaggaagcgg aggaagcggc   360
ggctattgcc agaagtggat gtggacctgc gatagcgaac ggaaatgttg cgaaggcatg   420
gtgtgccgct gtggtgcaa gaagaaactc tggggcggcg gaggaagcgg aggaagctct   480
tatacctaca attatgaatg gcatgtggat gtctggggac agggcctgct ggtgacagtc   540
tctagtgcta gc                                                        552
```

SEQ ID NO: 855          moltype = DNA  length = 582
FEATURE                 Location/Qualifiers
source                  1..582

```
                        mol_type = other DNA
                        organism = synthetic construct
SEQUENCE: 855
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag cgggtggaag tggtggcgga   360
ggtagcggag gatactgcca gaagtggatg tggacctgcg acagcgagag gaagtgctgc   420
gagggcatgg tgtgcaggct gtggtgcaag aagaagctgt ggggaggtgg tggatctggt   480
ggaggaggca gtgaggtgg tggcagctct tatacctaca attatgaatg gcatgtggat   540
gtctggggcc aaggaaccct ggtcaccgtc tcctcagcta gc                     582

SEQ ID NO: 856          moltype = DNA   length = 597
FEATURE                 Location/Qualifiers
source                  1..597
                        mol_type = other DNA
                        organism = synthetic construct
SEQUENCE: 856
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag cgggtggaag tggtggcgga   360
ggtagcggag gaaggagctg catcgacacc atccccaaga gccgatgcac cgccttccag   420
tgcaagcaca gcatgaagta caggctgagc ttctgcagga gacctgcgg cacctgcgga   480
ggtggtggat ctggtggagg aggcagtgga ggtggtggca gctcttatac ctacaattat   540
gaatggcatg tggatgtctg gggccaagga accctggtca ccgtctcctc agctagc      597

SEQ ID NO: 857          moltype = DNA   length = 606
FEATURE                 Location/Qualifiers
source                  1..606
                        mol_type = other DNA
                        organism = synthetic construct
SEQUENCE: 857
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag cgggtggaag tggtggcgga   360
ggtagcggag gaggcgtgat catcaacgtg aagtgcaaga tcagcaggca gtgcctgaag   420
ccctgcaagg acgccggcat gaggttcggt aagtgcatga cggcaagtg ccactgcacc   480
cccaagggag gtggtggatc tggtggagga ggcagtggag gtggtggcag ctcttatacc   540
tacaattatg aatggcatgt ggatgtctgg ggccaaggaa ccctggtcac cgtctcctca   600
gctagc                                                              606

SEQ ID NO: 858          moltype = DNA   length = 606
FEATURE                 Location/Qualifiers
source                  1..606
                        mol_type = other DNA
                        organism = synthetic construct
SEQUENCE: 858
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag cgggtggaag tggtggcgga   360
ggtagcggag gaggcgtgat catcaacgtg aaatgcaaga tcagcccca gtgcctgaag   420
ccctgcaagg acgccggcat gaggttcggg aagtgcatga cggcaagtg ccactgcacc   480
cccaagggag gtggtggatc tggtggagga ggcagtggag gtggtggcag ctcttatacc   540
tacaattatg aatggcatgt ggatgtctgg ggccaaggaa ccctggtcac cgtctcctca   600
gctagc                                                              606

SEQ ID NO: 859          moltype = DNA   length = 594
FEATURE                 Location/Qualifiers
source                  1..594
                        mol_type = other DNA
                        organism = synthetic construct
SEQUENCE: 859
caggtccagc tgagagagag cggcccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag cgggtggaag tggtggcgga   360
```

-continued

```
ggtagcggag gagactgcct gggcttcatg aggaagtgca tccccgacaa cgacaagtgc  420
tgcaggccca acctggtgtg cagcaggacc cacaagtggt gcaagtacgt gttcggaggt  480
ggtggatctg gtggaggagg cagtggaggt ggtggcagct cttataccta caattatgaa  540
tggcatgtgg atgtctgggg ccaaggaacc ctggtcaccg tctcctcagc tagc        594

SEQ ID NO: 860          moltype = DNA   length = 486
FEATURE                 Location/Qualifiers
source                  1..486
                        mol_type = other DNA
                        organism = synthetic construct
SEQUENCE: 860
caggtccagc tgagagagag cggcccttca ctggtcaagc catcccagac actgagcctg  60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggtggagga ggttctggag gcggtggaag tggtggcgga  360
ggtagcggag gaggtggatc tggtggagga ggcagtggag gtggtggcag ctcttatacc  420
tacaattatg aatggcatgt ggatgtctgg ggccaaggaa ccctggtcac cgtctcctca  480
gctagc                                                            486

SEQ ID NO: 861          moltype = DNA   length = 459
FEATURE                 Location/Qualifiers
source                  1..459
                        mol_type = other DNA
                        organism = synthetic construct
SEQUENCE: 861
caggtccagc tgagagagag cggcccttca ctggtcaagc catcccagac actgagcctg  60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggtggagga ggttctggag gatgagacct actatggttc  360
agggtctctg gaggtggtgg atcttcttat acctacaatt atgaatggca tgtggatgtc  420
tggggccaag gaaccctggt caccgtctcc tcagctagc                         459

SEQ ID NO: 862          moltype = DNA   length = 582
FEATURE                 Location/Qualifiers
source                  1..582
                        mol_type = other DNA
                        organism = synthetic construct
SEQUENCE: 862
caggtccagc tgagagagag cggcccttca ctggtcaagc catcccagac actgagcctg  60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggtggagga ggttctggag gcggtggaag tggtggcgga  360
ggtagcggag gatactgcca gaagtggatg tggacctgcg acagcgagag gaagtgctgc  420
gagggcatgg tgtgcaggct gtggtgcaag aagaagctgt ggggaggtgg tggatctggt  480
ggaggaggca gtggaggtgg tggcagctct tatacctaca attatgaatg gcatgtggat  540
gtctggggac agggcctggt ggacagtc tctagtgcta gc                       582

SEQ ID NO: 863          moltype = DNA   length = 597
FEATURE                 Location/Qualifiers
source                  1..597
                        mol_type = other DNA
                        organism = synthetic construct
SEQUENCE: 863
caggtccagc tgagagagag cggcccttca ctggtcaagc catcccagac actgagcctg  60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
cccggactga agagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag cggtggagga ggttctggag gcggtggaag tggtggcgga  360
ggtagcggag gaaggagctg catcgacacc atccccaaga gccgatgcac cgccttccag  420
tgcaagcaca gcatgaagta caggctgagc ttctgcagga gacctgcgg cacctgcgga  480
ggtggtggat ctggtggagg aggcagtgga ggtggtggca gctcttatac ctacaattat  540
gaatggcatg tggatgtctg gggacagggc ctgctggtga cagtctctag tgctagc     597

SEQ ID NO: 864          moltype = DNA   length = 606
FEATURE                 Location/Qualifiers
source                  1..606
                        mol_type = other DNA
                        organism = synthetic construct
SEQUENCE: 864
caggtccagc tgagagagag cggcccttca ctggtcaagc catcccagac actgagcctg  60
acatgcacag caagcgggtt ttcactgagc gacaaggcag tgggatgggt ccgacaggca  120
ccaggaaaag ccctggaatg gctgggcagc atcgataccg gcgggaacac agggtacaat  180
```

```
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag gcggtggaag tggtggcgga   360
ggtagcggag gaggcgtgat catcaacgtg aagtgcaaga tcagcaggca gtgcctgaag   420
ccctgcaagg acgccggcat gaggttcggt aagtgcatga agtgcaagtg ccactgcacc   480
cccaagggag gtggtggatc tggtggagga ggcagtggag gtggtggcag ctcttatacc   540
tacaattatg aatggcatgt ggatgtctgg ggacagggcc tgctggtgac agtctctagt   600
gctagc                                                              606
```

SEQ ID NO: 865          moltype = DNA   length = 606
FEATURE                 Location/Qualifiers
source                  1..606
                        mol_type = other DNA
                        organism = synthetic construct
SEQUENCE: 865

```
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag gcggtggaag tggtggcgga   360
ggtagcggag gaggcgtgat catcaacgtg aaatgcaaga tcagccccca gtgcctgaag   420
ccctgcaagg acgccggcat gaggttcggt aagtgcatga acggcaagtg ccactgcacc   480
cccaagggag gtggtggatc tggtggagga ggcagtggag gtggtggcag ctcttatacc   540
tacaattatg aatggcatgt ggatgtctgg ggacagggcc tgctggtgac agtctctagt   600
gctagc                                                              606
```

SEQ ID NO: 866          moltype = DNA   length = 594
FEATURE                 Location/Qualifiers
source                  1..594
                        mol_type = other DNA
                        organism = synthetic construct
SEQUENCE: 866

```
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag gcggtggaag tggtggcgga   360
ggtagcggag gagactgcct gggcttcatg aggaagtgca tccccgacaa cgacaagtgc   420
tgcaggccca acctggtgtg cagcaggacc cacaagtggt gcaagtacgt gttcggaggt   480
ggtggatctg tgtgaggagg cagtggaggt ggtggcagct cttataccta caattatgaa   540
tggcatgtgg atgtctgggg acagggcctg ctggtgacag tctctagtgc tagc          594
```

SEQ ID NO: 867          moltype = DNA   length = 627
FEATURE                 Location/Qualifiers
source                  1..627
                        mol_type = other DNA
                        organism = synthetic construct
SEQUENCE: 867

```
caggtgcagc tacagcagtg gggcgcagga ctgttgaagc cttcggagac gctgtccctc   60
acctgcacag caagcgggtt ttcactgagc gacaaggcag tgggatggat tcgccagccc   120
ccagggaagg ggctggagtg gattgggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cccaaggagt gctaaagaac ttagatgtca gtgcataaag   360
acatactcca aacctttcca ccccaagttc atcaaggagc tgagagtgat tgagagtgga   420
ccacactgcg ccaacacaga gattattgta aagctttctg atgggagaga gctctgcctg   480
gaccccaagg aaaactgggt gcagagggtc gtggagaagt tcttgaagag ggctgagaac   540
tcaggcagcg gttcttatac ctacaattat gaatggcatg tggatgtctg gggacagggc   600
ctgctggtga cagtctctag tgctagc                                       627
```

SEQ ID NO: 868          moltype = DNA   length = 627
FEATURE                 Location/Qualifiers
source                  1..627
                        mol_type = other DNA
                        organism = synthetic construct
SEQUENCE: 868

```
caggtgcagc tacagcagtg gggcgcagga ctgttgaagc cttcggagac gctgtccctc   60
acctgcacag caagcgggtt ttcactgagc gacaaggcag tgggatggat tcgccagccc   120
ccagggaagg ggctggagtg gctgggcagc atcgataccg gcgggaacac agggtacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cccaaggagt gctaaagaac ttagatgtca gtgcataaag   360
acatactcca aacctttcca ccccaagttc atcaaggagc tgagagtgat tgagagtgga   420
ccacactgcg ccaacacaga gattattgta aagctttctg atgggagaga gctctgcctg   480
gaccccaagg aaaactgggt gcagagggtc gtggagaagt tcttgaagag ggctgagaac   540
tcaggcagcg gttcttatac ctacaattat gaatggcatg tggatgtctg gggacagggc   600
ctgctggtga cagtctctag tgctagc                                       627
```

```
SEQ ID NO: 869          moltype = DNA  length = 627
FEATURE                 Location/Qualifiers
source                  1..627
                        mol_type = other DNA
                        organism = synthetic construct
SEQUENCE: 869
caggtgcagc tacagcagtg gggcgcagga ctgttgaagc cttcggagac gctgtccctc   60
acctgcacag caagcgggtt ttcactgagc gacaaggcag tgggatggat tcgccagccc  120
ccagggaagg ggctggagtg gctgggcagc atcgataccg gcgggaacac agggtacaac  180
ccgtccctca agagtcgagt caccatatca gtagacacgt ccaagaacca gttctccctg  240
aagctgagct ctgtgaccgc cgcggacacg gctgtgtatt actgtacctc tgtgcaccag  300
gaaactaaga aataccagag cccaaggagt gctaaagaac ttagatgtca gtgcataaag  360
acatactcca aacctttcca ccccaagttc atcaaggagc tgagagtgat tgagagtgga  420
ccacactgcg ccaacacaga gattattgta aagctttctg atgggagaga gctctgcctg  480
gaccccaagg aaaactgggt gcagagggtc gtggagaagt tcttgaagag ggctgagaac  540
tcaggcagcg gttcttatac ctacaattat gaatggcatg tggatgtctg gggacagggc  600
ctgctggtga cagtctctag tgctagc                                      627

SEQ ID NO: 870          moltype = DNA  length = 627
FEATURE                 Location/Qualifiers
source                  1..627
                        mol_type = other DNA
                        organism = synthetic construct
SEQUENCE: 870
caggtgcagc tacagcagtg gggcgcagga ctgttgaagc cttcggagac gctgtccctc   60
acctgcgctg tctatggtgg gtccttcagt gacaagtact ggagctggat tcgccagccc  120
ccagggaagg ggctggagtg gattgggagc atcaatcata gtggaagcac caactacaac  180
ccgtccctca agagtcgagt caccatatca gtagacacgt ccaagaacca gttctccctg  240
aagctgagct ctgtgaccgc cgcggacacg gctgtgtatt actgtacctc tgtgcaccag  300
gaaactaaga aataccagag cccaaggagt gctaaagaac ttagatgtca gtgcataaag  360
acatactcca aacctttcca ccccaagttc atcaaggagc tgagagtgat tgagagtgga  420
ccacactgcg ccaacacaga gattattgta aagctttctg atgggagaga gctctgcctg  480
gaccccaagg aaaactgggt gcagagggtc gtggagaagt tcttgaagag ggctgagaac  540
tcaggcagcg gttcttatac ctacaattat gaatggcatg tggatgtctg gggacagggc  600
ctgctggtga cagtctctag tgctagc                                      627

SEQ ID NO: 871          moltype = DNA  length = 627
FEATURE                 Location/Qualifiers
source                  1..627
                        mol_type = other DNA
                        organism = synthetic construct
SEQUENCE: 871
caggtgcagc tacagcagtg gggcgcagga ctgttgaagc cttcggagac gctgtccctc   60
acctgcacag caagcgggtt ttcactgagc gacaaggcag tgggatggat tcgccagccc  120
ccagggaagg ggctggagtg gctgggcagc atcgataccg gcgggaacac agggtacaac  180
ccgtccctca agagtcgagt caccatatca gtagacacgt ccaagaacca gttctccctg  240
aagctgagct ctgtgaccgc cgcggacacg gctgtgtatt actgtacctc tgtgcaccag  300
gaaactaaga aataccagag cccaaggagt gctaaagaac ttagatgtca gtgcataaag  360
acatactcca aacctttcca ccccaagttc atcaaggagc tgagagtgat tgagagtgga  420
ccacactgcg ccaacacaga gattattgta aagctttctg atgggagaga gctctgcctg  480
gaccccaagg aaaactgggt gcagagggtc gtggagaagt tcttgaagag ggctgagaac  540
tcaggcagcg gttcttatac ctacaattat gaatggcatg tggatgtctg gggacagggc  600
ctgctggtga cagtctctag tgctagc                                      627

SEQ ID NO: 872          moltype = DNA  length = 513
FEATURE                 Location/Qualifiers
source                  1..513
                        mol_type = other DNA
                        organism = synthetic construct
SEQUENCE: 872
caggtccagc tgagagagag cggcccttca ctggtcaagc catcccagac actgagcctg   60
acatgcacag caagcgggtt ttcactgagc gacaaggcag tgggatgggt ccgacaggca  120
ccaggaaaag ccctggaatg gctgggcagc atcgataccg gcgggaacac agggtacaact  180
cccggactga gagcagact gtccattacc aaggacaact ctaaaagtca ggtgtcactg  240
agcgtgagct ccgtcaccac agaggatagt gcaacttact attgcacctc tgtgcaccag  300
gaaactaaga aataccagag ctgtcctgac ggctatcggg agagatctga ttgcagtaat  360
aggccagctt gtggcacatc cgactgctgt cgcgtgtctc tcttcgggaa ctgcctgact  420
accctgcctg tgtcctactc ttatacctac aattatgaat ggcatgtgga tgtctgggga  480
cagggcctgc tggtgacagt ctctagtgct agc                               513

SEQ ID NO: 873          moltype = DNA  length = 627
FEATURE                 Location/Qualifiers
source                  1..627
                        mol_type = other DNA
                        organism = synthetic construct
SEQUENCE: 873
caggtccagc tgagagagag cggcccttca ctggtcaagc catcccagac actgagcctg   60
acatgcacag caagcgggtt ttcactgagc gacaaggcag tgggatgggt ccgacaggca  120
```

```
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cccaaggagt gctaaagaac ttagatgtca gtgcataaag   360
acatactcca aacctttcca ccccaagttc atcaaggagc tgagagtgat tgagagtgga   420
ccacactgcg ccaacacaga gattattgta aagctttctg atgggagaga gctctgcctg   480
gaccccaagg aaaactgggt gcagagggtc gtggagaagt cttgaagag ggctgagaac   540
tcaggcagcg gttcttatac ctacaattat gaatggcatg tggatgtctg gggacagggc   600
ctgctggtga cagtctctag tgctagc                                      627
```

```
SEQ ID NO: 874           moltype = DNA  length = 654
FEATURE                  Location/Qualifiers
source                   1..654
                         mol_type = other DNA
                         organism = synthetic construct
SEQUENCE: 874
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag gaccaaggag tgctaaagaa   360
cttagatgtc agtgcataaa gacatactcc aaacctttcc accccaagtt catcaaggag   420
ctgagagtga ttgagagtgg accacactgc gccaacacag agattattgt aaagctttct   480
gatgggagag agctctgcct ggaccccaag gaaaactggg tgcagagggt cgtggagaag   540
ttcttgaaga gggctgagaa ctcaggaggt ggtggatctt cttataccta caattatgaa   600
tggcatgtgg atgtctgggg acagggcctg ctggtgacag tctctagtgc tagc          654
```

```
SEQ ID NO: 875           moltype = DNA  length = 714
FEATURE                  Location/Qualifiers
source                   1..714
                         mol_type = other DNA
                         organism = synthetic construct
SEQUENCE: 875
caggtccagc tgagagagag cggcccttca ctggtcaagc catcccagac actgagcctg   60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga agagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggag gcggtggaag tggtggcgga   360
ggtagcggag gaccaaggag tgctaaagaa cttagatgtc agtgcataaa gacatactcc   420
aaacctttcc accccaagtt catcaaggag ctgagagtga ttgagagtgg accacactgc   480
gccaacacag agattattgt aaagctttct gatgggagag agctctgcct ggaccccaag   540
gaaaactggg tgcagagggt cgtggagaag ttcttgaaga gggctgagaa ctcaggaggt   600
ggtggatctg gtgaggagg cagtggaggt ggtggcagct cttataccta caattatgaa   660
tggcatgtgg atgtctgggg acagggcctg ctggtgacag tctctagtgc tagc          714
```

```
SEQ ID NO: 876           moltype = DNA  length = 714
FEATURE                  Location/Qualifiers
source                   1..714
                         mol_type = other DNA
                         organism = synthetic construct
SEQUENCE: 876
caggtgcagc taagagagtg gggcgcagga ctgttgaagc cttcggagac gctgtccctc   60
acctgcgctg tctatggtgg gtccttcagt gacaagtact ggagctggat cgccagccct   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaccaaggag tgctaaagaa cttagatgtc agtgcataaa gacatactcc   420
aaacctttcc accccaagtt catcaaggag ctgagagtga ttgagagtgg accacactgc   480
gccaacacag agattattgt aaagctttct gatgggagag agctctgcct ggaccccaag   540
gaaaactggg tgcagagggt cgtggagaag ttcttgaaga gggctgagaa ctcaggaggt   600
ggtggatctg gtgaggagg cagtggaggt ggtggcagct cttataccta caattatgaa   660
tggcatgtgg atgtctgggg acagggcctg ctggtgacag tctctagtgc tagc          714
```

```
SEQ ID NO: 877           moltype = DNA  length = 597
FEATURE                  Location/Qualifiers
source                   1..597
                         mol_type = other DNA
                         organism = synthetic construct
SEQUENCE: 877
caggtgcagc taagagagtg gggcgcagga ctgttgaagc cttcggagac gctgtccctc   60
acctgcgctg tctatggtgg gtccttcagt gacaagtact ggagctggat cgccagccc    120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaaggagctg catcgacacc atccccaaga gccgatgcac cgcccttccag   420
```

```
tgcaagcaca gcatgaagta caggctgagc ttctgcagga agacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc      597

SEQ ID NO: 878              moltype = DNA   length = 555
FEATURE                    Location/Qualifiers
source                     1..555
                           mol_type = other DNA
                           organism = synthetic construct
SEQUENCE: 878
caggtgcagc taagagagtg gggcgcagga ctgttgaagc cttcggagac gctgtccctc   60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggaggaagc ggaggaagcg gaggaagcgg catcaacgtg   360
aagtgcagcc tgccccagca gtgcatcaag ccctgcaagg acgccggcat gagattcggc   420
aagtgcatga acaagaagtg cagatgctac agcggaggaa gcggaggaag cggaggaagc   480
tcttatacct acaattatga atggcatgtg gatgtctggg gacagggcct gctggtgaca   540
gtctctagtg ctagc                                                     555

SEQ ID NO: 879              moltype = DNA   length = 597
FEATURE                    Location/Qualifiers
source                     1..597
                           mol_type = other DNA
                           organism = synthetic construct
SEQUENCE: 879
caggtgcagc taagagagtg gggcgcagga ctgttgaagc cttcggagac gctgtccctc   60
acctgcacag caagcgggtt ttcactgagc gacaaggcag tgggatggat tcgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggtggagga ggttctggag gcggtggaag tggtggcgga   360
ggtagcggag gaaggagctg catcgacacc atccccaaga gccgatgcac cgccttccag   420
tgcaagcaca gcatgaagta caggctgagc ttctgcagga agacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc      597

SEQ ID NO: 880              moltype = DNA   length = 714
FEATURE                    Location/Qualifiers
source                     1..714
                           mol_type = other DNA
                           organism = synthetic construct
SEQUENCE: 880
caggtgcagc taagagagtg gggcgcagga ctgttgaagc cttcggagac gctgtccctc   60
acctgcacag caagcgggtt ttcactgagc gacaaggcag tgggatggat tcgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggtggagga ggttctggag gcggtggaag tggtggcgga   360
ggtagcggag gaccaaggag tgctaaagaa cttagatgc agtgcataaa gacatactcc   420
aaacctttcc accccaagtt catcaaggag ctgagagtga ttgagagtgg accacactgc   480
gccaacacag agattattgt aaagctttct gatgggagag agctctgcct ggaccccaag   540
gaaaactggg tgcagagggt cgtggagaag ttcttgaaga gggctgagaa ctcaggaggt   600
ggtggatctg gtgaggagg cagtggaggt ggtggcagct cttataccta caattatgaa   660
tggcatgtgg atgtctgggg acagggcctg ctggtgacag tctctagtgc tagc         714

SEQ ID NO: 881              moltype = DNA   length = 555
FEATURE                    Location/Qualifiers
source                     1..555
                           mol_type = other DNA
                           organism = synthetic construct
SEQUENCE: 881
caggtgcagc taagagagtg gggcgcagga ctgttgaagc cttcggagac gctgtccctc   60
acctgcacag caagcgggtt ttcactgagc gacaaggcag tgggatggat tcgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggaggaagc ggaggaagcg gaggaagcgg catcaacgtg   360
aagtgcagcc tgccccagca gtgcatcaag ccctgcaagg acgccggcat gagattcggc   420
aagtgcatga acaagaagtg cagatgctac agcggaggaa gcggaggaag cggaggaagc   480
tcttatacct acaattatga atggcatgtg gatgtctggg gacagggcct gctggtgaca   540
gtctctagtg ctagc                                                     555

SEQ ID NO: 882              moltype = DNA   length = 582
FEATURE                    Location/Qualifiers
source                     1..582
                           mol_type = other DNA
                           organism = synthetic construct
```

```
SEQUENCE: 882
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggtggagga ggttctggag gcggtggaag tggtggcgga   360
ggtagcggag gatactgcca gaagtggatg tggacctgcg acagcgagag gaagtgctgc   420
gagggcatgg tgtgtgcaggct gtggtgcaag aagaagctgt ggggaggtgg tggatctggt   480
ggaggaggca gtggaggtgg tggcagctct tatacctaca attatgaatg gcatgtggat   540
gtctggggac agggcctgct ggtgacagtc tctagtgcta gc                       582

SEQ ID NO: 883        moltype = DNA   length = 594
FEATURE               Location/Qualifiers
source                1..594
                      mol_type = other DNA
                      organism = synthetic construct
SEQUENCE: 883
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggtggagga ggttctggag gcggtggaag tggtggcgga   360
ggtagcggag gagactgcct gggcttcatg aggaagtgca tccccgacaa cgacaagtgc   420
tgcaggccca acctggtgtg cagcaggacc cacaagtggt gcaagtacgt gttcggaggt   480
ggtggatctg gtggaggagg cagtggaggt ggtggcagct cttataccta caattatgaa   540
tggcatgtgg atgtctgggg acagggcctg ctggtgacag tctctagtgc tagc          594

SEQ ID NO: 884        moltype = DNA   length = 423
FEATURE               Location/Qualifiers
source                1..423
                      mol_type = other DNA
                      organism = synthetic construct
SEQUENCE: 884
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggaggaagc ggaggaagcg gaggaagctc ttatacctac   360
aattatgaat ggcatgtgga tgtctgggga cagggcctgc tggtgacagt ctctagtgct   420
agc                                                                   423

SEQ ID NO: 885        moltype = DNA   length = 537
FEATURE               Location/Qualifiers
source                1..537
                      mol_type = other DNA
                      organism = synthetic construct
SEQUENCE: 885
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggtggagga ggttctggag gaaggagctg catcgacacc   360
atccccaaga gccgatgcac cgccttccag tgcaagcaca gcatgaagta caggctgagc   420
ttctgcagga agacctgcgg cacctgcgga ggtggtggat cttcttatac ctacaattat   480
gaatggcatg tggatgtctg gggacagggc ctgctggtga cagtctctag tgctagc       537

SEQ ID NO: 886        moltype = DNA   length = 537
FEATURE               Location/Qualifiers
source                1..537
                      mol_type = other DNA
                      organism = synthetic construct
SEQUENCE: 886
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgtcaccag   300
gaaactaaga aataccagag cggtggagga ggttctggag gaaggagctg catcgacacc   360
atccccaaga gccgatgcac cgccttcaag tgcaagcaca gcatgaagta caggctgagc   420
ttctgcagga agacctgcgg cacctgcgga ggtggtggat cttcttatac ctacaattat   480
gaatggcatg tggatgtctg gggacagggc ctgctggtga cagtctctag tgctagc       537

SEQ ID NO: 887        moltype = DNA   length = 597
FEATURE               Location/Qualifiers
source                1..597
```

```
                        mol_type = other DNA
                        organism = synthetic construct
SEQUENCE: 887
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaaggagctg catcgacacc atccccaaga gccgatgcac cgccttcaag   420
tgcaagcaca gcatgaagta caggctgagc ttctccagga gacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc     597

SEQ ID NO: 888          moltype = DNA  length = 501
FEATURE                 Location/Qualifiers
source                  1..501
                        mol_type = other DNA
                        organism = synthetic construct
SEQUENCE: 888
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag caggagctgc atcgacaca tccccaagag ccgatgacc   360
gccttccagt gcaagcacag catgaagtac aggctgagct tctgcaggaa gacctgcggc   420
acctgctctt atacctacaa ttatgaatgg catgtggatg tctggggaca gggcctgctg   480
gtgacagtct ctagtgctag c                                            501

SEQ ID NO: 889          moltype = DNA  length = 507
FEATURE                 Location/Qualifiers
source                  1..507
                        mol_type = other DNA
                        organism = synthetic construct
SEQUENCE: 889
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggcaggagc tgcatcgaca ccatccccaa gagccgatgc   360
accgccttcc agtgcaagca cagcatgaag tacaggctga gcttctgcag gaagacctgc   420
ggcacctgcg gatcttatac ctacaattat gaatggcatg tggatgtctg gggacagggc   480
ctgctggtga cagtctctag tgctagc                                      507

SEQ ID NO: 890          moltype = DNA  length = 513
FEATURE                 Location/Qualifiers
source                  1..513
                        mol_type = other DNA
                        organism = synthetic construct
SEQUENCE: 890
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggcgggagg agctgcatcg acaccatccc caagagccga   360
tgcaccgcct tccagtgcaa gcacagcatg aagtacaggc tgagcttctg caggaagacc   420
tgcggcacct gcgcgaggctc ttatacctac aattatgaat ggcatgtgga tgtctgggga   480
cagggcctgc tggtgacagt ctctagtgct agc                               513

SEQ ID NO: 891          moltype = DNA  length = 525
FEATURE                 Location/Qualifiers
source                  1..525
                        mol_type = other DNA
                        organism = synthetic construct
SEQUENCE: 891
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggttctgga ggaaggagct gcatcgacac catccccaag   360
agccgatgca ccgccttcca gtgcaagcac agcatgaaga caggctgag cttctgcagg   420
aagacctgcg gcacctgcgg aggtggtgga tcttatacct acaattatga atggcatgtg   480
gatgtctggg gacagggcct gctggtgaca gtctctagtg ctagc                  525

SEQ ID NO: 892          moltype = DNA  length = 525
```

-continued

```
FEATURE              Location/Qualifiers
source               1..525
                     mol_type = other DNA
                     organism = synthetic construct
SEQUENCE: 892
caggtgcagc taagagagtg gggcgcagga ctgttgaagc cttcggagac gctgtccctc   60
acctgcgctg tctatggtgg gtccttcagt gacaagtact ggagctggat tcgccagccc  120
ccagggaagg ggctggagtg gattgggagc atcaatcata gtggaagcac caactacaac  180
ccgtccctca agagtcgagt caccatatca gtagacacgt ccaagaacca gttctcccctc  240
aagctgagct ctgtgaccgc cgcggacacg gctgtgtatt actgtacctc tgtgcaccag  300
gaaactaaga aataccagag cggtggagga ggtaggagct gcatcgacac catccccaag  360
agccgatgca ccgccttcca gtgcaagcac agcatgaagt acaggctgag cttctgcagg  420
aagacctgcg gcacctgcgg aggtggtgga tcttatacct acaattatga atggcatgtg  480
gatgtctggg gacagggcct gctggtgaca gtctctagtg ctagc                  525

SEQ ID NO: 893        moltype = DNA   length = 519
FEATURE              Location/Qualifiers
source               1..519
                     mol_type = other DNA
                     organism = synthetic construct
SEQUENCE: 893
caggtgcagc taagagagtg gggcgcagga ctgttgaagc cttcggagac gctgtccctc   60
acctgcgctg tctatggtgg gtccttcagt gacaagtact ggagctggat tcgccagccc  120
ccagggaagg ggctggagtg gattgggagc atcaatcata gtggaagcac caactacaac  180
ccgtccctca agagtcgagt caccatatca gtagacacgt ccaagaacca gttctcccctg  240
aagctgagct ctgtgaccgc cgcggacacg gctgtgtatt actgtacctc tgtgcaccag  300
gaaactaaga aataccagag cggaggaggt aggagctgca tcgacaccat ccccaagagc  360
cgatgcaccg ccttccagtg caagcacagc atgaagtaca ggctgagctt ctgcaggaag  420
acctgcggca cctgcggtgg tggatcttat acctacaatt atgaatggca tgtggatgtc  480
tggggacagg gcctgctggt gacagtctct agtgctagc                         519

SEQ ID NO: 894        moltype = DNA   length = 597
FEATURE              Location/Qualifiers
source               1..597
                     mol_type = other DNA
                     organism = synthetic construct
SEQUENCE: 894
caggtgcagc taagagagtg gggcgcagga ctgttgaagc cttcggagac gctgtccctc   60
acctgcgctg tctatggtgg gtccttcagt gacaagtact ggagctggat tcgccagccc  120
ccagggaagg ggctggagtg gattgggagc atcaatcata gtggaagcac caactacaac  180
ccgggcctca agagtcgagt caccatatca gtagacacgt ccaagaacca gttctcccctg  240
aagctgagct ctgtgaccgc cgcggacacg gctgtgtatt actgtacctc tgtgcaccag  300
gaaactaaga aataccagag cggtggagga ggttctggag gcggtggaag tggtggcgga  360
ggtagcggag gaaggagctg catcgacacc atccccaaga gccgatgcac cgccttccag  420
tgcaagcaca gcatgaagta caggctgagc ttctgcagga gacctgcggg cacctgcgga  480
ggtggtggat ctggtggagg aggcagtgga ggtggtggca gctcttatac ctacaattat  540
gaatggcatg tggatgtctg gggacagggc ctgctggtga cagtctctag tgctagc     597

SEQ ID NO: 895        moltype = DNA   length = 567
FEATURE              Location/Qualifiers
source               1..567
                     mol_type = other DNA
                     organism = synthetic construct
SEQUENCE: 895
caggtgcagc taagagagtg gggcgcagga ctgttgaagc cttcggagac gctgtccctc   60
acctgcgctg tctatggtgg gtccttcagt gacaagtact ggagctggat tcgccagccc  120
ccagggaagg ggctggagtg gattgggagc atcaatcata gtggaagcac caactacaac  180
ccgtccctca agagtcgagt caccatatca gtagacacgt ccaagaacca gttctcccctg  240
aagctgagct ctgtgaccgc cgcggacacg gctgtgtatt actgtacctc tgtgcaccag  300
gaaactaaga aataccagag cggaggcggt ggaagtggtg gcggaggtag cggaggaagg  360
agctgcatcg acaccatccc caagagccga tgcaccgcct tccagtgcaa gcacagcatg  420
aagtacaggc tgagcttctg caggaagacc tgcggcacct gcggtggagg aggcagtgga  480
ggtggtggca gctcttatac ctacaattat gaatggcatg tggatgtctg gggacagggc  540
ctgctggtga cagtctctag tgctagc                                      567

SEQ ID NO: 896        moltype = DNA   length = 597
FEATURE              Location/Qualifiers
source               1..597
                     mol_type = other DNA
                     organism = synthetic construct
SEQUENCE: 896
caggtgcagc taagagagtg gggcgcagga ctgttgaagc cttcggagac gctgtccctc   60
acctgcgctg tctatggtgg gtccttcagt gacaagtact ggagctggat tcgccagccc  120
ccagggaagg ggctggagtg gattgggagc atcaatcata gtggaagcac caactacaac  180
ccgtccctca agagtcgagt caccatatca gtagacacgt ccaagaacca gttctcccctg  240
aagctgagct ctgtgaccgc cgcggacacg gctgtgtatt actgtacctc tgtgcaccag  300
gaaactaaga aataccagag cggtggagga ggttctggag gcggtggaag tggtggcgga  360
ggtagcggag gaaggagctg catcgacacc atccccaaga gccgatgcac cgccttccag  420
tgcaagcaca gccagaagta caggctgagc ttctgcagga gacctgcggg cacctgcgga  480
```

-continued

```
ggtggtggat ctggtggagg aggcagtgga ggtggtggca gctcttatac ctacaattat   540
gaatggcatg tggatgtctg gggacagggc ctgctggtga cagtctctag tgctagc       597

SEQ ID NO: 897           moltype = DNA  length = 597
FEATURE                  Location/Qualifiers
source                   1..597
                         mol_type = other DNA
                         organism = synthetic construct
SEQUENCE: 897
caggtgcagc taagagagtg gggcgcagga ctgttgaagc cttcggagac gctgtccctc   60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaaggagctg catcgacacc atccccaaga gccgatgcac cgccttccag   420
tgcaagcaca gcctgaagta caggctgagc ttctgcagga agacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc       597

SEQ ID NO: 898           moltype = DNA  length = 597
FEATURE                  Location/Qualifiers
source                   1..597
                         mol_type = other DNA
                         organism = synthetic construct
SEQUENCE: 898
caggtgcagc taagagagtg gggcgcagga ctgttgaagc cttcggagac gctgtccctc   60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaaggagctg catcgacacc atccccaaga gccgatgcac cgccttccag   420
tgcaagcaca gcttcaagta caggctgagc ttctgcagga agacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc       597

SEQ ID NO: 899           moltype = DNA  length = 597
FEATURE                  Location/Qualifiers
source                   1..597
                         mol_type = other DNA
                         organism = synthetic construct
SEQUENCE: 899
caggtgcagc taagagagtg gggcgcagga ctgttgaagc cttcggagac gctgtccctc   60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaaggagctg catcgacacc atccccaaga gccgatgcac cgccttccag   420
tgcaagcaca gcatcaagta caggctgagc ttctgcagga agacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc       597

SEQ ID NO: 900           moltype = DNA  length = 597
FEATURE                  Location/Qualifiers
source                   1..597
                         mol_type = other DNA
                         organism = synthetic construct
SEQUENCE: 900
caggtgcagc taagagagtg gggcgcagga ctgttgaagc cttcggagac gctgtccctc   60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cggtggagga ggttctggag gcggtggaag tggtggcgga   360
ggtagcggag gaaggagctg catcgacacc atccccaaga gccgatgcac cgccttccag   420
tgcaagcaca gcgccaagta caggctgagc ttctgcagga agacctgcgg cacctgcgga   480
ggtggtggat ctggtggagg aggcagtgga ggtggtggca gctcttatac ctacaattat   540
gaatggcatg tggatgtctg gggacagggc ctgctggtga cagtctctag tgctagc       597

SEQ ID NO: 901           moltype = DNA  length = 522
FEATURE                  Location/Qualifiers
source                   1..522
                         mol_type = other DNA
                         organism = synthetic construct
SEQUENCE: 901
caggtgcagc taagagagtg gggcgcagga ctgttgaagc cttcggagac gctgtccctc   60
acctgcgctg tctatggtgg gtccttcagt gacaagtact ggagctggat tcgccagccc   120
```

-continued

```
ccagggaagg ggctggagtg gattgggagc atcaatcata gtggaagcac caactacaac  180
ccgtccctca agagtcgagt caccatatca gtagacacgt ccaagaacca gttctccctg  240
aagctgagct ctgtgaccgc cgcggacacg gctgtgtatt actgtacctc tgtgcaccag  300
gaaactaaga aataccagag cggtggagga ggttctggag atactgcca  gaagtggatg  360
tggacctgcg acagcgagag gaagtgctgc gagggcatgg tgtgcaggct gtggtgcaag  420
aagaagctgt ggggaggtgg tggatcttct tatacctaca attatgaatg gcatgtggat  480
gtctggggac agggcctgct ggtgacagtc tctagtgcta gc  522
```

```
SEQ ID NO: 902          moltype = DNA  length = 534
FEATURE                 Location/Qualifiers
source                  1..534
                        mol_type = other DNA
                        organism = synthetic construct
SEQUENCE: 902
caggtgcagc taagagagtg gggcgcagga ctgttgaagc cttcggagac gctgtccctc  60
acctgcgctg tctatggtgg gtccttcagt gacaagtact ggagctggat tcgccagccc  120
ccagggaagg ggctggagtg gattgggagc atcaatcata gtggaagcac caactacaac  180
ccgtccctca agagtcgagt caccatatca gtagacacgt ccaagaacca gttctccctg  240
aagctgagct ctgtgaccgc cgcggacacg gctgtgtatt actgtacctc tgtgcaccag  300
gaaactaaga aataccagag cggtggagga ggttctggag gagactgcct gggcttcatg  360
aggaagtgca tccccgacaa cgacaagtgc tgcaggccca acctggtgtg cagcaggacc  420
cacaagtggt gcaagtacgt gttcggaggt ggtggatctt cttataccta caattatgaa  480
tggcatgtgg atgtctgggg acagggcctg ctggtgcaca tctctagtgc tagc  534
```

```
SEQ ID NO: 903          moltype = AA  length = 168
FEATURE                 Location/Qualifiers
source                  1..168
                        mol_type = protein
                        organism = synthetic construct
SEQUENCE: 903
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGS YCQKWMWTCD  120
SERKCCEGMV CRLWCKKKLW GGSSYTYNYE WHVDVWGQGL LVTVSSAS  168
```

```
SEQ ID NO: 904          moltype = AA  length = 171
FEATURE                 Location/Qualifiers
source                  1..171
                        mol_type = protein
                        organism = synthetic construct
SEQUENCE: 904
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGS YCQKWMWTCD  120
SERKCCEGMV CRLWCKKKLW GGSGGSSYTY NYEWHVDVWG QGLLVTVSSA S  171
```

```
SEQ ID NO: 905          moltype = AA  length = 171
FEATURE                 Location/Qualifiers
source                  1..171
                        mol_type = protein
                        organism = synthetic construct
SEQUENCE: 905
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGS GGSYCQKWMW  120
TCDSERKCCE GMVCRLWCKK KLWGGSSYTY NYEWHVDVWG QGLLVTVSSA S  171
```

```
SEQ ID NO: 906          moltype = AA  length = 172
FEATURE                 Location/Qualifiers
source                  1..172
                        mol_type = protein
                        organism = synthetic construct
SEQUENCE: 906
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGS GGYCQKWMWT  120
CDSERKCCEG MVCRLWCKKK LWGGGGSSYT NYEWHVDVW GQGLLVTVSS AS  172
```

```
SEQ ID NO: 907          moltype = AA  length = 175
FEATURE                 Location/Qualifiers
source                  1..175
                        mol_type = protein
                        organism = synthetic construct
SEQUENCE: 907
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGS GGYCQKWMWT  120
CDSERKCCEG MVCRLWCKKK LWGGGGSGGS SYTYNYEWHV DVWGQGLLVT VSSAS  175
```

```
SEQ ID NO: 908          moltype = AA  length = 175
FEATURE                 Location/Qualifiers
source                  1..175
                        mol_type = protein
                        organism = synthetic construct
```

-continued

```
SEQUENCE: 908
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSGGYCQKW   120
MWTCDSERKC CEGMVCRLWC KKKLWGGGGS SYTYNYEWHV DVWGQGLLVT VSSAS        175

SEQ ID NO: 909           moltype = AA  length = 174
FEATURE                  Location/Qualifiers
source                   1..174
                         mol_type = protein
                         organism = synthetic construct
SEQUENCE: 909
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSYCQKWMW   120
TCDSERKCCE GMVCRLWCKK KLWGGSGGSS YTYNYEWHVD VWGQGLLVTV SSAS         174

SEQ ID NO: 910           moltype = AA  length = 180
FEATURE                  Location/Qualifiers
source                   1..180
                         mol_type = protein
                         organism = synthetic construct
SEQUENCE: 910
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSYCQKWMW   120
TCDSERKCCE GMVCRLWCKK KLWGGSGGSG GSGGSSYTYN YEWHVDVWGQ GLLVTVSSAS   180

SEQ ID NO: 911           moltype = AA  length = 180
FEATURE                  Location/Qualifiers
source                   1..180
                         mol_type = protein
                         organism = synthetic construct
SEQUENCE: 911
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSGGSGGSY   120
CQKWMWTCDS ERKCCEGMVC RLWCKKKLWG GSGGSSYTYN YEWHVDVWGQ GLLVTVSSAS   180

SEQ ID NO: 912           moltype = AA  length = 178
FEATURE                  Location/Qualifiers
source                   1..178
                         mol_type = protein
                         organism = synthetic construct
SEQUENCE: 912
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSGGYCQKW   120
MWTCDSERKC CEGMVCRLWC KKKLWGGGGS GGSSYTYNYE WHVDVWGQGL LVTVSSAS     178

SEQ ID NO: 913           moltype = AA  length = 181
FEATURE                  Location/Qualifiers
source                   1..181
                         mol_type = protein
                         organism = synthetic construct
SEQUENCE: 913
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSGGYCQKW   120
MWTCDSERKC CEGMVCRLWC KKKLWGGGGS GGSGGSSYTY NYEWHVDVWG QGLLVTVSSA   180
S                                                                   181

SEQ ID NO: 914           moltype = AA  length = 184
FEATURE                  Location/Qualifiers
source                   1..184
                         mol_type = protein
                         organism = synthetic construct
SEQUENCE: 914
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSGGYCQKW   120
MWTCDSERKC CEGMVCRLWC KKKLWGGGGS GGSGGSGGSS YTYNYEWHVD VWGQGLLVTV   180
SSAS                                                                184

SEQ ID NO: 915           moltype = AA  length = 181
FEATURE                  Location/Qualifiers
source                   1..181
                         mol_type = protein
                         organism = synthetic construct
SEQUENCE: 915
QVQLRESGPS LVKPSQTLSL TCTASGFSLS DKAVGWVRQA PGKALEWLGS IDTGGNTGYN    60
PGLKSRLSIT KDNSKSQVSL SVSSVTTEDS ATYYCTSVHQ ETKKYQSGGS GGSGGSGGYC   120
QKWMWTCDSE RKCCEGMVCR LWCKKKLWGG GGSGGSSYTY NYEWHVDVWG QGLLVTVSSA   180
S                                                                   181

SEQ ID NO: 916           moltype = AA  length = 184
```

-continued

```
FEATURE                Location/Qualifiers
source                 1..184
                       mol_type = protein
                       organism = synthetic construct
SEQUENCE: 916
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGS GGSGGSGGYC     120
QKWMWTCDSE RKCCEGMVCR LWCKKKLWGG GGSGGSGGSS YTYNYEWHVD VWGQGLLVTV     180
SSAS                                                                  184

SEQ ID NO: 917         moltype = AA  length = 184
FEATURE                Location/Qualifiers
source                 1..184
                       mol_type = protein
                       organism = synthetic construct
SEQUENCE: 917
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGS GGSGGSGGSG     120
GYCQKWMWTC DSERKCCEGM VCRLWCKKKL WGGGGSGGSS YTYNYEWHVD VWGQGLLVTV     180
SSAS                                                                  184

SEQ ID NO: 918         moltype = AA  length = 194
FEATURE                Location/Qualifiers
source                 1..194
                       mol_type = protein
                       organism = synthetic construct
SEQUENCE: 918
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGG GSGGGGSGGG     120
GSGGYCQKWM WTCDSERKCC EGMVCRLWCK KKLWGGGGSG GGGSGGGGSS YTYNYEWHVD     180
VWGQGTLVTV SSAS                                                      194

SEQ ID NO: 919         moltype = AA  length = 199
FEATURE                Location/Qualifiers
source                 1..199
                       mol_type = protein
                       organism = synthetic construct
SEQUENCE: 919
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGG GSGGGGSGGG     120
GSGGRSCIDT IPKSRCTAFQ CKHSMKYRLS FCRKTCGTCG GGGSGGGGSG GGGSSYTYNY     180
EWHVDVWGQG TLVTVSSAS                                                 199

SEQ ID NO: 920         moltype = AA  length = 202
FEATURE                Location/Qualifiers
source                 1..202
                       mol_type = protein
                       organism = synthetic construct
SEQUENCE: 920
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGG GSGGGGSGGG     120
GSGGGVIINV KCKISRQCLK PCKDAGMRFG KCMNGKCHCT PKGGGGSGGG GSGGGGSSYT     180
YNYEWHVDVW GQGTLVTVSS AS                                             202

SEQ ID NO: 921         moltype = AA  length = 202
FEATURE                Location/Qualifiers
source                 1..202
                       mol_type = protein
                       organism = synthetic construct
SEQUENCE: 921
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGG GSGGGGSGGG     120
GSGGGVIINV KCKISPQCLK PCKDAGMRFG KCMNGKCHCT PKGGGGSGGG GSGGGGSSYT     180
YNYEWHVDVW GQGTLVTVSS AS                                             202

SEQ ID NO: 922         moltype = AA  length = 198
FEATURE                Location/Qualifiers
source                 1..198
                       mol_type = protein
                       organism = synthetic construct
SEQUENCE: 922
QVQLRESGPS LVKPSQTLSL TCTASGFSLS DKAVGWVRQA PGKALEWLGS IDTGGNTGYN      60
PGLKSRLSIT KDNSKSQVSL SVSSVTTEDS ATYYCTSVHQ ETKKYQSGGG GSGGGGSGGG     120
GSGGDCLGFM RKCIPDNDKC CRPNLVCSRT HKWCKYVFGG GGSGGGGSGG GGSSYTYNYE     180
WHVDVWGQGT LVTVSSAS                                                  198

SEQ ID NO: 923         moltype = AA  length = 162
FEATURE                Location/Qualifiers
source                 1..162
```

```
                              mol_type = protein
                              organism = synthetic construct
SEQUENCE: 923
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGG GSGGGGSGGG  120
GSGGGGSGGG GSGGGGSSYT YNYEWHVDVW GQGTLVTVSS AS                      162

SEQ ID NO: 924          moltype = AA  length = 152
FEATURE                 Location/Qualifiers
source                  1..152
                        mol_type = protein
                        organism = synthetic construct
SEQUENCE: 924
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGG GSGGDLLWFR  120
VSGGGGSSYT YNYEWHVDVW GQGTLVTVSS AS                                 152

SEQ ID NO: 925          moltype = AA  length = 171
FEATURE                 Location/Qualifiers
source                  1..171
                        mol_type = protein
                        organism = synthetic construct
SEQUENCE: 925
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSCPD GYRERSDCSN  120
RPACGTSDCC RVSVFGNCLT TLPVSYSYTY NYEWHVDVWQ QGLLVTVSSA S            171

SEQ ID NO: 926          moltype = AA  length = 209
FEATURE                 Location/Qualifiers
source                  1..209
                        mol_type = protein
                        organism = synthetic construct
SEQUENCE: 926
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSPRS AKELRCQCIK  120
TYSKPFHPKF IKELRVIESG PHCANTEIIV KLSDGRELCL DPKENWVQRV VEKFLKRAEN  180
SGSGSYTYNY EWHVDVWGQG LLVTVSSAS                                     209

SEQ ID NO: 927          moltype = AA  length = 218
FEATURE                 Location/Qualifiers
source                  1..218
                        mol_type = protein
                        organism = synthetic construct
SEQUENCE: 927
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGG GSGGPRSAKE  120
LRCQCIKTYS KPFHPKFIKE LRVIESGPHC ANTEIIVKLS DGRELCLDPK ENWVQRVVEK  180
FLKRAENSGG GGSSYTYNYE WHVDVWGQGL LVTVSSAS                           218

SEQ ID NO: 928          moltype = AA  length = 238
FEATURE                 Location/Qualifiers
source                  1..238
                        mol_type = protein
                        organism = synthetic construct
SEQUENCE: 928
QVQLRESGPS LVKPSQTLSL TCTASGFSLS DKAVGWVRQA PGKALEWLGS IDTGGNTGYN  60
PGLKSRLSIT KDNSKSQVSL SVSSVTTEDS ATYYCTSVHQ ETKKYQSGGG GSGGGGSGGG  120
GSGGPRSAKE LRCQCIKTYS KPFHPKFIKE LRVIESGPHC ANTEIIVKLS DGRELCLDPK  180
ENWVQRVVEK FLKRAENSGG GGSGGGGSGG GGSSYTYNYE WHVDVWGQGL LVTVSSAS     238

SEQ ID NO: 929          moltype = AA  length = 238
FEATURE                 Location/Qualifiers
source                  1..238
                        mol_type = protein
                        organism = synthetic construct
SEQUENCE: 929
QVQLREWGAG LLKPSETLSL TCAVYGGSFS DKYWSWIRQP PGKGLEWIGS INHSGSTNYN  60
PSLKSRVTIS VDTSKNQFSL KLSSVTAADT AVYYCTSVHQ ETKKYQSGGG GSGGGGSGGG  120
GSGGPRSAKE LRCQCIKTYS KPFHPKFIKE LRVIESGPHC ANTEIIVKLS DGRELCLDPK  180
ENWVQRVVEK FLKRAENSGG GGSGGGGSGG GGSSYTYNYE WHVDVWGQGL LVTVSSAS     238

SEQ ID NO: 930          moltype = AA  length = 199
FEATURE                 Location/Qualifiers
source                  1..199
                        mol_type = protein
                        organism = synthetic construct
SEQUENCE: 930
QVQLREWGAG LLKPSETLSL TCAVYGGSFS DKYWSWIRQP PGKGLEWIGS INHSGSTNYN  60
PSLKSRVTIS VDTSKNQFSL KLSSVTAADT AVYYCTSVHQ ETKKYQSGGG GSGGGGSGGG  120
```

-continued

```
GSGGRSCIDT IPKSRCTAFQ CKHSMKYRLS FCRKTCGTCG GGGSGGGGSG GGGSSYTYNY    180
EWHVDVWGQG LLVTVSSAS                                                  199

SEQ ID NO: 931           moltype = AA  length = 185
FEATURE                  Location/Qualifiers
source                   1..185
                         mol_type = protein
                         organism = synthetic construct
SEQUENCE: 931
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGS GGSGGSGINV    120
KCSLPQQCIK PCKDAGMRFG KCMNKKCRCY SGGSGGSGGS SYTYNYEWHV DVWGQGLLVT    180
VSSAS                                                                185

SEQ ID NO: 932           moltype = AA  length = 199
FEATURE                  Location/Qualifiers
source                   1..199
                         mol_type = protein
                         organism = synthetic construct
SEQUENCE: 932
QVQLREWGAG LLKPSETLSL TCTASGFSLS DKAVGWIRQP PGKGLEWIGE INHSGSTNYN    60
PSLKSRVTIS VDTSKNQFSL KLSSVTAADT AVYYCTSVHQ ETKKYQSGGG GSGGGGSGGG    120
GSGGRSCIDT IPKSRCTAFQ CKHSMKYRLS FCRKTCGTCG GGGSGGGGSG GGGSSYTYNY    180
EWHVDVWGQG LLVTVSSAS                                                  199

SEQ ID NO: 933           moltype = AA  length = 238
FEATURE                  Location/Qualifiers
source                   1..238
                         mol_type = protein
                         organism = synthetic construct
SEQUENCE: 933
QVQLREWGAG LLKPSETLSL TCTASGFSLS DKAVGWIRQP PGKGLEWIGE INHSGSTNYN    60
PSLKSRVTIS VDTSKNQFSL KLSSVTAADT AVYYCTSVHQ ETKKYQSGGG GSGGGGSGGG    120
GSGGGPRSAKE LRCQCIKTYS KPFHPKFIKE LRVIESGPHC ANTEIIVKLS DGRELCLDPK    180
ENWVQRVVEK FLKRAENSGG GGSGGGGSGG GGSSYTYNYE WHVDVWGQGL LVTVSSAS      238

SEQ ID NO: 934           moltype = AA  length = 185
FEATURE                  Location/Qualifiers
source                   1..185
                         mol_type = protein
                         organism = synthetic construct
SEQUENCE: 934
QVQLREWGAG LLKPSETLSL TCTASGFSLS DKAVGWIRQP PGKGLEWIGE INHSGSTNYN    60
PSLKSRVTIS VDTSKNQFSL KLSSVTAADT AVYYCTSVHQ ETKKYQSGGS GGSGGSGINV    120
KCSLPQQCIK PCKDAGMRFG KCMNKKCRCY SGGSGGSGGS SYTYNYEWHV DVWGQGLLVT    180
VSSAS                                                                185

SEQ ID NO: 935           moltype = AA  length = 194
FEATURE                  Location/Qualifiers
source                   1..194
                         mol_type = protein
                         organism = synthetic construct
SEQUENCE: 935
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGG GSGGGGSGGG    120
GSGGGYCQKWM WTCDSERKCC EGMVCRLWCK KKLWGGGSGG GGGSGGGGSS YTYNYEWHVD    180
VWGQGLLVTV SSAS                                                      194

SEQ ID NO: 936           moltype = AA  length = 198
FEATURE                  Location/Qualifiers
source                   1..198
                         mol_type = protein
                         organism = synthetic construct
SEQUENCE: 936
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGS GGSGGGGSGGG    120
GSGGDCLGFM RKCIPDNDKC CRPNLVCSRT HKWCKYVFGG GGSGGGGSGG GGSSYTYNYE    180
WHVDVWGQGL LVTVSSAS                                                  198

SEQ ID NO: 937           moltype = AA  length = 141
FEATURE                  Location/Qualifiers
source                   1..141
                         mol_type = protein
                         organism = synthetic construct
SEQUENCE: 937
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGS GGSGGSSYTY    120
NYEWHVDVWG QGLLVTVSSA S                                              141
```

-continued

```
SEQ ID NO: 938                moltype = AA   length = 179
FEATURE                       Location/Qualifiers
source                        1..179
                              mol_type = protein
                              organism = synthetic construct
SEQUENCE: 938
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGRSCIDT  120
IPKSRCTAFQ CKHSMKYRLS FCRKTCGTCG GGGSSYTYNY EWHVDVWGQG LLVTVSSAS   179

SEQ ID NO: 939                moltype = AA   length = 179
FEATURE                       Location/Qualifiers
source                        1..179
                              mol_type = protein
                              organism = synthetic construct
SEQUENCE: 939
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGRSCIDT  120
IPKSRCTAFK CKHSMKYRLS FCRKTCGTCG GGGSSYTYNY EWHVDVWGQG LLVTVSSAS   179

SEQ ID NO: 940                moltype = AA   length = 199
FEATURE                       Location/Qualifiers
source                        1..199
                              mol_type = protein
                              organism = synthetic construct
SEQUENCE: 940
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGSG GSGGGGSGGG  120
GSGGRSCIDT IPKSRCTAFK CKHSMKYRLS FCRKTCGTCG GGGSGGGGSG GGGSSYTYNY  180
EWHVDVWGQG LLVTVSSAS                                               199

SEQ ID NO: 941                moltype = AA   length = 167
FEATURE                       Location/Qualifiers
source                        1..167
                              mol_type = protein
                              organism = synthetic construct
SEQUENCE: 941
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSRSC IDTIPKSRCT  120
AFQCKHSMKY RLSFCRKTCG TCSYTYNYEW HVDVWGQGLL VTVSSAS                167

SEQ ID NO: 942                moltype = AA   length = 169
FEATURE                       Location/Qualifiers
source                        1..169
                              mol_type = protein
                              organism = synthetic construct
SEQUENCE: 942
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGRS CIDTIPKSRC  120
TAFQCKHSMK YRLSFCRKTC GTCGSYTYNY EWHVDVWGQG LLVTVSSAS              169

SEQ ID NO: 943                moltype = AA   length = 171
FEATURE                       Location/Qualifiers
source                        1..171
                              mol_type = protein
                              organism = synthetic construct
SEQUENCE: 943
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGR SCIDTIPKSR  120
CTAFQCKHSM KYRLSFCRKT CGTCGGSTY NYEWHVDVWG QGLLVTVSSA S           171

SEQ ID NO: 944                moltype = AA   length = 175
FEATURE                       Location/Qualifiers
source                        1..175
                              mol_type = protein
                              organism = synthetic construct
SEQUENCE: 944
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGSG GRSCIDTIPK  120
SRCTAFQCKH SMKYRLSFCR KTCGTCGGGG SYTYNYEWHV DVWGQGLLVT VSSAS        175

SEQ ID NO: 945                moltype = AA   length = 175
FEATURE                       Location/Qualifiers
source                        1..175
                              mol_type = protein
                              organism = synthetic construct
SEQUENCE: 945
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GRSCIDTIPK  120
```

```
SRCTAFQCKH SMKYRLSFCR KTCGTCGGGG SYTYNYEWHV DVWGQGLLVT VSSAS          175

SEQ ID NO: 946          moltype = AA   length = 173
FEATURE                 Location/Qualifiers
source                  1..173
                        mol_type = protein
                        organism = synthetic construct
SEQUENCE: 946
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG RSCIDTIPKS  120
RCTAFQCKHS MKYRLSFCRK TCGTCGGGSY TYNYEWHVDV WGQGLLVTVS SAS          173

SEQ ID NO: 947          moltype = AA   length = 199
FEATURE                 Location/Qualifiers
source                  1..199
                        mol_type = protein
                        organism = synthetic construct
SEQUENCE: 947
QVQLREWGAG LLKPSETLSL TCAVYGGSFS DKYWSWIRQP PGKGLEWIGS INHSGSTNYN   60
PGLKSRVTIS VDTSKNQFSL KLSSVTAADT AVYYCTSVHQ ETKKYQSGGG GSGGGGSGGG  120
GSGGRSCIDT IPKSRCTAFQ CKHSMKYRLS FCRKTCGTCG GGGSGGGGSG GGGSSYTYNY  180
EWHVDVWGQG LLVTVSSAS                                                199

SEQ ID NO: 948          moltype = AA   length = 189
FEATURE                 Location/Qualifiers
source                  1..189
                        mol_type = protein
                        organism = synthetic construct
SEQUENCE: 948
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGGGSGGR  120
SCIDTIPKSR CTAFQCKHSM KYRLSFCRKT CGTCGGGSG GGGSSYTYNY EWHVDVWGQG   180
LLVTVSSAS                                                          189

SEQ ID NO: 949          moltype = AA   length = 199
FEATURE                 Location/Qualifiers
source                  1..199
                        mol_type = protein
                        organism = synthetic construct
SEQUENCE: 949
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGGGSGGG  120
GSGGRSCIDT IPKSRCTAFQ CKHSQKYRLS FCRKTCGTCG GGGSGGGGSG GGGSSYTYNY  180
EWHVDVWGQG LLVTVSSAS                                                199

SEQ ID NO: 950          moltype = AA   length = 199
FEATURE                 Location/Qualifiers
source                  1..199
                        mol_type = protein
                        organism = synthetic construct
SEQUENCE: 950
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGGGSGGG  120
GSGGRSCIDT IPKSRCTAFQ CKHSLKYRLS FCRKTCGTCG GGGSGGGGSG GGGSSYTYNY  180
EWHVDVWGQG LLVTVSSAS                                                199

SEQ ID NO: 951          moltype = AA   length = 199
FEATURE                 Location/Qualifiers
source                  1..199
                        mol_type = protein
                        organism = synthetic construct
SEQUENCE: 951
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGGGSGGG  120
GSGGRSCIDT IPKSRCTAFQ CKHSFKYRLS FCRKTCGTCG GGGSGGGGSG GGGSSYTYNY  180
EWHVDVWGQG LLVTVSSAS                                                199

SEQ ID NO: 952          moltype = AA   length = 199
FEATURE                 Location/Qualifiers
source                  1..199
                        mol_type = protein
                        organism = synthetic construct
SEQUENCE: 952
QVQLREWGAG LLKPSETLSL TCAVYGGSFS DKYWSWIRQP PGKGLEWIGS INHSGSTNYN   60
PSLKSRVTIS VDTSKNQFSL KLSSVTAADT AVYYCTSVHQ ETKKYQSGGG GSGGGGSGGG  120
GSGGRSCIDT IPKSRCTAFQ CKHSIKYRLS FCRKTCGTCG GGGSGGGGSG GGGSSYTYNY  180
EWHVDVWGQG LLVTVSSAS                                                199

SEQ ID NO: 953          moltype = AA   length = 199
```

```
FEATURE              Location/Qualifiers
source               1..199
                     mol_type = protein
                     organism = synthetic construct
SEQUENCE: 953
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGG GSGGGGSGGG   120
GSGGRSCIDT IPKSRCTAFQ CKHSAKYRLS FCRKTCGTCG GGGSGGGGSG GGGSSYTYNY   180
EWHVDVWGQG LLVTVSSAS                                                 199

SEQ ID NO: 954       moltype = AA  length = 174
FEATURE              Location/Qualifiers
source               1..174
                     mol_type = protein
                     organism = synthetic construct
SEQUENCE: 954
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGG GSGGGYCQKWM   120
WTCDSERKCC EGMVCRLWCK KKLWGGGGSS YTYNYEWHVD VWGQGLLVTV SSAS          174

SEQ ID NO: 955       moltype = AA  length = 178
FEATURE              Location/Qualifiers
source               1..178
                     mol_type = protein
                     organism = synthetic construct
SEQUENCE: 955
QVQLREWGAG LLKPSETLSL TCAVYGGSFS DKYWSWIRQP PGKGLEWIGS INHSGSTNYN    60
PSLKSRVTIS VDTSKNQFSL KLSSVTAADT AVYYCTSVHQ ETKKYQSGGG GSGGDCLGFM   120
RKCIPDNDKC CRPNLVCSRT HKWCKYVFGG GGSSYTYNYE WHVDVWGQGL LVTVSSAS     178

SEQ ID NO: 956       moltype = AA  length = 110
FEATURE              Location/Qualifiers
source               1..110
                     mol_type = protein
                     organism = synthetic construct
SEQUENCE: 956
QAVLNQPSSV SGSLGQRVSI TCSGSSSNVG NGYVSWYQLI PGSAPRTLIY GDTSRASGVP    60
DRFSGSRSGN TATLTISSLQ AEDEADYFCA SAEDSSSNAV FGSGTTLTVL              110

SEQ ID NO: 957       moltype = DNA  length = 420
FEATURE              Location/Qualifiers
source               1..420
                     mol_type = other DNA
                     organism = synthetic construct
SEQUENCE: 957
caggtgcagc taagagagtg gggcgcagga ctgttgaagc cttcggagac gctgtccctc    60
acctgcgctg tctatggtgg gtccttcagt gacaagtact ggagctggat tcgccagccc   120
ccagggaagg ggctggagtg gattgggagc atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtacctc tgtgcaccag   300
gaaactaaga aataccagag cgagacctac tatggttcgg gtctctctta tacctacaat   360
tatgaatggc atgtggatgt ctggggacag ggcctgctgg tgacagtctc tagtgctagc   420

SEQ ID NO: 958       moltype = DNA  length = 519
FEATURE              Location/Qualifiers
source               1..519
                     mol_type = other DNA
                     organism = synthetic construct
SEQUENCE: 958
caggtccagc tgagagagag cggccccttca ctggtcaagc catcccagac actgagcctg    60
acatgcacag caagcgggtt ttcactgagc gacaaggcag tgggatgggt ccgacaggca   120
ccaggaaaag ccctggaatg gctgggcagc atcgataccg gcgggaacac agggtacaat   180
cccggactga gagcagact gtccattacc aaggacaact ctaaaagtca ggtgtcactg   240
agcgtgagct ccgtcaccac agaggatagt gcaacttact attgcacctc tgtgcaccag   300
gaaactaaga aataccagag cggtggagga ggttctggaa ggtggcggga tggtggcgga   360
ggtagcggag gatgagacct actatggttc agggtctctg gaggtggtgg atctggtgga   420
ggaggcagtg gaggtggtgg cagctcttat acctacaatt atgaatggca tgtggatgtc   480
tggggccaag gaaccctggt caccgtctcc tcagctagc                          519

SEQ ID NO: 959       moltype = AA  length = 110
FEATURE              Location/Qualifiers
source               1..110
                     mol_type = protein
                     organism = synthetic construct
SEQUENCE: 959
QAVLNQPSSV SGSLGQKVTI SCSGSSSNIG NNYVSWYQQL PGTAPRTLIY GDTKRPSGIP    60
DRFSGSKSGT SATLGITGLQ TGDEADYYCA SAEDSSSNAV FGSGTTLTVL              110
```

HUMANIZED ANTIBODIES WITH ULTRALONG COMPLEMENTARY DETERMINING REGIONS

CROSS REFERENCE

This application is a continuation of U.S. application Ser. No. 16/831,508, filed Mar. 26, 2020, which is a continuation of U.S. application Ser. No. 14/905,765, filed Jan. 15, 2016, which is a U. S. National Stage Application under 35 U.S.C. § 371 of International Patent Application No. PCT/US2014/047315, filed Jul. 18, 2014, which claims the benefit of priority of U.S. Provisional Application Ser. No. 61/856,010, filed Jul. 18, 2013, the entire contents of which are each incorporated here by reference.

FIELD

The present disclosure relates to humanized antibodies, including antibodies comprising an ultralong CDR3.

INCORPORATION BY REFERENCE OF SEQUENCE LISTING

The instant application contains a Sequence Listing XML, "TAUR-003CON2 SequenceListing" created on Nov. 7, 2022 and having a size of 1,171 kilobytes. The contents of the Sequence Listing XML are incorporated by reference herein in their entirety.

BACKGROUND

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Some bovine antibodies have unusually long VH CDR3 sequences compared to other vertebrates. For example, about 10% of IgM contains "ultralong" CDR3 sequences, which can be up to 61 amino acids long. These unusual CDR3s often have multiple cysteines. Functional VH genes form through a process called V(D)J recombination, wherein the D-region encodes a significant proportion of CDR3. A unique D-region encoding an ultralong sequence has been identified in cattle. Ultralong CDR3s are partially encoded in the cattle genome, and provide a unique characteristic of their antibody repertoire in comparison to humans. Kaushik et al. (U.S. Pat. Nos. 6,740,747 and 7,196,185) disclose several bovine germline D-gene sequences unique to cattle stated to be useful as probes and a bovine VDJ cassette stated to be useful as a vaccine vector.

SUMMARY

The present disclosure provides humanized antibodies, including antibodies comprising an ultralong CDR3, methods of making same, and uses thereof.

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3.

In some embodiments, the humanized antibody or binding fragment thereof comprises one or more human variable region framework sequences.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75),

3

$CX_{10}CX_3CX_3CX_5CX_7CXCX_6C$ (SEQ ID NO: 76),
$CX_{10}CX_4CX_5CX_{12}CX_2C$ (SEQ ID NO: 77),
$CX_{12}CX_4CX_5CXCXCX_9CX_3C$ (SEQ ID NO: 78),
$CX_{12}CX_4CX_5CX_{12}CX_2C$ (SEQ ID NO: 79),
$CX_{10}CX_6CX_5CXCX_{11}C$ (SEQ ID NO: 80),
$CX_{16}CX_5CXCXCX_{14}C$ (SEQ ID NO: 81),
$CX_{10}CX_5CXCX_8CX_6C$ (SEQ ID NO: 82),
$CX_{12}CX_4CX_5CX_8CX_2C$ (SEQ ID NO: 83),
$CX_{12}CX_5CX_5CXCX_8C$ (SEQ ID NO: 84),
$CX_{10}CX_6CX_5CXCX_4CXCX_9C$ (SEQ ID NO: 85),
$CX_{11}CX_4CX_5CX_8CX_2C$ (SEQ ID NO: 86),
$CX_{10}CX_6CX_5CX_8CX_2C$ (SEQ ID NO: 87),
$CX_{10}CX_6CX_5CXCX_8C$ (SEQ ID NO: 88),
$CX_{10}CX_6CX_5CXCX_3CX_8CX_2C$ (SEQ ID NO: 89),
$CX_{10}CX_6CX_5CX_3CX_8C$ (SEQ ID NO: 90),
$CX_{10}CX_6CX_5CXCX_2CX_6CX_5C$ (SEQ ID NO: 91),
$CX_7CX_6CX_3CX_3CX_9C$ (SEQ ID NO: 92),
$CX_9CX_8CX_5CX_6CX_5C$ (SEQ ID NO: 93),
$CX_{10}CX_2CX_2CX_7CXCX_{11}CX_5C$ (SEQ ID NO: 94), and
$CX_{10}CX_6CX_5CXCX_2CX_8CX_4C$ (SEQ ID NO: 95).

In some embodiments of each or any of the above or below mentioned embodiments, the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CCX_4C$ (SEQ ID NO: 139),

4

$CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_5CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

In some embodiments of each or any of the above or below mentioned embodiments, the ultralong CDR3 comprises 2 to 6 disulfide bonds.

In some embodiments of each or any of the above or below mentioned embodiments, the ultralong CDR3 comprises SEQ ID NO: 40 or a derivative thereof.

In some embodiments of each or any of the above or below mentioned embodiments, the ultralong CDR3 comprises amino acid residues 3-6 of any of one SEQ ID NO: 1-4.

In some embodiments of each or any of the above or below mentioned embodiments, the ultralong CDR3 comprises a non-human DH or a derivative thereof.

In some embodiments of each or any of the above or below mentioned embodiments, the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

In some embodiments of each or any of the above or below mentioned embodiments, the ultralong CDR3 comprises a JH sequence or a derivative thereof.

In some embodiments of each or any of the above or below mentioned embodiments, the JH sequence comprises amino acids at positions 5-15 of SEQ ID NO: 13, SEQ ID NO: 14, SEQ ID NO: 15, SEQ ID NO: 16, or SEQ ID NO: 17.

In some embodiments of each or any of the above or below mentioned embodiments, the ultralong CDR3 comprises: a sequence derived from a non-human or human VH sequence (e.g., a germline VH) or a derivative thereof; a sequence derived from a non-human DH sequence or a derivative thereof; and/or a sequence derived from a JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the additional amino acid sequence is selected from the group consisting of: IR, IF, SEQ ID NO: 18, SEQ ID NO: 19, SEQ ID NO: 20 or SEQ ID NO: 21.

In some embodiments of each or any of the above or below mentioned embodiments, the ultralong CDR3 comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

In some embodiments of each or any of the above or below mentioned embodiments, the ultralong CDR3 comprises a bovine sequence, a non-bovine sequence, an antibody sequence, or a non-antibody sequence.

In some embodiments of each or any of the above or below mentioned embodiments, the non-antibody sequence is a synthetic sequence.

In some embodiments of each or any of the above or below mentioned embodiments, the non-antibody sequence is a cytokine sequence, a lymphokine sequence, a chemokine sequence, a growth factor sequence, a hormone sequence, or a toxin sequence.

In some embodiments of each or any of the above or below mentioned embodiments, the non-antibody sequence is an IL-8 sequence, an IL-21 sequence, an IL-1 sequence, an IL-2 sequence, an IL-4 sequence, an IL-10 sequence, an IL-17 sequence, an GLP-1 sequence, an SDF-1 (alpha) sequence, a somatostatin sequence, a chlorotoxin sequence, a Pro-TxII sequence, a ziconotide sequence, an ADWX-1 sequence, an HsTx1 sequence, an OSK1 sequence, a Pi2 sequence, a Hongotoxin (HgTX) sequence, a Margatoxin sequence, an Agitoxin-2 sequence, a Pi3 sequence, a Kaliotoxin sequence, an Anuroctoxin sequence, a Charybdotoxin sequence, a Tityustoxin-K-alpha sequence, a Maurotoxin sequence, a Ceratotoxin 1 (CcoTx1) sequence, a CcoTx2 sequence, a CcoTx3 sequence, a Phrixotoxin 3 (PaurTx3) sequence, a Hanatoxin 1 sequence, a Phrixotoxin 1 sequence, a Huwentoxin-IV sequence, an α-conotoxin Iml sequence, an α-conotoxin Epl sequence, an α-conotoxin PnIA sequence, an α-conotoxin PnlB sequence, an α-conotoxin MII sequence, an α-conotoxin AulA sequence, an α-conotoxin AulB sequence, an α-conotoxin AulC sequence, a conotoxin κ-PVIIA sequence, a charybdotoxin sequence, a neurotoxin B-IV sequence, a crotamine sequence, a ω-GVIA (conotoxin) sequence, a κ-hefutoxin 1 sequence, a Css4 sequence, a Bj-xtrlT sequence, a BcIV sequence, a Hm-1 sequence, a Hm-2 sequence, a GsAF-I (β-theraphotoxin-Gr1b) sequence, a Protoxin I (ProTx-I sequence, a β-theraphotoxin-Tp1a) sequence, a Protoxin II (ProTx II) sequence, a Huwentoxin I sequence, a μ-Conotoxin PIIIA sequence, a Jingzhaotoxin-III (β-TRTX-Cj1α) sequence, a GsAF-II (Kappa-theraphotoxin-Gr2c) sequence, a ShK (Stichodactyla toxin) sequence, a HsTx1 sequence, a Guangxitoxin 1E (GxTx-1E) sequence, a Maurotoxin sequence, a Charybdotoxin (ChTX) sequence, an Iberiotoxin (IbTx) sequence, a Leiurotoxin 1 (scyllatoxin) sequence, a Tamapin sequence, a Kaliotoxin-1 (KTX) sequence, a Purotoxin1 (PT-1) sequence, or a GpTx-1 sequence, a MOKA Toxin sequence, a OSK1 (P12, K16, D20) sequence, a OSK1 (K16, D20) sequence, a HmK sequence, a ShK (K16, Y26, K29) sequence, a ShK (K16) sequence, a ShK-A (K16) sequence, a ShK (K16,E30) sequence, a ShK (Q21) sequence, a ShK (L21) sequence, a ShK (F21) sequence, a ShK (121) sequence, or a ShK (A21) sequence.

In some embodiments of each or any of the above or below mentioned embodiments, the non-antibody sequence is any one of SEQ ID NOS: 475-481, 599-655, 666-698, 727-733, 808-810 and 831-835.

In some embodiments of each or any of the above or below mentioned embodiments, the humanized antibody or binding fragment thereof comprises an antibody heavy chain variable region comprising an amino acid sequence selected from the group consisting of SEQ ID NO: 770-779, 784-791, 903-922 and 925-955.

In some embodiments of each or any of the above or below mentioned embodiments, the humanized antibody or binding fragment thereof comprises a light chain variable region comprising an amino acid sequence SEQ ID NO: 780 or 807.

In some embodiments of each or any of the above or below mentioned embodiments, the humanized antibody or binding fragment thereof comprises an antibody heavy chain variable region comprising an amino acid sequence selected from the group consisting of SEQ ID NO: 770-779, 784-791, 903-922 and 925-955.

In some embodiments of each or any of the above or below mentioned embodiments, the humanized antibody or binding fragment thereof comprises a light chain variable region comprising an amino acid sequence of SEQ ID NO: 956 or 959.

In some embodiments of each or any of the above or below mentioned embodiments, the humanized antibody or binding fragment thereof comprises a heavy chain variable region and a light chain variable region, wherein the antibody heavy chain variable region comprises an amino acid sequence selected from the group consisting of SEQ ID NO: 770-779, 784-791, 903-922 and 925-955, and the light chain variable region comprising the amino acid sequence of SEQ ID NO: 959. In some aspects, the antibody heavy chain variable region comprises the amino acid sequence of SEQ ID NO: 941, and the light chain variable region comprising the amino acid sequence of SEQ ID NO: 959.

In some embodiments of each or any of the above or below mentioned embodiments, the humanized antibody or binding fragment thereof comprises a heavy chain variable region and a light chain variable region, wherein the antibody heavy chain variable region comprises an amino acid sequence selected from the group consisting of SEQ ID NO: 770-779, 784-791, 903-922 and 925-955, and wherein the light chain variable region comprising the amino acid sequence of SEQ ID NO: 956.

In some embodiments of each or any of the above or below mentioned embodiments, the non-antibody sequence replaces at least a portion of the ultralong CDR3.

In some embodiments of each or any of the above or below mentioned embodiments, the non-antibody sequence (e.g., a non-antibody human sequence) is inserted into the CDR3, including optionally, wherein a portion of CDR3 (e.g., one or more amino acids of the CDR3) or the entire CDR3 sequence (e.g., all or substantially all of the amino acids of the CDR3) is removed.

In some embodiments of each or any of the above or below mentioned embodiments, the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

In some embodiments of each or any of the above or below mentioned embodiments, the $X^1X^2X^3X^4X^5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the ultralong CDR3 comprises a $CX^1X^2X^3X^4X^5$ motif.

In some embodiments of each or any of the above or below mentioned embodiments, the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

In some embodiments of each or any of the above or below mentioned embodiments, the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the $(X^aX^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the $(X^aX^b)_z$ motif is YXYXYX.

In some embodiments of each or any of the above or below mentioned embodiments, the ultralong CDR3 comprises a $X_1X_2X_3X_4X_5X_n$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), and wherein n is 27-54.

In some embodiments of each or any of the above or below mentioned embodiments, the ultralong CDR3 comprises $X_n(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (VW), and histidine (H), wherein n is 27-54, and wherein z is 1-4.

In some embodiments of each or any of the above or below mentioned embodiments, the $X^1X^2X^3X^4X^5$ motif is TTVHQ (SEQ ID NO: 153) or TSVHQ (SEQ ID NO: 154), and wherein the $(X^aX^b)_z$ motif is YXYXYX.

In some embodiments of each or any of the above or below mentioned embodiments, the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75),
$CX_{10}CX_3CX_3CX_5CX_7CXCX_6C$ (SEQ ID NO: 76),
$CX_{10}CX_4CX_5CX_{12}CX_2C$ (SEQ ID NO: 77),
$CX_{12}CX_4CX_5CXCXCX_9CX_3C$ (SEQ ID NO: 78),
$CX_{12}CX_4CX_5CX_{12}CX_2C$ (SEQ ID NO: 79),
$CX_{10}CX_6CX_5CXCX_{1}C$ (SEQ ID NO: 80),
$CX_{16}CX_5CXCXCX_{14}C$ (SEQ ID NO: 81),
$CX_{10}CX_5CXCX_8CX_6C$ (SEQ ID NO: 82),
$CX_{12}CX_4CX_5CX_8CX_2C$ (SEQ ID NO: 83),
$CX_{12}CX_5CX_5CXCX_8C$ (SEQ ID NO: 84),
$CX_1CCX_6CX_5CXCX_4CXCX_9C$ (SEQ ID NO: 85),
$CX_{11}CX_4CX_5CX_8CX_2C$ (SEQ ID NO: 86),
$CX_{10}CX_6CX_5CX_8CX_2C$ (SEQ ID NO: 87),
$CX_{10}CX_6CX_5CXCX_8C$ (SEQ ID NO: 88),
$CX_{10}CX_6CX_5CXCX_3CX_8CX_2C$ (SEQ ID NO: 89),
$CX_{10}CX_6CX_5CX_3CX_8C$ (SEQ ID NO: 90),
$CX_{10}CX_6CX_5CXCX_2CX_6CX_5C$ (SEQ ID NO: 91),
$CX_7CX_6CX_3CX_3CX_9C$ (SEQ ID NO: 92),
$CX_9CX_8CX_5CX_6CX_5C$ (SEQ ID NO: 93),
$CX_{10}CX_2CX_2CX_7CXCX_{11}CX_5C$ (SEQ ID NO: 94), and
$CX_{10}CX_6CX_5CXCX_2CX_8CX_4C$ (SEQ ID NO: 95), and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of:
$CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CCX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises an additional sequence that is a linker.

In some embodiments of each or any of the above or below mentioned embodiments, the linker is linked to a C-terminus, a N-terminus, or both C-terminus and N-terminus of the non-antibody sequence.

In some embodiments of each or any of the above or below mentioned embodiments, the ultralong CDR3 is a ruminant CDR3.

In some embodiments of each or any of the above or below mentioned embodiments, the ruminant is a cow.

In some embodiments of each or any of the above or below mentioned embodiments, the humanized antibody or binding fragment thereof comprises a human heavy chain variable region framework sequence.

In some embodiments of each or any of the above or below mentioned embodiments, the humanized antibody or binding fragment thereof comprises a human heavy chain germline sequence or is a derived from a human heavy chain germline sequence.

In some embodiments of each or any of the above or below mentioned embodiments, the heavy chain variable region comprises an amino acid sequence of SEQ ID NO: 735.

In some embodiments of each or any of the above or below mentioned embodiments, the heavy chain variable region comprises an amino acid sequence of SEQ ID NO: 737.

In some embodiments of each or any of the above or below mentioned embodiments, the heavy chain variable region comprises an amino acid sequence of SEQ ID NO: 739.

In some embodiments of each or any of the above or below mentioned embodiments, the heavy chain variable region comprises an amino acid sequence of SEQ ID NO: 741.

In some embodiments of each or any of the above or below mentioned embodiments, the heavy chain variable region comprises an amino acid sequence of SEQ ID NO: 743.

In some embodiments of each or any of the above or below mentioned embodiments, the heavy chain variable region comprises an amino acid sequence of SEQ ID NO: 745.

In some embodiments of each or any of the above or below mentioned embodiments, the heavy chain variable region comprises an amino acid sequence of SEQ ID NO: 747.

In some embodiments of each or any of the above or below mentioned embodiments, the heavy chain variable region comprises an amino acid sequence of SEQ ID NO: 749.

In some embodiments of each or any of the above or below mentioned embodiments, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515); (iii) any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529); (v) any one of DKGDSDYDYNL (SEQ ID NO: 530), DKGDSDYDYN (SEQ ID NO: 531), DKGDSDYDY (SEQ ID NO: 532), DKGDSDYD (SEQ ID NO: 533), DKGDSDY (SEQ ID NO: 534), DKGDSD (SEQ ID NO: 535); (vi) TSVHQETKKYQS (SEQ ID NO: 498).

In some embodiments of each or any of the above or below mentioned embodiments, the ultralong CDR3 comprises an amino acid sequence of: (i) any one of YGPNYEEWGDYLATLDV (SEQ ID NO: 536), GPNYEEWGDYLATLDV (SEQ ID NO: 537), PNYEEWGDYLATLDV (SEQ ID NO: 538), NYEEWGDYLATLDV (SEQ ID NO: 539), YEEWGDYLATLDV (SEQ ID NO: 540), or EEWGDYLATLDV (SEQ ID NO: 541); (ii) any one of YDFYDGYYNYHYMDV (SEQ ID NO: 542), DFYDGYYNYHYMDV (SEQ ID NO: 543), FYDGYYNYHYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of YDFNDGYYNYHYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNYHYMDV (SEQ ID NO: 553), or GYYNYHYMDV (SEQ ID NO: 554); (iv) any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569); or (vi) SYTYNYEWHVDV (SEQ ID NO: 499).

In some embodiments of each or any of the above or below mentioned embodiments, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507), and any one of YGPNYEEWGDYLATLDV (SEQ ID NO: 536), GPNYEEWGDYLATLDV (SEQ ID NO: 537), PNYEEWGDYLATLDV (SEQ ID NO: 538), NYEEWGDYLATLDV (SEQ ID NO: 539), YEEWGDYLATLDV (SEQ ID NO: 540), or EEWGDYLATLDV (SEQ ID NO: 541); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515), and any one of YDFYDGYYNYHYMDV (SEQ ID NO: 542), DFYDGYYNYHYMDV (SEQ ID NO: 543), FYDGYYNYHYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523), and any one of YDFNDGYYNYHYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNYHYMDV (SEQ ID NO: 553), or GYYNYHYMDV (SEQ ID NO: 554); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529), and any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569); or (vi) TSVHQETKKYQS (SEQ ID NO: 498) and SYTYNYEWHVDV (SEQ ID NO: 499).

In some embodiments of each or any of the above or below mentioned embodiments, the humanized antibody or binding fragment thereof comprises a human light chain variable region framework sequence.

In some embodiments of each or any of the above or below mentioned embodiments, the humanized antibody or binding fragment thereof comprises a light chain variable region comprising a sequence selected from the group of: (i) SEQ ID NO: 750, (ii) SEQ ID NO: 751, (iii) SEQ ID NO: 752, and (iv) SEQ ID NO: 753.

In some embodiments of each or any of the above or below mentioned embodiments, the light chain variable comprises a lambda light chain variable region sequence or derived from a lambda light chain variable region sequence.

In some embodiments of each or any of the above or below mentioned embodiments, the light chain variable region sequence comprises a human lambda light chain variable region sequence or derived from a human lambda light chain variable region sequence.

In some embodiments of each or any of the above or below mentioned embodiments, the light chain variable region comprises a VL1-51 germline sequence.

In some embodiments of each or any of the above or below mentioned embodiments, the light chain variable region is derived from a VL1-51 germline sequence.

In some embodiments of each or any of the above or below mentioned embodiments, the VL1-51 germline sequence comprises a CDR1 comprising Ile29Val and Asn32Gly substitution based on Kabat numbering.

In some embodiments of each or any of the above or below mentioned embodiments, the VL1-51 germline sequence comprises a CDR2 comprising a substitution of DNN to GDT.

In some embodiments of each or any of the above or below mentioned embodiments, the VL1-51 germline sequence comprises a CDR2 comprising a substitution of DNNKRP (SEQ ID NO: 471) to GDTSRA (SEQ ID NO: 472).

In some embodiments of each or any of the above or below mentioned embodiments, the VL1-51 germline sequence comprises a S2A, T5N, P8S, A12G, A13S, and P14L substitution based on Kabat numbering.

In some embodiments of each or any of the above or below mentioned embodiments, the VL1-51 germline sequence comprises a S2A, T5N, P8S, A12G, A13S, and P14L substitution based on Kabat numbering, and a CDR2 comprising a substitution of DNN to GDT.

In some embodiments of each or any of the above or below mentioned embodiments, the humanized antibody or binding fragment thereof comprising: (a) a heavy chain variable region comprising a sequence selected from the group consisting of SEQ ID NO: 740, SEQ ID NO: 741, SEQ ID NO:742, and SEQ ID NO: 743; and (b) a light chain variable region comprising SEQ ID NO: 750.

The present disclosure also provides polynucleotides encoding the heavy chain variable region of the humanized antibody or binding fragment thereof disclosed herein.

The present disclosure also provides polynucleotides encoding the light chain variable region of the humanized antibody or binding fragment thereof disclosed herein.

The present disclosure also provides polynucleotides encoding a heavy chain variable region that comprises an ultralong CDR3, wherein the polynucleotide comprises a sequence selected from the group consisting of SEQ ID NO: 490, SEQ ID NO: 491, SEQ ID NO: 492, SEQ ID NO: 493, SEQ ID NO: 494, SEQ ID NO: 495, SEQ ID NO: 496, and SEQ ID NO: 497.

The present disclosure also provides vectors that comprise the polynucleotides disclosed herein.

The present disclosure also provides host cells comprising the vectors disclosed herein.

The present disclosure also provides a nucleic acid library comprising a plurality of polynucleotides comprising sequences coding for humanized antibodies or binding fragments thereof, wherein the antibodies or binding fragments thereof comprise a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3.

The present disclosure also provides a library of humanized antibodies or binding fragments thereof, wherein the antibodies or binding fragments thereof comprise (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_1C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

In some embodiments of each or any of the above or below mentioned embodiments, the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CCX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

In some embodiments of each or any of the above or below mentioned embodiments, the ultralong CDR3 comprises 2 to 6 disulfide bonds.

In some embodiments of each or any of the above or below mentioned embodiments, the ultralong CDR3 comprises SEQ ID NO: 40 or a derivative thereof.

In some embodiments of each or any of the above or below mentioned embodiments, the ultralong CDR3 comprises amino acid residues 3-6 of any of one SEQ ID NO: 1-4.

In some embodiments of each or any of the above or below mentioned embodiments, the ultralong CDR3 comprises a non-human DH or a derivative thereof.

In some embodiments of each or any of the above or below mentioned embodiments, the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

In some embodiments of each or any of the above or below mentioned embodiments, the ultralong CDR3 comprises a JH sequence or a derivative thereof.

In some embodiments of each or any of the above or below mentioned embodiments, the JH sequence comprises amino acids as positions 5-15 of SEQ ID NO: 13, SEQ ID NO: 14, SEQ ID NO: 15, SEQ ID NO: 16, or SEQ ID NO: 17.

In some embodiments of each or any of the above or below mentioned embodiments, the ultralong CDR3 comprises: a sequence derived from a non-human VH sequence or a derivative thereof; a sequence derived from a non-human DH sequence or a derivative thereof; and/or a sequence derived from JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the additional amino acid sequence is selected from the group consisting of: IR, IF, SEQ ID NO: 18, SEQ ID NO: 19, SEQ ID NO: 20 or SEQ ID NO: 21.

In some embodiments of each or any of the above or below mentioned embodiments, the ultralong CDR3 comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

In some embodiments of each or any of the above or below mentioned embodiments, the ultralong CDR3 comprises a non-bovine sequence or a non-antibody sequence. For example, the non-antibody sequence (e.g., a non-antibody human sequence) is inserted into the CDR3, including optionally, wherein a portion of CDR3 (e.g., one or more amino acids of the CDR3) or the entire CDR3 sequence (e.g., all or substantially all of the amino acids of the CDR3) is removed.

In some embodiments of each or any of the above or below mentioned embodiments, the non-antibody sequence is a synthetic sequence.

In some embodiments of each or any of the above or below mentioned embodiments, the non-antibody sequence is a cytokine sequence, a lymphokine sequence, a chemokine sequence, a growth factor sequence, a hormone sequence, or a toxin sequence.

In some embodiments of each or any of the above or below mentioned embodiments, the non-antibody sequence is an IL-8 sequence, an IL-21 sequence, an SDF-1 (alpha) sequence, a somatostatin sequence, a chlorotoxin sequence, a Pro-TxII sequence, a ziconotide sequence, an ADWX-1 sequence, an HsTx1 sequence, an OSK1 sequence, a Pi2 sequence, a Hongotoxin (HgTX) sequence, a Margatoxin sequence, an Agitoxin-2 sequence, a Pi3 sequence, a Kaliotoxin sequence, an Anuroctoxin sequence, a Charybdotoxin sequence, a Tityustoxin-K-alpha sequence, a Maurotoxin sequence, a Ceratotoxin 1 (CcoTx1) sequence, a CcoTx2 sequence, a CcoTx3 sequence, a Phrixotoxin 3 (PaurTx3) sequence, a Hanatoxin 1 sequence, a Phrixotoxin 1 sequence, a Huwentoxin-IV sequence, an α-conotoxin Iml sequence, an α-conotoxin Epl sequence, an α-conotoxin PnIA sequence, an α-conotoxin PnIB sequence, an α-conotoxin MII sequence, an α-conotoxin AuIA sequence, an α-conotoxin AuIB sequence, an α-conotoxin AuIC sequence, a conotoxin κ-PVIIA sequence, a charybdotoxin sequence, a neurotoxin B-IV sequence, a crotamine sequence, a ω-GVIA (conotoxin) sequence, a κ-hefutoxin 1 sequence, a Css4 sequence, a Bj-xtrlT sequence, a BcIV sequence, a Hm-1 sequence, a Hm-2 sequence, a GsAF-I (β-theraphotoxin-Gr1b) sequence, a Protoxin I (ProTx-I sequence, a β-theraphotoxin-Tp1a) sequence, a Protoxin II (ProTx II) sequence, a Huwentoxin I sequence, a μ-Conotoxin PIIIA sequence, a Jingzhaotoxin-III (β-TRTX-Cj1α) sequence, a GsAF-II (Kappa-theraphotoxin-Gr2c) sequence, a ShK (Stichodactyla toxin) sequence, a HsTx1 sequence, a Guangxitoxin 1E (GxTx-1E) sequence, a Maurotoxin sequence, a Charybdotoxin (ChTX) sequence, an Iberiotoxin (IbTx) sequence, a Leiurotoxin 1 (scyllatoxin) sequence, a Tamapin sequence, a Kaliotoxin-1 (KTX) sequence, a Purotoxin1 (PT-1) sequence, or a GpTx-1 sequence, a MOKA Toxin sequence, a OSK1 (P12, K16, D20) sequence, a OSK1 (K16, D20) sequence, a HmK sequence, a ShK (K16, Y26, K29) sequence, a ShK (K16) sequence, a ShK-A (K16) sequence, a ShK (K16,E30) sequence, a ShK (Q21) sequence, a ShK (L21) sequence, a ShK (F21) sequence, a ShK (121) sequence, or a ShK (A21) sequence.

In some embodiments of each or any of the above or below mentioned embodiments, the non-antibody sequence is any one of SEQ ID NOS: 475-481, 599-655, 666-698, 727-733, 808-810 and 831-835.

In some embodiments of each or any of the above or below mentioned embodiments, the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

In some embodiments of each or any of the above or below mentioned embodiments, the $X^1X^2X^3X^4X^5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the ultralong CDR3 comprises a $CX^1X^2X^3X^4X^5$ motif.

In some embodiments of each or any of the above or below mentioned embodiments, the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

In some embodiments of each or any of the above or below mentioned embodiments, the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the $(X^aX^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the $(X^a X^b)_z$ motif is YXYXYX.

In some embodiments of each or any of the above or below mentioned embodiments, the ultralong CDR3 comprises a $X^1 X^2 X^3 X^4 X^5 X_n$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), and wherein n is 27-54.

In some embodiments of each or any of the above or below mentioned embodiments, the ultralong CDR3 comprises $X_n (X^a X^b)_z$ motif, wherein $X^a$ is any amino acid residue, $X^b$ is an aromatic amino acid selected from the group consisting of: tyrosine (Y), phenylalanine (F), tryptophan (V), and histidine (H), wherein n is 27-54, and wherein z is 1-4.

In some embodiments of each or any of the above or below mentioned embodiments, the ultralong CDR3 comprises a $X^1 X^2 X^3 X^4 X^5 X_n (X^a X^b)_z$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), $X^a$ is any amino acid residue, $X^b$ is an aromatic amino acid selected from the group consisting of: tyrosine (Y), phenylalanine (F), tryptophan (VW), and histidine (H), wherein n is 27-54, and wherein z is 1-4.

In some embodiments of each or any of the above or below mentioned embodiments, the $X^1 X^2 X^3 X^4 X^5$ motif is TTVHQ (SEQ ID NO: 153) or TSVHQ (SEQ ID NO: 154), and wherein the $(X^a X^b)_z$ motif is YXYXYX.

In some embodiments of each or any of the above or below mentioned embodiments, the ultralong CDR3 comprises: a $CX^1 X^2 X^3 X^4 X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_1CCX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_1CCX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_1CCX_6CX_5CXCX_1'C$ (SEQ ID NO: 80), $CX_{16}CX_5CXCXCX_{14}C$ (SEQ ID NO: 81), $CX_1CCX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95); and a $(X^a X^b)_z$ motif, $X^a$ is any amino acid residue, $X^b$ is an aromatic amino acid selected from the group consisting of: tyrosine (Y), phenylalanine (F), tryptophan (VW), and histidine (H), and wherein z is 1-4.

In some embodiments of each or any of the above or below mentioned embodiments, the ultralong CDR3 comprises: a $CX^1 X^2 X^3 X^4 X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_1CCXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCX_1CCX_2CX_3C$ (SEQ ID NO: 125), $CX_3CX_5CX_5CX_4CCX_1CCX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CCX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); andba $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises an additional sequence that is a linker.

In some embodiments of each or any of the above or below mentioned embodiments, the linker is linked to a C-terminus, a N-terminus, or both C-terminus and N-terminus of the non-antibody sequence.

In some embodiments of each or any of the above or below mentioned embodiments, the ultralong CDR3 is a ruminant CDR3.

In some embodiments of each or any of the above or below mentioned embodiments, the ruminant is a cow.

In some embodiments of each or any of the above or below mentioned embodiments, the humanized antibody or binding fragment thereof comprises a human heavy chain variable region framework sequence.

In some embodiments of each or any of the above or below mentioned embodiments, the humanized antibody or binding fragment thereof comprises a human heavy chain germline sequence or is a derived from a human heavy chain germline sequence.

In some embodiments of each or any of the above or below mentioned embodiments, the heavy chain variable region comprises an amino acid sequence of SEQ ID NO: 735.

In some embodiments of each or any of the above or below mentioned embodiments, the heavy chain variable region comprises an amino acid sequence of SEQ ID NO: 737.

In some embodiments of each or any of the above or below mentioned embodiments, the heavy chain variable region comprises an amino acid sequence of SEQ ID NO: 739.

In some embodiments of each or any of the above or below mentioned embodiments, the heavy chain variable region comprises an amino acid sequence of SEQ ID NO: 741.

In some embodiments of each or any of the above or below mentioned embodiments, the heavy chain variable region comprises an amino acid sequence of SEQ ID NO: 743.

In some embodiments of each or any of the above or below mentioned embodiments, the heavy chain variable region comprises an amino acid sequence of SEQ ID NO: 745.

In some embodiments of each or any of the above or below mentioned embodiments, the heavy chain variable region comprises an amino acid sequence of SEQ ID NO: 747.

In some embodiments of each or any of the above or below mentioned embodiments, the heavy chain variable region comprises an amino acid sequence of SEQ ID NO: 749.

In some embodiments of each or any of the above or below mentioned embodiments, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515); (iii) any one of EAGGPIWHDDDVKY (SEQ ID NO: 516), EAGGPIWHDDDVK (SEQ ID NO: 517), EAGGPIWHDDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529); (v) any one of DKGDSDYDYNL (SEQ ID NO: 530), DKGDSDYDYN (SEQ ID NO: 531), DKGDSDYDY (SEQ ID NO: 532), DKGDSDYD (SEQ ID NO: 533), DKGDSDY (SEQ ID NO: 534), DKGDSD (SEQ ID NO: 535); or (vi) TSVHQETKKYQS (SEQ ID NO: 498).

In some embodiments of each or any of the above or below mentioned embodiments, the ultralong CDR3 comprises an amino acid sequence of: (i) any one of YGPNY-EEWGDYLATLDV (SEQ ID NO: 536), GPNYEEWGDY-LATLDV (SEQ ID NO: 537), PNYEEWGDYLATLDV (SEQ ID NO: 538), NYEEWGDYLATLDV (SEQ ID NO: 539), YEEWGDYLATLDV (SEQ ID NO: 540), or EEWGDYLATLDV (SEQ ID NO: 541); (ii) any one of YDFYDGYYNYHYMDV (SEQ ID NO: 542), DFYDGYYNYHYMDV (SEQ ID NO: 543), FYDGYYNY-HYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of YDFNDGYYNY-HYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNY-HYMDV (SEQ ID NO: 553), or GYYNYHYMDV (SEQ ID NO: 554); (iv) any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569); or (vi) SYTYNYE-WHVDV (SEQ ID NO: 499).

In some embodiments of each or any of the above or below mentioned embodiments, the humanized antibody or binding fragment thereof comprises a light chain variable region sequence.

In some embodiments of each or any of the above or below mentioned embodiments, the humanized antibody or binding fragment thereof comprises a light chain variable region comprising a sequence selected from the group of: (i) SEQ ID NO: 750, (ii) SEQ ID NO: 751, (iii) SEQ ID NO: 752, and (iv) SEQ ID NO: 753.

In some embodiments of each or any of the above or below mentioned embodiments, the light chain variable region sequence is a lambda light chain variable region sequence.

In some embodiments of each or any of the above or below mentioned embodiments, the light chain variable region sequence is a human lambda light chain variable region sequence.

In some embodiments of each or any of the above or below mentioned embodiments, the light chain variable region sequence comprises a VL1-51 germline sequence.

In some embodiments of each or any of the above or below mentioned embodiments, the light chain variable region is derived from a VL1-51 germline sequence.

In some embodiments of each or any of the above or below mentioned embodiments, the VL1-51 germline sequence comprises a CDR1 comprising Ile29Val and Asn32Gly substitution based on Kabat numbering.

In some embodiments of each or any of the above or below mentioned embodiments, the VL1-51 germline sequence comprises a CDR2 comprising a substitution of DNN to GDT.

In some embodiments of each or any of the above or below mentioned embodiments, the VL1-51 germline sequence comprises a CDR2 comprising a substitution of DNNKRP (SEQ ID NO: 471) to GDTSRA (SEQ ID NO: 472).

In some embodiments of each or any of the above or below mentioned embodiments, the VL1-51 germline sequence comprises a S2A, T5N, P8S, A12G, A13S, and P14L substitution based on Kabat numbering.

In some embodiments of each or any of the above or below mentioned embodiments, the VL1-51 germline sequence comprises a S2A, T5N, P8S, A12G, A13S, and P14L substitution based on Kabat numbering, and a CDR2 comprising a substitution of DNN to GDT.

In some embodiments of each or any of the above or below mentioned embodiments, the humanized antibody or binding fragment thereof comprising (a) a heavy chain variable region comprising a sequence selected from the group consisting of SEQ ID NO: 740, SEQ ID NO: 741, SEQ ID NO:742, and SEQ ID NO: 743; and (b) a light chain variable region comprising SEQ ID NO: 750.

In some embodiments of each or any of the above or below mentioned embodiments, the humanized antibodies or binding fragments thereof are present in a spatially addressed format.

The present disclosure also provides a method of humanizing an antibody variable region comprising the step of genetically combining a nucleic acid sequence encoding an ultralong CDR3 with a nucleic acid sequence encoding a variable region sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO: 747, and (viii) SEQ ID NO: 748 or SEQ ID NO: 749.

The present disclosure also provides a method of generating a library of humanized antibodies that comprises an ultralong CDR3, the method comprising: combining a nucleic acid sequence encoding an ultralong CDR3 with a nucleic acid sequence encoding a variable region sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO: 747, and (viii) SEQ ID NO: 748 or SEQ ID NO: 749, to produce nucleic acids encoding for humanized antibodies that comprises an ultralong CDR3; and expressing the nucleic acids encoding for humanized antibodies that comprises an ultralong CDR3 to generate a library of humanized antibodies that comprises an ultralong CDR3.

The present disclosure also provides a method of generating a library of humanized antibodies or binding fragments thereof comprising an ultralong CDR3 and which comprises a non-antibody sequence, the method comprising: combining a nucleic acid sequence encoding an ultralong CDR3, a nucleic acid sequence encoding a variable region sequence selected from the group consisting of: (i) SEQ ID NO: 734 or SEQ ID NO: 735, (ii) SEQ ID NO: 736 or SEQ ID NO:

737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO: 747, and (viii) SEQ ID NO: 748 or SEQ ID NO: 749, and a nucleic acid sequence encoding a non-antibody sequence to produce nucleic acids encoding humanized antibodies or binding fragments thereof comprising an ultralong CDR3 and a non-antibody sequence, and expressing the nucleic acids encoding humanized antibodies or binding fragments thereof comprising an ultralong CDR3 and a non-antibody sequence to generate a library of humanized antibodies or binding fragments thereof comprising an ultralong CDR3 and a non-antibody sequence. In some embodiments, the ultralong CDR3 comprises a bovine, a non-bovine, an antibody, or a non-antibody sequence.

The present disclosure also provides a library of humanized antibodies or binding fragments thereof comprising an ultralong CDR3 which comprises a non-bovine or a non-antibody sequence. For example, the non-antibody sequence (e.g., a non-antibody human sequence) is inserted into the CDR3, including optionally, wherein a portion of CDR3 (e.g., one or more amino acids of the CDR3) or the entire CDR3 sequence (e.g., all or substantially all of the amino acids of the CDR3) is removed.

The present disclosure also provides a method of generating a library of humanized antibodies or binding fragments thereof comprising an ultralong CDR3 which comprises a cysteine motif, the method comprising: combining a human variable region framework (FR) sequence, and a nucleic acid sequence encoding an ultralong CDR3 and a cysteine motif; introducing one or more nucleotide changes to the nucleic acid sequence encoding one or more amino acid residues that are positioned between one or more cysteine residues in the cysteine motif for nucleotides encoding different amino acid residues to produce nucleic acids encoding humanized antibodies or binding fragments thereof comprising an ultralong CDR3 and a cysteine motif with one or more nucleotide changes introduced between one or more cysteine residues in the cysteine domain; and expressing the nucleic acids encoding humanized antibodies or binding fragments thereof comprising an ultralong CDR3 and a cysteine motif with one or more nucleotide changes introduced between one or more cysteine residues in the cysteine domain to generate a library of humanized antibodies or binding fragments thereof comprising an ultralong CDR3 and a cysteine motif with one or more amino acid changes introduced between one or more cysteine residues in the cysteine domain.

The present disclosure also provides a library of humanized antibodies or binding fragments thereof comprising an ultralong CDR3 which comprises a cysteine motif, wherein the antibodies or binding fragments comprise one or more substitutions of amino acid residues that are positioned between cysteine residues in the cysteine motif.

The present disclosure also provides a method of generating a library of humanized antibodies or binding fragments thereof comprising a bovine ultralong CDR3, the method comprising: combining a nucleic acid sequence encoding a human variable region framework (FR) sequence and a nucleic acid encoding a bovine ultralong CDR3, and expressing the nucleic acids encoding a human variable region framework (FR) sequence and a nucleic acid encoding a bovine ultralong CDR3 to generate a library of humanized antibodies or binding fragments thereof comprising a bovine ultralong CDR3.

The present disclosure also provides a library of humanized antibodies or binding fragments thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO: 747, and (viii) SEQ ID NO: 748 or SEQ ID NO: 749; and (b) a bovine ultralong CDR3.

The present disclosure also provides an antibody heavy chain variable region comprising a sequence of the formula V1-X-V2, wherein V1 comprises an amino acid sequence selected from the group consisting of: (i) QVQLREW-GAGLLKPSETLSLTCAVYGGSFSGYYWSWIRQPPGK-GLEWIGEINHSGSTNY NPSLKSRVTISVDTSKNQFSLKLSSVTAADTAVYYC (SEQ ID NO: 735), (ii) QVQLREWGAGLLKPSETLSLT-CAVYGGSFSDKYWSWIRQPPGKGLEWIGEINHSG-STNY NPSLKSRVTISVDTSKNQFSLKLSSVTAAD-TAVYYC (SEQ ID NO: 737), (iii) QVQLREWGAGLLKPSETLSLTCA-VYGGSFSGYYWSWIRQPPGKGLEWIGSINHSGSTNY NPSLKSRVTISVDTSKNQFSLKLSSVTAADTAVYYC (SEQ ID NO: 739), (iv) QVQLREWGAGLLKPSETLSLT-CAVYGGSFSDKYWSWIRQPPGKGLEWIGSINHSG-STNY NPSLKSRVTISVDTSKNQFSLKLSSVTAAD-TAVYYC (SEQ ID NO: 741), (v) QVQLREWGAGLLKPSETLSLTC-TASGFSLSDKAVGWIRQPPGKGLEWIGEINHSG-STNYN PSLKSRVTISVDTSKNQFSLKLSSVTAAD-TAVYYC (SEQ ID NO: 743), (vi) QVQLREWGAGLLKPSETLSLTCAVYGGLGSIDTGG-NTGSFSGYYWSWIRQPPGKGLEW YNPSLKSRVTISVDTSKNQFSLKLSSVTAADTAVYYC (SEQ ID NO: 745), (vii) QVQLREWGAGLLKP-SETLSLTCTASGFSLSDKAVGWIRQPPGKGLEWIGS-INHSGSTNYN PSLKSRVTISVDTSKNQFSLKLSSVTAADTAVYYC (SEQ ID NO: 747), and (viii) QVQLREWGAGLLKP-SETLSLTCTASGFSLSDKAVGWIRQPPGKGLEW-LGSIDTGGNTGY NPSLKSRVTISVDTSKNQFSLKLSSVTAADTAVYYC (SEQ ID NO: 749); wherein X comprises an ultralong CDR3, wherein X comprises an ultralong CDR3, which can include a non-human sequence or a non-antibody sequence (e.g., a non-antibody human sequence) that has been inserted into the CDR3 sequence of the antibody, including optionally, removing a portion of CDR3 (e.g., one or more amino acids of the CDR3) or the entire CDR3 sequence (e.g., all or substantially all of the amino acids of the CDR3); and wherein V2 comprises an amino acid sequence selected from the group consisting of: (i) WGHGTAVTVSS (SEQ ID NO: 570), (ii) WGKGTTVTVSS (SEQ ID NO: 571), (iii) WGKGTTVTVSS (SEQ ID NO: 572), (iv) WGRGTLVTVSS (SEQ ID NO: 573), (v) WGKGTTVTVSS (SEQ ID NO: 574), and (vi) WGQGLL-VTVSS (SEQ ID NO: 500).

In some embodiments of each or any of the above or below mentioned embodiments, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515); (iii) any one of EAGGPIWHDDVKY (SEQ ID NO: 516), EAGG-PIWHDDVK (SEQ ID NO: 517), EAGGPIWHDDV (SEQ ID NO: 518), EAGGPIWHDD (SEQ ID NO: 519), EAGG-PIWHD (SEQ ID NO: 520), EAGGPIWH (SEQ ID NO: 521), EAGGPIW (SEQ ID NO: 522), or EAGGPI (SEQ ID NO: 523); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529); (v) any one of DKGDSDYDYNL (SEQ ID NO: 530), DKGDSDYDYN (SEQ ID NO: 531), DKGDSDYDY (SEQ ID NO: 532), DKGDSDYD (SEQ ID NO: 533), DKGDSDY (SEQ ID NO: 534), DKGDSD (SEQ ID NO: 535); or (vi) TSVHQETKKYQS (SEQ ID NO: 498).

In some embodiments of each or any of the above or below mentioned embodiments, the ultralong CDR3 comprises an amino acid sequence of: (i) any one of YGPNY-EEWGDYLATLDV (SEQ ID NO: 536), GPNYEEWGDY-LATLDV (SEQ ID NO: 537), PNYEEWGDYLATLDV (SEQ ID NO: 538), NYEEWGDYLATLDV (SEQ ID NO: 539), YEEWGDYLATLDV (SEQ ID NO: 540), or EEWGDYLATLDV (SEQ ID NO: 541); (ii) any one of YDFYDGYYNYHYMDV (SEQ ID NO: 542), DFYDGYYNYHYMDV (SEQ ID NO: 543), FYDGYYNY-HYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of YDFNDGYYNY-HYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNY-HYMDV (SEQ ID NO: 553), or GYYNYHYMDV (SEQ ID NO: 554); (iv) any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569); or (vi) SYTYNYE-WHVDV (SEQ ID NO: 499).

In some embodiments of each or any of the above or below mentioned embodiments, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507), and any one of YGPNYEEWGDYLATLDV (SEQ ID NO: 536), GPNYEEWGDYLATLDV (SEQ ID NO: 537), PNYEEWGDYLATLDV (SEQ ID NO: 538), NYEEWGDYLATLDV (SEQ ID NO: 539), YEEWGDY-LATLDV (SEQ ID NO: 540), or EEWGDYLATLDV (SEQ ID NO: 541); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515), and any one of YDFYDGYYNYHYMDV (SEQ ID NO: 542), DFYDGYYNYHYMDV (SEQ ID NO: 543), FYDGYYNY-HYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523), and any one of YDFNDGYYNYHYMDV (SEQ ID NO: 549), DFYDGYYNYHYMDV (SEQ ID NO: 550), FYDGYYNY-HYMDV (SEQ ID NO: 551), YDGYYNYHYMDV (SEQ ID NO: 552), DGYYNYHYMDV (SEQ ID NO: 553), or GYYNYHYMDV (SEQ ID NO: 554); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529), and any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), and any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569); or (vi) TSVHQETKKYQS (SEQ ID NO: 498) and SYTYNYE-WHVDV (SEQ ID NO: 499).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507), and an amino acid sequence of any one of YGPNYEEWGDYLATLDV (SEQ ID NO: 536), GPNY-EEWGDYLATLDV (SEQ ID NO: 537), PNYEEWGDY-LATLDV (SEQ ID NO: 538), NYEEWGDYLATLDV (SEQ ID NO: 539), YEEWGDYLATLDV (SEQ ID NO: 540), or EEWGDYLATLDV (SEQ ID NO: 541), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515), and an amino acid sequence of any one of YDFYDGYYNYHYMDV (SEQ ID NO: 542), DFYDGYYNYHYMDV (SEQ ID NO: 543), FYDGYYNYHYMDV (SEQ ID NO: 544), YDGYYNY-HYMDV (SEQ ID NO: 545), DGYYNYHYMDV (SEQ ID NO: 546), GYYNYHYMDV (SEQ ID NO: 547), or YYNY-HYMDV (SEQ ID NO: 548), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of EAGG-PIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523), and an amino acid sequence of any one of YDFNDGYYNY-HYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNY-HYMDV (SEQ ID NO: 553), or GYYNYHYMDV (SEQ ID NO: 554), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529), and an amino acid sequence of any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), and any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), and wherein V2 comprises an amino acid sequence selected of WGQGLLVTVSS (SEQ ID NO: 500).

In some embodiments of each or any of the above or below mentioned embodiments, the antibody heavy chain variable region includes wherein the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the antibody heavy chain variable region includes wherein the ultralong CDR3 is 35 amino acids in length or longer.

In some embodiments of each or any of the above or below mentioned embodiments, the antibody heavy chain variable region includes wherein the ultralong CDR3 comprises a cysteine motif.

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507), a cysteine motif, and an amino acid sequence of any one of YGPNYEEWGDYLATLDV (SEQ ID NO: 536), GPNYEEWGDYLATLDV (SEQ ID NO: 537), PNY-EEWGDYLATLDV (SEQ ID NO: 538), NYEEWGDY-LATLDV (SEQ ID NO: 539), YEEWGDYLATLDV (SEQ ID NO: 540), or EEWGDYLATLDV (SEQ ID NO: 541), and and wherein V2 comprises an amino acid sequence of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515), a cysteine motif, and an amino acid sequence of any one of YDFYDGYYNY-HYMDV (SEQ ID NO: 542), DFYDGYYNYHYMDV (SEQ ID NO: 543), FYDGYYNYHYMDV (SEQ ID NO: 544), YDGYYNYHYMDV (SEQ ID NO: 545), DGYYNY-HYMDV (SEQ ID NO: 546), GYYNYHYMDV (SEQ ID NO: 547), or YYNYHYMDV (SEQ ID NO: 548), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523), a cysteine motif, and an amino acid sequence of any one of YDFNDGYYNYHYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNYHYMDV (SEQ ID NO: 553), or GYYNYHYMDV (SEQ ID NO: 554), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529), a cysteine motif, and an amino acid sequence of any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), a cysteine motif, and an amino acid sequence of any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), and wherein V2 comprises an amino acid sequence selected of WGQGLLVTVSS (SEQ ID NO: 500).

In some embodiments of each or any of the above or below mentioned embodiments, the antibody heavy chain variable region includes wherein VI comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence that is SEQ ID NO: 498 and an amino acid sequence that is SEQ ID NO: 499, and wherein V2 comprises an amino acid sequence that is SEQ ID NO: 500.

In some embodiments of each or any of the above or below mentioned embodiments, the antibody heavy chain variable region includes wherein the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_1CCX_6CX_5CXCX_{17}C$ (SEQ ID NO: 80), $CX_{16}CX_5CXCXCX_{14}C$ (SEQ ID NO: 81), $CX_1CCX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_1CCX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

In some embodiments of each or any of the above or below mentioned embodiments, the antibody heavy chain variable region includes wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_1CCX_3CX_4CCX_4C$ (SEQ ID NO: 139), $CX_9CX_4CCX_5CX_4C$ (SEQ ID NO: 140), $CX_1CCX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

In some embodiments of each or any of the above or below mentioned embodiments, the antibody heavy chain variable region includes wherein the ultralong CDR3 comprises 2 to 6 disulfide bonds.

In some embodiments of each or any of the above or below mentioned embodiments, the antibody heavy chain variable region includes wherein the ultralong CDR3 comprises a non-antibody sequence.

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507), a non-antibody sequence, and an amino acid sequence of any one of YGPNYEEWGDYLATLDV (SEQ ID NO: 536), GPNYEEWGDYLATLDV (SEQ ID NO: 537), PNYEEWGDYLATLDV (SEQ ID NO: 538), NYEEWGDYLATLDV (SEQ ID NO: 539), YEEWGDYLATLDV (SEQ ID NO: 540), or EEWGDYLATLDV (SEQ ID NO: 541), and wherein V2 comprises an amino acid sequence of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515), a non-antibody sequence, and an amino acid sequence of any one of YDFYDGYYNYHYMDV (SEQ ID NO: 542), DFYDGYYNYHYMDV (SEQ ID NO: 543), FYDGYYNYHYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523), a non-antibody sequence, and an amino acid sequence of any one of YDFNDGYYNYHYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNYHYMDV (SEQ ID NO: 553), or GYYNYHYMDV (SEQ ID NO: 554), and wherein V2 comprises an amino acid sequence selected of WGQGLLVTVSS (SEQ ID NO: 500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO:

741, SEQ ID NO: 743, SEQ ID NO: 745, SEQ ID NO: 747, and SEQ ID NO: 749, wherein the ultralong CDR3 comprises an amino acid sequence of any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529), a non-antibody sequence, and an amino acid sequence of any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563), and wherein V2 comprises an amino acid sequence selected of WGQGLLVTVSS (SEQ ID NO:500).

In some embodiments of each or any of the above or below mentioned embodiments, the antibody heavy chain variable region includes wherein V1 comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence of any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), a non-antibody sequence, and an amino acid sequence of any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), and wherein V2 comprises an amino acid sequence selected of WGQGLLVTVSS (SEQ ID NO:500).

In some embodiments of each or any of the above or below mentioned embodiments, the antibody heavy chain variable region includes wherein VI comprises an amino acid sequence selected from the group consisting of SEQ ID NO:735, SEQ ID NO: 737, SEQ ID NO: 739, SEQ ID NO: 741, SEQ ID NO: 743, SEQ ID NO: 745, SEQ ID NO: 747, and SEQ ID NO: 749, wherein the ultralong CDR3 comprises an amino acid sequence that is SEQ ID NO: 498 and an amino acid sequence that is SEQ ID NO: 499, and wherein V2 comprises an amino acid sequence that is SEQ ID NO: 500.

In some embodiments of each or any of the above or below mentioned embodiments, the antibody heavy chain variable region includes wherein the non-antibody sequence is a synthetic sequence.

In some embodiments of each or any of the above or below mentioned embodiments, the antibody heavy chain variable region includes wherein the non-antibody sequence is a cytokine sequence, a lymphokine sequence, a chemokine sequence, a growth factor sequence, a hormone sequence, or a toxin sequence.

In some embodiments of each or any of the above or below mentioned embodiments, the antibody heavy chain variable region includes wherein the non-antibody sequence is an IL-8 sequence, an IL-21 sequence, an SDF-1 (alpha) sequence, a somatostatin sequence, a chlorotoxin sequence, a Pro-TxII sequence, a ziconotide sequence, an ADWX-1 sequence, an HsTx1 sequence, an OSK1 sequence, a Pi2 sequence, a Hongotoxin (HgTX) sequence, a Margatoxin sequence, an Agitoxin-2 sequence, a Pi3 sequence, a Kaliotoxin sequence, an Anuroctoxin sequence, a Charybdotoxin sequence, a Tityustoxin-K-alpha sequence, a Maurotoxin sequence, a Ceratotoxin 1 (CcoTx1) sequence, a CcoTx2 sequence, a CcoTx3 sequence, a Phrixotoxin 3 (PaurTx3) sequence, a Hanatoxin 1 sequence, a Phrixotoxin 1 sequence, a Huwentoxin-IV sequence, an α-conotoxin Iml sequence, an α-conotoxin Epl sequence, an α-conotoxin PnIA sequence, an α-conotoxin PnlB sequence, an α-conotoxin MII sequence, an α-conotoxin AulA sequence, an α-conotoxin AulB sequence, an α-conotoxin AulC sequence, a conotoxin κ-PVIIA sequence, a charybdotoxin sequence, a neurotoxin B-IV sequence, a crotamine sequence, a ω-GVIA (conotoxin) sequence, a κ-hefutoxin 1 sequence, a Css4 sequence, a Bj-xtrlT sequence, a BcIV sequence, a Hm-1 sequence, a Hm-2 sequence, a GsAF-I (β-theraphotoxin-Gr1b) sequence, a Protoxin I (ProTx-I sequence, a β-theraphotoxin-Tp1a) sequence, a Protoxin II (ProTx II) sequence, a Huwentoxin I sequence, a μ-Conotoxin PIIIA sequence, a Jingzhaotoxin-III (β-TRTX-Cj1α) sequence, a GsAF-II (Kappa-theraphotoxin-Gr2c) sequence, a ShK (Stichodactyla toxin) sequence, a HsTx1 sequence, a Guangxitoxin 1E (GxTx-1E) sequence, a Maurotoxin sequence, a Charybdotoxin (ChTX) sequence, an Iberiotoxin (IbTx) sequence, a Leiurotoxin 1 (scyllatoxin) sequence, a Tamapin sequence, a Kaliotoxin-1 (KTX) sequence, a Purotoxin1 (PT-1) sequence, or a GpTx-1 sequence, a MOKA Toxin sequence, a OSK1 (P12, K16, D20) sequence, a OSK1 (K16, D20) sequence, a HmK sequence, a ShK (K16, Y26, K29) sequence, a ShK (K16) sequence, a ShK-A (K16) sequence, a ShK (K16,E30) sequence, a ShK (Q21) sequence, a ShK (L21) sequence, a ShK (F21) sequence, a ShK (121) sequence, or a ShK (A21) sequence.

In some embodiments of each or any of the above or below mentioned embodiments, the antibody heavy chain variable region includes wherein the non-antibody sequence is any one of SEQ ID NOS: 475-481, 599-655, 666-698, 727-733, 808-810, and 831-835.

In some embodiments of each or any of the above or below mentioned embodiments, the antibody heavy chain variable region includes wherein the antibody heavy chain variable region comprises an amino acid sequence selected from the group consisting of SEQ ID NO: 770-779, 784-791, 903-922 and 925-955. Accordingly, in some aspects, the antibody heavy chain variable region comprises the amino acid sequence of SEQ ID NO: 941.

In some embodiments of each or any of the above or below mentioned embodiments, the antibody heavy chain variable region includes wherein the ultralong CDR3 comprises a linker sequence.

In some embodiments of each or any of the above or below mentioned embodiments, the antibody heavy chain variable region includes wherein the linker is linked to a N-terminus, a C-terminus, or both N-terminus and C-terminus of the non-antibody sequence.

In some embodiments of each or any of the above or below mentioned embodiments, the antibody heavy chain variable region includes wherein the linker comprises one or more amino acid sequence selected from the group consisting of SEQ ID NO: 575 to 598, 699 to 726 and 813 to 830, or any combination thereof.

In some embodiments of each or any of the above or below mentioned embodiments, the antibody heavy chain variable region includes wherein the linkers linked to both N-terminus and C-terminus have the same or different amino acid sequence.

The present disclosure also provides antibody or binding fragment thereof comprising the antibody heavy chain variable region disclosed herein.

In some embodiments of each or any of the above or below mentioned embodiments, the heavy chain variable region further comprises a constant heavy chain 1 (CH1) region.

In some embodiments of each or any of the above or below mentioned embodiments, the heavy chain variable region further comprises an amino acid sequence of SEQ ID NO: 390.

In some embodiments of each or any of the above or below mentioned embodiments, the antibody or binding fragment further comprises a light chain variable region.

In some embodiments of each or any of the above or below mentioned embodiments, the light chain variable region further comprising a constant light chain (CL) region.

The present disclosure also provides an isolated polynucleotide encoding the antibody heavy chain variable region described herein.

The present disclosure also provides a vector comprising the polynucleotide described herein.

The present disclosure also provides a host cell comprising the vector described herein.

The present disclosure also provides a nucleic acid library comprising a plurality of polynucleotides comprising nucleic acid sequences encoding for an antibody heavy chain variable region comprising a sequence of the formula V1-X-V2, wherein V1 comprises an amino acid sequence selected from the group consisting of:

(i) QVQLREWGAGLLKPSETLSLTCA-VYGGSFSGYYWSWIRQPPG KGLEWIGEINHSG-STNYNPSLKSRVTISVDTSKNQFSLKLSSVTAAD-TAVYYC (SEQ ID NO: 735), (ii) QVQLREWGAGLLKPSETLSLTCA-VYGGSFSDKYWSWIRQPPGKGLEWIGE INHSG-STNYNPSLKSRVTISVDTSKNQFSLKLSSVTAAD-TAVYYC (SEQ ID NO: 737), (iii) QVQLREWGAGLLKPSETLSLTCA-VYGGSFSGYYWSWIRQPPGKGLEWIGSINHSGSTNY NPSLKSRVTISVDTSKNQFSLKLSSVTAADTAVYYC (SEQ ID NO: 739), (iv) QVQLREWGAGLLKPSETLSLT-CAVYGGSFSDKYWSWIRQPPGKGLEWIGSINHSG-STNY NPSLKSRVTISVDTSKNQFSLKLSSVTAAD-TAVYYC (SEQ ID NO: 741), (v) QVQLREWGAGLLKPSETLSLTC-TASGFSLSDKAVGWIRQPPGKGLEWIGEINHSG-STNYN PSLKSRVTISVDTSKNQFSLKLSSVTAAD-TAVYYC (SEQ ID NO: 743), (vi) QVQLREWGAGLLKPSETLSLTCAVYGGLGSIDTGG-NTGSFSGYYWSWIRQPPGKGLEW YNPSLKSRVTISVDTSKNQFSLKLSSVTAADTAVYYC (SEQ ID NO: 745), (vii) QVQLREWGAGLLKP-SETLSLTCTASGFSLSDKAVGWIRQPPGKGLEWIGS-INHSGSTNYN PSLKSRVTISVDTSKNQFSLKLSSVTAADTAVYYC (SEQ ID NO: 747), and (viii) QVQLREWGAGLLKP-SETLSLTCTASGFSLSDKAVGWIRQPPGKGLEW-LGSIDTGGNTGY NPSLKSRVTISVDTSKNQFSLKLSSVTAADTAVYYC (SEQ ID NO: 749); wherein X comprises an ultralong CDR3, wherein X comprises an ultralong CDR3, which can include a non-human sequence or a non-antibody sequence (e.g., a non-antibody human sequence) that has been inserted into the CDR3 sequence of the antibody, including optionally, removing a portion of CDR3 (e.g., one or more amino acids of the CDR3) or the entire CDR3 sequence (e.g., all or substantially all of the amino acids of the CDR3); and wherein V2 comprises an amino acid sequence selected from the group consisting of: (i) WGHGTAVTVSS (SEQ ID NO: 570), (ii) WGKGTTVTVSS (SEQ ID NO: 571), (iii) WGKGTTVTVSS (SEQ ID NO: 572), (iv) WGRGTLVTVSS (SEQ ID NO: 573), (v) WGKGTTVTVSS (SEQ ID NO: 574), and (vi) WGQGLL-VTVSS (SEQ ID NO: 500).

The present disclosure also provides a library of antibodies comprising antibody heavy chain variable regions comprising a sequence of the formula V1-X-V2, wherein V1 comprises an amino acid sequence selected from the group consisting of: (i) QVQLREWGAGLLKPSETLSLTCA-VYGGSFSGYYWSWIRQPPGKGLEWI GEINHSG-STNYNPSLKSRVTISVDTSKNQFSLKLSSVTAAD-TAVYYC (SEQ ID NO: 735), (ii) QVQLREWGAGLLKPSETLSLTCA-VYGGSFSDKYWSWIRQPPGKGLEWIGEINHSGST NYNPSLKSRVTISVDTSKNQFSLKLSSVTAAD-TAVYYC (SEQ ID NO: 737), (iii) QVQLREWGAGLLKP-SETLSLTCAVYGGSFSGYYWSWIRQPPGKGLEWIGS-INHSGSTNY NPSLKSRVTISVDTSKNQFSLKLSSVTAADTAVYYC (SEQ ID NO: 739), (iv) QVQLREWGAGLLKPSETLSLT-CAVYGGSFSDKYWSWIRQPPGKGLEWIGSINHSG-STNY NPSLKSRVTISVDTSKNQFSLKLSSVTAAD-TAVYYC (SEQ ID NO: 741), (v) QVQLREWGAGLLKPSETLSLTC-TASGFSLSDKAVGWIRQPPGKGLEWIGEINHSG-STNYN PSLKSRVTISVDTSKNQFSLKLSSVTAAD-TAVYYC (SEQ ID NO: 743), (vi) QVQLREWGAGLLKPSETLSLTCAVYGGLGSIDTGG-NTGSFSGYYWSWIRQPPGKGLEW YNPSLKSRVTISVDTSKNQFSLKLSSVTAADTAVYYC (SEQ ID NO: 745), (vii) QVQLREWGAGLLKP-SETLSLTCTASGFSLSDKAVGWIRQPPGKGLEWIGS-INHSGSTNYN PSLKSRVTISVDTSKNQFSLKLSSVTAADTAVYYC (SEQ ID NO: 747), and (viii) QVQLREWGAGLLKP-SETLSLTCTASGFSLSDKAVGWIRQPPGKGLEW-LGSIDTGGNTGY NPSLKSRVTISVDTSKNQFSLKLSSVTAADTAVYYC (SEQ ID NO: 749); wherein X comprises an ultralong CDR3, wherein X comprises an ultralong CDR3, which can include a non-human sequence or a non-antibody sequence (e.g., a non-antibody human sequence) that has been inserted into the CDR3 sequence of the antibody, including optionally, removing a portion of CDR3 (e.g., one or more amino acids of the CDR3) or the entire CDR3 sequence (e.g., all or substantially all of the amino acids of the CDR3); and wherein V2 comprises an amino acid sequence selected from the group consisting of: (i) WGHGTAVTVSS (SEQ ID NO: 570), (ii) WGKGTTVTVSS (SEQ ID NO: 571), (iii) WGKGTTVTVSS (SEQ ID NO: 572), (iv) WGRGTLVTVSS (SEQ ID NO: 573), (v) WGKGTTVTVSS (SEQ ID NO: 574), and (vi) WGQGLL-VTVSS (SEQ ID NO:500).

In some embodiments, the ultralong CDR3 comprises a $X_1X_2X_3X_4X_5$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), and wherein $X_5$ is glutamine (Q).

In some embodiments of each or any of the above or below mentioned embodiments, the antibody heavy chain variable region includes wherein the $X_1X_2X_3X_4X_5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the antibody heavy chain variable region includes wherein the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the antibody heavy chain variable region includes wherein the $(X^aX^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the antibody heavy chain variable region includes wherein the ultralong CDR3 comprises a $X^1X^2X^3X^4X^5X_n$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), and wherein n is 27-54.

In some embodiments of each or any of the above or below mentioned embodiments, the antibody heavy chain variable region includes wherein the ultralong CDR3 comprises $X_n(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the antibody heavy chain variable region includes wherein the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

The present disclosure also provides an antibody heavy chain variable region comprising a sequence of the formula V1-X, wherein V1 comprises an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and wherein X comprises an ultralong CDR3, wherein X comprises an ultralong CDR3, which can include a non-human sequence or a non-antibody sequence (e.g., a non-antibody human sequence) that has been inserted into the CDR3 sequence of the antibody, including optionally, removing a portion of CDR3 (e.g., one or more amino acids of the CDR3) or the entire CDR3 sequence (e.g., all or substantially all of the amino acids of the CDR3).

In some embodiments of each or any of the above or below mentioned embodiments, the antibody heavy chain variable region includes wherein the ultralong CDR3 comprises a $X^1X^2X^3X^4X^5$ motif, wherein $X^1$ is threonine (T), glycine (G), alanine (A), serine (S), or valine (V), wherein X2 is serine (S), threonine (T), proline (P), isoleucine (I), alanine (A), valine (V), or asparagine (N), wherein X3 is valine (V), alanine (A), threonine (T), or aspartic acid (D), wherein X4 is histidine (H), threonine (T), arginine (R), tyrosine (Y), phenylalanine (F), or leucine (L), and wherein X5 is glutamine (Q).

In some embodiments of each or any of the above or below mentioned embodiments, the antibody heavy chain variable region includes wherein the X1X2X3X4X5 motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the antibody heavy chain variable region includes wherein the ultralong CDR3 comprises a $CX1X2X^3X4X5$ motif.

In some embodiments of each or any of the above or below mentioned embodiments, the antibody heavy chain variable region includes wherein the $CX1X2X3X4X5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

In some embodiments of each or any of the above or below mentioned embodiments, the antibody heavy chain variable region includes wherein the ultralong CDR3 comprises a (XaXb)z motif, wherein Xa is any amino acid residue, Xb is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the antibody heavy chain variable region includes wherein the (XaXb)z motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the antibody heavy chain variable region includes wherein the (XaXb)z motif is YXYXYX.

In some embodiments of each or any of the above or below mentioned embodiments, the antibody heavy chain variable region includes wherein the ultralong CDR3 comprises a X1X2X3X4X5Xn motif, wherein X1 is threonine (T), glycine (G), alanine (A), serine (S), or valine (V), wherein X2 is serine (S), threonine (T), proline (P), isoleucine (I), alanine (A), valine (V), or asparagine (N), wherein X3 is valine (V), alanine (A), threonine (T), or aspartic acid (D), wherein X4 is histidine (H), threonine (T), arginine (R), tyrosine (Y), phenylalanine (F), or leucine (L), wherein X5 is glutamine (Q), and wherein n is 27-54.

In some embodiments of each or any of the above or below mentioned embodiments, the antibody heavy chain variable region includes wherein the ultralong CDR3 comprises Xn(XaXb)z motif, wherein Xa is any amino acid residue, Xb is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the antibody heavy chain variable region includes wherein the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4. 206.) The antibody heavy chain variable region includes wherein V1 comprises an amino acid sequence of SEQ ID NO: 737, wherein the ultralong CDR3 comprises an amino acid sequence of SEQ ID NO: 498 and SEQ ID NO: 499, and wherein V2 comprises an amino acid sequence of SEQ ID NO: 500.

In some embodiments of each or any of the above or below mentioned embodiments, the antibody heavy chain variable region includes wherein V1 comprises an amino acid sequence of SEQ ID NO: 739, wherein the ultralong CDR3 comprises an amino acid sequence of SEQ ID NO: 498 and SEQ ID NO: 499, and wherein V2 comprises an amino acid sequence of SEQ ID NO: 500.

In some embodiments of each or any of the above or below mentioned embodiments, the humanized antibody or binding fragment thereof includes wherein the light chain variable region comprises an amino acid sequence of SEQ ID NO: 750, an amino acid sequence of SEQ ID NO: 754, and an amino acid sequence of SEQ ID NO: 755.

In some embodiments of each or any of the above or below mentioned embodiments, the humanized antibody or binding fragment thereof includes an amino acid sequence of SEQ ID NO: 756.

In some embodiments of each or any of the above or below mentioned embodiments, the humanized antibody or binding fragment thereof includes wherein the light chain variable region comprises an amino acid sequence of SEQ ID NO: 751, an amino acid sequence of SEQ ID NO: 754, and an amino acid sequence of SEQ ID NO: 755.

In some embodiments of each or any of the above or below mentioned embodiments, the humanized antibody or binding fragment thereof includes further comprising an amino acid sequence of SEQ ID NO: 756.

In some embodiments of each or any of the above or below mentioned embodiments, the humanized antibody or binding fragment thereof includes wherein the light chain variable region comprises an amino acid sequence of SEQ ID NO: 752, an amino acid sequence of SEQ ID NO: 754, and an amino acid sequence of SEQ ID NO: 755.

In some embodiments of each or any of the above or below mentioned embodiments, the humanized antibody or binding fragment thereof includes further comprising an amino acid sequence of SEQ ID NO: 756.

In some embodiments of each or any of the above or below mentioned embodiments, the humanized antibody or binding fragment thereof includes wherein the light chain variable region comprises an amino acid sequence of SEQ ID NO: 753, an amino acid sequence of SEQ ID NO: 754, and an amino acid sequence of SEQ ID NO: 755.

In some embodiments of each or any of the above or below mentioned embodiments, the humanized antibody or binding fragment thereof includes further comprising an amino acid sequence of SEQ ID NO: 756.

In some embodiments of each or any of the above or below mentioned embodiments, the humanized antibody or binding fragment thereof includes wherein the heavy chain variable region comprises an amino acid sequence of SEQ ID NO: 737 and SEQ ID NO: 500, wherein the ultralong CDR3 comprises an amino acid sequence of SEQ ID NO: 498 and SEQ ID NO: 499.

In some embodiments of each or any of the above or below mentioned embodiments, the humanized antibody or binding fragment thereof includes further comprising a light chain variable region comprising an amino acid sequence of SEQ ID NO: 750, an amino acid sequence of SEQ ID NO: 754, and an amino acid sequence of SEQ ID NO: 755.

In some embodiments of each or any of the above or below mentioned embodiments, the humanized antibody or binding fragment thereof includes wherein the heavy chain variable region comprises an amino acid sequence of SEQ ID NO: 739 and SEQ ID NO: 500, wherein the ultralong CDR3 comprises an amino acid sequence of SEQ ID NO: 498 and SEQ ID NO: 499.

In some embodiments of each or any of the above or below mentioned embodiments, the humanized antibody or binding fragment thereof includes further comprising a light chain variable region comprising an amino acid sequence of SEQ ID NO: 750, an amino acid sequence of SEQ ID NO: 754, and an amino acid sequence of SEQ ID NO: 755.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 1 shows a sequence alignment of exemplary bovine-derived antibody variable region sequences designated BLV1H12, BLV5B8, BLV5D3, BLV8C11, BF4E9, BF1H1, or F18 that comprise an ultralong CDR3 sequence.

FIG. 2A-C depicts ultralong CDR3 sequences. (Top) Translation from the germline $V_H$BUL, $D_H$2, and $J_H$. The 5 full length ultralong CDR H3s reported in the literature contain between four and eight cysteines and are not highly homologous to one another; however, some conservation of cysteine residues with $D_H$2 could be found when the first cysteine of these CDR H3s was "fixed" prior to alignment. Four of the seven sequences (BLV1H12, BLV5D3, BLV8C11, and BF4E9) contain four cysteines in the same positions as $D_H$2, but also have additional cysteines. BLV5B8 has two cysteines in common with the germline $D_H$2. This limited homology with some cysteine conservation suggests that mutation of $D_H$2 could generate these sequences. B-L1 and B-L2 are from initial sequences from bovine spleen, and the remaining are selected ultralong CDR H3 sequences from deep sequencing data. The first group contains the longest CDR H3s identified, and appear clonally related. The * indicates a sequence represented 167 times, suggesting it was strongly selected for function. Several of the eight-cysteine sequences appear selected for function as they were represented multiple times, indicated in parentheses. Other representative sequences of various lengths are indicated in the last group. The framework cysteine and tryptophan residues that define the CDR H3 boundaries are double-underlined. The sequences BLV1H12 through UL-77 (left-most column) presented in Tables 2A-C are depicted broken apart into four segments to identify the segments of amino acid residues that are derived from certain germline sequences and V/D/J joining sequences. Moving from left to right, the first segment is derived from the $V_H$ germline and is represented in the disclosure as a $X^1X^2X^3X^4X^5$ motif. The second segment represents sequences from V-D joining and is represented in the disclosure as $X_n$. The third segment is a string of amino acid residues derived from $D_H$2 germline, and the fourth segment is a string of amino acid residues derived from $J_H$1 germline region.

FIG. 3 depicts a sequence alignment of exemplary bovine-derived ultralong CDR3 sequences designated BLV1H12, BLV5B8, BLV5D3, BLV8C11, BF4E9, BF1H1, or F18.

FIG. 4 shows an exemplary bovine germline heavy chain variable region ($V_H$) sequence designated VH-UL suitable for modification or use with an ultralong CDR3 sequence.

FIG. 5A-B shows exemplary human germline heavy chain variable region sequences designated 4-39, 4-59*03, 4-34*09, and 4-34*02 that are suitable for modification or use with an ultralong CDR3 sequence (A) and an alignment of these sequences (B).

FIG. 6 shows an exemplary bovine light chain variable region sequence designated BLV1H12 suitable for modification or use with an ultralong CDR 3 sequence (e.g., a heavy chain variable region sequence comprising an ultralong CDR3 sequence).

FIG. 7A-B shows exemplary light chain variable region sequences designated VI1-47, VI1-40*1, VI1-51*01, and VI2-18*02 that are suitable for modification or use with an ultralong CDR 3 sequence (A) and an alignment of these sequences (B).

FIG. 8 shows exemplary heavy chain variable region sequences.

FIG. 9 shows exemplary light chain variable region sequences.

FIG. 10 shows exemplary heavy chain variable region sequences having IL-8 non-antibody sequences.

FIG. 11 shows exemplary light chain variable and constant region sequences.

FIG. 12 shows exemplary amino acids sequences.

FIG. 13 shows exemplary nucleic acid Linker-Bsal-Linker sequences introduced into BLV1H12 sequences.

FIG. 14 shows exemplary BLV1H12 heavy chain amino acid sequences with toxin sequences inserted at CDR3 with a variety of linkers.

FIG. 15 shows exemplary amino acids sequences of heavy variable regions and light chains (VL-CL).

FIG. 16 shows exemplary linker amino acid sequences.

FIG. 17 shows exemplary amino acid sequences for toxins.

FIG. 18 shows exemplary nucleic acid sequences for toxins.

FIG. 19 shows exemplary A regions, D regions and V2 regions of variable heavy chains from HIV-1 neutralizing antibodies.

FIG. 21 shows exemplary amino acid and nucleic acid sequences for heavy chain variable regions described and referenced herein by BID number, IgG Name and/or Heavy Chain Name.

FIG. 22 shows_shows exemplary amino acid and nucleic acid sequences for light chain variable regions described and referenced herein by BID number, IgG Name and/or Light Chain Name.

DETAILED DESCRIPTION

Figure 20:
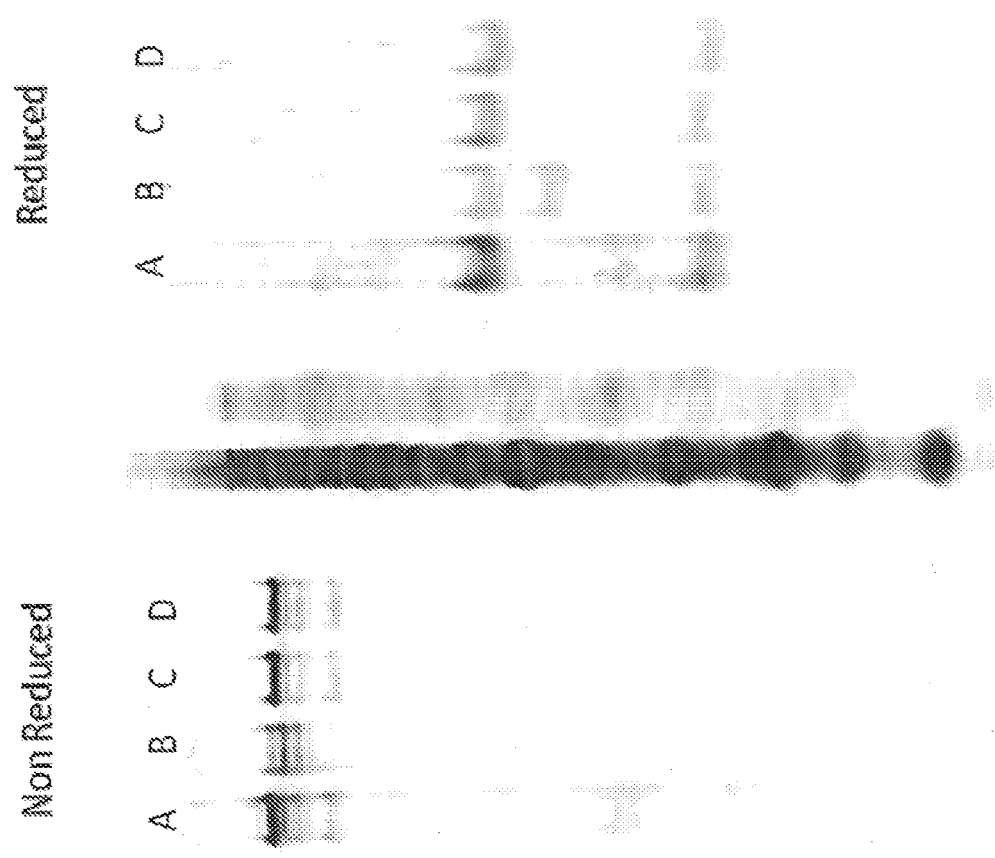
FIG. 20 shows exemplary sodium dodecyl sulfate polyacrylamide gel electrophoresis (SDS-PAGE) of antibody samples (VH4-34 MutE 1×G4S ShK (BID #56) and VH4-34 MutE NoLinker ShK (BID #59)) purified from CHO (e.g., CHO-S) and HEK (e.g., 293F) cells.

The present disclosure provides humanized antibodies comprising heavy chain variable regions comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence, along with materials for (e.g., protein sequences, genetic sequences, cells, libraries) and methods of making the antibodies (e.g., humanizing methods, library methods). Such humanized antibodies may be useful for the treatment or prevention of a variety of diseases, disorders, or conditions, including inflammatory diseases, disorders or conditions, autoimmune diseases, disorders or conditions, metabolic diseases, disorders or conditions, neoplastic diseases, disorders or conditions, and cancers.

The present disclosure also provides humanized antibodies comprising heavy chain variable regions comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence, wherein the CDR3 sequences are 35 amino acids in length or longer (e.g., 40 or longer, 45 or longer, 50 or longer, 55 or longer, 60 or longer) and/or wherein the CDR3 sequences have at least 3 cysteine residues or more (e.g., 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues). Such antibodies, as described herein, bind (e.g., specifically or selectively bind) a variety of targets, including, for example protein targets such as transmembrane proteins (e.g., GPCRs, ion channels, transporter, cell surface receptors).

The present disclosure also provides methods and materials for the preparation or making of humanized antibodies comprising heavy chain variable regions comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence. Such materials include proteins, genetic sequences, cells and libraries. Such methods include methods of humanization and method of making and screening libraries.

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3. In some embodiments, the ultralong CDR3 may be 35 amino acids in length or longer, 40 amino acids in length or longer, 45 amino acids in length or longer, 50 amino acids in length or longer, 55 amino acids in length or longer, or 60 amino acids in length or longer. In some embodiments, the ultralong CDR3 may comprise 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues. The ultralong CDR3 may comprise a cysteine motif including, for example, where the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_1CCX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_1CCX_6CX_5CXCX_{17}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95). Alternatively, the ultralong CDR3 may comprise a cysteine motif including, for example, where the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_5CX_7CX_5CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_1CCX_3CX_4CCX_4C$ (SEQ ID NO: 139), $CX_9CX_4CCX_5CX_4C$ (SEQ ID NO: 140), $CX_1CCX_3CX_4CX_7CXC$ (SEQ ID NO: 141), $CX_7CX_7CX_2CX_2CX_3C$ (SEQ ID NO: 142), $CX_5CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3, wherein the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q). In some embodiments, the $X^1X^2X^3X^4X^5$ motif may be TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3, wherein the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4. In some embodiments, the $(X^aX^b)_z$ motif may be CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3, wherein the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_1C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CXCX_8C$ (SEQ ID NO: 84), $CX_1CCX_6CX_5CXCX_4CXCX_9C$ (SEQ ID NO: 85), $CX_{11}CX_4CX_5CX_8CX_2C$ (SEQ ID NO: 86), $CX_1CCX_6CX_5CX_8CX_2C$ (SEQ ID NO: 87), $CX_{10}CX_6CX_5CXCX_8C$ (SEQ ID NO: 88), $CX_1CCX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95), and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

The present disclosure provides a humanized antibody or binding fragment thereof comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCX_4CX_4CX_{12}C$ (SEQ ID NO: 104), $CX_6CX_2CX_3CCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCCX_1CCX_2CX_3C$ (SEQ ID NO: 125), $CX_3CX_5CX_5CX_4CCX_1CCX_6C$ (SEQ ID NO: 126), $CX_9CX_5CX_4CCXCX_5CX_4C$ (SEQ ID NO: 127), $CX_7CXCX_6CX_4CCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_1CCX_3CX_4CCX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

The present disclosure also provides methods of generating a library of humanized antibodies that comprises an ultralong CDR3, comprising: combining a nucleic acid sequence encoding an ultralong CDR3 with a nucleic acid sequence encoding a human variable region framework (FR) sequence to produce nucleic acids encoding for humanized antibodies that comprises an ultralong CDR3; and expressing the nucleic acids encoding for humanized antibodies that comprises an ultralong CDR3 to generate a library of humanized antibodies that comprises an ultralong CDR3.

The present disclosure also provides methods of generating a library of humanized antibodies or binding fragments thereof comprising an ultralong CDR3 that comprises a non-antibody sequence, comprising: combining a nucleic acid sequence encoding an ultralong CDR3, a nucleic acid sequence encoding a human variable region framework (FR) sequence, and a nucleic acid sequence encoding a non-antibody sequence to produce nucleic acids encoding humanized antibodies or binding fragments thereof comprising an ultralong CDR3 and a non-antibody sequence, and expressing the nucleic acids encoding humanized antibodies or binding fragments thereof comprising an ultralong CDR3 and a non-antibody sequence to generate a library of humanized antibodies or binding fragments thereof comprising an ultralong CDR3 and a non-antibody sequence.

The present disclosure also provides libraries of humanized antibodies or binding fragments thereof comprising an ultralong CDR3 that comprises a non-antibody sequence.

The present disclosure also provides methods of generating a library of humanized antibodies or binding fragments thereof comprising an ultralong CDR3 that comprises a cysteine motif, comprising: combining a human variable region framework (FR) sequence, and a nucleic acid sequence encoding an ultralong CDR3 and a cysteine motif; introducing one or more nucleotide changes to the nucleic acid sequence encoding one or more amino acid residues that are positioned between one or more cysteine residues in the cysteine motif for nucleotides encoding different amino acid residues to produce nucleic acids encoding humanized antibodies or binding fragments thereof comprising an ultralong CDR3 and a cysteine motif with one or more nucleotide changes introduced between one or more cysteine residues in the cysteine domain; and expressing the nucleic acids encoding humanized antibodies or binding fragments thereof comprising an ultralong CDR3 and a cysteine motif with one or more nucleotide changes introduced between one or more cysteine residues in the cysteine domain to generate a library of humanized antibodies or binding fragments thereof comprising an ultralong CDR3 and a cysteine motif with one or more amino acid changes introduced between one or more cysteine residues in the cysteine domain.

The present disclosure also provides libraries of humanized antibodies or binding fragments thereof comprising an ultralong CDR3 that comprises a cysteine motif, wherein the antibodies or binding fragments comprise one or more substitutions of amino acid residues that are positioned between cysteine residues in the cysteine motif.

The present disclosure also provides methods of generating a library of humanized antibodies or binding fragments thereof comprising a bovine ultralong CDR3, comprising: combining a nucleic acid sequence encoding a human variable region framework (FR) sequence and a nucleic acid encoding a bovine ultralong CDR3, and expressing the nucleic acids encoding a human variable region framework (FR) sequence and a nucleic acid encoding a bovine ultralong CDR3 to generate a library of humanized antibodies or binding fragments thereof comprising a bovine ultralong CDR3.

Proteins

The present disclosure provides humanized antibodies comprising heavy chain variable regions comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence.

In an embodiment, the present disclosure provides a humanized antibody comprising an ultralong CDR3, wherein the CDR3 is 35 amino acids in length or more (e.g., 40 or more, 45 or more, 50 or more, 55 or more, 60 or more). Such a humanized antibody may comprise at least 3 cysteine residues or more (e.g., 4 or more, 6 or more, 8 or more) within the ultralong CDR3.

In another embodiment, the present disclosure provides a humanized antibody comprising an ultralong CDR3, wherein the CDR3 is 35 amino acids in length or more and is derived from or based on a non-human sequence. The ultralong CDR3 sequence may be derived from any species that naturally produces ultralong CDR3 antibodies, including ruminants such as cattle (*Bos taurus*).

In another embodiment, the present disclosure provides a humanized antibody comprising an ultralong CDR3, wherein the CDR3 is 35 amino acids in length or more and is derived from a non-antibody sequence. The non-antibody sequence may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be of human or non-human origin and may comprise a portion of a non-antibody protein such as a peptide or domain. The non-antibody sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the humanized antibody.

In another embodiment, the present disclosure provides a humanized antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides for a humanized antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides a humanized antibody comprising an ultralong CDR3, wherein the CDR3 is 35 amino acids in length or more and comprises at least 3 cysteine residues or more, wherein the partially human ultralong CDR3 is a component of an immunoconjugate.

In another embodiment, the present disclosure provides a humanized antibody comprising an ultralong CDR3, wherein the CDR3 is 35 amino acids in length or more and comprises at least 3 cysteine residues or more, wherein the humanized antibody comprising an ultralong CDR3 binds to a transmembrane protein target. Such transmembrane targets may include, but are not limited to, GPCRs, ion channels, transporters, and cell surface receptors.

Genetic Sequences

The present disclosure provides genetic sequences (e.g., genes, nucleic acids, polynucleotides) encoding humanized antibodies comprising a heavy chain variable region comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence.

The present disclosure also provides genetic sequences (e.g., genes, nucleic acids, polynucleotides) encoding an ultralong CDR3.

In an embodiment, the present disclosure provides genetic sequences encoding a humanized antibody comprising an ultralong CDR3, wherein the CDR3 is 35 amino acids in length or more (e.g., 40 or more, 45 or more, 50 or more, 55 or more, 60 or more). Such a humanized antibody may comprise at least 3 cysteine residues or more (e.g., 4 or more, 6 or more, 8 or more) within the ultralong CDR3.

In another embodiment, the present disclosure provides genetic sequences encoding a humanized antibody comprising an ultralong CDR3, wherein the CDR3 is 35 amino acids in length or more and is derived from or based on a non-human sequence. The genetic sequences encoding the ultralong CDR3 may be derived from any species that naturally produces ultralong CDR3 antibodies, including ruminants such as cattle (*Bos taurus*).

In another embodiment, the present disclosure provides genetic sequences encoding a humanized antibody comprising an ultralong CDR3, wherein the CDR3 is 35 amino acids in length or more and is derived from a non-antibody protein sequence. The genetic sequences encoding the non-antibody protein sequences may be derived from any protein family including, but not limited to, chemokines, growth factors, peptides, cytokines, cell surface proteins, serum proteins, toxins, extracellular matrix proteins, clotting factors, secreted proteins, etc. The non-antibody protein sequence may be of human or non-human origin and may comprise a portion of a non-antibody protein such as a peptide or domain. The non-antibody protein sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the humanized antibody.

In another embodiment, the present disclosure provides genetic sequences encoding a humanized antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides genetic sequences encoding a humanized antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides genetic sequences encoding a humanized antibody comprising an ultralong CDR3, wherein the CDR3 is 35 amino acids in length or more and comprises at least 3 cysteine residues or more, wherein the ultralong CDR3 is a component of an immunoconjugate.

In another embodiment, the present disclosure provides genetic sequences encoding a humanized antibody comprising an ultralong CDR3 wherein the CDR3 is 35 amino acids in length or more and comprises at least 3 cysteine residues or more and wherein the humanized antibody comprising an ultralong CDR3 binds to a transmembrane protein target. Such transmembrane targets may include, but are not limited to, GPCRs, ion channels, transporters, and cell surface receptors.

Libraries and Arrays

The present disclosure provides collections, libraries, and arrays of humanized antibodies comprising ultralong CDR3 sequences.

In an embodiment, the present disclosure provides a library or an array of humanized antibodies comprising ultralong CDR3 sequences wherein at least two members of the library or array differ in the positions of at least one of the cysteines in the ultralong CDR3 sequence. Structural diversity may be enhanced through different numbers of cysteines in the ultralong CDR3 sequence (e.g., at least 3 or more cysteine residues such as 4 or more, 6 or more and 8 or more) and/or through different disulfide bond formation, and hence different loop structures.

In another embodiment, the present disclosure provides for a library or an array of humanized antibodies comprising ultralong CDR3 sequences wherein at least two members of the library or the array differ in at least one amino acid located between cysteines in the ultralong CDR3. In this regard, members of the library or the array can contain cysteines in the same positions of CDR3, resulting in similar overall structural folds, but with fine differences brought about through different amino acid side chains. Such libraries or arrays may be useful for affinity maturation.

In another embodiment, the present disclosure provides libraries or arrays of humanized antibodies comprising ultralong CDR3 sequences wherein at least two of the ultralong CDR3 sequences differ in length (e.g., 35 amino acids in length or more such as 40 or more, 45 or more, 50 or more, 55 or more and 60 or more). The amino acid and cysteine content may or may not be altered between the members of the library or the array. Different lengths of ultralong CDR3 sequences may provide for unique binding sites, including, for example, due to steric differences, as a result of altered length.

In another embodiment, the present disclosure provides libraries or arrays of humanized antibodies comprising ultralong CDR3 sequences wherein at least two members of the library differ in the human framework used to construct the humanized antibody comprising an ultralong CDR3.

In another embodiment, the present disclosure provides libraries or arrays of humanized antibodies comprising ultralong CDR3 sequences wherein at least two members of the library or the array differ in having a non-antibody protein sequence that comprises a portion of the ultralong CDR3. Such libraries or arrays may contain multiple non-antibody protein sequences, including for chemokines, growth factors, peptides, cytokines, cell surface proteins, serum proteins, toxins, extracellular matrix proteins, clotting factors, secreted proteins, viral or bacterial proteins, etc. The non-antibody protein sequence may be of human or non-human origin and may be comprised of a portion of a non-antibody protein such as a peptide or domain. The non-antibody protein sequence of the ultralong CDR3 may contain mutations from its natural sequence, including amino acid changes (e.g., substitutions), or insertions or deletions. Engineering additional amino acids at the junction between the non-antibody sequence within the ultralong CDR3 may be done to facilitate or enhance proper folding of the non-antibody sequence within the humanized antibody.

The libraries or the arrays of the present disclosure may be in several formats well known in the art. The library or the array may be an addressable library or an addressable array. The library or array may be in display format, for example, the antibody sequences may be expressed on phage, ribosomes, mRNA, yeast, or mammalian cells.

Cells

The present disclosure provides cells comprising genetic sequences encoding humanized antibodies comprising heavy chain variable regions comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence.

In an embodiment, the present disclosure provides cells expressing a humanized antibody comprising an ultralong CDR3. The cells may be prokaryotic or eukaryotic, and a humanized antibody comprising an ultralong CDR3 may be expressed on the cell surface or secreted into the media. When displayed on the cell surface a humanized antibody preferentially contains a motif for insertion into the plasmid membrane such as a membrane spanning domain at the C-terminus or a lipid attachment site. For bacterial cells, a humanized antibody comprising an ultralong CDR3 may be secreted into the periplasm. When the cells are eukaryotic, they may be transiently transfected with genetic sequences encoding a humanized antibody comprising an ultralong CDR3. Alternatively, a stable cell line or stable pools may be created by transfecting or transducing genetic sequences encoding a humanized antibody comprising an ultralong CDR3 by methods well known to those of skill in the art. Cells can be selected by fluorescence activated cell sorting (FACS) or through selection for a gene encoding drug resistance. Cells useful for producing humanized antibodies comprising ultralong CDR3 sequences include prokaryotic cells like *E. coli*, eukaryotic cells like the yeasts *Saccharomyces cerevisiae* and *Pichia pastoris*, chinese hamster ovary (CHO) cells, monkey cells like COS-1, or human cells like HEK-293, HeLa, SP-1.

Humanization Methods

The present disclosure provides methods for making humanized antibodies comprising ultralong CDR3 sequences, comprising the steps of engineering an ultralong CDR3 sequence derived from a non-human CDR3 into a human framework. The human framework may be of germline origin, or may be derived from non-germline (e.g. mutated or affinity matured) sequences. Genetic engineering techniques well known to those in the art, including as disclosed herein, may be used to generate a hybrid DNA sequence containing a human framework and a non-human ultralong CDR3. Unlike human antibodies which may be encoded by V region genes derived from one of seven families, bovine antibodies which produce ultralong CDR3 sequences appear to utilize a single V region family which may be considered to be most homologous to the human VH4 family. In a preferred embodiment where ultralong CDR3 sequences derived from cattle are to be humanized to produce an antibody comprising an ultralong CDR3, human V region sequences derived from the VH4 family may be genetically fused to a bovine-derived ultralong CDR3 sequence. Exemplary VH4 germline gene sequences in the human antibody locus are shown in FIG. 5A (e.g., SEQ ID NOS: 31-34; and 368-371).

The present disclosure also provides methods of humanizing an antibody variable region comprising the step of genetically combining a nucleic acid sequence encoding a non-human ultralong CDR3 (ULCDR3) with a nucleic acid sequence encoding a human variable region framework (FR) sequence. Also provided are methods of making a humanized antibody variable region comprising selecting a human framework sequence comprising FR1, FR2, and FR3; selecting a CDR1 sequence; selecting a CDR2 sequence; selecting an ultralong CDR3 sequence; and combining the sequences as FR1-CDR1-FR2-CDR2-FR3-ULCDR3. Also provided are methods of making a humanized antibody variable region sequence comprising selecting a human antibody variable region sequence comprising a sequence encoding FR1-CDR1-FR2-CDR2-FR3; selecting a sequence encoding a non-human ultralong CDR3 (ULCDR3); and genetically fusing the human sequence of step (a) in frame with the non-human sequence of step (b) to generate a sequence encoding FR1-CDR1-FR2-CDR2-FR3-ULCDR3.

In an embodiment, the present disclosure provides a fusion of a human VH4 framework sequence to a bovine-derived ultralong CDR3, for example, as may be accomplished through the following steps. First, the second cysteine of a V region genetic sequence is identified along with the nucleotide sequence encoding the second cysteine. Generally, the second cysteine marks the boundary of the framework and CDR3 two residues upstream (N-terminal) of the CDR3. Second, the second cysteine in a bovine-derived V region sequence is identified which similarly marks 2 residues upstream (N-terminal) of the CDR3. Third, the genetic material encoding the human V region is combined with the genetic sequence encoding the ultralong CDR3. Thus, a genetic fusion may be made, wherein the ultralong CDR3 sequence is placed in frame of the human V region sequence. Preferably a humanized antibody comprising an ultralong CDR3 is as near to human in amino acid composition as possible. Optionally, a J region sequence may be mutated from bovine-derived sequence to a human sequence. Also optionally, a humanized heavy chain may be paired with a human light chain.

In another embodiment, the present disclosure provides pairing of a human ultralong CDR3 heavy chain with a non-human light chain.

In another embodiment, the present disclosure provides pairing of a humanized heavy chain comprising an ultralong CDR3 with a human light chain. Preferably the light chain is homologous to a bovine light chain known to pair with a bovine ultralong CDR3 heavy chain. An exemplary bovine light chain is shown in FIG. 7A (e.g., SEQ ID NO: 36-39; and 373-376).

Library Methods

The present disclosure provides methods for making libraries comprising humanized antibodies comprising heavy chain variable regions comprising: (a) an amino acid sequence selected from the group consisting of: (i) SEQ ID NO: 734 or SEQ ID NO: 735, (ii) SEQ ID NO: 736 or SEQ ID NO: 737, (iii) SEQ ID NO: 738 or SEQ ID NO: 739, (iv) SEQ ID NO: 740 or SEQ ID NO: 741, (v) SEQ ID NO: 742 or SEQ ID NO: 743, (vi) SEQ ID NO: 744 or SEQ ID NO: 745, (vii) SEQ ID NO: 746 or SEQ ID NO 747, and (viii) SEQ ID NO: 748 or SEQ ID NO:749; and (b) an ultralong CDR3 sequence. Methods for making libraries of spatially addressed libraries are described in WO 2010/054007. Methods of making libraries in yeast, phage, E. coli, or mammalian cells are well known in the art.

The present disclosure also provides methods of screening libraries of humanized antibodies comprising ultralong CDR3 sequences.

Definitions

An "ultralong CDR3" or an "ultralong CDR3 sequence", used interchangeably herein, comprises a CDR3 or CDR3 sequence that is not derived from a human antibody sequence. An ultralong CDR3 may be 35 amino acids in length or longer, for example, 40 amino acids in length or longer, 45 amino acids in length or longer, 50 amino acids in length or longer, 55 amino acids in length or longer, or 60 amino acids in length or longer. The length of the ultralong CDR3 may include a non-antibody sequence. An ultralong CDR3 may comprise a non-antibody sequence, including, for example, an interleukin sequence, a hormone sequence, a cytokine sequence, a toxin sequence, a lymphokine sequence, a growth factor sequence, a chemokine sequence, a toxin sequence, or combinations thereof. Preferably, the ultralong CDR3 is a heavy chain CDR3 (CDR-H3 or CDRH3). Preferably, the ultralong CDR3 is a sequence derived from or based on a ruminant (e.g., bovine) sequence. Preferably, the ultralong CDR3 comprises an amino acid sequence of SEQ ID NO: 498, SEQ ID NO: 499 or both. Alternatively or additionally, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515); (iii) any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529); or (v) any one of DKGDSDYDYNL (SEQ ID NO: 530), DKGDSDYDYN (SEQ ID NO: 531), DKGDSDYDY (SEQ ID NO: 532), DKGDSDYD (SEQ ID NO: 533), DKGDSDY (SEQ ID NO: 534), DKGDSD (SEQ ID NO: 535). Alternatively or additionally, the ultralong CDR3 comprises an amino acid sequence of: (i) any one of YGPNYEEWGDYLATLDV (SEQ ID NO: 536), GPNYEEWGDYLATLDV (SEQ ID NO: 537), PNYEEWGDYLATLDV (SEQ ID NO: 538), NYEEWGDYLATLDV (SEQ ID NO: 539), YEEWGDYLATLDV (SEQ ID NO:

540), or EEWGDYLATLDV (SEQ ID NO: 541); (ii) any one of YDFYDGYYNYHYMDV (SEQ ID NO: 542), DFYDGYYNYHYMDV (SEQ ID NO: 543), FYDGYYNY-HYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of YDFNDGYYNY-HYMDV (SEQ ID NO: 549), DFYDGYYNYHYMDV (SEQ ID NO: 550), FYDGYYNYHYMDV (SEQ ID NO: 551), YDGYYNYHYMDV (SEQ ID NO: 552), DGYYNY-HYMDV (SEQ ID NO: 553), or GYYNYHYMDV (SEQ ID NO: 554); (iv) any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); or (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569). Alternatively or addition-ally, the ultralong CDR3 comprises an amino acid sequence of: (i) any one of GSKHRLRDYFLYNE (SEQ ID NO: 501), GSKHRLRDYFLYN (SEQ ID NO: 502), GSKHRLRDYFLY (SEQ ID NO: 503), GSKHRLRDYFL (SEQ ID NO: 504), GSKHRLRDYF (SEQ ID NO: 505), GSKHRLRDY (SEQ ID NO: 506), or GSKHRLRD (SEQ ID NO: 507), and any one of YGPNYEEWGDYLATLDV (SEQ ID NO: 536), GPNYEEWGDYLATLDV (SEQ ID NO: 537), PNYEEWGDYLATLDV (SEQ ID NO: 538), NYEEWGDYLATLDV (SEQ ID NO: 539), YEEWGDY-LATLDV (SEQ ID NO: 540), or EEWGDYLATLDV (SEQ ID NO: 541); (ii) any one of EAGGPDYRNGYNY (SEQ ID NO: 508), EAGGPDYRNGYN (SEQ ID NO: 509), EAGGPDYRNGY (SEQ ID NO: 510), EAGGPDYRNG (SEQ ID NO: 511), EAGGPDYRN (SEQ ID NO: 512), EAGGPDYR (SEQ ID NO: 513), EAGGPDY (SEQ ID NO: 514), or EAGGPD (SEQ ID NO: 515), and any one of YDFYDGYYNYHYMDV (SEQ ID NO: 542), DFYDGYYNYHYMDV (SEQ ID NO: 543), FYDGYYNY-HYMDV (SEQ ID NO: 544), YDGYYNYHYMDV (SEQ ID NO: 545), DGYYNYHYMDV (SEQ ID NO: 546), GYYNYHYMDV (SEQ ID NO: 547), or YYNYHYMDV (SEQ ID NO: 548); (iii) any one of EAGGPIWHDDVKY (SEQ ID NO: 516), EAGGPIWHDDVK (SEQ ID NO: 517), EAGGPIWHDDV (SEQ ID NO: 518), EAGGPIWHDD (SEQ ID NO: 519), EAGGPIWHD (SEQ ID NO: 520), EAGGPIWH (SEQ ID NO: 521), EAGGPIW (SEQ ID NO: 522), or EAGGPI (SEQ ID NO: 523), and any one of YDFNDGYYNYHYMDV (SEQ ID NO: 549), DFYDGYYNYHYMDV (SEQ ID NO: 550), FYDGYYNY-HYMDV (SEQ ID NO: 551), YDGYYNYHYMDV (SEQ ID NO: 552), DGYYNYHYMDV (SEQ ID NO: 553), or GYYNYHYMDV (SEQ ID NO: 554); (iv) any one of GTDYTIDDQGI (SEQ ID NO: 524), GTDYTIDDQG (SEQ ID NO: 525), GTDYTIDDQ (SEQ ID NO: 526), GTDYTIDD (SEQ ID NO: 527), GTDYTID (SEQ ID NO: 528), or GTDYTI (SEQ ID NO: 529), and any one of QGIRYQGSGTFWYFDV (SEQ ID NO: 555), GIRYQGSGTFWYFDV (SEQ ID NO: 556), IRYQGSGTFWYFDV (SEQ ID NO: 557), RYQGSGTFWYFDV (SEQ ID NO: 558), YQGSGTFWYFDV (SEQ ID NO: 559), QGSGTFWYFDV (SEQ ID NO: 560), GSGTFWYFDV (SEQ ID NO: 561), SGTFWYFDV (SEQ ID NO: 562), or GTFWYFDV (SEQ ID NO: 563); or (v) any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569), and any one of YNLGYSYFYYMDG (SEQ ID NO: 564), NLGYSYFYYMDG (SEQ ID NO: 565), LGYSYFYYMDG (SEQ ID NO: 566), GYSYFYYMDG (SEQ ID NO: 567), YSYFYYMDG (SEQ ID NO: 568), or SYFYYMDG (SEQ ID NO: 569). An ultralong CDR3 may comprise at least 3 or more cysteine residues, for example, 4 or more cysteine residues, 6 or more cysteine residues, 8 or more cysteine residues, 10 or more cysteine residues, or 12 or more cysteine residues (e.g., 3, 4, 5, 6, 7, 8, 9, 10, 11, 12 or more). An ultralong CDR3 may comprise one or more of the following motifs: a cysteine motif, a $X^1X^2X^3X^4X^5$ motif, a $CX^1X^2X^3X^4X^5$ motif, or a $(X^aX^b)_z$ motif. A "cys-teine motif" is a segment of amino acid residues in an ultralong CDR3 that comprises 3 or more cysteine residues including, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues. A cysteine motif may comprise an amino acid sequence selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_1CCX_6CX_5CXCX_{11}C$ (SEQ ID NO: 80), $CX_{16}CX_5CXCXCX_{14}C$ (SEQ ID NO: 81), $CX_1CCX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), CX$_{10}$CX$_6$CX$_5$CXCX$_8$C (SEQ ID NO: 88), CX$_{10}$CX$_6$CX$_5$CXCX$_3$CX$_8$CX$_2$C (SEQ ID NO: 89), CX$_{10}$CX$_6$CX$_5$CX$_3$CX$_8$C (SEQ ID NO: 90), CX$_{10}$CX$_6$CX$_5$CXCX$_2$CX$_6$CX$_5$C (SEQ ID NO: 91), CX$_7$CX$_6$CX$_3$CX$_3$CX$_9$C (SEQ ID NO: 92), CX$_9$CX$_8$CX$_5$CX$_6$CX$_5$C (SEQ ID NO: 93), CX$_{10}$CX$_2$CX$_2$CX$_7$CXCX$_{11}$CX$_5$C (SEQ ID NO: 94), and CX$_{10}$CX$_6$CX$_5$CXCX$_2$CX$_8$CX$_4$C (SEQ ID NO: 95). Alternatively, a cysteine motif may comprise an amino acid sequence selected from the group consisting of: CCX$_3$CXCX$_3$CX$_2$CCXCX$_5$CX$_9$CX$_5$CXC (SEQ ID NO: 96), CX$_6$CX$_2$CX$_5$CX$_4$CCXCX$_4$CX$_6$CXC (SEQ ID NO: 97), CX$_7$CXCX$_5$CX$_4$CCX$_4$CX$_6$CXC (SEQ ID NO: 98), CX$_9$CX$_3$CXCX$_2$CXCCCX$_6$CX$_4$C (SEQ ID NO: 99), CX$_5$CX$_3$CXCX$_4$CX$_4$CCX$_{10}$CX$_2$CC (SEQ ID NO: 100), CX$_5$CXCX$_1$CXCX$_3$CCX$_3$CX$_4$CX$_{10}$C (SEQ ID NO: 101), CX$_9$CCCX$_3$CX$_4$CCCX$_5$CX$_6$C (SEQ ID NO: 102), CCX$_8$CX$_5$CX$_4$CX$_3$CX$_4$CCXCX$_1$C (SEQ ID NO: 103), CCX$_6$CCX$_5$CCX$_4$CX$_4$CX$_{12}$C (SEQ ID NO: 104), CX$_6$CX$_2$CX$_3$CCX$_4$CX$_5$CX$_3$CX$_3$C (SEQ ID NO: 105), CX$_3$CX$_5$CX$_6$CX$_4$CCXCX$_5$CX$_4$CXC (SEQ ID NO: 106), CX$_4$CX$_4$CCX$_4$CX$_4$CXCX$_{11}$CX$_2$CXC (SEQ ID NO: 107), CX$_5$CX$_2$CCX$_5$CX$_4$CCX$_3$CCX$_7$C (SEQ ID NO: 108), CX$_5$CX$_5$CX$_3$CX$_2$CXCCX$_4$CX$_7$CXC (SEQ ID NO: 109), CX$_3$CX$_7$CX$_3$CX$_4$CCXCX$_2$CX$_5$CX$_2$C (SEQ ID NO: 110), CX$_9$CX$_3$CXCX$_4$CCX$_5$CCCX$_6$C (SEQ ID NO: 111), CX$_9$CX$_3$CXCX$_2$CXCCX$_6$CX$_3$CX$_3$C (SEQ ID NO: 112), CX$_8$CCXCX$_3$CCX$_3$CXCX$_3$CX$_4$C (SEQ ID NO: 113), CX$_9$CCX$_4$CX$_2$CXCCXCX$_4$CX$_3$C (SEQ ID NO: 114), CX$_{10}$CXCX$_3$CX$_2$CXCCX$_4$CX$_5$CXC (SEQ ID NO: 115), CX$_9$CXCX$_3$CX$_2$CXCCX$_4$CX$_5$CXC (SEQ ID NO: 116), CX$_6$CCXCX$_5$CX$_4$CCXCX$_5$CX$_2$C (SEQ ID NO: 117), CX$_6$CCXCX$_3$CXCCX$_3$CX$_4$CC (SEQ ID NO: 118), CX$_6$CCXCX$_3$CXCX$_2$CXCX$_4$CX$_8$C (SEQ ID NO: 119), CX$_4$CX$_2$CCX$_3$CXCX$_4$CCX$_2$CX$_3$C (SEQ ID NO: 120), CX$_3$CX$_5$CX$_3$CCX$_4$CX$_9$C (SEQ ID NO: 121), CCX$_9$CX$_3$CXCCX$_3$CX$_5$C (SEQ ID NO: 122), CX$_9$CX$_2$CX$_3$CX$_4$CCX$_4$CX$_5$C (SEQ ID NO: 123), CX$_9$CX$_7$CX$_4$CCXCX$_7$CX$_3$C (SEQ ID NO: 124), CX$_9$CX$_3$CCX$_{10}$CX$_2$CX$_3$C (SEQ ID NO: 125), CX$_3$CX$_5$CX$_5$CX$_4$CCX$_{10}$CX$_6$C (SEQ ID NO: 126), CX$_9$CX$_5$CX$_4$CCXCX$_5$CX$_4$C (SEQ ID NO: 127), CX$_7$CXCX$_6$CX$_4$CCX$_{10}$C (SEQ ID NO: 128), CX$_8$CX$_2$CX$_4$CCX$_4$CX$_3$CX$_3$C (SEQ ID NO: 129), CX$_7$CX$_5$CXCX$_4$CCX$_7$CX$_4$C (SEQ ID NO: 130), CX$_{11}$CX$_3$CX$_4$CCCX$_8$CX$_2$C (SEQ ID NO: 131), CX$_2$CX$_3$CX$_4$CCX$_4$CX$_5$CX$_{15}$C (SEQ ID NO: 132), CX$_9$CX$_5$CX$_4$CCX$_7$C (SEQ ID NO: 133), CX$_9$CX$_7$CX$_3$CX$_2$CX$_6$C (SEQ ID NO: 134), CX$_9$CX$_5$CX$_4$CCX$_{14}$C (SEQ ID NO: 135), CX$_9$CX$_5$CX$_4$CCX$_8$C (SEQ ID NO: 136), CX$_9$CX$_6$CX$_4$CCXC (SEQ ID NO: 137), CX$_5$CCX$_7$CX$_4$CX$_{12}$ (SEQ ID NO: 138), CX$_1$CCX$_3$CX$_4$CCX$_4$C (SEQ ID NO: 139), CX$_9$CX$_4$CCX$_5$CX$_4$C (SEQ ID NO: 140), CX$_1$CCX$_3$CX$_4$CX$_7$CXC (SEQ ID NO: 141), CX$_7$CX$_7$CX$_2$CX$_2$CX$_3$C (SEQ ID NO: 142), CX$_9$CX$_4$CX$_4$CCX$_6$C (SEQ ID NO: 143), CX$_7$CXCX$_3$CXCX$_6$C (SEQ ID NO: 144), CX$_7$CXCX$_4$CXCX$_4$C (SEQ ID NO: 145), CX$_9$CX$_5$CX$_4$C (SEQ ID NO: 146), CX$_3$CX$_6$CX$_8$C (SEQ ID NO: 147), CX$_{10}$CXCX$_4$C (SEQ ID NO: 148), CX$_{10}$CCX$_4$C (SEQ ID NO: 149), CX$_{15}$C (SEQ ID NO: 150), CX$_{10}$C (SEQ ID NO: 151), and CX$_9$C (SEQ ID NO: 152). A cysteine motif is preferably positioned within an ultralong CDR3 between a X$^1$X$^2$X$^3$X$^4$X$^5$ motif and a (X$^a$X$^b$)$_z$ motif. A "X$^1$X$^2$X$^3$X$^4$X$^5$ motif" is a series of five consecutive amino acid residues in an ultralong CDR3, wherein X$^1$ is threonine (T), glycine (G), alanine (A), serine (S), or valine (V), wherein X$^2$ is serine (S), threonine (T), proline (P), isoleucine (I), alanine (A), valine (V), or asparagine (N), wherein X$^3$ is valine (V), alanine (A), threonine (T), or aspartic acid (D), wherein X$^4$ is histidine (H), threonine (T), arginine (R), tyrosine (Y), phenylalanine (F), or leucine (L), and wherein X$^5$ is glutamine (Q). In some embodiments, the X$^1$X$^2$X$^3$X$^4$X$^5$ motif may be TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184). A "CX$^1$X$^2$X$^3$X$^4$X$^5$ motif" is a series of six consecutive amino acid residues in an ultralong CDR3, wherein the first amino acid residue is cysteine, wherein X$^1$ is threonine (T), glycine (G), alanine (A), serine (S), or valine (V), wherein X$^2$ is serine (S), threonine (T), proline (P), isoleucine (I), alanine (A), valine (V), or asparagine (N), wherein X$^3$ is valine (V), alanine (A), threonine (T), or aspartic acid (D), wherein X$^4$ is histidine (H), threonine (T), arginine (R), tyrosine (Y), phenylalanine (F), or leucine (L), and wherein X$^5$ is glutamine (Q). In some embodiments, the CX$^1$X$^2$X$^3$X$^4$X$^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216). A "(X$^a$X$^b$)$_z$" motif is a repeating series of two amino acid residues in an ultralong CDR3, wherein X$^a$ is any amino acid residue, X$^b$ is an aromatic amino acid selected from the group consisting of: tyrosine (Y), phenylalanine (F), tryptophan (W), and histidine (H), and wherein z is 1-4. In some embodiments, the (X$^a$X$^b$)$_z$ motif may comprise CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273). In some embodiments, the $(X^aX^b)_z$ motif is YXYXYX. An ultralong CDR3 may comprise an amino acid sequence that is derived from or based on SEQ ID NO: 40 (see, e.g., amino acid residues 3-6 of SEQ ID NO: 1-4; see also, e.g., VH germline sequences in FIGS. 2A-C). A variable region that comprises an ultralong CDR3 may include an amino acid sequence that is SEQ ID NO: 1 (CTTVHQ), SEQ ID NO:2 (CTSVHQ), SEQ ID NO:3 (CSSVTQ) or SEQ ID NO: 4 (CTTVHP). Such a sequence may be derived from or based on a bovine germline VH gene sequence (e.g., SEQ ID NO: 1). An ultralong CDR3 may comprise a sequence derived from or based on a non-human DH gene sequence, for example, SEQ ID NO: 5 (see also, e.g., Koti, et al. (2010) *Mol. Immunol.* 47: 2119-2128), or alternative sequences such as SEQ ID NO: 6, 7, 8, 9, 10, 11 or 12 (see also, e.g., DH2 germline sequences in FIGS. 2A-C). An ultralong CDR3 may comprise a sequence derived from or based on a JH sequence, for example, SEQ ID NO: 13 (see also, e.g., Hosseini, et al. (2004) *Int. Immunol.* 16: 843-852), or alternative sequences such as SEQ ID NO: 14, 15, 16 or 17 (see also, e.g., JH1 germline sequences in FIGS. 2A-C). In an embodiment, an ultralong CDR3 may comprise a sequence derived from or based on a non-human VH sequence (e.g., SEQ ID NO: 1, 2, 3 or 4; alternatively VH sequences in FIGS. 2A-C) and/or a sequence derived from or based on a non-human DH sequence (e.g., SEQ ID NO: 5, 6, 7, 8, 9, 10, 11 or 12; alternatively DH sequences in FIGS. 2A-C) and/or a sequence derived from or based on a JH sequence (e.g., SEQ ID NO: 13, 14, 15, 16, or 17; alternatively JH sequences in FIGS. 2A-C), and optionally an additional sequence comprising two to six amino acids or more (e.g., IR, IF, SEQ ID NO: 18, 19, 20 or 21) such as, for example, between the VH derived sequence and the DH derived sequence. In another embodiment, an ultralong CDR3 may comprise a sequence derived from or based on SEQ ID NO: 22, 23, 24, 25, 26, 27, or 28 (see also, e.g., SEQ ID NOs: 276-359 in FIGS. 2A-C).

An "isolated" biological molecule, such as the various polypeptides, polynucleotides, and antibodies disclosed herein, refers to a biological molecule that has been identified and separated and/or recovered from at least one component of its natural environment.

"Antagonist" refers to any molecule that partially or fully blocks, inhibits, or neutralizes an activity (e.g., biological activity) of a polypeptide. Also encompassed by "antagonist" are molecules that fully or partially inhibit the transcription or translation of mRNA encoding the polypeptide. Suitable antagonist molecules include, e.g., antagonist antibodies or antibody fragments; fragments or amino acid sequence variants of a native polypeptide; peptides; antisense oligonucleotides; small organic molecules; and nucleic acids that encode polypeptide antagonists or antagonist antibodies. Reference to "an" antagonist encompasses a single antagonist or a combination of two or more different antagonists.

"Agonist" refers to any molecule that partially or fully mimics a biological activity of a polypeptide. Also encompassed by "agonist" are molecules that stimulate the transcription or translation of mRNA encoding the polypeptide. Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

An "isolated" antibody refers to one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody (e.g., as determined by the Lowry method), and preferably to more than 99% by weight, (2) to a degree sufficient to obtain at least 15 residues of N-terminal or internal amino acid sequence (e.g., by use of a spinning cup sequenator), or (3) to homogeneity by SDS-PAGE under reducing or nonreducing conditions (e.g., using Coomassie™ blue or, preferably, silver stain). Isolated antibody includes the antibody in situ within recombinant cells since at least one component of the antibody's natural environment will not be present. Similarly, isolated antibody includes the antibody in medium around recombinant cells. An isolated antibody may be prepared by at least one purification step.

An "isolated" nucleic acid molecule refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that express an antibody where, for example, the nucleic acid molecule is in a chromosomal location different from that of natural cells.

Variable domain residue numbering as in Kabat or amino acid position numbering as in Kabat, and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (e.g., residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Substantially similar," or "substantially the same", refers to a sufficiently high degree of similarity between two numeric values (generally one associated with an antibody disclosed herein and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, "binding affinity" refers to intrinsic binding affinity which reflects a 1:1 interaction between members of a binding pair (e.g., antibody and antigen). The affinity of a molecule X for its partner Y can generally be represented by the dissociation constant. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

An "on-rate" or "rate of association" or "association rate" or "$k_{on}$" can be determined with a surface plasmon resonance technique such as Biacore (e.g., Biacore A100, Biacore™-2000, Biacore™-3000, Biacore, Inc., Piscataway, N.J.) carboxymethylated dextran biosensor chips (CM5, Biacore Inc.) and according to the supplier's instructions.

"Vector" refers to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. Accordingly, "plasmid" and "vector" may, at times, be used interchangeably as the plasmid is a commonly used form of vector.

"Gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

"Polynucleotide," or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide" refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Stringent hybridization conditions" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. For example, recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this disclosure. It is understood that once a recombinant nucleic acid is made and introduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, e.g., through the expression of a recombinant nucleic acid as depicted above.

"Percent (%) amino acid sequence identity" with respect to a peptide or polypeptide sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MegAlign (DNASTAR) software. Those skilled in the art can determine appropriate parameters for measuring alignment, including any algorithms needed to achieve maximal alignment over the full length of the sequences being compared.

"Polypeptide," "peptide," "protein," and "protein fragment" may be used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a function-ally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, pep-tide, polypeptide, or protein sequence which alters, adds or deletes a single amino acid or a small percentage of amino acids in the encoded sequence is a "conservatively modified variant" including where the alteration results in the substi-tution of an amino acid with a chemically similar amino acid. Conservative substitution tables providing functionally similar amino acids are well known in the art. Such conser-vatively modified variants are in addition to and do not exclude polymorphic variants, interspecies homologs, and alleles disclosed herein. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Antibodies" (Abs) and "immunoglobulins" (Igs) are glycoproteins having similar structural characteristics. While antibodies may exhibit binding specificity to a spe-cific antigen, immunoglobulins may include both antibodies and other antibody-like molecules which generally lack antigen specificity. Polypeptides of the latter kind are, for example, produced at low levels by the lymph system and at increased levels by myelomas.

"Antibody" and "immunoglobulin" are used interchange-ably in the broadest sense and include monoclonal antibod-ies (e.g., full length or intact monoclonal antibodies), poly-clonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured. An antibody may refer to immunoglobulins and immunoglobulin portions, whether natural or partially or wholly synthetic, such as recombinantly produced, includ-ing any portion thereof containing at least a portion of the variable region of the immunoglobulin molecule that is sufficient to form an antigen binding site. Hence, an antibody or portion thereof includes any protein having a binding domain that is homologous or substantially homologous to an immunoglobulin antigen binding site. For example, an antibody may refer to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g. heavy chains include, but are not limited to, VH, chains VH-CH1 chains and VH-CH1-CH2-CH3 chains), and each light chain can be a full-length light chain or a thereof sufficient to form an antigen binding site (e.g. light chains include, but are not limited to, VL chains and VL-CL chains). Each heavy chain (H and H') pairs with one light chain (L and L', respectively). Typically, antibodies mini-mally include all or at least a portion of the variable heavy (VH) chain and/or the variable light (VL) chain. The anti-body also can include all or a portion of the constant region. For example, a full-length antibody is an antibody having two full-length heavy chains (e.g. VH-CH1-CH2-CH3 or VH-CH1-CH2-CH3-CH4) and two full-length light chains (VL-CL) and hinge regions, such as antibodies produced by antibody secreting B cells and antibodies with the same domains that are produced synthetically. Additionally, an "antibody" refers to a protein of the immunoglobulin family or a polypeptide comprising fragments of an immunoglobu-lin that is capable of noncovalently, reversibly, and in a specific manner binding a corresponding antigen. An exem-plary antibody structural unit comprises a tetramer. Each tetramer is composed of two identical pairs of polypeptide chains, each pair having one "light" (about 25 kD) and one "heavy" chain (about 50-70 kD), connected through a dis-ulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a vari-able region of about 100 to 110 or more amino acids primarily responsible for antigen recognition. The terms variable light chain (VL) and variable heavy chain (VH) refer to these regions of light and heavy chains respectively.

"Variable" refers to the fact that certain portions of the variable domains (also referred to as variable regions) differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. CDRs include those specified as Kabat, Chothia, and IMGT as shown herein within the variable region sequences. The more highly conserved portions of variable domains are called the framework (FR). The variable domains of native heavy and light chains each comprise four FR regions, largely adopting a β-sheet configuration, con-nected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" refers to an antibody fragment which contains an antigen-recognition and antigen-binding site. In a two-chain Fv species, this region consists of a dimer of one heavy and one light chain variable domain in non-covalent association. In a single chain Fv (scFv) species, one heavy chain and one light chain variable domain can be covalently linked by a flexible peptide linker such that the light and heavy chains can associate in a "dimeric" structure analogous to that in a two-chain Fv (scFv) species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, single-chain Fvs (scFv), Fv, dsFv, diabody, Fd and Fd' fragments Fab fragments, Fd fragments, scFv fragments, linear antibodies, single-chain antibody molecules, and multispecific antibodies formed from antibody fragments (see, for example, Methods in Molecular Biology, Vol 207: Recombinant Antibodies for Cancer Therapy Methods and Protocols (2003); Chapter 1; p 3-25, Kipriyanov). Other known fragments include, but are not limited to, scFab fragments (Hust et al., BMC Biotechnology (2007), 7:14). In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment. For another example, an antibody fragment or antibody portion refers to any portion of a full-length antibody that is less than full length but contains at least a portion of the variable region of the antibody sufficient to form an antigen binding site (e.g. one or more CDRs) and thus retains the a binding specificity and/or an activity of the full-length antibody; antibody fragments include antibody derivatives produced by enzymatic treatment of full-length antibodies, as well as synthetically, e.g. recombinantly produced derivatives.

A "dsFv" refers to an Fv with an engineered intermolecular disulfide bond, which stabilizes the VH-VL pair.

A "Fd fragment" refers to a fragment of an antibody containing a variable domain (VH) and one constant region domain (CH1) of an antibody heavy chain.

A "Fab fragment" refers to an antibody fragment that contains the portion of the full-length antibody that would results from digestion of a full-length immunoglobulin with papain, or a fragment having the same structure that is produced synthetically, e.g. recombinantly. A Fab fragment contains a light chain (containing a VL and CL portion) and another chain containing a variable domain of a heavy chain (VH) and one constant region domain portion of the heavy chain (CH1); it can be recombinantly produced.

A "F(ab')2 fragment" refers to an antibody fragment that results from digestion of an immunoglobulin with pepsin at pH 4.0-4.5, or a synthetically, e.g. recombinantly, produced antibody having the same structure. The F(ab')2 fragment contains two Fab fragments but where each heavy chain portion contains an additional few amino acids, including cysteine residues that form disulfide linkages joining the two fragments; it can be recombinantly produced.

A "Fab' fragment" refers to a fragment containing one half (one heavy chain and one light chain) of the F(ab')2 fragment.

A "Fd' fragment refers to a fragment of an antibody containing one heavy chain portion of a F(ab')2 fragment.

A "Fv' fragment" refers to a fragment containing only the VH and VL domains of an antibody molecule.

A "scFv fragment" refers to an antibody fragment that contains a variable light chain (VL) and variable heavy chain (VH), covalently connected by a polypeptide linker in any order. The linker is of a length such that the two variable domains are bridged without substantial interference. Exemplary linkers are (Gly-Ser)n residues with some Glu or Lys residues dispersed throughout to increase solubility.

Diabodies are dimeric scFv; diabodies typically have shorter peptide linkers than scFvs, and they preferentially dimerize.

"HsFv" refers to antibody fragments in which the constant domains normally present in a Fab fragment have been substituted with a heterodimeric coiled-coil domain (see, e.g., Arndt et al. (2001) J Mol Biol. 7:312:221-228).

"Hypervariable region", "HVR", or "HV", as well as "complementary determing region" or "CDR", may refer to the regions of an antibody variable domain which are hypervariable in sequence and/or form structurally defined loops. Generally, antibodies comprise six hypervariable or CDR regions; three in the VH (H1, H2, H3), and three in the VL (L1, L2, L3). A number of hypervariable region or CDR delineations are in use and are encompassed herein. The Kabat Complementarity Determining Regions (Kabat CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, (Chothia "CDRs") and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

IMGT refers to the international ImMunoGeneTics Information System, as described by Lefrace et al., Nucl. Acids, Res. 37; D1006-D1012 (2009), including for example, IMGT designated CDRs for antibodies.

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al, Supra for each of these definitions.

"Framework" or "FR" residues are those variable domain residues other than the hypervariable region residues as herein defined. "Framework regions" (FRs) are the domains within the antibody variable region domains comprising framework residues that are located within the beta sheets; the FR regions are comparatively more conserved, in terms of their amino acid sequences, than the hypervariable regions.

"Monoclonal antibody" refers to an antibody from a population of substantially homogeneous antibodies, that is, for example, the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations which typically include different antibodies directed against different determinants (e.g., epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5):1073-1093 (2004); Fellouse, Proc. Nat. Acad. Sci. USA 101(34):12467-12472 (2004); and Lee et al. J. Immunol. Methods 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806; 5,569,825; 5,591,669; 5,545,807; WO 1997/17852; U.S. Pat. Nos. 5,545,807; 5,545,806; 5,569,825; 5,625,126; 5,633,425; and U.S. Pat. No. 5,661,016; Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995)).

"Humanized" or "Human engineered" forms of non-human (e.g., murine) antibodies are chimeric antibodies that contain amino acids represented in human immunoglobulin sequences, including, for example, wherein minimal sequence is derived from non-human immunoglobulin. For example, humanized antibodies may be human antibodies in which some hypervariable region residues and possibly some FR residues are substituted by residues from analogous sites in non-human (e.g., rodent) antibodies. Alternatively, humanized or human engineered antibodies may be non-human (e.g., rodent) antibodies in which some residues are substituted by residues from analoguous sites in human antibodies (see, e.g., U.S. Pat. No. 5,766,886). Humanized antibodies include human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody, including, for example non-antibody sequences such as a chemokine, growth factor, peptide, cytokine, cell surface protein, serum protein, toxin, extracellular matrix protein, clotting factor, or secreted protein sequence. These modifications may be made to further refine antibody performance. Humanized antibodies include human engineered antibodies, for example, as described by U.S. Pat. No. 5,766,886, including methods for preparing modified antibody variable domains. A humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. A humanized antibody optionally may also comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994).

"Hybrid antibodies" refer to immunoglobulin molecules in which pairs of heavy and light chains from antibodies with different antigenic determinant regions are assembled together so that two different epitopes or two different antigens can be recognized and bound by the resulting tetramer.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). Humanized antibody refers to a subset of chimeric antibodies.

"Single-chain Fv" or "scFv" antibody fragments may comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see e.g., Pluckthun, in The Pharmacology of Monoclonal Antibodies, vol. 113, Rosenburg and Moore eds., Springer-Verlag, New York, pp. 269-315 (1994).

An "antigen" refers to a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

"Epitope" or "antigenic determinant", used interchangeably herein, refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. Antibodies may bind to the same or a different epitope on an antigen. Antibodies may be characterized in different epitope bins. Whether an antibody binds to the same or different epitope as another antibody (e.g., a reference antibody or benchmark antibody) may be determined by competition between antibodies in assays (e.g., competitive binding assays).

Competition between antibodies may be determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay or enzyme-linked immunosorbent assay (EIA or ELISA), sandwich competition assay including an ELISA assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using 1-125 label (see Morel et al., Molec. Immunol. 25(1): 7-15 (1988)); solid phase direct biotin-avidin EIA (Cheung et al., Virology 176:546-552 (1990)); and direct labeled RIA (Moldenhauer et al., Scand. J. Immunol., 32:77-82 (1990)). Competition binding assays may be performed using Surface Plasmon Resonance (SPR), for example, with a Biacore® instrument for kinetic analysis of binding interactions. In such an assay, a humanized antibody comprising an ultralong CDR3 of unknown epitope specificity may be evaluated for its ability to compete for binding against a comparator antibody (e.g., a BA1 or BA2 antibody as described herein). An assay may involve the use of purified antigen bound to a solid surface or cells bearing either of these, an unlabeled test immunoglobulin and a labeled reference immunoglobulin. Competitive inhibition may be measured by determining the amount of label bound to the solid surface or cells in the presence of the test immunoglobulin. Usually the test immunoglobulin is present in excess. An assay (competing antibodies) may include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50%, or at least about 70%, or at least about 80%, or least about 90%, or at least about 95%, or at least about 99% or about 100% for a competitor antibody.

That an antibody "selectively binds" or "specifically binds" means that the antibody reacts or associates more frequently, more rapidly, with greater duration, with greater affinity, or with some combination of the above to an antigen or an epitope than with alternative substances, including unrelated proteins. "Selectively binds" or "specifically binds" may mean, for example, that an antibody binds to a protein with a $K_D$ of at least about 0.1 mM, or at least about 1 µM or at least about 0.1 µM or better, or at least about 0.01 µM or better. Because of the sequence identity between homologous proteins in different species, specific binding can include an antibody that recognizes a given antigen in more than one species.

"Non-specific binding" and "background binding" when used in reference to the interaction of an antibody and a protein or peptide refer to an interaction that is not dependent on the presence of a particular structure (e.g., the antibody is binding to proteins in general rather that a particular structure such as an epitope).

"Diabodies" refer to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et. al., Proc. Natl. Acad. Sci. USA, 90:6444-6448 (1993).

A "human antibody" refers to one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody refers to one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992) describes affinity maturation by VH and VL domain shuffling. Random mutagenesis of CDR and/or framework residues is described by: Barbas et al., Proc Nat. Acad. Sci. USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Natl. Acad. Sci. USA 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulates homeostasis of immunoglobulins. For example, antibody variants with improved or diminished binding to FcRs have been described (see, e.g., Shields et al. J. Biol. Chem. 9(2): 6591-6604 (2001)).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, for example, as described in Gazzano-Santoro et al., J. Immunol. Methods 202:163 (1996), may be performed.

Polypeptide variants with altered Fc region amino acid sequences and increased or decreased Clq binding capability have been described (e.g., see, also, Idusogie et al. J. Immunol. 164: 4178-4184 (2000)).

"Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide.

"Blocking" antibody or an "antagonist" antibody refers to one which inhibits or reduces biological activity of the antigen it binds. Preferred blocking antibodies or antagonist antibodies substantially or completely inhibit the biological activity of the antigen.

"Agonist" antibody refers to an antibody which mimics (e.g., partially or fully) at least one of the functional activities of a polypeptide of interest.

"Acceptor human framework" refers to a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present.

A "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Disorder" or "disease" refers to any condition that would benefit from treatment with a substance/molecule (e.g., a humanized antibody comprising an ultralong CDR3 as disclosed herein) or method disclosed herein. This includes chronic and acute disorders or diseases including those pathological conditions which predispose the mammal to the disorder in question.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies disclosed herein are used to delay development of a disease or disorder.

"Individual" (e.g., a "subject") refers to a vertebrate, preferably a mammal, more preferably a human. Mammals include, but are not limited to, farm animals (such as cows), sport animals, pets (such as cats, dogs and horses), primates, mice and rats.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

"Providing a prognosis", "prognostic information", or "predictive information" refer to providing information, including for example the presence of cancer cells in a subject's tumor, regarding the impact of the presence of cancer (e.g., as determined by the diagnostic methods of the present disclosure) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented.

"Providing a diagnosis" or "diagnostic information" refers to any information, including for example the presence of cancer cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

A "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein refers to a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Antigen-binding site" refers to the interface formed by one or more complementary determining regions. An antibody molecule has two antigen combining sites, each containing portions of a heavy chain variable region and portions of a light chain variable region. The antigen combining sites can contain other portions of the variable region domains in addition to the CDRs.

An "antibody light chain" or an "antibody heavy chain" refers to a polypeptide comprising the VL or VH, respectively. The VL is encoded by the minigenes V (variable) and J (junctional), and the VH by minigenes V, D (diversity), and J. Each of VL or VH includes the CDRs as well as the framework regions. In this application, antibody light chains and/or antibody heavy chains may, from time to time, be collectively referred to as "antibody chains." These terms encompass antibody chains containing mutations that do not disrupt the basic structure of VL or VH, as one skilled in the art will readily recognize.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide bonded. From N- to C-terminus, each heavy chain has a variable region (V H), also called a variable heavy domain or a heavy chain variable domain, followed by three constant domains (CH1, CH2, and CH3). Similarly, from N- to C-terminus, each light chain has a variable region (V L), also called a variable light domain or a light chain variable domain, followed by a constant light (CL) domain. The light chain of an antibody may be assigned to one of two types, called kappa (κ) and lambda (λ), based on the amino acid sequence of its constant domain.

"Combinatorial library" refers to collections of compounds formed by reacting different combinations of interchangeable chemical "building blocks" to produce a collection of compounds based on permutations of the building blocks. For an antibody combinatorial library, the building blocks are the component V, D and J regions (or modified forms thereof) from which antibodies are formed. For purposes herein, the terms "library" or "collection" are used interchangeably.

A "combinatorial antibody library" refers to a collection of antibodies (or portions thereof, such as Fabs), where the antibodies are encoded by nucleic acid molecules produced by the combination of V, D and J gene segments, particularly human V, D and J germline segments. The combinatorial libraries herein typically contain at least 50 different antibody (or antibody portions or fragment) members, typically at or about 50, 100, 500, 103, 1×103, 2×103, 3×103, 4×103, 5×103, 6×103, 7×103, 8×103, 9×103, 1×104, 2×104, 3×104, 4×104, 5×104, 6×104, 7×104, 8×104, 9×104, 1×105, 2×105, 3×105, 4×105, 5×105, 6×105, 7×105, 8×105, 9×105, 106, 107, 108, 109, 1010, or more different members. The resulting libraries or collections of antibodies or portions thereof, can be screened for binding to a target protein or modulation of a functional activity.

A "human combinatorial antibody library" refers to a collection of antibodies or portions thereof, whereby each member contains a VL and VH chains or a sufficient portion thereof to form an antigen binding site encoded by nucleic acid containing human germline segments produced as described herein.

A "variable germline segment" refers to V, D and J groups, subgroups, genes or alleles thereof. Gene segment sequences are accessible from known database (e.g., National Center for Biotechnology Information (NCBI), the international ImMunoGeneTics information System® (IMGT), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). Tables 3-5 list exemplary human variable germline segments. Sequences of exemplary VH, DH, JH, Vκ, Jκ, Vλ and or Jλ, germline segments are set forth in SEQ ID NOS: 10-451 and 868. For purposes herein, a germline segment includes modified sequences thereof, that are modified in accord with the rules of sequence compilation provided herein to permit practice of the method. For example, germline gene segments include those that contain one amino acid deletion or insertion at the 5' or 3' end compared to any of the sequences of nucleotides set forth in SEQ ID NOS:10-451, 868.

"Compilation," "compile," "combine," "combination," "rearrange," "rearrangement," or other similar terms or grammatical variations thereof refers to the process by which germline segments are ordered or assembled into nucleic acid sequences representing genes. For example, variable heavy chain germline segments are assembled such that the VH segment is 5' to the DH segment which is 5' to the JH segment, thereby resulting in a nucleic acid sequence encoding a VH chain. Variable light chain germline segments are assembled such that the VL segment is 5' to the JL segment, thereby resulting in a nucleic acid sequence encoding a VL chain. A constant gene segment or segments also can be assembled onto the 3' end of a nucleic acid encoding a VH or VL chain.

"Linked," or "linkage" or other grammatical variations thereof with reference to germline segments refers to the joining of germline segments. Linkage can be direct or indirect. Germline segments can be linked directly without additional nucleotides between segments, or additional nucleotides can be added to render the entire segment in-frame, or nucleotides can be deleted to render the resulting segment in-frame. It is understood that the choice of linker nucleotides is made such that the resulting nucleic acid molecule is in-frame and encodes a functional and productive antibody.

"In-frame" or "linked in-frame" with reference to linkage of human germline segments means that there are insertions and/or deletions in the nucleotide germline segments at the joined junctions to render the resulting nucleic acid molecule in-frame with the 5' start codon (ATG), thereby producing a "productive" or functional full-length polypeptide. The choice of nucleotides inserted or deleted from germline segments, particularly at joints joining various VD, DJ and VJ segments, is in accord with the rules provided in the method herein for V(D)J joint generation. For example, germline segments are assembled such that the VH segment is 5' to the DH segment which is 5' to the JH segment. At the junction joining the VH and the DH and at the junction joining the DH and JH segments, nucleotides can be inserted or deleted from the individual VH, DH or JH segments, such that the resulting nucleic acid molecule containing the joined VDJ segments are in-frame with the 5' start codon (ATG).

A portion of an antibody includes sufficient amino acids to form an antigen binding site.

A "reading frame" refers to a contiguous and non-overlapping set of three-nucleotide codons in DNA or RNA. Because three codons encode one amino acid, there exist three possible reading frames for given nucleotide sequence, reading frames 1, 2 or 3. For example, the sequence ACTGGTCA will be ACT GGT CA for reading frame 1, A CTG GTC A for reading frame 2 and AC TGG TCA for reading frame 3. Generally for practice of the method described herein, nucleic acid sequences are combined so that the V sequence has reading frame 1.

A "stop codon" refers to a three-nucleotide sequence that signals a halt in protein synthesis during translation, or any sequence encoding that sequence (e.g. a DNA sequence encoding an RNA stop codon sequence), including the amber stop codon (UAG or TAG)), the ochre stop codon (UAA or TAA)) and the opal stop codon (UGA or TGA)). It is not necessary that the stop codon signal termination of translation in every cell or in every organism. For example, in suppressor strain host cells, such as amber suppressor strains and partial amber suppressor strains, translation proceeds through one or more stop codon (e.g. the amber stop codon for an amber suppressor strain), at least some of the time.

A "variable heavy" (VH) chain or a "variable light" (VL) chain (also termed VH domain or VL domain) refers to the polypeptide chains that make up the variable domain of an antibody. For purposes herein, heavy chain germline segments are designated as VH, DH and JH, and compilation thereof results in a nucleic acid encoding a VH chain. Light chain germline segments are designated as VL or JL, and include kappa and lambda light chains (Vκ and Jκ; Vλ and Jλ.) and compilation thereof results in a nucleic acid encoding a VL chain. It is understood that a light chain is either a kappa or lambda light chain, but does not include a kappa/lambda combination by virtue of compilation of a Vκ and Jλ.

A "degenerate codon" refers to three-nucleotide codon that specifies the same amino acid as a codon in a parent nucleotide sequence. One of skill in the art is familiar with degeneracy of the genetic code and can identify degenerate codons.

"Diversity" with respect to members in a collection refers to the number of unique members in a collection. Hence, diversity refers to the number of different amino acid sequences or nucleic acid sequences, respectively, among the analogous polypeptide members of that collection. For example, a collection of polynucleotides having a diversity of 104 contains 104 different nucleic acid sequences among the analogous polynucleotide members. In one example, the provided collections of polynucleotides and/or polypeptides have diversities of at least at or about 102, 103, 104, 105, 106, 107, 108, 109, 1010 or more.

"Sequence diversity" refers to a representation of nucleic acid sequence similarity and is determined using sequence alignments, diversity scores, and/or sequence clustering. Any two sequences can be aligned by laying the sequences side-by-side and analyzing differences within nucleotides at every position along the length of the sequences. Sequence alignment can be assessed in silico using Basic Local Alignment Search Tool (BLAST), an NCBI tool for comparing nucleic acid and/or protein sequences. The use of BLAST for sequence alignment is well known to one of skill in the art. The Blast search algorithm compares two sequences and calculates the statistical significance of each match (a Blast score). Sequences that are most similar to each other will have a high Blast score, whereas sequences that are most varied will have a low Blast score.

A "polypeptide domain" refers to a part of a polypeptide (a sequence of three or more, generally 5 or 7 or more amino acids) that is a structurally and/or functionally distinguishable or definable. Exemplary of a polypeptide domain is a part of the polypeptide that can form an independently folded structure within a polypeptide made up of one or more structural motifs (e.g. combinations of alpha helices and/or beta strands connected by loop regions) and/or that is recognized by a particular functional activity, such as enzymatic activity or antigen binding. A polypeptide can have one, typically more than one, distinct domains. For example, the polypeptide can have one or more structural domains and one or more functional domains. A single polypeptide domain can be distinguished based on structure and function. A domain can encompass a contiguous linear sequence of amino acids. Alternatively, a domain can encompass a plurality of non-contiguous amino acid portions, which are non-contiguous along the linear sequence of amino acids of the polypeptide. Typically, a polypeptide contains a plurality of domains. For example, each heavy chain and each light chain of an antibody molecule contains a plurality of immunoglobulin (Ig) domains, each about 110 amino acids in length.

An "Ig domain" refers to a domain, recognized as such by those in the art, that is distinguished by a structure, called the Immunoglobulin (Ig) fold, which contains two beta-pleated sheets, each containing anti-parallel beta strands of amino acids connected by loops. The two beta sheets in the Ig fold are sandwiched together by hydrophobic interactions and a conserved intra-chain disulfide bond. Individual immunoglobulin domains within an antibody chain further can be distinguished based on function. For example, a light chain contains one variable region domain (VL) and one constant region domain (CL), while a heavy chain contains one variable region domain (VH) and three or four constant region domains (CH). Each VL, CL, VH, and CH domain is an example of an immunoglobulin domain.

A "variable domain" with reference to an antibody refers to a specific Ig domain of an antibody heavy or light chain that contains a sequence of amino acids that varies among different antibodies. Each light chain and each heavy chain has one variable region domain (VL, and, VH). The variable domains provide antigen specificity, and thus are responsible for antigen recognition. Each variable region contains CDRs that are part of the antigen binding site domain and framework regions (FRs).

A "constant region domain" refers to a domain in an antibody heavy or light chain that contains a sequence of amino acids that is comparatively more conserved among antibodies than the variable region domain. Each light chain has a single light chain constant region (CL) domain and each heavy chain contains one or more heavy chain constant region (CH) domains, which include, CH1, CH2, CH3 and CH4. Full-length IgA, IgD and IgG isotypes contain CH1, CH2 CH3 and a hinge region, while IgE and IgM contain CH1, CH2 CH3 and CH4. CH1 and CL domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g. through interactions with various cells, biomolecules and tissues.

An "antibody or portion thereof that is sufficient to form an antigen binding site" means that the antibody or portion thereof contains at least 1 or 2, typically 3, 4, 5 or all 6 CDRs of the VH and VL sufficient to retain at least a portion of the binding specificity of the corresponding full-length antibody containing all 6 CDRs. Generally, a sufficient antigen binding site at least requires CDR3 of the heavy chain (CDRH3). It typically further requires the CDR3 of the light chain (CDRL3). As described herein, one of skill in the art knows and can identify the CDRs based on Kabat or Chothia numbering (see, e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). For example, based on Kabat numbering, CDR-LI corresponds to residues L24-L34; CDR-L2 corresponds to residues L50-L56; CDR-L3 corresponds to residues L89-L97; CDR-H1 corresponds to residues H31-H35, 35a or 35b depending on the length; CDR-H2 corresponds to residues H50-H65; and CDR-H3 corresponds to residues H95-H102.

A "peptide mimetic" refers to a peptide that mimics the activity of a polypeptide. For example, an erythropoietin (EPO) peptide mimetic is a peptide that mimics the activity of Epo, such as for binding and activation of the EPO receptor.

An "address" refers to a unique identifier for each locus in a collection whereby an addressed member (e.g. an antibody) can be identified. An addressed moiety is one that can be identified by virtue of its locus or location. Addressing can be effected by position on a surface, such as a well of a microplate. For example, an address for a protein in a microwell plate that is F9 means that the protein is located in row F, column 9 of the microwell plate. Addressing also can be effected by other identifiers, such as a tag encoded with a bar code or other symbology, a chemical tag, an electronic, such RF tag, a color-coded tag or other such identifier.

An "array" refers to a collection of elements, such as antibodies, containing three or more members.

A "spatial array" refers to an array where members are separated or occupy a distinct space in an array. Hence, spatial arrays are a type of addressable array. Examples of spatial arrays include microtiter plates where each well of a plate is an address in the array. Spacial arrays include any arrangement wherein a plurality of different molecules, e.g., polypeptides, are held, presented, positioned, situated, or supported. Arrays can include microtiter plates, such as 48-well, 96-well, 144-well, 192-well, 240-well, 288-well, 336-well, 384-well, 432-well, 480-well, 576-well, 672-well, 768-well, 864-well, 960-well, 1056-well, 1152-well, 1248-well, 1344-well, 1440-well, or 1536-well plates, tubes, slides, chips, flasks, or any other suitable laboratory apparatus. Furthermore, arrays can also include a plurality of sub-arrays. A plurality of sub-arrays encompasses an array where more than one arrangement is used to position the polypeptides. For example, multiple 96-well plates could constitute a plurality of sub-arrays and a single array.

An "addressable library" or "spatially addressed library" refers to a collection of molecules such as nucleic acid molecules or protein agents, such as antibodies, in which each member of the collection is identifiable by virtue of its address.

An "addressable array" refers to one in which the members of the array are identifiable by their address, the position in a spatial array, such as a well of a microtiter plate, or on a solid phase support, or by virtue of an identifiable or detectable label, such as by color, fluorescence, electronic signal (i.e. RF, microwave or other frequency that does not substantially alter the interaction of the molecules of interest), bar code or other symbology, chemical or other such label. Hence, in general the members of the array are located at identifiable loci on the surface of a solid phase or directly or indirectly linked to or otherwise associated with the identifiable label, such as affixed to a microsphere or other particulate support (herein referred to as beads) and suspended in solution or spread out on a surface.

"An addressable combinatorial antibody library" refers to a collection of antibodies in which member antibodies are identifiable and all antibodies with the same identifier, such as position in a spatial array or on a solid support, or a chemical or RF tag, bind to the same antigen, and generally are substantially the same in amino acid sequence. For purposes herein, reference to an "addressable arrayed combinatorial antibody library" means that the antibody members are addressed in an array.

"In silico" refers to research and experiments performed using a computer. In silico methods include, but are not limited to, molecular modeling studies, biomolecular docking experiments, and virtual representations of molecular structures and/or processes, such as molecular interactions. For purposes herein, the antibody members of a library can be designed using a computer program that selects component V, D and J germline segments from among those input into the computer and joins them in-frame to output a list of nucleic acid molecules for synthesis. Thus, the recombination of the components of the antibodies in the collections or libraries provided herein, can be performed in silico by combining the nucleotide sequences of each building block in accord with software that contains rules for doing so. The process could be performed manually without a computer, but the computer provides the convenience of speed.

A "database" refers to a collection of data items. For purposes herein, reference to a database is typically with reference to antibody databases, which provide a collection of sequence and structure information for antibody genes and sequences. Exemplary antibody databases include, but are not limited to, IMGT®, the international ImMunoGeneTics information system (imgt.cines.fr; see e.g., Lefranc et al. (2008) Briefings in Bioinformatics, 9:263-275), National Center for Biotechnology Information (NCBI), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). A database also can be created by a user to include any desired sequences. The database can be created such that the sequences are inputted in a desired format (e.g., in a particular reading frame; lacking stop codons; lacking signal sequences). The database also can be created to include sequences in addition to antibody sequences.

"Screening" refers to identification or selection of an antibody or portion thereof from a collection or library of antibodies and/or portions thereof, based on determination of the activity or property of an antibody or portion thereof. Screening can be performed in any of a variety of ways, including, for example, by assays assessing direct binding (e.g. binding affinity) of the antibody to a target protein or by functional assays assessing modulation of an activity of a target protein.

"Activity towards a target protein" refers to binding specificity and/or modulation of a functional activity of a target protein, or other measurements that reflects the activity of an antibody or portion thereof towards a target protein.

A "target protein" refers to candidate proteins or peptides that are specifically recognized by an antibody or portion thereof and/or whose activity is modulated by an antibody or portion thereof. A target protein includes any peptide or protein that contains an epitope for antibody recognition. Target proteins include proteins involved in the etiology of a disease or disorder by virtue of expression or activity. Exemplary target proteins are described herein.

"Hit" refers to an antibody or portion thereof identified, recognized or selected as having an activity in a screening assay.

"Iterative" with respect to screening means that the screening is repeated a plurality of times, such as 2, 3, 4, 5 or more times, until a "Hit" is identified whose activity is optimized or improved compared to prior iterations.

"High-throughput" refers to a large-scale method or process that permits manipulation of large numbers of molecules or compounds, generally tens to hundred to thousands of compounds. For example, methods of purification and screening can be rendered high-throughput. High-throughput methods can be performed manually. Generally, however, high-throughput methods involve automation, robotics or software.

Basic Local Alignment Search Tool (BLAST) is a search algorithm developed by Altschul et al. (1990) to separately search protein or DNA databases, for example, based on sequence identity. For example, blastn is a program that compares a nucleotide query sequence against a nucleotide sequence database (e.g. GenBank). BlastP is a program that compares an amino acid query sequence against a protein sequence database.

A BLAST bit score is a value calculated from the number of gaps and substitutions associated with each aligned sequence. The higher the score, the more significant the alignment.

A "human protein" refers to a protein encoded by a nucleic acid molecule, such as DNA, present in the genome of a human, including all allelic variants and conservative variations thereof. A variant or modification of a protein is a human protein if the modification is based on the wildtype or prominent sequence of a human protein.

"Naturally occurring amino acids" refer to the 20 L-amino acids that occur in polypeptides. The residues are those 20 α-amino acids found in nature which are incorporated into protein by the specific recognition of the charged tRNA molecule with its cognate mRNA codon in humans.

"Non-naturally occurring amino acids" refer to amino acids that are not genetically encoded. For example, a non-natural amino acid is an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

"Nucleic acids" include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

A "peptide" refers to a polypeptide that is from 2 to 40 amino acids in length.

The amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

An "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

"Amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3552-3559 (1969), and adopted 37 C.F.R. □§§ 1.821-1.822, abbreviations for amino acid residues are shown below:

| SYMBOL | | |
| --- | --- | --- |
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues, to an amino-terminal group such as NH2 or to a carboxyl-terminal group such as COOH. The abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:1726). Each naturally occurring L-amino acid is identified by the standard three letter code (or single letter code) or the standard three letter code (or single letter code) with the prefix "L-"; the prefix "D-" indicates that the stereoisomeric form of the amino acid is D.

An "immunoconjugate" refers to an antibody conjugated to one or more heterologous molecule(s), including but not limited to a cytotoxic agent. An immunoconjugate may include non-antibody sequences.

General Techniques

The present disclosure relies on routine techniques in the field of recombinant genetics. Basic texts disclosing the general methods of use in this present disclosure include Sambrook and Russell, Molecular Cloning: A Laboratory Manual 3d ed. (2001); Kriegler, Gene Transfer and Expression: A Laboratory Manual (1990); and Ausubel et al., Current Protocols in Molecular Biology (1994).

For nucleic acids, sizes are given in either kilobases (Kb) or base pairs (bp). These are estimates derived from agarose or polyacrylamide gel electrophoresis, from sequenced nucleic acids, or from published DNA sequences. For proteins, sizes are given in kilo-Daltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage and Caruthers, Tetrahedron Letters, 22:1859-1862 (1981), using an automated synthesizer, as described in Van Devanter et al., Nucleic Acids Res., 12:6159-6168 (1984). Purification of oligonucleotides is by either native polyacrylamide gel electrophoresis or by anion-exchange chromatography as described in Pearson & Reanier, J. Chrom., 255:137-149 (1983). The sequence of the cloned genes and synthetic oligonucleotides can be verified after cloning using, e.g., the chain termination method for sequencing double-stranded templates of Wallace et al., Gene, 16:21-26 (1981).

The nucleic acids encoding recombinant polypeptides of the present disclosure may be cloned into an intermediate vector before transformation into prokaryotic or eukaryotic cells for replication and/or expression. The intermediate vector may be a prokaryote vector such as a plasmid or shuttle vector.

Humanized Antibodies with Ultralong CDR3 Sequences

To date, cattle are the only species where ultralong CDR3 sequences have been identified. However, other species, for example other ruminants, may also possess antibodies with ultralong CDR3 sequences.

Exemplary antibody variable region sequences comprising an ultralong CDR3 sequence identified in cattle include those designated as: BLV1H12 (see, SEQ ID NO: 22), BLV5B8 (see, SEQ ID NO: 23), BLV5D3 (see, SEQ ID NO: 24) and BLV8C11 (see SEQ ID NO: 25) (see, e.g., Saini, et al. (1999) Eur. J. Immunol. 29: 2420-2426; and Saini and Kaushik (2002) Scand. J. Immunol. 55: 140-148); BF4E9 (see, SEQ ID NO: 26) and BF1H1 (see, SEQ ID NO: 27) (see, e.g., Saini and Kaushik (2002) Scand. J. Immunol. 55:140-148); and F18 (see, SEQ ID NO: 28) (see, e.g., Berens, et al. (1997) Int. Immunol. 9: 189-199).

In an embodiment, bovine antibodies are identified and humanized. Multiple techniques exist to identify antibodies.

Antibodies of the present disclosure may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Phage display libraries of bovine antibodies may be a source of bovine antibody gene sequences, including ultralong CDR3 sequences.

Typically, a non-human antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005); Klimka et al., Br. J. Cancer, 83:252-260 (2000) (describing the "guided selection" approach to FR shuffling); and Studnicka et al., U.S. Pat. No. 5,766,886.

Human variable region framework sequences that may be used for humanization include but are not limited to: framework sequences selected using the "best-fit" method (see, e.g., Sims et al. J. Immunol. 151:2296 (1993)); framework sequences derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151: 2623 (1993)); human mature (somatically mutated) framework sequences or human germline framework sequences (see, e.g., Almagro and Fransson, Front. Biosci. 13:1619-1633 (2008)); and framework sequences derived from screening FR libraries (see, e.g., Baca et al., Biol. Chem. 272:10678-10684 (1997) and Rosok et al., J. Biol. Chem. 271:22611-22618 (1996)).

Humanized antibodies with ultralong CDR3 sequences may also include engineered non-antibody sequences, such as cytokines or growth factors, into the CDR3 region, such that the resultant humanized antibody is effective, for example, in inhibiting tumor metastasis. Non-antibody sequences may include an interleukin sequence, a hormone sequence, a cytokine sequence, a toxin sequence, a lymphokine sequence, a growth factor sequence, a chemokine sequence, or combinations thereof. Non-antibody sequences may be human, non-human, or synthetic. In some embodiments, the cytokine or growth factor may be shown to have an antiproliferative effect on at least one cell population. Such cytokines, lymphokines, growth factors, or other hematopoietic factors include M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFo1, TNF1, TNF2, G-CSF, Meg-CSF, GM-CSF, thrombopoietin, stem cell factor, and erythropoietin. Additional growth factors for use in humanized antibodies and/or pharmaceutical compositions of the present disclosure include: angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-S, latent transforming growth factor-1, transforming growth factor-1 binding protein I, transforming growth factor-1 binding protein II, transforming growth factor-1 binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Exemplary hormone sequences include a glucagon-like peptide-1 (GLP-1), Melatonin (MT), Thyroxine (T4), Triiodothyronine (T3), Adrenaline (EPI), Noradrenaline (NRE), Dopamine (DA), Antimullerian Hormone, Adrenocorticotropic (ACTH), Angiotensin (AGT), Antidiuretic Hormone (ADH), Calcitonin (CT), Cholecystokinin (CCK), Corticotropin-releasing hormone (CRH), Erythropoietin (EPO), FollicLe-Stimulating Hormone (FSH), Gastrin (GRP), Ghrelin, Glucagon (GCG), Gonadotropin-releasing Hormone (GnRH), Growth-Hormone Releasing Hormone (GNRH), Human Chorionic Gonadotropin (hCG), Growth Hormone (GH), Insulin (INS), Insuin-like Growth Factor (or Somatomedin) (IGF), Leptin (LEP), Luteinizing Hormone (LH), Melanocyte Stimulating Hormone (MSH), Oxytocin (OXT), Parathyroid Hormone (PTH), Prolactin (PRL), Secretin (SCT), Somatostatin (SRIF), Thrombopoietin (TPO), Thyroid-Stimulating Hormone (TSH), Thyrotropin-releasing Hormone (TRH), Cortisol, Aldosterone, Testosterone, Dehydroepiandrosterone (DHEA), Estradiol (Oestrogen), Progesterone, Calcitriol (1,25-dihydroxyvitamin D3), Calcidiol (25-hydroxyvitamin D3), Prolactin releasing hormone (PRH), Lipotropin (LRH), Brain Natriuretic Peptide (BNP), Neuropeptide Y (NPY), Histamine, Endothelin, Renin, or Enkephalin. Exemplary toxin sequences include an ADWX-1 sequence, an HsTx1 sequence, an OSK1 sequence, a Pi2 sequence, a Hongotoxin (HgTX) sequence, a Margatoxin sequence, an Agitoxin-2 sequence, a Pi3 sequence, a Kaliotoxin sequence, an Anuroctoxin sequence, a Charybdotoxin sequence, a Tityustoxin-K-alpha sequence, a Maurotoxin sequence, a Ceratotoxin 1 (CcoTx1) sequence, a CcoTx2 sequence, a CcoTx3 sequence, a Phrixotoxin 3 (PaurTx3) sequence, a Hanatoxin 1 sequence, a Phrixotoxin 1 sequence, a Huwentoxin-IV sequence, an α-conotoxin Iml sequence, an α-conotoxin Epl sequence, an α-conotoxin PnlA sequence, an α-conotoxin PnlB sequence, an α-conotoxin MII sequence, an α-conotoxin AulA sequence, an α-conotoxin AulB sequence, an α-conotoxin AulC sequence, a conotoxin κ-PVIIA sequence, a charybdotoxin sequence, a neurotoxin B-IV sequence, a crotamine sequence, a ω-GVIA (conotoxin) sequence, a κ-hefutoxin 1 sequence, a Css4 sequence, a Bj-xtrlT sequence, a BcIV sequence, a Hm-1 sequence, a Hm-2 sequence, a GsAF-I (β-theraphotoxin-Gr1b) sequence, a Protoxin I (ProTx-I sequence, a β-theraphotoxin-Tp1a) sequence, a Protoxin II (ProTx II) sequence, a Huwentoxin I sequence, a μ-Conotoxin PIIIA sequence, a Jingzhaotoxin-III (β-TRTX-Cj1α) sequence, a GsAF-II (Kappa-theraphotoxin-Gr2c) sequence, a ShK (Stichodactyla toxin) sequence, a HsTx1 sequence, a Guangxitoxin 1E (GxTx-1E) sequence, a Maurotoxin sequence, a Charybdotoxin (ChTX) sequence, an Iberiotoxin (IbTx) sequence, a Leiurotoxin 1 (scyllatoxin) sequence, a Tamapin sequence, a Kaliotoxin-1 (KTX) sequence, a Purotoxin1 (PT-1) sequence, or a GpTx-1 sequence, a MOKA Toxin sequence, a OSK1 (P12, K16, D20) sequence, a OSK1 (K16, D20) sequence, a HmK sequence, a ShK (K16, Y26, K29) sequence, a ShK (K16) sequence, a ShK-A (K16) sequence, a ShK (K16,E30) sequence, a ShK (Q21) sequence, a ShK (L21) sequence, a ShK (F21) sequence, a ShK (121) sequence, or a ShK (A21) sequence. Exemplary toxin sequences include SEQ ID NOS: 475-481, 599-655, 666-698, 727-733, 808-810 and 831-835 (see, e.g., FIG. 17). Exemplary non-antibody sequences include interleukin 8 (IL-8, SEQ ID NO: 475), interleukin 21 (IL-21, SEQ ID NO: 480), CXCL12/SDF-1alpha (SEQ ID NO: 479), somatostain (SEQ ID NO: 477), ProTx-II (SEQ ID NO: 481), chlorotoxin (SEQ ID NO: 478), and ziconotide (SEQ ID NO: 476).

A non-human antibody may be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

The humanized antibodies comprising an ultralong CDR3 as disclosed herein are preferably monoclonal. Also encompassed within the scope of the disclosure are Fab, Fab', Fab'-SH and F(ab')$^2$ fragments of the humanized antibodies comprising an ultralong CDR3 as provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, e.g., the individual antibodies comprising the population are identical except for possible naturally occurring mutations that may be present in minor amounts. Thus, the modifier "monoclonal" indicates the character of the antibody as not being a mixture of discrete antibodies.

The humanized antibodies comprising an ultralong CDR3 as disclosed herein can be made using a hybridoma cell-based method first described by Kohler et al, Nature, 256: 495 (1975), or may be made by recombinant DNA methods.

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed.

The hybridoma cells may be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, myeloma cell lines may be murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of humanized antibodies comprising an ultralong CDR3. For example, the binding specificity of monoclonal antibodies produced by hybridoma cells may be determined by immunoprecipitation or by an in vitro binding assay, such as an enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The humanized antibodies comprising an ultralong CDR3 as disclosed herein may be made by using combinatorial libraries to screen for synthetic antibody clones with the desired activity or activities. For example, synthetic antibody clones are selected by screening phage libraries containing phage that display various fragments of antibody variable regions (e.g., scFv or Fab) fused to phage coat protein. Such phage libraries may be panned, for example, by affinity chromatography against the desired antigen. Clones expressing antibody fragments capable of binding to the desired antigen may be adsorbed to the antigen and thus separated from the non-binding clones in the library. The binding clones may then be eluted from the antigen, and can be further enriched by additional cycles of antigen adsorption/elution. Any of the humanized antibodies comprising an ultralong CDR3 as disclosed herein may be obtained by designing a suitable antigen screening procedure to select for the phage clone of interest followed by construction of a full length antibody comprising an ultralong CDR3 clone using the VH and VL (e.g., from scFv or Fab) sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions, one each from the light (VL) and heavy (VH) chains, that both present three hypervariable loops or complementarity-determining regions (CDRs). Variable domains may be displayed functionally on phage, either as single-chain Fv (scFv, also referred to as single-chain antibody (SCA)) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). scFv or SCA encoding phage clones and Fab encoding phage clones may be separately or collectively referred to as "Fv phage clones" or "Fv clones".

Repertoires of VH and VL genes may be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire may be cloned to provide a single source of human antibodies to a wide range of non-self and also self antigens without any immunization as described by Griffiths et al., EMBO J. 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. Protein pIII may include truncated forms of pIII. The antibody fragments can be displayed as single chain Fv fragments, in which VH and VL domains are connected on the same polypeptide chain by a flexible polypeptide spacer, (e.g., as described by Marks et al., J. Mol. Biol., 222: 581-597 (1991)), or as Fab fragments, in which one chain is fused to pIII (e.g., a truncated pII) and the other is secreted into the bacterial host cell periplasm where assembly of a Fab-coat protein structure which becomes displayed on the phage surface by displacing some of the wild type coat proteins, (e.g., as described in Hoogenboom et al., Nucl. Acids Res., 19: 4133-4137 (1991)).

Nucleic acid encoding antibody variable gene segments (including VH and VL segments) are recovered from the cells of interest and may be amplified or copies made by recombinant DNA techniques (e.g., Kunkel mutagenesis). For example, in the case of rearranged VH and VL gene libraries, the desired DNA may be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes may be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). For amplifying from cDNA, back primers can also be based in the leader exon as described in Jones et al., Biotechnol., 9: 88-89 (1991), and forward primers within the constant region as described in Sastry et al., Proc. Natl. Acad. Sci.

(USA), 86: 5728-5732 (1989). To enhance or maximize complementarity, degeneracy may be incorporated in the primers as described in Orlandi et al. (1989) or Sastry et al. (1989). Library diversity may be enhanced or maximized by using PCR primers targeted to each V-gene family in order to amplify available VH and VL arrangements present in the immune cell nucleic acid sample, for example, as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction may can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes may be derived in vitro from V gene segments. Most of the human VH-gene segments have been cloned and sequenced (e.g., reported in Tomlinson et al., J. Mol. Biol., 227: 776-798 (1992)), and mapped (e.g., reported in Matsuda et al., Nature Genet., 3: 88-94 (1993); these cloned segments (including all the major conformations of the H1 and H2 loop) may be used to generate diverse VH gene repertoires with PCR primers encoding H3 loops of diverse sequence and length as described in Hoogenboom and Winter, J. Mol. Biol., 227: 381-388 (1992). VH repertoires may also be made with all the sequence diversity focused in a long H3 loop of a single length as described in Barbas et al., Proc. Natl. Acad. Sci. USA, 89: 4457-4461 (1992). Human Vκ and Vλ. segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments may be constructed by combining VH and VL gene repertoires together in several ways. Each repertoire may be created in different vectors, and the vectors recombined in vitro, for example, as described in Hogrefe et al., Gene, 128: 119-126 (1993), or in vivo by combinatorial infection, for example, the loxP system described in Waterhouse et al., Nucl. Acids Res., 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These large libraries may provide large numbers of diverse antibodies of good affinity ($K_d^{-1}$ of about $10^{-8}$ M).

Alternatively, the repertoires may be cloned sequentially into the same vector, for example, as described in Barbas et al., Proc. Natl. Acad. Sci. USA, 88: 7978-7982 (1991), or assembled together by PCR and then cloned, for example, as described in Clackson et al., Nature, 352: 624-628 (1991). PCR assembly may also be used to join VH and VL DNAs with DNA encoding a flexible peptide spacer to form single chain Fv (scFv) repertoires. In yet another technique, "in cell PCR assembly" may be used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7 M^{-1}$), but affinity maturation may also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation may be performed by randomly mutating one or more CDRs, for example, using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the $10^{-9}$ M range.

The phage library samples are contacted with an immobilized protein under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g., as described in Barbas et al., Proc. Natl. Acad. Sci. USA, 88: 7978-7982 (1991), or by alkali, (e.g., as described in Marks et al., J. Mol. Biol., 222: 581-597 (1991)), or by antigen competition, (e.g., in a procedure similar to the antigen competition method of Clackson et al., Nature, 352: 624-628 (1991)). Phages may be enriched 20-1,000-fold in a single round of selection. Moreover, the enriched phages may be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) may be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) may be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

DNA encoding the hybridoma-derived monoclonal antibodies or phage display Fv clones disclosed herein is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Recombinant expression in bacteria of antibody-encoding DNA has been described by Better et al., U.S. Pat. No. 6,204,023 (see also, e.g., Skerra et al., Curr. Opinion in Immunol., 5: 256 (1993) and Pluckthun, Immunol. Revs, 130: 151 (1992)).

DNA encoding Fv clones as disclosed herein may be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions may be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred Fv clone embodiment, aFv clone derived from human variable DNA is fused to human constant region DNA to form coding sequence(s) for all human, full or partial length heavy and/or light chains.

DNA encoding a humanized antibody comprising an ultralong CDR3 derived from a hybridoma disclosed herein may also be modified, for example, by substituting the coding sequence for human heavy- and light-chain constant domains in place of homologous murine sequences derived from the hybridoma clone (e.g., as in the method of Morrison et al., Proc. Natl. Acad. Sci. USA, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies disclosed herein.

Antibody Genes and Proteins

The present disclosure provides antibody genes and proteins including, for example, humanized antibody genes or proteins that comprise an ultralong CDR3 sequence and/or a CDR3 scaffold. The present disclosure additionally provides VH, DH, and JH sequences useful in the preparation of ultralong CDR3 sequences. Such sequences may comprise motifs (e.g., cysteine motifs) as described herein including those as described in the many embodiments disclosed herein. In some embodiments, the antibodies disclosed herein may selectively or specifically bind to an epitope of a target protein. In some embodiments, the antibody may be an antagonist (e.g., blocking) antibody or an agonist antibody.

The variable region of the heavy and light chains are encoded by multiple germline gene segments separated by non-coding regions, or introns, and often are present on different chromosomes. For example, the genes for the human immunoglobulin heavy chain region contains approximately 65 variable (VH) genes, 27 Diversity (DH) genes, and 6 Joining (JH) genes. The human kappa (κ) and lambda (λ) light chains are also each encoded by a similar number of VL and JL gene segments, but do not include any D gene segments. Exemplary VH, DH, JH and VL (Vκ or Vλ) and JL (Jκ or Jλ) germline gene segments are set forth in WO 2010/054007.

During B cell differentiation germline DNA is rearranged whereby one DH and one JH gene segment of the heavy chain locus are recombined, which is followed by the joining of one VH gene segment forming a rearranged VDJ gene that encodes a VH chain. The rearrangement occurs only on a single heavy chain allele by the process of allelic exclusion. Allelic exclusion is regulated by in-frame or "productive" recombination of the VDJ segments, which occurs in only about one-third of VDJ recombinations of the variable heavy chain. When such productive recombination events first occur in a cell, this result in production of a μ heavy chain that gets expressed on the surface of a pre-B cell and transmits a signal to shut off further heavy chain recombination, thereby preventing expression of the allelic heavy chain locus. The surface-expressed μ heavy chain also acts to activate the kappa (κ) locus for rearrangement. The lambda (λ) locus is only activated for rearrangement if the κ recombination is unproductive on both loci. The light chain rearrangement events are similar to the heavy chain, except that only the VL and JL segments are recombined. Before primary transcription of each, the corresponding constant chain gene is added. Subsequent transcription and RNA splicing leads to mRNA that is translated into an intact light chain or heavy chain.

The variable regions of antibodies confer antigen binding and specificity due to recombination events of individual germline V, D and J segments, whereby the resulting recombined nucleic acid sequences encoding the variable region domains differ among antibodies and confer antigen-specificity to a particular antibody. The variation, however, is limited to three complementarity determining regions (CDR1, CDR2, and CDR3) found within the N-terminal domain of the heavy (H) and (L) chain variable regions. The CDRs are interspersed with regions that are more conserved, termed "framework regions" (FR). The extent of the framework region and CDRs has been precisely defined (see e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Each VH and VL is typically composed of three CDRs and four FRs arranged from the amino terminus to carboxy terminus in the following order: FR1, CDR1, FR2, CDR2, FR3, CDR3 and FR4. Sequence variability among VL and VH domains is generally limited to the CDRs, which are the regions that form the antigen binding site. For example, for the heavy chain, generally, VH genes encode the N-terminal three framework regions, the first two complete CDRs and the first part of the third CDR), the DH gene encodes the central portion of the third CDR, and the JH gene encodes the last part of the third CDR and the fourth framework region. For the light chain, the VL genes encode the first CDR and second CDR. The third CDR (CDRL3) is formed by the joining of the VL and JL gene segments. Hence, CDRs 1 and 2 are exclusively encoded by germline V gene segment sequences. The VH and VL chain CDR3s form the center of the Ag-binding site, with CDRs 1 and 2 form the outside boundaries; the FRs support the scaffold by orienting the H and L CDRs. On average, an antigen binding site typically requires at least four of the CDRs make contact with the antigen's epitope, with CDR3 of both the heavy and light chain being the most variable and contributing the most specificity to antigen binding (see, e.g., Janis Kuby, Immunology, Third Edition, New York, W.H. Freeman and Company, 1998, pp. 115-118). CDRH3, which includes all of the D gene segment, is the most diverse component of the Ab-binding site, and typically plays a critical role in defining the specificity of the Ab. In addition to sequence variation, there is variation in the length of the CDRs between the heavy and light chains.

The constant regions, on the other hand, are encoded by sequences that are more conserved among antibodies. These domains confer functional properties to antibodies, for example, the ability to interact with cells of the immune system and serum proteins in order to cause clearance of infectious agents. Different classes of antibodies, for example IgM, IgD, IgG, IgE and IgA, have different constant regions, allowing them to serve distinct effector functions.

These natural recombination events of V, D, and J, can provide nearly $2×10^7$ different antibodies with both high affinity and specificity. Additional diversity is introduced by nucleotide insertions and deletions in the joining segments and also by somatic hypermutation of V regions. The result is that there are approximately $10^{10}$ antibodies present in an individual with differing antigen specificities.

Antibodies include bovine antibody BLVH12 (e.g., heavy chain variable region set forth in SEQ ID NO: 482, and light chain variable region set forth in SEQ ID NO: 483); and bovine antibody BLV5B8 (e.g., heavy chain variable region set forth in SEQ ID NO: 484, and light chain variable region set forth in SEQ ID NO: 485)

Antibody Fragments

The present disclosure encompasses antibody fragments. In certain circumstances there are advantages of using antibody fragments, rather than whole antibodies. The smaller size of the fragments allows for rapid clearance, and may lead to improved access to solid tumors. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046.

Diabodies are antibody fragments with two antigen binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9: 129134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516). Antibody fragments can be made by various techniques, including but not limited to proteolytic digestion of an intact antibody as well as production by recombinant host cells (e.g. E. coli or phage), as described herein.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments (see, e.g., U.S. Pat. No. 6,204,023). Antibody fragments can be isolated from antibody phage libraries as discussed above. Alternatively, Fab'-SH fragments can be directly recovered from *E. coli* and chemically coupled to form $F(ab')_2$ fragments (see, e.g., Carter et al., Bio/Technology 10: 163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues (see, e.g., in U.S. Pat. No. 5,869,046). Other techniques for the production of antibody fragments will be apparent to the skilled practitioner. In other embodiments, the antibody of choice is a single chain Fv fragment (scFv or single chain antibody (SCA)). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, Supra. The antibody fragment may also be a "linear antibody", for example, as described in U.S. Pat. No. 5,641,870. Such linear antibody fragments may be monospecific or bispecific.

Humanized Antibodies

The present disclosure provides humanized antibodies comprising an ultralong CDR3. Humanized antibodies may include human engineered antibodies (see, e.g., Studnicka et al. (1994) Protein Eng. 7(6) 805-814; and U.S. Pat. No. 5,766,886). Various methods for humanizing non-human antibodies are known in the art. For example, a humanized antibody can have one or more amino acid residues introduced into it from a source which is human or non-human. Humanization may be performed following the method of Studnicka (see, e.g., Studnicka et al. (1994) Protein Eng. 7(6) 805-814; and U.S. Pat. No. 5,766,886), including the preparation of modified antibody variable domains. Humanization may alternatively be performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" or "human engineered" antibodies are chimeric antibodies, including wherein substantially less than an intact human variable domain has been substituted by or incorporated into the corresponding sequence from a non-human species. For example, humanized antibodies may be human antibodies in which some hypervariable region residues and possibly some FR residues are substituted by residues from analogous sites in rodent antibodies. Alternatively, humanized or human engineered antibodies may be non-human (e.g, rodent) antibodies in which some residues are substituted by residues from analoguous sites in human antibodies (see, e.g., Studnicka et al. (1994) Protein Eng. 7(6) 805-814; and U.S. Pat. No. 5,766,886).

The choice of human variable domains, both light and heavy, to be used in making the humanized antibodies is important to reduce antigenicity. For example, to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901). Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In some embodiments, the humanized antibodies comprising an ultralong CDR3 may be deimmunized. Methods of deimmunizing an antibody or protein are well known in the art. The immunogenicity of therapeutic proteins such as antibodies is thought to result from the presence of T-cell epitopes which can bind MHC class II molecules and generate a proliferative and cytokine response in CD4+ helper T-cells. These CD4+ helper cells then collaborate with B-cells to generate an antibody response against the therapeutic protein. Removal of the T-cell epitopes are thought to be key steps in deimmunizing a recombinant protein. T-cell epitopes can be predicted by in silico algorithms that identify residues required for binding MHC. Alternatively, epitopes can be identified directly by utilizing peripheral blood mononuclear cells from panels of human donors and measuring their response against the therapeutic protein when incubated with antigen presenting cells. Such in silico and in vitro systems are well known in the art [Jones T D, Crompton L J, Carr F J, Baker M P. Methods Mol Biol. 2009; 525:405-23, Deimmunization of monoclonal antibodies; and Baker M, and Jones T D. The identification and removal of immunogenicity in therapeutic proteins. *Curr. Opin. Drug Discovery Dev.* 2007; (2007); 10(2): 219-227]. When peptides are identified that bind MHC II or otherwise stimulate CD4+ cell activation, the residues of the peptide can be mutated one by one and tested for T-cell activation until a mutation is found which disrupts MHC II binding and T-cell activation. Such mutations, when found in an individual peptide, can be encoded directly in the recombinant therapeutic protein. Incubation of the whole protein with antigen presenting cells will not induce a significant CD4+ response, indicating successful deimmunization.

Bispecific Antibodies

Bispecific antibodies are monoclonal, preferably human or humanized, antibodies that have binding specificities for at least two different antigens. For example, one of the binding specificities may be for a first antigen and the other may be for any other antigen. Exemplary bispecific antibodies may bind to two different epitopes of the same protein. Bispecific antibodies may also be used to localize cytotoxic agents to cells which express a particular protein. These antibodies possess a binding arm specific for the particular protein and an arm which binds the cytotoxic agent (e.g., saporin, anti-interferon-α, *vinca* alkaloid, ricin A chain, methotrexate or radioactive isotope hapten). Bispecific antibodies may be prepared as full length antibodies or antibody fragments (e.g., F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, and in Traunecker et al., EMBO J., 10: 3655 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are not of particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure may facilitate the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules may can be engineered to maximize the percentage of heterodimers which are recovered from recombinant cell culture. The preferred interface comprises at least a part of the $C_{H3}$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate may be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies may be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced may be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. See, e.g., Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol., 152:5368 (1994).

Antibodies with more than two valencies are contemplated. For example, trispecific antibodies can be prepared. See, e.g., Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present disclosure may be multivalent antibodies (which are other than of the IgM class) with three or more antigen binding sites (e.g., tetravalent antibodies), which may be produced by recombinant expression of nucleic acid encoding the polypeptide chains of the antibody. The multivalent antibody may comprise a dimerization domain and three or more antigen binding sites. A preferred dimerization domain may comprise (or consist of) an Fc region or a hinge region. In this scenario, the antibody will comprise an Fc region and three or more antigen binding sites amino-terminal to the Fe region. A preferred multivalent antibody may comprise (or consist of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. A multivalent antibody may preferably further comprises at least two (and preferably four) light chain variable domain polypeptides. A multivalent antibody may, for instance, comprise from about two to about eight light chain variable domain polypeptides. The light chain variable domain polypeptides may comprise a light chain variable domain and, optionally, further comprise a CL domain.

Antibody Variants

In some embodiments, amino acid sequence modification(s) of the humanized antibodies comprising an ultralong CDR3 as described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody have been described (see, e.g., US 2003/0157108, US 2004/0093621. Antibodies with a bisecting N-acetylglucosamine (GlcNAc) in the carbohydrate attached to an Fc region of the antibody have been described (see, e.g., WO 2003/011878, and U.S. Pat. No. 6,602,684). Antibodies with at least one galactose residue in the oligosaccharide attached to an Fc region of the antibody WO 1997/30087; see, also, WO 1998/58964 and WO 1999/22764 concerning antibodies with altered carbohydrate attached to the Fc region thereof). Antigen-binding molecules with modified glycosylation have been described (see, e.g., WO 99/54342, U.S. Pat. Nos. 6,602,684 and 7,517,670, and US 2004/0072290; see also, e.g., U.S. Pat. Nos. 7,214,775 and 7,682,610).

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614 (now U.S. Pat. No. 6,946,292) US 2002/0164328 (now U.S. Pat.

No. 7,064,191); US 2004/0093621; US 2004/0132140; US 2004/0110704; US 2004/0110282 (now U.S. Pat. No. 7,749, 753); US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: Cys, Ser, Thr, Asn, Gln; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides disclosed herein, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods disclosed herein may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (e.g., either improved or diminished) Clq binding and/or Complement Dependent Cytotoxicity (CDC), e.g., as described in WO99/51642. See also Duncan & Winter Nature 322:738-40 (1988); U.S. Pat. Nos. 5,648,260; 5,624, 821; and WO94/29351 concerning other examples of Fc region variants. WO00/42072 and WO 2004/056312 describe antibody variants with improved or diminished binding to FcRs. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). These antibodies comprise an Fc reg on with one or more substitutions therein which improve binding of the Fc region to FcRn. Polypeptide variants with altered Fc region amino acid sequences and increased or decreased Clq binding capability are described in U.S. Pat. No. 6,194,551, WO99/51642. See, also, Idusogie et al. J. Immunol. 164:4178-4184 (2000).

In certain embodiments, the present disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see, Bruggemann, M. et al., Exp. Med. 166:1351-1361 (1987)). Alternatively, non-radioactive assays methods may be employed (see, for example, ACTI™ non-radioactive cytotoxicity assay for flow cytometry (CellTecl1r1ology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., Immunol. Methods 202:163 (1996); Cragg, M. S. et al., Blood 101:1045-1052 (2003); and Cragg, M. S, and M. J. Glennie, Blood 103:27382743 (2004)). FcRn binding and in vivo clearance/half life determinations can also be performed using methods known in the art (see, e.g., Petkova, S. B. et al., Int'l Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. Immunol. 164: 41784184 (2000).

Antibodies with increased half lives and improved binding to the neonatal Fc receptor (FcRn), which is responsible for the transfer of maternal IgGs to the fetus (Guyer et al., Immunol. 117:587 (1976) and Kim et al., Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

Antibody Derivatives

The humanized antibodies comprising an ultralong CDR3 as disclosed herein may be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Vectors, Host Cells and Recombinant Methods

For recombinant production of an antibody or fragment thereof as disclosed herein, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). In an exemplary embodiment, nucleic acid encoding a humanized antibody comprising an ultralong CDR3, a variable region comprising an ultralong CDR3, or an ultralong CDR3, is isolated and inserted into a replicable vector for further cloning (amplification of the DNA) or for expression. Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a partially human ultralong CDR3 antibody chain under the direction of the polyhedrin promoter or other strong baculovirus promoters.

a. Generating Antibodies Using Prokaryotic or Eukaryotic Host Cells:

i. Vector Construction

Polynucleotide sequences encoding polypeptide components of the antibodies disclosed herein can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence. Additionally, V regions comprising an ultralong CDR3 may optionally be fused to a C-region to produce an antibody comprising constant regions.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies have been described (see, e.g., U.S. Pat. No. 5,648,237).

In addition, phage vectors containing replicon and control sequences that are compatible with the host microorganism can be used as transforming vectors in connection with these hosts. For example, bacteriophage such as AGEM™-11 may be utilized in making a recombinant vector which can be used to transform susceptible host cells such as E. coli LE392.

The expression vectors disclosed herein may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector disclosed herein. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include: an ara B promoter, a PhoA promoter, β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (e.g., Siebenlist et al. (1980) Cell 20: 269) using linkers or adaptors to supply any required restriction sites.

Suitable bacterial promoters are well known in the art and fully described in scientific literature such as Sambrook and Russell, supra, and Ausubel et al, supra. Bacterial expression systems for expressing antibody chains of the recombinant catalytic polypeptide are available in, e.g., E. coli, Bacillus sp., and Salmonella (Palva et al., Gene, 22:229-235 (1983); Mosbach et al., Nature, 302:543-545 (1983)).

In one aspect disclosed herein, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence should be one that is recognized and processed (e.g., cleaved by a signal peptidase) by the host cell. For prokaryotic host cells that do not recognize and process the signal sequences native to the heterologous polypeptides, the signal sequence is substituted by a prokaryotic signal sequence selected, for example PeIB, OmpA, alkaline phosphatase, penicillinase, Ipp, or heat-stable enterotoxin II (STII) leaders, LamB, PhoE, and MBP. In one embodiment disclosed herein, the signal sequences used in both cistrons of the expression system are STII signal sequences or variants thereof.

In another aspect, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits (see e.g., Proba and Pluckthun Gene, 159:203 (1995)).

Suitable host cells for cloning or expression of antibody-encoding vectors include prokaryotic or eukaryotic cells described herein. In one embodiment, the host cell is eukaryotic, e.g. a Chinese Hamster Ovary (CHO) cell, Human Embryonic Kidney (HEK) cell or lymphoid cell (e.g., YO, NSO, Sp20 cell). For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22: 1409-1414 (2004), and Li et al., Nat. Biotech. 24:210-215 (2006). Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Plant cell cultures can also be utilized as hosts. See, e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., Gen VII'01. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (V ERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., Annals NI'. Acad. Sci. 383:44-68 (1982); MRC 5 cells; and FS4 cells. Other useful mammalian host cell lines include Chinese hamster ovary (CHO) cells, including DHFR' CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody.

ii. Antibody Production

For recombinant production of a partially human ultralong CDR3 antibody, nucleic acid encoding a humanized antibody comprising an ultralong CDR3 is inserted into one or more expression vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Host cells are transformed with such expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides disclosed herein are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector disclosed herein, protein expression is induced under conditions suitable for the activation of the promoter. For example, an ara B or phoA promoter may be used for controlling transcription of the polypeptides. A variety of inducers may be used, according to the vector construct employed, as is known in the art.

The expressed polypeptides of the present disclosure are secreted into and recovered from the periplasm of the host cells or transported into the culture media. Protein recovery from the periplasm typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins that are transported into the culture media may be isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Antibody production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides disclosed herein, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells. (see e.g., Chen et al. (1999) J Bio Chem 274:19601-19605; U.S. Pat. Nos. 6,083,715; 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210).

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available (see, e.g., Joly et al. (1998), supra; U.S. Pat. Nos. 5,264,365; 5,508,192; Hara et al., Microbial Drug Resistance, 2:63-72 (1996)).

*E. coli* strains deficient for proteolytic enzymes and transformed with plasmids overexpressing one or more chaperone proteins may be used as host cells in the expression systems disclosed herein.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products disclosed herein. Protein A is a 41 kD cell wall protein from *Staphylococcus aureus* which binds with a high affinity to the Fc region of antibodies (see, e.g., Lindmark et al (1983) J. Immunol. Meth. 62:1-13). The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (e.g., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this disclosure by higher eukaryotes is often increased by inserting an enhancer sequence into the vector. Many enhancer sequences are now known from mammalian genes (globin, elastase, albumin, α-fetoprotein, and insulin). An enhancer from a eukaryotic cell virus may also be used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least both genes into the host cell capable of expressing germline antibody polypeptide.

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Reissue 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma$1, $\gamma$2, or $\gamma$4 heavy chains (Lindmark et al., J. Immunol. Meth. 62:1-13 (1983)). Protein G is recommended for all mouse isotypes and for human $\gamma$3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Soluble forms of antibody or fragment present either in the cytoplasm or released from the periplasmic space may be further purified using methods known in the art, for example Fab fragments are released from the bacterial periplasmic space by osmotic shock techniques.

If inclusion bodies comprising an antibody or fragment have formed, they can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The soluble antibody or fragment can then be analyzed using gel electrophoresis, immunoprecipitation or the like. If it is desired to isolate a solubilized antibody or antigen binding fragment isolation may be accomplished using standard methods such as those set forth below and in Marston et al. (Meth. Enz., 182:264-275 (1990)).

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

In some cases, an antibody or fragment may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

Immunoconjugates

The disclosure also provides immunoconjugates (interchangeably termed "antibody-drug conjugates" or "ADC"), comprising any of the humanized antibodies comprising an ultralong CDR3 as described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (e.g., a radioconjugate).

The use of antibody-drug conjugates for the local delivery of cytotoxic or cytostatic agents. For example, drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) Supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10: 1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

a. Maytansine and Maytansinoids

In some embodiments, the immunoconjugate comprises a humanized antibody (full length or fragments) comprising an ultralong CDR3 as disclosed herein conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and EP 0 425 235. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. Nos. 5,208,020, 6,441, 163, or EP Patent 0 425 235, Chari et al., Cancer Research 52:127-131 (1992). Antibody-maytansinoid conjugates comprising the linker component SMCC may be prepared. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

b. Auristatins and Dolastatins

In some embodiments, the immunoconjugate comprises an antibody disclosed herein conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, (see, e.g., U.S. Pat. No. 7,498,298).

Typically, peptide-based drug moieties can be prepared by forming a peptide bond between two or more amino acids and/or peptide fragments. Such peptide bonds can be prepared, for example, according to the liquid phase synthesis method (see, e.g., E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al. (1998) Anti-Cancer Drug Design 13:243-277; Pettit, G. R., et al. Synthesis, 1996, 719-725; and Pettit et al. (1996) J. Chem. Soc. Perkin Trans. 1 5:859-863. See also Doronina (2003) Nat Biotechnol 21(7):778-784; U.S. Pat. No. 7,498,289, (disclosing, linkers and methods of preparing monomethylvaline compounds such as MMAE and MMAF conjugated to linkers).

c. Calicheamicin

In other embodiments, the immunoconjugate comprises an antibody disclosed herein conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Structural analogues of calicheamicin which may be used include, but are not limited to, $\gamma_1{}'$, $\alpha_2{}'$, $\alpha_3{}'$, N-acetyl-$\gamma_1{}'$, PSAG and $\theta_1{}'$ (see, e.g., Hinman et al., Cancer Research 53:3336-3342 (1993), Lode et al., Cancer Research 58:2925-2928 (1998) and the aforementioned U.S. patents). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

d. Other Cytotoxic Agents

Other antitumor agents that can be conjugated to the antibodies disclosed herein include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present disclosure further contemplates an immuno-conjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic reso-nance imaging, mri), such as iodine-123 again, iodine-131, indium-111, fluorine-19, carbon-13, nitrogen-15, oxygen-17, gadolinium, manganese or iron.

The radiolabels or other labels may be incorporated in the conjugate in known ways. For example, the peptide may be biosynthesized or may be synthesized by chemical amino acid synthesis using suitable amino acid precursors involv-ing, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), alde-hydes (such as glutaraldehyde), bis-azido compounds (such as bis (p-azidobenzoyl) hexanediamine), bis-diazonium derivatives (such as bis-(p-diazoniumbenzoyl)-ethylenedi-amine), diisocyanates (such as toluene 2,6-diisocyanate), and bis-active fluorine compounds (such as 1,5-difluoro-2, 4-dinitrobenzene). For example, a ricin immunotoxin can be prepared as described in Vitetta et al., Science 238:1098 (1987). Carbon-14-labeled 1-isothiocyanatobenzyl-3-meth-yldiethylene triaminepentaacetic acid (MX-DTPA) is an exemplary chelating agent for conjugation of radionucle-otide to the antibody. See WO94/11026. The linker may be a "cleavable linker" facilitating release of the cytotoxic drug in the cell. For example, an acid-labile linker, peptidase-sensitive linker, photolabile linker, dimethyl linker or dis-ulfide-containing linker (Chari et al., Cancer Research 52:127-131 (1992); U.S. Pat. No. 5,208,020) may be used.

The compounds disclosed herein expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succin-imidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

e. Preparation of Antibody Drug Conjugates

In the antibody drug conjugates (ADC) disclosed herein, an antibody (Ab) is conjugated to one or more drug moieties (D), e.g., about 1 to about 20 drug moieties per antibody, through a linker (L). An ADC of Formula I $[Ab-(L-D)_p]$ may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-male-imidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-ma-leimidomethyl)cyclohexane-1 carboxylate ("SMCC"), and N-Succinimidyl (4-iodo-acetyl)aminobenzoate ("SIAB"). Additional linker components are known in the art and some are disclosed herein (see, e.g., U.S. Pat. No. 7,498,298).

In some embodiments, the linker may comprise amino acid residues. Exemplary amino acid linker components include a dipeptide, a tripeptide, a tetrapeptide or a penta-peptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid resi-dues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated pro-tease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cys-teine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, e.g., cysteine bridges. Antibodies may be made reactive for conjugation with linker reagents by treatment with a reducing agent such as DTT (dithiothreitol). Each cysteine bridge will thus form, theo-retically, two reactive thiol nucleophiles. Additional nucleo-philic groups can be introduced into antibodies through the reaction of lysines with 2-iminothiolane (Traut's reagent) resulting in conversion of an amine into a thiol. Reactive thiol groups may be introduced into the antibody (or frag-ment thereof) by introducing one, two, three, four, or more cysteine residues (e.g., preparing mutant antibodies com-prising one or more non-native cysteine amino acid resi-dues).

Antibody drug conjugates disclosed herein may also be produced by modification of the antibody to introduce electrophilic moieties, which can react with nucleophilic substituents on the linker reagent or drug. The sugars of glycosylated antibodies may be oxidized, e.g., with perio-date oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Engineered Hybridomas

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed. Hybridomas. Including bovine hybridomas, may be a source of bovine antibody gene sequences, including ultralong CDR3 sequences.

Transgenic Mammals

A nucleic acid sequence encoding a germline antibody polypeptide of the present disclosure can be introduced into a non-human mammal to generate a transgenic animal that expresses the germline antibody polypeptide. Unlike the transgenic animal models more commonly seen, the transgene expressed by the transgenic mammals of the present disclosure need not replace at least one allele of the endogenous coding sequence responsible for the variable regions of antibody chains following somatic recombination. Due to allelic exclusion, the presence of an exogenous, post-somatic rearrangement version of the germline V region DNA will inhibit the endogenous alleles of pre-somatic rearrangement V minigenes from undergoing somatic rearrangement and contributing to the makeup of antibody chains this mammal may produce. Thus, when exposed to a particular antigen, the mammal will generate heterologous antibodies comprising one endogenously rearranged antibody chain, and one transgenic gene which was rearranged a priori. Such heterologous antibodies are invaluable in research and in treating certain conditions in live subjects. On the other hand, a method that directs the integration of the transgene to the locus of an endogenous allele will fully serve the purpose of practicing the present disclosure as well.

The general methods of generating transgenic animals have been well established and frequently practiced. For reviews and protocols for generating transgenic animals and related methods for genetic manipulations, see, e.g., Mansour et al., Nature 336:348-352 (1988); Capecchi et al., Trends Genet. 5:70-76 (1989); Capecchi, Science 244:1288-1292 (1989); Capecchi et al., Current Communications in Molecular Biology, pp 45-52, Capecchi, M. R. (ed.), Cold Spring Harbor Press, Cold Spring Harbor, N.Y. (1989); Frohman et al., Cell 56: 145-147 (1989); Brinster et al., Proc. Natl. Acad. Sci. USA 82:4438-4442 (1985); Evans et. al., Nature 292:154-156 (1981); Bradley et al., Nature 309:255-258 (1984); Gossler et al., Proc. Natl. Acad. Sci. USA 83:9065-9069 (1986); Robertson et al., Nature 322: 445-448 (1986); Jaenisch Science 240:1468-1474 (1988); and Siedel, G. E., Jr., "Critical review of embryo transfer procedures with cattle" in Fertilization and Embryonic Development in Vitro, page 323, L. Mastroianni, Jr. and J. D. Biggers, ed., Plenum Press, New York, N.Y. (1981).

An exemplary transgenic animal of the present disclosure is mouse, whereas a number of other transgenic animals can also be produced using the same general method. These animals include, but are not limited to: rabbits, sheep, cattle, and pigs (Jaenisch Science 240:1468-1474 (1988); Hammer et al., J. Animal. Sci. 63:269 (1986); Hammer et al. Nature 315:680 (1985); Wagner et al., Theriogenology 21:29 (1984)).

Pharmaceutical Compositions

Humanized antibodies comprising an ultralong CDR3, antibody fragments, nucleic acids, or vectors disclosed herein can be formulated in compositions, especially pharmaceutical compositions. Such compositions with humanized antibodies comprising an ultralong CDR3 comprise a therapeutically or prophylactically effective amount of a humanized antibodies comprising an ultralong CDR3, antibody fragment, nucleic acid, or vector disclosed herein in admixture with a suitable carrier, e.g., a pharmaceutically acceptable agent. Typically, humanized antibodies comprising an ultralong CDR3, antibody fragments, nucleic acids, or vectors disclosed herein are sufficiently purified for administration before formulation in a pharmaceutical composition.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecularweight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of humanized antibodies comprising an ultralong CDR3, antibody fragments, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., humanized antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(-)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(-)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141). Exemplary hyaluronic acid containing compositions of the present disclosure comprise a hyaluronic acid ester polymer in an amount of approximately 0.1% to about 40% (w/w) of a humanized antibody comprising an ultralong CDR3 to hyaluronic acid polymer.

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which a humanized antibody comprising an ultralong CDR3, antibody fragment, nucleic acid, or vector disclosed herein has been absorbed or encapsulated. Where an implantation device is used, the device may be implanted into any suitable tissue or organ, and delivery of a humanized antibody comprising an ultralong CDR3 antibody fragment, nucleic acid, or vector disclosed herein can be directly through the device via bolus, or via continuous administration, or via catheter using continuous infusion.

A pharmaceutical composition comprising a humanized antibody comprising an ultralong CDR3, antibody fragment, nucleic acid, or vector disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Certain formulations containing humanized antibodies comprising an ultralong CDR3, antibody fragments, nucleic acids, or vectors disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of a humanized antibody comprising an ultralong CDR3, antibody fragment, nucleic acid, or vector disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

In some embodiments, humanized antibodies comprising an ultralong CDR3 or fragments thereof are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., IgG1, IgG2, IgG3, or IgG4) that is responsible for increasing the in vivo serum half-life of the IgG molecule.

A salvage receptor binding epitope may include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also WO 97/34631 and WO 96/32478 which describe Fc variants and their interaction with the salvage receptor.

Mutation of residues within Fc receptor binding sites may result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g., replacing an IgG1 residue with a corresponding IgG2 residue at that position). For example, it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., Mol. Immunol. 30:105-8, 1993).

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g., a composition comprising a humanized antibody comprising an ultralong CDR3 alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises a humanized antibody comprising an ultralong CDR3 as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the humanized antibody comprising an ultralong CDR3 composition.

The following are examples of the methods and compositions of the disclosure. It is understood that various other embodiments may be practiced, given the general description provided above.

EXAMPLES

Example 1

At least 7 antibody heavy chain variable region sequences are publicly available that comprise an ultralong CDR3 of bovine origin. These sequences are shown in the alignment in FIG. 1. As shown in FIG. 1, the ultralong CDR3s present within these variable region sequences range in length from 56 to 61 amino acids. Strikingly, the sequence alignment indicates that the amino acid residues positioned in the N-terminal ends of the CDR3s are particularly conserved. Following the first cysteine residue in each of these variable region sequences, an amino acid sequence pattern of "TTVHQ" and variants thereof are found. This is unusual in that most heavy chain variable regions of most species end with the amino acid sequence "CAK" or "CAR". This unusual sequence motif (e.g., "TTVHQ") may be characteristic of the structure of an ultralong CDR3.

Additionally, the *Bos taurus* genome was searched and an undescribed heavy chain variable region DNA sequence in the antibody locus was found that encodes a "CTTVHQ" motif (e.g., SEQ ID NO: 1). This variable region sequence is designated herein as VH-UL (SEQ ID NO: 29). This sequence motif, discovered for the first time in searching the cow genome, is important in antibodies that comprise an ultralong CDR3.

To produce a humanized antibody comprising an ultralong CDR3, human variable regions for acceptor human frameworks were identified that are homologous to the bovine-derived VH-UL sequence (SEQ ID NO: 29). Several members of the human VH4 family were identified as being homologous to the VH-UL sequence, however none of VH4 family members contained a "CTTVHQ" motif. The sequences VH4-34*02 (SEQ ID NO: 33), VH4-39 (SEQ ID NO: 31), and VH4-59*03 (SEQ ID NO: 32) are the most homologous to the VH-UL sequence (see, e.g., FIG. 4B).

In a first exemplary method to produce a humanized antibody comprising an ultralong CDR3, a VH4-39 human acceptor framework (SEQ ID NO: 31) is used. The nucleotides encoding the last two amino acid residues of VH4-39 (e.g., "AR") are removed from the VH4-39 human acceptor framework, and nucleotides encoding a "TTVHQ" motif are added to the 3' end of the DNA sequence encoding the VH4-39 human acceptor framework after the nucleotides that encode the second cysteine residue of the VH4-39 human acceptor framework (e.g., after the nucleotides that code for amino acid position 97 of SEQ ID NO: 31). Next, the DNA encoding a portion of the ultralong CDR3 from BLV1H12 (e.g., the portion of the ultralong CDR3 beginning at the first glutamic acid residue (E) in BLV1H12, ETKKYQSCPDGYRERSDCSNRPACGTSDC-CRVSVFGNCLTTLPVSYSYTYNYEWHVD) is fused to the 3' end of the polynucleotide encoding the "TTVHQ" motif. Finally, DNA encoding a partial human JH4 region, beginning with the conserved tryptophan residue common to J region sequences, is added to the 3' end of the portion of the ultralong CDR3 sequence derived from BLV1H12. The following antibody gene encoding a partially human antibody comprising an ultralong CDR3 is derived:

(SEQ ID NO: 377)

```
cagctgcagctgcaggagtcgggcccaggactggtgaagccttcggagac cctgtccctcacctgcactgtctctggtggctccatcagcagtagtagtt actactggggctggatccgccagcccccagggaaggggctggagtggatt gggagtatctattatagtgggagcacctactacaacccgtccctcaagag tcgagtcaccatatccgtagacacgtccaagaaccagttctccctgaagc tgagctctgtgaccgccgcagacacggctgtgtattactgtactactgtg caccagGAAACAAAAAAATACCAAAGTTGTCCTGATGGGTATAGAGAACG

TTCGGATTGTAGTAACAGACCTGCTTGTGGTACTAGTGATTGTTGTCGTG

TTAGTGTTTTTGGTAATTGTCTTACTACTCTTCCTGTGAGTTATAGTTAT

ACTTACAATTACGAATGGCACGTCGATGTC*TGGGGCCAGGGAACCCTGGT*

*CACCGTCTCCTCAG*
```

Regular Font-derived from human VH4-39
Underlined-derived from VH-UL
BOLD BLACK-ultralong CDR3, derived from cow BLVH12
ITALICS-derived from human JH4

The amino acid sequence as translated from this partially human variable region gene is:

```
cagctgcagctgcaggagtcgggcccaggactggtgaagccttcggag
 Q   L   Q   L   Q   E   S   G   P   G   L   V   K   P   S   E accctgtccctcacctgcactgtctctggtggctccatcagcagtagt
 T   L   S   L   T   C   T   V   S   G   G   S   I   S   S agttactactggggctggatccgccagcccccagggaaggggctggag
 S   Y   Y   W   G   W   I   R   Q   P   P   G   K   G   L   E
```

-continued

```
tggattgggagtatctattatagtgggagcacctactacaaacccgtcc
 W   I   G   S   I   Y   Y   S   G   S   T   Y   Y   N   P   S ctcaagagtcgagtcaccatatccgtagacacgtccaagaaccagttc
 L   K   S   R   V   T   I   S   V   D   T   S   K   N   Q   F tccctgaagctgagctctgtgaccgccgcagacacggctgtgtattac
 S   L   K   L   S   S   V   T   A   A   D   T   A   V   Y   Y tgtactactgtgcaccaggaaacaaaaaaataccaaagttgtcctgat
 C   T   T   V   H   Q   E   T   K   K   Y   Q   S   C   P   D gggtatagagaacgttcggattgtagtaacagacctgcttgtggtact
 G   Y   R   E   R   S   D   C   S   N   R   P   A   C   G   T agtgattgttgtcgtgttagtgtttttggtaattgtcttactactctt
 S   D   C   C   R   V   S   V   F   G   N   C   L   T   T   L cctgtgagttatagttatacttacaattacgaatggcacgtcgatgtc
 P   V   S   Y   S   Y   T   Y   N   Y   E   W   H   V   D   V tggggccagggaaccctggtcaccgtctcctcag (SEQ ID NO: 377)
 W   G   Q   G   T   L   V   T   V   S   S    (SEQ ID NO: 378)
```

In an embodiment, this humanized VH sequence is recombinantly fused in-frame with a human heavy chain constant region and paired with a light chain for recombinant antibody production.

In another exemplary method to produce a humanized antibody comprising an ultralong CDR3, an ultralong CDR3 derived from BLV5B8 (SEQ ID NO: 7) is incorporated into the VH4-34 human acceptor framework (e.g., 4-34*02 (SEQ ID NO: 33); or 4-34*09 (SEQ ID NO: 34), along with a portion of the human JH2 region to produce a humanized antibody comprising an ultralong CDR3. Next, the nucleotides encoding the last two amino acid residues of the VH4-34 human acceptor framework (e.g., "AR") are removed from the VH4-34 human acceptor framework, and nucleotides encoding a "TTVHQ" motif are added to the 3' end of the VH4-34 human acceptor framework after the nucleotides that code for the second conserved cysteine residue in the VH4-34 human acceptor framework (e.g., after the nucleotides that code for amino acid position 95 of SEQ ID NOS: 33 or 34). Finally, DNA encoding a partial human JH2 region, beginning with the conserved tryptophan residue common to J region sequences, is added to the 3' end of the portion of the ultralong CDR3 sequence derived from BLV5B8. Thus, the following sequence encoding a humanized antibody variable region comprising an ultralong CDR3 is produced:

```
                                      (SEQ ID NO: 379)
caggtgcagctacaacagtggggcgcaggactgttgaagccttcggagac cctgtccctcacctgcgctgtctatggtgggtccttcagtggttactact ggagctggatccgccagcccccagggaaggggctggagtggattggggaa atcaatcatagtggaagcaccaactacaacccgtccctcaagagtcgagt caccatatcagtagacacgtccaagaaccagttctccctgaagctgagct ctgtgaccgccgcggacacggctgtgtattactgtActactgtgcaccag

GAAACCAGAAAAACCTGTTCTGATGGTTATATGGCTGTAGATAGTTGTGG

TCGTGGTCAGAGTGATGGTTGTGTCAATGATTGCAATTGTTGTTATTATG

GTTGGCGGAACTGTCGCAGGCAGCCTGCAATTCAAAGTTACGAATTTCAC

GTCGATGCCTGGGGCCGTGGCACCCTGGTCACTGTCTCCTCAG
Regular Font-derived from human VH4-39
Underlined-derived from VH-UL
```

-continued

```
BOLD BLACK-ultralong CDR3, derived from cow BLVH12
ITALICS-derived from human JH2
```

The amino acid sequence as translated from this partially human variable region gene is:

```
caggtgcagctacaacagtggggcgcaggactgttgaagccttcggag
 Q   V   Q   L   Q   Q   W   G   A   G   L   L   K   P   S   E accctgtccctcacctgcgctgtctatggtgggtccttcagtggttac
 T   L   S   L   T   C   A   V   Y   G   G   S   F   S   G   Y tactggagctggatccgccagcccccagggaaggggctggagtggatt
 Y   W   S   W   I   R   Q   P   P   G   K   G   L   E   W   I ggggaaatcaatcatagtggaagcaccaactacaacccgtccctcaag
 G   E   I   N   H   S   G   S   T   N   Y   N   P   S   L   K agtcgagtcaccatatcagtagacacgtccaagaaccagttctccctg
 S   R   V   T   I   S   V   D   T   S   K   N   Q   F   S   L aagctgagctctgtgaccgccgcggacacggctgtgtattactgtact
 K   L   S   S   V   T   A   A   D   T   A   V   Y   Y   C   T actgtgcaccaggaaaccagaaaaacctgttctgatggttatatggct
 T   V   H   Q   E   T   R   K   T   C   S   D   G   Y   M   A gtagatagttgtggtcgtggtcagagtgatggttgtgtcaatgattgc
 V   D   S   C   G   R   G   Q   S   D   G   C   V   N   D   C aattgttgttattatggttggcggaactgtcgcaggcagcctgcaatt
 N   C   C   Y   Y   G   W   R   N   C   R   R   Q   P   A   I caaagttacgaatttcacgtcgatgcctggggccgtggcaccctggtc
 Q   S   Y   E   F   H   V   D   A   W   G   R   G   T   L   V Actgtctcctcag (SEQ ID NO: 379)
 T   V   S   S    (SEQ ID NO: 380)
```

In an embodiment, this humanized VH sequence is then recombinantly fused in-frame with a human heavy chain constant region and paired with a light chain for recombinant antibody production.

Thus, any heavy chain variable region can be paired with a light chain variable region to produce a recombinant antibody. Bovine antibodies containing ultralong VH CDR3s typically pair with a restricted set of lambda light chains. Several human VL sequences can be used to pair with the sequences above, including VL1-47, VL1-40, VL1-51, VL2-18, which are homologous to the lambda region derived from *Bos taurus*.

Example 2

Libraries of polynucleotides encoding antibodies that comprise an ultralong CDR3 may be constructed by any method known in the art. Such polynucleotide libraries may be present within a plurality of vectors (e.g., a library of vectors) including, for example, vectors present within a plurality of host cells (e.g., a library of host cells). The libraries may present in any known format including, in a spatially addressed format (see, e.g., WO 11/056997; and Mao et al. (2010) Nat Biotech 28:1195-1202).

In an exemplary method, bovine spleen and lymph nodes were obtained from Animal Technologies (Tyler, TX), or from Texas A&M University. Total RNA was isolated from bovine tissues from three different cows (MID1, MID10, and MID 11) using TRIzol reagent (Invitrogen, Carlsbad, CA, USA) followed by on column digestion of DNA using the RNeasy Mini Kit (Qiagen, Valencia, CA, USA). Alternatively, cDNA may be obtained from the lymph nodes of a bovine immunized with an antigen (e.g., BVDV). Next, RNA quantity and quality were assessed with Nanodrop (Thermal Scientific), Qubit RNA and Agilent 2100 Bioanalyzer (Agilent, Santa Clara, CA, USA), following the manufacturer's protocols. Total RNA was used as a template for cDNA synthesis catalyzed by Superscript II (Invitrogen).

The library of amplified antibody variable regions were then subjected to deep sequencing. Briefly, bar-coded primers (Table 1) for each of the three cows (MID1, MID10, and MID11) were used to amplify $V_H$ from bovine spleen cDNA.

TABLE 1

Bar-coded primers for deep sequencing

| Primer # | Isotype | Primers |
|---|---|---|
| MID1 FW | IgG | CCTATCCCCTGTGTGCCTTGGCAGT CTCAGACGAGTGCGTTTGAGCGACA AGGCTGTAGGCTG (SEQ ID NO: 381) |
| MID1 RV | IgG | CCATCTCATCCCTGCGTGTCTCCGA CTCAGACGAGTGCGTCTTTCGGGGC TGTGGTGGAGGC (SEQ ID NO: 382) |
| MID10 FW | IgM | CCTATCCCCTGTGTGCCTTGGCAGT CTCAGTCTCTATGCGTTGAGCGACA AGGCTGTAGGCTG (SEQ ID NO: 383) |
| MID10 RV | IgM | CCATCTCATCCCTGCGTGTCTCCGA CTCAGTCTCTATGCGAGTGAAGACT CTCGGGTGTGATTCAC (SEQ ID NO: 384) |
| MID11 FW | IgM | CCTATCCCCTGTGTGCCTTGGCAGT CTCAGTGATACGTCTTTGAGCGACA AGGCTGTAGGCTG (SEQ ID NO: 385) |
| MID11 RV | IgM | CCATCTCATCCCTGCGTGTCTCCGA CTCAGTGATACGTCTAGTGAAGACT CTCGGGTGTGATTCAC (SEQ ID NO: 386) |

Next, the amplicons of $V_H$ were purified from 2% agarose gels and deep sequenced according to Roche 454 GS FLX instructions. Multiple alignments were performed with the MUSCLE algorithm (Edgar (2004) Nucleic Acids Research 32:1792-1797). MUSCLE was executed to generate multiple long CDR H3 nucleotide alignments with relatively high gap open (−20.0) and gap extend (−10.0) penalties due to the large amount of heterogeneity observed in the sequences. Local alignment was executed using the Smith-Waterman algorithm with the following settings, match score=2.0, mismatch penalty=−1.0, gap opening penalty=−2.0, and gap extension penalty=−0.5. CDR H3s were defined by the third residue following the conserved cysteine in framework 3 to the residue immediately preceding the conserved tryptophan in framework 4. $V_H$BUL was identified by BLAST searching the bovine genome (assembly Btau_4.6.1) with multiple ultralong $V_H$ sequences identified by deep sequencing. The deep sequencing identified a total of 11,728 ultralong CDR3 sequences with having a length between 44 and 69 amino acid residues. The results of the deep sequencing are summarized in Table 2 below.

TABLE 2

Summary of deep sequencing results from bovine spleen

| Source (Bar code) | Cow#1 (MID1) | Cow#1 (MID10) | Cow#2 (MID11) |
|---|---|---|---|
| Ig Class | IgG | IgM | IgM |
| CDR H3 length range | 44-66 | 44-68 | 44-69 |
| Number of unique cysteine patterns | 655 | 449 | 847 |
| Total number of unique long CDR H3 sequences | 5633 | 1639 | 4456 |

The results of the deep sequencing also revealed that ultralong CDR3 comprise a cysteine motif (e.g., a pattern of cysteine residues) that comprises between 3 and 12 cysteine residues. Representative examples of cysteine patterns are shown for the deep sequencing run for three different cows (MID1, MID10, and MID11) as well as their abundance in the run (Tables 3-5). The cysteines in the ultralong CDR3 regions are symbolized as "C". The amino acids between two cysteines are symbolized as "$X_n$". Exemplary sequences comprising cysteine motifs identified from the deep sequencing are presented in FIGS. 2A-C.

TABLE 3

Cysteine patterns identified in ultralong CDR3s from MID1

| Cysteine pattern (MID1) | Abundance (%) |
|---|---|
| $CX_{10}CX_5CX_5CXCX_7C$ | 10.44% |
| $CX_{10}CX_6CX_5CXCX_{15}C$ | 8.11% |
| $CX_{11}CXCX_5C$ | 5.22% |
| $CX_{11}CX_5CX_5CXCX_7C$ | 2.56% |
| $CX_{10}CX_6CX_5CXCX_{13}C$ | 1.47% |
| $CX_{10}CX_5CXCX_4CX_8C$ | 1.19% |
| $CX_{10}CX_6CX_6CXCX_7C$ | 1.08% |
| $CX_{10}CX_4CX_7CXCX_8C$ | 1.05% |
| $CX_{10}CX_4CX_7CXCX_7C$ | 0.91% |
| $CX_{13}CX_8CX_8C$ | 0.91% |
| $CX_{10}CX_6CX_5CXCX_7C$ | 0.59% |
| $CX_{10}CX_5CX_5C$ | 0.57% |
| $CX_{10}CX_5CX_6CXCX_7C$ | 0.50% |
| $CX_{10}CX_6CX_5CX_7CX_9C$ | 0.43% |
| $CX_9CXCX_5CXCX_7C$ | 0.41% |
| $CX_{10}CX_6CX_5CXCX_9C$ | 0.36% |
| $CX_{10}CXCX_4CX_5CX_{11}C$ | 0.32% |
| $CX_7CX_3CX_6CX_5CXCX_5CX_{10}C$ | 0.32% |
| $CX_{10}CXCX_4CX_5CXCX_2CX_3C$ | 0.30% |
| $CX_{16}CX_5CXC$ | 0.23% |

TABLE 4

Cysteine patterns identified in ultralong CDR3s from MID10

| Cysteine pattern (MID10) | Abundance (%) |
|---|---|
| $CX_{10}CXCX_4CX_5CXCX_2CX_3C$ | 2.87% |
| $CX_{10}CX_5CX_5C$ | 0.73% |
| $CX_{10}CXCX_4CX_5CX_{11}C$ | 0.67% |
| $CX_6CX_4CXCX_4CX_5C$ | 0.61% |
| $CX_{11}CX_4CX_5CX_6CX_3C$ | 0.55% |
| $CX_8CX_2CX_6CX_5C$ | 0.43% |
| $CX_{10}CX_5CX_5CXCX_{10}C$ | 0.37% |
| $CX_{10}CXCX_6CX_4CXC$ | 0.31% |
| $CX_{10}CX_5CX_5CXCX_2C$ | 0.31% |
| $CX_{14}CX_2CX_3CXCXC$ | 0.31% |
| $CX_{15}CX_5CXC$ | 0.31% |
| $CX_4CX_6CX_9CX_2CX_{11}C$ | 0.31% |
| $CX_6CX_4CX_5CX_5CX_{12}C$ | 0.31% |
| $CX_7CX_3CXCXCX_4CX_5CX_9C$ | 0.31% |
| $CX_{10}CX_6CX_5C$ | 0.24% |
| $CX_7CX_3CX_5CX_5CX_9C$ | 0.24% |
| $CX_7CX_5CXCX_2C$ | 0.24% |
| $CX_{10}CXCX_6C$ | 0.18% |

TABLE 4-continued

| Cysteine patterns identified in ultralong CDR3s from MID10 | |
| --- | --- |
| Cysteine pattern (MID10) | Abundance (%) |
| $CX_{10}CX_3CX_3CX_5CX_7CXCX_6C$ | 0.18% |
| $CX_{10}CX_4CX_5CX_{12}CX_2C$ | 0.18% |

TABLE 5

| Cysteine patterns identified in ultralong CDR3s from MID11 | |
| --- | --- |
| Cysteine pattern (MID11) | Abundance (%) |
| $CX_{12}CX_4CX_5CXCXCX_9CX_3C$ | 1.19% |
| $CX_{12}CX_4CX_5CX_{12}CX_2C$ | 0.96% |
| $CX_{10}CX_6CX_5CXCX_{11}C$ | 0.92% |
| $CX_{16}CX_5CXCXCX_{14}C$ | 0.70% |
| $CX_{10}CX_5CXCX_8CX_6C$ | 0.52% |
| $CX_{12}CX_4CX_5CX_8CX_2C$ | 0.49% |
| $CX_{12}CX_5CX_5CXCX_8C$ | 0.47% |
| $CX_{10}CX_6CX_5CXCX_4CXCX_9C$ | 0.45% |
| $CX_{11}CX_4CX_5CX_8CX_2C$ | 0.45% |
| $CX_{10}CX_6CX_5CX_8CX_2C$ | 0.43% |
| $CX_{10}CX_6CX_5CXCX_8C$ | 0.36% |
| $CX_{10}CX_6CX_5C$ | 0.31% |
| $CX_{10}CX_6CX_5CXCX_3CX_8CX_2C$ | 0.29% |
| $CX_{10}CX_6CX_5CX_3CX_8C$ | 0.29% |
| $CX_{10}CX_6CX_5CXCX_2CX_6CX_5C$ | 0.25% |
| $CX_7CX_6CX_3CX_3CX_9C$ | 0.25% |
| $CX_9CX_8CX_5CX_6CX_5C$ | 0.22% |
| $CX_{10}CX_2CX_2CX_7CXCX_{11}CX_5C$ | 0.20% |
| $CX_{10}CX_6CX_5CXCX_{13}C$ | 0.20% |
| $CX_{10}CX_6CX_5CXCX_2CX_8CX_4C$ | 0.20% |

Bovine $V_H$ regions were amplified from cDNA prepared in example 9 using primers 5'-TT-GAGCGACAAGGCTGTAGGCTG-3' (SEQ ID NO: 387) and 5'-CTTTCGGGGCTGTGGTGG-AGGC-3' (SEQ ID NO: 388) producing a library of antibody variable region cDNA biased for ultralong CDRs. Next, the mixture of $V_H$ regions was assembled by overlap PCR with bovine $C_H1$ and human IgG Fc. Briefly, EcoRI and NheI sites were incorporated for ligation into pFUSE expression vector, to afford a full-length heavy chain library ready for expression in mammalian cells. The ligation product was transformed into *E. coli* and 500 single E. colitransformants were picked. Each transformant was then grown overnight in a separate vessel and DNA from each colony was extracted using Qiagen minprep kits (Qiagen, Inc.) and sequenced by BATJ, Inc. (San Diego, CA) using the oligo 5'-AGATC-CAAGCTGTGACCGGC-3' (SEQ ID NO: 389). Sequences were analyzed using VectorNTI (Invitrogen, Inc. Carlsbad, CA). Duplicative sequences, sequences with no insert, and sequences encoding a CDR shorter than 35 residues were excluded. 132 clones containing unique long CDR heavy chain sequences were selected. Each heavy chain in the 132 member library was then co-transfected in parallel with pFUSE expression vector encoding the invariant bovine light chain BLV1H12 (SEQ ID NO: 412) into 293T cells, to generate a small spatially addressed library (Mao et al. (2010) Nat Biotech 28:1195-1202). 130,000 293T cells per well were plated in 24 well plates and grown overnight in 500 ul DMEM media (Invitrogen) with 10% FBS (Invitrogen), and Penicillin/streptomycin/glutamine (Invitrogen) at 37° C. and 5% $CO_2$. 0.5 µg of Hc-encoding pFuse vector and 0.5 µg of Lc-encoding pFuse vector were added to 25 µl of optimem (Invitrogen). 1 µl of Lipofectamine 2000 or 293Fectin transfection reagent (Invitrogen) was added to 25 µl of optimem, and incubated 5 minutes. Next, the DNA-optimem mix and transfection reagent-optimem mix were combined and incubated 15 minutes, added to 293T cells, and allowed to incubate on cells 4-6 hours. Then media was aspirated from wells and replaced with fresh media, and cells were allowed to grow and secrete IgG into the media for 4 days. Cell-culture supernatants containing IgG were harvested in 96 well format for further testing. The chimeric antibodies were quantified by sandwich ELISA detecting human Fc and screened for binding to BVDV by ELISA.

Antibodies were then secreted into culture media and harvested in a 96 well format to generate a small spatially addressed library for further testing including, screening for binding to BVDV by ELISA. For example, an ELISA was conducted to screen the antibody library for binding to BVDV. Briefly, killed BVDV (0.2 µg) in 100 µL DPBS was coated on 96-well MaxiSorp ELISA plates (Nunc) for 1 hour at 37° C. Next, the plates were blocked with 200 µL 3% BSA solution in DPBST, Dulbecco's phosphate buffered saline, 0.25% Tween 20) for 1 hour at 37° C. Samples were then incubated with 3% BSA in DPBST for 1 hour at 37° C. Subsequently, wells were washed 5 times with 200 µL DPBST. Next, Goat Anti-Human IgG (Fc)-HRP conjugated antibody (KPL Inc.) was added at a 1:1,000 dilution in blocking solution and incubated for 1 hour at 37° C. Wells were then washed 10 times with 200 µL DPBST. A 100 µL working solution of QuantaBlu (Pierce) was added to each well and incubated for 5 minutes at room temperature before plates were read in a SpectraMax M5 plate reader at ex325/em420 nm. Several candidate binders were identified. Clone H12 has a 63-residue CDR3 with 6 cysteine residues and was able to strongly bind BVDV in a dose dependent fashion.

Additionally, binding of the chimeric recombinant antibodies to BVDV antigens was evaluated by immunocytometric analysis of transfected human embryonic kidney (HEK) 293A cells (Invitrogen), as previously described (see, e.g., Njongmeta et al. (2012) *Vaccine* 30:1624-1635). Briefly, HEK 293A monolayers grown in 6-well tissue culture plates were transfected with 2 µg/well of plasmid (pCDNA3.3, Invitrogen) encoding BVDV antigens ($N^{pro}$, E2, or non-structural proteins NS2-3) using Lipofectamine 2000 reagent (Invitrogen), and incubated for 48 hr at 37° C. with 5% $CO_2$. The monolayers were fixed with ice-cold 100% methanol for 10 minutes, rinsed with PBS, and after blocking for 1 hour with PBS containing 5% fetal bovine serum (blocking buffer), the monolayers were incubated at room temperature for 1 hr with 10 µg/ml of a mouse anti-FLAG M2-alkaline phosphatase (AP)-conjugate (Sigma) in blocking buffer or 10 µg/ml of the chimeric recombinant antibodies (H12 or B8). Monolayers transfected with empty vector were similarly reacted to serve as negative controls and, following washes in blocking buffer, the monolayers probed with the chimeric recombinant antibodies were incubated with a 1/200 dilution of AP-conjugated goat anti-Human IgG (Fc specific) mAb (Sigma) in blocking buffer for 1 hr. Following washes in blocking buffer, the AP activity in all the wells was detected using Fast Red AS-MX substrate (Sigma). Stained cells were visualized and photographed using an IS70 inverted optical microscope (Olympus, Japan) equipped with a camera. H12 strongly binds HEK293A cells transfected with the NS2-3 non-structural proteins of BVDV but weakly bound to untransfected cells while B8 had weak binding to both HEK293A cells transfected with the NS2-3 non-structural proteins of BVDV and untransfected cells.

Example 3

Any vector known in the art may be used, or may be modified to be used, for cloning and/or expression of a nucleotide sequence encoding a heavy chain variable region that comprises an ultralong CDR3. Such vectors may optionally comprise, or be modified to comprise, a nucleotide sequence encoding the Fc portion of a human immunoglobulin (e.g., IgG) linked to the nucleotide sequence encoding the heavy chain variable region comprising an ultralong CDR3. Additionally, the nucleotide sequence encoding the heavy chain variable region comprising the ultralong CDR3 may be modified according to known methods such that the ultralong CDR3 can accept a nucleotide sequence encoding a non-bovine (e.g., non-antibody or human) sequence including, for example, by unidirectional cloning with restriction enzymes. Any vector known in the art may also be used, or may be modified to be used, for cloning and/or expression of a nucleotide sequence encoding a light chain variable region.

In an exemplary method, a vector may be modified by recombinant techniques to comprise a nucleotide sequence encoding a heavy chain variable region having an ultralong CDR3 linked to a nucleotide sequence encoding an IgG Fc. Briefly, a nucleotide sequence encoding CH1-CH2-CH3 of human IgG1 (SEQ ID NO: 390) was amplified by PCR and assembled via strand overlap elongation. Next, a compatible cohesive-end strategy was employed to replace the human Fc sequence encoded in vector pFUSE-hIgG2-Fc2 (SEQ ID NO: 457, InVivogen, San Diego CA) with CH1-CH2-CH3 of human IgG1, which destroyed the existing 3' NheI site in the pFUSE-hIgG2-Fc2 vector and generated an NheI site at the 5' end of SEQ ID NO: 390. The modified pFUSE-hIgG2-Fc2 vector ("HC pFuse", SEQ ID NO: 458) allows insertion of VH fragments between the signal sequence and the nucleotide sequence encoding CH1-CH2-CH3 of human IgG1 using the existing EcoRI site and the newly introduced NheI site. For example, the VH region from bovine antibody BLV1H12 (SEQ ID NO: 392) was amplified by PCR and subcloned in-frame between the signal sequence and nucleotide sequence encoding CH1-CH2-CH3 of human IgG1 in the HC pFuse vector using EcoRI and NheI restriction enzymes generating SEQ ID NO: 393.

Alternatively, nucleotide sequences encoding non-bovine sequences were inserted into the nucleotide sequence encoding the CDR3 of BLV1H12 heavy chain. Briefly, a pair of BsaI sites were introduced by PCR strand overlap extension into the nucleotide sequence encoding the CDR3 of BLV1H12 (SEQ ID NO: 395). The modified nucleotide sequence incorporating the BsaI sites within the CDR3 encoding sequence of BLV1H12 was then subcloned in-frame between the signal sequence and the nucleotide sequence encoding CH1-CH2-CH3 of human IgG1 in the HC pFuse vector described above using EcoRI and NheI restriction enzymes. Next, non-antibody sequences including cDNA encoding for interleukin 8 (IL-8, SEQ ID NO: 475), interleukin 21 (IL-21, SEQ ID NO: 480) and CXCL12/SDF-1alpha (SEQ ID NO: 479) (Origene) and oligoprimers encoding the peptide hormone somatostain (SEQ ID NO: 477), the venom peptides ProTx-II (SEQ ID NO: 481) and chlorotoxin (SEQ ID NO: 478), and the synthetic conotoxin peptide ziconotide (SEQ ID NO: 476) (IDTDNA) were modified by PCR amplification using oligoprimers with BsaI flanks to comprise BsaI flanks to produce non-bovine sequences with BsaI flanks for insertion into the CDR3 of BLV1H12. Next, the BsaI flanks in the modified non-antibody sequences were cut with BsaI and ligated, in frame, with the BLV1H12 BsaI digested vector, thereby inserting the nucleotide sequence encoding the non-antibody sequence into the BLV1H12 heavy chain variable region and replacing a portion (e.g., cysteine-rich portion) of the ultralong CDR3, and in-frame with the sequence encoding BVL1H12 variable region and CH1-CH2-CH3.

Similarly, a vector was modified by recombinant techniques to comprise a nucleotide sequence encoding a light chain. Briefly, the BLV1H12 light chain sequence (SEQ ID NO: 412) was amplified by PCR to introduce EcoRI and NheI ends. The BLV1H12 light chain variable region sequence was then digested with EcoRI and NheI and subcloned into pFUSE-hIgG2-Fc2, deleting the portion of pFUSE-hIgG2-Fc2 encoding Fc, and replacing it with only light chain sequence (SEQ ID NO: 459).

In addition, overlap PCR was used to amplify and join sequence from BLV1H12 light chain variable region and human lambda light chain constant region (SEQ ID NO: 474). This was amplified by PCR to introduce EcoRI and NheI ends. The hybrid BLV1H12 with human lambda sequence was then digested with EcoRI and NheI and subcloned into pFUSE-hIgG2-Fc2, deleting the portion of pFUSE-hIgG2-Fc2 encoding Fc, and replacing it with only light chain sequence.

Example 4

Polynucleotides coding for antibodies comprising an ultralong CDR3 may be expressed including, transiently expressed, in a host cell by any method known in the art.

In an exemplary method, the vectors comprising the heavy and light chains generated in Example 2 may be transfected into human embryonic kidney (HEK) 293 cells, for example, 293T cells or Freestyle™ 293-F cells.

For example, 130,000 293T cells per well were plated in 24 well plates and grown overnight in 500 µl DMEM media (Invitrogen) with 10% FBS (Invitrogen), and penicillin/streptomycin/glutamine (Invitrogen) at 37° C. and 5% $CO_2$. Next, 0.5 µg of Heavy chain-encoding pFuse vector (e.g., generated in Example 2) and 0.5 µg of Light chain-encoding pFuse vector (e.g., generated in Example 2) were added to 25 µl of Opti-MEM (Invitrogen). Subsequently, 1 µl of Lipofectamine 2000 or 293Fectin transfection reagent (Invitrogen) was added to 25 µl of Opti-MEM, and incubated 5 minutes. Then the dna-Opti-MEM solution and transfection reagent-Opti-MEM solution were combined and incubated for 15 minutes, added to 293T cells, and allowed to incubate on cells for 4-6 hours. Then media was aspirated from wells and replaced with fresh media, and the cells were allowed to grow and secrete IgG into the media for 2-6 days.

Additionally, for example, $1 \times 10^6$ 293Freestyle suspension cells/ml were grown overnight in Freestyle™293 Expression Medium (Invitrogen), and penicillin/streptomycin/glutamine (Invitrogen) at 37° C. and 5% $CO_2$. Next, for each milliliter of cells, a 30 µl solution was made in buffer PBS comprising 0.5 µg Heavy chain-encoding pFuse DNA and 0.5 µg of Lc-encoding pFuse. Additionally, for each milliliter of cells, a solution comprising 1 µl of 293Fectin transfection reagent was added to 30 µl PBS and incubated 5 minutes. Subsequently, the DNA and lipofectamine solutions were combined and incubated 15 minutes before adding the mixture to the cells. The cells were then allowed to grow and secrete IgG into media for 2-6 days.

After the growth period for the 293T cells or Freestyle™ 293-F suspension cells, media was harvested, and IgG secreted into the supernatant was evaluated by sandwich ELISA. Briefly, Fc-specific anti Human IgG (Cat 12136, Sigma-Aldrich) was diluted 1:1000 in PBS and coated onto maxisorp plates (Nunc). Next, plates were blocked with 2% BSA in TBST, washed, and IgG secreted supernatants were incubated for 1 hour. After washing with TBST, the appropriate HRP conjugated anti-Light chain antibody is diluted 1:1000 in TBST and incubated 1 hour (anti kappa-HRP, Cat #A-7164, Sigma-Aldrich; anti-lambda-HRP, Cat #2070-05, Southern Biotech). After washing with TBST, HRP was detected with TMB (Cat #TMBS-1000-01, BioFX), and neutralized with 0.6M $H_2SO_4$. Subsequently, absorbance (A450) was measured, and compared to a standard curve of known IgG concentration to determine the concentration of human antibody in cell culture supernatant.

The yield of antibody from supernatants from cells transfected with heavy chain constructs encoding BLV1H12 with human CH1-CH2-CH3 and a replacement of at least a portion of CDR3 (generated in Example 3) and a light chain construct encoding BLV1H12 LV-human lambda LC was determined by ELISA, and normalized to the yield of BLV1H12-IL8 (Table 6). The ELISA indicated that some sequences (e.g., zinconotide) that were used to replace a portion of CDR3 have a minor impact on expression of the antibody, while some sequences (e.g., somatostatin, chlorotoxin, SDF1(alpha), IL21) that were used to replace a portion of CDR3 had a modest impact on expression of the antibody, and other sequences (ProTxII) had an even greater impact on expression of the antibody, as compared to BLV1H12-IL8 (the highest expressor) (Table 6).

TABLE 6

Expression yield of BLV1H12 with replacements to Long CDR3

| Heavy Chain V region | Light Chain | Normalized Yield (% of highest expressor) |
|---|---|---|
| BLV1H12-IL8 | BLV1H12-HuLambdaC | 100 |
| BLV1H12-Ziconotide | BLV1H12-HuLambdaC | 94.7 |
| BLV1H12-Somatostatin | BLV1H12-HuLambdaC | 46.5 |
| BLV1H12-Chlorotoxin | BLV1H12-HuLambdaC | 39.7 |
| BLV1H12-SDF1(alpha) | BLV1H12-HuLambdaC | 38.9 |
| BLV1H12-IL21 | BLV1H12-HuLambdaC | 32.3 |
| BLV1H12-ProTxII | BLV1H12-HuLambdaC | 2.1 |

Example 5

Human germline sequences that comprise an ultralong CDR3 may be evaluated by any method known in the art to identify those human germline sequences that permit expression of an ultralong CDR3 that comprises a non-bovine sequence.

In an exemplary method, overlap PCR was used to insert Bsal sites into human germline variable regions VH1-24, VH1-46, VH1-69, VH3-23, VH4-4, and VH4-34. Next, PCR was used to introduce EcoRI and NheI sites for sub-cloning in between the signal sequence and CH1-CH2-CH3 region of the HC pFuse vector comprising BLV1H12 generated in Example 2. Subsequently, the IL-8-GSG cassette (SEQ ID NO: 399) was introduced into the Bsal sites of each human germline construct, giving VH1-24+CDR3-IL8 (SEQ ID NO: 425), VH1-46+CDR3-IL8 (SEQ ID NO: 426), VH1-69+CDR3-IL8 (SEQ ID NO: 427), VH3-23+CDR3-IL8 (SEQ ID NO: 428), VH4-4+CDR3-IL8 (SEQ ID NO: 429), and VH4-34+CDR3-IL8 (SEQ ID NO: 430). Next, each pFuse vector encoding a human germline heavy chain and CDR3-IL8 construct was co-transfected with pFuse vector encoding BLV1H12 LV (SEQ ID NO: 474), and allowed to express and secrete these IgGs into the media as described in Example 4. ELISA was then used to determine IgG yield as described in Example 4. Yields of the constructs were determined, and normalized to the highest expressing construct. Surprisingly, the CDR3 from cow is not readily transposable to any human heavy chain variable region. VH4-4 had the highest yield, despite VH4-34 having the closest sequence homology to the BLV1H12 sequence (Table 7).

TABLE 7

Expression Yield of Humanized Heavy Chains with Ultralong CDR3s (removed last column of values, with IgG nM, only showing normalized values.

| Heavy Chain Variable Region: | Normalized Yield (% of highest expressor) |
|---|---|
| BLV1H12 + CDR3IL8 | 100 |
| BLV1H12 | 58.4 |
| VH1-24 BLVCDR3IL8 | 4.4 |
| VH1-46 BLVCDR3IL8 | 2.4 |
| VH1-69 BLVCDR3IL8 | 1.4 |
| VH3-23 BLVCDR3IL8 | 14.7 |
| VH4-4 BLVCDR3IL8 | 22.5 |
| VH4-34 BLVCDR3IL8 | 5.4 |

Example 6

Antibodies comprising an ultralong CDR3 with a non-bovine sequence (e.g., a replacement of at least a portion of the CDR3 with a non-bovine sequence) including, humanized antibodies, may be evaluated by any method known in the art for binding of the non-bovine sequence to its binding partner including, for example, flow cytometry.

In an exemplary method, BLV1H12 IgG comprising a CDR3 with an IL-8 insert (e.g., the IL-8 sequence replaced a portion of the CDR3) was evaluated for binding to CXCR1 expressing cells by flow cytometry. Briefly, a cell line expressing functionally validated CXCR1 derived from U2OS cells was obtained from DiscoveRx and cultured per manufacturer's instructions (Cat #93-0226C3, DiscoveRx Corporation, Freemont, CA). The parental cell line U2OS was obtained from ATCC and cultured under the same conditions as the CXCR1 cells. Cell culture supernatants were then tested for binding to cells by flow cytometry. The adherent U2OS or CXCR1-U2OS cells were dissociated with Accutase (Innovative Cell Technologies, Inc., San Diego, CA), neutralized with an equal volume of media containing 10% serum, centrifuged at 1000 g, and resuspended in PBS with 2% BSA. Next, cells were dispensed into microtiter plates to achieve between 30,000 to 300,000 cells per well, centrifuged again, and resuspended in cell culture supernatant containing expressed IgG, or a dilution of IgG-containing cell culture supernatant. A fluorescent-conjugated anti-Human Fc antibody was used to detect binding of the expressed antibody to cells. Subsequently, cell fluorescence was measured by flow cytometry (e.g., FACS), and median Arbitrary Fluorescence Units (AFU) were calculated for each combination of antibody and cell type tested, revealing the extent of IgG binding to those cells. The ratio of median fluorescence (IgG binding) of CXCR1-U2OS cells versus U2OS parental cells shows that the BLV1H12 IgG comprising a CDR3 with an IL-8 insert has specificity for CXCR1 (Table 8).

TABLE 8

| | ULcowV (Median Arbitrary Fluorescence Units (AFU)) | ULcowV + IL8 (Median Arbitrary Fluorescence Units (AFU)) |
|---|---|---|
| Parental U2OS | 4 | 76 |
| CXCR1-U2OS | 4 | 707 |

Binding of BLV1H12 frameworks to CXCR1 U2OS cells

Additionally, the human germline CDR3-IL8 IgGs described in Example 5 were evaluated for binding to CXCR1 expressing cells by flow cytometry as described above. IgG binding to CXCR1-U2OS cells is indicated by higher fluorescence values, but non-specific binding to U2OS parental cells is also detectable. For a given IgG with CDR3-IL-8, specific binding to CXCR1 is revealed by the ratio of fluorescence on CXCR1-U2OS cells to the fluorescence on parental U2OS cells (Table 9). While the BLV1H12 supported strong and specific binding to CXCR1 (Table 8), the IL-8 in human germline IgGs showed either weaker binding to CXCR1, or non-specific interaction as seen in strong binding to both CXCR1-U2OS cells as well as the parental control cells. The most specific interaction to CXCR1 of IL-8 within a human germline IgG was seen with VH4-34.

TABLE 9

Binding of IgGs with CDR3-IL8 to CXCR1 U2OS cells

| IgG with HC V region: | Parental U2OS | CXCR1-U2OS | Ratio of CXCR1/ Parental |
|---|---|---|---|
| BLV1H12 | 5 | 9 | 1.9 |
| VH1-24 + CDR3-IL8 | 5 | 23 | 4.3 |
| VH1-46 + CDR3-IL8 | 5 | 6 | 1.1 |
| VH1-69 + CDR3-IL8 | 20 | 78 | 4.0 |
| VH3-23 + CDR3-IL8 | 534 | 1443 | 2.7 |
| VH4-4 + CDR3-IL8 | 1007 | 3079 | 3.1 |
| VH4-34 + CDR3-IL8 | 70 | 648 | 9.3 |

In another exemplary method, IL-8 activation of the CXCR1 receptor was tested using the CXCR1-U2OS DiscoveRx cells described above (Cat #93-0226C3, DiscoveRx). The DiscoveRx cells are engineered such that upon activation by ligand, the resultant beta-arrestin recruitment to the GPCR also causes activation of a luminescent reporter enzyme present cell line. Lysis reagents and luminescence substrate are included in the PathHunter Detection Kit (Cat #93-001, DiscoveRx) which was used following manufacturer's instructions. U2OS-CXCR1 cells were plated at 15,000 cells per well and serum starved overnight in EMEM media without serum. Next, media was removed and cells were incubated 1 hour at 37° C. with 80 μl of 1:1 EMEM and PBS, containing dilutions of either IL-8 or IgG with IL-8 insertion in CDR3, or control antibody. After 1 hour, 40 μl of PathHunter Detection reagent mix was added. Subsequently, after an hour at room temperature the luminescence in each well was measured using a luminescence plate reader. Higher luminescence signal reveals more activation of the CXCR1 receptor at the tested concentrations of IL-8 or IgG. IgGs were purified by scaling up the transfection method of Example 4, and purification of the IgG from media using protein A sepharose following manufacturer's instructions (Cat #17-1279-03 GE Healthcare) and dialysis post-elution into PBS. Protein yield was determined by A280 and calculated molar extinction coefficient. Increasing concentrations of BLV1H12-IL8 IgG activated CXCR1 somewhat similarly to the activation observed with IL-8, whereas increasing concentration of BLV1H12 IgG had no effect on CXCR1 activation (Table 10).

TABLE 10

Activation of CXCR1 by IL-8 as soluble cytokine or as CDR3 replacement

| nM | IL-8 (average RLU) | BLV1H12-IL8 IgG (average RLU) | IgG_ BVL1H12 IgG (average RLU) |
|---|---|---|---|
| 500.00 | 5720 | 6641 | 484 |
| 166.67 | 6770 | 6207 | 525 |
| 55.56 | 7365 | 5509 | 511 |
| 18.52 | 7295 | 5071 | 529 |
| 6.17 | 5869 | 4428 | 517 |
| 2.06 | 4110 | 3645 | 495 |
| 0.69 | 1939 | 2651 | 516 |
| 0.23 | 940 | 1515 | 455 |
| 0.08 | 504 | 822 | 461 |
| 0.01 | 440 | 435 | 460 |

Additionally, antibodies in which IL-8 was grafted into the VH4-4 human germline variable region were tested for activation of CXCR1. IgG with VH4-4+CDR3-IL8 (SEQ ID NO: 429) was compared to BLV1H12+CDR3-IL8, and IgGVH4-4 CDR3 Bsal (lacking the IL-8 insert) (SEQ ID NO: 431). A single concentration of soluble IL-8 was tested as a positive control for assay function at 31.5 nM and gave activation of 55525 average RLU. (Table 11). Although the IgG with insertion of IL-8 into the human VH4-4 variable region did activate CXCR1, it was not as potent in equal dose to the IgG with BLV1H12 sequence.

TABLE 11

Activation of CXCR1 by IgGs with CDR3 IL-8

| IgG (nM) | BLV1H12 + CDR3-IL8 (average RLU) | VH4-4 + CDR3-IL8 (average RLU) | VH4-4 + CDR3-Bsal (average RLU) |
|---|---|---|---|
| 261.500 | 56349 | 36481 | 7545 |
| 87.167 | 52128 | 29623 | 7139 |
| 29.056 | 47621 | 24889 | 7104 |
| 9.685 | 39280 | 15545 | 7174 |
| 3.228 | 34544 | 10233 | 7034 |
| 1.076 | 23700 | 8012 | 7184 |
| 0.359 | 13278 | 7338 | 6687 |
| 0.120 | 8867 | 7513 | 7331 |
| 0.040 | 7736 | 7323 | 6973 |
| 0.013 | 7329 | 6956 | 7048 |
| 0.004 | 7240 | 7067 | 7387 |
| 0.001 | 7437 | 7142 | 7500 |

Example 7

Humanized antibodies generated in Example 5 may be modified to comprise one or more amino acid substitutions in heavy chain CDR1 and/or CDR2. Such amino acid substitutions may be introduced into a human germline CDR1 and CDR2 at positions that are hypothesized to interact with CDR3.

In an exemplary method, certain residues in VH4-34 CDR1 and/or CDR2 were substituted with corresponding CDR1 and/or CDR2 residues from BLV1H12. Briefly, the pFuse vector encoding heavy chain VH4-34 CDR3-IL8 was modified by overlap PCR to replace all of CDR1 with sequence from BLV1H12 (VH4-34+CDR3-IL8_CDR1 Cow, SEQ ID NO: 432) or all of CDR2 with sequence from BLV1H12 (VH4-34+CDR3-IL8_CDR2 Cow, SEQ ID NO: 433). Additionally, overlap PCR was used to introduce point mutants G31D and Y32K into CDR1 (VH4-34+IL8_CDR1 G31D, Y32K, SEQ ID NO: 434) or point mutant E50S into CDR2 (VH4-34+CDR3-IL8_CDR2 E50S, SEQ ID NO: 435). These heavy chain constructs were paired with BLV1H12 light chain and were expressed as described in Example 4. Yield and CXCR1 binding were determined as described in Example 6 (Table 12).

TABLE 12

CDR1 and 2 modification of VH4-34 CDR3-IL8 IgG

| Heavy chain | IgG Yield normalized | FACS CXCR1/Parental Ratio |
|---|---|---|
| BLV1H12 | 100 | 1.9 |
| VH4-34 + CDR3-IL8 | 20 | 9.3 |
| VH4-34 + CDR3-IL8 + Cow CDR1 | 29 | 2.1 |
| VH4-34 + CDR3-IL8 + Cow CDR2 | 9 | 8.0 |
| VH4-34 + CDR3-IL8 + E31D, Y32K | 19 | 8.1 |
| VH4-34 + CDR3-IL8 + E50S | 27 | 4.0 |

Example 8

Antibodies that comprise an ultralong CDR3 including, antibodies that comprise an ultralong CDR3 where at least a portion of the CDR3 has been replaced by a non-bovine sequence, may be paired with a human light chain.

In an exemplary method, BLV1H12+CDR3-IL8 flexibility to pair productively with human germline light chains was explored by co-transfecting pFuse vector encoding heavy chain BLV1H12+CDR3-IL8 with pFuse vectors encoding each of several human germline light chains (e.g., SEQ ID NOs: 445-456), or BLV1H12 light chain (SEQ ID NO: 412). These human germline light chain sequences were synthesized (Genscript, Inc) and amplified by PCR as in Example 3 for subcloning via EcoRI and NheI into the pFUSE LC vector. BLV1H12+CDR3-IL8 encoding pFUSE vector was cotransfected with pFUSE vectors encoding light chains as in Example 3. Secreted IgGs were then tested by FACS as in Example 5 for specific binding to CXCR1 cells (Table 13). Human germ line light chains did not readily support the function of IL-8 when expressed as BLV1H12+CDR3.

TABLE 13

Evaluation of BLV1H12 + CDR3-IL8 when paired with germline human light chains

| Light chain | FACS CXCR1/Parental Ratio |
|---|---|
| A20J1 | 0.8 |
| A27J3 | 0.9 |
| L6J1 | 0.8 |
| L25J1 | 1.3 |
| V1-2J7 | 0.8 |
| V1-7J1 | 0.6 |
| V1-11J2 | 0.8 |
| V1-13J5 | 2.9 |
| V1-16J6 | 0.6 |
| V2-13J2 | 0.9 |
| V2-14J4 | 1.0 |
| V2-15J7 | 1.1 |
| V2-17J2 | 2.0 |
| V3-4J1 | 1.2 |

TABLE 13-continued

Evaluation of BLV1H12 + CDR3-IL8 when paired with germline human light chains

| Light chain | FACS CXCR1/Parental Ratio |
|---|---|
| V5-4J2 | 0.8 |
| BLV1H12 | 5.0 |

Alternatively, using the BLV1H12 light chain variable region as a guide, the human germline sequences identified with closest homology were V1-47 and V1-51. These light chain sequences were synthesized (SEQ ID NO: 455, 456) (IDTDNA, Inc.) with the desired EcoRI and NheI restriction sites for subcloning into the pFuse vector. Subsequently, pFuse vector encoding V1-47 or V1-51 were paired with pFuse vectors encoding VH4-34+CDR3-IL8, the VH4-34+CDR3-IL8 with the CDR1 or CDR2 modifications described in Example 6 (SEQ ID NOs: 432-435), as well as vectors encoding the combinations of both CDR1 and CDR2 modifications (e.g., VH4-34+CDR3-IL8_CDR1 Cow_CDR2 Cow, SEQ ID NO: 436; VH4-34+CDR3-IL8_CDR1 Cow-_CDR2 E50S, SEQ ID NO: 437; VH4-34+CDR3-IL8_CDR1 G31D, Y32K_CDR2 Cow, SEQ ID NO: 438; VH4-34+CDR3-IL8_CDR1 G31D, Y32K_CDR2 E50S, SEQ ID NO: 439). These IgGs were expressed, yield was determined by ELISA, and CXCR1 binding specificity was measured by flow cytometry as described above (Table 14).

TABLE 14

Expression yield and CXCR1 specificity for VH4-34 CDR3-IL8 IgGs having CDR1 and CDR2 modifications and paired with Lc V1-47 or V1-51

| HC VH4-34 CDR3-IL8+ | | nM IgG | | CXCR1/Parental Ratio | |
|---|---|---|---|---|---|
| Hc-CDR1 | Hc-CDR2 | V1-47 | V1-51 | V1-47 | V1-51 |
| G31D Y32K | VH4-34 | 1 | 2.5 | 3.6 | 3 |
| Cow | VH4-34 | 3 | 8.5 | 5.1 | 2.4 |
| VH4-34 | VH4-34 | 1.5 | −0.4 | 2.6 | 2.9 |
| G31D Y32K | E50S | 2 | 4.6 | 1.4 | 3 |
| Cow | E50S | — | 22.8 | 2.6 | 3.1 |
| VH4-34 | E50S | 3.3 | 3.3 | 3.3 | 1.8 |
| G31D Y32K | Cow | −0.1 | 2.3 | 2 | 2.6 |
| Cow | Cow | 0.7 | 4.9 | 4.6 | 3.1 |
| VH4-34 | Cow | 0.6 | 0.6 | 2.5 | 3.9 |

Example 9

Human germline light chains including, light chains that may be paired with a heavy chain comprising an ultralong CDR3, may be modified by any method known in the art. Such modifications may include the substitution of certain amino acid residues in the human light chain to those residues at corresponding positions in a bovine light chain sequence. The modified light chains may improve the yield of the antibody comprising the ultralong CDR3 and/or increase its binding specificity.

In an exemplary method, variants of V1-51 were made by overlap PCR and subcloned into pFuse vector for expression as described in Example 4. The engineered variants of V1-51 had: i) substitutions I29V and N32G introduced in CDR1 (SEQ ID NO: 440), ii) residues DNN (amino acids 51-53) in CDR2 changed to GDT (SEQ ID NO: 441), iii) residues DNNKRP (SEQ ID NO: 471) in and near CDR2 changed to GDTSRA (SEQ ID NO: 472), or iv) the 14 residues at the N-terminus were made identical to the first 14 resides of BLV1H12 light chain with point mutations S2A, T5N, P8S, A12G, A13S, and P14L (SEQ ID NO: 443) or v) combining the changes set forth in ii) and iv) (SEQ ID NO: 444). These V1-51 variants were paired with heavy chains encoding VH4-34+CDR3-IL8 (SEQ ID NO: 430), VH4-34+CDR3-IL8_CDR1 Cow (SEQ ID NO: 432), VH4-34+CDR3-IL8_CDR2 Cow (SEQ ID NO: 433), or VH4-34+CDR3-IL8_CDR1 Cow_CDR2 Cow, (SEQ ID NO: 436). Transfections and ELISA were carried out as described above, and flow cytometry was used to evaluate CXCR1 binding specificity as previously described, with the modification that cells were resuspended in 2% BSA in PBS plus 2 ug/ml Heparin sulfate, and IgGs were normalized to 10 nM during incubation on cells. Only certain combinations of heavy and light chains supported detectable expression (Table 15). Those combinations that expressed heavy and light chains were tested for CXCR1 binding specificity (Table 16).

Example 10

Libraries may be generated that comprise an ultralong CDR3 including, for example libraries that comprise at least a portion of an ultralong CDR3, within an antibody framework (e.g., a heavy chain framework). Such libraries may comprise a diversity of ultralong CDR3 sequences, a diversity of one or more residues that are positioned between one or more cysteine residues in the cysteine domain of the ultralong CDR3, or a diversity of non-bovine peptides that may be inserted (e.g., replace a portion of) in the ultralong CDR3. The antibody framework may be derived from a bovine sequence such as VH-UL, a human germline sequence, or a modified human germline sequence such as described in Example 7. Heavy chains with diverse ultralong CDR3 may be paired with light chains of bovine, human, or modified composition (see, e.g., Example 9) for expression of a library of antibody or antibody fragments comprising a diverse ultralong CDR3.

TABLE 15

| | VH4-34 CDR3-IL8 | VH4-34 CDR3-IL8 CDR1-Cow | VH4-34 CDR3-IL8 CDR2-Cow | VH4-34 CDR3-IL8 CDR1-Cow &CDR2-Cow |
|---|---|---|---|---|
| Hc CDR1: | | | | |
| | Human | Cow | Human | Cow |
| CDR2: | | | | |
| | Human | Human | Cow | Cow |
| V1-51 | 1 | 5 | 0 | 13 |
| V1-51 CDR1 129V, N32G | −1 | 5 | 0 | 3 |
| V1-51 CDR2 DNN to GDT | −1 | 23 | −1 | 5 |
| V1-51 CDR2 DNNKRP (SEQ ID NO: 471) to GDTSRA (SEQ ID NO: 472) | −1 | 4 | 1 | 23 |
| V1-51 S2A, T5N, P8S, A12G, A13S, P14L | 0 | 38 | −1 | 22 |
| V1-51 S2A, T5N, P8S, A12G, A13S, P14L & DNN to GDT | 0 | 37 | 0 | 1 |

TABLE 16

| | VH4-34 CDR3-IL8 | VH4-34 CDR3-IL8 CDR1-Cow | VH4-34 CDR3-IL8 CDR2-Cow | VH4-34 CDR3-IL8 CDR1-Cow &CDR2-Cow |
|---|---|---|---|---|
| Hc CDR1: | | | | |
| | Human | Cow | Human | Cow |
| CDR2: | | | | |
| | Human | Human | Cow | Cow |
| V1-51 | nt | 7.2 | nt | 11.1 |
| V1-51 CDR1 129V, N32G | nt | 8.9 | nt | 11.8 |
| V1-51 CDR2 DNN to GDT | nt | 5.6 | nt | 16.7 |
| V1-51 CDR2 DNNKRP (SEQ ID NO: 471) to GDTSRA (SEQ ID NO: 472) | nt | 8.0 | nt | 6.9 |
| V1-51 S2A, T5N, P8S, A12G, A13S, P14L | nt | 4.7 | nt | 12.2 |
| V1-51 S2A, T5N, P8S, A12G, A13S, P14L & DNN to GDT | nt | 6.8 | nt | |

In an exemplary method, a library is generated in which the library comprises a diversity of ultralong CDR3 sequences (e.g., the diversity in the library resides in that the library contains a plurality of diverse ultralong CDR3 sequences). For example, a plurality of diverse ultralong CDR3 sequences is obtained from cDNA extracted from the spleen and/or lymph nodes from either immunized or non-immunized cows. Alternatively, a plurality of diverse ultralong CDR3 sequences is captured as information from cDNA by sequencing technology, such as described in Example 2. cDNA-derived cow sequences are then amplified from the isolated cDNA or synthesized from sequencing of cDNA, and diverse CDR3 sequences are inserted into an antibody framework for expression of IgGs with ultralong CDR3 sequences, producing a library of IgGs with CDR3s derived from cows. The IgG library can exist in any format, including as a spatially addressed array see, e.g., WO 11/056997; and Mao et al. (2010) Nat Biotech 28:1195-1202).

In another exemplary method, a library is generated in which members of the library comprise an ultralong CDR3 with a certain cysteine domain, or multiple cysteine domains, wherein the members are diverse in one or more residues that are positioned between one or more cysteine residues in the cysteine domain. For example, in the sequence $CX_{10}CX_5CX_5CXCX_7C$ (SEQ ID NO: 41), a library is generated whereby any X residue is changed, or combination of X residues are changed, to produce diversity within CDR3. Such diversity is introduced by degenerate nucleotide synthesis, error prone PCR, gene synthesis, or any other method known in the art to make changes in nucleotide sequences. These ultralong CDR3 loops are then integrated with sequence encoding the antibody framework. Heavy chain sequences are then paired with human or modified human light chain sequences for co-transfection and expression to comprise an antibody library engineered from bovine CDR3s.

In another exemplary method, a library is generated in which members of the library comprise an ultralong CDR3 with diversity in a non-bovine sequence inserted into (e.g., replace a portion of) the ultralong CDR3. Ultralong CDR3s tolerate large non-bovine sequence insertions (e.g., cytokines, peptide hormones, signaling domains, and constituent proteins of arthropod toxins or reptile venoms) including, for example, cysteine rich insertions, within an antibody framework, and support the independent function of the peptide encoded by the non-bovine sequence, as demonstrated in Example 4 and Example 6. Sequences encoding non-bovine sequences are amplified by PCR from cDNA or synthesized, and incorporated with or without linker sequences, into an antibody sequence such that they are expressed within, in place of, or replace at least a portion of, an ultralong CDR3. Exemplary methods to insert a non-bovine sequence into a vector for expression are set forth in Example 3 above. Heavy chain sequences are then paired with human or modified human light chain for co-transfection and expression. For example, a non-bovine sequence is inserted into HC pFUSE, encoding VH4-34*02 with CDR1 and CDR3 modifications from BLV1H12. Briefly, the portion of the HC pFuse vector comprising a Bsal cassette (see, Example 3; bolded in the sequence below) which is flanked on both sides by a portion of an ultralong CDR3 (underlined sequence below) is replaced by a non-bovine sequence.

```
                                       (SEQ ID NO: 472)
caggtgcagctacagcagtggggcgcaggactgttgaagccttcggaga cgctgtccctcacctgcacagcaagcgggttttcactgagcgacaaggc
```

-continued

```
agtgggatggattcgccagcccccagggaaggggctggagtggattggg gaaatcaatcatagtggaagcaccaactacaacccgtccctcaagagtc gagtcaccatatcagtagacacgtccaagaaccagttctccctgaagct gagctctgtgaccgccgcggacacggctgtgtattactgtacctctgtg caccaggaaactaagaaataccagagcgagacctactatggttcgggtc tctcttatacctacaattatgaatggcatgtggatgtctggggacaggg cctgctggtgacagtctctagtgctagc
```

After replacement of the Bsal cassette with the non-bovine sequence the non-bovine sequence (referred to as insert in bold text in the sequence below) is positioned such that it is flanked on both sides by a portion of the ultralong CDR3.

```
                                    (SEQ ID NO: 473)
qvqlqqwgagllkpsetlsltctasgfslsdkavgwirqppgkglewige inhsgstnynpslksrvtisvdtsknqfslklssvtaadtavyyctsvhq etkkyqs- insert -sytynyewhvdvwgqgllvtvssas
```

Heavy chain sequences are then paired with human or modified human light chain for co-transfection and expression.

Example 11

Human germline light chains, including light chains that may be paired with a heavy chain comprising an ultralong CDR3, may be modified by any method known in the art. Such modifications may include the substitution of certain amino acid residues in the human light chain.

Light Chain V1-51 variants as described in Example 9 were modified by overlap PCR and subcloned into pFuse vectors to introduce K46R and L47T mutations. As an example, V1-51 with the point mutations S2A, T5N, P8S, A12G, A13S, P14L, D51 G, N52D, and N53T (SEQ ID NO: 444; SEQ ID NO:792) was modified to also include mutations K46R and L47T, encoding V1-51 with point mutations S2A, T5N, P8S, A12G, A13S, P14L, K46R, L47T, D51G, N52D, and N53T (SEQ ID NO: 486; SEQ ID NO: 780). In further examples, overlap PCR was used to combine previous V1-51 point mutation groupings with the K46R and L47T point mutations, to make i) VL1-51 S2A, T5N, P8S, A12G, A13S, P14L, K46R, L47T, D51G, N52D, N53T, K54S, P56A (SEQ ID NO: 487; SEQ ID NO: 781), ii) VL1-51 I29V, N32G, K47R, L47T, D51G, N52D, N53T (SEQ ID NO: 488; SEQ ID NO: 782), iii) VL1-51 I29V, N32G, K47R, L47T, D51G, N52D, N53T, K54S, P56A (SEQ ID NO: 489; SEQ ID NO: 783).

Humanized antibodies, including those generated as described in Example 5, may be modified, for example, to comprise one or more amino acid changes/substitutions in the heavy chain variable region (see, e.g., Example 7). In an exemplary method, certain residues of VH-34 were selected for substitution or modification.

Using overlap PCR, VH4-34+CDR3-IL8 constructs with various mutations at CDR1 and CDR2 were further modified to encode point mutations Q5R and Q6E. As an example, the construct in example 5 encoding VH4-34+CDR3-IL8 (SEQ ID NO: 430; SEQ ID NO: 793), was modified to encode point mutations Q5R and Q6E (SEQ ID NO: 490; SEQ ID NO: 784). Related constructs with the CDR1 or CDR2 modifications described in Example 7 (SEQ ID NOs: 432-435; SEQ ID NO: 794-797), were also mutated to encode Q5R and Q6E, resulting in i) VH4-34+CDR3-IL8_CDR1-G31DY32K_Q5RQ6E (SEQ ID NO: 491; SEQ ID NO: 785), ii) VH4-34+CDR3-IL8_CDR2-E50S_Q5RQ6E (SEQ ID NO: 492; SEQ ID NO: 786), iii) VH4-34+CDR3-IL8_CDR1-Cow_Q5RQ6E (SEQ ID NO: 494; SEQ ID NO: 788), and iv) VH4-34+CDR3-IL8_CDR2-Cow_Q5RQ6E (SEQ ID NO: 495; SEQ ID NO: 789). CDR1-Cow refers to the group of mutations A23T, V24A, Y25S, G27F, F29L, G31 D, Y32K, Y33A, W34V, and S35G. CDR2-Cow refers to the group of point mutations I48L, E50S, N52D, H53T, S54G, S56N, and N58G.

Vectors, for example, as described in Example 8, encoding the combinations of both CDR1 and CDR2 modifications (SEQ ID NOs: 436, 437, and 439; SEQ ID NOs: 798, 799, 801) were also modified by PCR to add the additional point mutations Q5R and Q6E resulting in i) VH4-34+CDR3-IL8_CDR1-G31DY32K_CDR2-E50S_Q5RQ6E (SEQ ID NO: 493; SEQ ID NO: 787), ii) VH4-34+CDR3-IL8_CDR1-Cow_CDR2-E50S_Q5RQ6E (SEQ ID NO: 496; SEQ ID NO: 790), and iii) VH4-34+CDR3-IL8_CDR1-Cow_CDR2-Cow_Q5RQ6E (SEQ ID NO: 497; SEQ ID NO: 791). These new VH4-34 variants containing mutations Q5R and Q6E are summarized in Table 17.

CDR3 may be evaluated by any method known in the art to identify and characterize sequences that permit expression of an ultralong CDR3, including an ultralong CDR that comprises a non-antibody sequence.

Heavy chain constructs encoding variants of VH4-34+ CDR3-IL8 (SEQ ID NOs: 430, 432-437, 439; SEQ ID NOs: 793, 794-799, 800) were paired with light chain constructs encoding variants of V1-51 (SEQ ID NOs: 440, 441, 442, 443, 444, 456, and 486; SEQ ID NOs: 801, 802, 803, 804, 792, and 780) and transfected in 293Freestyle cells as described in Example 4. Yield of the resultant IgGs in supernatant was determined as in Example 4, and presented in Table 18. Heavy chains without mutations at CDR1 or CDR2 designated "Human" indicate that the sequence was unchanged from the VH4-34 human germline. CDR1-Cow refers to the group of mutations A23T, V24A, Y25S, G27F, F29L, G31 D, Y32K, Y33A, W34V, and S35G. CDR2-Cow refers to the group of point mutations I48L, E50S, N52D, H53T, S54G, S56N, and N58G. Point mutations in CDR1 or CDR2 are indicated as well (e.g. G31 D, Y32K; or E50S). The antibody expression yield in each square was determined by the level of IgG expression: higher numbers in squares exhibit better expression.

TABLE 17

| Nucleotide SEQ ID | VH4-34 + CDR3-IL8 with Q5R, Q6E and CDR1 and/or CDR2 mutation | | |
|---|---|---|---|
| NO: | Construct Name: | CDR1 | CDR2 |
| 490 | VH4-34 + CDR3-IL8_Q5RQ6E | Human | Human |
| 491 | VH4-34 + CDR3-IL8_CDR1-G31DY32K_Q5RQ6E | G31D, Y32K | Human |
| 492 | VH4-34 + CDR3-IL8_CDR2-E50S_Q5RQ6E | Human | E50S |
| 493 | VH4-34 + CDR3-IL8_CDR1-G31DY32K_CDR2-E50S_Q5RQ6E | G31D, Y32K | E50S |
| 494 | VH4-34 + CDR3-IL8_CDR1-Cow_Q5RQ6E | Cow | Human |
| 495 | VH4-34 + CDR3-IL8_CDR2-Cow_Q5RQ6E | Human | Cow |
| 496 | VH4-34 + CDR3-IL8_CDR1-Cow_CDR2-E50S_Q5RQ6E | Cow | E50S |
| 497 | VH4-34 + CDR3-IL8_CDR1-Cow_CDR2-Cow_Q5RQ6E | Cow | Cow |

Example 12

Humanized germline sequences, including modified human germline sequences, that comprise an ultralong

TABLE 18

| VH4-34 + CDR3-IL8 and Mutations at CDR1 and/or CDR2 | | | | | | | | |
|---|---|---|---|---|---|---|---|---|
| Heavy Chain SEQ ID NO: | | | | | | | | |
| 430 | 434 | 435 | | 439 | 432 | 433 | 437 | 436 |
| CDR1 | | | | | | | | |
| Human | G31D, Y32K | Human | | G31D, Y32K | Cow | Human | Cow | Cow |
| Light Chain SEQ ID NO: | | CDR2: | | | | | | |
| | | Human | Human | E50S | E50S | Human | Cow | E50S | Cow |
| 456 | VL1-51 | 0 | 0 | 0 | 0 | 0 | 1 | 0 | 0 |
| 440 | VL1-51 I29V, N32G | 1 | 1 | 1 | 1 | 1 | 1 | 1 | 0 |
| 441 | VL1-51 D51G, N52D, N53T | 1 | 1 | 1 | 19 | 0 | 1 | 3 | 4 |
| 442 | VL1-51 D51G, N52D, N53T, K54S, P56A | 2 | 2 | 3 | 3 | 5 | 2 | 2 | 19 |

TABLE 18-continued

| VH4-34 + CDR3-IL8 and Mutations at CDR1 and/or CDR2 | | | | | | | | | |
|---|---|---|---|---|---|---|---|---|---|
| 443 | VL1-51 S2A, T5N, P8S, A12G, A13S, P14L | 4 | 7 | 7 | 22 | 20 | 3 | 47 | 25 |
| 444 | VL1-51 S2A, T5N, P8S, A12G, A13S, P14L, D51G, N52D, N53T | 13 | 29 | 22 | 54 | 56 | 3 | 47 | 90 |
| 486 | VL1-51 S2A, T5N, P8S, A12G, A13S, P14L, K46R, L47T, D51G, N52D, N53T | 37 | 34 | 25 | 88 | 68 | 8 | 81 | 98 |
| | Antibody Expression Yield (nM IgG) | | | | | | | | |

Cell culture supernatants from selected IgGs showing unexpectedly improved IgG expression were then normalized to 5 nM IgG and flow cytometry was used to evaluate CXCR1 binding specificity as previously described in Example 5. The ability of IL-8 within CDR3 in these antibodies to specifically bind CXCR1 receptor was evaluated by comparing the median fluorescence of cells expressing CXCR1 as compared to the median fluorescence of parental cells. The ratio of these median AFU was calculated and shown in Table 19. Heavy chains without mutations at CDR1 or CDR2 designated "Human" indicate that the sequence was unchanged from the VH4-34 human germline. CDR1-Cow refers to the group of mutations A23T, V24A, Y25S, G27F, F29L, G31 D, Y32K, Y33A, W34V, and S35G. CDR2-Cow refers to the group of point mutations I48L, E50S, N52D, H53T, S54G, S56N, and N58G. Point mutations in CDR1 or CDR2 are indicated as well (e.g. G31 D, Y32K, or E50S). Specific binding was determined by the ratio of median AFU of CXCR1 cells to that of parental cells: higher numbers show a higher ratio and thus more specific binding.

(SEQ ID NO: 486; SEQ ID NO: 780) unexpectedly showed improvement in both IgG expression and specific antibody binding when paired with several heavy chains tested in Example 12. We examined the K46R and L47T pair of mutations in other V1-51 variant light chains described in Example 11 (SEQ ID NOs: 487-489; SEQ ID NO: 781-783). We also examined the addition of the Q5R, Q6E pair of mutations in VH4-34+CDR3-IL-8 variant heavy chains described in Example 11, Table 17 (SEQ ID NOs: 490-497; SEQ ID NO: 784-791). Heavy chain constructs encoding variants of VH4-34+CDR3-IL8 with mutations Q5R and Q6E (SEQ ID NOs: 490-497; SEQ ID NO: 784-791) were paired with light chain constructs encoding variants of V1-51, some of which had mutations K46R and L47T (SEQ ID NOs: 444, 486-489; SEQ ID NOs: 792, 780-783). These heavy and light chain pairs were each transfected in 293Freestyle cells as described in Example 4. Yield of the resultant IgGs in supernatant was determined as in Example 4, and presented in Table 20. Heavy chains without muta-

TABLE 19

| VH4-34 + CDR3-IL8 and Mutations at CDR1 and/or CDR2 | | | | | | | | | |
|---|---|---|---|---|---|---|---|---|---|
| | | Heavy Chain SEQ ID NO: | | | | | | | |
| Light Chain | | 430 | 434 | 435 | 439 | 432 | 433 | 437 | 436 |
| | | | | | CDR1: | | | | |
| SEQ ID | | Human | G31D, Y32K | Human | G31D,Y32K | Cow | Human | Cow | Cow |
| | | | | | CDR2: | | | | |
| NO: | | Human | Human | E50S | E50S | Human | Cow | E50S | Cow |
| 443 | VL1-51 S2A, T5N, P8S, A12G, A13S, P14L | | 4 | 4 | 5 | 4 | | 5 | 11 |
| 444 | VL1-51 S2A, T5N, P8S, A12G, A13S, P14L, D51G, N52D, N53T | 3 | | 2 | 17 | 4 | 4 | 6 | 10 |
| 486 | VL1-51 S2A, T5N, P8S, A12G, A13S, P14L, K46R, L47T, D51G, N52D, N53T | 12 | 15 | 5 | 18 | 10 | 3 | 6 | 13 |
| | Specific Binding: (CXCR1-Cell median AFU/Parental Cell median AFU) | | | | | | | | |

Example 13

Humanized germline sequences, including modified human germline sequences, that comprise an ultralong CDR3 may be evaluated by any method known in the art to identify and characterize sequences that permit expression of an ultralong CDR3, including an ultralong CDR that comprises a non-antibody sequence.

Light chain V1-51 S2A, T5N, P8S, A12G, A13S, P14L, D51G, N52D, N53T (SEQ ID NO:444), with the addition of mutations K46R, and L47T to produce VL1-51 S2A, T5N, P8S, A12G, A13S, P14L, K46R, L47T, D51G, N52D, N53T tions at CDR1 or CDR2 designated "Human" indicate that the sequence was unchanged from the VH4-34 human germline. CDR1-Cow refers to the group of mutations A23T, V24A, Y25S, G27F, F29L, G31 D, Y32K, Y33A, W34V, and S35G. CDR2-Cow refers to the group of point mutations I48L, E50S, N52D, H53T, S54G, S56N, and N58G. Point mutations in CDR1 or CDR2 are indicated as well (e.g., Q5R, Q6E; G31D, Y32K; or E50S). Expression yield in each square was determined by the level of IgG expression: higher numbers in squares exhibit better expression.

TABLE 20

| VH4-34 + CDR3-IL8, Q5R, Q6E, and Mutations at CDR1 and/or CDR2 | | | | | | | | |
|---|---|---|---|---|---|---|---|---|
| | Heavy Chain SEQ ID NO: | | | | | | | |
| | 490 | 491 | 492 | 493 | 494 | 495 | 496 | 497 |
| | | | | CDR1: | | | | |
| | Human | G31D, Y32K | Human | G31D, Y32K | Cow | Human | Cow | Cow |
| | | | | CDR2 | | | | |
| | Human | Human | E50S | E50S | Human | Cow | E50S | Cow |
| 444  VL1-51 S2A, T5N, P8S, A12G, A13S, P14L D51G, N52D, N53T | 7 | 19 | 8 | 25 | 4 | 2 | 32 | 18 |
| 486 VL1-51 S2A, T5N, P8S, A12G, A13S, P14L, K46R, L47T, D51G, N52D, N53T | 18 | 5 | 6 | 28 | 77 | 11 | 13 | 8 |
| 487  VL1-51 S2A, T5N, P8S, A12G, A13S, P14L, K46R, L47T, D51G, N52D, N53T, K54S, P56A | 18 | 13 | 20 | 31 | 52 | 12 | 38 | 23 |
| 488  VL1-51 I29V, N32G, K46R, L47T, D51G, N52D, N53T | 2 | 0 | 3 | 12 | 30 | 1 | 19 | 11 |
| 489  VL1-51 I29V, N32G, K46R, L47T, D51G, N52D, N53T, K54S, P56A | 2 | 1 | 5 | 7 | 31 | 1 | 29 | 2 |
| | Expression Yield, nM IgG | | | | | | | |

Cell culture supernatants from selected IgGs unexpectedly showing improved IgG expression were then normalized to 5 nM IgG and flow cytometry was used to evaluate CXCR1 binding specificity as previously described in Example 5. The ability of IL-8 within CDR3 in these antibodies to specifically bind CXCR1 receptor was evaluated by comparing the median fluorescence of cells expressing CXCR1 as compared to the median fluorescence of parental cells. The ratio of these median AFU was calculated as previously in Table 19. Heavy chains without mutations at CDR1 or CDR2 designated "Human" indicate that the sequence was unchanged from the VH4-34 human germline. CDR1-Cow refers to the group of mutations A23T, V24A, Y25S, G27F, F29L, G31 D, Y32K, Y33A, W34V, and S35G. CDR2-Cow refers to the group of point mutations I48L, E50S, N52D, H53T, S54G, S56N, and N58G. Point mutations in CDR1 or CDR2 are indicated as well (e.g. G31 D, Y32K; or E50S). Specific binding was determined by the ratio of median AFU of CXCR1 cells to that of parental cells: higher numbers show a higher ratio and thus more specific binding.

TABLE 21

| VH4-34 + CDR3-IL8, Q5R, Q6E, and Mutations at CDR1 and/or CDR2 | | | | | | | | | |
|---|---|---|---|---|---|---|---|---|---|
| | | Heavy Chain SEQ ID NO: | | | | | | | |
| Light chain | | 490 | 491 | 492 | 493 | 494 | 495 | 496 | 497 |
| | | | | | CDR1: | | | | |
| SEQ ID | | Human | G31D, Y32K | Human | G31D,Y32K | Cow | Human | Cow | Cow |
| | | | | | CDR2: | | | | |
| NO: | | Human | Human | E50S | E50S | Human | Cow | E50S | Cow |
| 444 | VL1-51 S2A, T5N, P8S, A12G, A13S, P14L, D51G, N52D, N53T | | 2 | | 1 | | | 2 | 4 |
| 486 | VL1-51 S2A, T5N, P8S, A12G, A13S, P14L, K46R, L47T, D51G, N52D, N53T | 10 | | | 4 | 10 | 5 | 2 | |
| 487 | VL-1-51 S2A, T5N, P8S, A12G, A13S, P14L, K46R, L47T, D51G, N52D, N53T, K54S, P56A | 3 | 2 | 1 | 3 | 3 | 1 | 2 | 2 |
| 488 | VL1-51, I29V, N32G, K46R, L47T, D51G, N52D, N53T | | | | 1 | 1 | | 1 | 1 |
| 489 | VL1-51 I29V, N32G, K46R, L47T, D51G, N52D, N53T, K54S, P56A | | | | | 2 | | 2 | |
| | Specific Binding: (CXCR1-Cell median AFU/Parental Cell median AFU) | | | | | | | | |

Example 14

Antibodies comprising an ultralong CDR3, including an ultralong CDR that comprises a non-antibody sequence, may be evaluated by any method known in the art for binding of the non-antibody sequence to its binding partner (e.g., via flow cytometry) and/or for activation (e.g., via cell-based luminescent assays).

In an exemplary method, IL-8 activation of the CXCR1 receptor was tested using the CXCR1-U2OS DiscoveRx cells described above (Cat #93-0226C3, DiscoveRx). The DiscoveRx cells are engineered such that upon activation by ligand, the resultant beta-arrestin recruitment to the GPCR also causes activation of a luminescent reporter enzyme present in the cell line. Lysis reagents and luminescence substrate are included in the PathHunter Detection Kit (Cat #93-001, DiscoveRx) which was used following manufacturer's instructions. U2OS-CXCR1 cells were plated at 15,000 cells per well and serum starved overnight in EMEM media without serum. Next, media was removed and cells were incubated 1 hour at 37° C. with 80 μl of 1:1 EMEM and PBS, containing dilutions of either IL-8 or IgG with IL-8 insertion in CDR3, or control antibody. After 1 hour, 40 μl of PathHunter Detection reagent mix was added. Subsequently, after an hour at room temperature the luminescence in each well was measured using a luminescence plate reader. Higher luminescence signal reveals more activation of the CXCR1 receptor at the tested concentrations of IL-8 or IgG. IgGs were purified by scaling up the transfection method of Example 4, and purification of the IgG from media using protein A sepharose following manufacturer's instructions (Cat #17-1279-03 GE Healthcare) and dialysis post-elution into PBS. Protein yield was determined by A280 and calculated molar extinction coefficient. The humanized antibodies in Table 22 were expressed and tested for activation of CXCR1.

TABLE 22

| BID# | HC SEQ ID NO: | Heavy Chain: | LC SEQ ID NO: | Light Chain |
|---|---|---|---|---|
| 34 | 432 | VH4-34 + CDR3-IL8_CDR1-Cow | 443 | VL1-51 S2A, T5N, P8S, A12G, A13S, P14L |
| 35 | 436 | VH4-34 + CDR3-IL8_CDR1-Cow_CDR2-Cow | 456 | VL1-51 |
| 36 | 436 | VH4-34 + CDR3-IL8_CDR1-Cow _CDR2-Cow | 443 | VL1-51 S2A, T5N, P8S, A12G, A13S, P14L |
| 37 | 439 | VH4-34 + CDR3-IL8_CDR1-G31DY32K_CDR2-E50S | 486 | VL1-51 S2A, T5N, P8S, A12G , A13S, P14L, K46R, L47T, D51G, N52D, N53T |
| 38 | 493 | VH4-34 + CDR3-IL8_CDR1-G31DY32K _CDR2-E50S_Q5RQ6E | 486 | VL1-51 S2A, T5N, P8S, A12G , A13S, P14L, K46R, L47T, D51G, N52D, N53T |
| 39 | 436 | VH4-34 + CDR3-IL8_CDR1-Cow _CDR2-Cow | 486 | VL1-51 S2A, T5N, P8S, A12G , A13S, P14L, K46R, L47T, D51G, N52D, N53T |
| 43 | 494 | VH4-34 + CDR3-IL8_CDR1-Cow _Q5RQ6E | 486 | VL1-51 S2A, T5N, P8S, A12G , A13S, P14L, K46R, L47T, D51G, N52D, N53T |
| 42 | 393 | BLV1H12 Hc | 474 | CowULVL, Human Lambda C |

As shown in Tables 23 and 24, cells were treated with increasing concentrations of IL-8, either as free IL-8 control or as IL-8 in CDR3 of the above antibodies. IgGs comprised of CDR3-IL8 activated CXCR1 significantly more than IgG without CDR3-IL8. Concentration of IL-8 treatment is plotted, with the understanding that each IgG with CDR3-IL-8 contributes 2 IL-8 domains.

TABLE 23

CXCR1 Activation by Humanized IgGs with CDR3-IL-8

| | | BID # | | | | |
|---|---|---|---|---|---|---|
| | IgG nM | 37 VH4-34 MutC IL-8 31D32K50S | 38 VH4-34 MutE IL-8 5R6E31D32K50S | 39 VH4-34 MutD IL-8 CDR1cow CDR2cow | (IL-8) IL-8 | 42 BLV1H12 |
| nM | 100 | 15490 ± 7356 | 25920 ± 10105 | 21618 ± 5915 | 70182 ± 19176 | 5732 |
| IL-8 | | | | | | |
| Domains | 25 | 11187 ± 2377 | 21049 ± 4878 | 15446 ± 2884 | 50500 ± 5922 | 5729 |
| | 6.25 | 7162 ± 1128 | 13509 ± 2708 | 10246 ± 252 | 28583 ± 3700 | 5776 |
| | 1.6 | 5712 ± 552 | 8161 ± 570 | 7398 ± 432 | 12230 ± 273 | 5820 |
| | 0.4 | 5419 ± 270 | 6188 ± 560 | 6307 ± 622 | 6527 ± 245 | 6485 |

TABLE 24

| | | CXCR1 Activation by Humanized IgGs with CDR3-IL-8 | | | |
| | | | BID # | | |
| | IgG nM | 36<br>VH4-34<br>MutB IL-8<br>CDR1cow<br>CDR2cow | 43<br>VH4-34 MutF<br>IL-8 5R6E<br>CD1cow | 42<br>BLV1H12 | (IL-8)<br>IL-8 |
|---|---|---|---|---|---|
| nM | 100 | 12253 ± 5812 | 18038 ± 9947 | 4347 ± 601 | 53969 ± 20263 |
| IL-8 | 25 | 9552 ± 2569 | 14550 ± 4095 | 4747 ± 747 | 42188 ± 12385 |
| Domains | 6.25 | 6166 ± 1377 | 10524 ± 1991 | 4546 ± 105 | 22259 ± 6430 |
| | 1.6 | 4991 ± 97 | 6407 ± 1086 | 4497 ± 437 | 8729 ± 1731 |
| | 0.4 | 4974 ± 398 | 5187 ± 468 | 4641 ± 698 | 4926 ± 760 |

Example 15

Humanized germline sequences, including modified human germline sequences, that comprise an ultralong CDR3, may be evaluated by any method known in the art to identify and characterize sequences that permit expression of an ultralong CDR3, including an ultralong CDR that comprises a non-antibody sequence.

As described in Example 3, a nucleotide sequence having a pair of Bsal sites (SEQ ID NO: 768) was introduced by PCR strand overlap extension into the nucleotide sequence encoding CDR3 of BLV1H12 (SEQ ID NO: 395). This sequence was then subcloned in-frame between the signal sequence and the nucleotide sequence encoding CH1-CH2-CH3 of human IgG1 in the HC pFuse vector (SEQ ID NO: 458) using EcoRI and NheI restriction enzymes. The nucleotide sequence containing Bsal sites was positioned between the codons expressing the ascending stalk portion of CDR3 (SEQ ID NO: 498), and the descending stalk portion of CDR3 (SEQ ID NO: 499), allowing the further insertion of nucleotide sequence in-frame with the ascending and descending stalk within CDR3.

For example, various linkers may be subcloned in frame with the ascending and descending stalk portions of CDR3, and such linker sequences may themselves have Bsal sites which can be used again for further insertion of, for example, more elaborate linkers, antibody knob libraries (e.g., cow knob libraries), or non-antibody sequences.

In an exemplary embodiment, sequences were designed for insertion between the Bsal sites in the heavy chain vector encoding BLV1H12 with Bsal sites at CDR3 (SEQ ID NO: 395) by directional cloning into the Bsal sites in frame with the ascending and descending stalk portions of CDR3. Nucleotides were synthesized (IDTDNA, Inc.) to encode linker sequences flanking a new internal pair of Bsal sites useful for subsequent insertions between the new linkers. These Linker-Bsal-Linker sequences were introduced into BLV1H12 having Bsal sites at CDR3 (SEQ ID NO: 395) to produce BLV1H12-CDR3-Linker-Bsal vectors (SEQ ID NOs: 757-767) for further insertions within CDR3. In one example, the Bsal containing Nucleotide sequence was GAGACCTACTATGGTTCGGGTCTC (SEQ ID NO: 768). In another example, the Bsal containing nucleotide sequence was GAGACCTACTATGGTTCAGGGTCTC (SEQ ID NO: 769). The linkers surrounding the Bsal sites were produced as listed in Table 25, between the ascending stalk portion of CDR3 (SEQ ID NO: 498), and the descending stalk portion of CDR3 (SEQ ID NO: 499).

TABLE 25

Linkers in BLV1H12 CDR3 with Bsal sites for insertion of functional domains in CDR3 of an IgG.

| BLV1H12-CDR3-Linker-Bsal vectors SEQ ID NO: | Linker Name | Ascending Linker SEQ ID NO: | Amino Acid Sequence | Bsal Pair SEQ ID NO: | Descending Linker SEQ ID NO: | Amino Acid Sequence |
|---|---|---|---|---|---|---|
| 757 | GGS1: 1 | 579 | GGS | 768 | 579 | GGS |
| 758 | GGS1: 2 | 579 | GGS | 768 | 580 | GGS GGS |
| 759 | GGS2: 1 | 580 | GGS GGS | 768 | 579 | GGS |
| 760 | GGS2: 2 | 580 | GGS GGS | 768 | 580 | GGS GGS |
| 761 | GGS2: 3 | 580 | GGS GGS | 768 | 581 | GGS GGS GGS |
| 762 | GGS2: 4 | 580 | GGS GGS | 768 | 582 | GGS GGS GGS GGS |
| 763 | GGS3: 2 | 581 | GGS GGS GGS | 768 | 580 | GGS GGS |
| 764 | GGS3: 3 | 581 | GGS GGS GGS | 768 | 581 | GGS GGS GGS |
| 765 | GGS4: 2 | 582 | GGS GGS GGS GGS | 768 | 580 | GGS GGS |
| 766 | G4Sx1 | 723 | GGGGS GG | 769 | 575 | GGGGS |
| 767 | G4Sx3 | 724 | GGGGS GGGGS GGGGS GG | 769 | 577 | GGGGS GGGGS GGGGS |

Sequence encoding MOKA toxin (SEQ ID NO: 727; SEQ ID NO: 806) was inserted into the GGS1:1, GGS1:2, GGS2:1, GGS2:2, an GGS3:3 versions of BLV1H12-CDR3-Linker-BsaI vectors (SEQ ID NOs: 757-760, 764) to produce BLV1H12 heavy chain vectors that express MOKA toxin at CDR3 with a variety of linkers (SEQ ID NOs: 770-774). These MOKA and linker combinations in CDR3 of BLV1H12 were paired with CowULVL-Human LambdaC (SEQ ID NO: 474; SEQ ID NO: 807) for expression of IgGs as described in Example 4. All versions were found to express well (see, e.g., Moka constructs in Tables 26 and 27), and the GGS3:3 linker version (SEQ ID NO:774) was paired with CowULVL-Human LambdaC (SEQ ID NO: 474; SEQ ID NO: 807) for large scale transfection as described in Example 4, and purified as described in Examples 6 and 14 (see, e.g., FIG. 20, BID #33).

TABLE 26

Expression Yield of Antibodies with Toxin Domains in CDR3 of BLV1H12

| BID# | CDR3 Insert in BLV1H12: | nM |
|------|--------------------------|------|
| 201 | GGS1:1 ProTxll | 1.0 |
| 202 | GGS1:2 ProTxll | 0.7 |
| 203 | GGS2:1 ProTxll | −0.1 |
| 208 | GGS1:1 GG-ProTxll-GG | 1.0 |
| 209 | GGS1:2 GG-ProTxll-GG | 1.1 |
| 210 | GGS2:1 GG-ProTxll-GG | 3.4 |
| 204 | GGS1:1 Moka | 30.5 |
| 205 | GGS1:2 Moka | 47.9 |
| 206 | GGS2:1 Moka | 28.4 |

TABLE 27

Expression Yield of Antibodies with Toxin Domains and Linker Combinations in CDR3 fo BLV1H12

| BID # | CDR3 Insert in BLV1H12: | Ascending linker | Toxin | Desceding linker | nM |
|-------|--------------------------|------------------|--------|------------------|-----|
| 201 | GGS 1:1 ProTxll | GGS | ProTxll | GGS | −2 |
| 202 | GGS 1:2 ProTxll | GGS | ProTxll | GGSGGS | −1 |
| 203 | GGS 2:1 ProTxll | GGSGGS | ProTxll | GGS | −2 |
| 204 | GGS 1:1 Moka | GGS | G-Moka | GGS | 106 |
| 205 | GGS 1:2 Moka | GGS | G-Moka | GGSGGS | 74 |
| 206 | GGS 2:1 Moka | GGSGGS | G-Moka | GGS | 99 |
| 207 | GGS 3:3 Moka | GGSGGSGGS | G-Moka | GGSGGSGGS | 81 |
| 208 | GGS 1:1 GG-ProTxll-GG | GGSGG | ProTxll | GGGGS | −1 |
| 209 | GGS 1:2 GG-ProTxll-GG | GGSGG | ProTxll | GGGGSGGS | −2 |
| 210 | GGS 2:1 GG-ProTxll-GG | GGSGGSGG | ProTxll | GGGGS | −1 |
| 211 | GGS 2:2 ProTxll | GGSGGS | ProTxll | GGSGGS | −1 |
| 212 | GGS 2:4 ProTxll | GGSGGS | ProTxll | GGSGGSGGSGGS | −1 |
| 213 | GGS 4:2 ProTxll | GGSGGSGGSGGS | ProTxll | GGSGGS | 3 |
| 214 | GGS 2:2 GG-ProTxll-GG | GGSGGSGG | ProTxll | GGGGSGGS | 0 |
| 215 | GGS 2:3 GG-ProTxll-GG | GGSGGSGG | ProTxll | GGGGSGGSGGS | −1 |
| 216 | GGS 2:4 GG-ProTxll-GG | GGSGGSGG | ProTxll | GGGGSGGSGGSGS | 0 |
| 217 | GGS 3:2 GG-ProTxll-GG | GGSGGSGGSGG | ProTxll | GGGGSGGS | −1 |
| 218 | GGS 3:3 GG-ProTxll-GG | GGSGGSGGSGG | ProTxll | GGGGSGGSGGS | 0 |
| 219 | GGS 4:2 GG-ProTxll-GG | GGSGGSGGSGGSGG | ProTxll | GGGGSGGS | 4 |
| 42 | BLV1H12 | n/a | n/a | n/a | 76 |

Sequences encoding ShK toxin (SEQ ID NO: 648; SEQ ID NO: 808), ProTxII (SEQ ID NO: 640; SEQ ID NO: 809), GPTX toxin (SEQ ID NO: 655; SEQ ID NO: 810), OSK1 toxin with mutations P12, K16, D20, (SEQ ID NO: 728; SEQ ID NO: 811) and OSK1 toxin with mutations K16 and D20 (SEQ ID NO: 729; SEQ ID NO: 812) were introduced into the BsaI sites of BLV1H12-CDR3-G4Sx3-BsaI (SEQ ID NO:767) to produce each of these toxins in the CDR3 of BLV1H12 flanked by (G$_4$S)$_3$ linkers (SEQ ID NOs: 775-779). These heavy chains were paired with Cow ULVL-Human LambdaC (SEQ ID NO: 474; SEQ ID NO: 807), and transfected as described in Example 4. Yield of the resultant IgGs in supernatant was determined as in Example 4, and presented in Table 27. Strand overlap elongation was used to modify the BLV1H12-CDR3-G4Sx3-BsaI (SEQ ID NO: 767), replacing the J region from Cow with the most similar Human J region (analogous to SEQ ID No. 14 and 15). Sequences encoding ShK toxin (SEQ ID NO: 648; SEQ ID NO: 808), ProTxII (SEQ ID NO: 640; SEQ ID NO: 809), GPTX toxin (SEQ ID NO: 655; SEQ ID NO: 810), OSK1 toxin with mutations P12, K16, D20, (SEQ ID NO: 782; SEQ ID NO: 811), and OSK1 toxin with mutations K16 and D20 (SEQ ID NO: 729; SEQ ID NO: 812) were introduced into the BsaI sites of

```
BLV1H12-HumanJ-CDR3-G4Sx3-Bsal
                              (SEQ ID NO: 957))
(caggtccagctgagagagagcggcccttcactggtcaagccatcccag acactgagcctgacatgcacagcaagcgggttttcactgagcgacaagg cagtgggatgggtccgacaggcaccaggaaaagccctggaatggctggg cagcatcgataccgggggaacacagggtacaatcccggactgaagagca
```

-continued

```
gactgtccattaccaaggacaactctaaaagtcaggtgtcactgagcgt gagctccgtcaccacagaggatagtgcaacttactattgcacctctgtg caccaggaaactaagaaataccagagcggtggaggaggttctggaggcg gtggaagtggtggcggaggtagcggaggatgagacctactatggttcag ggtctctggaggtggtggatctggtggaggaggcagtggaggtggtggc agctcttatacctacaattatgaatggcatgtggatgtctggggccaag gaaccctggtcaccgtctcctcagctagc
``` to produce each of these toxins in the CDR3 of BLV1H12 with Human J and flanked by (G4S)3 linkers (BID Nos 220-224 of FIGS. 21 and 22) These heavy chains were paired with Cow ULVL-Human LambdaC (SEQ ID NO: 474; SEQ ID NO: 807), and transfected as described in Example 4. Yield of the resultant IgGs in supernatant was determined as in Example 4, and presented in Table 28. The BLV1H12 CDR3 Toxin constructs without the Human J modification (SEQ ID NOs: 775-779) were paired with Cow ULVL-Human LambdaC (SEQ ID NO: 474; SEQ ID NO: 807) for large scale transfection as described in Example 4, and purified as described in Examples 6 and 14.

TABLE 28

Expression Yields of Antibodies with Toxins, Long Linkers and J region in CDR3 of BLV1H2

| BID# | CDR3 Insert in BLV1H12: | J region | nM IgG |
|---|---|---|---|
| 220 | 3xG4S ProTxll | Human | 10.7 |
| 221 | 3xG4S ShKtoxin | Human | 18.1 |
| 222 | 3xG4S OSK1 (K16, D20) | Human | 26.1 |
| 223 | 3xG4S OSK1 (P12, K16, D20) | Human | 33.4 |
| 224 | 3xG4S GPTX | Human | 34.2 |
| 227 | 1:2GGS G-Moka | Cow | 54.2 |
| 228 | 3xG4S ProTxll | Cow | 22.4 |
| 229 | 3xG4S ShKtoxin | Cow | 32.7 |
| 230 | 3xG4S OSK1 (K16, D20) | Cow | 19.5 |
| 231 | 3xG4S OSK1 (P12, K16, D20) | Cow | 27.9 |
| 232 | 3xG4S GPTX | Cow | 36.9 |
| 42 | BLV1H12 | Cow | 50.9 |

Using, for example, overlap PCR, the toxin inserts in BLV1H12 can be grafted to any of the described variants of VH4-34 heavy chains, or other desired Human VH or modified Human VH regions for expression and testing of these toxins in a humanized antibody.

Example 16

Antibodies comprising an ultralong CDR3, including an ultralong CDR that comprises a non-antibody sequence (e.g., a toxin), may be evaluated by any method known in the art (e.g., via cell-based inhibition assays).

Antibodies expressing ShK toxin (SEQ ID NO: 779) or MOKA toxin (SEQ ID NO: 774) were expressed in Example 15 using the method described in Example 4, and purified as described in Examples 6 and 14. These toxins are both reported to inhibit KV1.3, whose activity is required for T-cell stimulation. We sought to evaluate the ability of these toxins, when expressed in the CDR3 of an IgG, to inhibit the stimulation of T-cells in a manner similar to the free toxin.

To assay T-cell stimulation, T-cells were purified from peripheral blood mononucleocytes and cultured. Human Blood was collected from donors into sterile collection tubes pre-treated with EDTA to prevent coagulation. Each 15 ml of blood yielded approximately 107 peripheral blood mono-nucleocytes (PBMCs) and 5×10^6 T-cells. Blood sample volumes of 15 mL were then transferred to 50 mL tubes containing 20 mL of 2 mM EDTA in PBS. 14 mL of Lymphocyte Separation Media (Corning, Catalog #: 25-072-CI) was slowly pipetted into the bottom of each tube to create a clean layer of Ficoll below the diluted blood sample. Next, samples were centrifuged at room temperature in a swinging bucket rotor at 400×g for 35 minutes. During the centrifuge deceleration, no brake was set to minimize disruption of the buffer-Ficoll interface, and the PBMCs enriched at this interface. The now separated PBMCs were carefully pipetted into a new 50 mL conical tube containing 30 mL of 2 mM EDTA in PBS. These tubes were centrifuged at room temperature at 300×g for 10 minutes to remove excess platelets. The brake was reapplied to this and subsequent centrifugations. Supernatant was aspirated and the pellet was resuspended in 30 mL of 2 mM EDTA in PBS. Samples were centrifuged at room temperature at 200×g for 10 minutes for additional platelet removal. Supernatant was aspirated and pellets were resuspended in 5 mL of T-Cell Media (RPMI Media with 1% 100× Pen/Strep/Glutamine, 10% Heat Inactivated FBS, 25 mM HEPES 10 uM 2-mercaptothanol) and cells were counted in the resultant fraction enriched for PBMCs To purify T-cells from PBMCs a magnetic bead based isolation kit was used (Dynabeads Untouched Human T-cells, cat #11344D, Invitrogen). 1×107 PBMCs were pelleted in a 15 mL conical tube by spinning for 5 minutes in a clinical centrifuge. Manufacturers instructions were followed, scaled to the cell count above, with the modification that cells were kept at 4 degrees Celsius or on ice. Isolated cells were resuspended in 2.5 mL of T-cell Media, and transferred into culture flasks.

To activate T-cells, 96 well plates were coated overnight at 4 degrees Celsius with anti-CD3 (Ebiosciences, cat #160037-81), 1 μg/ml in PBS, 100 ul per well. Plates were emptied and blocked with T-cell media containing 5% serum for 1 hour at 37 degrees Celsius. In another plate, T-cells were pre-treated with IgGs having either ShK toxin or MOKA toxin at CDR3 for 1.5 hours before activation. 8×10^4 cells per well in T-cell media with 10% serum were combined 1:1 with IgG in PBS in a final volume of 100 ul. Anti-CD28 antibody (clone CD28.6, cat #16-0288-81, Ebiosciences) was diluted in T-cell media (5% serum) to 10 μg/ml. 10 ul was transferred to each well of pre-incubated T-cells with IgG. Wells were mixed and 100 ul of T-cells, test IgG, Anti-CD28 mix was transferred to the Anti-CD3 coated plates and incubated 20 hrs 37 C. After incubation, supernatants were assayed for markers of T-cell activation: secreted TNFα and IL-2. To assay TNFα in the T cell supernatants, the Human TNFα ELISA Read-SET-Go! (Catalog #: 88-7346-22, eBioscience) kit was used following manufacturers instructions. IL-2 in T cell supernatants was assayed by sandwich ELISA using a mouse anti-hIL-2 (cat #MAB602, R&D Systems) capture antibody, rabbit anti-hIL-2, (Abcam, cat #ab9618) detection antibody, and goat anti-rabbit IgG-HRP (Jackson ImmunoResearch, cat #111-035-144) for signal detection using TMB Substrate (BioFX Laboratories, Catalog #: TMBS-1000-01). T-cell activation was measured by ELISA of TNFα or IL-2 secreted into cell culture media. Results of T-cell activation in the presence of varying concentrations of BLV1H12 IgGs having either ShK toxin (SEQ ID NO: 779) or MOKA toxin (SEQ ID NO. 774) at CDR3 were plotted and data was fit to a 4 parameter sigmoidal dose response curve using Kaleida-Graph (Synergy Software, Reading PA) to determine EC50 concentrations (Table 29). Experiments were done in triplicate and repeated with multiple T-cell donors. Unstimulated T-cells were tested as a negative control and Stimulated T-cells with no antibody treatment were tested as positive controls. EC$_{50}$ concentrations were calculated separately for each donor, and for each of TNFα or IL-2 for each toxin.

TABLE 29

| EC50 for Toxins in CDR3 of IgG. | | | |
|---|---|---|---|
| | | | EC50 (nM) |
| ShK Toxin IgG | TNFα | Donor 1 | 6.5 |
| | | Donor 2 | 0.2 |
| | IL-2 | Donor 1 | 0.1 |
| | | Donor 2 | 0.03 |
| MOKA Toxin IgG | TNFα | Donor 1 | 19.3 |
| | | Donor 2 | 38.2 |
| | IL-2 | Donor 1 | 14.4 |
| | | Donor 2 | 40.2 |

Example 17

Antibodies comprising an ultralong CDR3, including an ultralong CDR that comprises a non-antibody sequence, may be evaluated by any method known in the art. For example, polynucleotides coding for humanized antibodies comprising an ultralong CDR3 may be expressed, including transiently expressed, in a host cell by any method known in the art. Exemplary humanized antibody sequences that comprise an ultralong CDR3, including an ultralong CDR that comprises a non-antibody sequence, were expressed and characterized.

As described in Example 15 for MOKA toxin, sequences encoding ProTxII (SEQ ID NO: 640; SEQ ID NO: 809) were inserted into the versions of BLV1H12-CDR3-Linker-Bsal vectors (SEQ ID NOs: 757-760, 762, 765) to produce BLV1H12 heavy chain vectors that express ProTxII toxin at CDR3 with a variety of linkers (BIDs 201-203, 211-213 of FIG. 21). In addition, sequences encoding ProTxII with the addition of two glycine residue on the n-terminal and c-terminal sides of the toxin were similarly inserted into the versions of BLV1H12-CDR3-Linker-Bsal vectors (SEQ ID NOs: 757-765) to produce BLV1H12 heavy chain vectors that express ProTxII toxin at CDR3 with a variety of linkers (BIDs 208-210, 214-219 of FIG. 21). These ProTxII and linker combinations in CDR3 of BLV1H12 were paired with CowULVL-Human LambdaC (SEQ ID NO: 474; SEQ ID NO: 807, see FIG. 22), and transfected as described in Example 4. Yield of the resultant IgGs in supernatant was determined as in Example 4, and presented in Tables 26 and 27.

Example 18

Antibodies comprising an ultralong CDR3, including an ultralong CDR that comprises a non-antibody sequence, may be evaluated by any method known in the art. For example, polynucleotides coding for humanized antibodies comprising an ultralong CDR3 may be expressed, including transiently expressed, in a host cell by any method known in the art. Exemplary humanized antibody sequences that comprise an ultralong CDR3, including an ultralong CDR that comprises a non-antibody sequence, were expressed and characterized.

Sequence encoding IL-8 (SEQ ID NO: 475) was introduced into the Bsal sites of BLV1H12-CDR3-G4Sx3-Bsal (SEQ ID NO: 767) and BLV1H12-CDR3-G4Sx1-Bsal (SEQ ID NO: 766) to produce heavy chains that express BLV1H12 with IL8 flanked by either 3×G4S or 1×G4S linker in CDR3 (BID 45 and 46 of FIG. 21). These were compared to the original BLV1H12 IL-8 with shorter linker, made by insertion of IL-8 (SEQ ID NO: 475) into the Bsal sites in CDR3 of BLV1H12 Heavy chain (SEQ ID NO: 395). All 3 of these IL-8 Heavy chains were paired with CowULVL-Human LambdaC (SEQ ID NO: 474; SEQ ID NO: 807), for large scale transfection as described in Example 4, and purified as described in Sample 6 and 14. These proteins were loaded on SDS-PAGE gel and coomassie stained for comparison with all the humanized Antibodies expressed and purified in Example 14, and listed in Table 22 as BID #s 34-39, 42, and 43, as well as the MOKA antibody used in Example 16. Table 30 specifies the IgG expression yield upon purification. SDS-PAGE followed by coomassie staining with both reduced and unreduced samples of BLV1H12 antibody (BID 42 of FIGS. 21 and 22), BLV1H12-IL8 (BID 44 of FIGS. 21 and 22), and Humanized IgG (BID 38 listed in Table 22) confirmed expression.

TABLE 30

| Expression Yield of Antibodies with Toxins in CDR3 | | |
|---|---|---|
| BID | IgG with CDR3 insert | nM Yield |
| 46 | BLV1H12 HC CowV, CDR3 IL-8, 3xG4S | 235 |
| 45 | BLV1H12 HC CowV, CDR3 IL-8, 1xG4S | 313 |
| 42 | BLV1H12 | 1100 |
| 44 | BLV1H12 HC CowV, CDR3 IL-8, | 796 |
| 38 | VH4-34 MutE IL-8 5R6E31D32K50S | 436 |
| 43 | VH4-34 MutF IL-8 5R6E CD1cow | 476 |
| 39 | VH4-34 MutD IL-8 CDR1cow CDR2cow | 335 |
| 36 | VH4-34 IL-8 CDR1cow CDR2cow | 281 |
| 37 | VH4-34 MutE IL-8 31D32K50S | 259 |
| 34 | VH4-34 MutA IL-8 CD1Cow | 258 |
| 35 | VH4-34 IL-8 CDR1cow CDR2cow | 208 |
| 33 | Moka 3:3 | 483 |

Example 19

Antibodies comprising an ultralong CDR3, including an ultralong CDR that comprises a non-antibody sequence, may be evaluated by any method known in the art (e.g., via activation assays, cell-based luminescent assays, Dynamic Light Scattering (DLS)).

As was described in Example 14, CXCR1 activation by IgGs with CDR3-embedded IL-8 was performed using CXCR1-U2OS DiscoveRx cells, and the PathHunter Detection Kit. Here, Humanized VH4-34 IgGs with IL-8 embedded in CDR3 (BID 38 and 43 FIGS. 21 and 22) are compared to the original BLV1H12-IL8 (BID 44 of FIGS. 21 and 22), with soluble IL-8 as positive control and BLV1H12 IgG (BID 42 of FIGS. 21 and 22) as negative control. Luminescence at each concentration of IgG or IL-8 tested is presented in Table 31. To assess the solubility and monodispersity of the humanized VH4-34 antibodies versus the BLV1H12 scaffold, we performed Dynamic Light Scattering (DLS) on the purified IgG samples. DLS was run on a Wyatt Dyna Pro Titan using disposable Uvettes. Laser power was adjusted to give intensity between 100,000 to 1,000,000 counts per second. Each sample was measured ten times for each measurement and ten measurements were made. Table 32 summarizes the results of the DLS studies, listing the radius in nM of particles in the sample. Only BID 43 had 2 discrete particle sizes in the sample, both with a radius much larger than expected for an antibody.

TABLE 31

| | | | 38 | 43 | | |
| | | | VH4-34 | VH4-34 MutF | | |
| | IgG | Soluble | MutE IL-8 | IL-8 5R6E | 44 | 42 |
| | nM | IL-8 | 5R6E31D32K50S | CD1cow | BLV1H12-IL8 | BLV1H12 |
|---|---|---|---|---|---|---|
| nM | 200 | 50410 ± 5819 | 22309 ± 4546 | 25033 ± 1218 | 32163 ± 331 | 3104 ± 110 |
| IL-8 | 44 | 54082 ± 12683 | 23287 ± 5576 | 24050 ± 3024 | 32601 ± 7899 | 3291 ± 50 |
| Domains | 9.9 | 50313 ± 16599 | 17087 ± 5177 | 21935 ± 4874 | 25342 ± 9111 | 3489 ± 199 |
| | 2.2 | 25708 ± 9802 | 10321 ± 3172 | 13518 ± 2311 | 17599 ± 5140 | 3711 ± 221 |
| | 0.5 | 9791 ± 3223 | 5296 ± 582 | 6615 ± 736 | 9942 ± 3804 | 3681 ± 15 |
| | 0.1 | 4201 ± 447 | 4063 ± 121 | 4181 ± 116 | 4520 ± 457 | 3744 ± 298 |

CDR3-IL-8 activation of CXCR1 with humanized IgGs (BID #)

TABLE 32

DLS data for IgG IL-8

| IgG | BID# | R(nm) | % Pd | % Mass |
|---|---|---|---|---|
| BLV1H12 | 42 | 8.3 | 9.6 | 84.9 |
| BLV1H12 CDR3 IL-8 | 44 | 5.7 | 10.9 | 99.8 |
| VH4-34 MutE IL-8 5R6E31D32K50S | 38 | 6.4 | 10.9 | 99.9 |
| VH4-34 MutF IL-8 5R6E CD1cow Peak1 | 43 | 36.3 | 6 | 36.8 |
| VH4-34 MutF IL-8 5R6E CD1cow Peak2 | 43 | 3260 | 2.9 | 63.2 |

Example 20

Antibodies comprising an ultralong CDR3, including an ultralong CDR that comprises a non-antibody sequence, may be evaluated by any method known in the art. For example, polynucleotides coding for humanized antibodies comprising an ultralong CDR3 may be expressed, including transiently expressed, in a host cell by any method known in the art. Exemplary humanized antibody sequences that comprise an ultralong CDR3, including an ultralong CDR that comprises a non-antibody sequence, were expressed and characterized.

Several CDR3 inserts previously expressed in BLV1H12-CDR3 were amplified by PCR and joined using an overlap PCR approach to insert them into CDR3 of VH4-34 Mut E, producing sequences that encode heavy chain VH4-34 MutE 3×G4S IL-8 (BID 47 of FIG. 21), VH4-34 MutE 3×G4S ShK (BID 48 of FIG. 21), VH4-34 MutE 3×GGS MOKA (BID 49 of FIG. 21), VH4-34 MutE 3×G4S ProTxII (BID 53 of FIG. 21), VH4-34 MutE 3×G4S GPTX (BID 54 of FIG. 21), VH4-34 MutE 3×GGS NoKnob (BID 55 of FIG. 21), VH4-34 MutE 1×G4S ShK (BID 56 of FIG. 21), VH4-34 MutE 1×G4S ShK 16K (BID 57 of FIG. 21), and VH4-34 MutE 3×G4S ShK 16K (BID 58 of FIG. 21). These vectors encoding heavy chains were paired with light chain VL1-51 S2A T5N P8S A12G A13S P14L K46R L47T D51G N52D N53LK (SEQ ID NO: 486, see FIG. 22) for large scale transfection as described in Example 4, and purified as described in Example 6 and 14. SDS-PAGE and coomassie stain was performed on samples from BID 53-58 confirming expression.

Example 21

Antibodies comprising an ultralong CDR3, including an ultralong CDR that comprises a non-antibody sequence, may be evaluated by any method known in the art. For example, polynucleotides coding for humanized antibodies comprising an ultralong CDR3 may be expressed, including transiently expressed, in a host cell by any method known in the art. Exemplary humanized antibody sequences that comprise an ultralong CDR3, including an ultralong CDR that comprises a non-antibody sequence, were expressed and characterized (e.g., via HPLC, DLS, and DSF).

Using an overlap PCR approach, the pair of BsaI sites in the nucleotide sequence encoding CDR3 of BLV1H12 (SEQ ID NO: 395) was incorporated into the nucleotide sequence encoding CDR3 of VH4-34 MutE (SEQ ID NO: 957))

```
(caggtccagctgagagagagcggcccttcactggtcaagccatcccag acactgagcctgacatgcacagcaagcgggttttcactgagcgacaagg cagtgggatgggtccgacaggcaccaggaaaagccctggaatggctggg cagcatcgataccgggggaacacagggtacaatcccggactgaagagca gactgtccattaccaaggacaactctaaaagtcaggtgtcactgagcgt gagctccgtcaccacagaggatagtgcaacttactattgcacctctgtg caccaggaaactaagaaataccagagcggtggaggaggttctggaggcg gtggaagtggtggcggaggtagcggaggatgagacctactatggttcag ggtctctggaggtggtggatctggtggaggaggcagtggaggtggtggc agctcttatacctacaattatgaatggcatgtggatgtctggggccaag gaaccctggtcaccgtctcctcagctagc.
```

Then, oligonucleotides encoding various linker sequences were used to amplify the ShK toxin sequence (SEQ ID NO: 648), and the resulting sequences, encoding ShK toxin (SEQ ID NO: 648) and flanking linkers, were introduced into VH4-34MutE-CDR3-BsaI to produce a series of progressively shorter linkers flanking ShK toxin in VH4-34 MutE CDR3 (BIDs 48, 104, 56 66, 65, 67, 61, 60, and 59 of FIG. 21), as well as a VH4-34 MutE encoding only stalk, with 3×GGS in place of the knob (BID 55 of FIG. 21). These vectors encoding heavy chains were paired with light chain VL1-51 S2A T5N P8S A12G A13S P14L K46R L47T D51G N52D N53LK (SEQ ID NO: 486, see FIG. 22) for large scale transfection as described in Example 4, and purified as described in Example 6 and 14, with the following modifications. The cell culture supernatant was separated from cells by spinning 5000×g for 10 minutes. Protein A sepharose Fast Flow (GE Healthcare, #17-1279-03) was dispensed into a disposable column. The amount of resin was determined by the size of the growth. Resin was washed with 20 column volumes of 1×PBS (137 mM NaCl, 2.7 mM KCl, 10 mM Sodium phosphate dibasic, 2 mM Potassium phosphate dibasic. After washing, the supernatant containing IgG was loaded onto the resin with the flow rate monitored not to exceed resin manufacturer specifications. A subsequent wash with 20 columns volumes of 1×PBS was conducted and the protein was eluted from the column using a 0.7 M arginine buffer pH 4.3. Fractions containing protein were combined and dialyzed into 1×PBS. After dialysis the protein solution was filtered over a 0.2 μm PES membrane. Samples were stored at 4° C.

SDS-PAGE and coomassie stain was performed on these purified IgGs in non-reducing conditions and SDS-PAGE and silver staining was performed in reducing conditions. These IgGs were also subjected to HPLC analysis, Dynamic Light Scattering (DLS) analysis, and Differential Scanning Fluorimetry (DSF). HPLC was run on an Agilent 1100 with a Sepax Zenix-C SEC-300 7.8×300 mm with a 3 μM bead size column held at 25° C. The running buffer was 0.28 M KPi and 0.3 M KCl pH 6.9 at a flow rate of 1 mL/min. A 20 μL sample injection was performed for each sample. Samples were monitored at 280 nm. Integration was achieved using Agilent software. In Table 33, the elution time for each IgG and the % monomer is tabulated.

As was described in Example 19, DLS was run on a Wyatt Dyna Pro Titan using disposable Uvettes. Laser power was adjusted to give intensity between 100,000 to 1,000,000 counts per second. Each sample was measured ten times for each measurement and ten measurements were made. Radius in nanometers of the particle, % polydispersity, and an estimate of % mass for the particle of indicated radius is tabulated in Table 33.

Differential scanning fluorimetry (DSF) was done on a BioRad iQ5 with a FAM (485 nm) filter for excitation and a ROX (625 nm) filter for emission. Analysis program was run starting at 25° C. and stopping at 100° C. Steps were at 1° C. intervals with a wait time of 30 seconds between steps with reads being done after waiting at the step. Prior to sample preparation a stock solution was made of 300 X Sypro Orange (Life Technologies, #S6650). 1 μL of this was added to 19 μL of sample. Each sample was run in duplicate. Control sample was 1×PBS. Once the melt curves were obtained the derivative of the curve was taken and the melting transitions were assigned. Melting transition temperatures are tabulated in Table 33. Some melting transitions could not be determined (--).

Example 22

Antibodies comprising an ultralong CDR3, including an ultralong CDR that comprises a non-antibody sequence, may be evaluated by any method known in the art. For example, polynucleotides coding for humanized antibodies comprising an ultralong CDR3 may be expressed, including transiently expressed, in a host cell by any method known in the art. Exemplary humanized antibody sequences that comprise an ultralong CDR3, including an ultralong CDR that comprises a non-antibody sequence, were expressed and characterized (e.g., via SDS-PAGE).

VH4-34 MutE 1×G4S ShK (BID 56 of FIG. 21) and VH4-34 MutE NoLinker ShK (BID59 of FIG. 21) were expressed and purified with light chain (SEQ ID NO: 486, see FIG. 22) as described in Example 21 from Freestyle 293 Cells. Additionally, CHO-S cells and MAXfectin transfection reagent were used per manufacturer instructions (Invitrogen, Carlsbad CA) to produce VH4-34 MutE 1×G4S ShK (BID 56 of FIGS. 21 and 22) and VH4-34 MutE NoLinker ShK (BID59 of FIGS. 21 and 22) from CHO-S cells. Supernatants from CHO-S cells were purified as described in Example 21. Samples purified from CHO-S cells and from 293F cells were subjected to SDS-PAGE and silver staining (FIG. 20). Cell-type specific cleavage of the heavy chain is seen in the case of 1×G4S linker, but not in the NoLinker ShK.

Example 23

Antibodies comprising an ultralong CDR3, including an ultralong CDR that comprises a non-antibody sequence (e.g., a toxin), may be evaluated by any method known in the art (e.g., via cell-based inhibition and ELISA assays).

Kv1.3 Toxins OSK1, ShK, and MOKA in CDR3 of BLV1H12 were assayed for T-cell inhibition. BLV1H12 GLLV 3×G4S OSK1 (K16,D20) (BID 26/230 of FIG. 21) BLV1H12 GLLV 3×G4S OSK1 (P12,K16,D20) (BID 27/231 of FIG. 21), BLV1H12 GLLV 3×G4S ShK (BID 29/229 of FIG. 21), BLV1H12 GGS1:2 Moka (BID 30/205 of FIG. 21), BLV1H12 GGS2:1 Moka (BID 31/206 of FIG. 21), BLV1H12 GGS1:1 Moka (BID 32/204 of FIG. 21), and BLV1H12 GGS3:3 Moka (BID 33/207 of FIG. 21) heavy chains were each paired with CowULVL-Human LambdaC (SEQ ID NO: 474; SEQ ID NO: 807, see FIG. 22), for large scale transfection as described in Example 4, and purified as

TABLE 33

| | Biophysical Data for VH4-34 IgGs with ShK toxin in CDR3 | | | | | | | | |
| | | HPLC Data | | | DLS Data | | | DSF Data | |
| | VH4-34 MutE | % | Elution | | | Pd | % | | | |
| BID# | ShK | monomer | time | R (nm) | % | Mass | Tm1 | Tm2 | Tm3 |
| 48 | 3×G4S | 95 | 8.215 | 4.2 | 10 | 98.6 | 66.8 | 73.6 | 80.4 |
| 104 | 2×G4S | 93 | 8.229 | 5.2 | 6.5 | 99.4 | 67.1 | — | — |
| 56 | 1×G4S | 88 | 8.391 | 6.1 | 9.7 | 91.5 | 67.3 | — | — |
| 66 | GGGG-ShK-GGGG | 68 | 8.742 | 7.1 | 10 | 79.4 | 67.5 | 73.7 | 80.9 |
| 65 | GSGG-ShK-GGGG | 72 | 8.749 | 4.8 | 9.7 | 94.5 | 67.5 | 73.7 | 80.9 |
| 67 | GGG-ShK-GGG | 64 | 8.824 | 4 | 0 | 91.5 | 67.5 | 73.7 | 80.9 |
| 61 | GG-ShK-GG | 72 | 8.888 | 6.6 | 7 | 95.7 | 67.5 | 73.7 | — |
| 60 | G-ShK-G | 70 | 8.774 | 5.1 | 10.6 | 51.9 | 67.5 | 73.7 | — |
| 59 | No linker | 75 | 9.106 | 5.2 | 8 | 96.5 | 67.5 | — | — |
| 55 | No Knob | 99 | 8.116 | 5.2 | 7.4 | 99.8 | 67.7 | — | — | described in Sample 6 and 14. T-cell inhibition assays were performed as described in Example 16, with 3 blood donors, and ELISA measurement of TNF-α secretion. Though responses vary in magnitude among donors, and for different toxins, the trend in Table 34 indicates that increasing concentrations of IgG-CDR3 toxin treatment results in less TNF-α secretion.

replacing the IL-8 and producing VH4-34 MutF 3×G4S ShK (BID50 of FIG. 21) and VH4-34 MutF 3×GGS MOKA (BID52 of FIG. 21), respectively. These heavy chain encoding sequences were paired with light chain VL1-51 S2A T5N P8S A12G A13S P14L K46R L47T D51G N52D N53LK (SEQ ID NO: 486, see FIG. 22) for large scale transfection as described in Example 4, and purified as

TABLE 34

T-Cell inhibition by BLV1H12 IgGs with Kv1.3 inhibitory toxins in CDR3. ELISA for TNF-α secretion

| | | | BID # | | | | | | |
|---|---|---|---|---|---|---|---|---|---|
| | | [IgG] | 26 BLV1H12 GLLV 3xG4S OSK1 (K16, D20) | 27 BLV1H12 GLLV 3xG4S OSK1 (P12, K16, D20) | 29 BLV1H12 GLLV 3xG4S ShK | 30 BLV1H12 GGS1:2 Moka | 31 BLV1H12 GGS2:1 Moka | 32 BLV1H12 GGS1:1 Moka | 33 BLV1H12 GGS3:3 Moka |
| TNF-α ELISA (A450) | Donor 1 | 150 nM | 0.253 ± 0.071 | 0.171 ± 0.079 | 0.057 ± 0.008 | 0.209 ± 0.067 | 0.174 ± 0.006 | 0.114 ± 0.004 | 0.164 ± 0.005 |
| | | 50 nM | 0.556 ± 0.011 | 0.58 ± 0.146 | 0.056 ± 0.016 | 0.488 ± 0.075 | 0.329 ± 0.004 | 0.324 ± 0.029 | 0.295 ± 0.046 |
| | | 17 nM | 0.698 ± 0.049 | 0.651 ± 0.038 | 0.106 ± 0.002 | 0.609 ± 0.056 | 0.447 ± 0.048 | 0.383 ± 0.018 | 0.398 ± 0.02 |
| | | 6 nM | 0.641 ± 0.031 | 0.666 ± 0.019 | 0.133 ± 0.002 | 0.667 ± 0.031 | 0.51 ± 0.008 | 0.493 ± 0.005 | 0.487 ± 0.017 |
| | Donor 2 | 150 nM | 0.027 ± 0.008 | 0.037 ± 0 | 0.034 ± 0 | 0.018 ± 0.004 | 0.027 ± 0.009 | 0.028 ± 0.005 | 0.024 ± 0.005 |
| | | 50 nM | 0.075 ± 0.005 | 0.097 ± 0.005 | 0.053 ± 0.018 | 0.028 ± 0.006 | 0.031 ± 0.002 | 0.073 ± 0.001 | 0.024 ± 0.006 |
| | | 17 nM | 0.094 ± 0.002 | 0.108 ± 0.012 | 0.042 ± 0.01 | 0.032 ± 0.002 | 0.031 ± 0.004 | 0.094 ± 0.007 | 0.032 ± 0.01 |
| | | 6 nM | 0.096 ± 0.009 | 0.121 ± 0.012 | 0.06 ± 0.01 | 0.053 ± 0.006 | 0.035 ± 0.007 | 0.115 ± 0.003 | 0.032 ± 0 |
| | Donor 3 | 150 nM | 0.029 ± 0.003 | 0.037 ± 0 | 0.029 ± 0.005 | 0.034 ± 0.004 | 0.014 ± 0.004 | 0.03 ± 0 | 0.018 ± 0.002 |
| | | 50 nM | 0.102 ± 0.002 | 0.122 ± 0.012 | 0.057 ± 0.014 | 0.056 ± 0 | 0.023 ± 0.01 | 0.093 ± 0.011 | 0.028 ± 0.006 |
| | | 17 nM | 0.144 ± 0.039 | 0.168 ± 0.01 | 0.066 ± 0.028 | 0.063 ± 0.004 | 0.028 ± 0.003 | 0.129 ± 0.016 | 0.044 ± 0.001 |
| | | 6 nM | 0.159 ± 0.003 | 0.191 ± 0.02 | 0.07 ± 0.012 | 0.075 ± 0.007 | 0.043 ± 0.008 | 0.175 ± 0.002 | 0.053 ± 0.006 |

Example 24

Antibodies comprising an ultralong CDR3, including an ultralong CDR that comprises a non-antibody sequence, may be evaluated by any method known in the art (e.g., via T-cell activation or inhibition assays).

Kv1.3 Toxins ShK and MOKA were tested for T-cell inhibition activity, and comparing the effects of expression in BLV1H12, VH4-34 MutE (mutations in IgG 38,) or VH4-34 MutF (Mutations in IgG 43).

Using an overlap PCR approach, sequence encoding 3×G4S ShK or 3×GGS MOKA was inserted into VH4-34+ CDR3-IL8_CDR1-Cow_Q5RQ6E (SEQ ID NO:494), described in Example 6 and 14. Using the same light chain, VH4-34 MutE 3×G4S ShK (BID48 of FIGS. 21 and 22) IgG was produced and purified as described in Example 21, and VH4-34 MutE 3×GGS MOKA (BID49 of FIGS. 21 and 22) IgG was produced and purified as described in Example 20. BLV1H12 3×G4S ShK IgG and BLV1H12 GGS3:3 Moka IgG were produced as described in Example 23. BLV1H12 IgG was produced as described in Example 14. These IgGs were tested for T-cell inhibition as described in Example 16, using ELISA of secreted IL-2 and TNF-alpha as a measure of T-cell activation or inhibition as indicated in Table 35. Another iteration of this experiment is shown in Table 36.

TABLE 35

T-Cell inhibition by VH4-34 IgGs with Kv1.3 inhibiting toxins in CDR3. ELISA for IL-2 and TNF-α secretion.

| | | | BID # | | | | | | |
|---|---|---|---|---|---|---|---|---|---|
| | | [IgG] | 40 BLV1H12 GLLV 3xG4S ShK | 48 VH4-34 MutE 3xG4S ShK | 41 BLV1H12 GGS3:3 Moka | 49 VH4-34 MutE 3xGGS MOKA | 50 VH4-34 MutF 3xG4S ShK | 52 VH4-34 MutF 3xGGS MOKA | 42 BLV1H12 |
| IL-2 ELISA (A450) | Donor 1 | 150 nM | 0.144 ± 0.017 | 0.134 ± 0.013 | 0.493 ± 0.069 | 0.125 ± 0.021 | 0.143 ± 0.013 | 0.158 ± 0.012 | 0.445 ± 0.034 |
| | | 50 nM | 0.163 ± 0.019 | 0.176 ± 0.017 | 0.707 ± 0.054 | 0.18 ± 0.03 | — | — | — |
| | | 17 nM | 0.204 ± 0.009 | 0.25 ± 0.024 | 0.75 ± 0.182 | 0.406 ± 0.052 | — | — | — |
| | | 6 nM | 0.325 ± 0.054 | 0.322 ± 0.029 | 0.759 ± 0.023 | 0.674 ± 0.084 | — | — | — |
| | Donor 2 | 150 nM | 0.196 ± 0.054 | 0.172 ± 0.004 | 0.965 ± 0.262 | 0.2 ± 0.029 | 0.186 ± 0.021 | — | 0.355 ± 0.004 |
| | | 50 nM | 0.337 ± 0.071 | 0.342 ± 0.032 | 1.004 ± 0.198 | 0.346 ± 0.01 | — | — | — |
| | | 17 nM | 0.439 ± 0.047 | 0.455 ± 0.076 | 0.834 ± 0.169 | 0.766 ± 0.226 | — | — | — |
| | | 6 nM | 0.574 ± 0.101 | 0.404 ± 0.049 | 0.747 ± 0.321 | 0.764 ± 0.099 | — | — | — |
| TNF-α ELISA (A450) | Donor 1 | 150 nM | 0.055 ± 0.005 | 0.077 ± 0.001 | 1.251 ± 0.015 | 0.086 ± 0.013 | 0.055 ± 0.009 | 0.109 ± 0.002 | 0.11 ± 0.008 |
| | | 50 nM | 0.08 ± 0.008 | 0.114 ± 0.017 | 1.418 ± 0.181 | 0.294 ± 0.041 | — | — | — |
| | | 17 nM | 0.207 ± 0.017 | 0.276 ± 0.079 | 1.443 ± 0.135 | 0.749 ± 0.044 | — | — | — |
| | | 6 nM | 0.559 ± 0.068 | 0.563 ± 0.105 | 1.45 ± 0.062 | 1.208 ± 0.062 | — | — | — |
| | Donor 2 | 150 nM | 0.043 ± 0.003 | 0.058 ± 0.003 | 0.271 ± 0.16 | 0.06 ± 0.005 | 0.036 ± 0.001 | — | 0.058 ± 0.001 |
| | | 50 nM | 0.049 ± 0.003 | 0.056 ± 0.005 | 0.278 ± 0.07 | 0.096 ± 0.006 | — | — | — |
| | | 17 nM | 0.055 ± 0.002 | 0.065 ± 0.003 | 0.2 ± 0.037 | 0.186 ± 0.085 | — | — | — |
| | | 6 nM | 0.09 ± 0.01 | 0.062 ± 0.001 | 0.204 ± 0.113 | 0.208 ± 0.064 | — | — | — |

TABLE 36

T-Cell inhibition by IgG-CDR3-Toxins. ShK vs. MOKA, Cow vs. Humanized.

| | | [IgG] nM | 40 BLV1H12 GLLV 3xG4S ShK | 48 VH4-34 MutE 3xG4S ShK | 33 BLV1H12 GGS3:3 Moka | 49 VH4-34 MutE 3xGGS MOKA | 55 VH4-34 MutE No Knob |
|---|---|---|---|---|---|---|---|
| IL-2 ELISA (A450) | Donor 1 | 150 | 0.122 ± 0.015 | 0.144 ± 0.025 | 0.1 ± 0.008 | 0.13 ± 0.067 | 0.232 ± 0.054 |
| | | 38 | 0.11 ± 0.003 | 0.124 ± 0.005 | 0.146 ± 0.051 | 0.205 ± 0.033 | — |
| | | 9.4 | 0.173 ± 0.015 | 0.186 ± 0.031 | 0.282 ± 0.041 | 0.251 ± 0.033 | 0.371 ± 0.01 |
| | | 2.3 | 0.171 ± 0.021 | 0.18 ± 0.016 | 0.272 ± 0.016 | 0.333 ± 0.039 | — |
| | | 0.6 | 0.25 ± 0.035 | 0.254 ± 0.012 | 0.355 ± 0.006 | 0.376 ± 0.015 | 0.356 ± 0.005 |
| | | 0.15 | 0.28 ± 0.072 | 0.256 ± 0.019 | 0.303 ± 0.023 | 0.373 ± 0.026 | — |
| | | 0.04 | 0.5 ± 0.056 | 0.405 ± 0.06 | 0.311 ± 0.057 | 0.353 ± 0.054 | 0.333 ± 0.014 |
| | | 0.01 | 0.414 ± 0.039 | 0.453 ± 0.059 | 0.307 ± 0.028 | 0.323 ± 0.076 | — |
| | Donor 2 | 150 | 0.209 ± 0.008 | 0.17 ± 0.012 | 0.252 ± 0.038 | 0.176 ± 0.019 | 0.475 ± 0.001 |
| | | 38 | 0.221 ± 0.01 | 0.217 ± 0.035 | 0.574 ± 0.03 | 0.465 ± 0.036 | — |
| | | 9.4 | 0.353 ± 0.052 | 0.324 ± 0.039 | 0.831 ± 0.071 | 0.718 ± 0.064 | 0.808 ± 0.16 |
| | | 2.3 | 0.391 ± 0.028 | 0.279 ± 0.029 | 0.667 ± 0.026 | 0.778 ± 0.044 | — |
| | | 0.6 | 0.534 ± 0.028 | 0.559 ± 0.078 | 0.902 ± 0.088 | 0.754 ± 0.108 | 0.795 ± 0.059 |
| | | 0.15 | 0.616 ± 0.034 | 0.498 ± 0.028 | 0.793 ± 0.041 | 0.734 ± 0.055 | — |
| | | 0.04 | 0.854 ± 0.02 | 0.688 ± 0.059 | 0.864 ± 0.077 | 0.675 ± 0.01 | 0.976 ± 0.034 |
| | | 0.01 | 0.892 ± 0.079 | 0.718 ± 0.085 | 0.928 ± 0.008 | 0.832 ± 0.06 | — |
| TNF-α ELISA (A450) | Donor 1 | 150 | 0.032 ± 0.002 | 0.049 ± 0.018 | 0.189 ± 0.051 | 0.087 ± 0.011 | 0.599 ± 0.079 |
| | | 38 | 0.108 ± 0.022 | 0.138 ± 0.019 | 0.506 ± 0.122 | 0.549 ± 0.012 | — |
| | | 9.4 | 0.281 ± 0.03 | 0.249 ± 0.01 | 0.801 ± 0.035 | 0.773 ± 0.011 | 0.821 ± 0.074 |
| | | 2.3 | 0.419 ± 0.051 | 0.362 ± 0.035 | 0.768 ± 0.057 | 0.954 ± 0.078 | — |
| | | 0.6 | 0.615 ± 0.096 | 0.634 ± 0.041 | 0.952 ± 0.075 | 0.917 ± 0.033 | 0.813 ± 0.007 |
| | | 0.15 | 0.746 ± 0.116 | 0.742 ± 0.033 | 0.829 ± 0.045 | 0.925 ± 0.082 | — |
| | | 0.04 | 1.077 ± 0.051 | 0.952 ± 0.093 | 0.766 ± 0.087 | 0.889 ± 0.056 | 0.76 ± 0.016 |
| | | 0.01 | 0.955 ± 0.012 | 1.017 ± 0.123 | 0.883 ± 0.236 | 0.776 ± 0.191 | — |
| | Donor 2 | 150 | 0.039 ± 0.01 | 0.049 ± 0.008 | 0.174 ± 0.017 | 0.083 ± 0.007 | 0.366 ± 0.014 |
| | | 38 | 0.06 ± 0.004 | 0.062 ± 0.003 | 0.526 ± 0.06 | 0.373 ± 0.01 | — |
| | | 9.4 | 0.1 ± 0.021 | 0.104 ± 0.007 | 0.721 ± 0.111 | 0.564 ± 0.039 | 0.622 ± 0.102 |
| | | 2.3 | 0.161 ± 0.02 | 0.14 ± 0.01 | 0.618 ± 0.09 | 0.575 ± 0.047 | — |
| | | 0.6 | 0.314 ± 0.047 | 0.281 ± 0.019 | 0.742 ± 0.121 | 0.57 ± 0.039 | 0.631 ± 0.053 |
| | | 0.15 | 0.385 ± 0.016 | 0.316 ± 0.014 | 0.717 ± 0.076 | 0.614 ± 0.072 | — |
| | | 0.04 | 0.554 ± 0.051 | 0.403 ± 0.041 | 0.745 ± 0.067 | 0.573 ± 0.026 | 0.736 ± 0.122 |
| | | 0.01 | 0.663 ± 0.058 | 0.487 ± 0.059 | 0.76 ± 0.058 | 0.627 ± 0.048 | — |

Example 25

Antibodies comprising an ultralong CDR3, including an ultralong CDR that comprises a non-antibody sequence, may be evaluated by any method known in the art (e.g., via T-cell inhibition assays).

We examined the effects of linker length on T-cell inhibition by ShK toxin in CDR3 of VH4-34 MutE IgGs. VH4-34 MutE 3xG4S ShK (BID 48 of FIGS. 21 and 22), VH4-34 MutE NoLinker ShK (BID59 of FIGS. 21 and 22), and the single and di-glycine linker versions VH4-34 MutE G-ShK-G (BID 60 of FIGS. 21 and 22), and VH4-34 MutE GG-ShK-GG (BID 61 of FIGS. 21 and 22). In addition the VH4-34 MutE 3xGGS NoKnob IgG (BID55 of FIGS. 21 and 22) and an irrelevant human IgG were used as negative controls. T-cell assays and ELISAs for IL-2 and TNF-alpha were performed as explained below in this Example, and the data is in Table 37. Seeing minor differences in linker Length on T-cell inhibition, we examined the intermediate linker length VH4-34 MutE ShK IgGs that we had previously purified. Samples of Purified IgGs VH4-34 MutE 1×G4S ShK (BID56 of FIGS. 21 and 22), VH4-34 MutE GSGG-Shk-GGGG (BID65 of FIGS. 21 and 22), VH4-34 MutE GGGG-Shk-GGGG (BID66 of FIGS. 21 and 22), VH4-34 MutE GGG-Shk-GGG (BID67 of FIGS. 21 and 22), and VH4-34 MutE GG-ShK-GG (BID61 of FIGS. 21 and 22) were tested for T-cell inhibition as described in Example 16. TNF alpha secretion was examined as described above. IL-2 secretion on the T cell supernatants was examined by ELISA using mouse anti-hIL2 (R&D Systems, cat #MAB602) coated on a maxisorp plate to capture IL-2 from the T-cell supernatants. Rabbit anti-hIL2, (Abcam, cat #ab9618) was used to detect bound IL-2, and goat anti-rabbit IgG-HRP (Sigma, cat #A 6154) was used with TMB Substrate (BioFX Laboratories, Catalog #: TMBS-1000-01) to develop the ELISA. A450 absorbance was measured with a TECAN Genios Plate reader, and tabulated in Table 38.

TABLE 37

T-Cell inhibition by IgG-CDR3-Toxins. Comparing Long and Short Linkers.

BID:

| | | [IgG] nM | BID # 48 VH4-34 MutE 3xG4S ShK | 59 VH4-34 MutE Shk-No Linker | 60 VH4-34 MutE G-ShK-G | 55 VH4-34 MutE No Knob | Negative Control IgG | BID # 55 — 48 VH4-34 MutE 3xG4S ShK | 61 VH4-34 MutE GG-ShK-GG | VH4-34 MutE No Knob | Negative Control IgG |
|---|---|---|---|---|---|---|---|---|---|---|---|
| IL-2 ELISA (A450) | Donor 1 | 68 | 0.424 ± 0.026 | 0.472 ± 0.031 | 0.494 ± 0.105 | 1.418 ± 0.151 | 1.475 ± 0.043 | 0.432 ± 0.01 | 0.46 ± 0.041 | 1.306 | 1.549 ± 0 |
| | | 15 | 0.6 ± 0.02 | 0.759 ± 0.069 | 0.709 ± 0.048 | — | — | 0.626 ± 0.011 | 0.697 ± 0.029 | — | — |
| | | 3.4 | 0.858 ± 0.046 | 1.078 ± 0.101 | 1.015 ± 0.016 | — | — | 0.752 ± 0.049 | 0.899 ± 0.003 | — | — |
| | | 0.75 | 0.944 ± 0.104 | 1.389 ± 0.024 | 1.407 ± 0.124 | 2.185 ± 0.239 | 2.112 ± 0.073 | 0.864 ± 0.032 | 1.246 ± 0.054 | 2.169 | 2.044 |
| | | 0.17 | 1.46 ± 0.092 | 1.874 ± 0.03 | 1.793 ± 0.004 | — | — | 1.332 ± 0.02 | 1.663 ± 0.122 | — | — |
| | | 0.04 | 1.751 ± 0.001 | 2.049 ± 0.101 | 1.953 ± 0.087 | — | — | 1.585 ± 0.038 | 1.906 ± 0.041 | — | — |
| | | 0.01 | 2.163 ± 0.057 | 2.251 ± 0.07 | 2.185 ± 0.089 | 2.182 ± 0.026 | 1.997 ± 0.105 | 1.931 ± 0.15 | 2.006 ± 0.063 | 2.228 | 2.154 |
| | | 0.00 | 2.001 ± 0.031 | 1.988 ± 0.034 | 1.937 ± 0.091 | — | — | 1.822 ± 0.007 | 1.81 ± 0.074 | — | — |
| | Donor 2 | 68 | 0.343 ± 0.017 | 0.369 ± 0.027 | 0.373 ± 0.038 | 1.317 ± 0.277 | 1.501 ± 0.159 | 0.378 ± 0.037 | 0.336 ± 0.027 | 0.934 | 1.367 |
| | | 15 | 0.407 ± 0.029 | 0.436 ± 0.022 | 0.402 ± 0.031 | — | — | 0.375 ± 0.007 | 0.4 ± 0.024 | — | — |
| | | 3.4 | 0.484 ± 0.047 | 0.506 ± 0.016 | 0.496 ± 0.02 | — | — | 0.454 ± 0.055 | 0.474 ± 0.017 | — | — |
| | | 0.75 | 0.479 ± 0.037 | 0.682 ± 0.045 | 0.674 ± 0.029 | 1.613 ± 0.063 | 1.563 ± 0.068 | 0.442 ± 0.035 | 0.612 ± 0.02 | 1.421 | 1.524 |
| | | 0.17 | 0.695 ± 0.087 | 0.936 ± 0.063 | 1.06 ± 0.072 | — | — | 0.615 ± 0.021 | 0.94 ± 0.069 | — | — |
| | | 0.04 | 1.039 ± 0.119 | 1.389 ± 0.042 | 1.484 ± 0.068 | — | — | 0.897 ± 0.021 | 1.338 ± 0.059 | — | — |
| | | 0.01 | 1.549 ± 0.019 | 1.643 ± 0.071 | 1.638 ± 0.087 | 1.75 ± 0.072 | 1.608 ± 0.077 | 1.306 ± 0.075 | 1.533 ± 0.09 | 1.752 | 1.482 |
| | | 0.00 | 1.616 ± 0.021 | 1.64 ± 0.063 | 1.62 ± 0.061 | — | — | 1.382 ± 0.018 | 1.431 ± 0.05 | — | — |
| TNF-α ELISA (A450) | Donor 1 | 68 | 0.151 ± 0.003 | 0.211 ± 0.027 | 0.186 ± 0.006 | 1.117 ± 0.153 | 1.022 ± 0.043 | 0.131 ± 0.029 | 0.179 ± 0.016 | 1.076 | 1.133 |
| | | 15 | 0.378 ± 0.022 | 0.526 ± 0.021 | 0.46 ± 0.04 | — | — | 0.309 ± 0.017 | 0.466 ± 0.03 | — | — |
| | | 3.4 | 0.668 ± 0.01 | 0.868 ± 0.026 | 0.917 ± 0.008 | — | — | 0.538 ± 0.047 | 0.766 ± 0.035 | — | — |
| | | 0.75 | 0.756 ± 0.003 | 1.135 ± 0.029 | 1.136 ± 0.128 | 1.757 ± 0.168 | 1.693 ± 0.101 | 0.661 ± 0.025 | 1.011 ± 0.037 | 1.672 | 1.647 |
| | | 0.17 | 1.347 ± 0.1 | 1.522 ± 0.022 | 1.56 ± 0.003 | — | — | 1.131 ± 0.055 | 1.371 ± 0.096 | — | — |
| | | 0.04 | 1.383 ± 0.015 | 1.641 ± 0.055 | 1.495 ± 0.063 | — | — | 1.25 ± 0.023 | 1.496 ± 0.034 | — | — |
| | | 0.01 | 1.877 ± 0.095 | 1.961 ± 0.056 | 1.844 ± 0.027 | 1.911 ± 0.019 | 1.623 ± 0.063 | 1.699 ± 0.037 | 1.766 ± 0.039 | 1.878 | 1.662 |
| | | 0.00 | 1.634 ± 0.072 | 1.652 ± 0.071 | 1.495 ± 0.014 | — | — | 1.537 ± 0 | 1.475 ± 0.026 | — | — |
| | Donor 2 | 68 | 0.231 ± 0.011 | 0.295 ± 0.03 | 0.34 ± 0.036 | 1.803 ± 0.209 | 1.881 ± 0.054 | 0.19 ± 0.022 | 0.228 ± 0.009 | 1.32 | 1.537 |
| | | 15 | 0.365 ± 0.063 | 0.511 ± 0.02 | 0.491 ± 0.018 | — | — | 0.336 ± 0.017 | 0.44 ± 0.013 | — | — |
| | | 3.4 | 0.628 ± 0.043 | 0.858 ± 0.004 | 0.848 ± 0.009 | — | — | 0.524 ± 0.093 | 0.615 ± 0.018 | — | — |
| | | 0.75 | 0.731 ± 0.056 | 1.18 ± 0.022 | 1.248 ± 0.018 | 2.098 ± 0.038 | 2.036 ± 0.034 | 0.615 ± 0.032 | 0.907 ± 0.043 | 1.875 | 1.855 |
| | | 0.17 | 1.264 ± 0.093 | 1.646 ± 0.052 | 1.776 ± 0.006 | — | — | 1.023 ± 0.063 | 1.45 ± 0.043 | — | — |
| | | 0.04 | 1.587 ± 0.012 | 1.878 ± 0.041 | 1.975 ± 0.056 | — | — | 1.324 ± 0.053 | 1.758 ± 0.021 | — | — |
| | | 0.01 | 1.973 ± 0.061 | 2.113 ± 0.035 | 2.117 ± 0.086 | 2.228 ± 0.023 | 2.066 ± 0.036 | 1.872 ± 0.04 | 1.971 ± 0.017 | 2.103 | 1.766 |
| | | 0.00 | 1.911 ± 0.017 | 1.867 ± 0.06 | 1.968 ± 0.069 | — | — | 1.667 ± 0.064 | 1.724 ± 0.043 | — | — |
| | | | T-cell growth and activation on same plate | | | | | T-cell growth and activation on same plate | | | |

TABLE 38

T-Cell inhibition by IgG-CDR3-Toxins: intermediate linker lengths

| | | [IgG] nM | BID # 56 VH4-34 MutE 1xG4S ShK | 65 VH4-34 MutE GSGG-Shk-GGGG | 66 VH4-34 MutE GGGG-Shk-GGGG | 67 VH4-34 MutE GGG-Shk-GGG | 61 VH4-34 MutE GG-ShK-GG |
|---|---|---|---|---|---|---|---|
| IL-2 ELISA (A450) | Donor 1 | 100 | — | 0.009 ± 0.002 | 0.019 ± 0.013 | 0.019 ± 0.001 | 0.032 ± 0.005 |
| | | 22 | 0.025 ± 0.012 | 0.011 ± 0.001 | 0.03 ± 0.01 | 0.034 ± 0.007 | 0.04 ± 0.004 |
| | | 4.9 | 0.018 ± 0.002 | 0.019 ± 0.009 | 0.032 ± 0.018 | 0.03 ± | 0.038 ± 0.001 |
| | | 1.10 | 0.04 ± 0.006 | 0.019 ± 0.009 | 0.05 ± 0.014 | 0.051 ± 0.012 | 0.044 ± 0.011 |
| | | 0.24 | 0.068 ± 0 | 0.083 ± 0.035 | 0.099 ± 0.007 | 0.075 ± 0.014 | 0.06 ± 0.001 |
| | | 0.05 | 0.121 ± 0.027 | 0.12 ± 0.027 | 0.142 ± 0.013 | 0.106 ± 0.03 | 0.105 ± 0.003 |
| | | 0.01 | 0.171 ± 0.017 | 0.179 ± 0.01 | 0.174 ± 0.033 | 0.155 ± 0.019 | 0.136 ± 0.037 |
| | | 0.00 | 0.158 ± 0.013 | 0.119 ± 0.031 | 0.146 ± 0.024 | 0.18 ± 0.021 | |
| | Donor 2 | 100 | — | 0.038 ± 0.04 | 0.011 ± 0.013 | 0.018 ± 0.002 | 0.016 ± 0.003 |
| | | 22 | 0.038 ± 0.016 | 0.028 ± 0.019 | 0.035 ± 0.018 | 0.044 ± 0.009 | 0.048 ± 0.017 |
| | | 4.9 | 0.061 ± 0.007 | 0.045 ± 0.01 | 0.051 ± 0.01 | 0.053 ± 0 | 0.059 ± 0.022 |
| | | 1.10 | 0.07 ± 0.001 | 0.056 ± 0.001 | 0.077 ± 0.022 | 0.072 ± 0.001 | 0.074 ± 0.012 |
| | | 0.24 | 0.108 ± 0.014 | 0.116 ± 0.003 | 0.131 ± 0.018 | 0.113 ± 0.006 | 0.123 ± 0.02 |
| | | 0.05 | 0.159 ± 0.016 | 0.163 ± 0.014 | 0.193 ± 0.001 | 0.155 ± 0.026 | 0.165 ± 0.017 |
| | | 0.01 | 0.21 ± 0.023 | 0.22 ± 0.001 | 0.224 ± 0.019 | 0.213 ± 0.023 | 0.22 ± 0.019 |
| | | 0.00 | 0.188 ± 0.032 | 0.185 ± 0.008 | 0.183 ± 0.005 | 0.189 ± 0.001 | — |

TABLE 38-continued

T-Cell inhibition by IgG-CDR3-Toxins: intermediate linker lengths

| | | | BID # | | | |
|---|---|---|---|---|---|---|
| | [IgG] nM | 56 VH4-34 MutE 1xG4S ShK | 65 VH4-34 MutE GSGG-Shk-GGGG | 66 VH4-34 MutE GGGG-Shk-GGGG | 67 VH4-34 MutE GGG-Shk-GGG | 61 VH4-34 MutE GG-ShK-GG |
| TNF-α ELISA (A450) | Donor 1   100 | — | 0.059 ± 0.015 | 0.069 ± 0.023 | 0.073 ± 0 | 0.091 ± 0.005 |
| | 22 | 0.214 ± 0.006 | 0.169 ± 0.039 | 0.191 ± 0.028 | 0.151 ± 0.013 | 0.216 ± 0.006 |
| | 4.9 | 0.245 ± 0.083 | 0.361 ± 0.138 | 0.315 ± 0.017 | 0.23 ± 0.026 | 0.298 ± 0.042 |
| | 1.10 | 0.481 ± 0.003 | 0.462 ± 0.018 | 0.566 ± 0.011 | 0.487 ± 0.019 | 0.509 ± 0.051 |
| | 0.24 | 0.786 ± 0.049 | 0.958 ± 0.169 | 0.96 ± 0.01 | 0.755 ± 0.116 | 0.819 ± 0.143 |
| | 0.05 | 1.231 ± 0.032 | 1.248 ± 0.128 | 1.309 ± 0.025 | 1.093 ± 0.019 | 1.266 ± 0.014 |
| | 0.01 | 1.433 ± 0.079 | 1.497 ± 0.014 | 1.489 ± 0.07 | 1.402 ± 0.064 | 1.448 ± 0.031 |
| | 0.00 | 1.322 ± 0.035 | 1.22 ± 0.071 | 1.339 ± 0.079 | 1.414 ± 0.009 | — |
| | Donor 2   100 | — | 0.031 ± 0.005 | 0.045 ± 0.006 | 0.062 ± 0.002 | 0.036 ± 0.003 |
| | 22 | 0.315 ± 0.026 | 0.273 ± 0.022 | 0.315 ± 0.01 | 0.303 ± 0.001 | 0.258 ± 0.026 |
| | 4.9 | 0.545 ± 0.056 | 0.58 ± 0.032 | 0.616 ± 0.094 | 0.515 ± 0.046 | 0.512 ± 0.042 |
| | 1.10 | 0.845 ± 0.021 | 0.812 ± 0.001 | 0.902 ± 0.06 | 0.785 ± 0.028 | 0.791 ± 0.031 |
| | 0.24 | 1.049 ± 0.027 | 1.181 ± 0.08 | 1.084 ± 0.052 | 0.985 ± 0.067 | 0.996 ± 0.023 |
| | 0.05 | 1.198 ± 0.048 | 1.192 ± 0.022 | 1.305 ± 0.029 | 1.237 ± 0.053 | 1.201 ± 0.083 |
| | 0.01 | 1.336 ± 0.087 | 1.378 ± 0.051 | 1.38 ± 0.009 | 1.327 ± 0.078 | 1.318 ± 0.017 |
| | 0.00 | 1.212 ± 0.094 | 1.193 ± 0.015 | 1.192 ± 0.018 | 1.198 ± 0.097 | — |

Example 26

Antibodies comprising an ultralong CDR3, including an ultralong CDR that comprises a non-antibody sequence, may be evaluated by any method known in the art (e.g., via Kv1.3 inhibition assays).

Kv1.3 inhibition by toxins in CDR3 of IgGs was assessed directly from PBMCs, without purifying T-cells. PBMCs were enriched as described in example 16, but not subjected to T-cell purification. The assay for T-cell inhibition using PBMCs was carried out as it was for purified T-cells in Example 16, with the modification that 1×10^5 PBMCs are dispensed per well. Cell were treated with Toxin CDR3 IgGs VH4-34 MutE 3×G4S ShK (BID48 of FIGS. 21 and 22), VH4-34 MutE GGG-Shk-GGG (BID067 of FIGS. 21 and 22), and VH4-34 MutE G-ShK-G (BID 60 of FIGS. 21 and 22) as described in Example 16. PBMC supernatants were evaluated for Granzyme B and IL-17 by ELISA. IL-17 was detected using Human IL-17 ELISA Ready-SET-Go! (eBioscience Catalog #: 88-7176-22). Granzyme B was detected using Capture Antibody: BD NA/LE Purified Anti-Human Granzyme B. Catalog #: 51-9005687, Detection Antibody: BD Biotinylated Anti-Human Granzyme B. Catalog #: 51-9000060, and Avidin-HRP: BD Streptavidin-HRP. Catalog #: 51-9000209, used per manufacturer directions with modifications for 384 well format. The results of these inhibition assays are tabulated in Table 39.

TABLE 39

T-Cell inhibition by IgG-CDR3-Toxins assayed via Granzyme B and IL-17

| | | BID # | | | |
|---|---|---|---|---|---|
| | [IgG] nM | 75 VH4-34 MutE 3xG4S ShK | 76 VH4-34 MutE G-ShK-G | 77 VH4-34 MutE GGG-Shk-GGG | 61 VH4-34 MutE GG-ShK-GG |
| Granzyme B ELISA (A450) | Donor 1   68 | 0.023 ± 0.004 | 0.03 ± 0.004 | 0.03 ± 0.007 | 0.837 ± 0.217 |
| | 17 | 0.059 ± 0.041 | 0.105 ± 0.012 | 0.166 ± 0.026 | — |
| | 4.2 | 0.94 ± 0.155 | 0.756 ± 0.14 | 1.057 ± 0.128 | 1.579 ± 0.01 |
| | 1.06 | 1.435 ± 0.068 | 1.448 ± 0.069 | 1.481 ± 0.059 | — |
| | 0.26 | 1.61 ± 0.079 | 1.615 ± 0.043 | 1.657 ± 0.013 | 1.602 ± 0.06 |
| | 0.07 | 1.642 ± 0.03 | 1.635 ± 0.058 | 1.644 ± 0.003 | — |
| | 0.02 | 1.665 ± 0.044 | 1.646 ± 0.037 | 1.644 ± 0.024 | 1.563 ± 0.065 |
| | 0.00 | 1.652 ± 0.054 | 1.61 ± 0.034 | 1.557 ± 0.06 | — |
| | Donor 2   68 | 0.02 ± 0.009 | 0.026 ± 0.005 | 0.028 ± 0.006 | 0.445 ± 0.041 |
| | 17 | 0.014 ± 0.001 | 0.034 ± 0.015 | 0.038 ± 0.011 | — |
| | 4.2 | 0.429 ± 0.059 | 0.308 ± 0.023 | 0.721 ± 0.091 | 1.478 ± 0.022 |
| | 1.1 | 1.286 ± 0.015 | 1.269 ± 0.039 | 1.366 ± 0.042 | — |
| | 0.26 | 1.43 ± 0.082 | 1.464 ± 0.02 | 1.42 ± 0.061 | 1.495 ± 0.076 |
| | 0.07 | 1.454 ± 0.034 | 1.507 ± 0.035 | 1.494 ± 0.005 | — |
| | 0.02 | 1.545 ± 0.036 | 1.541 ± 0.05 | 1.492 ± 0.027 | 1.488 ± 0.069 |
| | 0.00 | 1.553 ± 0.075 | 1.507 ± 0.042 | 1.494 ± 0.024 | — |
| IL-17 ELISA (A450) | Donor 1   68 | 0.019 ± 0.002 | 0.02 ± 0.005 | 0.023 ± 0.007 | 0.131 ± 0.024 |
| | 17 | 0.008 ± 0.003 | 0.028 ± 0.011 | 0.034 ± 0.012 | — |
| | 4.2 | 0.115 ± 0.023 | 0.088 ± 0.005 | 0.122 ± 0.05 | 0.456 ± 0.045 |
| | 1.1 | 0.263 ± 0.046 | 0.324 ± 0.058 | 0.388 ± 0.024 | — |
| | 0.26 | 0.361 ± 0.058 | 0.474 ± 0.052 | 0.53 ± 0.075 | 0.474 ± 0.055 |
| | 0.07 | 0.348 ± 0.064 | 0.514 ± 0.077 | 0.451 ± 0.031 | — |

TABLE 39-continued

T-Cell inhibition by IgG-CDR3-Toxins assayed via Granzyme B and IL-17

|  |  | BID # | | | |
|---|---|---|---|---|---|
|  |  | 75 | 76 | 77 | 61 |
|  | [IgG] nM | VH4-34 MutE 3xG4S ShK | VH4-34 MutE G-ShK-G | VH4-34 MutE GGG-Shk-GGG | VH4-34 MutE GG-ShK-GG |
|  | 0.02 | 0.505 ± 0.057 | 0.545 ± 0.028 | 0.492 ± 0.142 | 0.474 ± 0.101 |
|  | 0.00 | 0.45 ± 0.04 | 0.466 ± 0.053 | 0.375 ± 0.079 | — |
| Donor 68 | 0.017 ± 0.007 | 0.024 ± 0.001 | 0.02 ± 0.004 | 0.236 ± 0.012 |
| 2 | 17 | 0.013 ± 0.003 | 0.034 ± 0.006 | 0.035 ± 0.013 | — |
|  | 4.2 | 0.17 ± 0.042 | 0.122 ± 0.012 | 0.247 ± 0.02 | 0.854 ± 0.061 |
|  | 1.1 | 0.532 ± 0.013 | 0.572 ± 0.077 | 0.558 ± 0.023 | — |
|  | 0.26 | 0.608 ± 0.087 | 0.716 ± 0.046 | 0.673 ± 0.041 | 0.783 ± 0.033 |
|  | 0.07 | 0.679 ± 0.053 | 0.755 ± 0.066 | 0.692 ± 0.058 | — |
|  | 0.02 | 0.912 ± 0.102 | 0.908 ± 0.094 | 0.833 ± 0.037 | 0.825 ± 0.052 |
|  | 0.00 | 0.8 ± 0.01 | 0.809 ± 0.047 | 0.75 ± 0.009 | — |

Example 27

Antibodies comprising an ultralong CDR3, including an ultralong CDR that comprises a non-antibody sequence, may be evaluated by any method known in the art (e.g., via T-cell activation or inhibition assays).

The ability to inhibit T-cell activation was compared among several versions of IgG VH4-34 ShK with point mutations in the ShK toxin sequence at position 21 in ShK (SEQ ID NO: 648). Point mutations were generated using an overlap PCR method to modify the ShK sequence in VH4-34 MutE 3xG4S ShK (BID48 of FIG. 21), yielding VH4-34 MutE 3xG4S ShK(M21Q) (BID105 of FIG. 21), VH4-34 MutE 3xG4S ShK(M21L) (BID106 of FIG. 21), VH4-34 MutE 3xG4S ShK(M21F) (BID107 of FIG. 21), VH4-34 MutE 3xG4S ShK(M21I) (BID108 of FIG. 21), and VH4-34 MutE 3xG4S ShK(M21A) (BID109 of FIG. 21). These heavy chains encoding ShK mutations were paired with light chain VL1-51 S2A T5N P8S A12G A13S P14L K46R L47T D51G N52D N53LK (SEQ ID NO: 486, see FIG. 22) for large scale transfection as described in Example 4, and purified as described in Example 6 and 14. The resultant IgGs were tested with VH4-34 MutE 3xG4S (BID 48 of FIGS. 21 and 22) and VH4-34 MutE 3xGGS NoKnob IgG (BID55 of FIGS. 21 and 22) as positive and negative controls. T-cell inhibition was examined using PBMCs as described in Example 26 with the modification that cells were incubated 48 hours rather than 24 hours prior to harvest of supernatant. ELISAs to detect TNF-alpha and IL-17 were carried out using Human IL-17 ELISA Ready-SET-Go! (eBioscience Catalog #: 88-7176-22) and Human TNFα ELISA Ready-SET-Go! (eBioscience Catalog #: 88-7346-22) following manufacturer instructions with modification for 384 well assay. These results are shown in Table 40.

TABLE 40

Mutations to ShK Residue M21 in VH4-34 MutE CDR3.

|  |  |  | BID # | | | | | | |
|---|---|---|---|---|---|---|---|---|---|
|  |  |  | 102 | 80 | 105 | 106 | 107 | 108 | 109 |
|  |  | [IgG] nM | VH4-34 MutE No Knob | VH4-34 MutE 3xG4S ShK | VH4-34 MutE 3xG4S ShK (M21Q) | VH4-34 MutE 3xG4S ShK (M21L) | VH4-34 MutE 3xG4S ShK (M21F) | VH4-34 MutE 3xG4S ShK (M21I) | VH4-34 MutE 3xG4S ShK (M21A) |
| IL-17 ELISA (A450) | Donor 1 | 140 | 0.247 ± 0.128 | 0.02 ± 0.002 | 0.058 ± 0.002 | 0.123 ± 0.02 | 0.53 ± 0.01 | 0.078 ± 0.012 | 0.068 ± 0.003 |
|  |  | 31 | 0.453 ± 0.088 | 0.022 ± 0 | 0.541 ± 0.184 | 0.621 ± 0.167 | 1.114 ± 0.15 | 0.843 ± 0.068 | 0.665 ± 0.04 |
|  |  | 6.9 | 0.828 ± 0.024 | 0.641 ± 0.014 | 0.835 ± 0.024 | 0.786 ± 0.074 | 1.279 ± 0.215 | 1.28 ± 0.024 | 1.13 ± 0.031 |
|  |  | 1.54 | 1.183 ± 0.05 | 1.063 ± 0.045 | 1.216 ± 0.108 | 1.242 ± 0.071 | 1.294 ± 0.012 | 1.303 ± 0.049 | 1.326 ± 0.061 |
|  |  | 0.34 | 1.271 ± 0.015 | 1.417 ± 0.058 | 1.078 ± 0.322 | 1.257 ± 0.004 | 1.06 ± 0.397 | 1.237 ± 0.018 | 1.295 ± 0.078 |
|  |  | 0.08 | 1.338 ± 0.14 | 1.335 ± 0.051 | 1.369 ± 0.09 | 1.141 ± 0.406 | 1.054 ± 0.285 | 1.237 ± 0.042 | 1.194 ± 0.093 |
|  |  | 0.02 | 1.348 ± 0.071 | 1.261 ± 0.075 | 1.375 ± 0.02 | 1.161 ± 0.33 | 1.039 ± 0.091 | 0.96 ± 0.016 | 0.944 ± 0.07 |
|  |  | 0.00 | 0 ± 0.192 | 1.079 ± 0.077 | 1.069 ± 0.089 | 1.261 ± 0.208 | 0.993 ± 0.011 | 1.09 ± 0.007 | 1.05 ± 0.014 |
|  | Donor 2 | 140 | 0.096 ± 0.07 | 0.032 ± 0.005 | 0.048 ± 0.008 | 0.052 ± 0.005 | 0.278 ± 0.029 | 0.047 ± 0.004 | 0.043 ± 0.014 |
|  |  | 31 | 0.364 ± 0.054 | 0.033 ± 0.012 | 0.27 ± 0.015 | 0.278 ± 0.044 | 0.602 ± 0.224 | 0.335 ± 0.005 | 0.219 ± 0.019 |
|  |  | 6.9 | 0.641 ± 0.01 | 0.281 ± 0.038 | 0.707 ± 0.092 | 0.595 ± 0.028 | 0.647 ± 0.229 | 0.614 ± 0.061 | 0.592 ± 0.092 |
|  |  | 1.54 | 0.785 ± 0.024 | 0.785 ± 0.013 | 0.924 ± 0.022 | 0.795 ± 0.267 | 0.597 ± 0.22 | 0.733 ± 0.052 | 0.711 ± 0.009 |
|  |  | 0.34 | 0.82 ± 0.018 | 0.757 ± 0.058 | 0.859 ± 0.089 | 0.861 ± 0.066 | 0.765 ± 0.241 | 0.744 ± 0.241 | 0.897 ± 0.044 |
|  |  | 0.08 | 0.777 ± 0.137 | 0.772 ± 0.069 | 0.778 ± 0.012 | 0.654 ± 0.221 | 0.879 ± 0.013 | 0.91 ± 0.044 | 0.918 ± 0.054 |
|  |  | 0.02 | 0.959 ± 0.105 | 0.977 ± 0.052 | 1.022 ± 0.022 | 0.937 ± 0.259 | 0.831 ± 0.181 | 0.896 ± 0.061 | 0.984 ± 0.013 |
|  |  | 0.00 | 0 ± 0.002 | 1.03 ± 0.053 | 1.099 ± 0.003 | 1.107 ± 0.092 | 0.797 ± 0.11 | 0.836 ± 0.036 | 0.923 ± 0.063 |
| TNF-α ELISA (A450) | Donor 1 | 140 | 0.402 ± 0.152 | 0.024 ± 0.003 | 0.053 ± 0.008 | 0.164 ± 0.036 | 1.079 ± 0.277 | 0.074 ± 0.012 | 0.056 ± 0.008 |
|  |  | 31 | 0.808 ± 0.127 | 0.036 ± 0.007 | 1.48 ± 0.007 | 1.515 ± 0.089 | 1.494 ± 0.16 | 1.506 ± 0.006 | 1.473 ± 0.053 |
|  |  | 6.9 | 1.096 ± 0.075 | 1.624 ± 0.105 | 1.799 ± 0.041 | 1.762 ± 0.024 | 1.616 ± 0.155 | 1.854 ± 0.019 | 1.957 ± 0.062 |
|  |  | 1.54 | 1.334 ± 0.12 | 1.734 ± 0.082 | 1.69 ± 0.171 | 1.575 ± 0.087 | 1.466 ± 0.046 | 1.604 ± 0.009 | 1.696 ± 0.086 |
|  |  | 0.34 | 1.416 ± 0.074 | 1.542 ± 0.01 | 1.473 ± 0.013 | 1.495 ± 0.033 | 1.448 ± 0.008 | 1.591 ± 0.076 | 1.581 ± 0.004 |
|  |  | 0.08 | 1.451 ± 0.001 | 1.059 ± 0.281 | 1.26 ± 0.179 | 1.462 ± 0.045 | 1.389 ± 0.041 | 1.399 ± 0.019 | 1.397 ± 0.131 |
|  |  | 0.02 | 1.518 ± 0.123 | 1.188 ± 0.067 | 1.396 ± 0.11 | 1.493 ± 0.05 | 1.1 ± 0.036 | 1.384 ± 0.04 | 1.371 ± 0.06 |
|  |  | 0.00 | 0 ± 0.012 | 1.306 ± 0.082 | 1.408 ± 0.059 | 1.337 ± 0.079 | 1.241 ± 0.082 | 1.388 ± 0.065 | 1.379 ± 0.052 |
|  | Donor 2 | 140 | 0.167 ± 0.064 | 0.035 ± 0.013 | 0.036 ± 0.01 | 0.046 ± 0.001 | 0.942 ± 0.038 | 0.056 ± 0.007 | 0.042 ± 0.005 |
|  |  | 31 | 0.438 ± 0 | 0.035 ± 0.001 | 0.733 ± 0.016 | 0.726 ± 0.062 | 1.504 ± 0.102 | 1.028 ± 0.046 | 0.63 ± 0.044 |

TABLE 40-continued

Mutations to ShK Residue M21 in VH4-34 MutE CDR3.

| | BID # | | | | | | |
|---|---|---|---|---|---|---|---|
| [IgG] nM | 102 VH4-34 MutE No Knob | 80 VH4-34 MutE 3xG4S ShK | 105 VH4-34 MutE 3xG4S ShK (M21Q) | 106 VH4-34 MutE 3xG4S ShK (M21L) | 107 VH4-34 MutE 3xG4S ShK (M21F) | 108 VH4-34 MutE 3xG4S ShK (M211) | 109 VH4-34 MutE 3xG4S ShK (M21A) |
| 6.9 | 0.916 ± 0.004 | 0.953 ± 0.063 | 1.667 ± 0.052 | 1.623 ± 0.001 | 1.512 ± 0.219 | 1.777 ± 0 | 1.764 ± 0.014 |
| 1.54 | 1.293 ± 0.029 | 1.655 ± 0.023 | 1.749 ± 0.06 | 1.768 ± 0.038 | 1.423 ± 0.004 | 1.579 ± 0.065 | 1.715 ± 0.009 |
| 0.34 | 1.55 ± 0.13 | 1.586 ± 0.05 | 1.662 ± 0.041 | 1.661 ± 0.029 | 1.567 ± 0.009 | 1.597 ± 0.021 | 1.683 ± 0.003 |
| 0.08 | 1.424 ± 0.092 | 1.36 ± 0.049 | 1.433 ± 0.064 | 1.501 ± 0.01 | 1.523 ± 0.097 | 1.56 ± 0.045 | 1.599 ± 0.015 |
| 0.02 | 1.562 ± 0.109 | 1.483 ± 0.045 | 1.578 ± 0.018 | 1.57 ± 0.05 | 1.616 ± 0.05 | 1.623 ± 0.001 | 1.67 ± 0.022 |
| 0.00 | 0 ± 0.003 | 1.427 ± 0.009 | 1.626 ± 0.006 | 1.667 ± 0.053 | 1.49 ± 0.035 | 1.518 ± 0.059 | 1.576 ± 0.027 |

For the disclosure herein, the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the exemplary embodiments (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the exemplary embodiments and does not pose a limitation on the scope of the exemplary embodiments otherwise claimed. No language in the specification should be construed as indicating any non-claimed element essential to the practice of the exemplary embodiments.

Groupings of alternative elements or embodiments disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the exemplary embodiments. Of course, variations on these described embodiments will become apparent to those of ordinary skill in the art upon reading the foregoing description. The inventor expects skilled artisans to employ such variations as appropriate, and the inventors intend for the embodiments to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications. Each of the above-cited references is individually incorporated herein by reference in their entirety.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Exemplary embodiments so claimed are inherently or expressly described and enabled herein.

In closing, it is to be understood that the exemplary embodiments disclosed herein are illustrative of the principles of the present disclosure. Other modifications that can be employed are within the scope of the disclosure. Thus, by way of example, but not of limitation, alternative configurations of the present exemplary embodiments can be utilized in accordance with the teachings herein. Accordingly, the present exemplary embodiments are not limited to that precisely as shown and described.

The invention claimed is:

1. An antibody comprising:

(a) a modified heavy chain variable domain comprising, in order:

(i) a FR1-CDR1-FR2-CDR2-FR3 region comprising the FR1, FR2 and FR3 of the human germline VH4-34 variable domain (SEQ ID NO: 33) with the exception of at least one amino acid substitution selected from Q5R, Q6E, and E50S, and up to 5 additional amino acids substitutions at positions other than positions 5, 6, and 50;

(ii) an ultralong CDR3 that is at least 35 amino acids in length; and (iii) a framework region 4 (FR4); and (b) a light chain variable domain.

2. The antibody of claim 1, wherein the SEQ ID NO: 33 comprises at least two amino acid substitution selected from Q5R, Q6E, and E50S.

3. The antibody of claim 1, wherein the SEQ ID NO: 33 comprises three amino acid substitution selected from Q5R, Q6E, and E50S.

4. The antibody of claim 1, wherein the light chain variable domain is a VL1-51 light chain variable domain or a variant thereof.

5. The antibody of claim 4, wherein the light chain variable domain comprises the amino acid sequence of residues 1-90 of SEQ ID NO: 37 with the exception of one or more amino acid substitutions at positions corresponding to positions 2, 5, 8, 12, 13, 14, 46, 47, 51, 52, and 53 in SEQ ID NO: 37.

6. The antibody of claim 5, wherein the amino acid substitutions are selected from S2A, T5N, P8S, A12G, A13S, P14L, K46R, L47T, D51G, N52D, and N53T.

7. The antibody of claim 5, wherein the light chain variable region comprises at least two of the amino acid substitutions.

8. The antibody of claim 1, wherein the FR4 comprises an amino acid sequence selected from the group consisting of:

(i) WGHGTAVTVSS (SEQ ID NO: 570), (ii) WGKGTTVTVSS (SEQ ID NO: 571), (iii) WGRGTLVTVSS (SEQ ID NO: 573), and (iv) WGQGLLVTVSS (SEQ ID NO: 500).

9. The antibody of claim 1, wherein antibody is a single-chain variable fragment.

10. The antibody of claim 1, wherein heavy and light chain variable domains are on different polypeptides.

\* \* \* \* \*